US007238692B2

(12) United States Patent
Timmer et al.

(10) Patent No.: US 7,238,692 B2
(45) Date of Patent: *Jul. 3, 2007

(54) MEDICAL DEVICES EMPLOYING TRIAZINE COMPOUNDS AND COMPOSITIONS THEREOF

(75) Inventors: Richard T. Timmer, Decatur, GA (US); Christopher W. Alexander, Norcross, GA (US); Sivaram Pillarisetti, Norcross, GA (US); Uday Saxena, Atlanta, GA (US); Koteswar Rao Yeleswarapu, Hyderabad (IN); Manojit Pal, Hyderabad (IN); Jangalgar Tirupathy Reddy, Hyderabad (IN); Velagala Venkata Rama Murali Krisha Reddy, Hyderabad (IN); Sesha Sridevi Alluri, Hyderabad (IN); Potlapally Rajender Kumar, Hyderabad (IN); Gaddam Om Reddy, Hyderabad (IN)

(73) Assignee: Reddy US Therapeutics, Inc., Norcross, GA (US)

( * ) Notice: Subject to any disclaimer, the term of this patent is extended or adjusted under 35 U.S.C. 154(b) by 133 days.

This patent is subject to a terminal disclaimer.

(21) Appl. No.: 10/951,120

(22) Filed: Sep. 27, 2004

(65) Prior Publication Data

US 2005/0124619 A1 Jun. 9, 2005

Related U.S. Application Data

(60) Division of application No. 10/400,169, filed on Mar. 26, 2003, now Pat. No. 7,169,785, which is a continuation-in-part of application No. 10/390,485, filed on Mar. 17, 2003, now Pat. No. 7,173,032, which is a continuation of application No. 10/253,388, filed on Sep. 23, 2002, now abandoned.

(60) Provisional application No. 60/324,147, filed on Sep. 21, 2001.

(51) Int. Cl.
*A61M 31/00* (2006.01)
*A61F 2/86* (2006.01)
*C07D 251/70* (2006.01)
*C07D 251/52* (2006.01)
*C07D 251/30* (2006.01)

(52) U.S. Cl. .................. 514/245; 623/1.11; 623/1.2; 623/1.42

(58) Field of Classification Search ............... 514/241, 514/245; 623/1.11, 1.2, 1.42
See application file for complete search history.

(56) References Cited

U.S. PATENT DOCUMENTS

| | | | |
|---|---|---|---|
| 3,290,305 A | 12/1966 | Schmitz | |
| 3,758,471 A | 9/1973 | Irikura et al. | |
| 3,867,383 A | 2/1975 | Winter | |
| 4,617,390 A | 10/1986 | Hoppe et al. | |
| 5,062,882 A | 11/1991 | Newton et al. | |
| 5,346,691 A | 9/1994 | Raspanti | |
| 5,470,921 A | 11/1995 | Kaul et al. | |
| 5,599,576 A | 2/1997 | Opolski | |
| 5,651,174 A | 7/1997 | Schwartz et al. | |
| 5,725,568 A | 3/1998 | Hastings | |
| 5,759,525 A | 6/1998 | Raspanti et al. | |
| 5,801,224 A | 9/1998 | Narayan et al. | |
| 5,897,696 A | 4/1999 | Giodano et al. | |
| 5,980,551 A | 11/1999 | Summers et al. | |
| 5,981,568 A | 11/1999 | Kunz et al. | |
| 6,117,996 A | 9/2000 | Lowe et al. | |
| 6,123,763 A | 9/2000 | Kamikubo et al. | |
| 6,150,360 A | 11/2000 | Daeyaert et al. | |
| 6,153,252 A | 11/2000 | Hossainy et al. | |
| 6,179,817 B1 | 1/2001 | Zhong | |
| 6,187,370 B1 | 2/2001 | Dinh et al. | |
| 6,218,016 B1 | 4/2001 | Tedeschi et al. | |
| 6,239,071 B1 | 5/2001 | Giencke et al. | |
| 6,249,952 B1 | 6/2001 | Ding | |
| 6,273,913 B1 | 8/2001 | Wright et al. | |
| 6,284,710 B1 | 9/2001 | Riebel et al. | |
| 6,290,729 B1 | 9/2001 | Slepian et al. | |
| 6,491,617 B1 * | 12/2002 | Ogle et al. .................. 600/3 |
| 2002/0051730 A1 | 5/2002 | Bodnar et al. | |
| 2002/0065270 A1 | 5/2002 | Moriarty et al. | |

FOREIGN PATENT DOCUMENTS

DE 19531084 A1 2/1997

(Continued)

OTHER PUBLICATIONS

Bennet, J. Ed., et al., Cecil Textbook of Medicine, 20th Ed., 1996, 1001-1010, W. B. Saunders Company.

(Continued)

*Primary Examiner*—Venkataraman Balasubramanian
(74) *Attorney, Agent, or Firm*—Milagros A. Cepeda; Robert A. Franks

(57) ABSTRACT

The present invention relates to methods and compositions comprising compounds that treat pathophysiological conditions arising from inflammatory responses. In particular, the present invention is directed to compounds that inhibit or block glycated protein produced induction of the signaling-associated inflammatory response in endothelial cells. The present invention relates to compounds that inhibit smooth muscle proliferation. In particular, the present invention is directed to compounds that inhibit smooth muscle cell proliferation by modulating HSPGs such as Perlecan. The present invention further relates to the use of compounds to treat vascular occlusive conditions characterized by smooth muscle proliferation such as restenosis and atherosclerosis.

18 Claims, 86 Drawing Sheets

FOREIGN PATENT DOCUMENTS

| | | | |
|---|---|---|---|
| JP | WO 00/47567 | * | 8/2000 |
| WO | WO-97/08156 A1 | | 3/1997 |
| WO | WO-99/31088 A1 | | 6/1999 |
| WO | WO 99/36410 A1 | | 7/1999 |
| WO | WO-01/40218 A1 | | 6/2001 |
| WO | WO 01/47897 A1 | | 7/2001 |
| WO | WO 01/47921 A1 | | 7/2001 |
| WO | WO-02/26139 A1 | | 4/2002 |
| WO | WO-02/26271 A1 | | 4/2002 |
| WO | WO 03/024926 A2 | | 3/2003 |

OTHER PUBLICATIONS

Axford, J., "Glycosylation and Rheumatic Disease", Biochimica et Biophysica Acta, 1999, 219-229, 1455, Elsevier Science B.V.

Stern, R., "Devising A Pathway For Hyaluronan Catabolism: Are We There Yet?", Glycobiology, 2003, 105R-115R, vol. 13, No. 12, Oxford University Press.

Fattori, Rossella et al., "Drug-Eluting Stents in Vascular Intervention", The Lancet, 2003, vol. 361, pp. 247-249.

Van Der Hoeven, Barend L. et al., "Drug-Eluting Stents: Results, Promises and Problems", Int'l. Journal of Cardiology, 2005, vol. 99, pp. 9-17.

Indolfi, Ciro et al., "Molecular Mechanisms of In-Stent Restenosis and Approach to Therapy with Eluting Stents", TCM, 2003, vol. 13(4), pp. 142-148.

Javed, Qamar et al., "Tumor Necrosis Factor-alpha Antibody Eluting Stents Reduce Vascular Smooth Muscle Cell Proliferation in Saphenous Vein Organ Culture", Experimental and Molecular Pathology, 2002, vol. 73, pp. 104-111.

* cited by examiner

600 MHz, CDCl$_3$, TMS, 55 C

600 MHz, CDCl₃, TMS, 55 C

600 MHz, CDCl$_3$, TMS, 55 C

MEDICAL DEVICES EMPLOYING TRIAZINE COMPOUNDS AND COMPOSITIONS THEREOF

PRIOR RELATED U.S. APPLICATION DATA

This application is a divisional application of U.S. patent application Ser. No. 10/400,169 filed Mar. 26, 2003, now U.S. Pat. No. 7,169,785, which is a continuation-in-part of U.S. patent application Ser. No. 10/390,485 filed Mar. 17, 2003, now U.S. Pat. No. 7,173,032, which is a continuation of U.S. patent application Ser. No. 10/253,388 filed Sep. 23, 2002, now abandoned, which claims priority to U.S. Provisional Application Ser. No. 60/324,147 filed Sep. 21, 2001, all of which are incorporated, herein by reference.

FIELD OF THE INVENTION

The present invention relates to triazine compounds. More particularly, the invention relates to methods and compositions for making and using triazine compounds.

BACKGROUND OF THE INVENTION

Synthesis of novel compounds leads to new possibilities for discovery of novel therapeutic interventions. By using structure and activity relationship investigations, compounds can be tailored so that the compounds have at least one activity that can be predicted from its structure. Using high-throughput assays allows for the rapid determination of the activity of the newly synthesized compounds.

Novel compounds for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise in the population as a whole, with diabetes alone affecting 16 million people.

While inflammation in and of itself is a normal immune response, chronic inflammation leads to complications and ongoing system damage due to the interactions of unknown cellular factors. In particular, chronic inflammation can cause endothelial damage resulting in vascular complications. Coronary artery, cerbrovascular and peripheral vascular disease resulting from atherosclerotic and thromboembolic macroangiopathy are the primary causes of mortality in chronic inflammatory diseases.

Many humans and animals have limited lifespans and lifestyles because of conditions relating to lifestyle choices, such as diet and exercise, or because of genetic predispositions to develop a disease. For example, vascular smooth muscle cell proliferation is a common consequence of endothelial injury and is believed to be an early pathogenetic event in the formation of atherosclerotic plaques or complications related to vascular injury or as a result surgical interventions. Abnormal vascular smooth muscle cell (SMC) proliferation is thought to contribute to the pathogenesis of vascular occlusive lesions, including arteriosclerosis, atherosclerosis, restenosis, and graft atherosclerosis after organ transplantation.

Percutaneous coronary artery intervention (PTCA) procedures are the most common in-patient hospital procedure in the United States. According to the American Heart Association, about one-third of the patients that undergo balloon angioplasty have restenosis of the widened segment of the vessel within approximately 6 months. It may be necessary to perform another angioplasty or coronary artery bypass surgery on restenosed arteries. A key feature of restenosis is an injury response that results in activation of an inflammatory cascade and remodeling of the cells both inside and outside the carotid artery wall. This includes excessive growth of connective tissue and smooth muscle into the lumen of the artery known as neointimal hyperplasia. Currently there are no effective pharmacological treatments available that control the pathogenesis of vascular occlusive lesions, such as, but not limited to, arteriosclerosis, atherosclerosis, restenosis, and graft atherosclerosis after organ transplantation. Identification of effective therapeutics with minimal side effects will restore quality of life without requiring additional surgical procedures such as coronary artery bypass surgery.

Control or modulation of factors produced by the body in response to injury, surgery, metabolic factors or loss of control of in feedback mechanisms, leading to too much or too little of a factor has long been the goal of administering pharmacological agents. One disease that rapidly growing in the industrialized countries is the occurrence of diabetes and all of its attendant sequellae. One of the factors important in the damage associated with diabetes is the presence of glycated proteins.

Glycated proteins and advanced glycation end products (AGE) contribute to cellular damage, particularly, diabetic tissue injury, by at least by two major mechanisms; modulation of cellular functions through interactions with specific cell surface receptors, and alteration of the extracellular matrix leading to the formation of protein cross-links. Studies suggest that glycated protein and AGE interactions with cells may promote inflammatory processes and oxidative cellular injury. AGE increases lipoprotein oxidisability and atherogenicity. Its binding to matrix proteins induces synthesis of cytokines and activates cellular messangers. Diseases where glycated protein and AGE accumulation is a suspected etiological factor include vascular complications of diabetes, microangiopathies, renal insufficiency and Alzheimer's disease.

The exact mechanisms by which high plasma glucose, as seen in diabetes, causes microvascular damage are not completely understood. One potential mechanism by which hyperglycemia can be linked to microangiopathies is through the process of non-enzymatic glycation of critical proteins. Non-enzymatic glycation, i.e. the linking of proteins with glucose, leads to the formation of glycated proteins. The first step in this glycation pathway involves the non-enzymatic condensation of glucose with free amino groups in the protein, primarily the epsilon-amino groups of lysine residues, forming the Amadori adducts. These early glycation products can undergo further reactions such as rearrangements, dehydration and condensations to form irreversible advanced glycation end products (AGE). These are a highly reactive group of molecules whose interaction with specific receptors on the cell-surface which are thought to lead to pathogenic outcomes.

Other major area of disease of where treatments are needed and for which adequate and effective therapies do not exist are cellular proliferative disorders, or disorders caused by unwanted or unintended cellular growth. As mentioned, smooth muscle cell (SMC) hyperplasia is a major event in the development of atherosclerosis and is also responsible for the significant number of failure rates following vascular procedures such as angioplasty, stent implantation and coronary artery bypass surgery. In the normal vessel, SMC are quiescent, but they proliferate when damage to the endothelium occurs. Naturally occurring growth modulators, many of which are derived from the endothelium, tightly control SMC proliferation in vivo. When the control becomes unregulated, a pathological state is induced in the subject.

Another major area of unwanted cellular growth, that is unchecked by the body's regulatory systems, is cancer or oncological conditions. Many therapies have been used and are being used in an effort to restore health or at least stop the unwanted cell growth. Many times, therapeutic agents can have an effect individually, but often, therapeutic regimes require combinations of different pharmacological agents with treatments such as surgery or radiation.

There is a present need for treatments of chronic or acute diseases, such as atherosclerosis, unwanted cellular growth or cellular proliferation, diabetes, inflammatory conditions and vascular occlusive pathologic conditions, because occurrence is frequent, the currently available treatments are costly and the conditions are refractory to many pharmacological therapies. The mechanisms involved in the control or prevention of such diseases are not clear and there exists a need for preventive and therapeutic treatments of these and other diseases Thus, what is presently needed are novel compounds that find utility in methods and compositions for treatment and prevention of chronic and acute diseases.

SUMMARY OF THE INVENTION

The present invention is directed to methods and compositions comprising novel compounds, primarily based on a substituted triazine core. Disclosed herein are methods for making novel compounds, the compounds, compositions comprising the compounds, and methods and compositions for using the compounds. The compounds and compositions comprising the compounds have utility in treatment of a variety of diseases.

Compositions in accordance with the present invention comprise triazine compounds, analogs, derivatives, and mixtures thereof. Such triazine compounds comprise the following structure, where $N^A$, $N^B$ and $N^C$ are typically used to represent pendant substituted amino groups attached to 1,3,5-triazine at the 2, 4 and 6 positions:

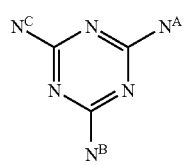

An example of such triazine compounds includes compounds having the following structure.

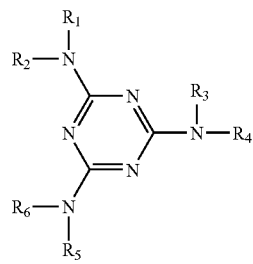

In this example, each pendent amino (NRR') group can represent simply an $NH_2$ group or a secondary or tertiary amino group, including a cyclic secondary amide, and a range of other substituents as described herein. Compositions in accordance with the present invention also comprise analogs of the tris(amino) compounds, that include intermediate compounds in the synthesis of the tris(amino) triazine compounds indicated above, for example diamino chlorotriazine compounds, or amino diclorotriazine compounds shown below, where $N^A$ and $N^B$ are pendant substituted amino groups as described above.

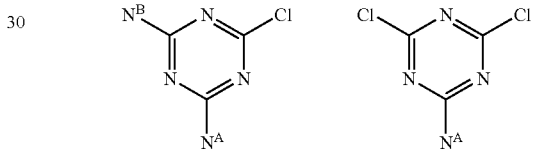

Compositions in accordance with the present invention also comprise analogs of the tris(amino) triazine compounds indicated above, including compounds that are isolated as byproducts in the synthesis of the tris(amino) triazine compounds, such as bis(amino)alkoxy triazine compounds as shown below, where E=O or S and the like.

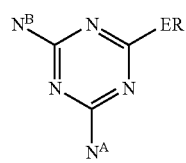

The present invention also comprises compositions used in making the novel compounds and methods of making the novel compounds disclosed herein.

The present invention is directed to methods and compositions comprising compounds that have utility in treatment of pathological conditions. One aspect of the present invention comprises compounds and compositions comprising such compounds in methods for treating diseases related to unwanted cellular proliferation. Many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis are caused by or have collateral damage due to unwanted cellular proliferation, such as smooth muscle cell (SMC) hyperplasia. At least one activity of one or more of these compounds is that the compound has the activity of effecting the synthesis of proteoglycans including induction and synthesis of proteoglycans and active fragments of proteoglycans. Methods comprise administration of compositions comprising compounds that have at least the activity of effecting cellular proliferation and effecting proteoglycan synthesis and activity.

The present invention also comprises methods and compositions comprising compounds described herein that have an activity associated with modulation of glycosidase enzymes and thus, effecting the substrates for such enzymes. Glycosidase enzymes and their activity with their substrates, such as proteoglycans or glycated proteins, are aspects of a variety of diseases such as vascular conditions, proteoglycan-associated diseases, kidney disease; autoimmune disease and inflammatory diseases. Compounds described herein that have an activity that effects the concentrations of substrates of glycosidase enzymes are used in methods of treatment of such vascular, inflammatory, metastatic and systemic diseases.

An embodiment of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. Methods of treatment comprise administration of compositions comprising having compounds having at least the activity of modulating inflammatory reactions that are components of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. An aspect of the present invention comprises methods and compositions for the treatment of diseases, preconditions or pathologies associated with inflammatory cytokines and other inflammation related molecules.

Another embodiment of the present invention comprises methods and compositions comprising compounds that have at least the activity of causing cellular death or a cessation of cellular activity, referred to herein as cytotoxic activity. This activity can be used in methods for in vitro or in vivo cytotoxicity. For example, compounds having this activity can be selectively delivered to an area within a living organism to selectively kill cells in that area. Such methods are using in treating hyperproliferative cells, such as cancers, or other unwanted cellular growth or cellular activities. One aspect of the invention provides compositions comprising compounds that nonselectively kill cells. Another aspect of the invention provides compounds that selectively kill cells, for example, cells that have a particular cellular marker or other identifying characteristic such as metabolic rate or uptake of a particular compound.

The present invention also comprises pharmaceutical compositions comprising the compounds disclosed herein. Routes of administration and dosages of effective amounts of the compounds and pharmaceutical compositions are also disclosed. For example, the compounds of the present invention can be administered in combination with other pharmaceutical agents in a variety of protocols for effective treatment of disease.

In another aspect, the present invention relates to drug delivering or eluting medical devices that contain or are coated with at least one compound disclosed herein. The medical device suitable for use with the compounds of the present invention include, but are not limited to, stents and other medical devices that can provide a substrate for delivery of at least one compound.

Other aspects of the present invention comprise compositions and methods for microarray devices. Such microarray devices and methods comprise a variety of microarrays that may be used, for example, to study and monitor gene expression in response to treatment with the compounds of the present invention. The microarrays may comprise nucleic acid sequences, carbohydrates or proteins that are determinative for specific cells, tissues, species, disease states, prognoses, disease progression, or any other combination of molecules that can be used to determine an effect of one or more of the compounds of the present invention. Other embodiments of the present invention comprise methods using databases and computer applications.

DETAILED DESCRIPTION OF THE INVENTION

Figure 1:
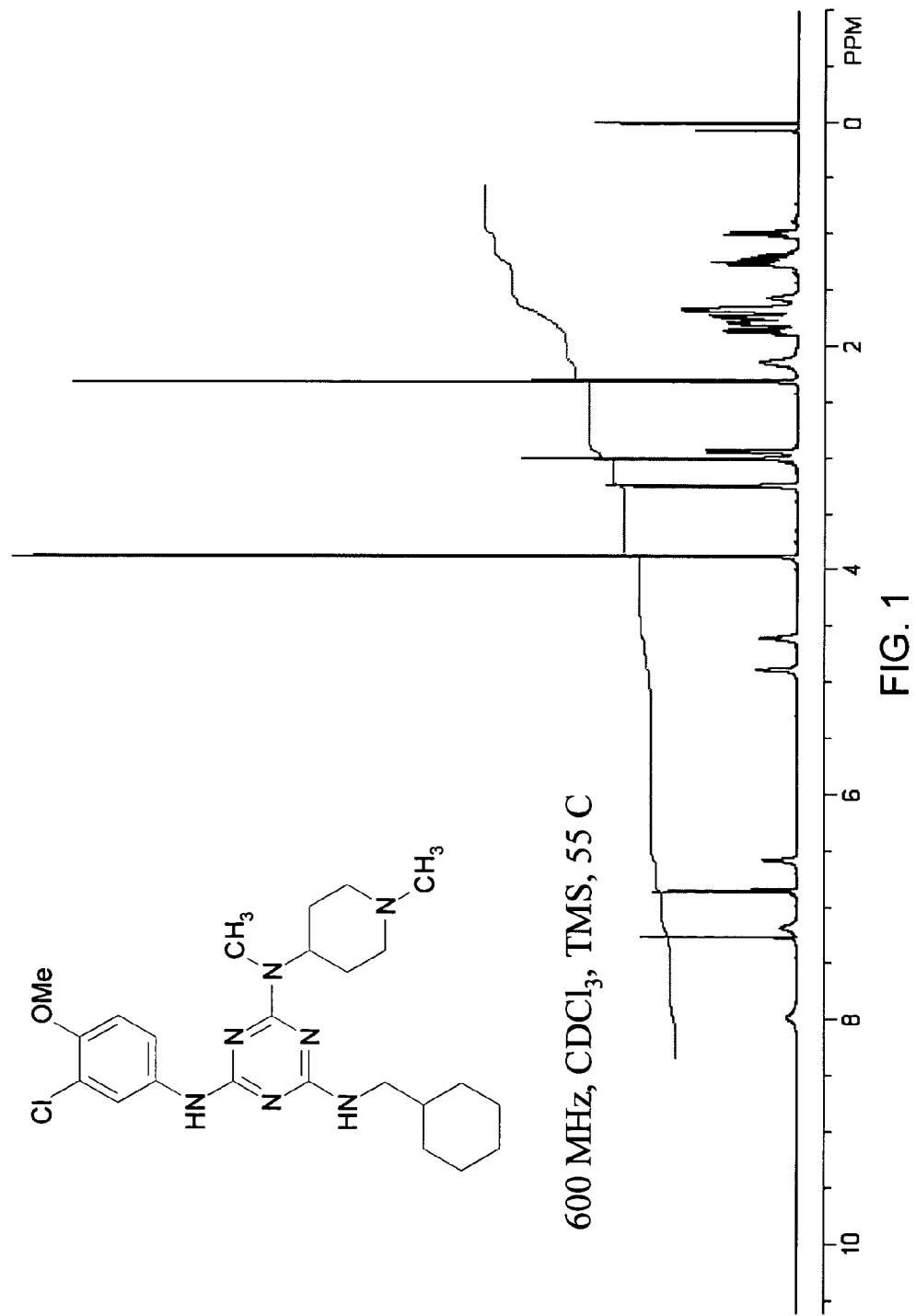
FIG. 1. $^1$H NMR of N-(3-Chloro-4-methoxy-phenyl)-N'-cyclohexylmethyl-N"-methyl-N"-(1-methyl-piperidin-4-yl)-[1,3,5]triazine-2,4,6-triamine.
Figure 2:
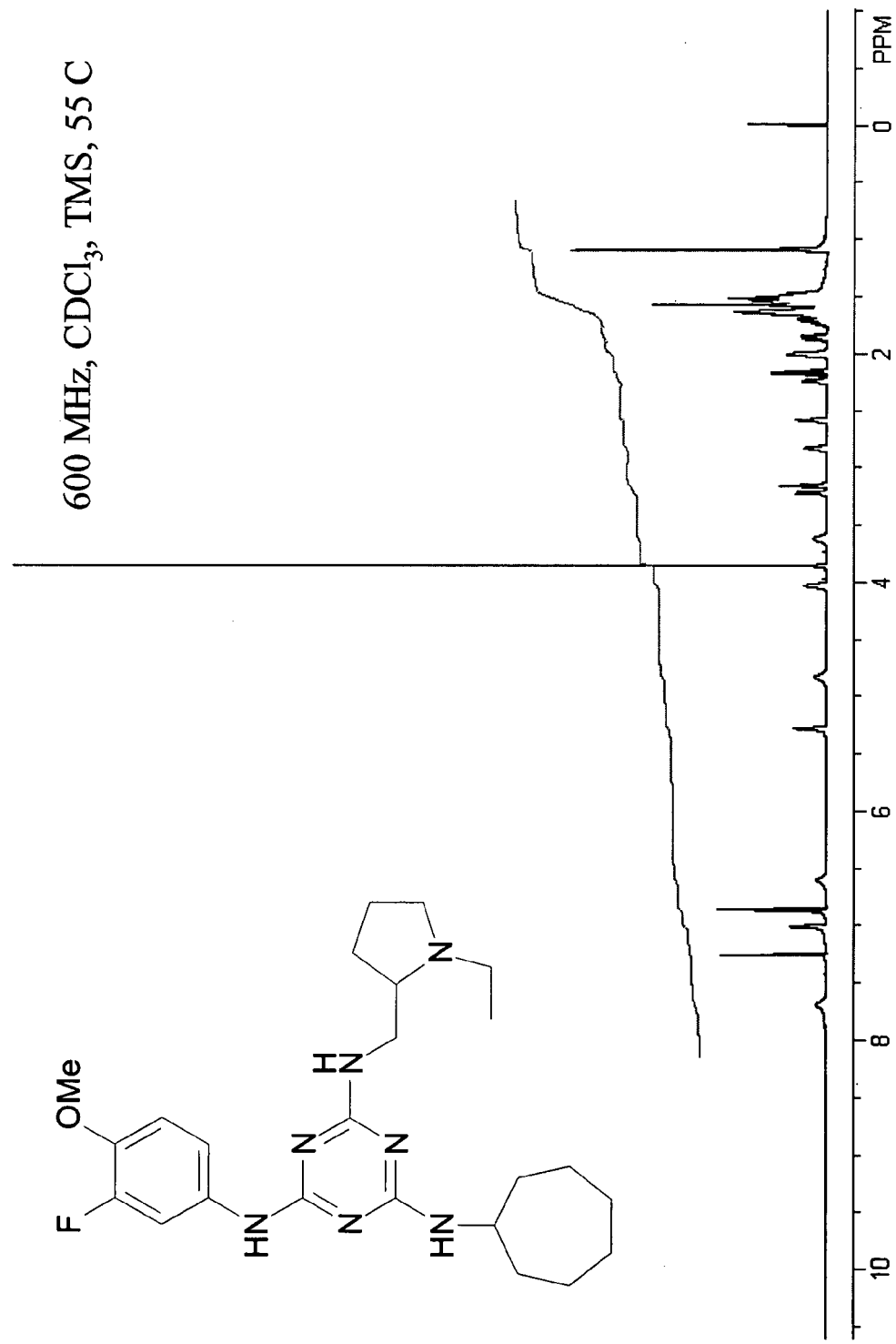
FIG. 2. $^1$H NMR of N-Cycloheptyl-N'-(1-ethyl-pyrrolidin-2-ylmethyl)-N"-(3-fluoro-4-methoxy-phenyl)-[1,3,5]triazine-2,4,6-triamine.
Figure 3:
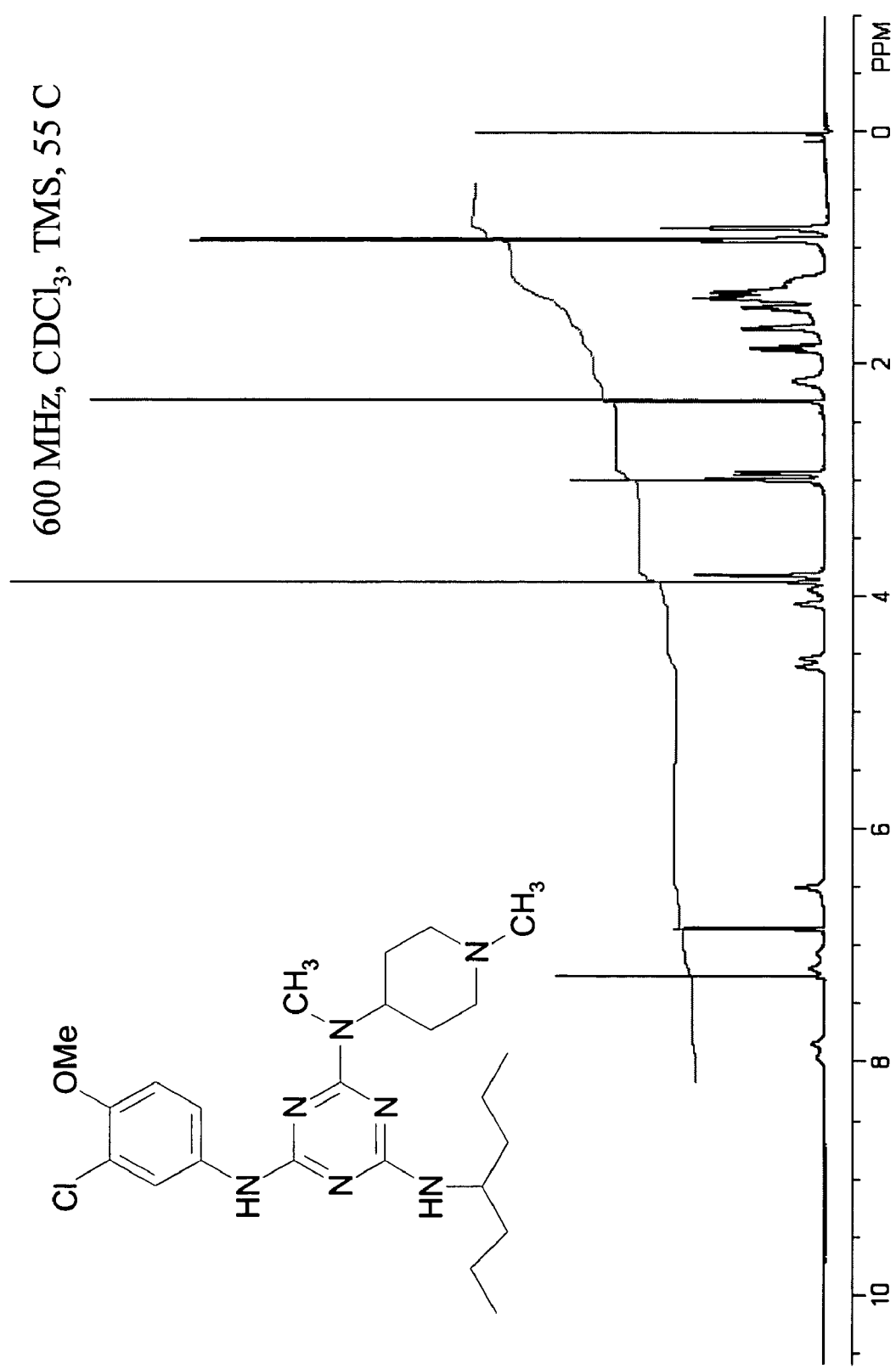
FIG. 3. $^1$H NMR of N-(3-Chloro-4-methoxy-phenyl)-N'-methyl-N'-(1-methyl-piperidin-4-yl)-N"-(1-propyl-butyl)-[1,3,5]triazine-2,4,6-triamine.
Figure 4:
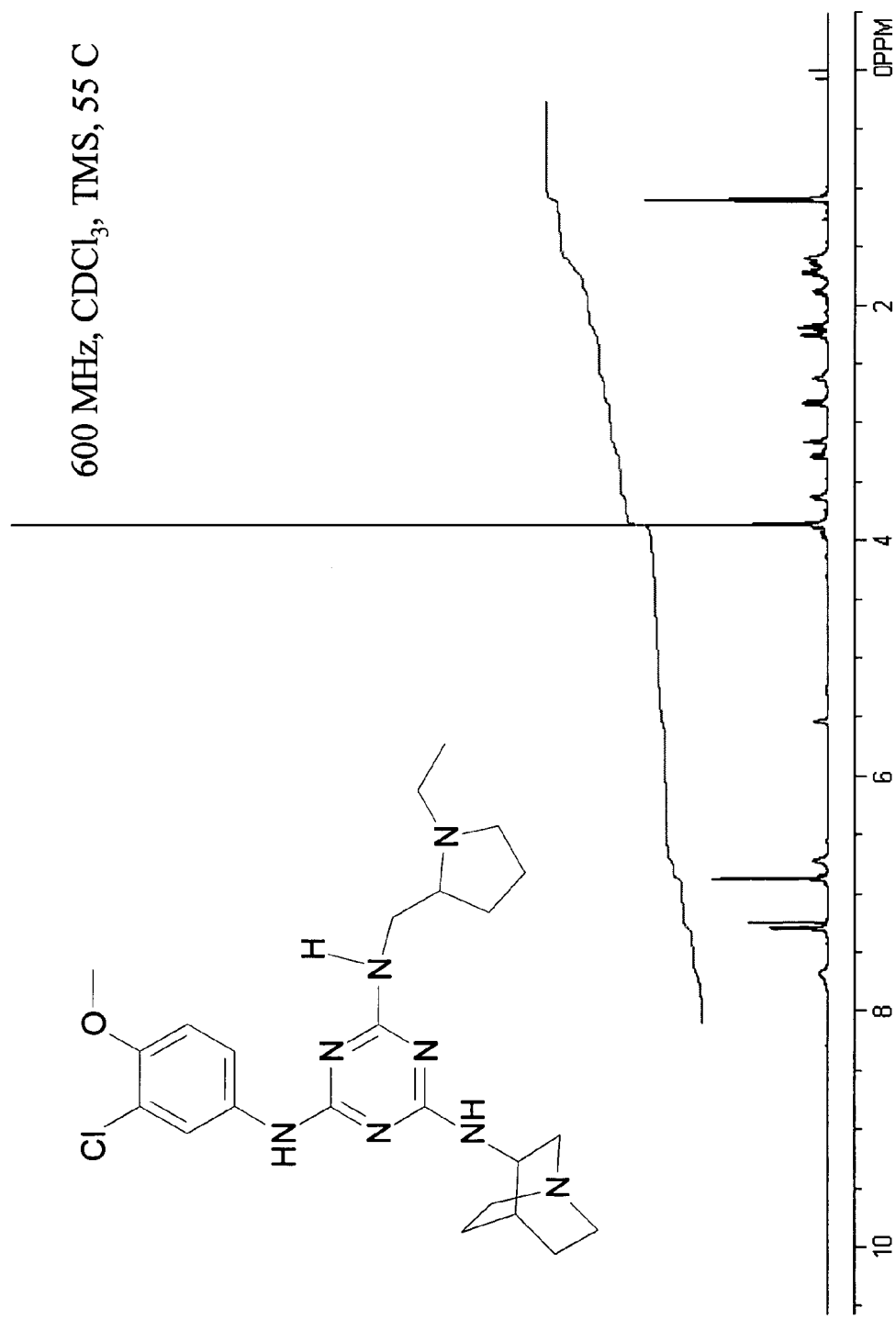
FIG. 4. $^1$H NMR of N-(1-Aza-bicyclo[2.2.2]oct-3-yl)-N'-(3-chloro-4-methoxy-phenyl)-N"-)1-ethyl-pyrrolidin-2-ylmethyl)-[1,3,5]triazine-2,4,6-triamine.
Figure 5:
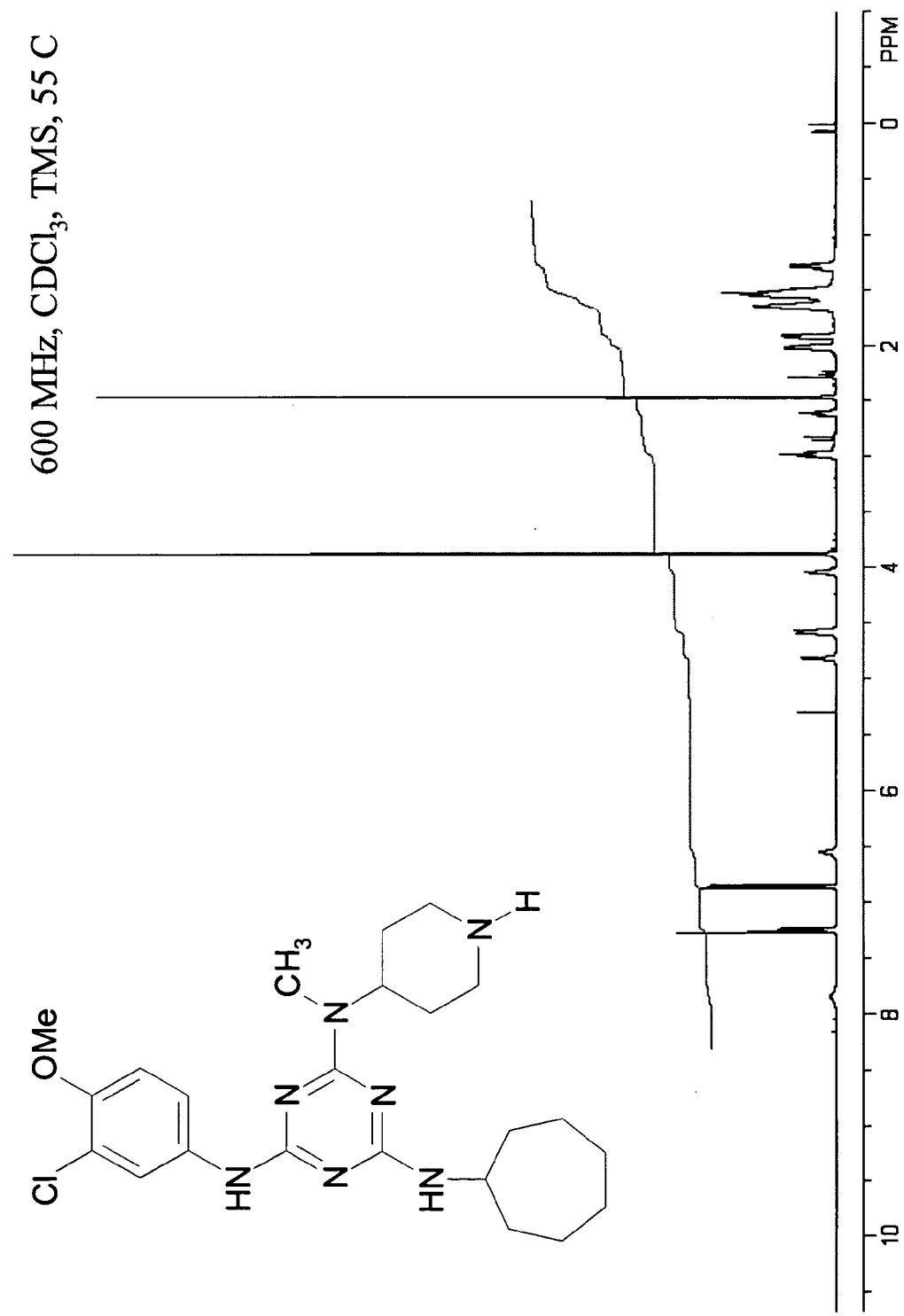
FIG. 5. $^1$H NMR of N2-(3-chloro-4-methoxy-phenyl)-N4-cycloheptyl-N6-methyl-N6-piperidin-4-yl-1,3,5-triazine-2,4,6-triamine.
Figure 6:
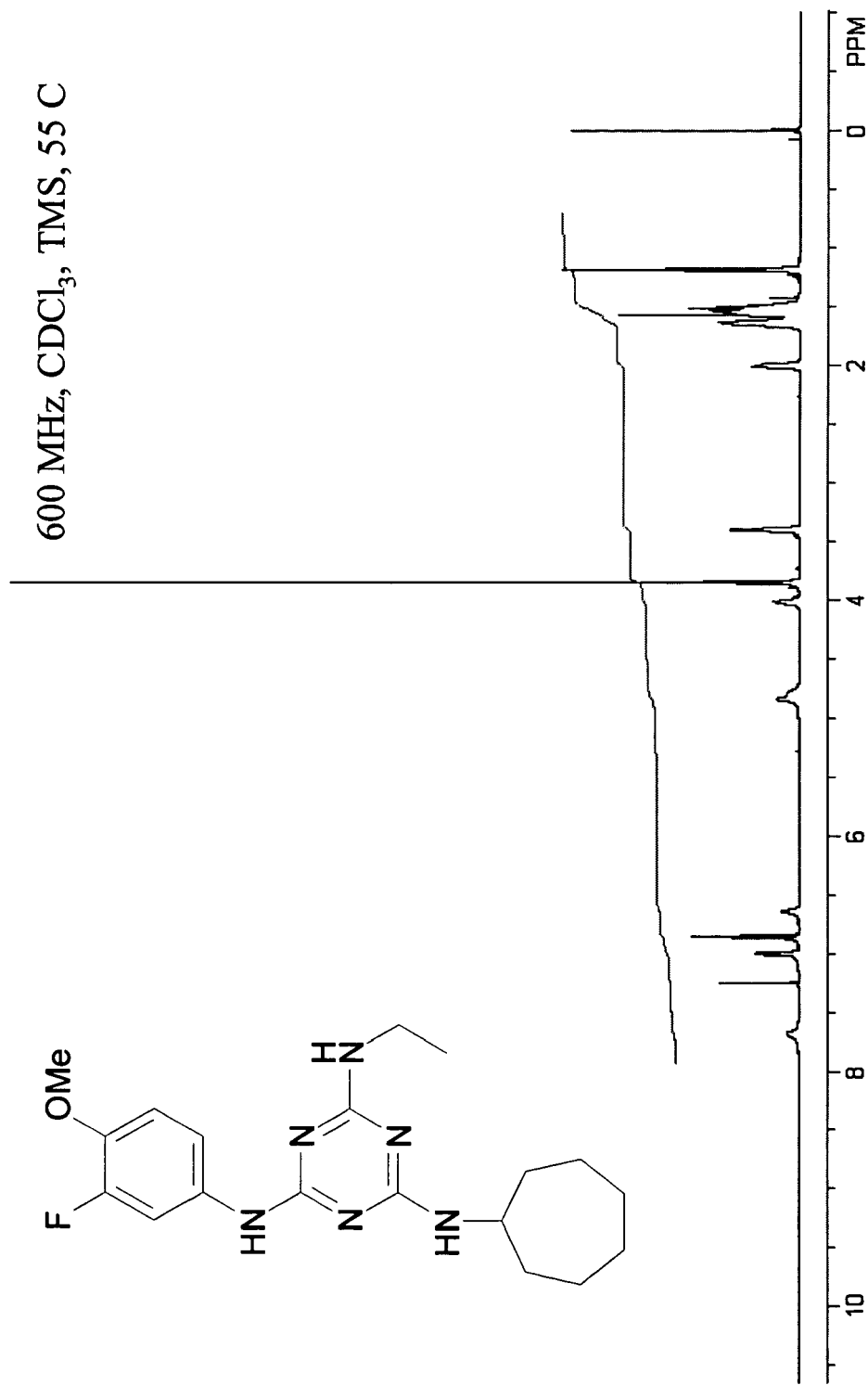
FIG. 6. $^1$H NMR of N-Cycloheptyl-N'-ethyl-N"-(3-fluoro-4-methoxy-phenyl)-[1,3,5]triazine-2,4-diamine.
Figure 7:
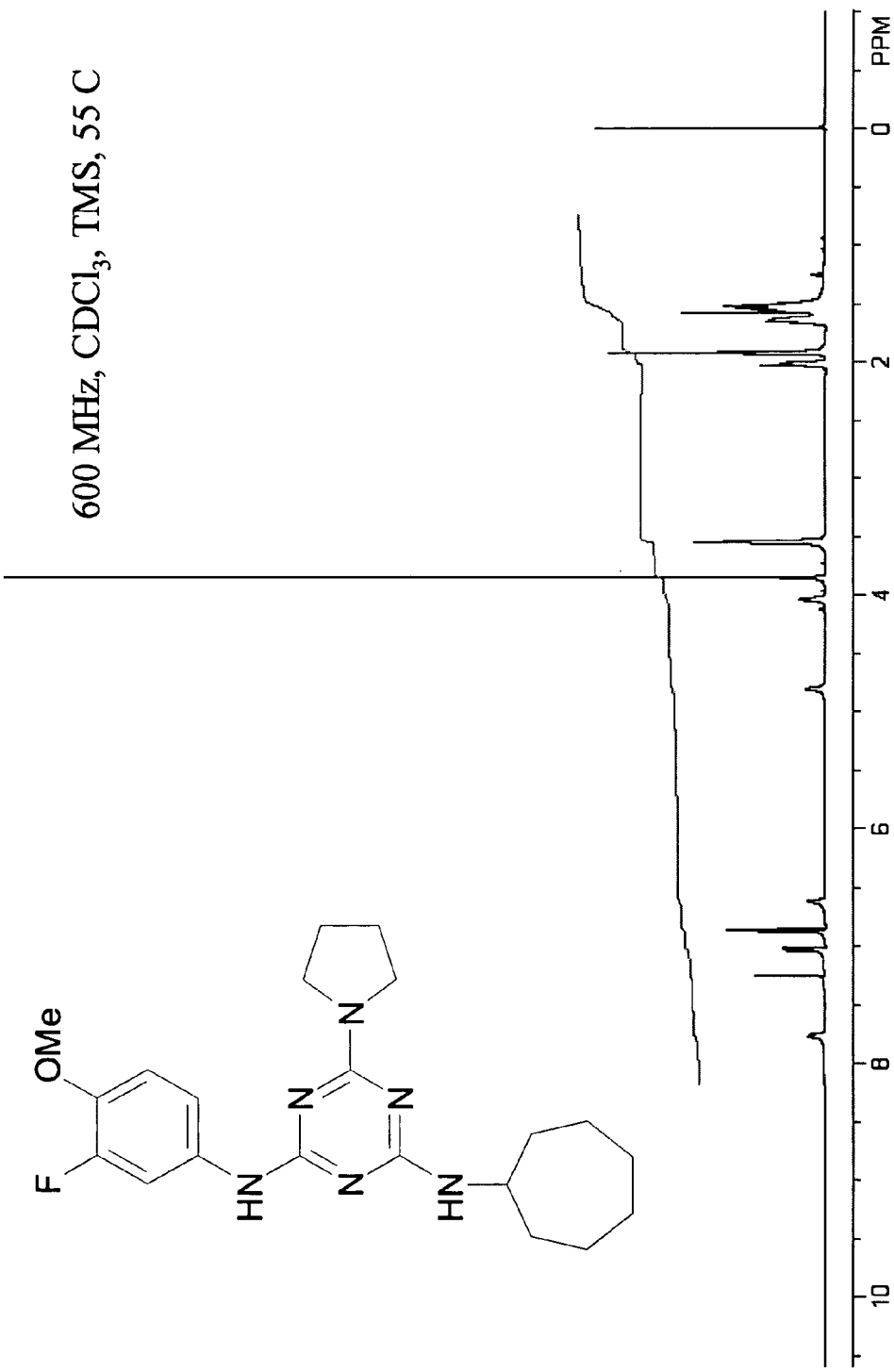
FIG. 7. $^1$H NMR of N-Cycloheptyl-N'-(3-fluoro-4-methoxy-phenyl)-6-pyrrolidin-1-yl-[1,3,5]triazine-2,4-diamine.
Figure 8:
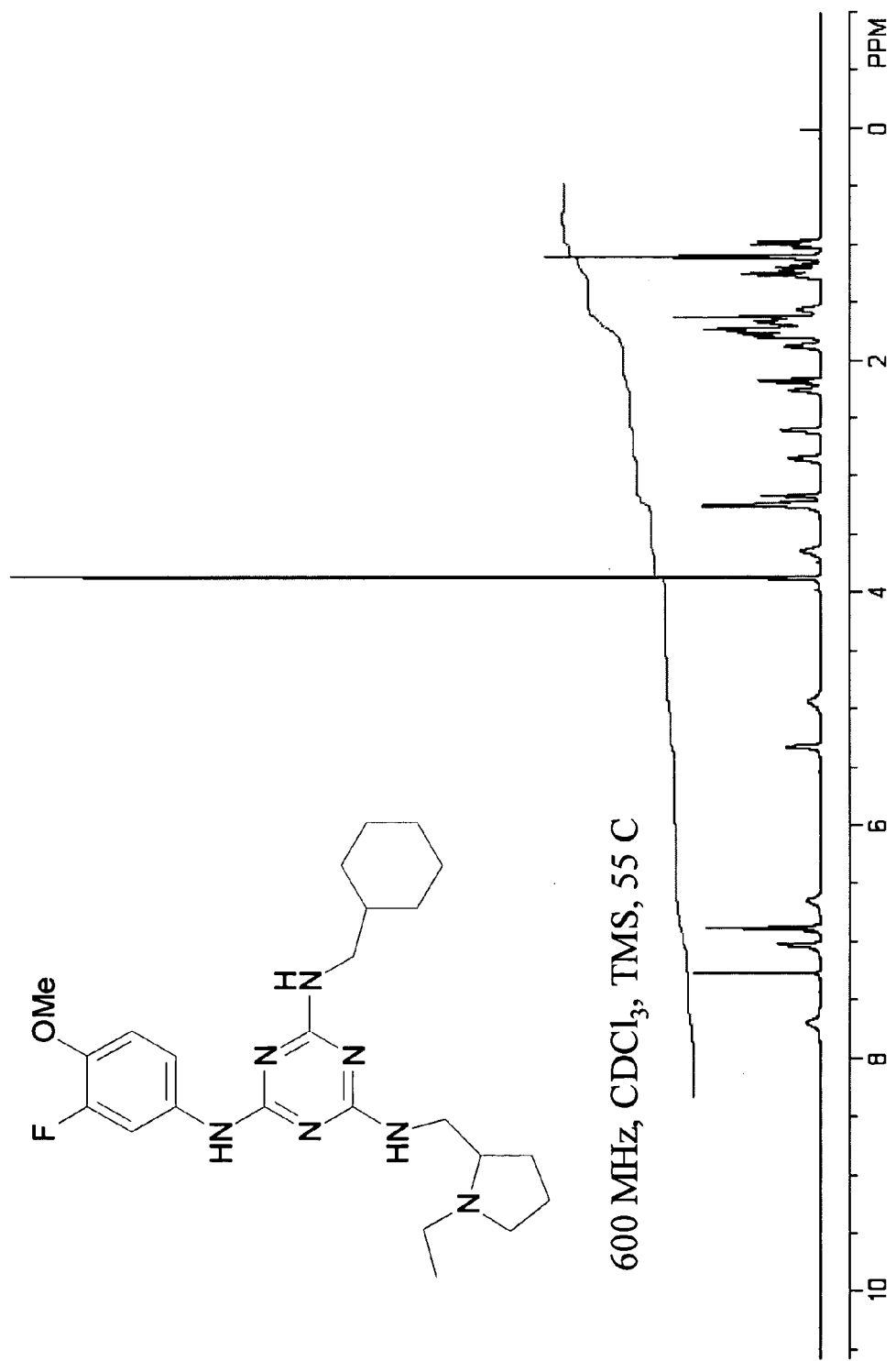
FIG. 8. $^1$H NMR of N-Cyclohexylmethyl-N'-(1-ethyl-pyrrolidin-2-ylmethyl)-N"-(3-fluoro-4-methoxy-phenyl)-[1,3,5]triazine-2,4,6-triamine.
Figure 9:
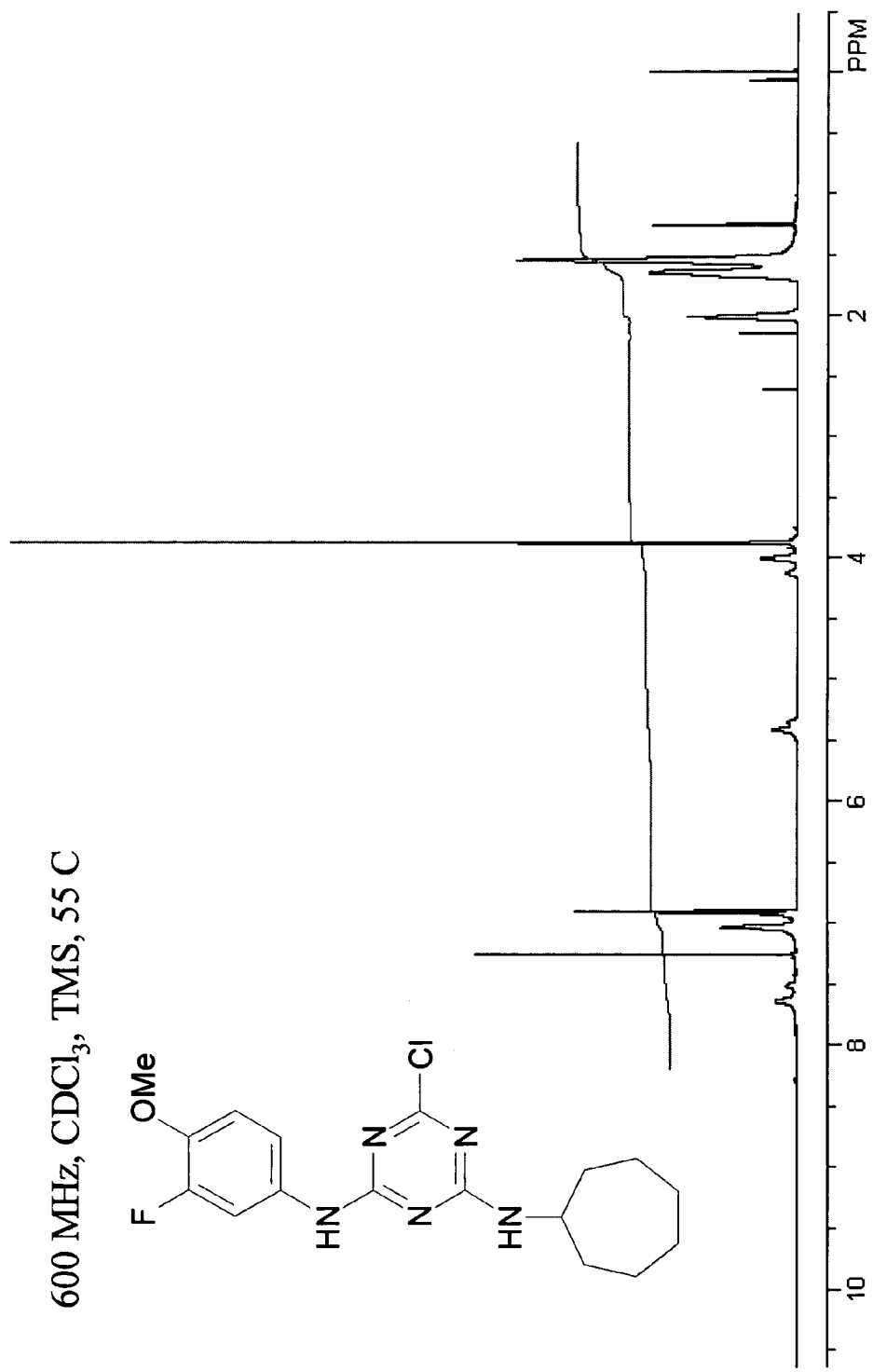
FIG. 9. $^1$H NMR of 6-Chloro-N-cycloheheptyl-N'-(3-fluoro-4-methoxy-phenyl)-[1,3,5]triazine-2,4-diamine.
Figure 10:
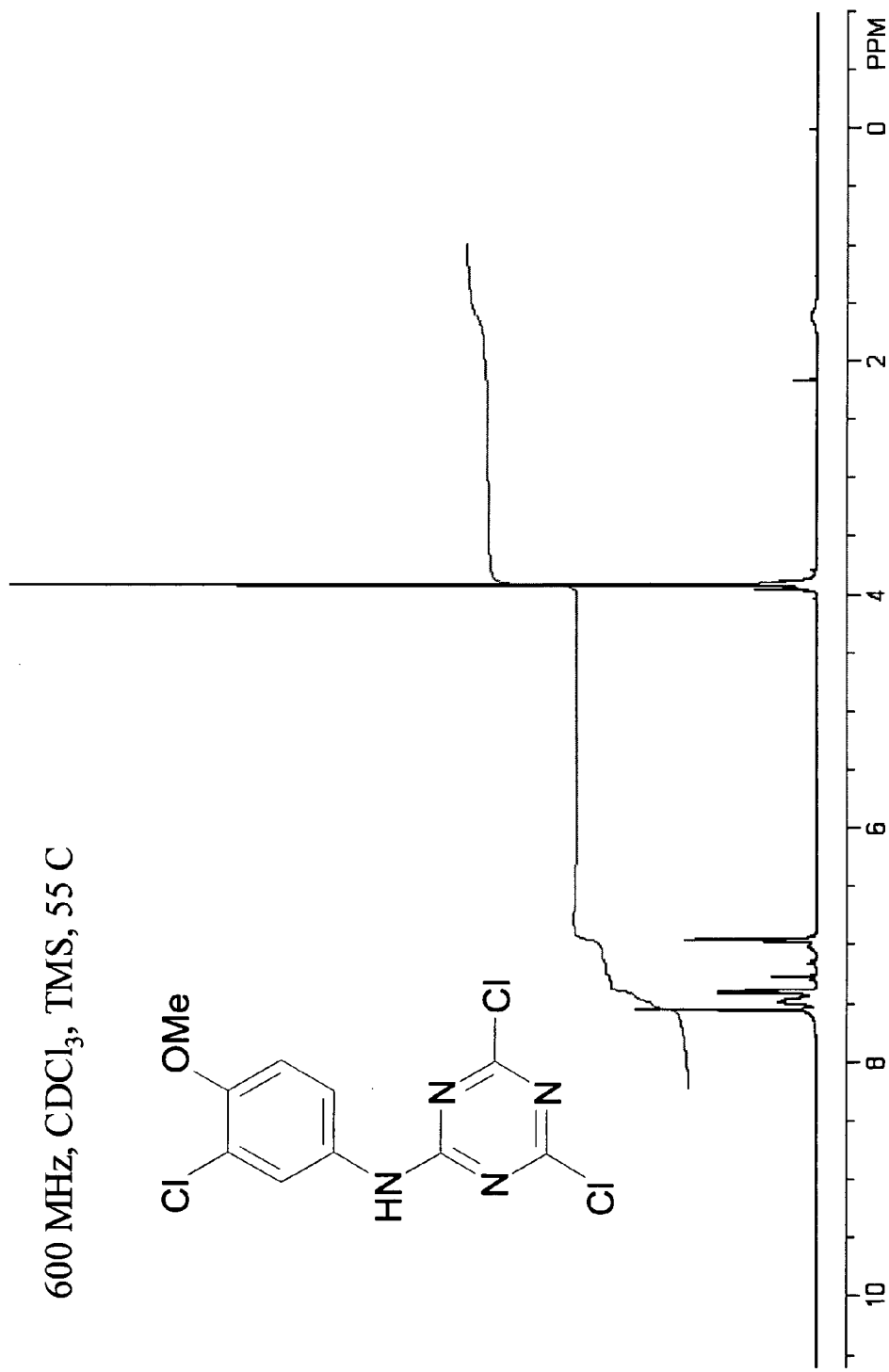
FIG. 10. $^1$H NMR of (3-Chloro-4-methoxy-phenyl)-(4,6-dichloro-[1,3,5]triazin-2-yl)-amine.
Figure 11:
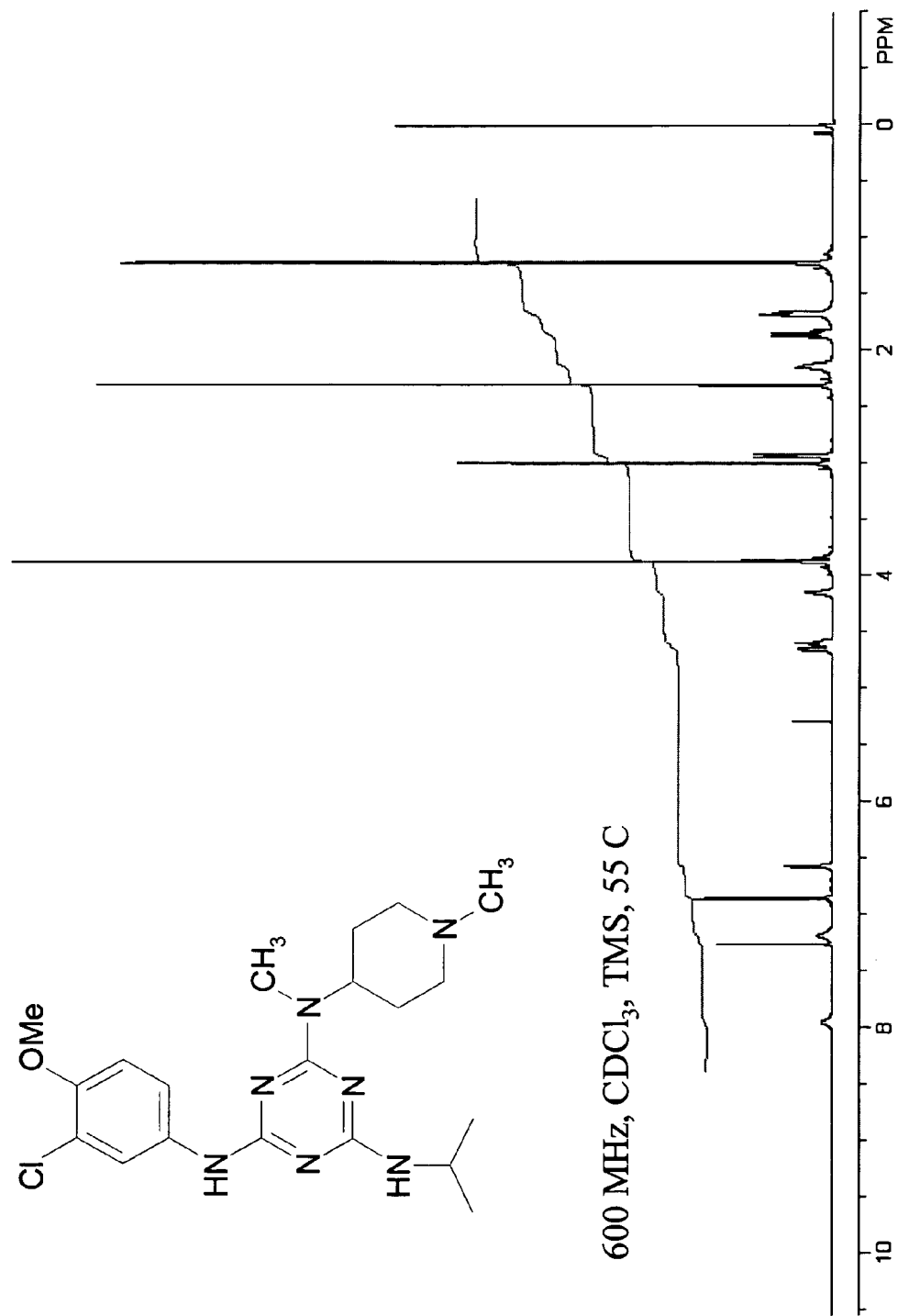
FIG. 11. $^1$H NMR of N-(3-Chloro-4-methoxy-phenyl)-N'-isopropyl-N"-methyl-N"-(1-methyl-piperidin-4-yl)-[1,3,5]triazine-2,4,6-triamine.
Figure 12:
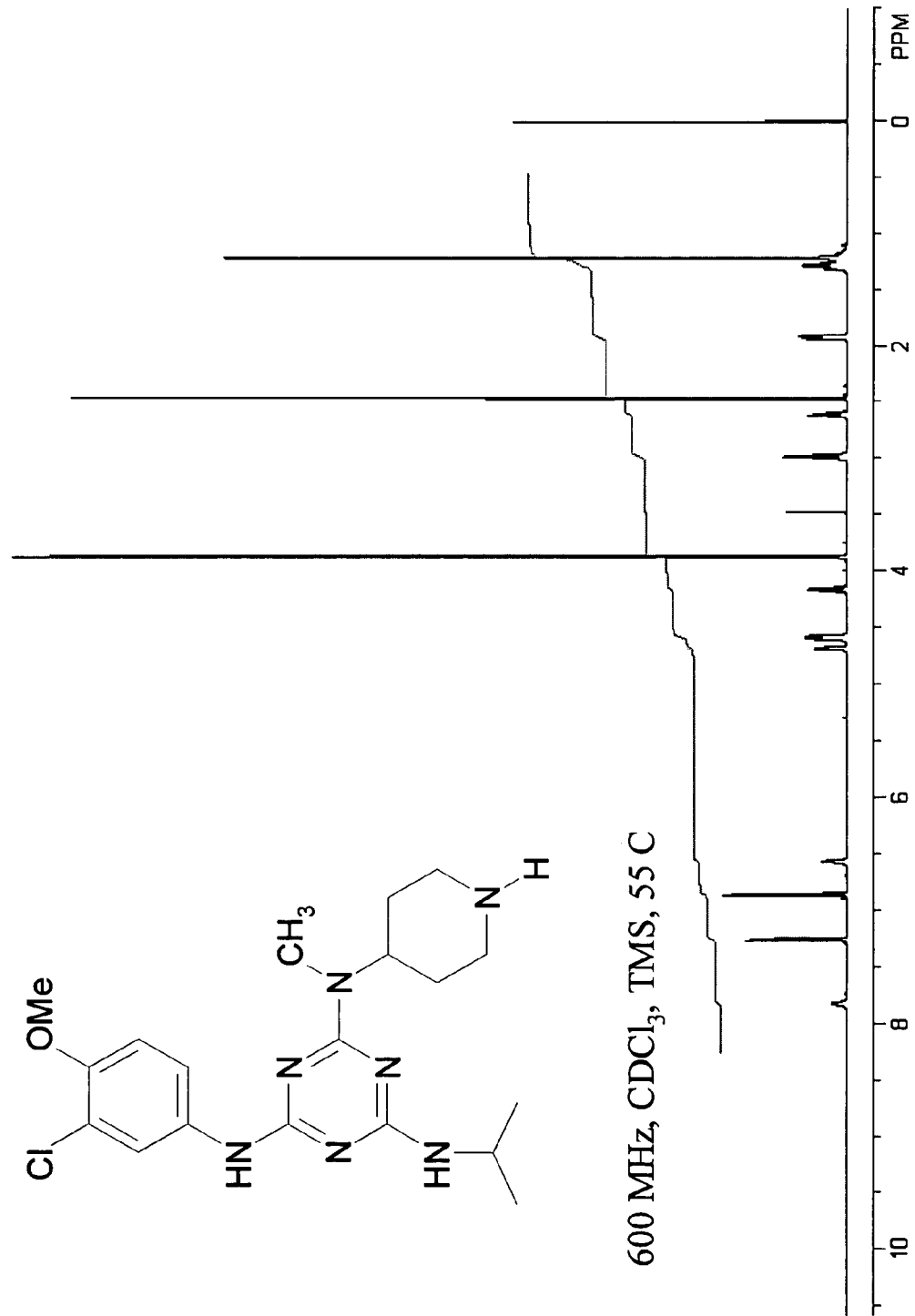
FIG. 12. $^1$H NMR of N2-(3-chloro-4-methoxy-phenyl)-N4-isopropyl-N6-methyl-N6-piperidin-4-yl-1,3,5-triazine-2,4,6-triamine.
Figure 13:
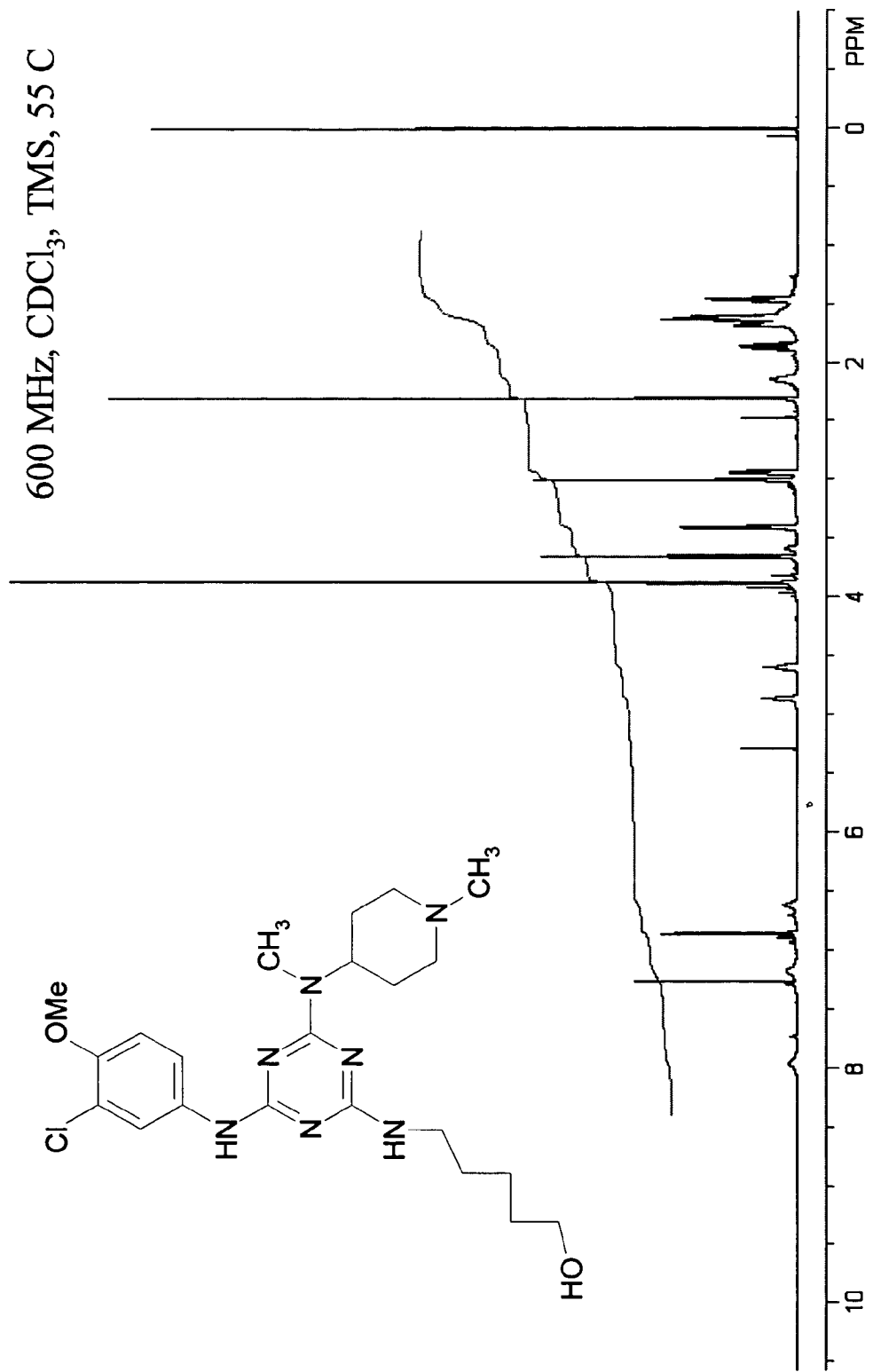
FIG. 13. $^1$H NMR of 5-{4-(3-Chloro-4-methoxy-phenylamino)-6-[methyl-(1-methyl-piperidin-4-yl)-amino]-[1,3,5]triazin-2-ylamino}-pentan-1-ol.
Figure 14:
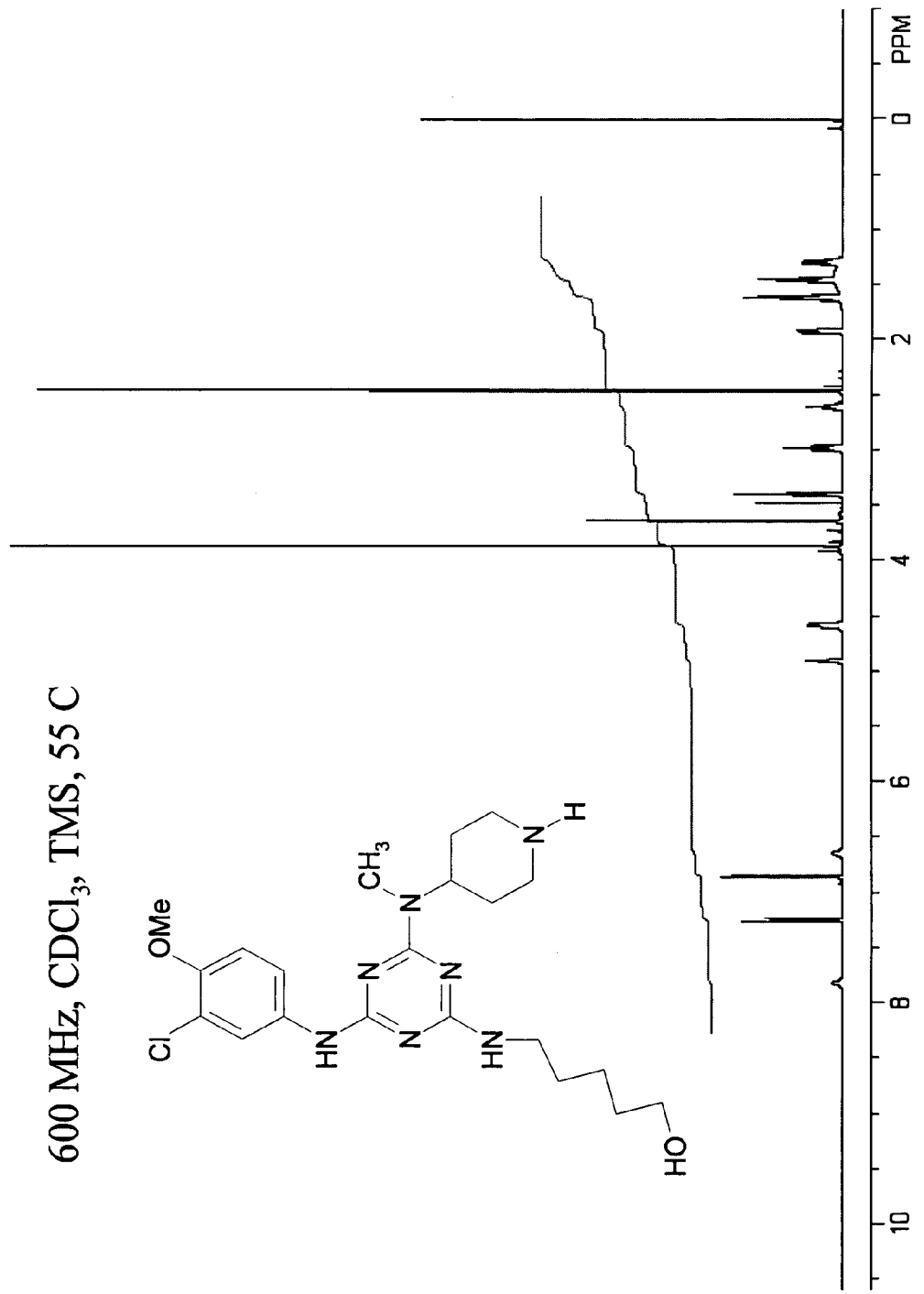
FIG. 14. $^1$H NMR of 5-[4-(3-chloro-4-methoxy-phenylamino)-6-(methyl-piperidin-4-yl-amino)-1,3,5-triazin-2-ylamino]-pentan-1-ol.
Figure 15:
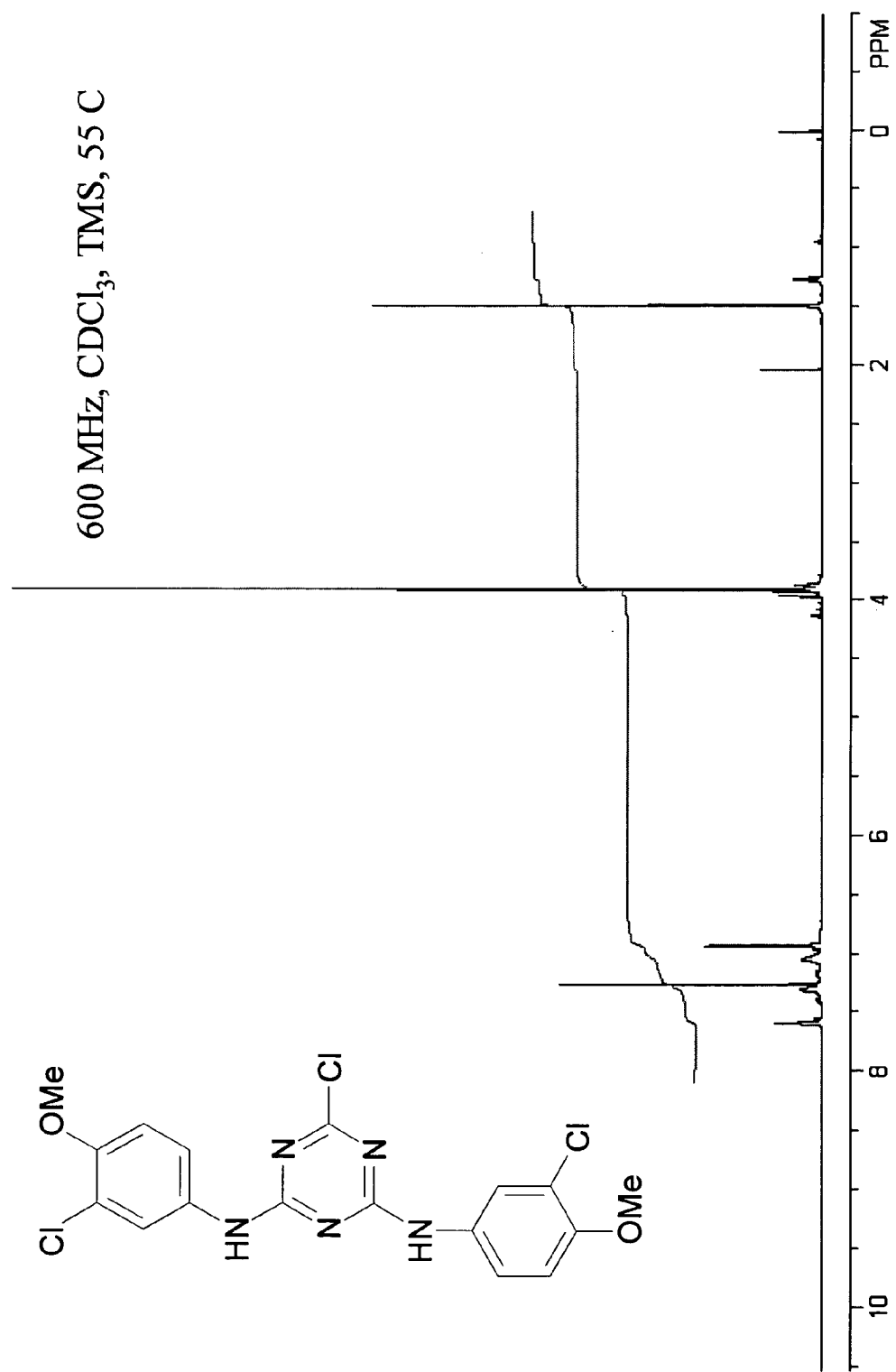
FIG. 15. $^1$H NMR of 6-Chloro-N,N"-bis-(3-chloro-4-methoxy-phenyl)-[1,3,5]triazine-2,4-diamine.
Figure 16:
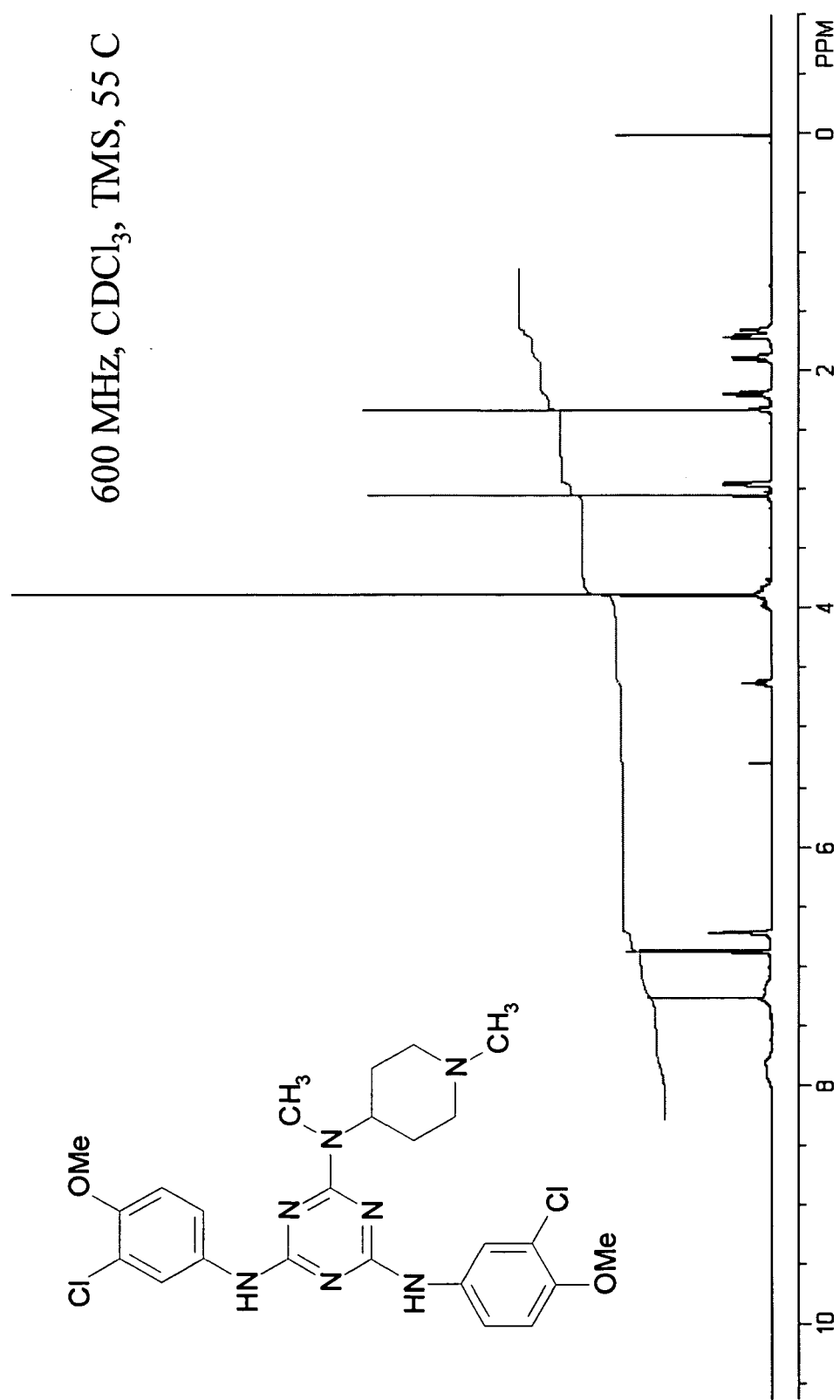
FIG. 16. ¹H NMR of N,N'-Bis-(3-chloro-4-methoxy-phenyl)-N''-methyl-N''-(4-methyl-cyclohexyl)-[1,3,5]triazine-2,4,6-triamine.
Figure 17:
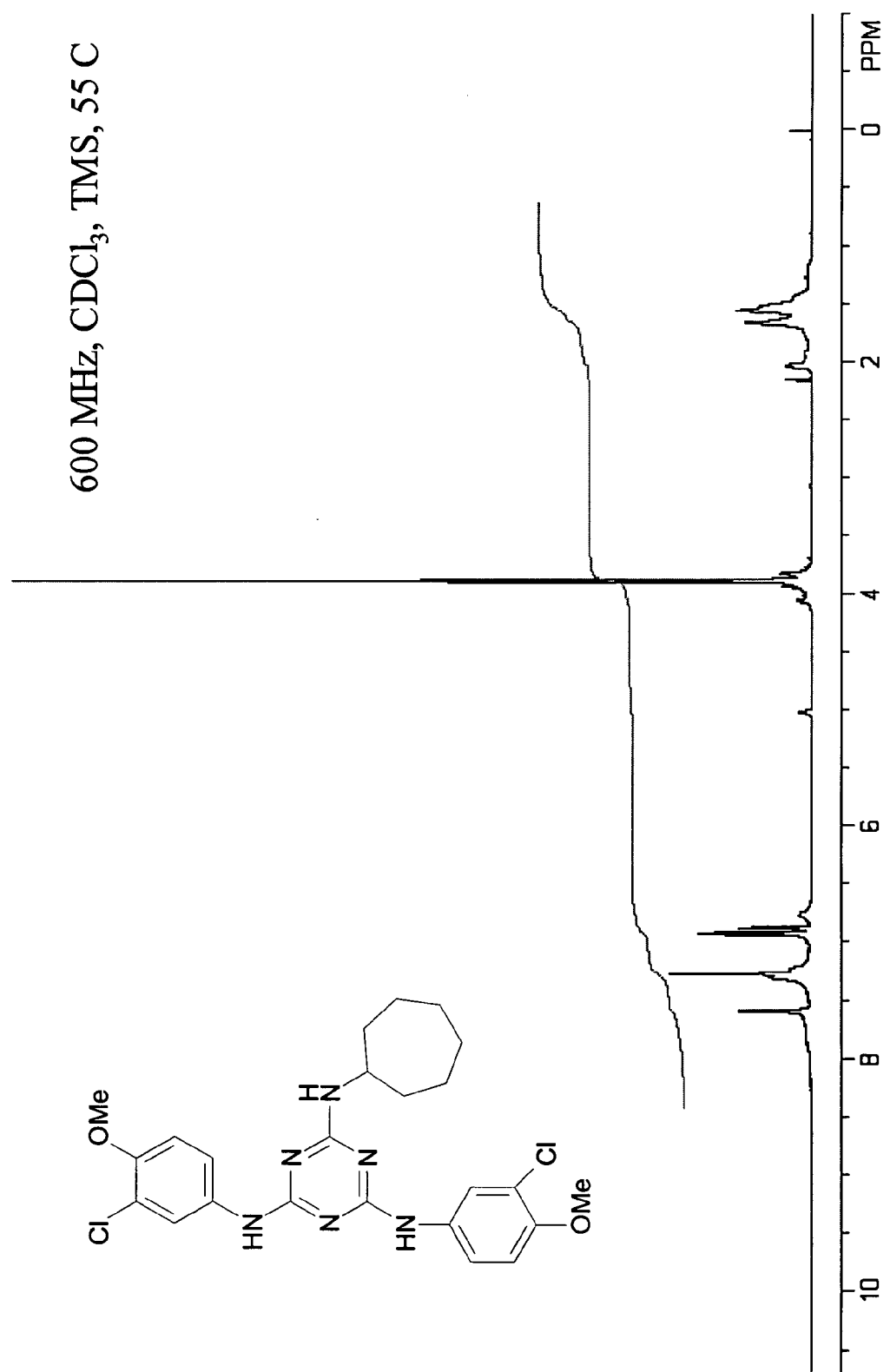
FIG. 17. ¹H NMR of N,N'-Bis-(3-chloro-4-methoxy-phenyl)-N''-cycloheptyl-[1,3,5]triazine-2,4,6-triamine.
Figure 18:
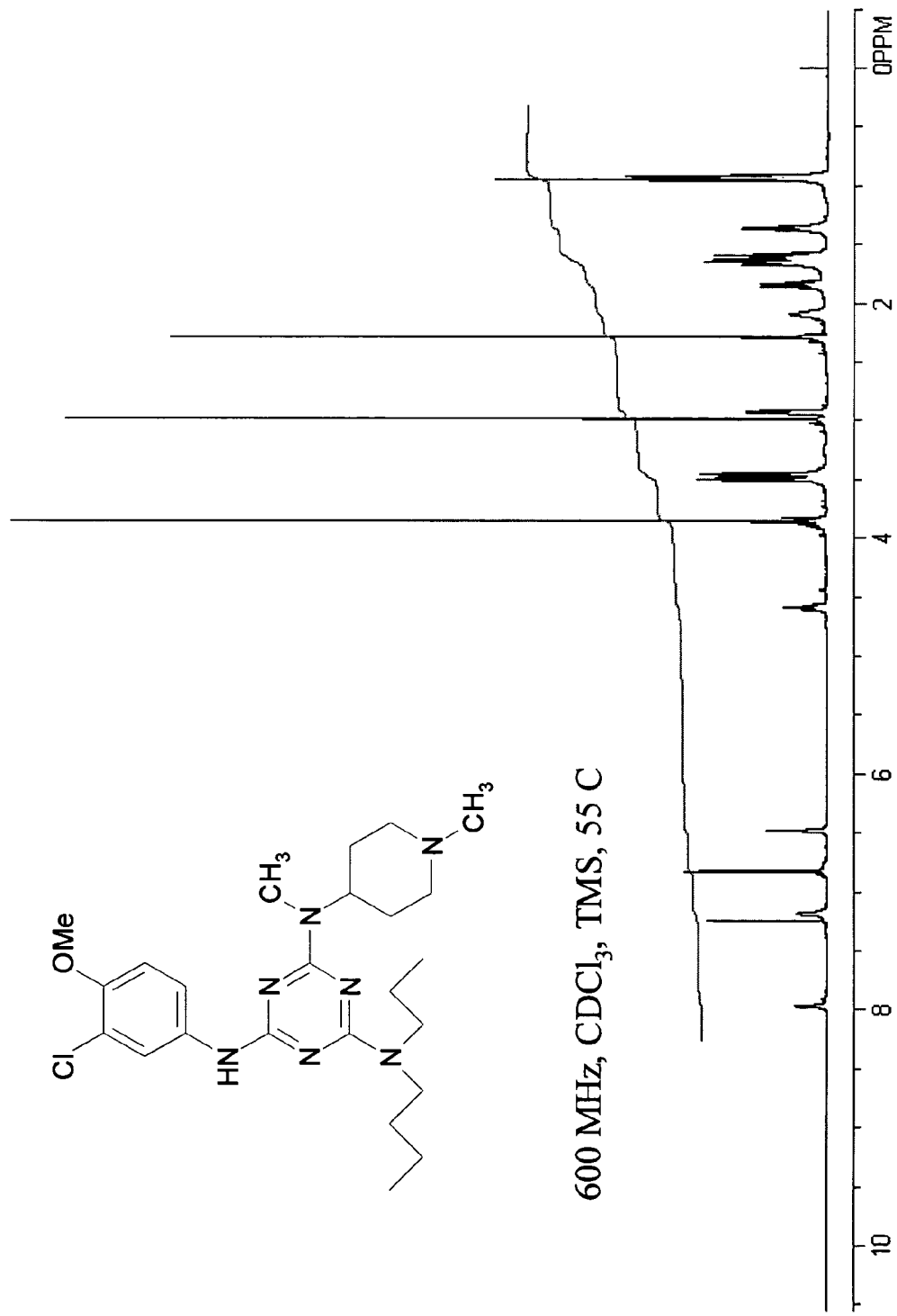
FIG. 18. ¹H NMR of N-Butyl-N'-(3-chloro-4-methoxy-phenyl)-N''-(1-methyl-piperidin-4-yl)-N-propyl-[1,3,5]triazine-2,4,6-triamine.
Figure 19:
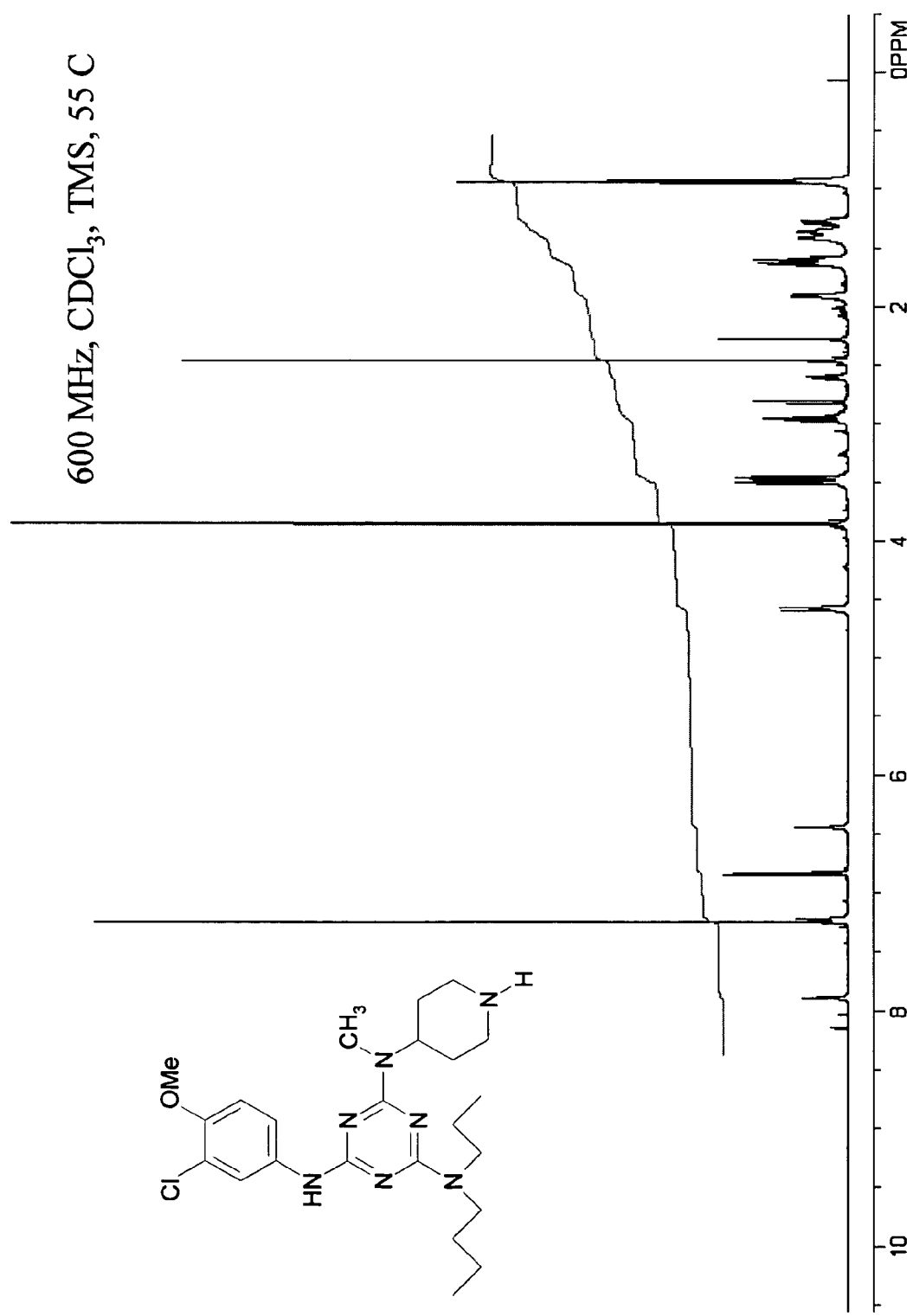
FIG. 19. ¹H NMR of N2-Butyl-N4-(3-chloro-4-methoxy-phenyl)-N6-methyl-N6-piperidin-4-yl-N2-propyl-1,3,5-triazine-2,4,6-triamine.
Figure 20:
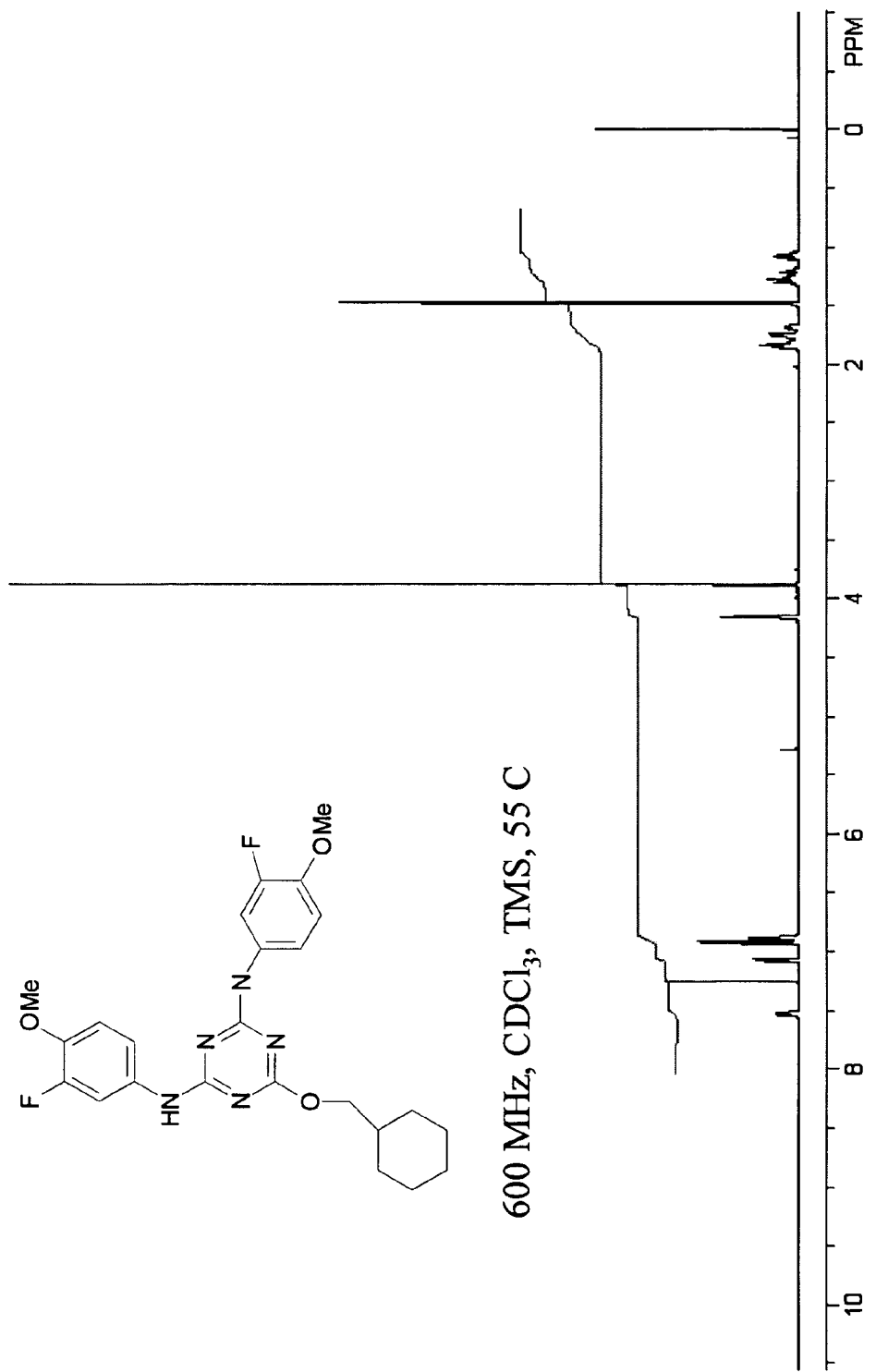
FIG. 20. ¹H NMR of 6-Cyclohexylmethoxy-N,N'-bis-(3-fluoro-4-methoxy-phenyl)-1,3,5-triazine-2,4-diamine.
Figure 21:
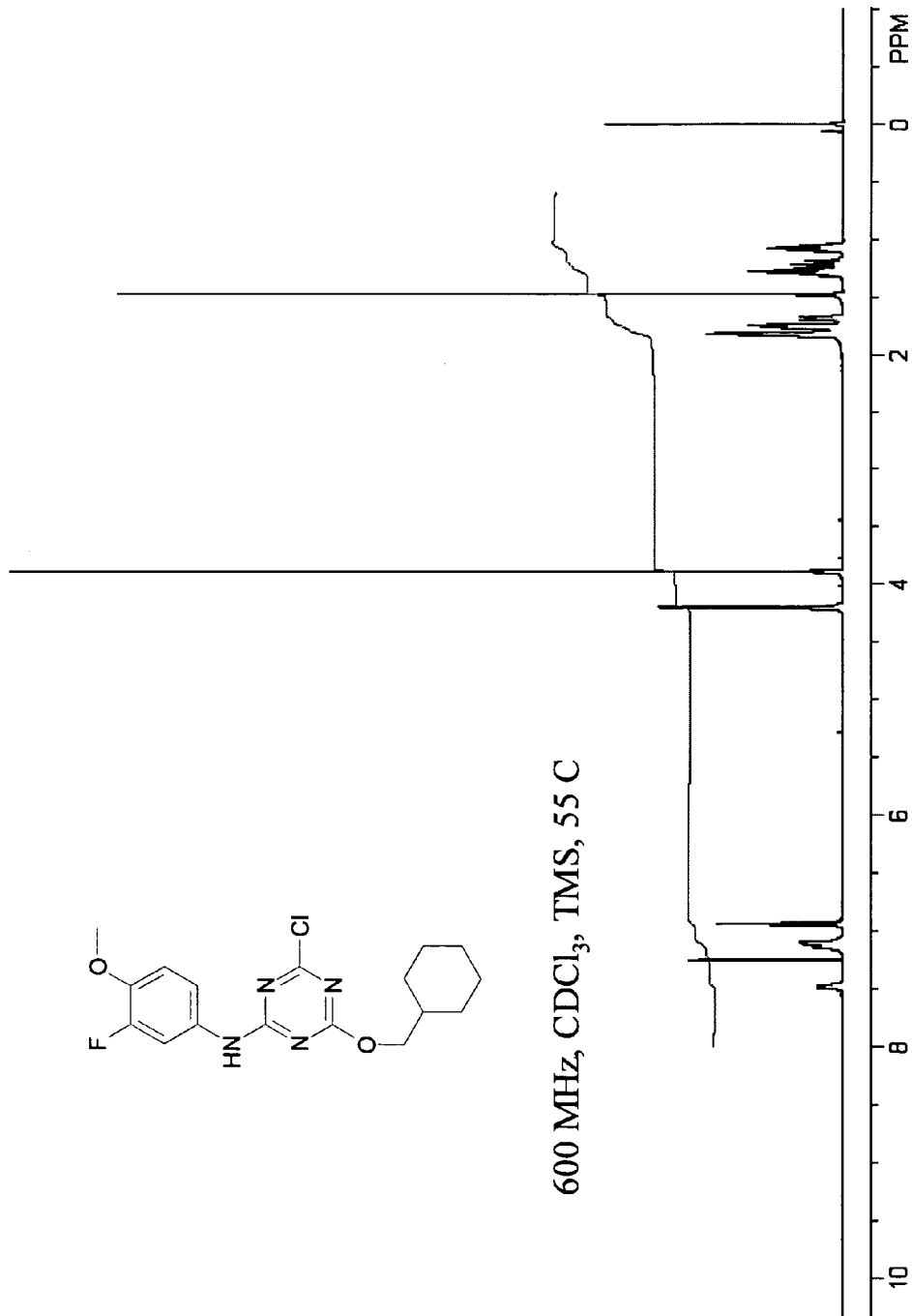
FIG. 21. ¹H NMR of (4-Chloro-6-cyclohexylmethoxy-[1,3,5]triazin-2-yl)-(3-fluoro-4-methoxy-phenyl)-amine.
Figure 22:
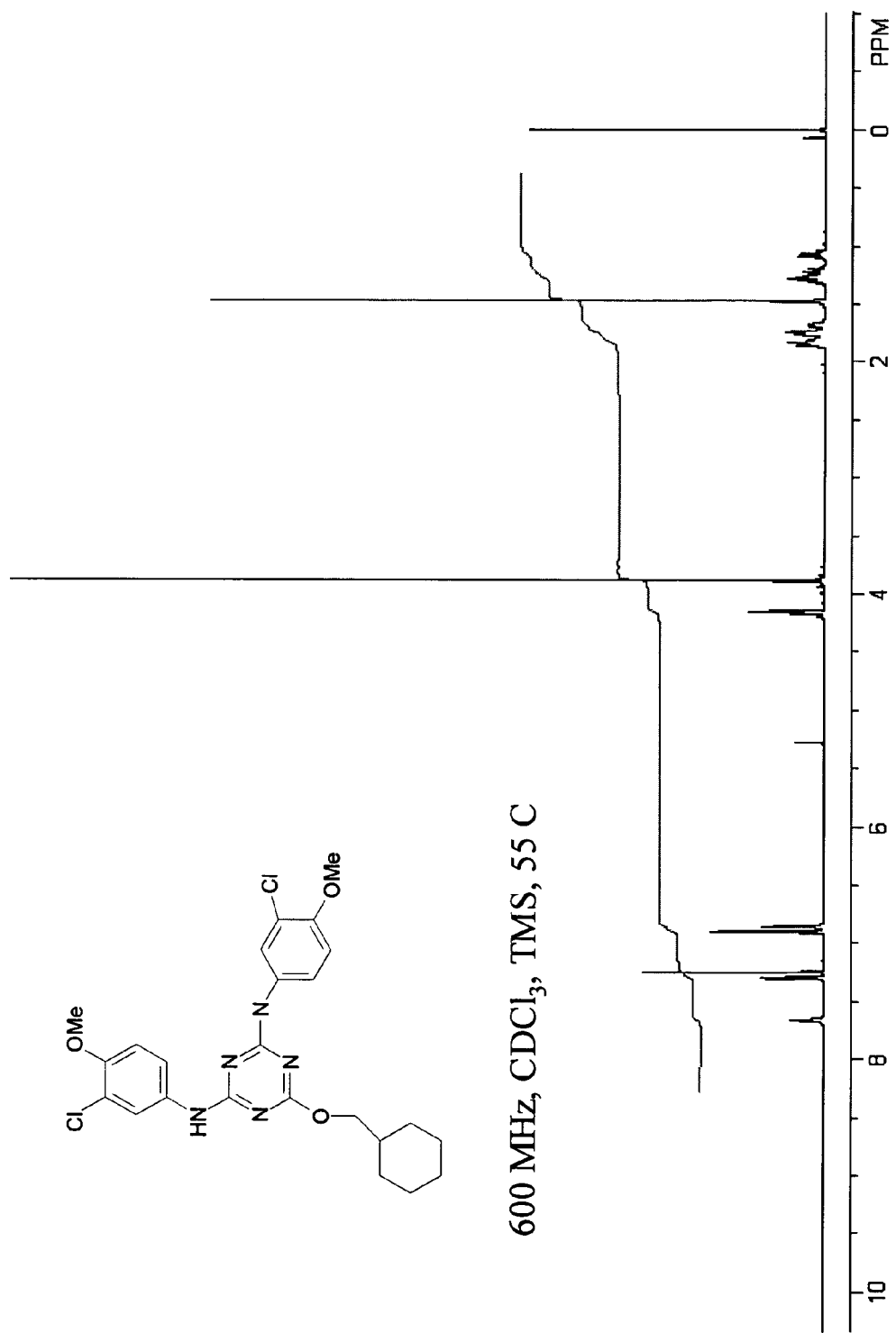
FIG. 22. ¹H NMR of N,N'-Bis-(3-chloro-4-methoxy-phenyl)-6-cyclohexylmethoxy-1,3,5-triazine-2,4-diamine.
Figure 23:
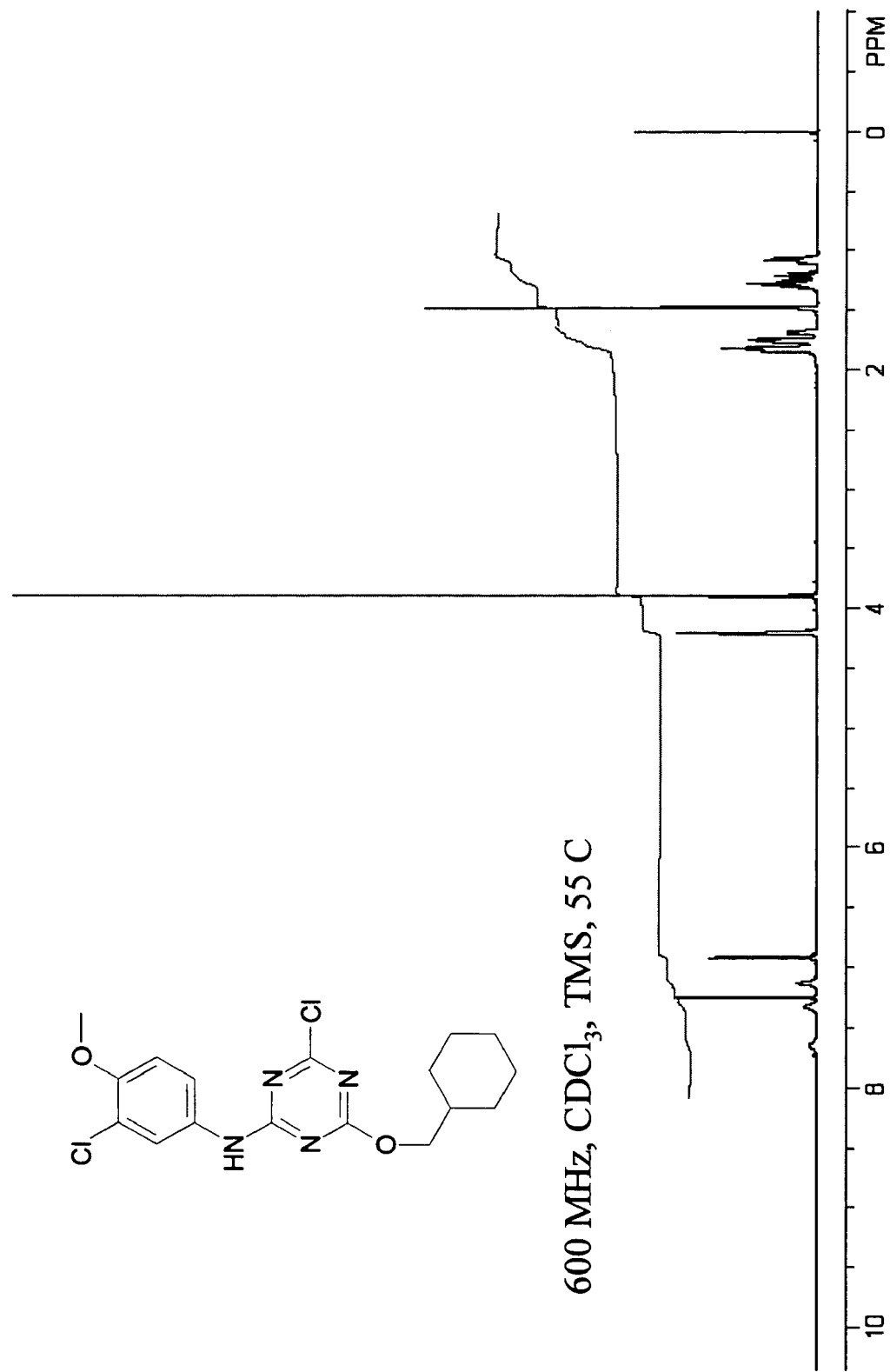
FIG. 23. ¹H NMR of (4-Chloro-6-cyclohexylmethoxy-[1,3,5]triazin-2-yl)-(3-chloro-4-methoxy-phenyl)-amine.
Figure 24:
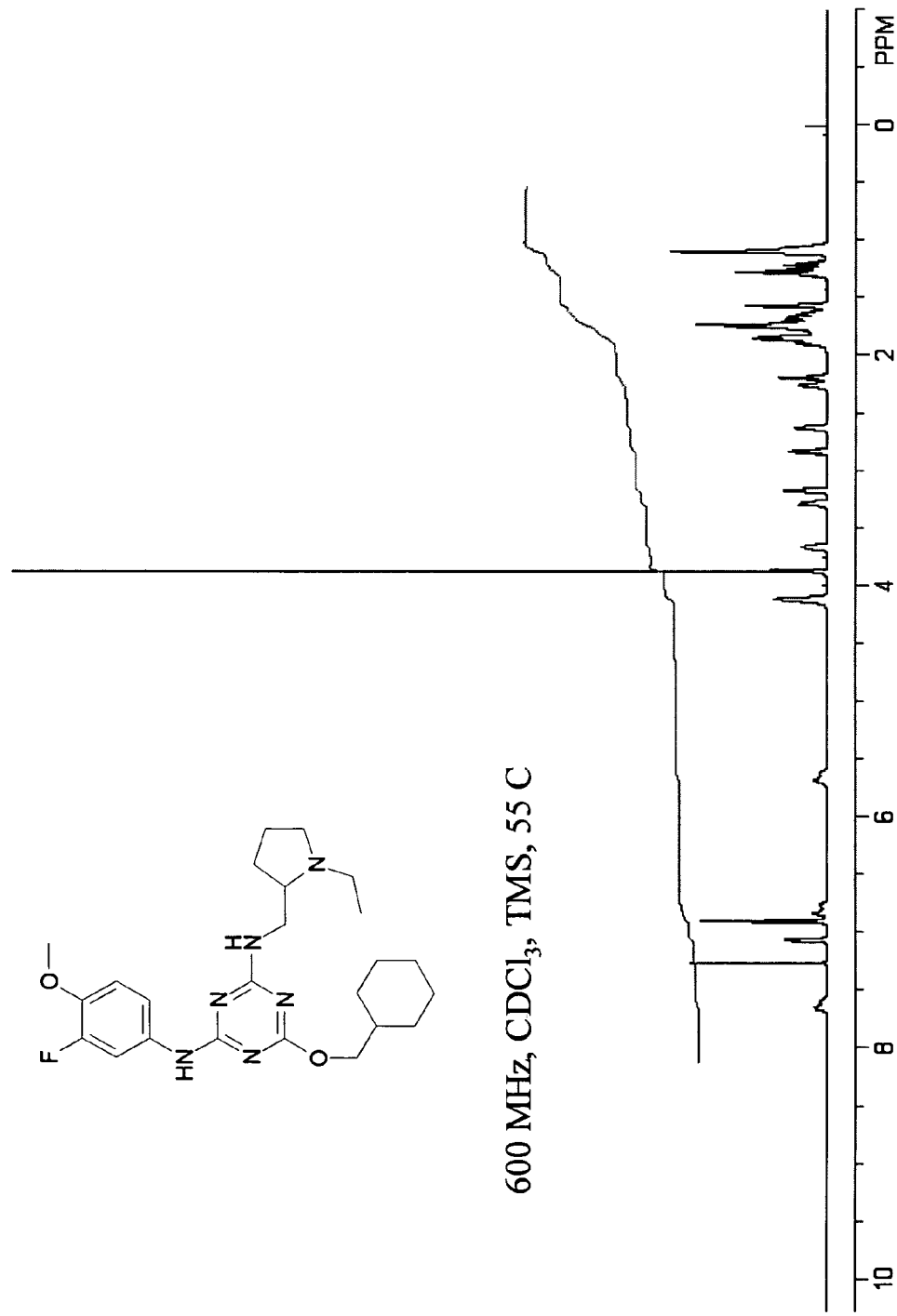
FIG. 24. ¹H NMR of 6-Cyclohexylmethoxy-N-(1-ethyl-pyrrolidin-2-ylmethyl)-N'-(3-fluoro-4-methoxy-phenyl)-[1,3,5]triazine-2,4-diamine.
Figure 25:
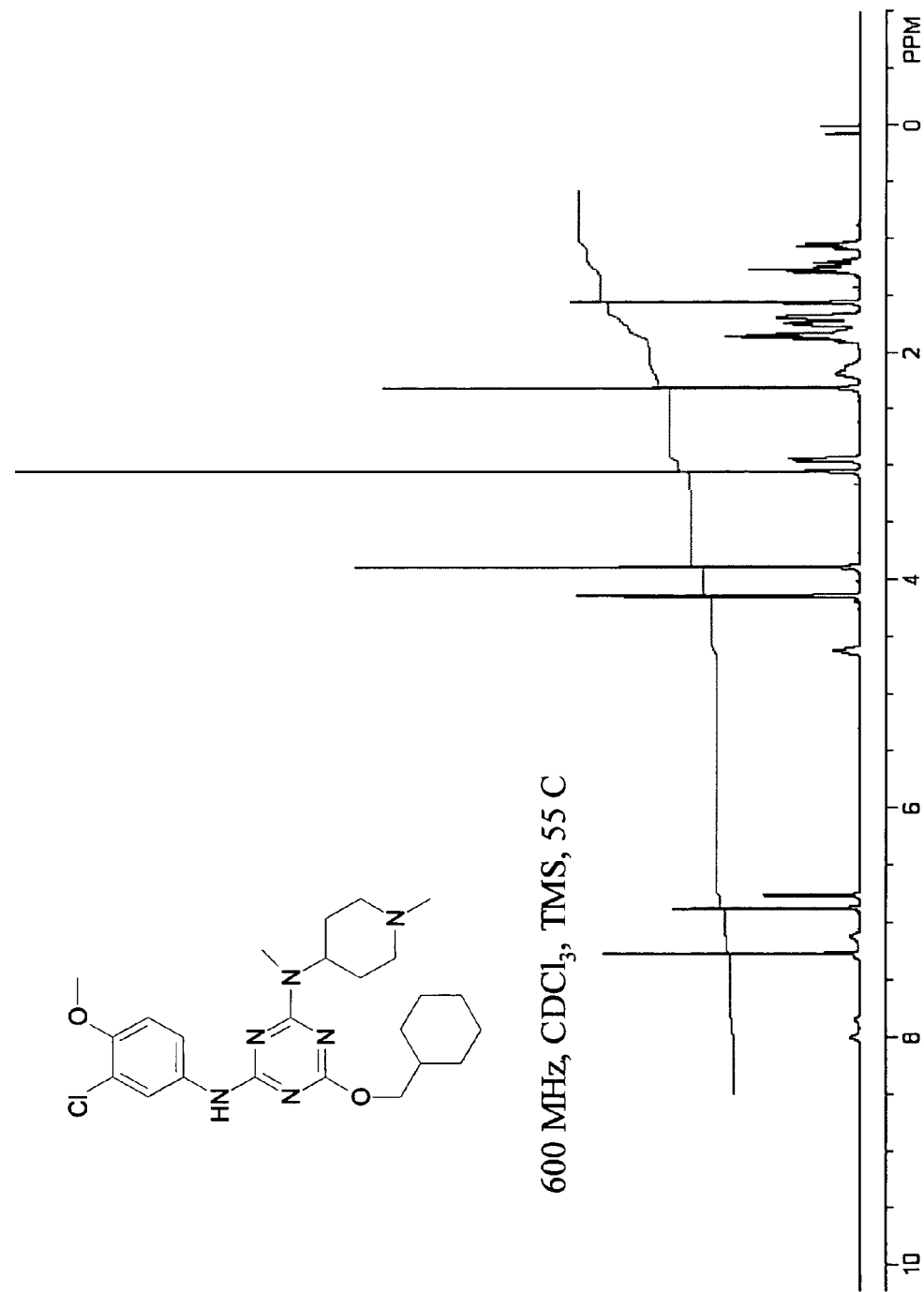
FIG. 25. ¹H NMR of N-(3-Chloro-4-methoxy-phenyl)-6-cyclohexylmethoxy-N'-methyl-N'-(1-methyl-piperidin-4-yl)-[1,3,5]triazine-2,4-diamine.
Figure 26:
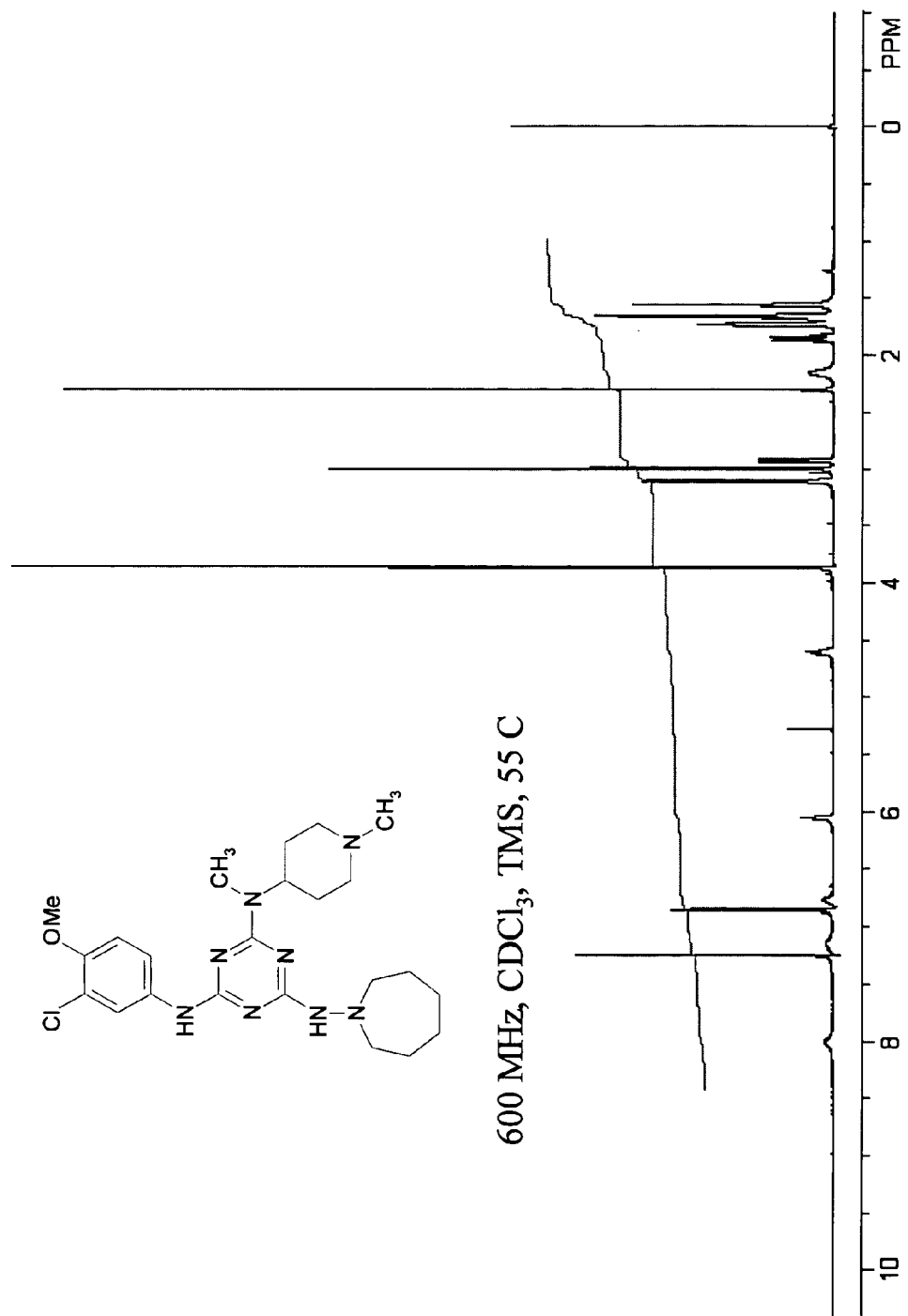
FIG. 26. ¹H NMR of N-Azepan-1-yl-N'-(3-chloro-4-methoxy-phenyl)-N''-(1-methyl-piperidin-4-yl)-[1,3,5]triazine-2,4,6-triamine.
Figure 27:
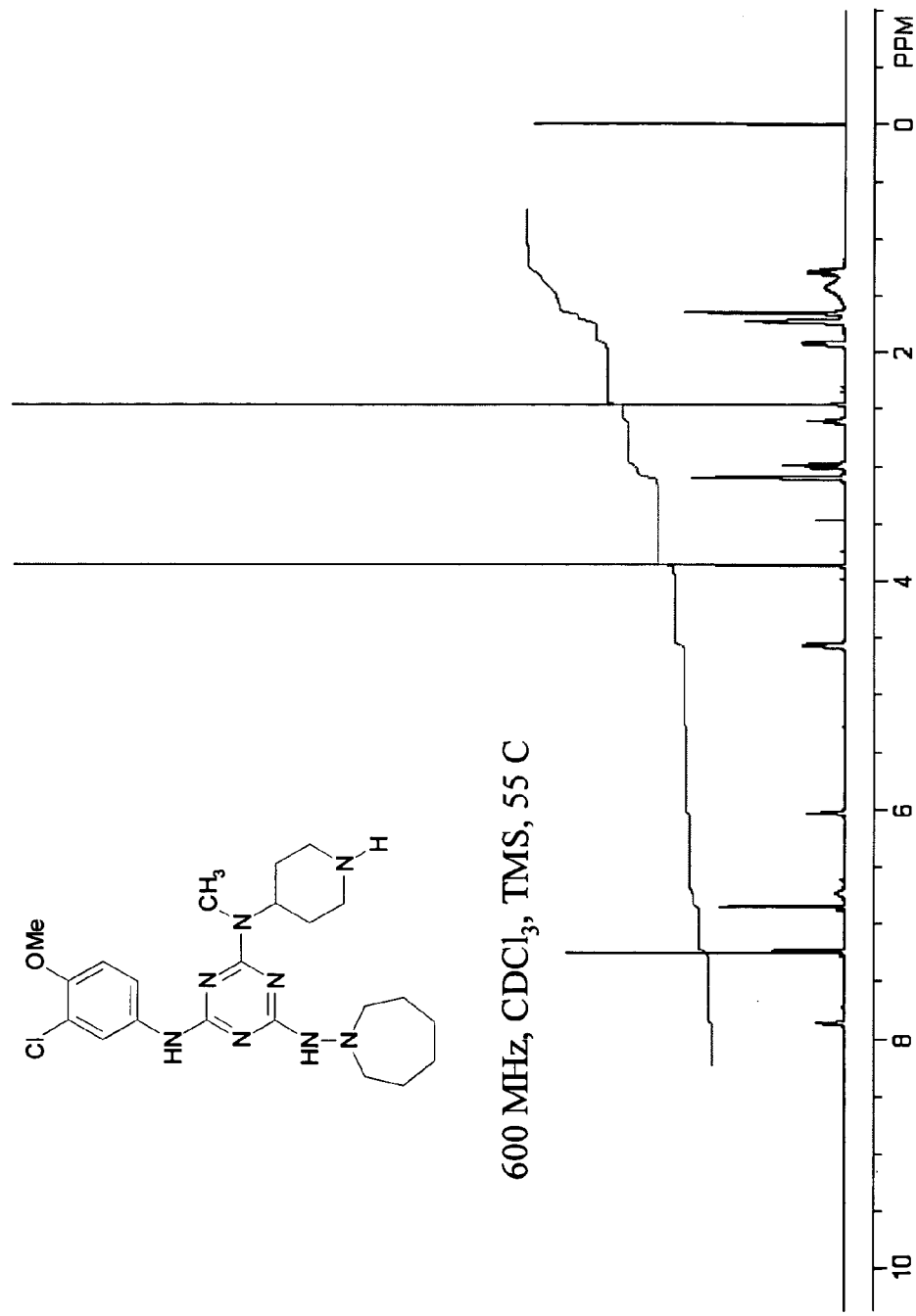
FIG. 27. ¹H NMR of N4-(3-chloro-4-methoxy-phenyl)-N6-methyl-N2-perhydro-azepin-1-yl-N6-piperidin-4-yl-1,3,5-triazine-2,4,6-triamine.
Figure 28:
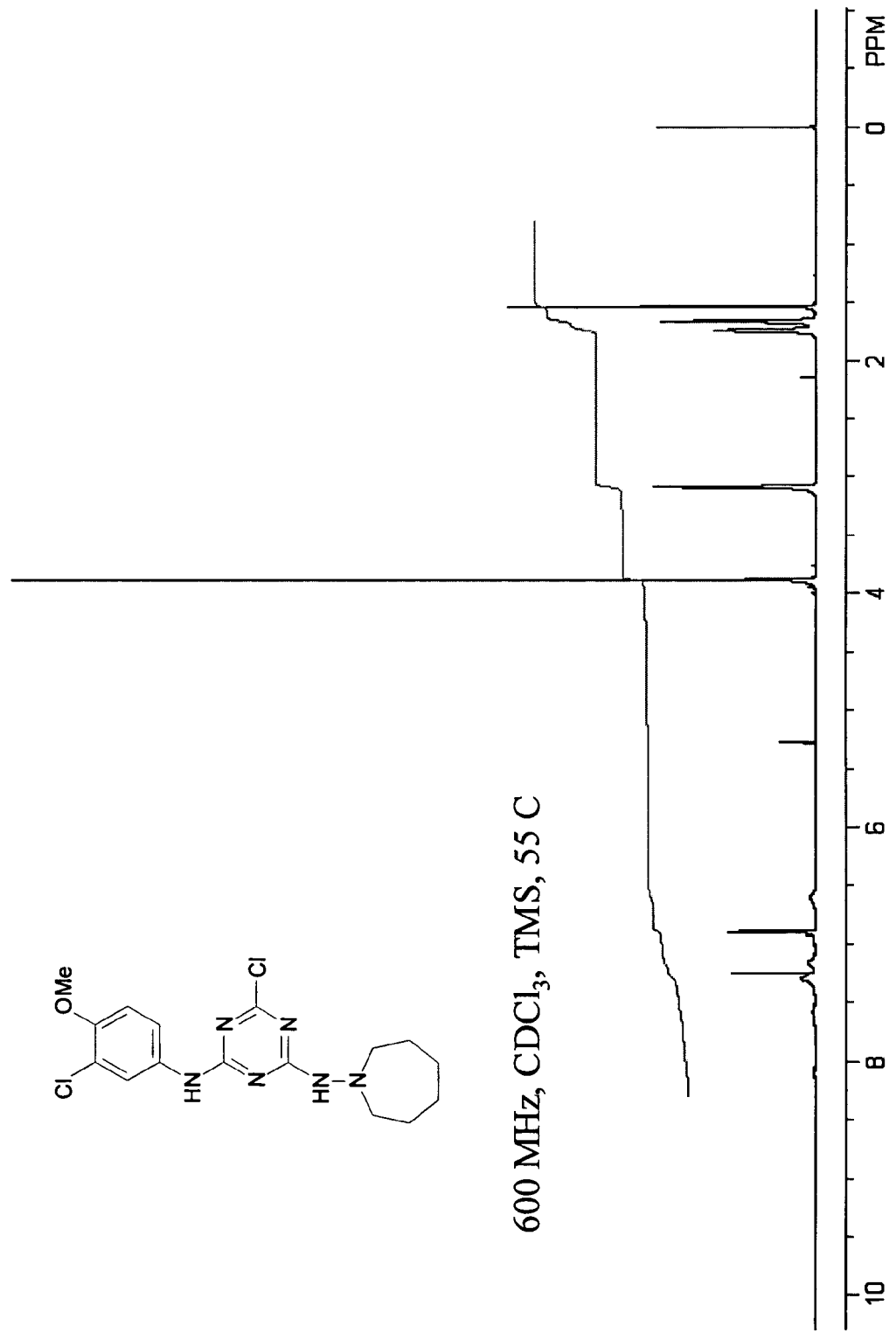
FIG. 28. ¹H NMR of N-Azepan-1-yl-6-chloro-N'-(3-chloro-4-methoxy-phenyl)-[1,3,5]triazine-2,4-diamine.
Figure 29:
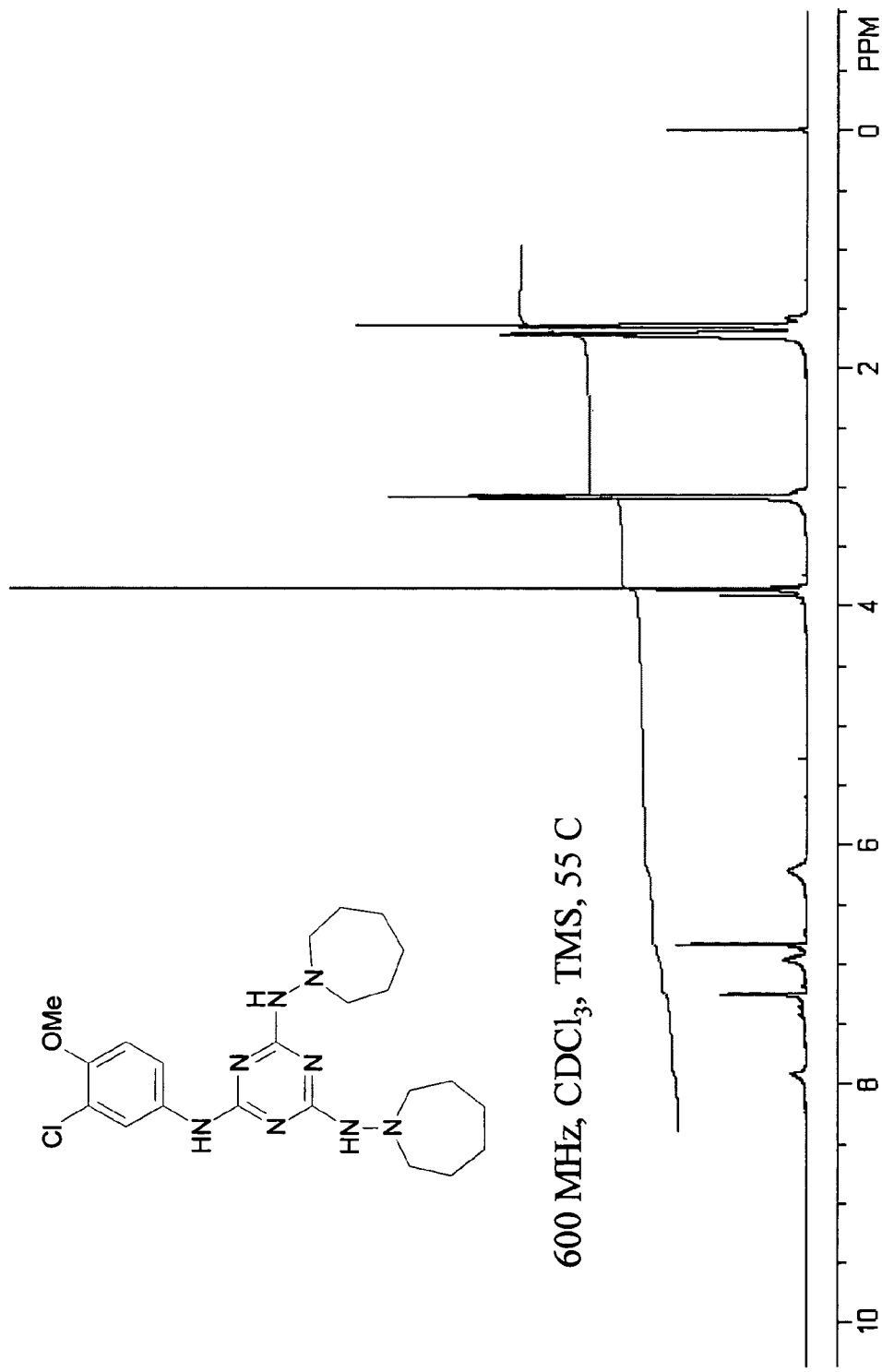
FIG. 29. ¹H NMR of N''-(3-chloro-4-methoxy-phenyl)-N,N'-bis-perhydro-azepin-1-yl-1,3,5-triazine-2,4,6-triamine.
Figure 30:
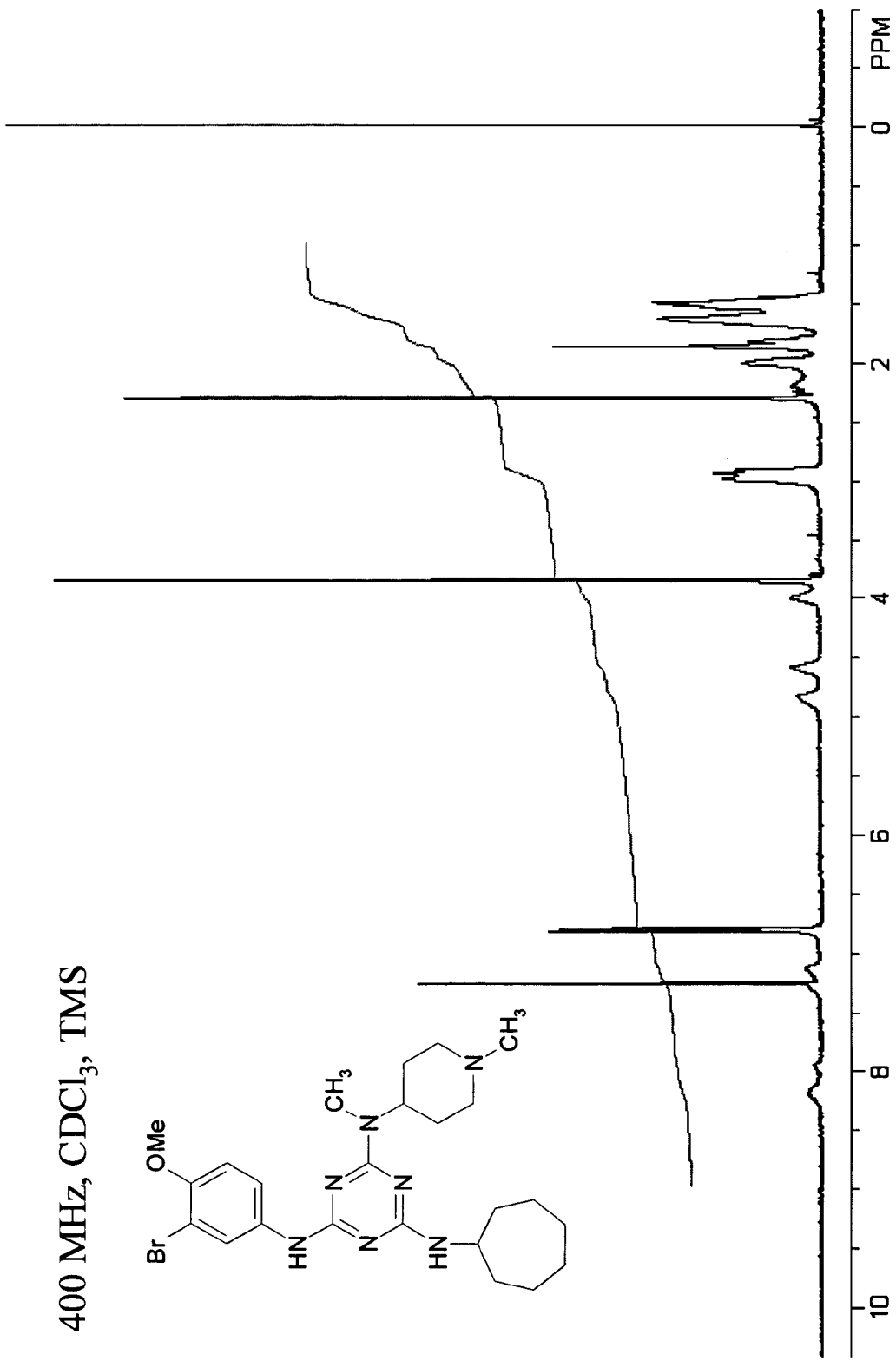
FIG. 30. ¹H NMR of N-(3-Bromo-4-methoxy-phenyl)-N'-cycloheptyl-N''-methyl-N''-(1-methyl-piperidin-4-yl)-[1,3,5]triazine-2,4,6-triamine.
Figure 31:
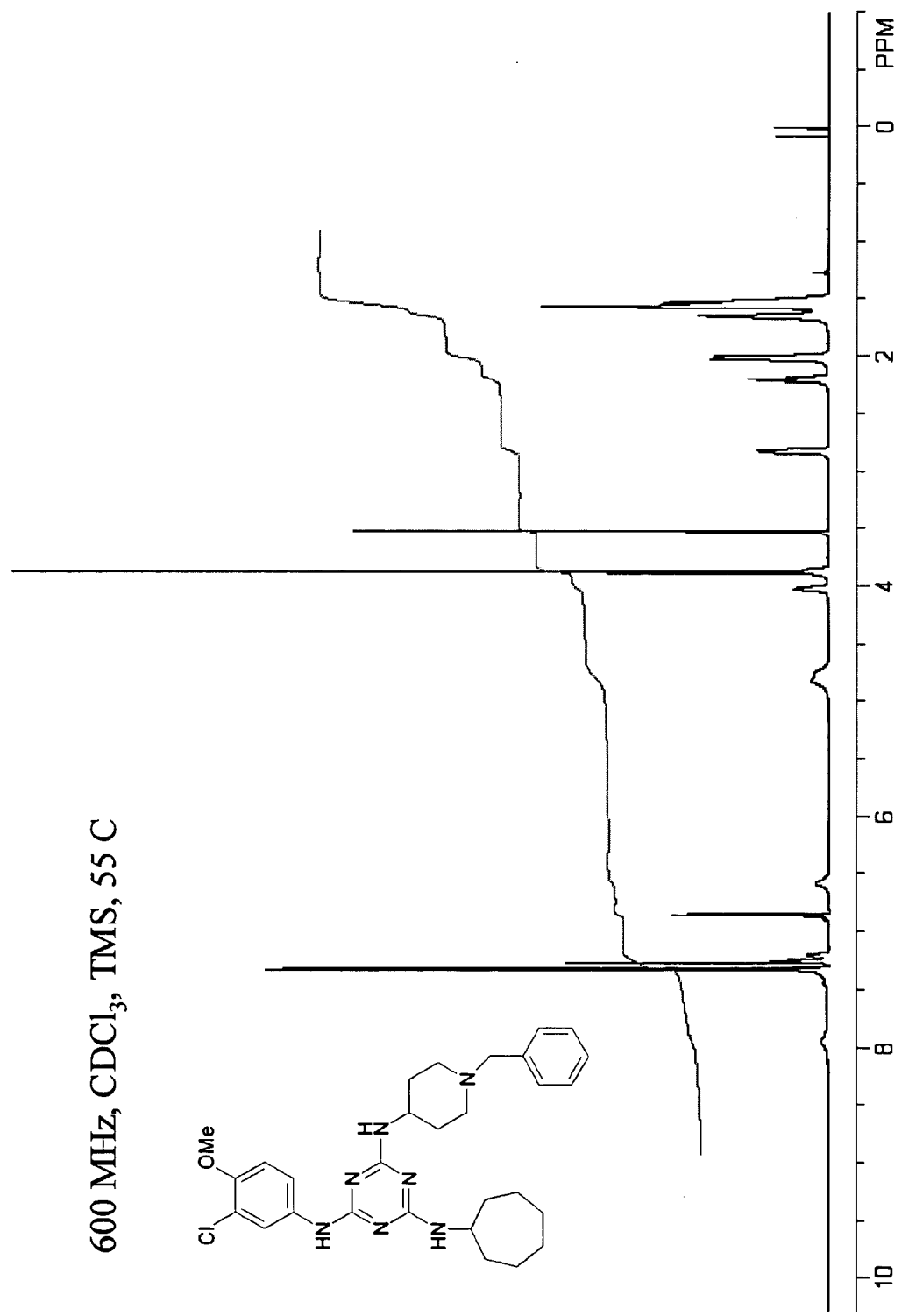
FIG. 31. ¹H NMR of N-(1-benzyl-piperidin-4-yl)-N'-(3-chloro-4-methoxy-phenyl)-N''-cycloheptyl-[1,3,5]-2,4,6-triamine.
Figure 32:
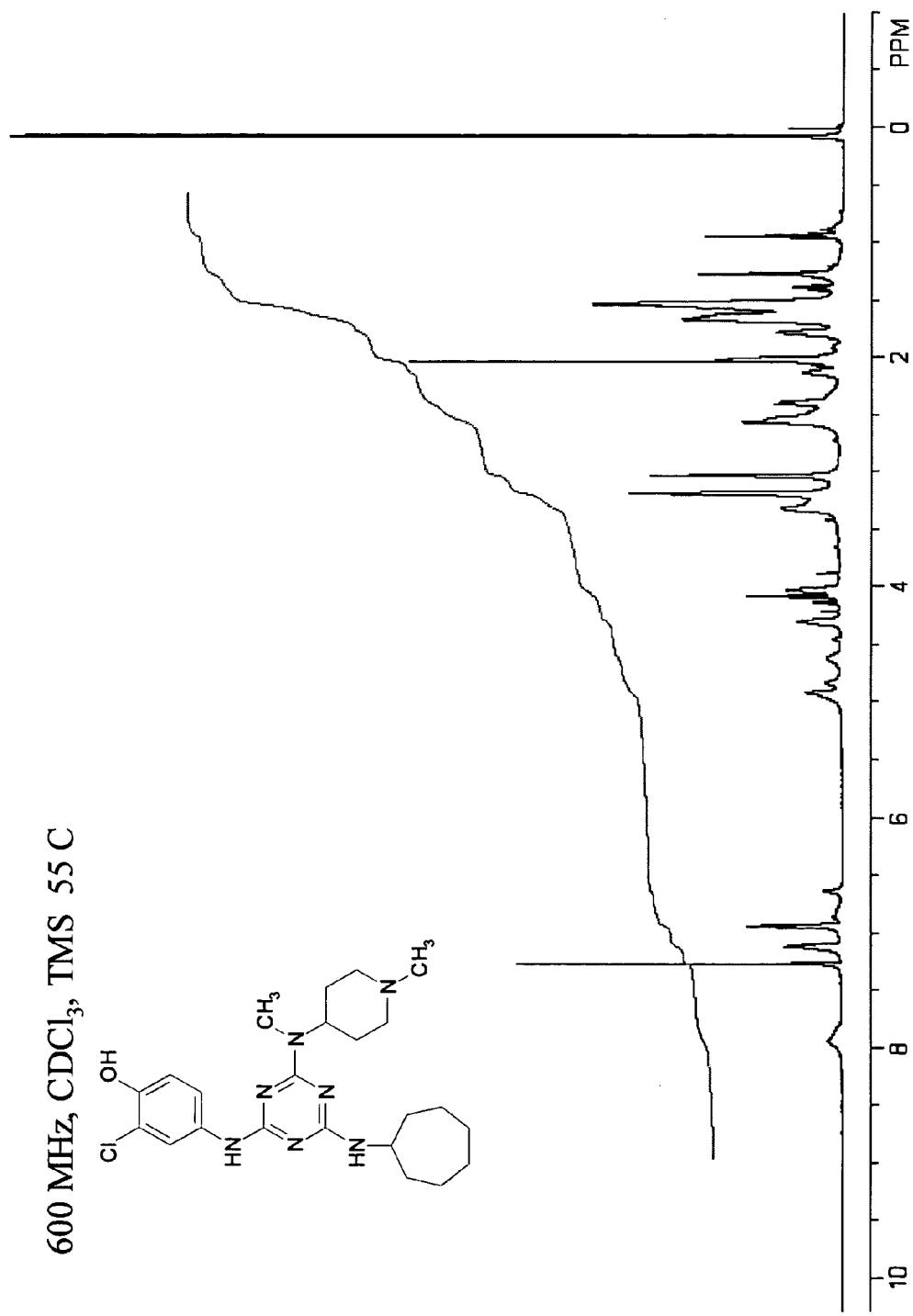
FIG. 32. ¹H NMR of 2-chloro-4-{4-cycloheptylamino-6-[methyl-(1-methyl-piperidin-4-yl-amino]-1,3,5-triazin-2-ylamino}-phenyl.
Figure 33:
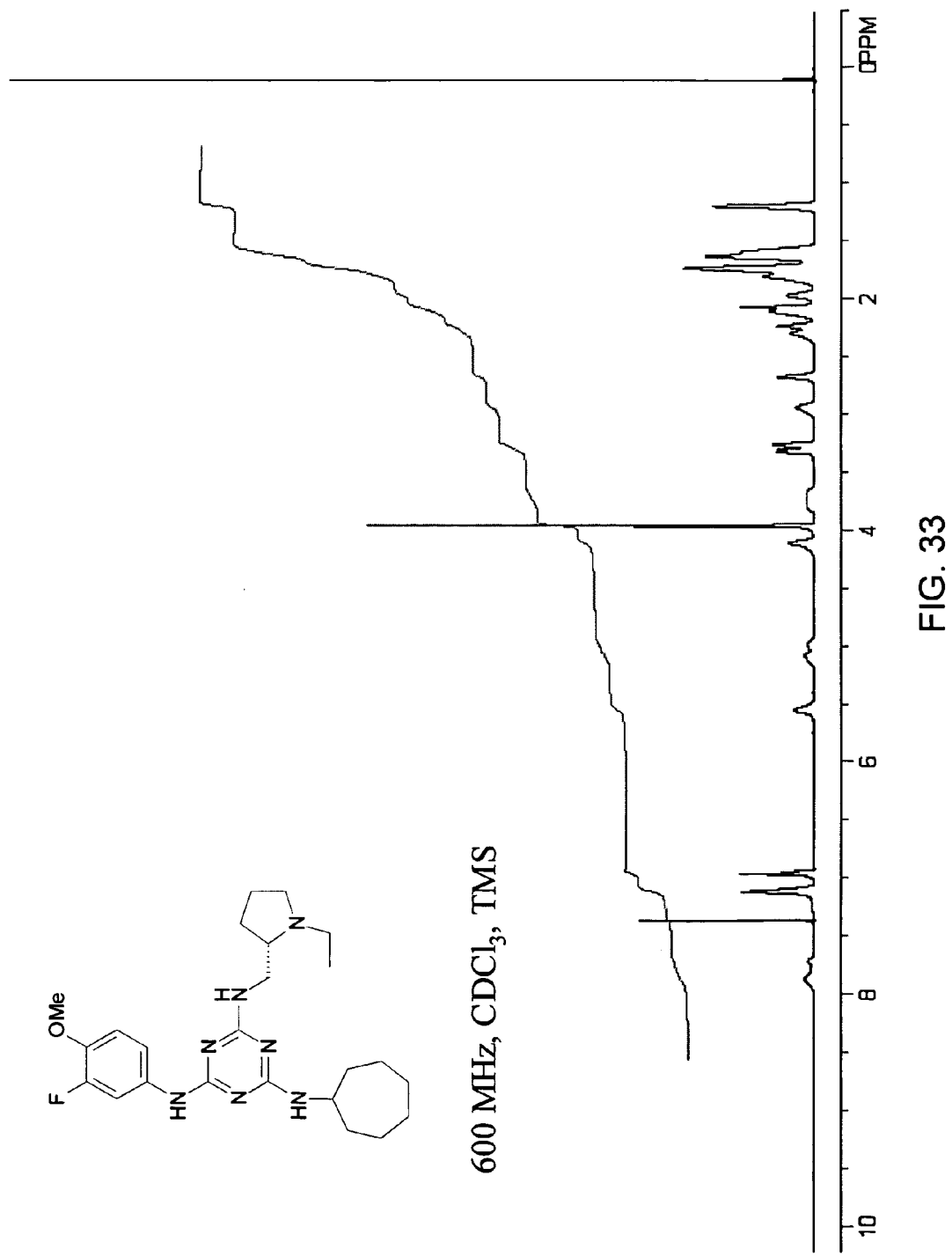
FIG. 33. ¹H NMR of N2-cycloheptyl-N4-((S)-1-ethyl-pyrrolidin-2-ylmethyl)-N6-(3-fluoro-4-methoxyphenyl)-1,3,5-triazine-2,4,6-triamine.
Figure 34:
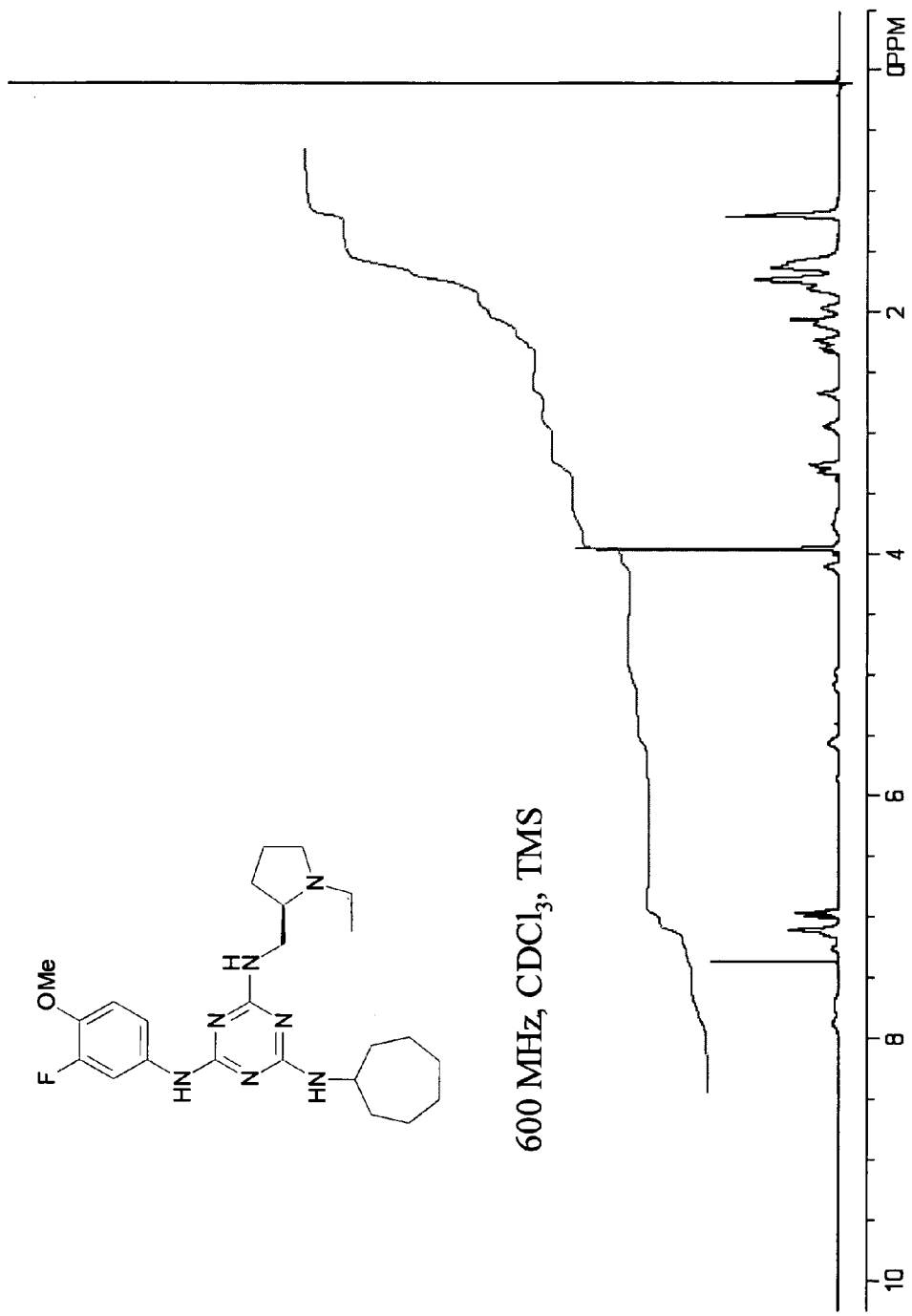
FIG. 34. ¹H NMR of N2-cycloheptyl-N4-((R)-1-ethyl-pyrrolidin-2-ylmethyl)-N6-(3-fluoro-4-methoxyphenyl)-1,3,5-triazine-2,4,6-triamine.
Figure 35:
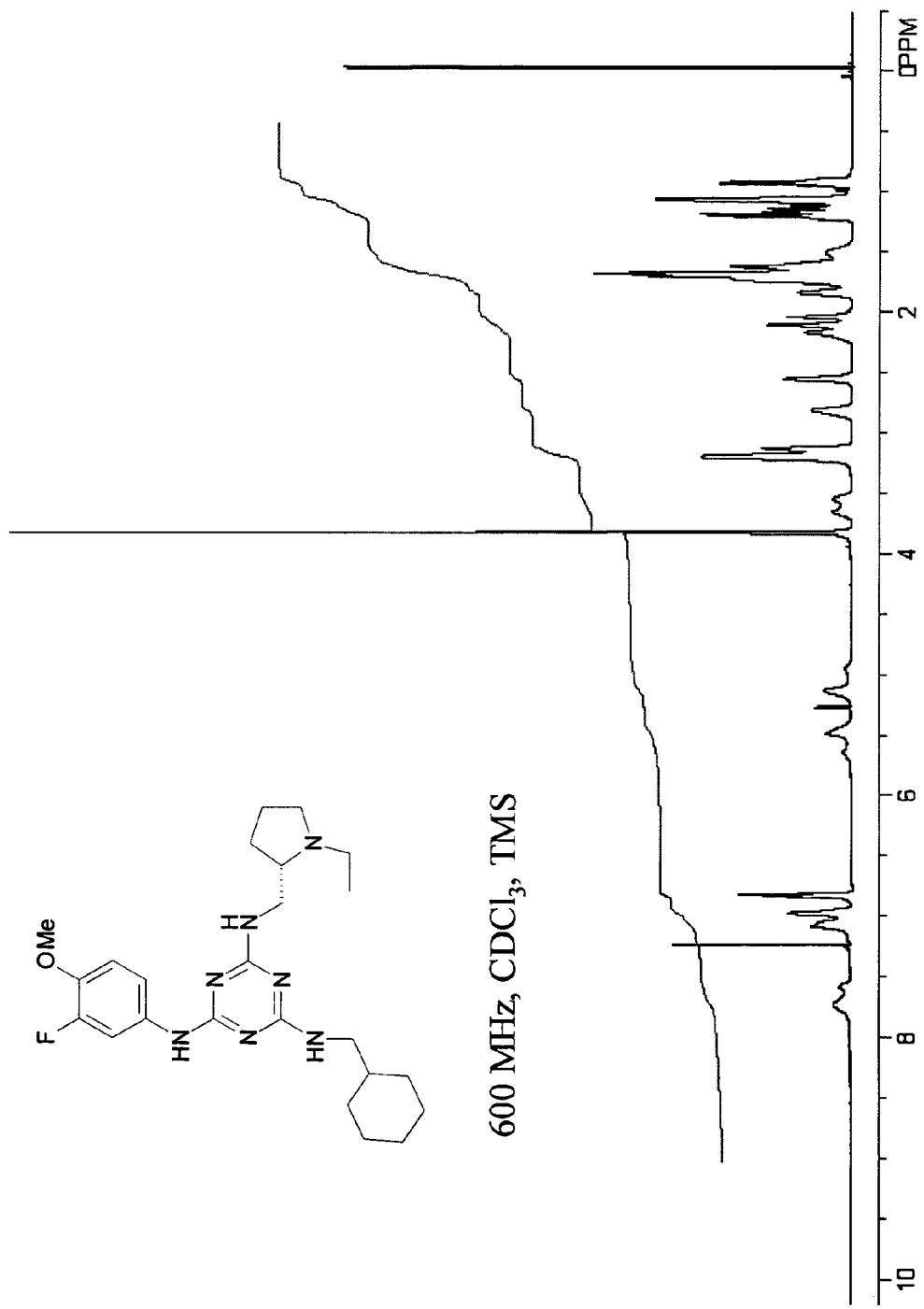
FIG. 35. ¹H NMR of N2-cyclohexylmethyl-N4-((S)-1-ethyl-pyrrolidin-2-ylmethyl)-N6-(3-fluoro-4-methoxyphenyl)-1,3,5-triazine-2,4,6-triamine.
Figure 36:
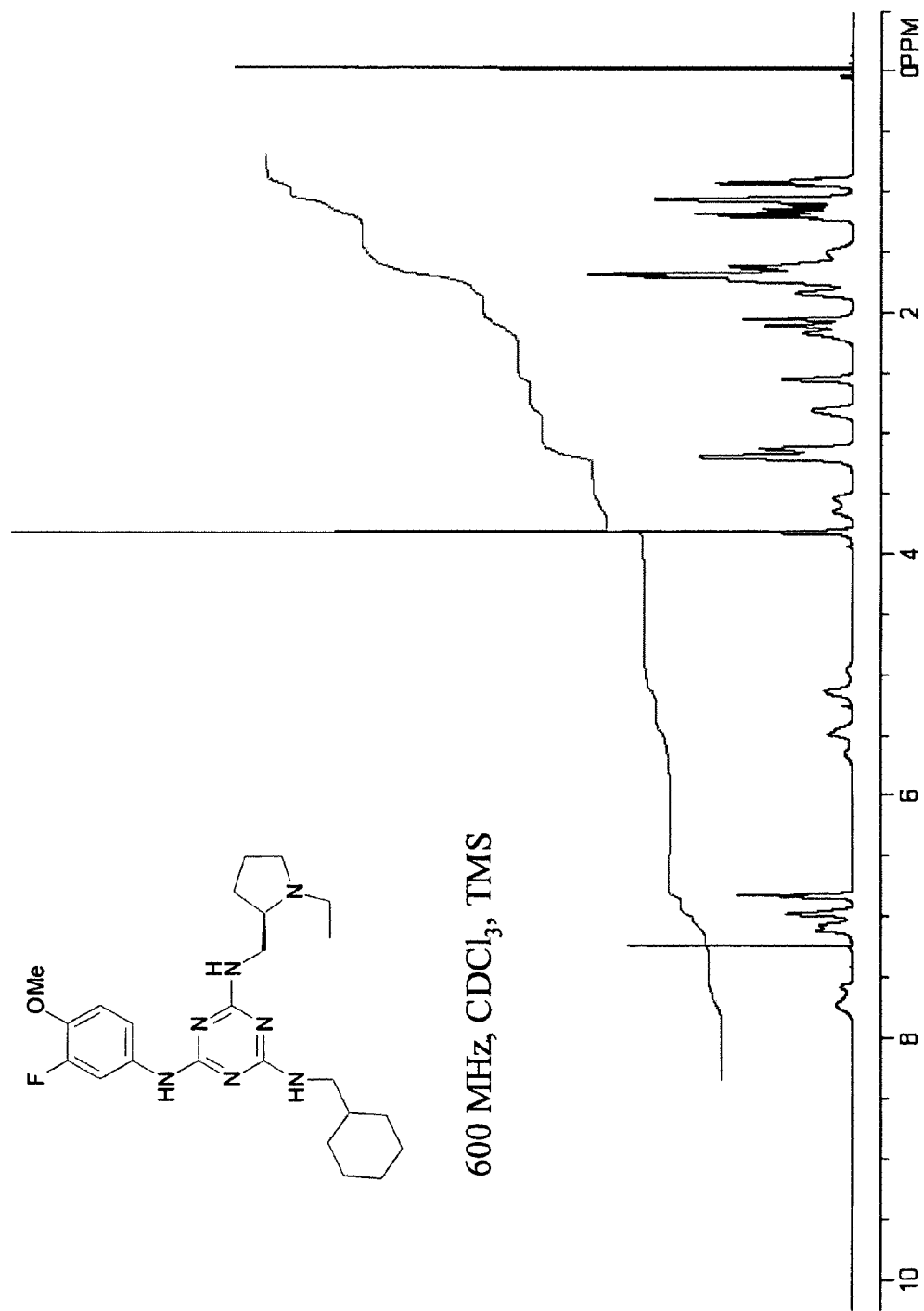
FIG. 36. ¹H NMR of N2-cyclohexylmethyl-N4-((R)-1-ethyl-pyrrolidin-2-ylmethyl)-N6-(3-fluoro-4-methoxyphenyl)-1,3,5-triazine-2,4,6-triamine.
Figure 37:
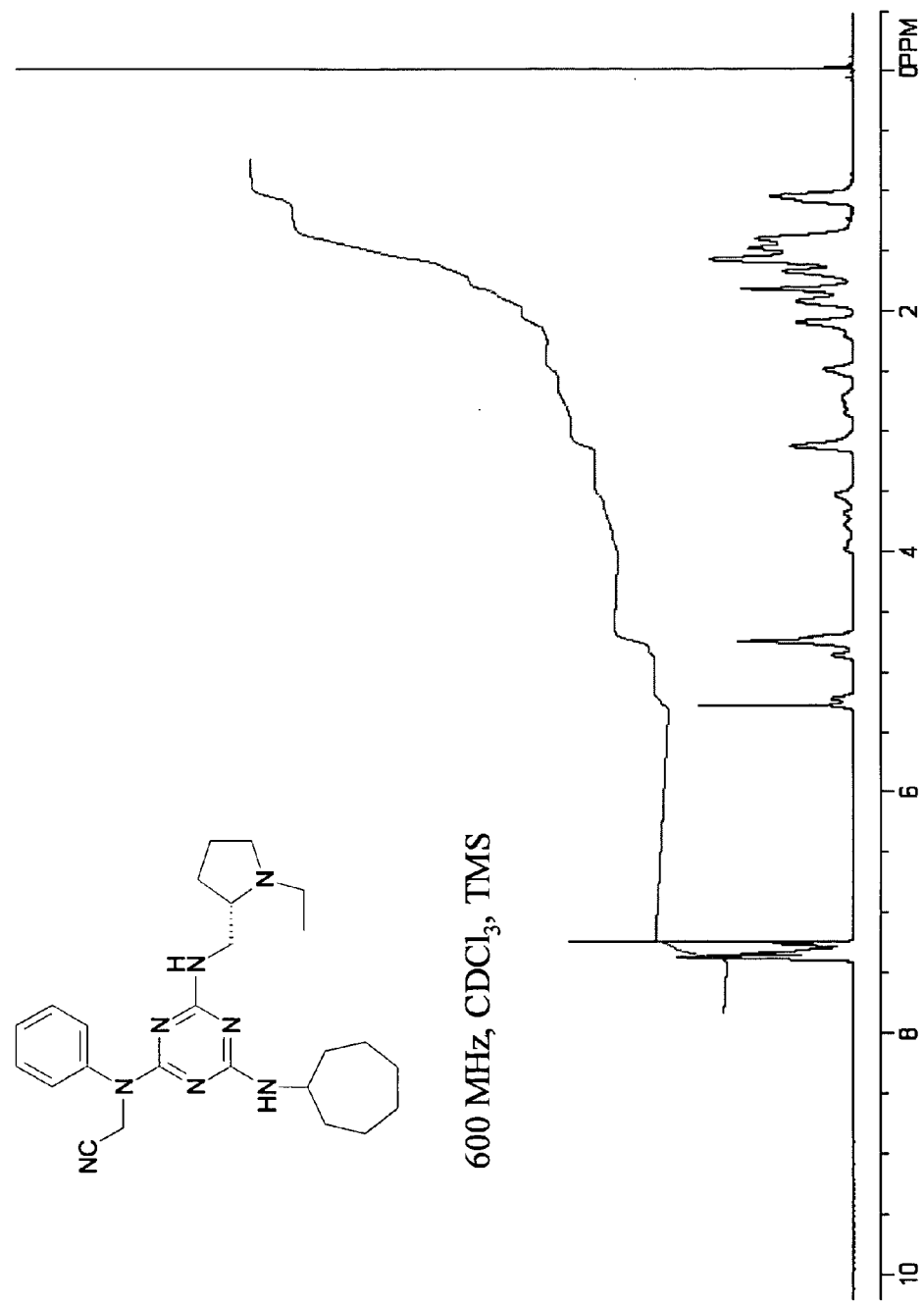
FIG. 37. ¹H NMR of ({4-cycloheptylamino-6-[((S)-1-ethyl-pyrrolidin-2-ylmethyl)-amino]-1,3,5-triazin-2-yl}-phenyl-amino)-acetonitrile.
Figure 38:
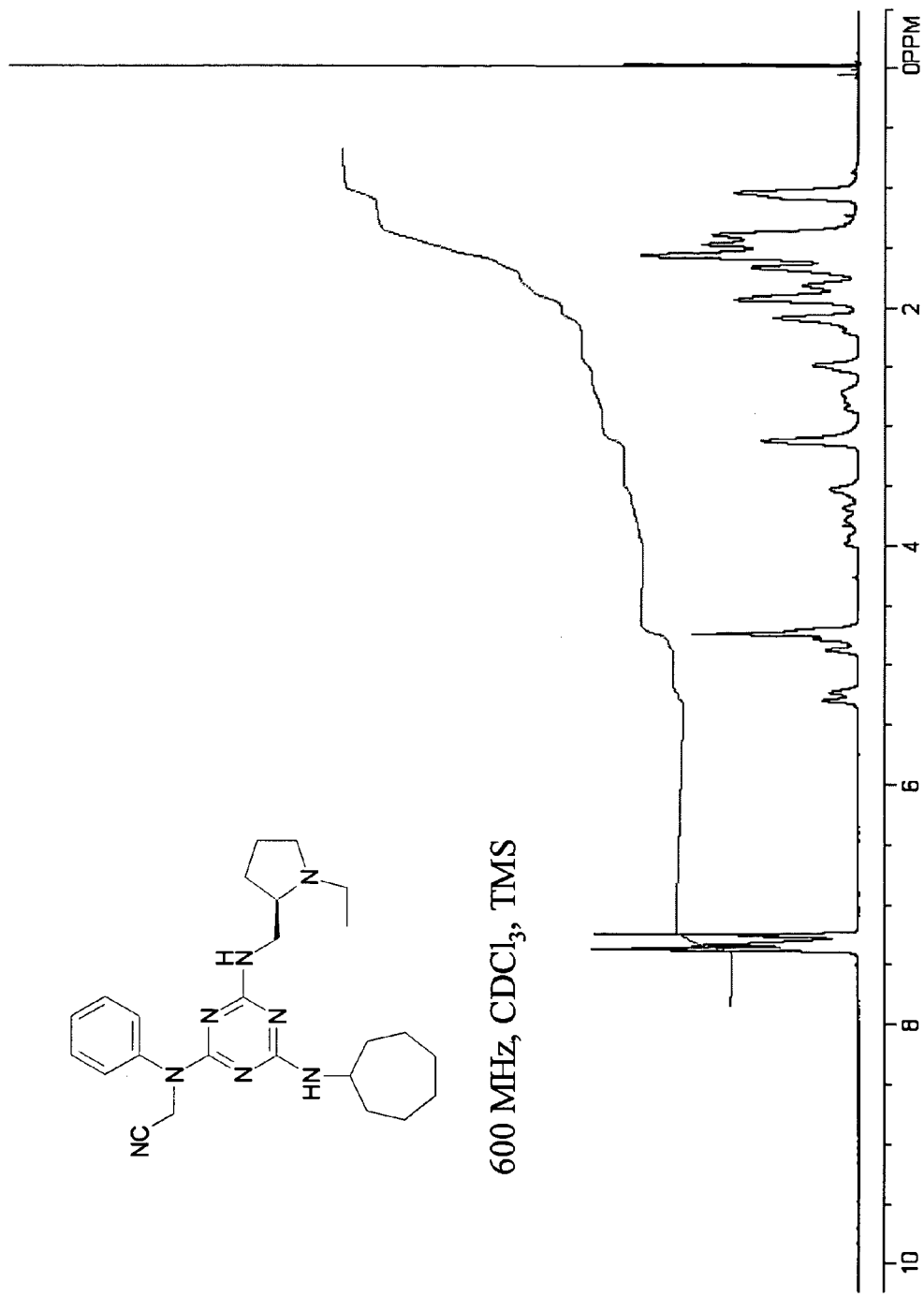
FIG. 38. ¹H NMR of ({4-cycloheptylamino-6-[((R)-1-ethyl-pyrrolidin-2-ylmethyl)-amino]-1,3,5-triazin-2-yl}-phenyl-amino)-acetonitrile.
Figure 39:
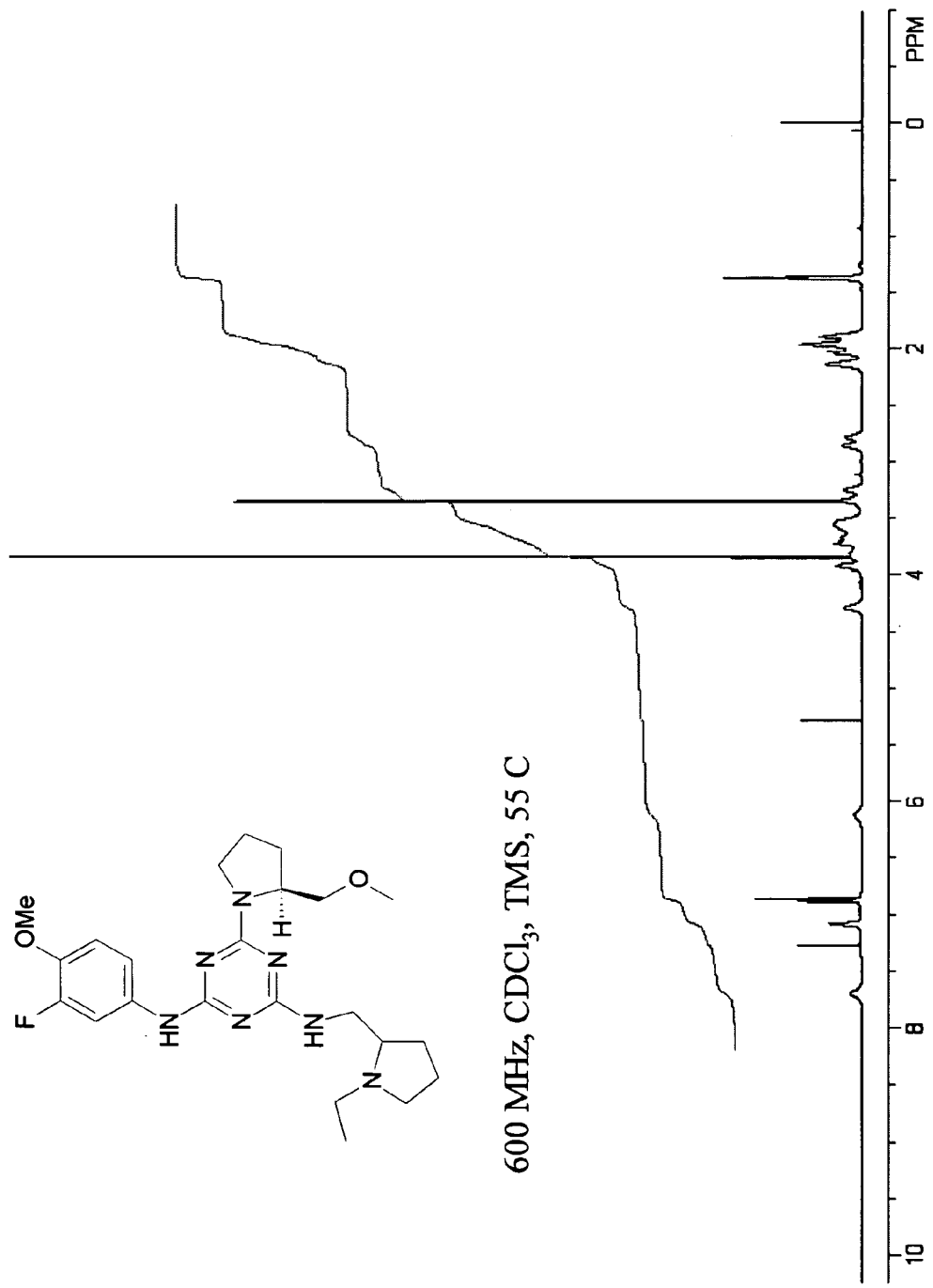
FIG. 39. ¹H NMR of N2-[(1-ethyl-2-pyrrolidinyl]-N4-(3-fluoro-4-methoxyphenyl)-6-[(S)-2-(methoxymethyl)-1-pyrrolidinyl]-1,3,5-triazine-2,4-diamine.
Figure 40:
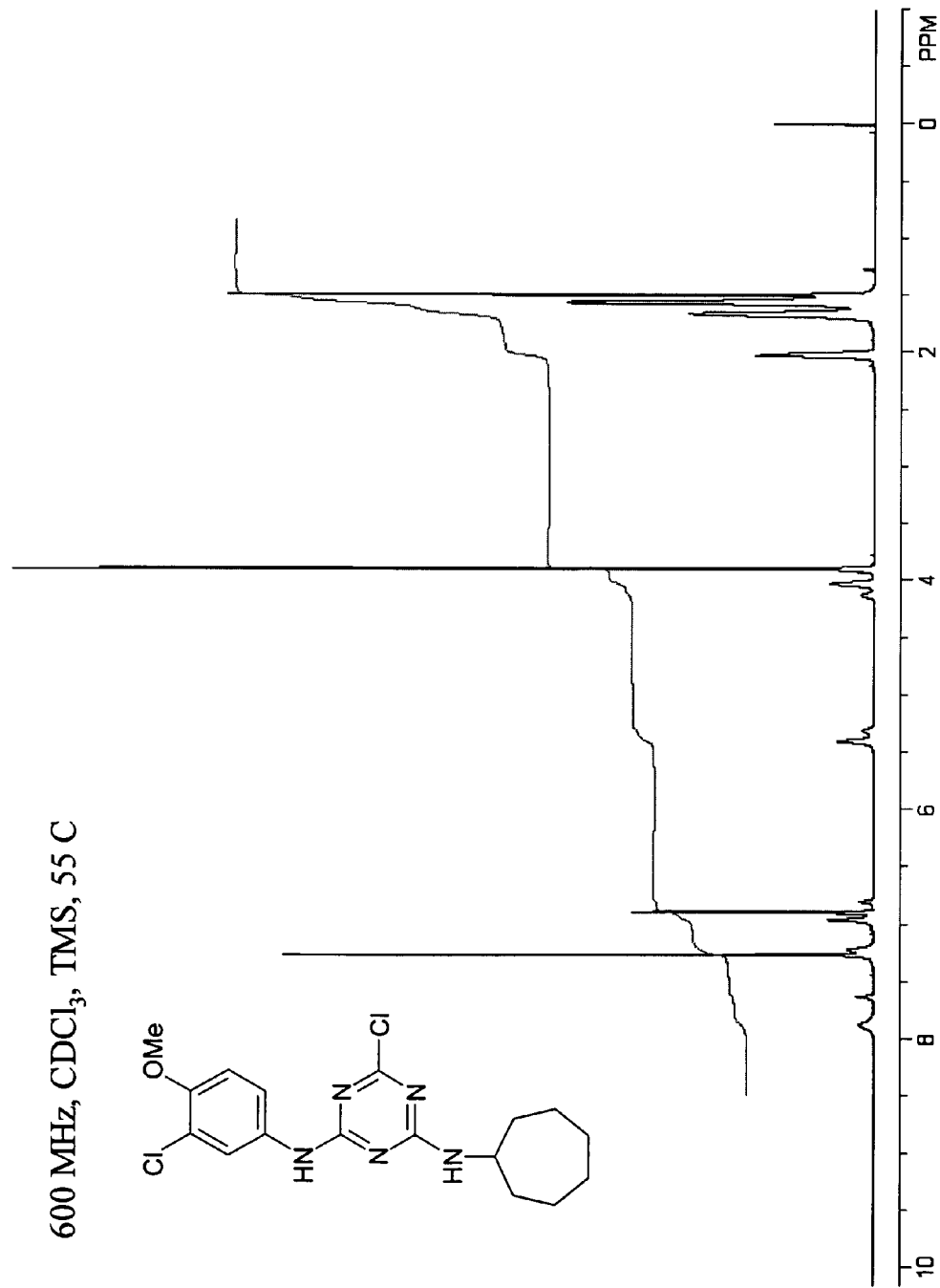
FIG. 40. ¹H NMR of 6-Chloro-N-(3-chloro-4-methoxy-phenyl)-N'-cycloheptyl-[1,3,5]triazine-2,4-diamine.
Figure 41:
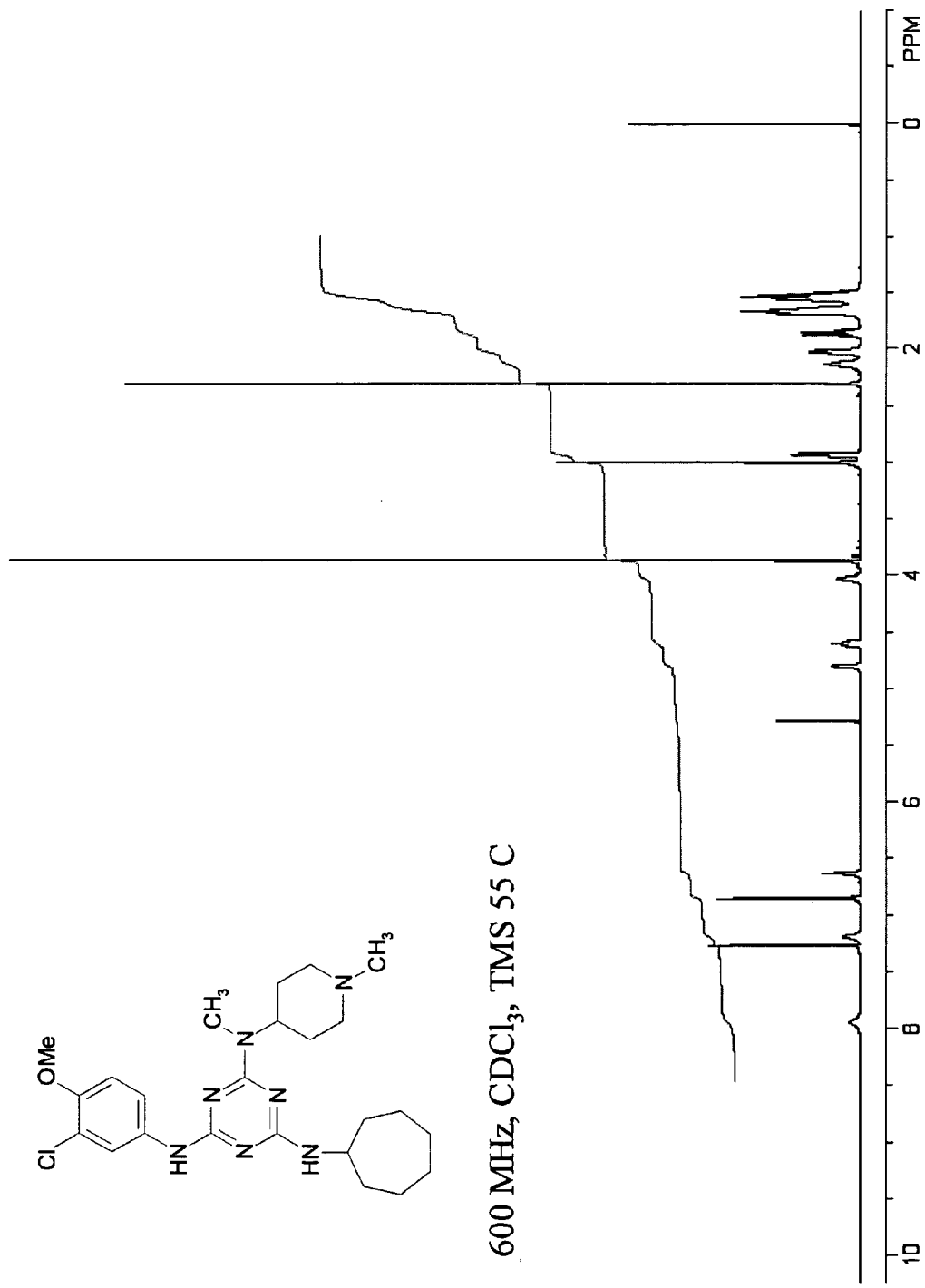
FIG. 41. ¹H NMR of N-(3-Chloro-4-methoxy-phenyl)-N'-cycloheptyl-N''-methyl-N''-(1-methyl-piperidin-4-yl)-[1,3,5]triazine-2,4,6-triamine.
Figure 42:
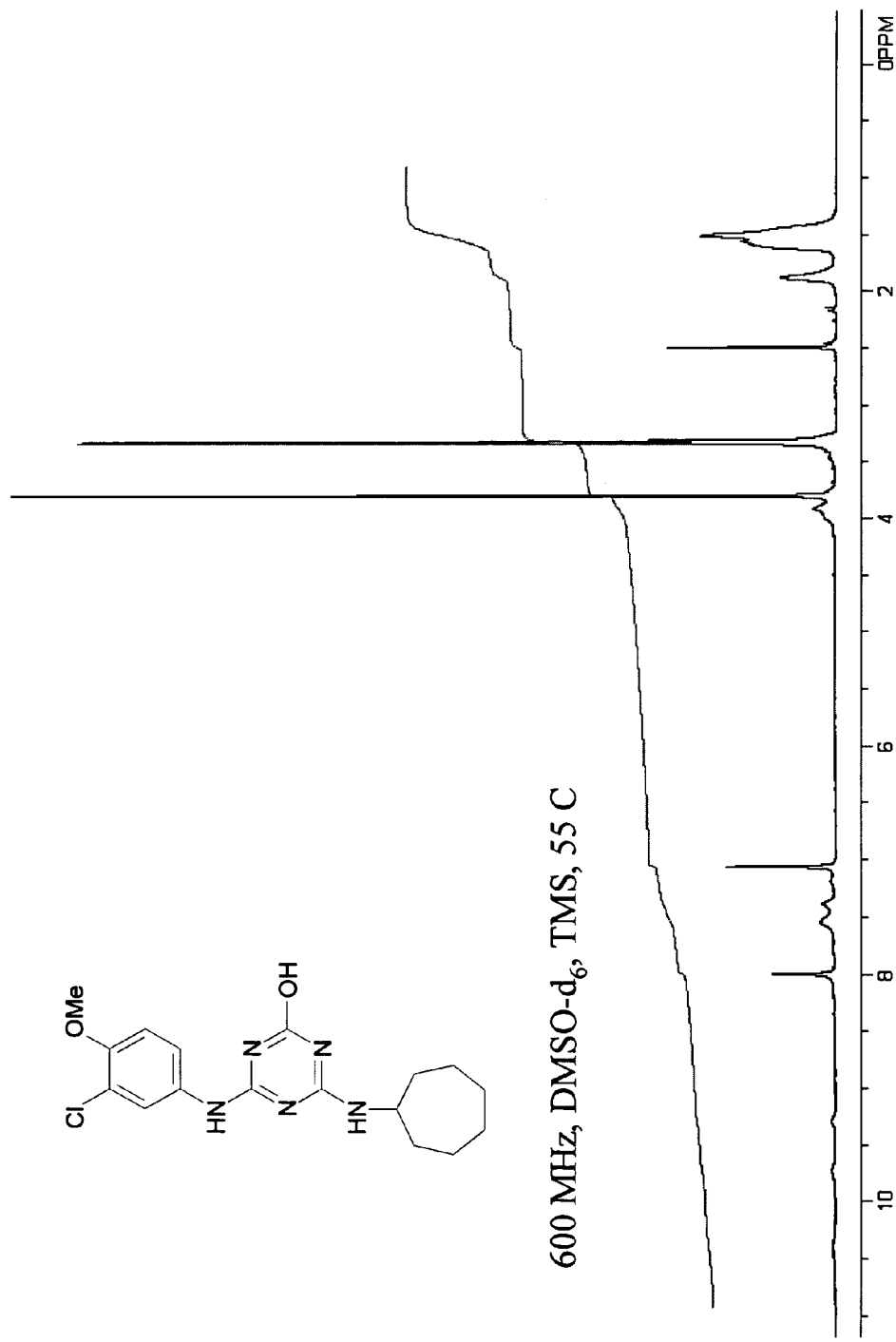
FIG. 42. ¹H NMR of 4-(3-Chloro-4-methoxy-phenylamino)-6-cycloheptylamino-1,3,5-triazin-2-ol.
Figure 43:
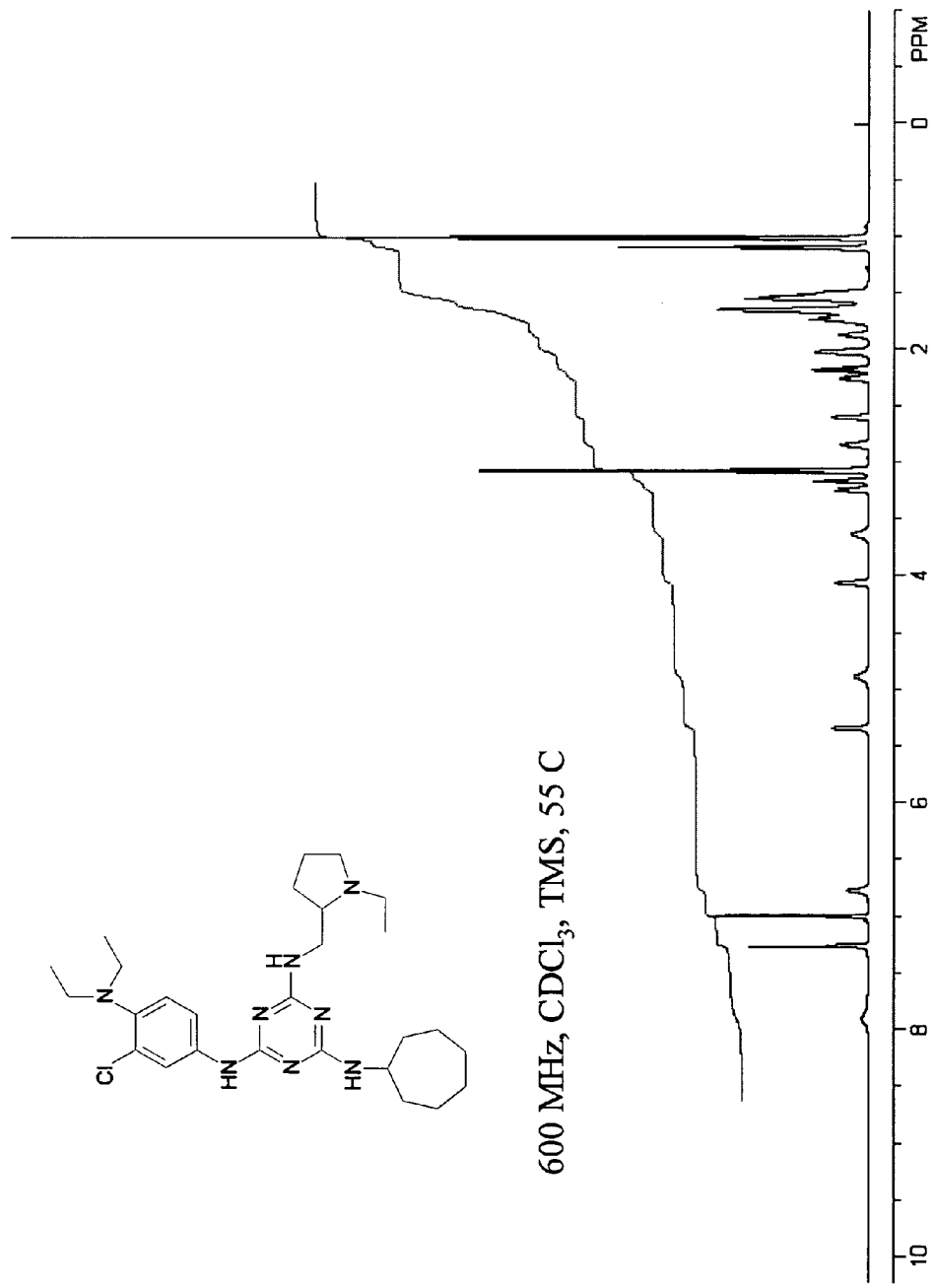
FIG. 43. ¹H NMR of N2-(3-chloro-4-diethylamino-phenyl)-N4-cycloheptyl-N6-(1-ethyl-pyrrolidin-2-ylmethyl)-1,3,5-triazine-2,4,6-triamine.
Figure 44:
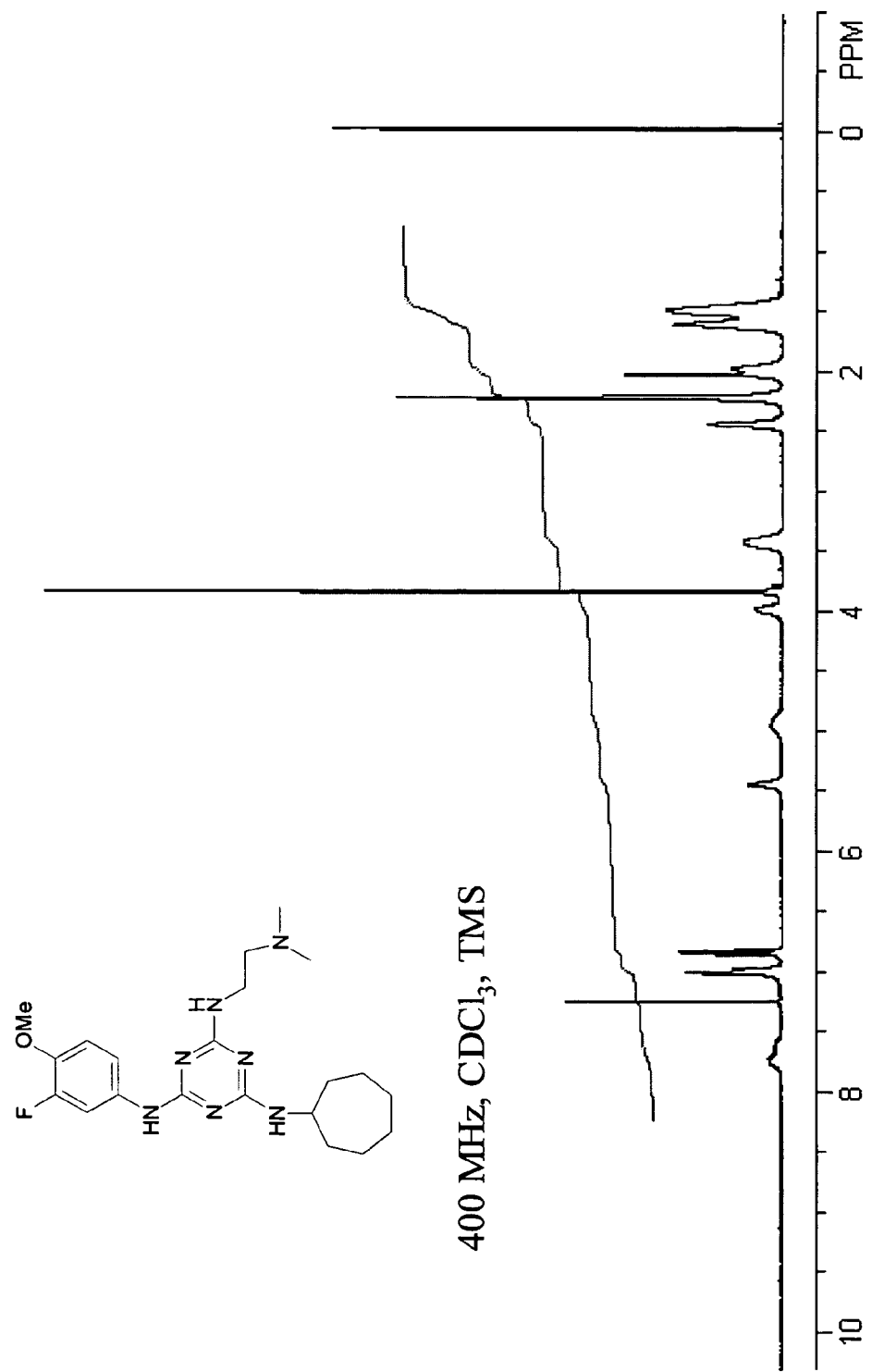
FIG. 44. ¹H NMR of N2-cycloheptyl-N4-(2-dimethylamino-ethyl)-N6-(3-fluoro-4-methoxy-phenyl)-1,3,5-triazine-2,4,6-triamine.
Figure 45:
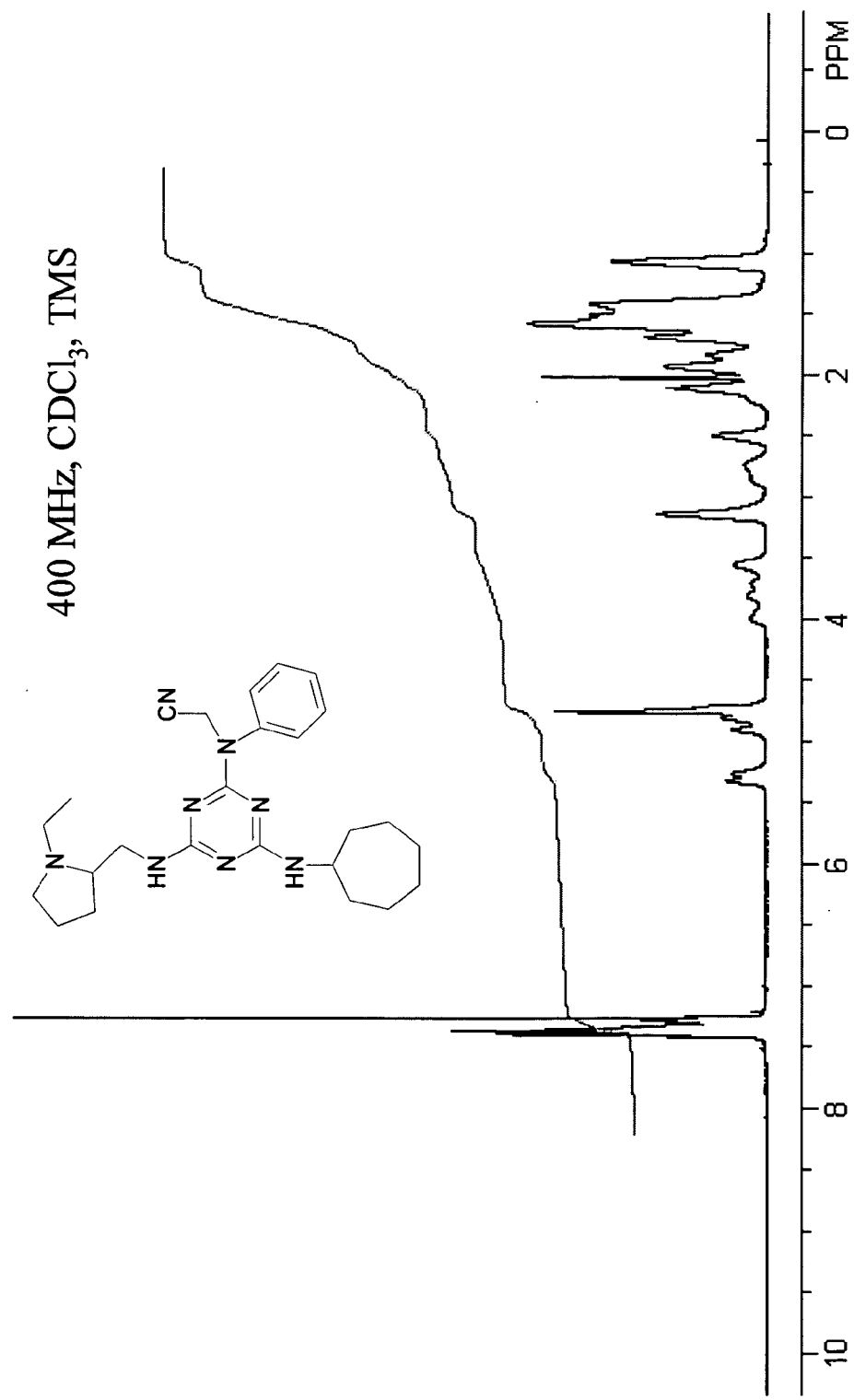
FIG. 45. ¹H NMR of ({4-cycloheptylamino-6-[1-ethyl-pyrrolidin-2-ylmethyl)-amino]-1,3,5-triazin-2-yl}-phenyl-amino)-acetonitrile.
Figure 46:
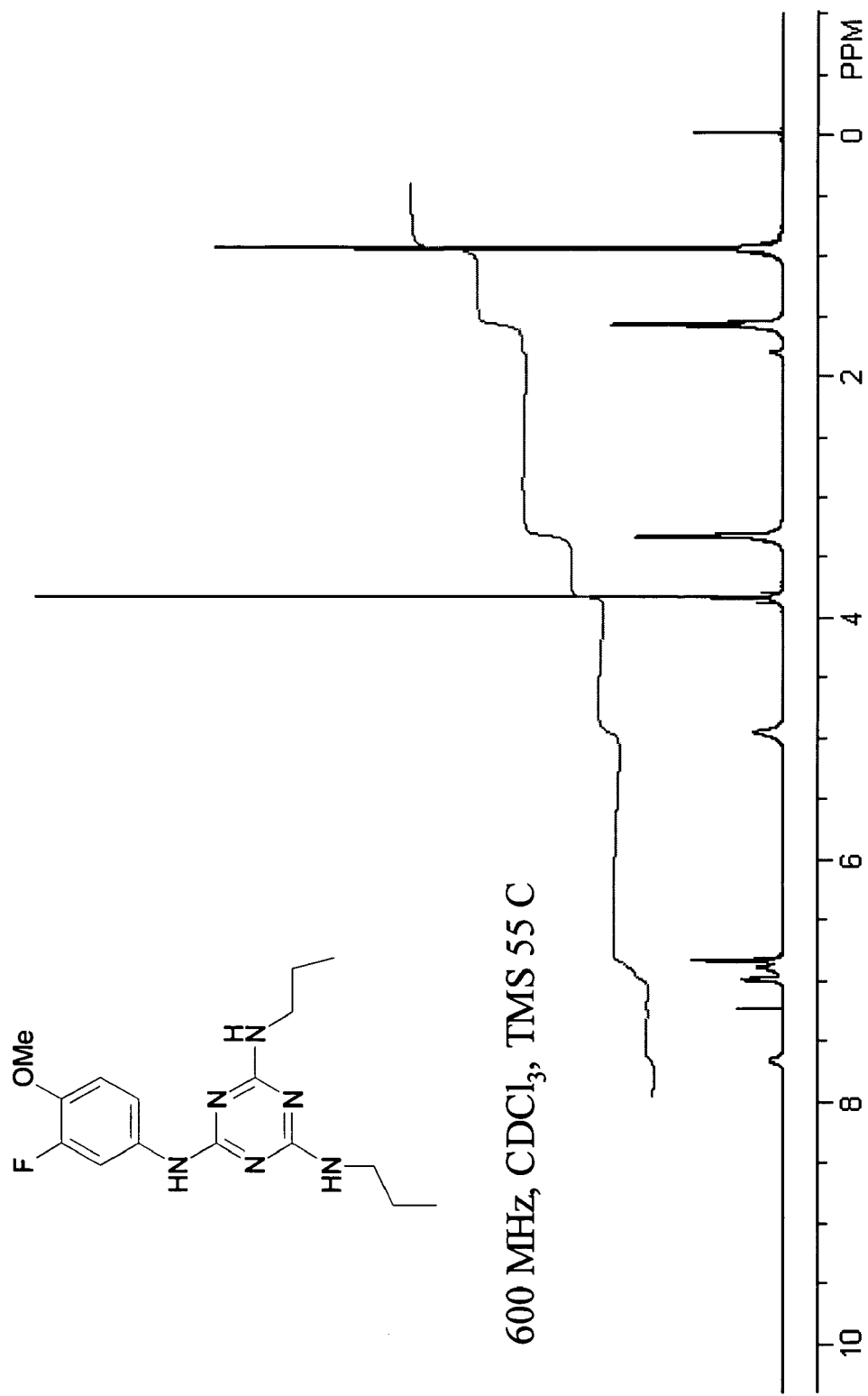
FIG. 46. ¹H NMR of N,N'-di-n-propyl-N''-(3-fluoro-4-methoxy-phenyl)-1,3,5-triazine-2,4,6-triamine.
Figure 47:
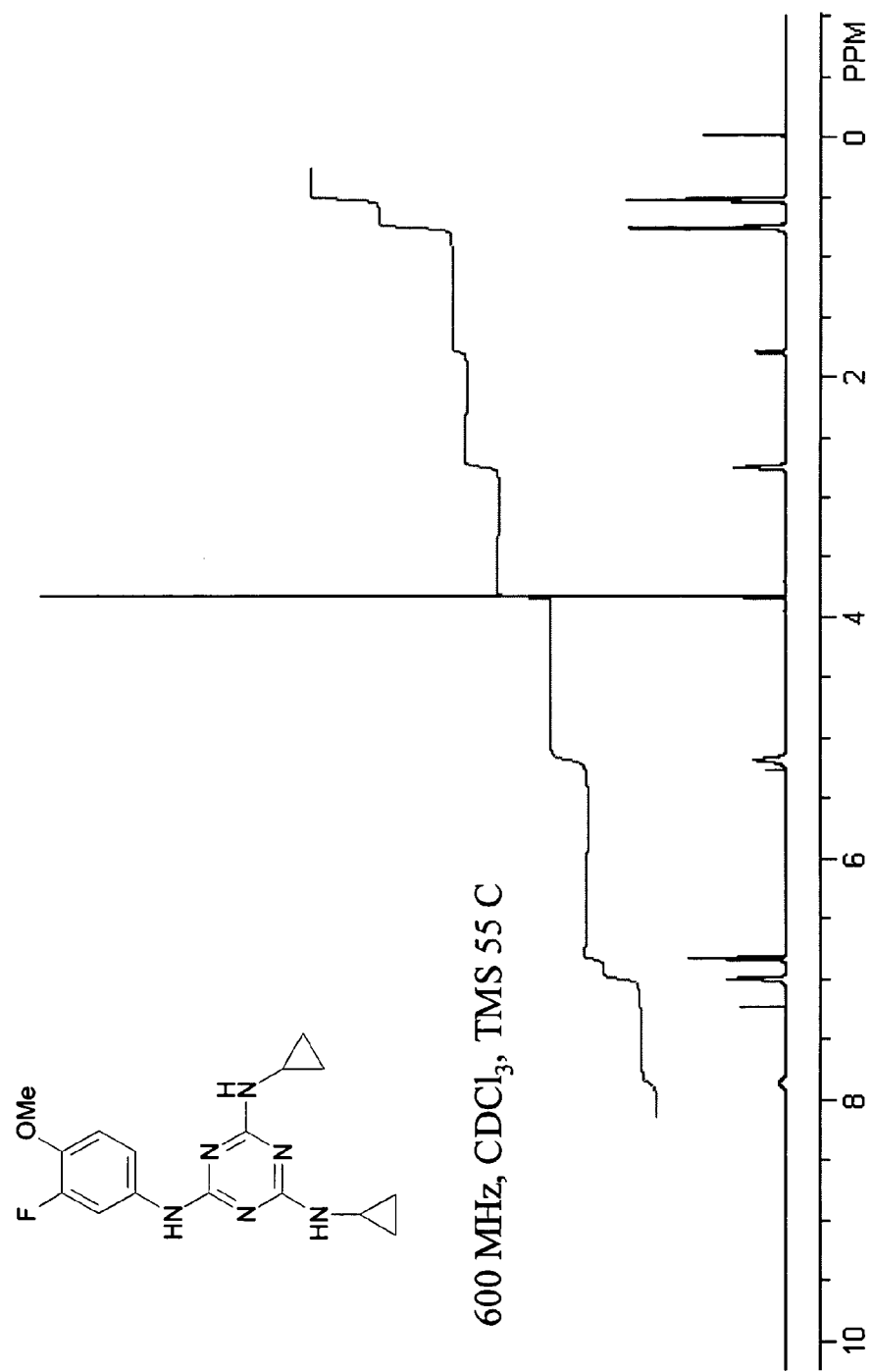
FIG. 47. ¹H NMR of N,N'-dicyclopropyl-N''-(3-fluoro-4-methoxy-phenyl)-1,3,5-triazine-2,4,6-triamine.
Figure 48:
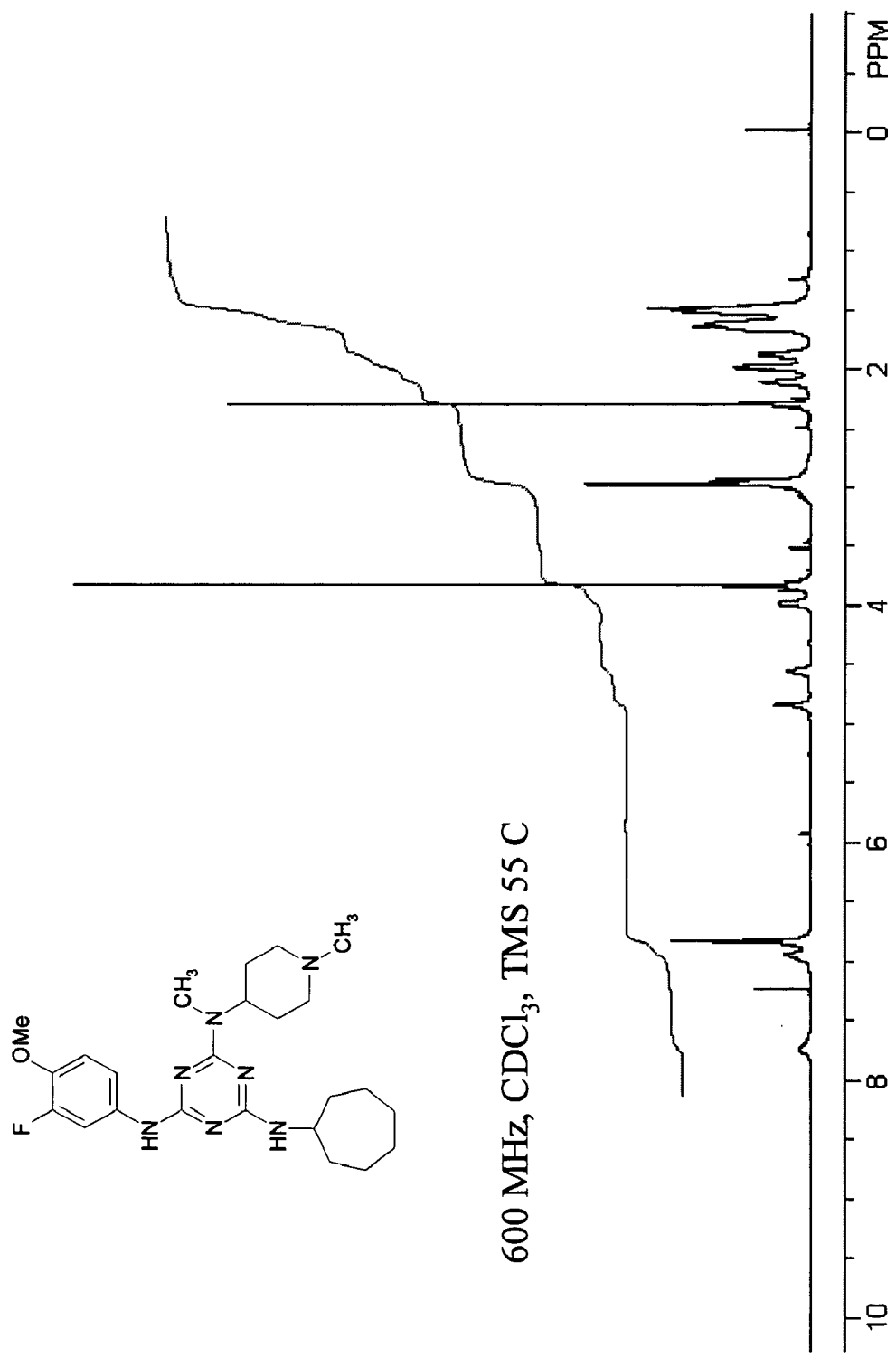
FIG. 48. ¹H NMR of N2-Cycloheptyl-N4-(3-fluoro-4-methoxy-phenyl)-N6-methyl-N6-(1-methyl-piperidin-4-yl)-1,3,5-triazine-2,4,6-triamine.
Figure 49:
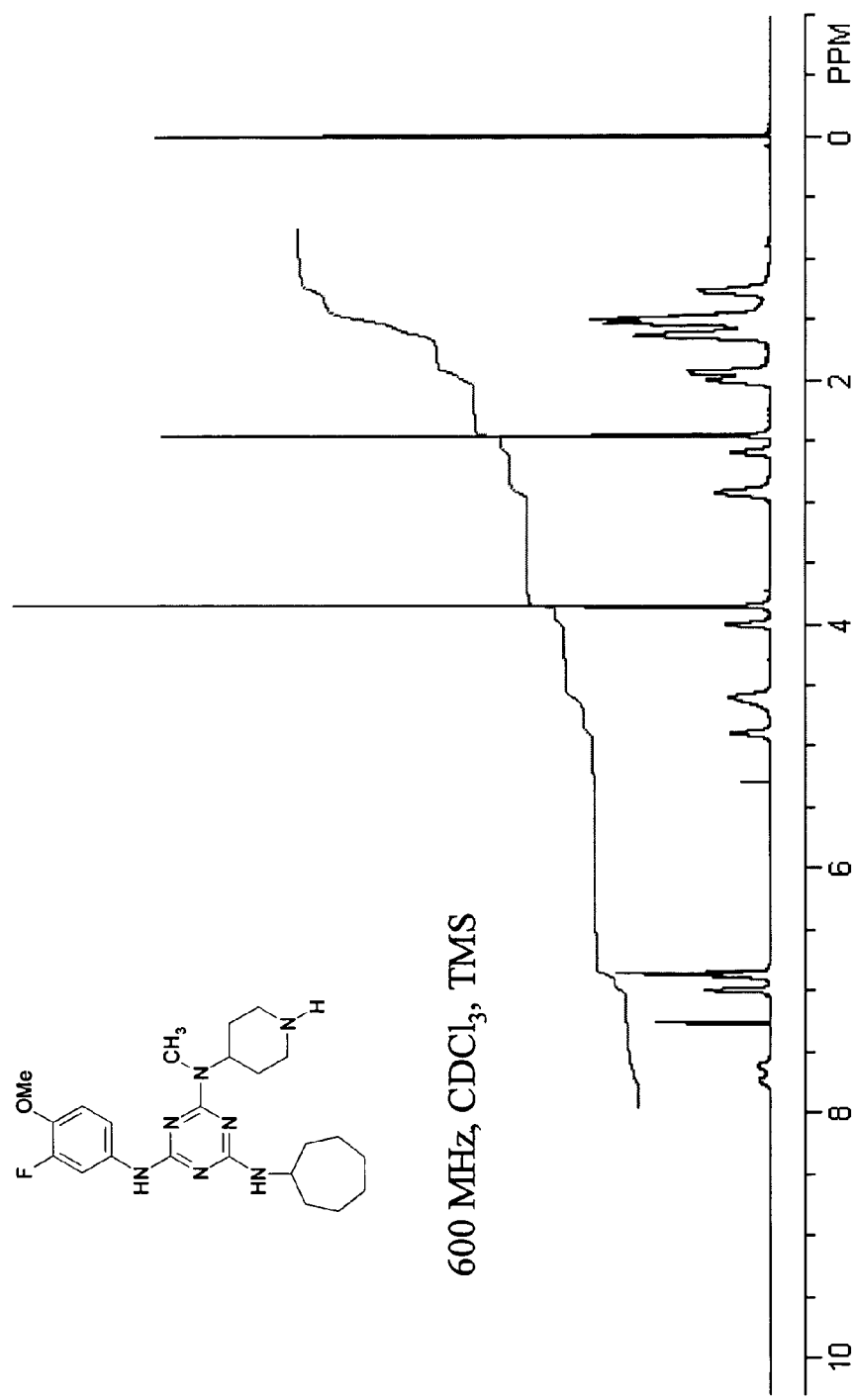
FIG. 49. ¹H NMR of N2-Cycloheptyl-N4-(3-fluoro-4-methoxy-phenyl)-N6-methyl-N6-piperidin-4-yl-1,3,5-triazine-2,4,6-triamine.
Figure 50:
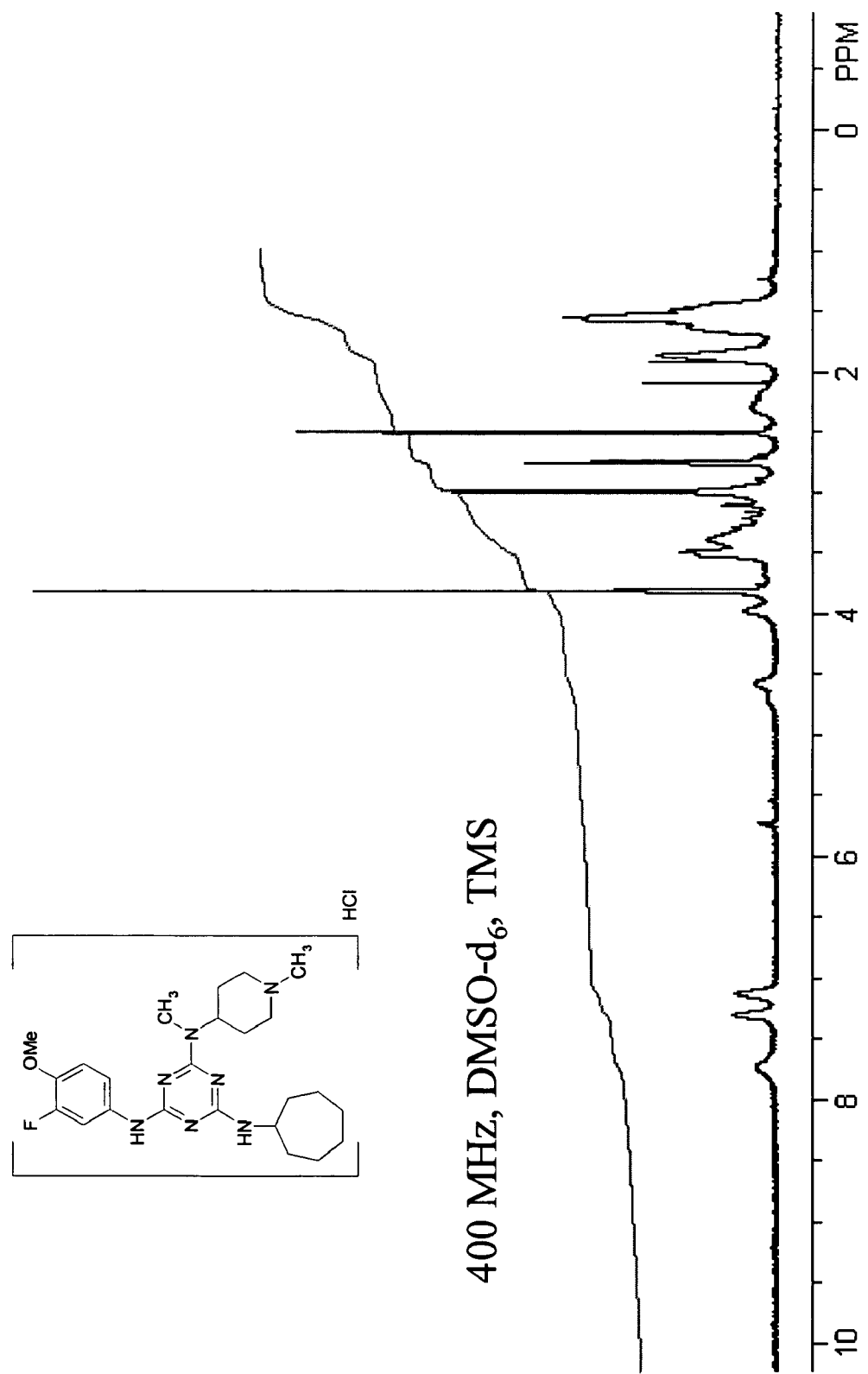
FIG. 50. ¹H NMR of N2-cycloheptyl-N4-(3-fluoro-4-methoxyphenyl)-N6-methyl-N6-(1-methyl-piperidin-4-yl)-1,3,5-triazine-2,4,6-triamine, hydrogen chloride salt.
Figure 51:
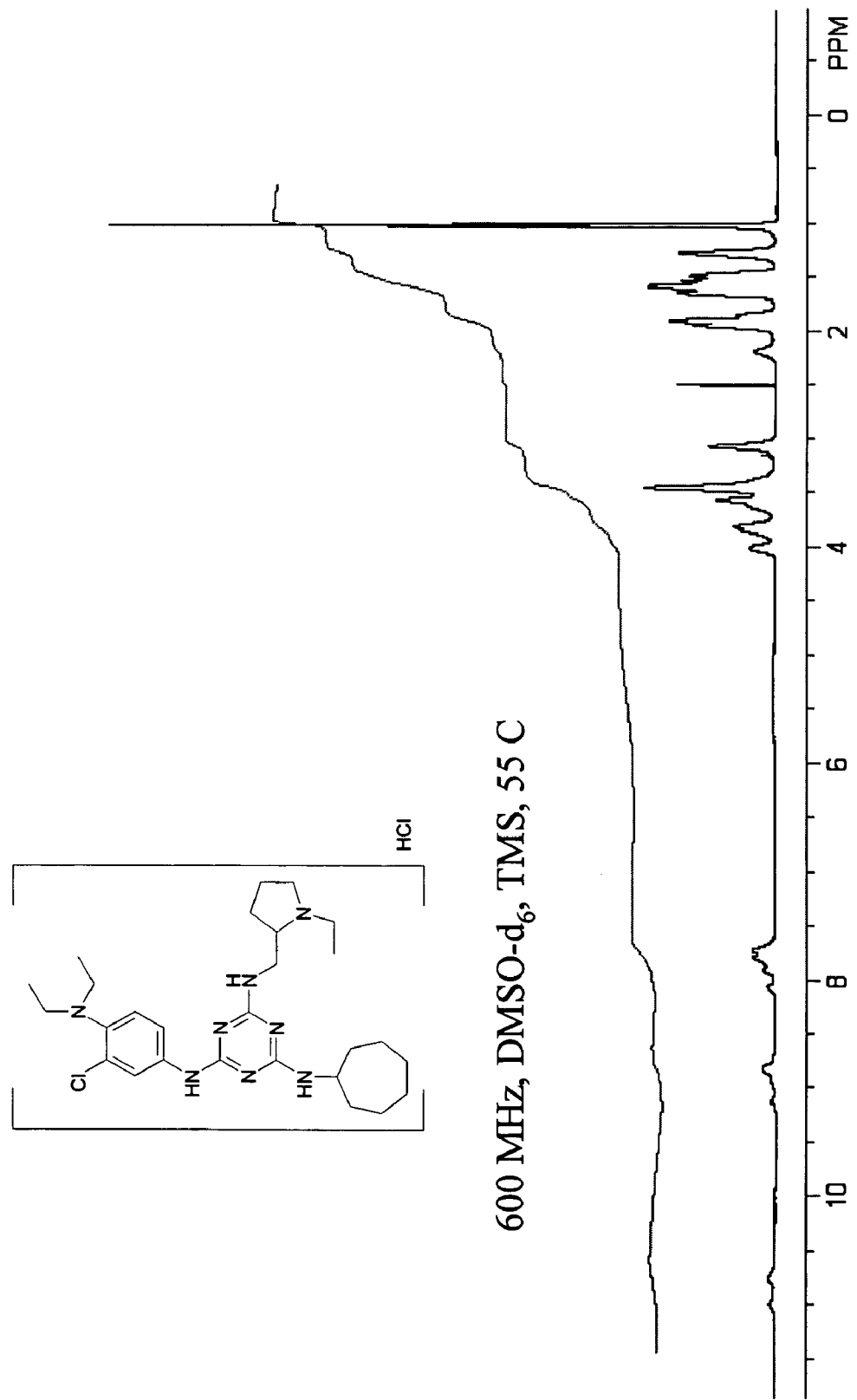
FIG. 51. ¹H NMR of N2-(3-chloro-4-diethylamino-phenyl)-N4-cycloheptyl-N6-(1-ethyl-pyrrolidin-2-ylmethyl)-1,3,5-triazine-2,4,6-triamineS42-63 hydrogen chloride salt.
Figure 52:
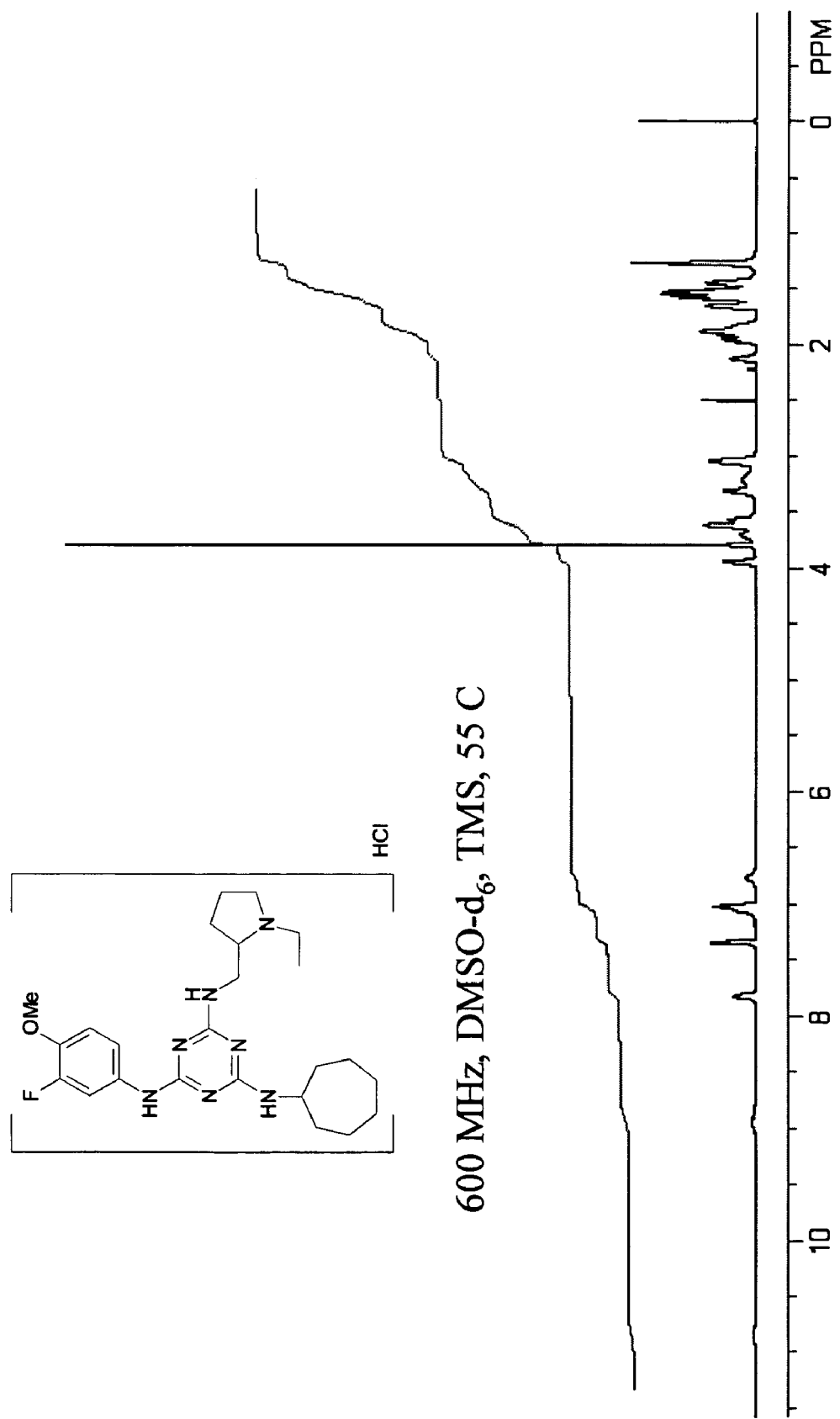
FIG. 52. ¹H NMR of N2-cycloheptyl-N4-(1-ethyl-pyrrolidin-2-ylmethyl)-N6-(3-fluoro-4-methoxyphenyl)-1,3,5-triazine-2,4,6-triamine hydrogen chloride salt.
Figure 53:
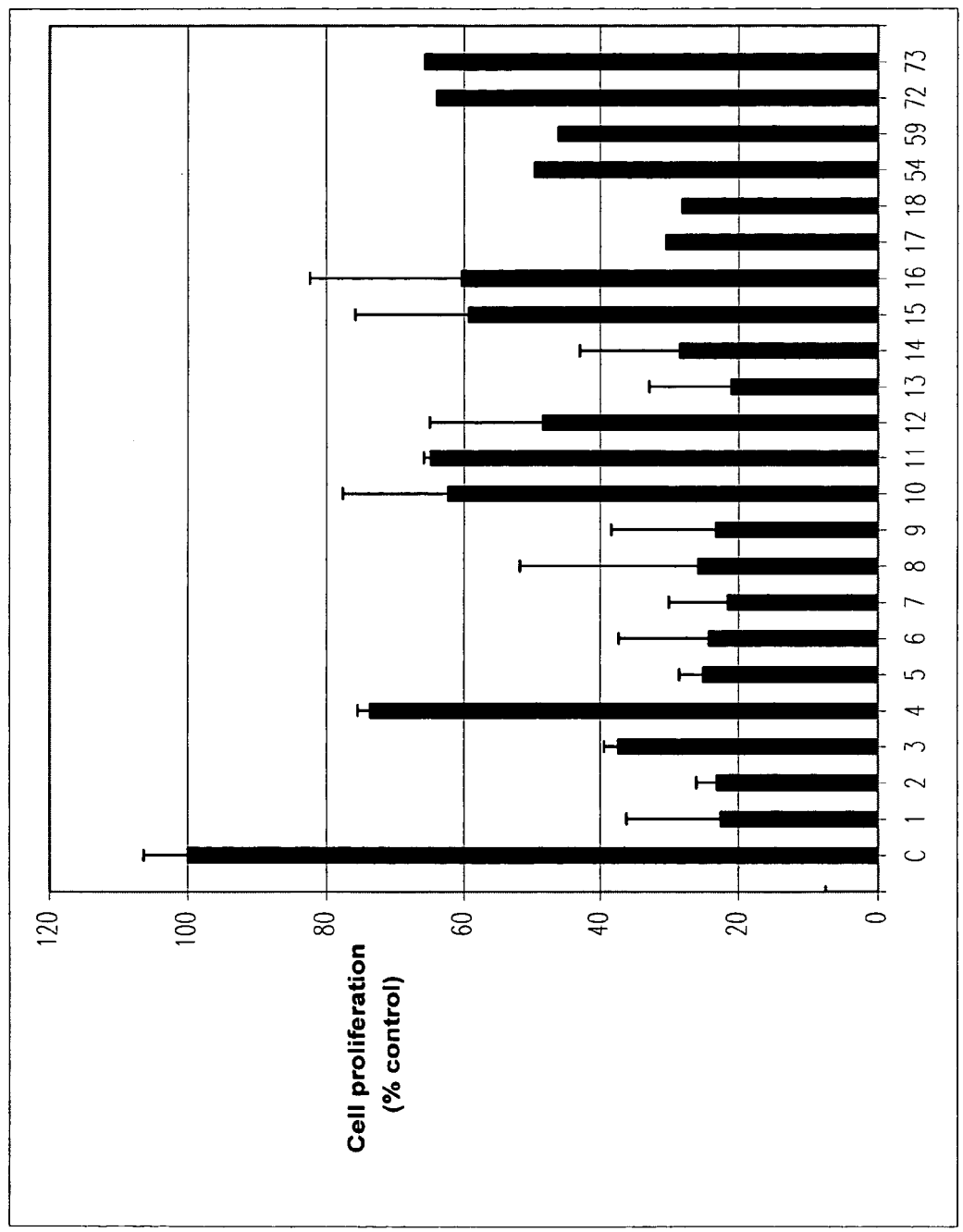
FIG. 53. Chart showing the effects of compounds in an assay where glycated human serum albumin (G-HSA) induces IL-6 production.
Figure 54:
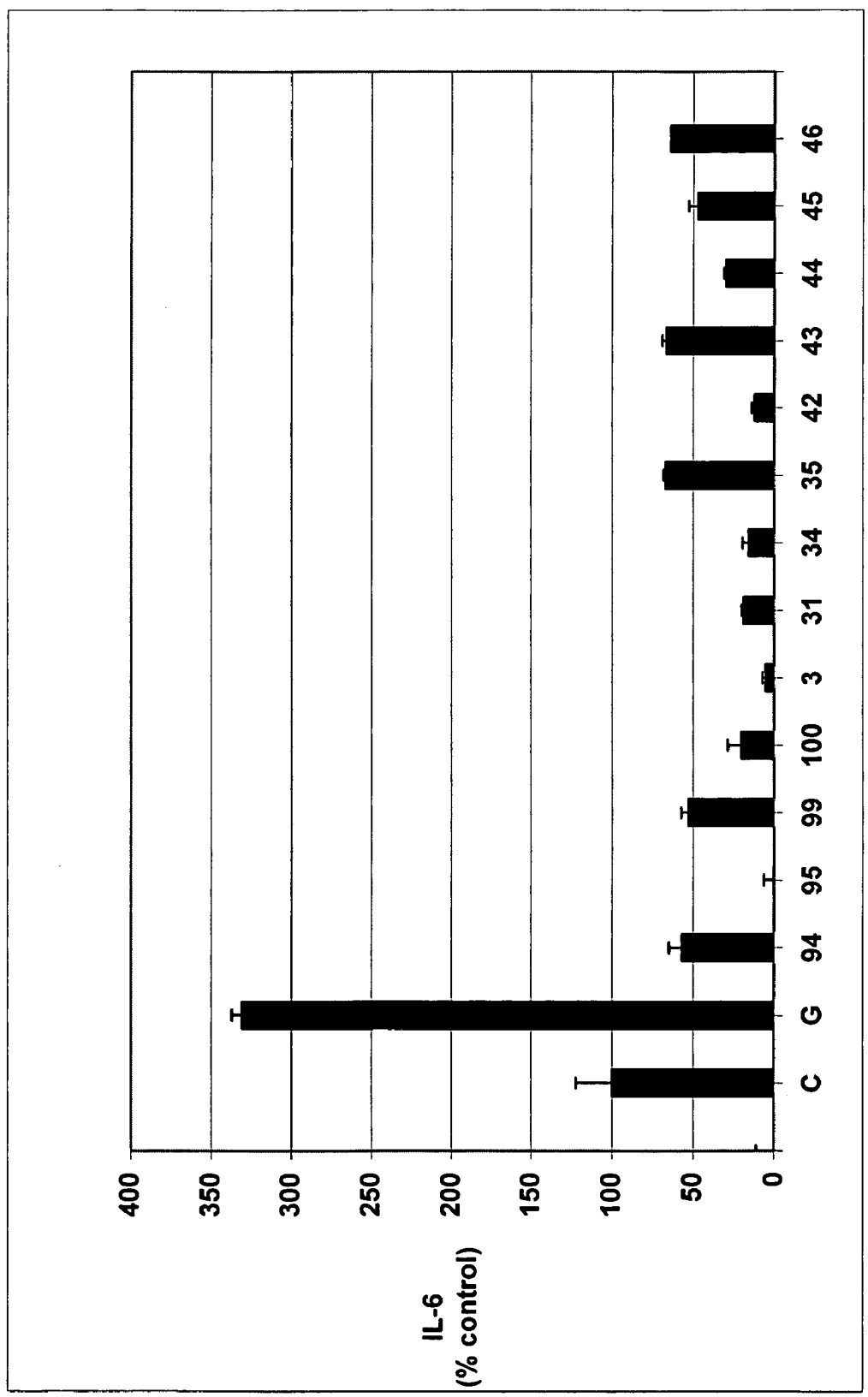
FIG. 54. Chart showing the effects of compounds in an antiproliferative assay.
Figure 55:
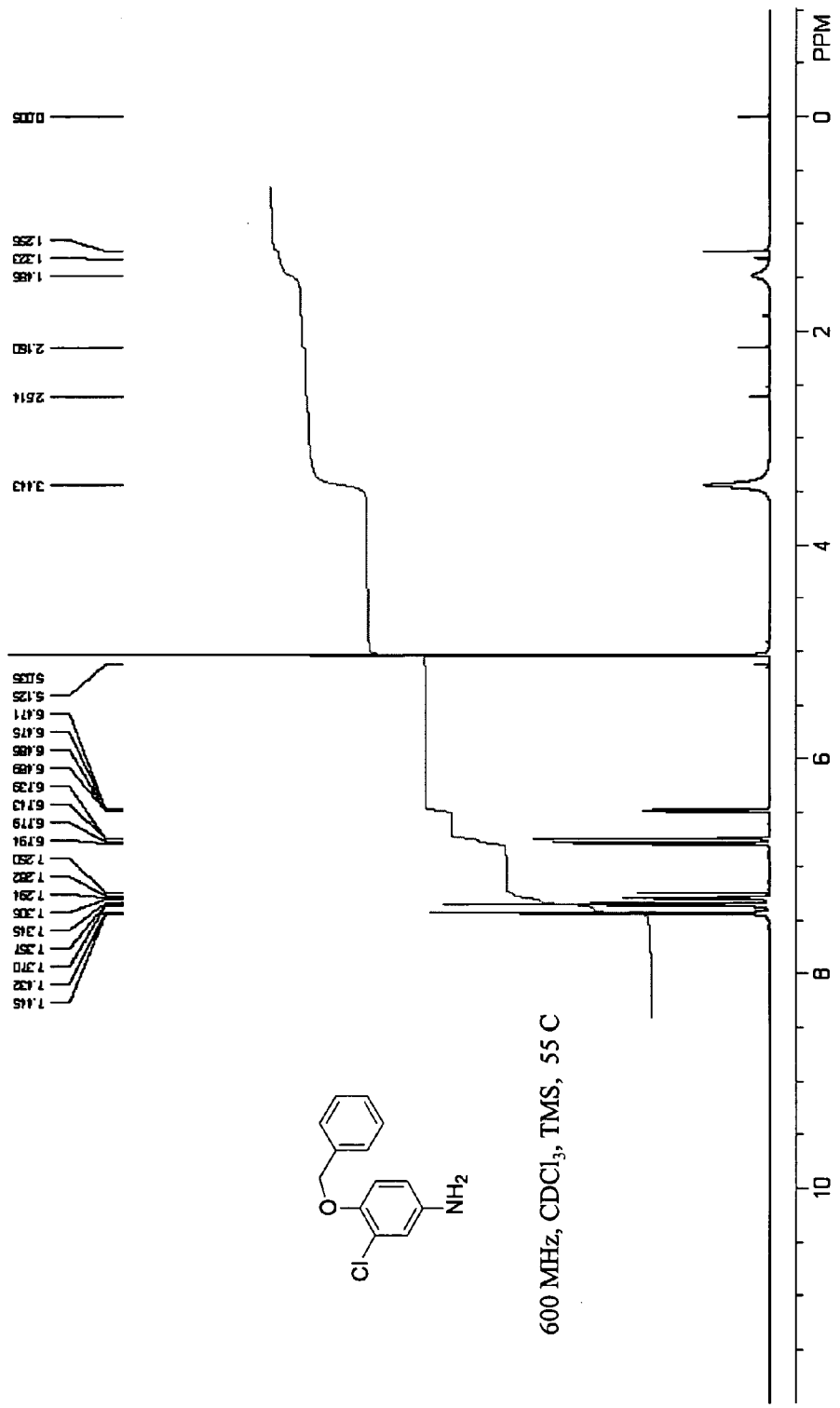
FIG. 55. ¹H NMR of 4-benzyloxy-3-chloro-phenylamine.
Figure 56:
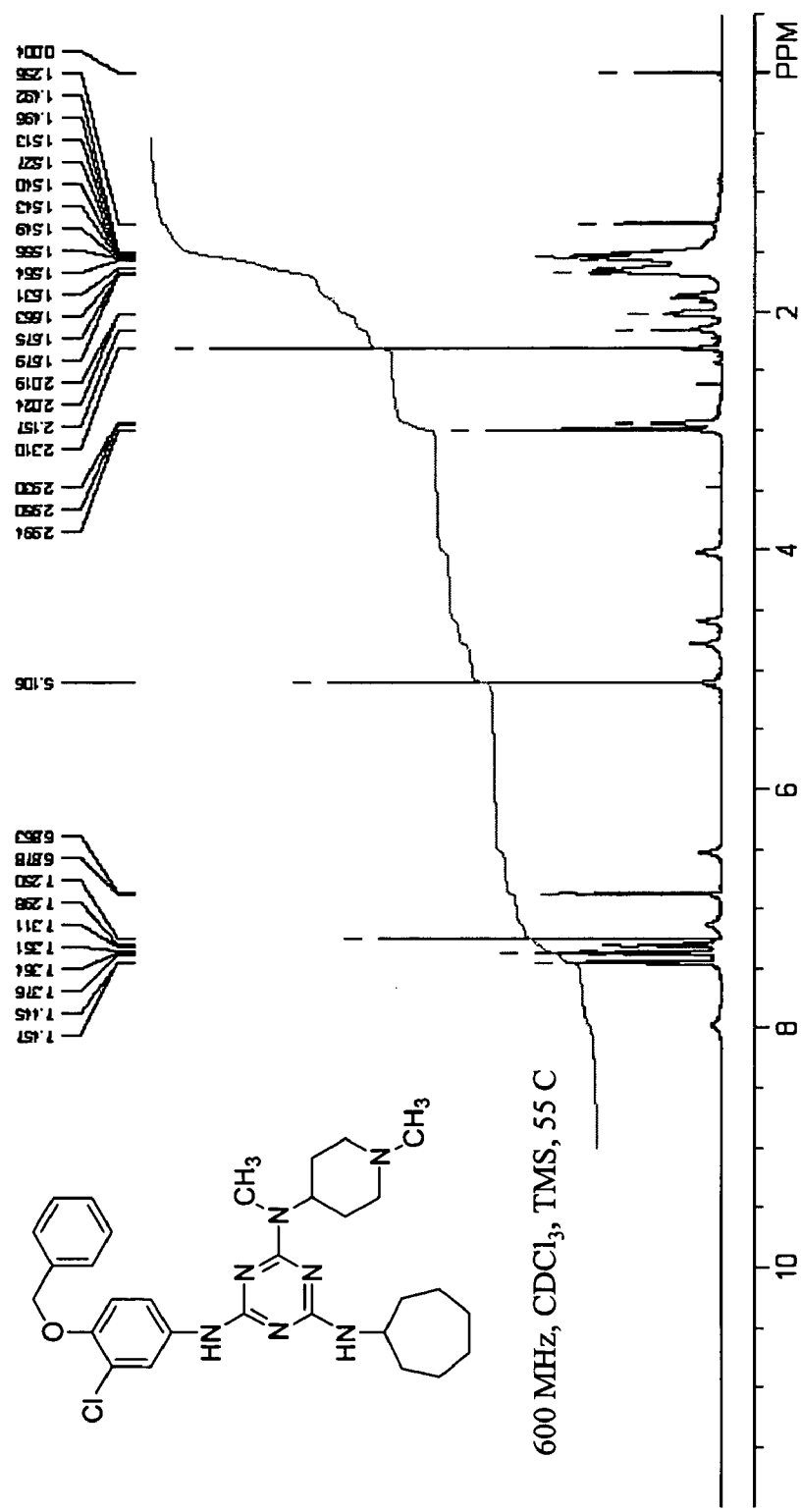
FIG. 56. ¹H NMR of N-(4-benzyloxy-3-chloro-phenyl)-N'-cycloheptyl-N''-methyl-N''-(1-methyl-piperidin-4-yl)-[1,3,5]triazine-2,4,6-triamine.
Figure 57:
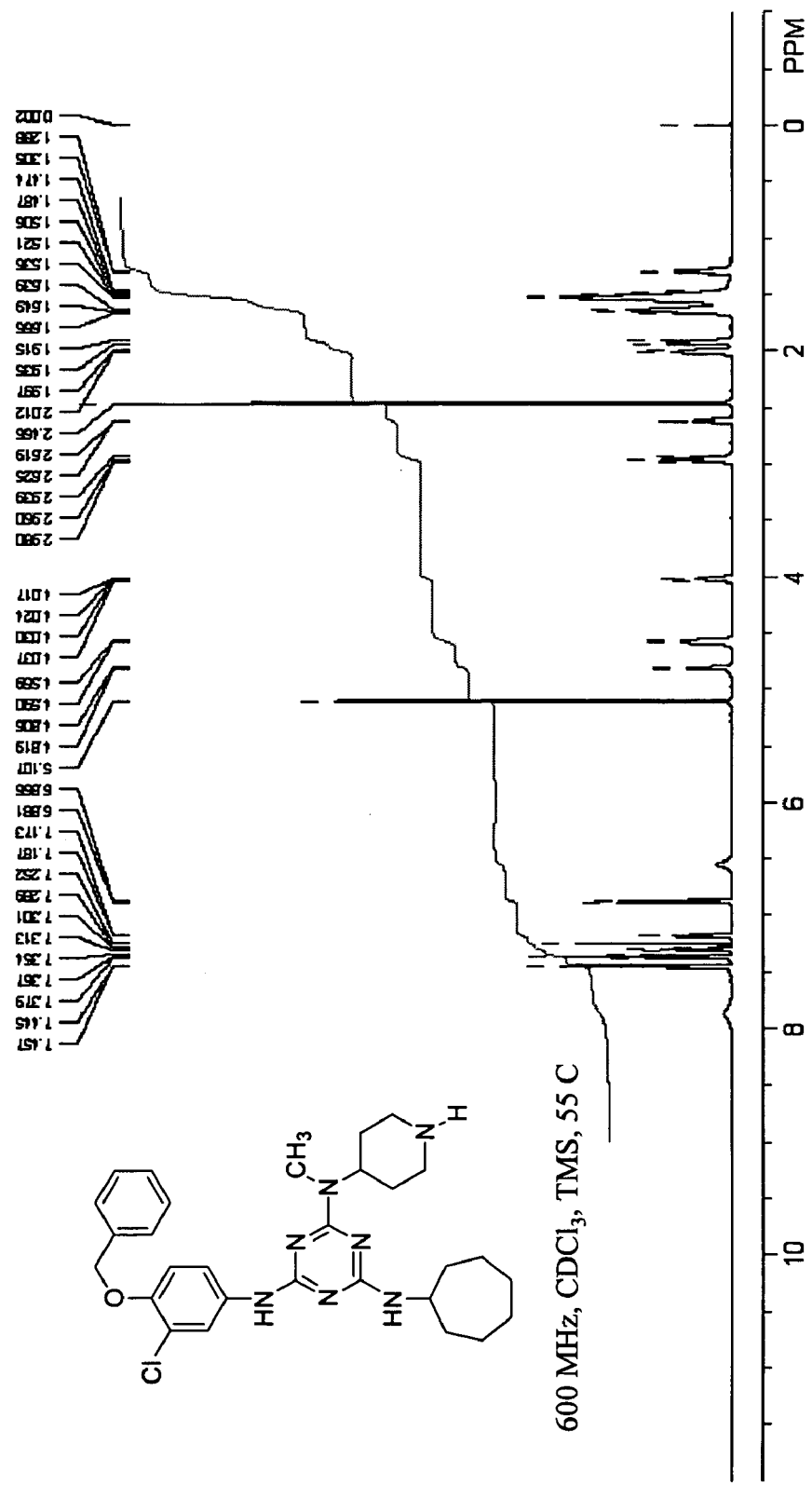
FIG. 57. ¹H NMR of N-(4-benzyloxy-3-chloro-phenyl)-N'-cycloheptyl-N''-methyl-N''-piperidin-4-yl)-[1,3,5]triazine-2,4,6-triamine.
Figure 58:
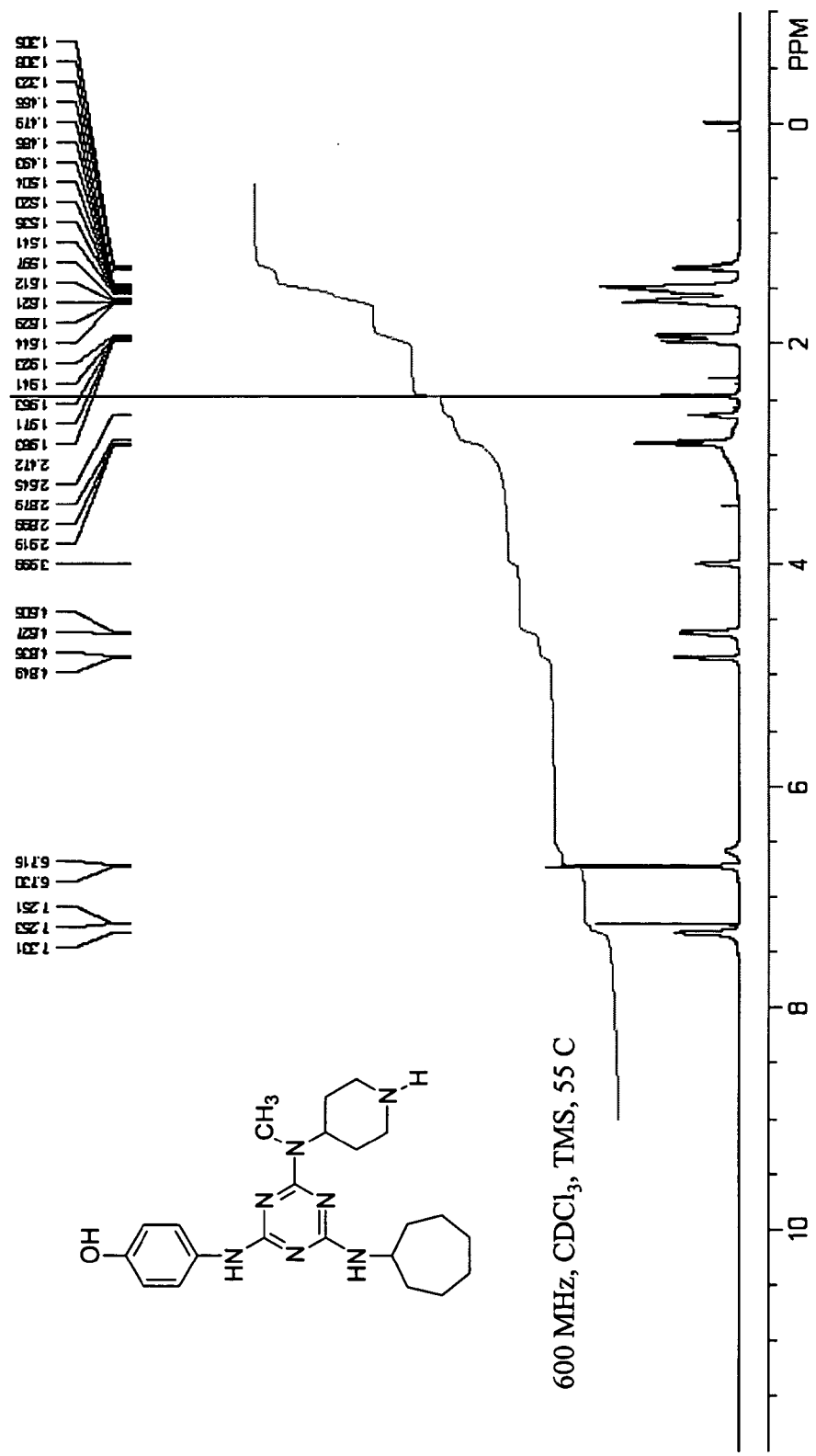
FIG. 58. ¹H NMR of 4-[4-cycloheptylamino-6-(methyl-piperidin-4-yl-amino)-[1,3,5]triazin-2-ylamino]-phenyl.
Figure 59:
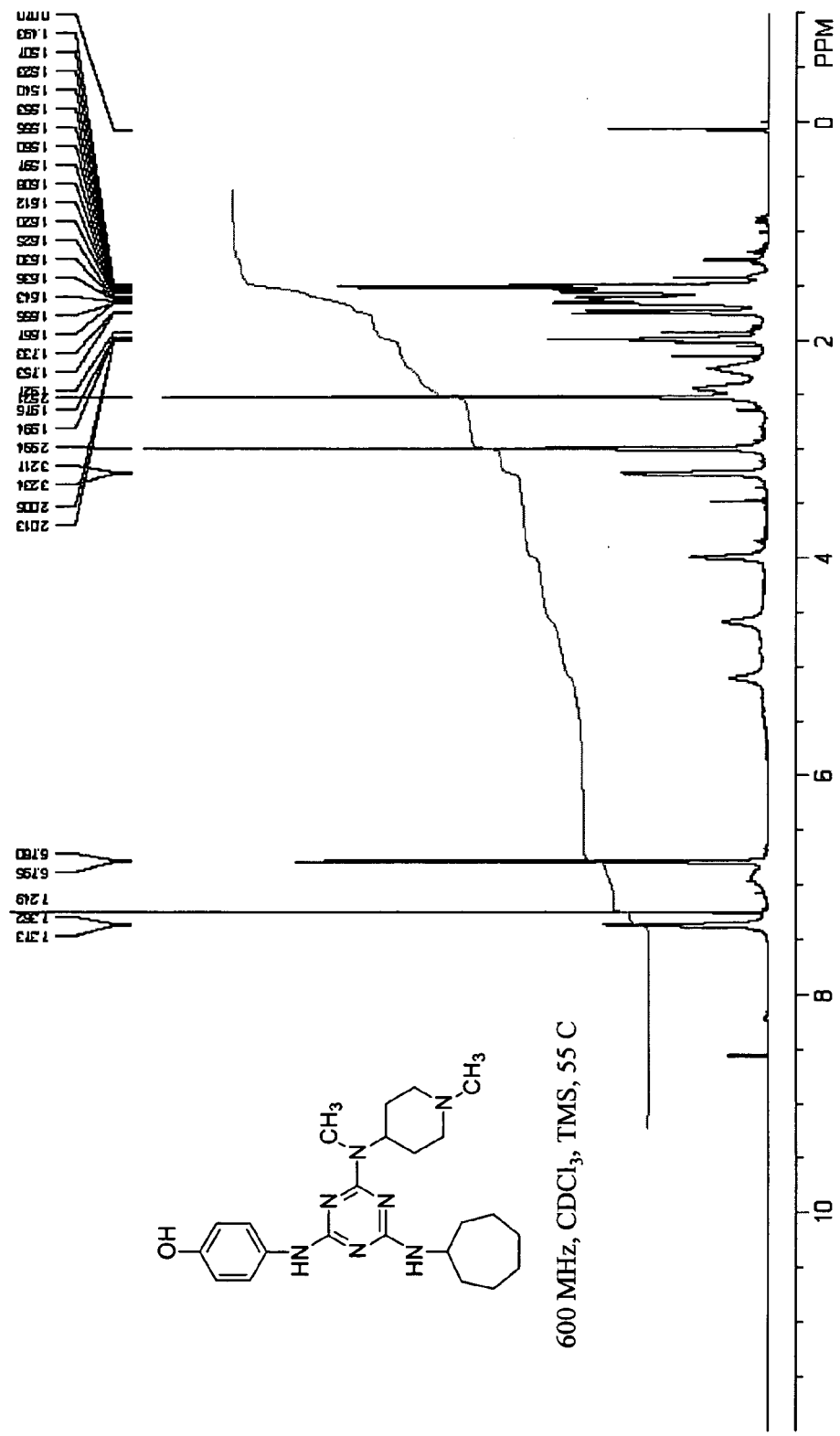
FIG. 59. ¹H NMR of 4-{4-cycloheptylamino-6-[methyl-(1-methyl-piperidin-4-yl)-amino]-[1,3,5-triazin-2-ylamino}-phenyl.
Figure 60:
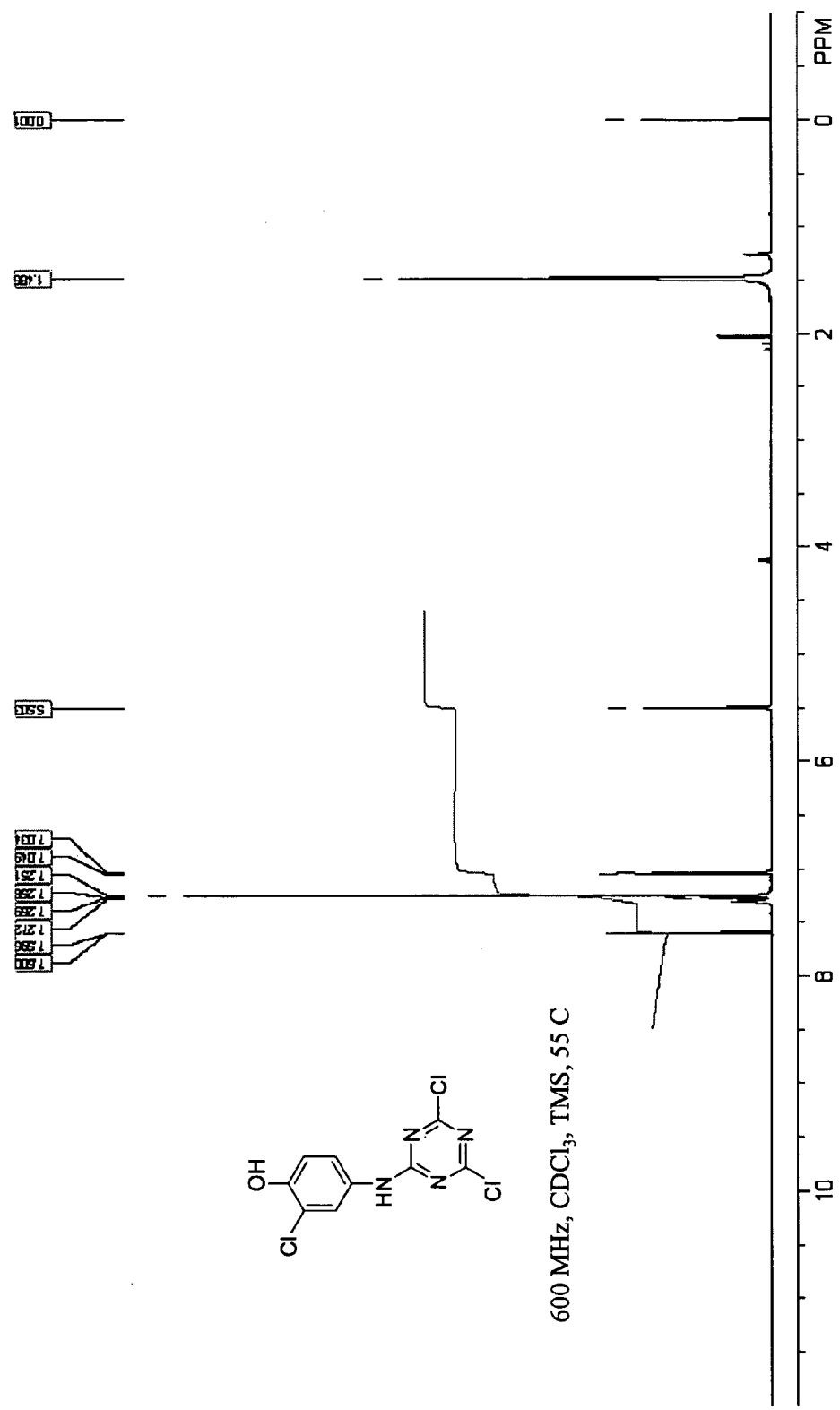
FIG. 60. ¹H NMR of 2-Chloro-4-(4,6-dichloro-[1,3,5]triazin-2-ylamino)-phenyl.
Figure 61:
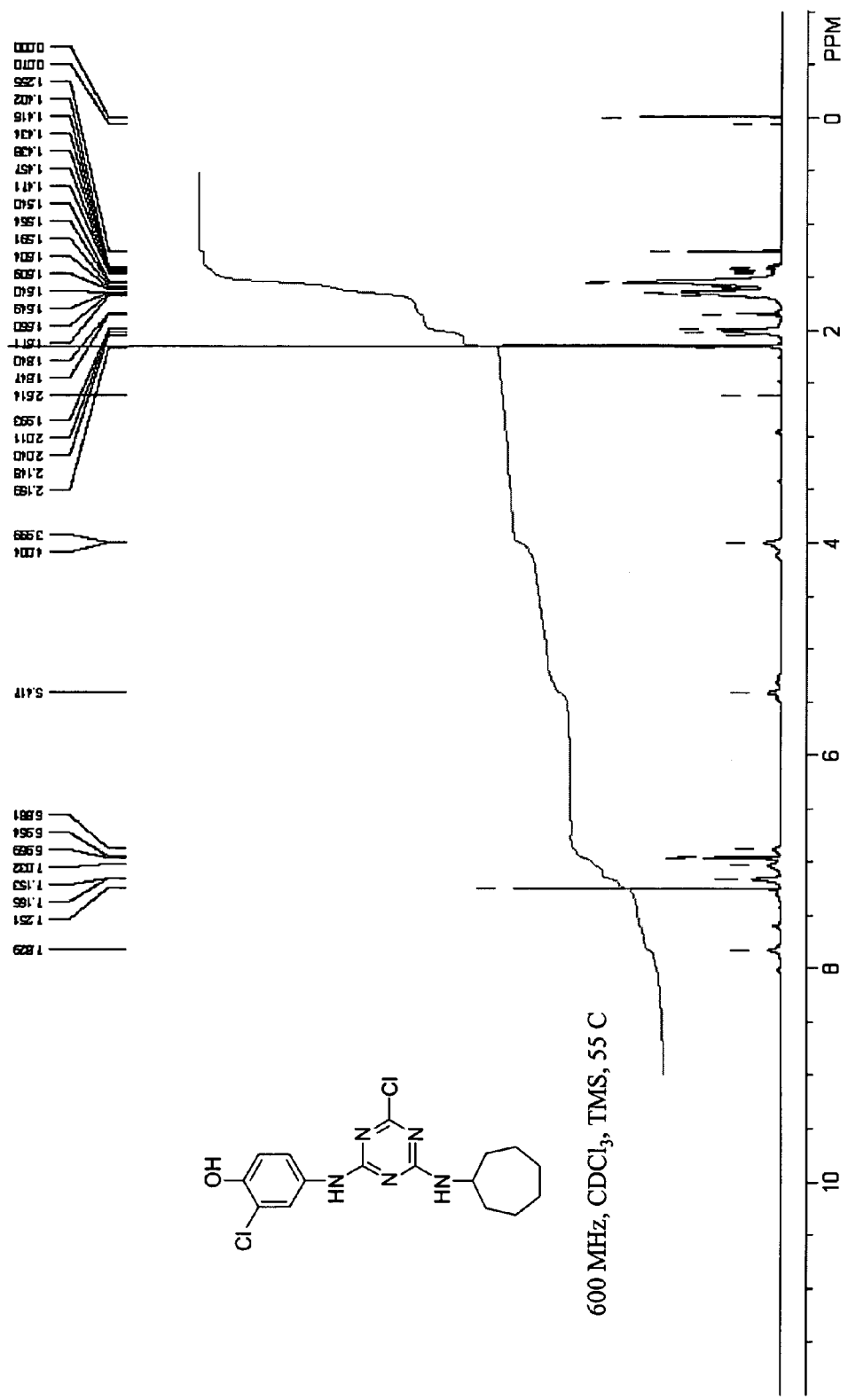
FIG. 61. ¹H NMR of 2-Chloro-4-(4-chloro-6-cycloheptylamino-[1,3,5]triazin-2-ylamino)-phenyl.
Figure 62:
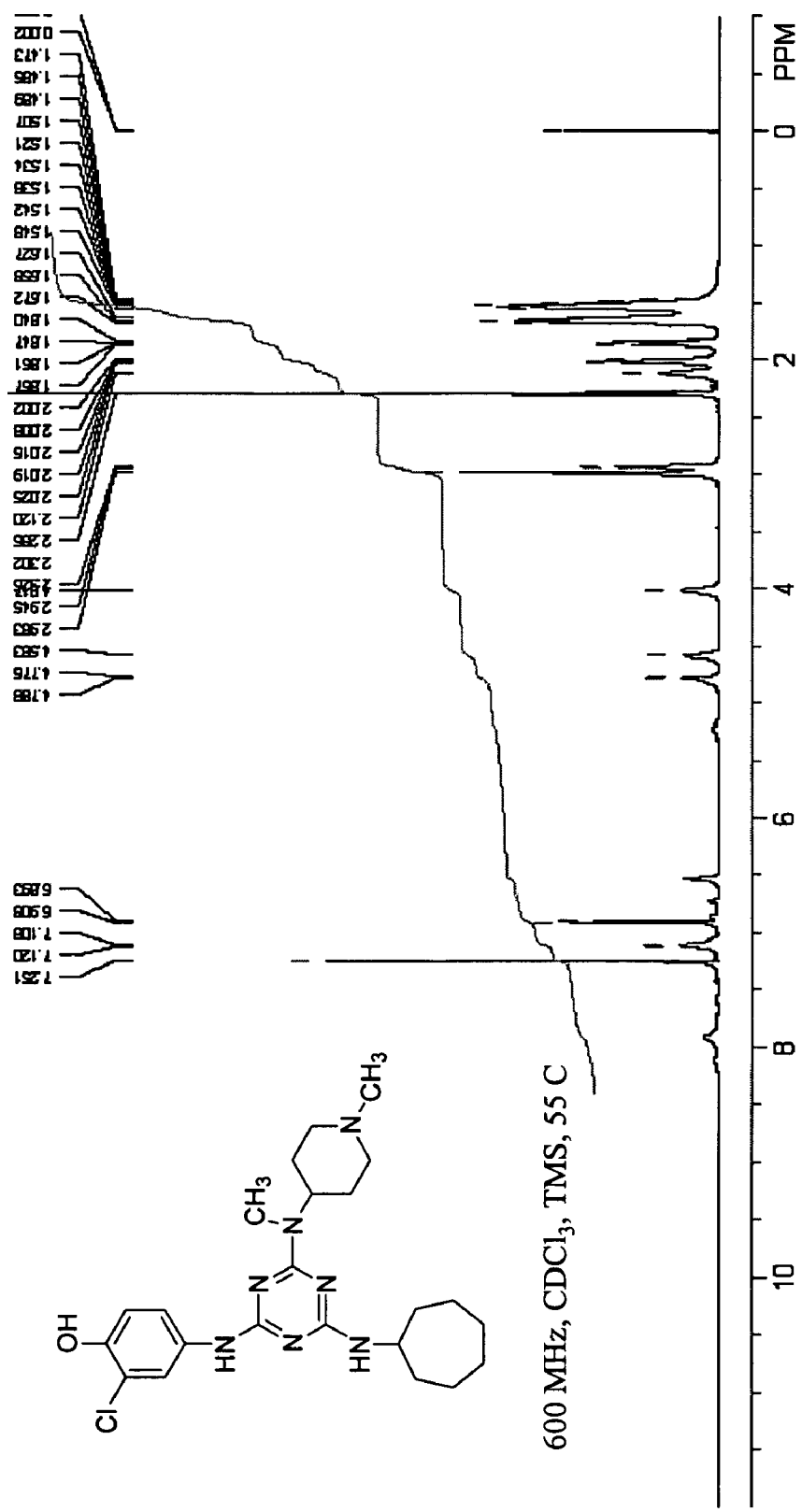
FIG. 62. ¹H NMR of 2-Chloro-4-{4-cycloheptylamino-6-[methyl-(1-methyl-piperidin-4-yl)-amino]-[1,3,5]triazin-2-ylamino}-phenyl.
Figure 63:
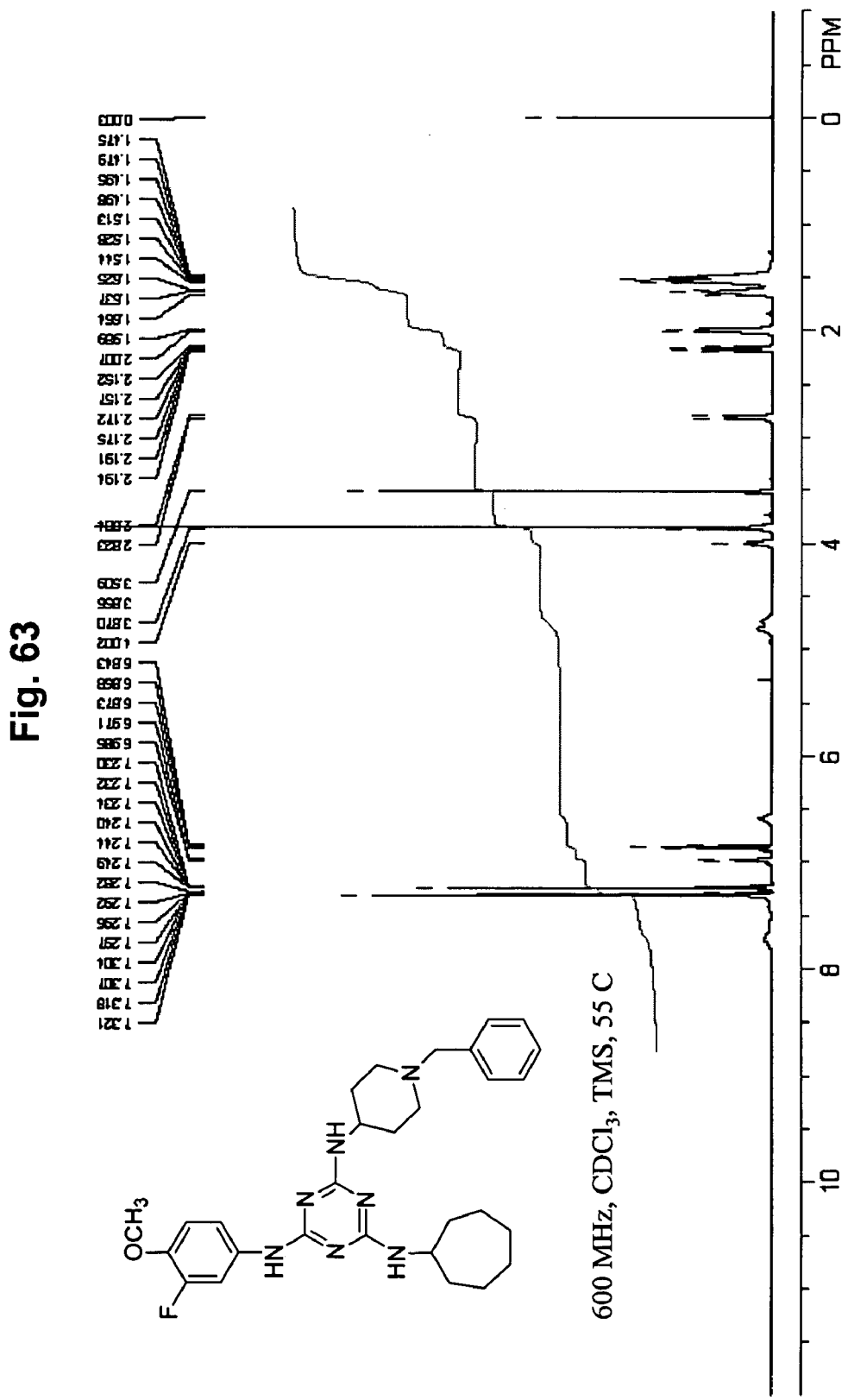
FIG. 63. ¹H NMR of N-(1-Benzyl-piperidin-4-yl)-N'-(3-fluoro-4-methoxy-phenyl)-N''-cycloheptyl-[1,3,5]triazine-2,4,6-diamine.
Figure 64:
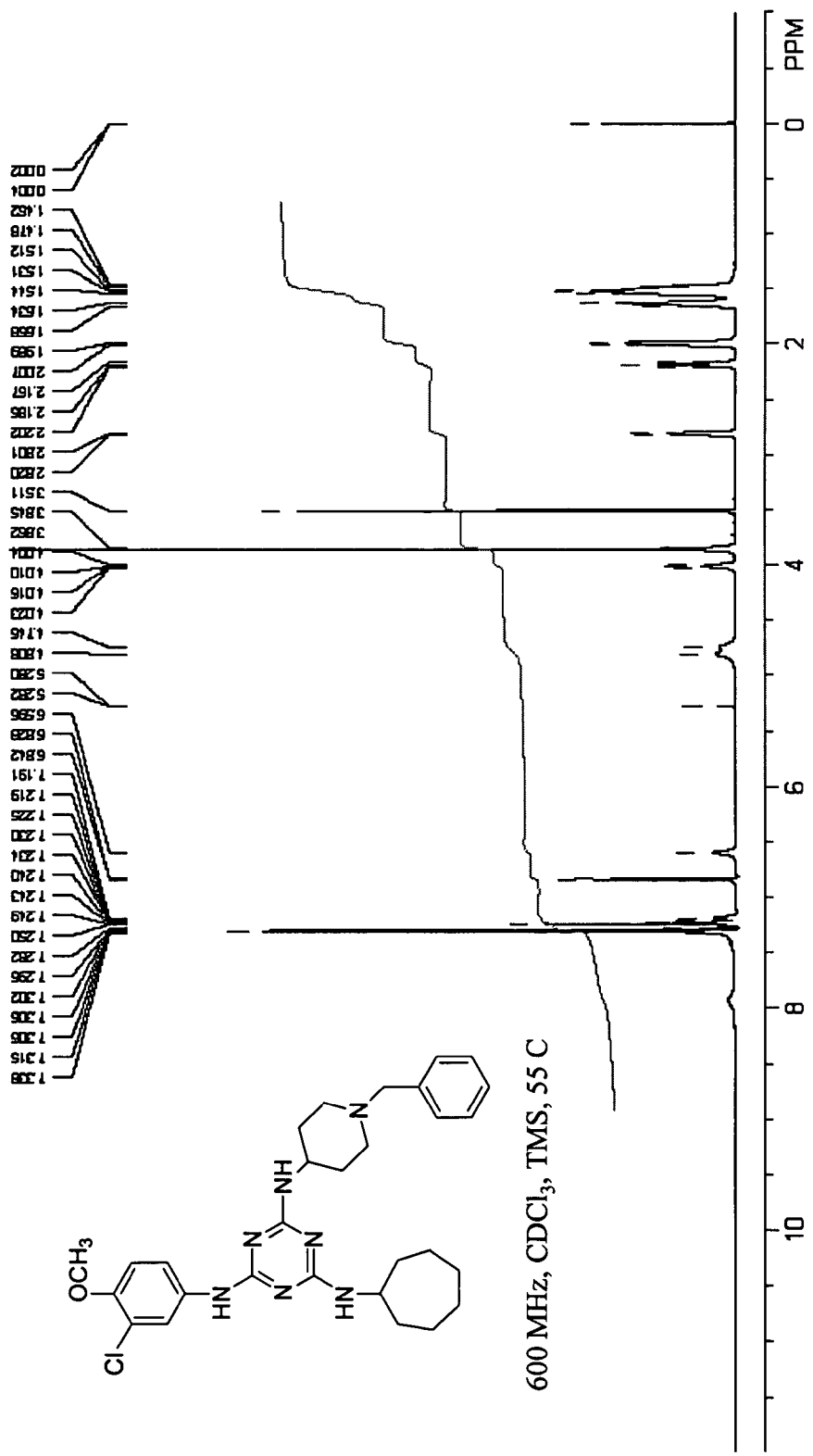
FIG. 64. ¹H NMR of N-(1-Benzyl-piperidin-4-yl)-N'-(3-chloro-4-methoxy-phenyl)-N''-cycloheptyl-[1,3,5]triazine-2,4,6-diamine.
Figure 65:
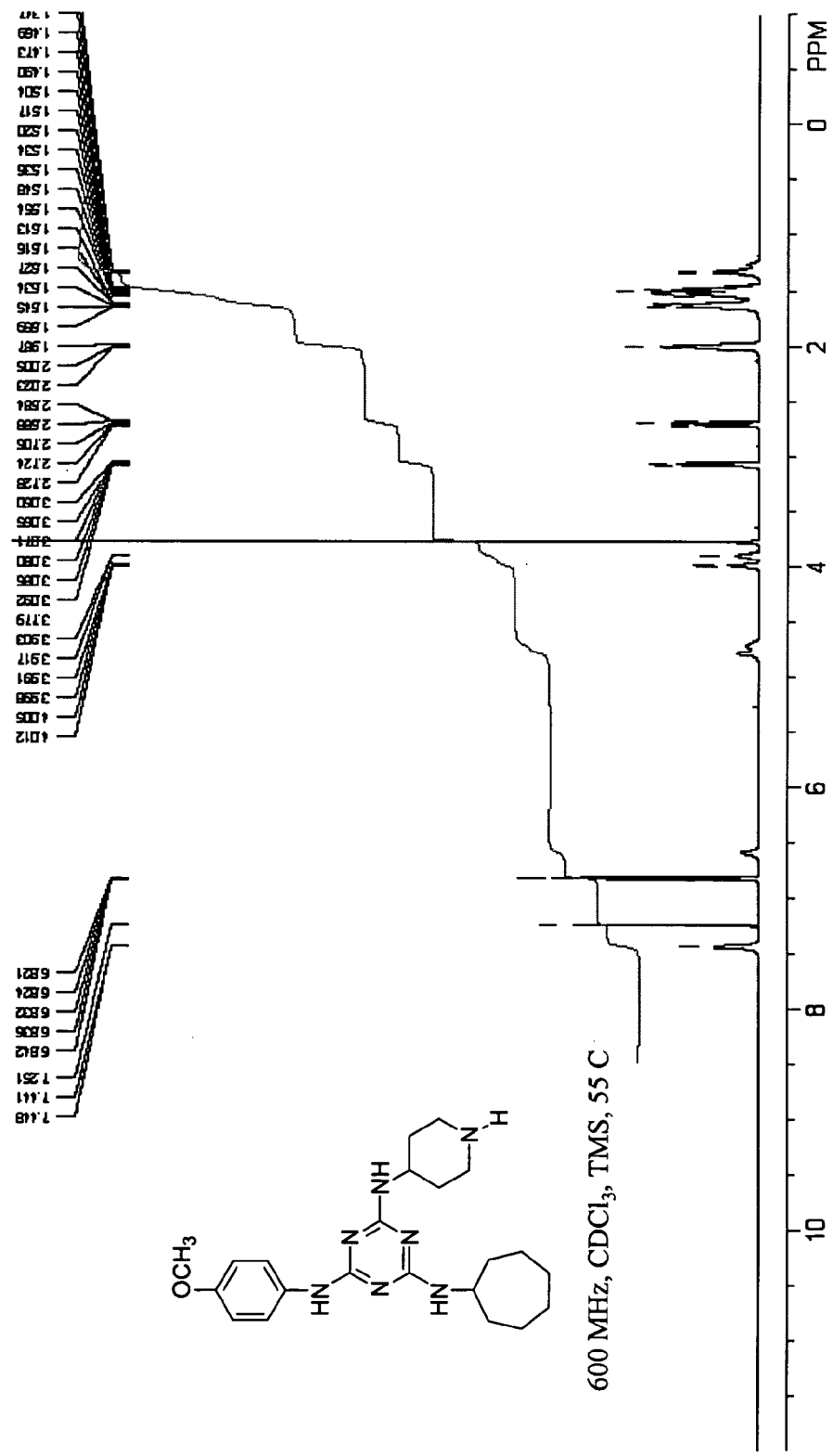
FIG. 65. ¹H NMR of N-Cycloheptyl-N'-(4-methoxy-phenyl)-N''-piperidin-4-yl-[1,3,5]triazine-2,4,6-triamine.
Figure 66:
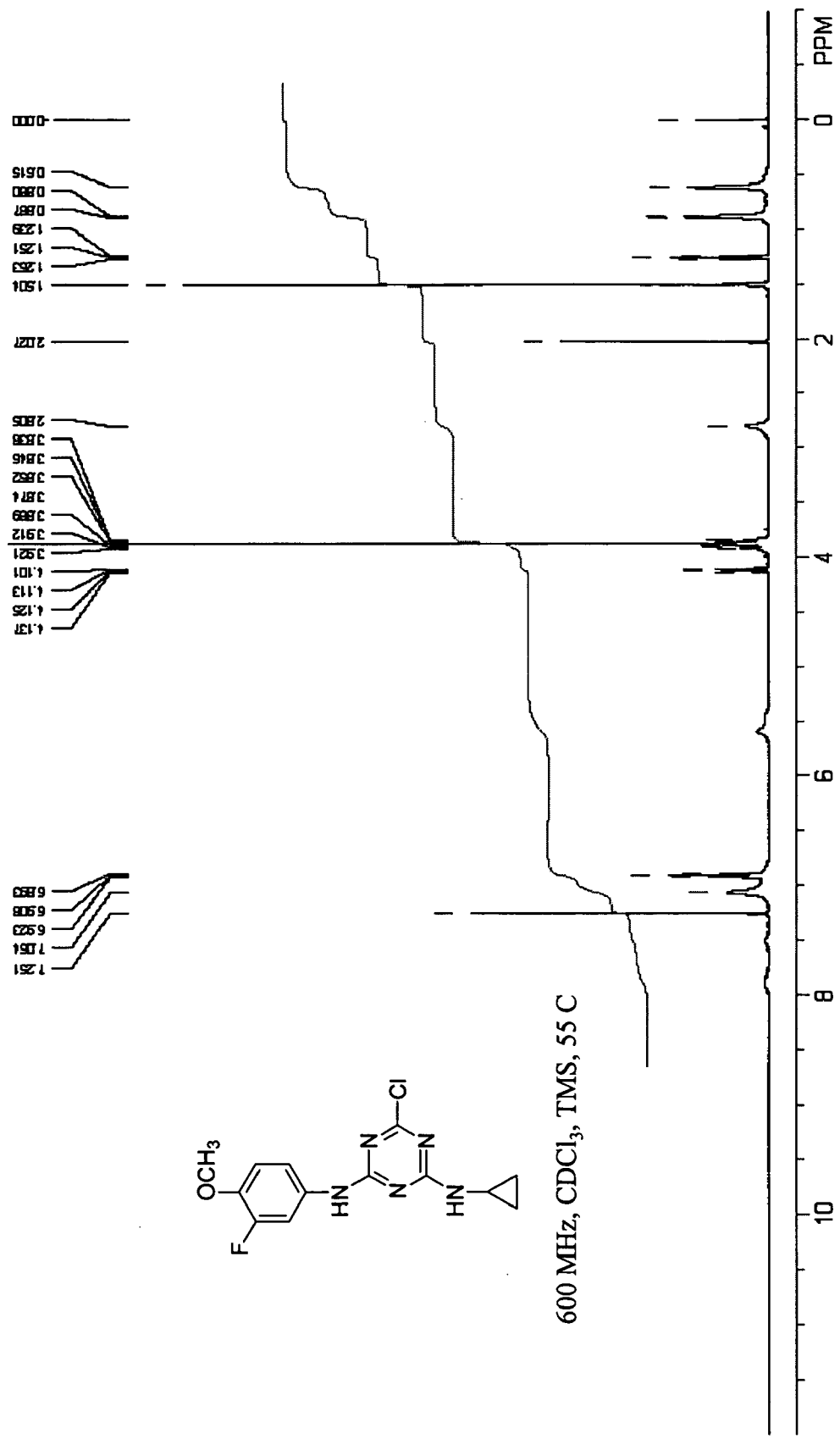
FIG. 66. ¹H NMR of 6-Chloro-N-cyclopropyl-N'-(3-fluoro-4-methoxy-phenyl)-[1,3,5]triazine-2,4-diamine.
Figure 67:
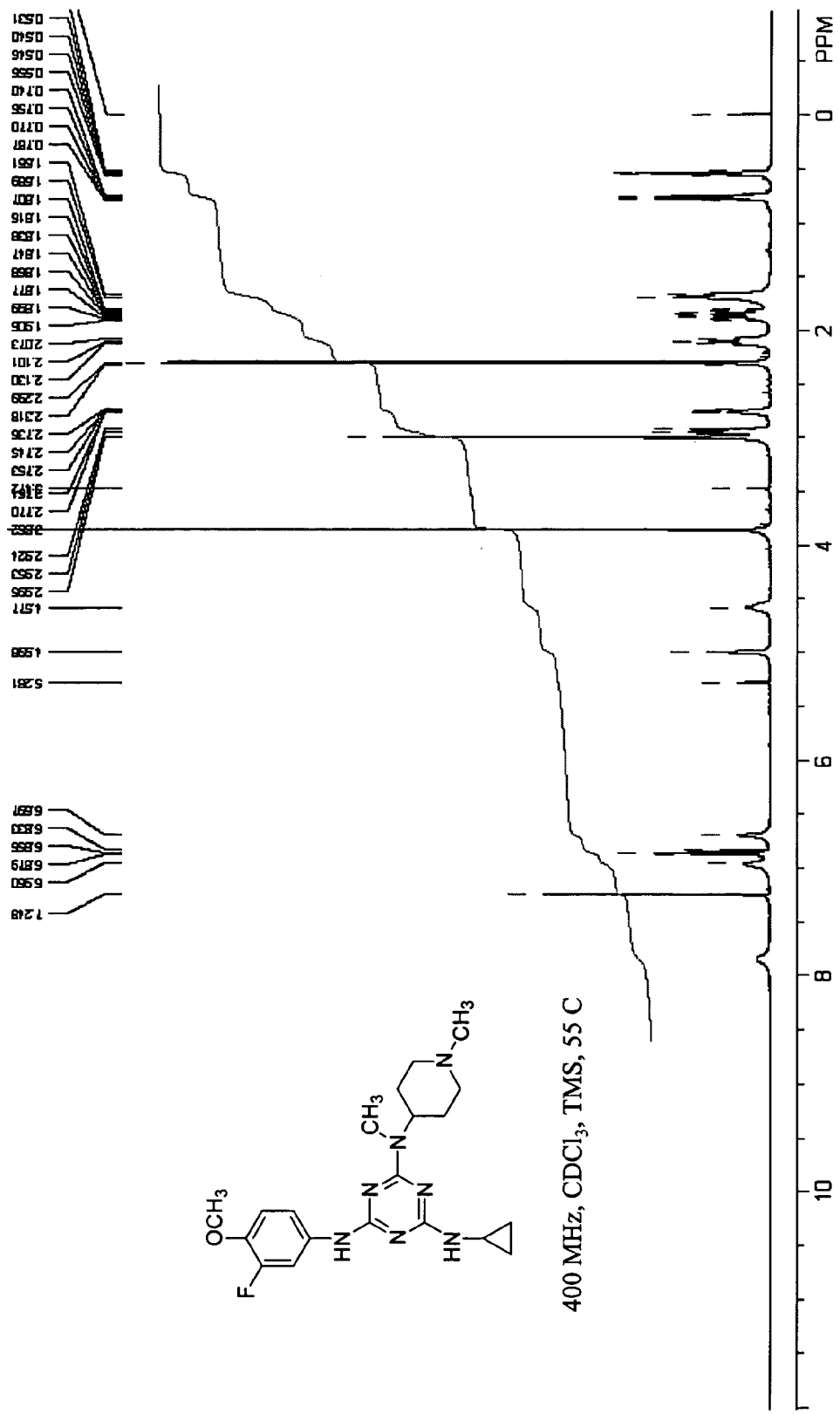
FIG. 67. ¹H NMR of N-Cyclopropyl-N'-(3-flouro-4-methoxy-phenyl)-N"-methyl-N"-(1-methyl-piperidin-4-yl)-[1,3,5]triazine-2,4,6-triamine.
Figure 68:
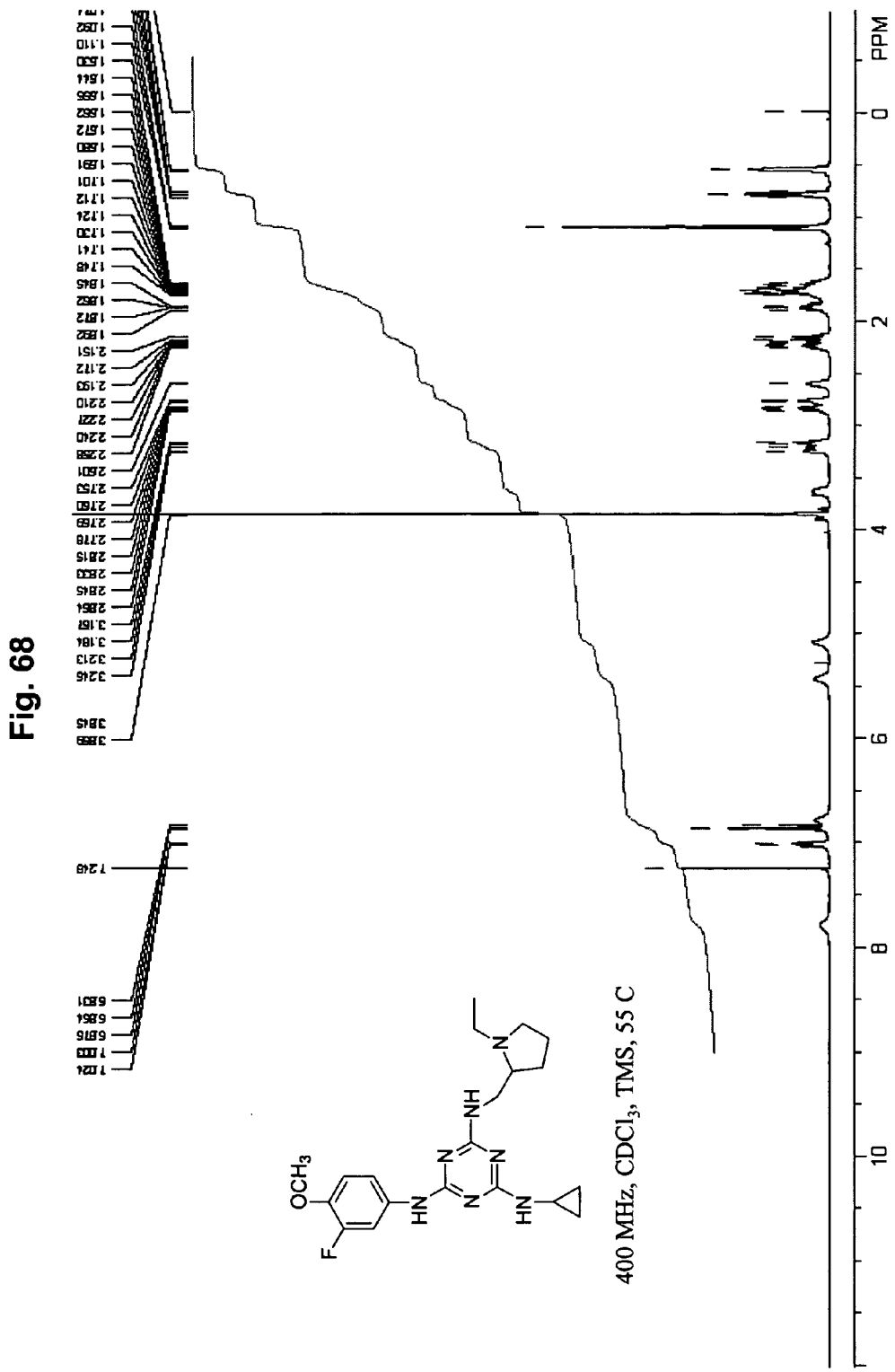
FIG. 68. ¹H NMR of N-Cyclopropyl-N'-(1-ethyl-pyrrolidin-2-ylmethyl)-N"-(3-fluoro-4-methoxy-phenyl)-[1,3,5]triazine-2,4,6-triamine.
Figure 69:
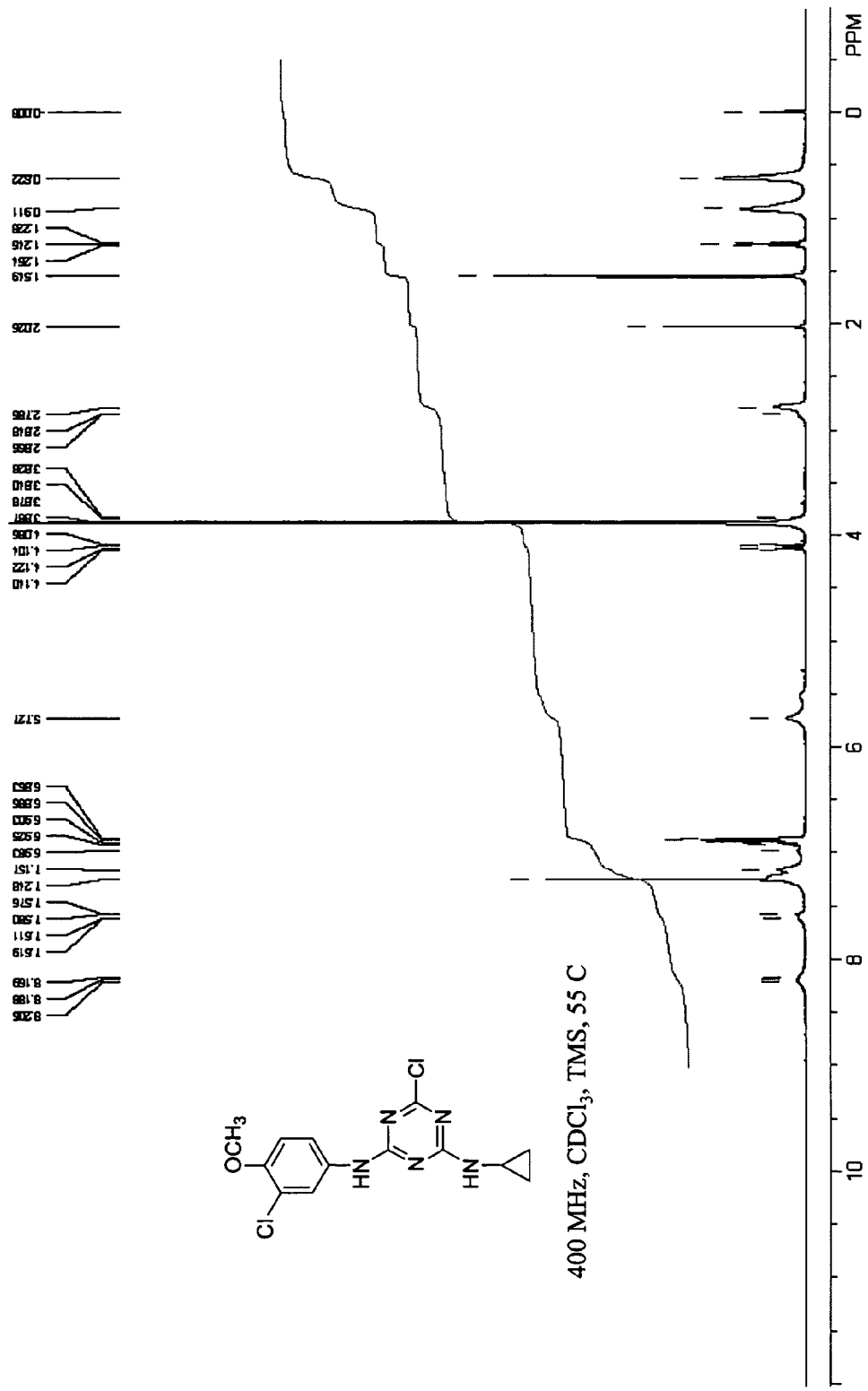
FIG. 69. ¹H NMR of 6-Chloro-N'-(3-chloro-4-methoxy-phenyl)-N'-cyclopropyl-[1,3,5]triazine-2,4-diamine.
Figure 70:
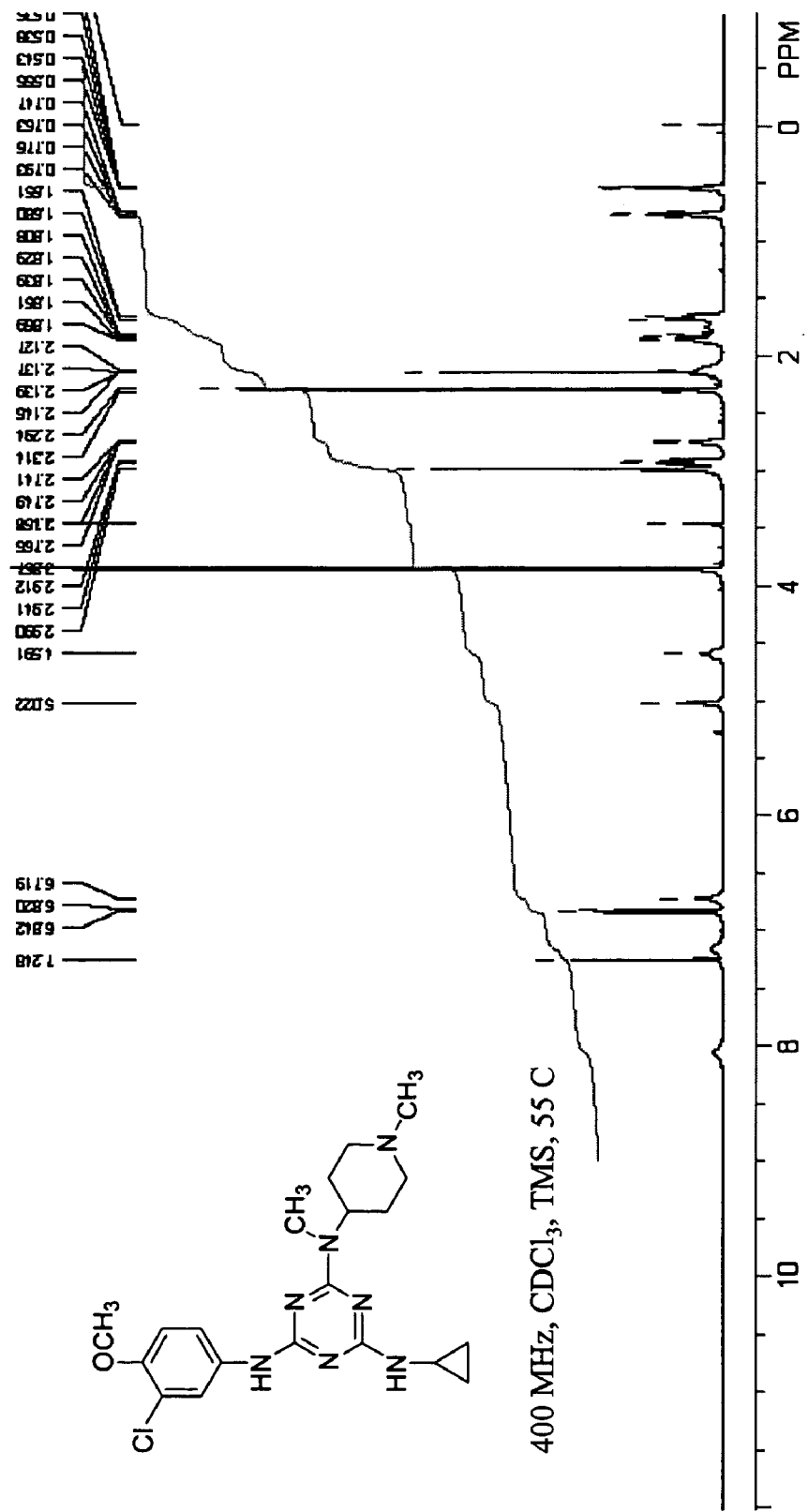
FIG. 70. ¹H NMR of N-Cyclopropyl-N'-(3-chloro-4-methoxy-phenyl)-N"-methyl-"N-(1-methyl-piperidin-4-yl)-[1,3,5]triazine-2,4,6-triamine.
Figure 71:
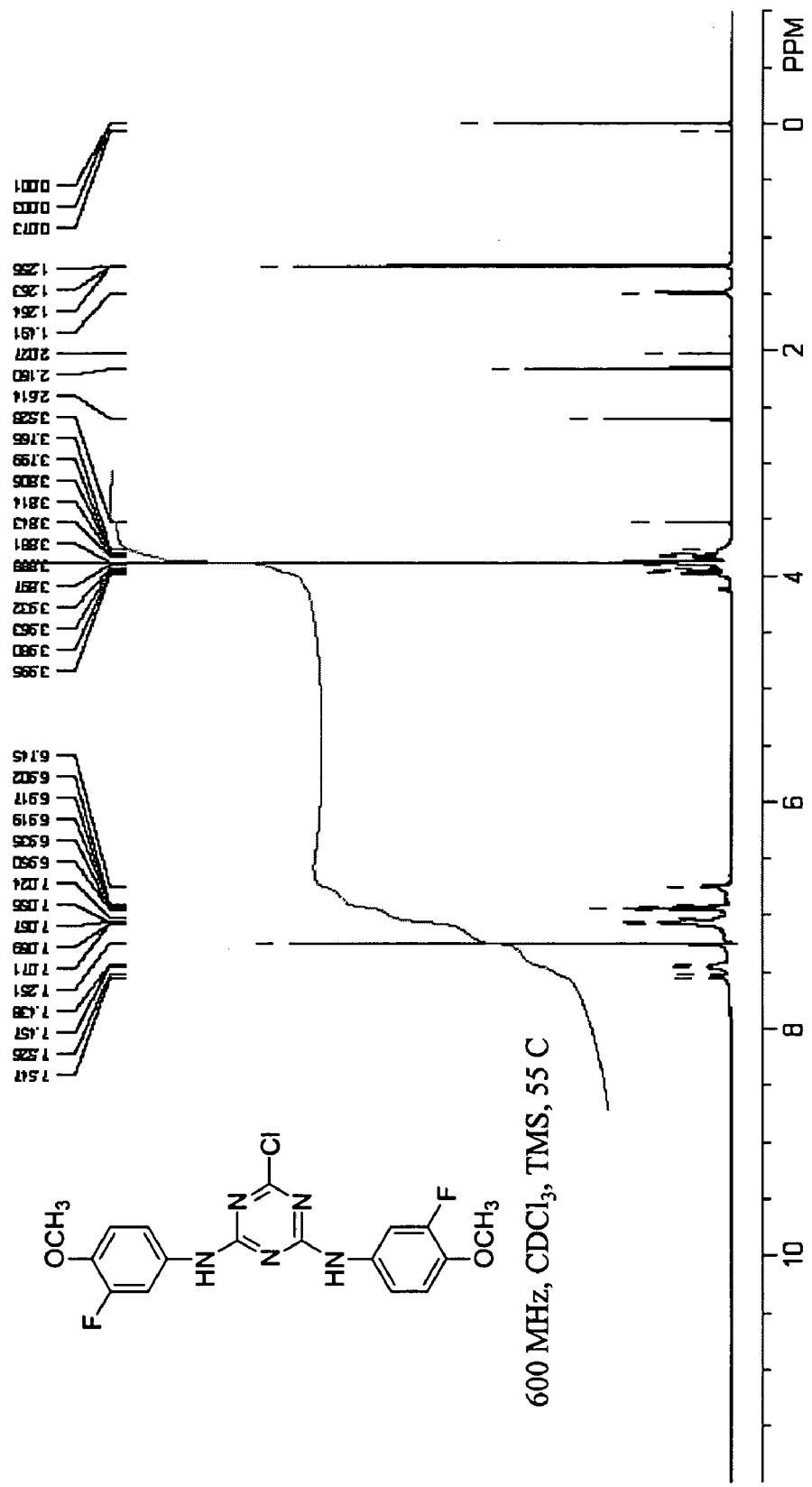
FIG. 71. ¹H NMR of 6-Chloro-N,N'-bis-(3-fluoro-4-methoxy-phenyl)-[1,3,5]triazine-2,4-diamine.
Figure 72:
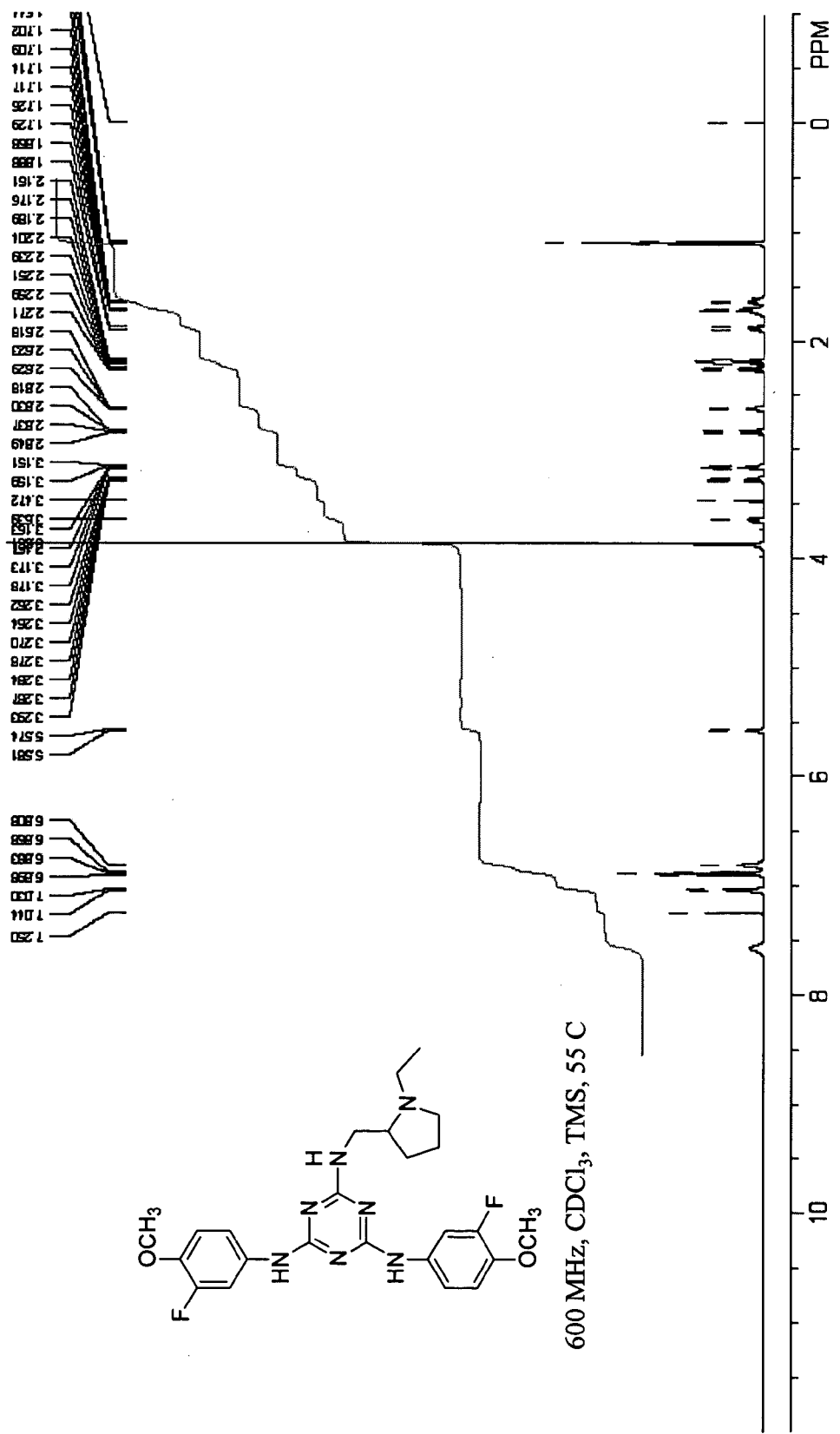
FIG. 72. ¹H NMR of N-(1-Ethyl-pyrrolidin-2-ylmethyl)-N',N"-bis-(3-fluoro-4-methoxy-phenyl)-[1,3,5]triazine-2,4,6-triamine.
Figure 73:
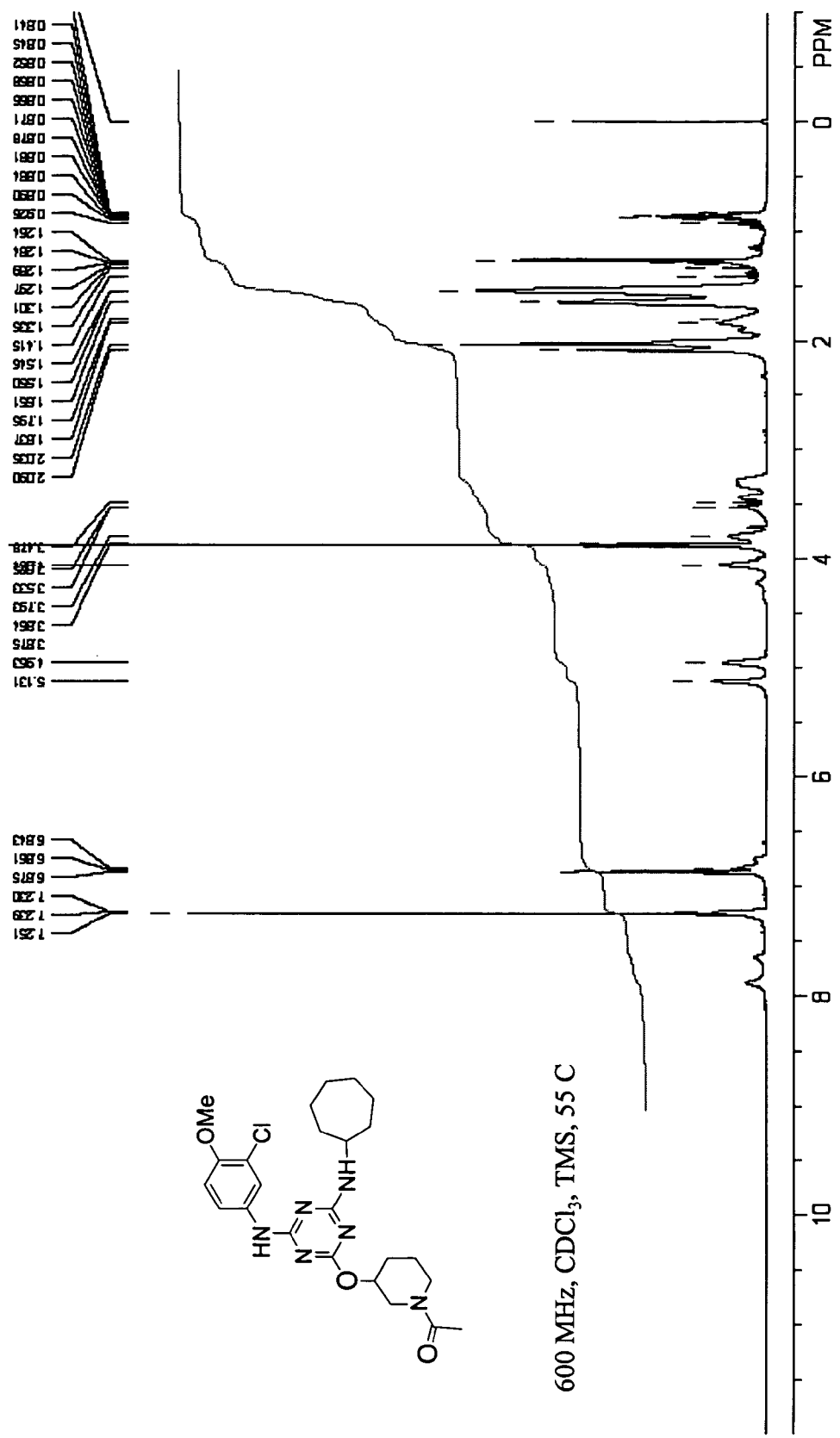
FIG. 73. ¹H NMR of 1-[3-{4-(3-chloro-4-methoxyanilino)-6-cycloheptylamino-1,3,5-triazine-2-yloxy}piperidino]-1-ethanone.
Figure 74:
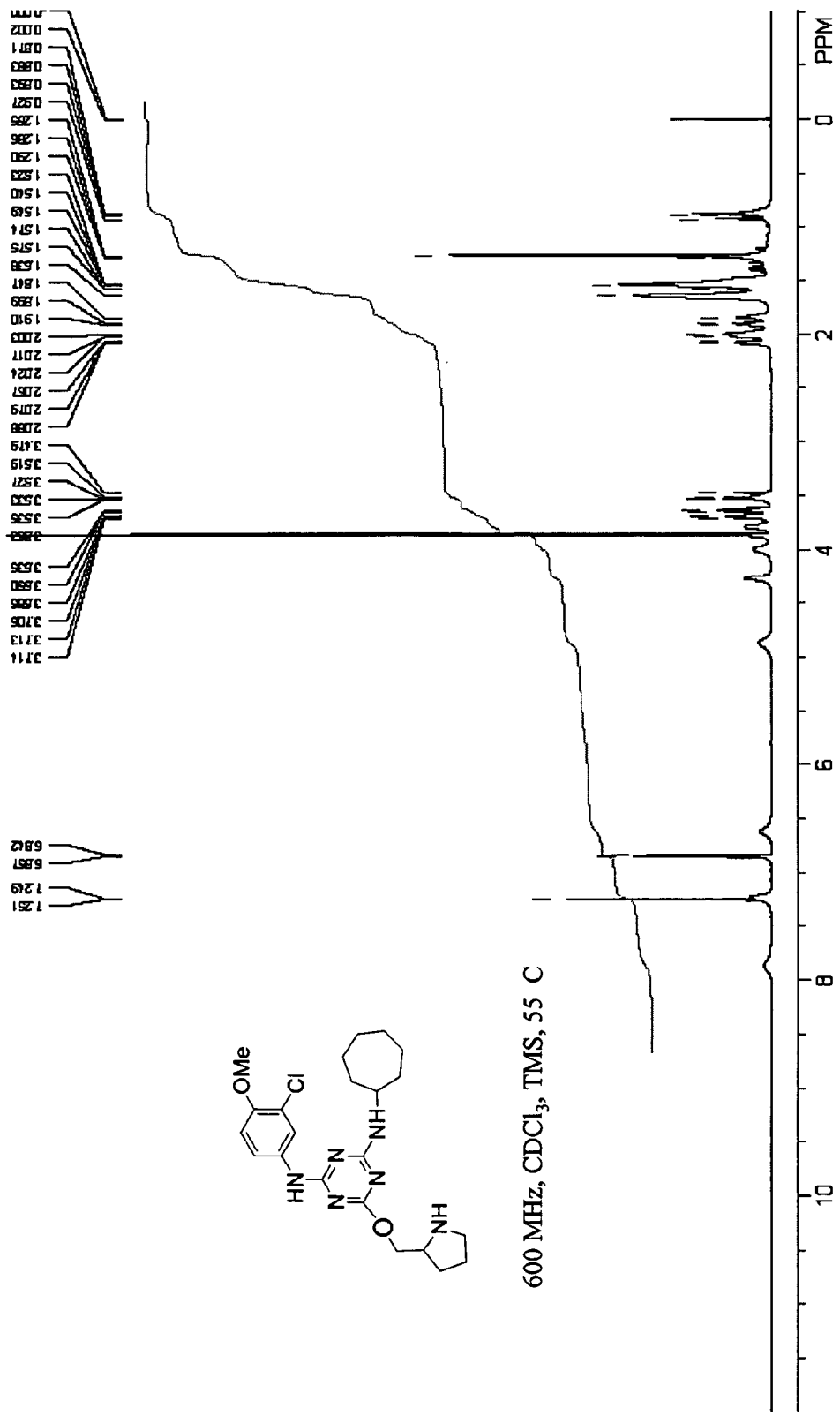
FIG. 74. ¹H NMR of $N^2$-(3-chloro-4-methoxyphenyl)-$N^4$-cycloheptyl-6-(2-azolanylmethoxy)-1,3,5-triazine-2,4-diamine.
Figure 75:
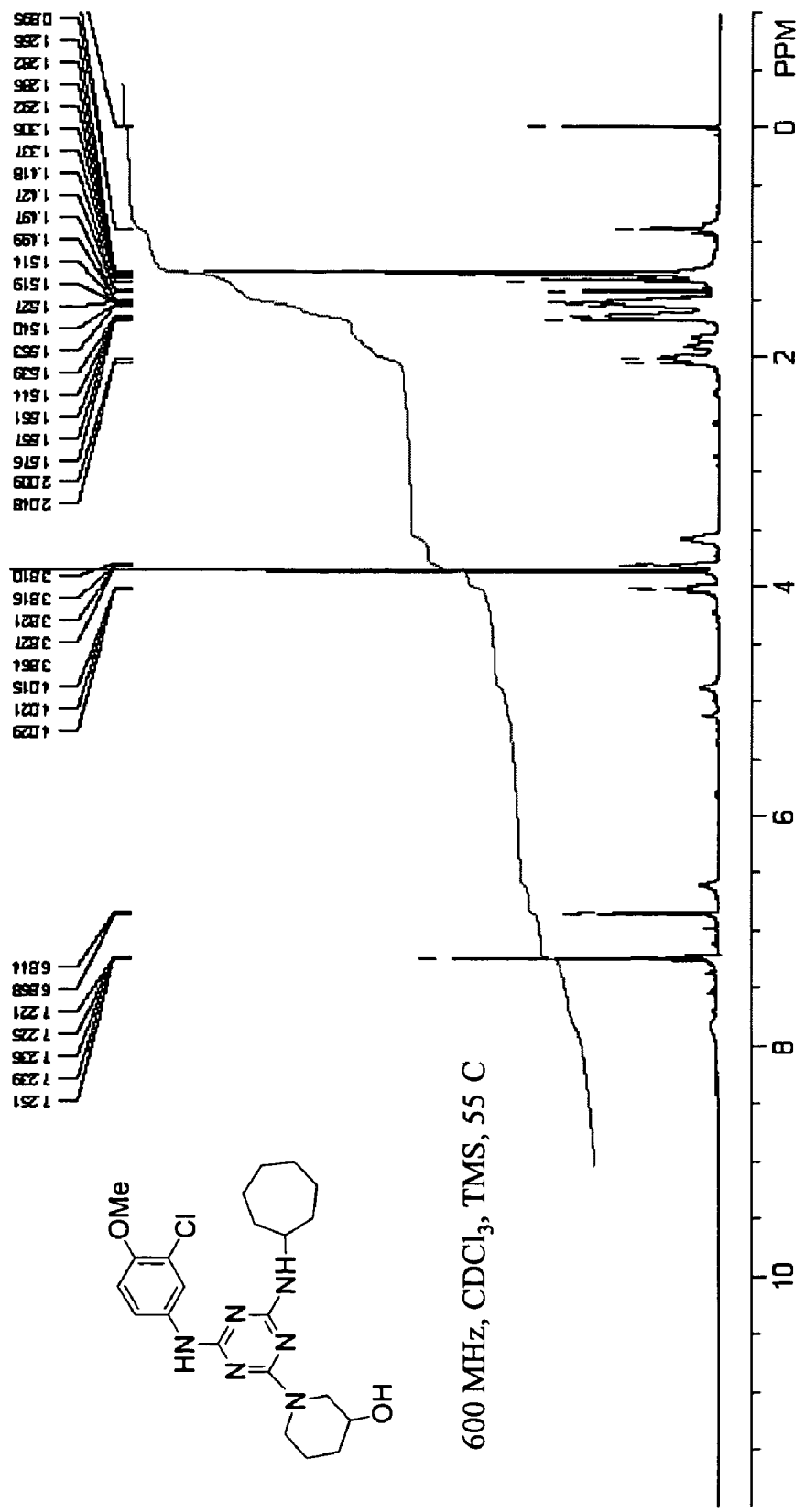
FIG. 75. ¹H NMR of 1-[4-(3-chloro-4-methoxy-phenylamino)-6-cycloheptylamino-[1,3,5]triazine-2-yl]-piperidin-3-ol.
Figure 76:
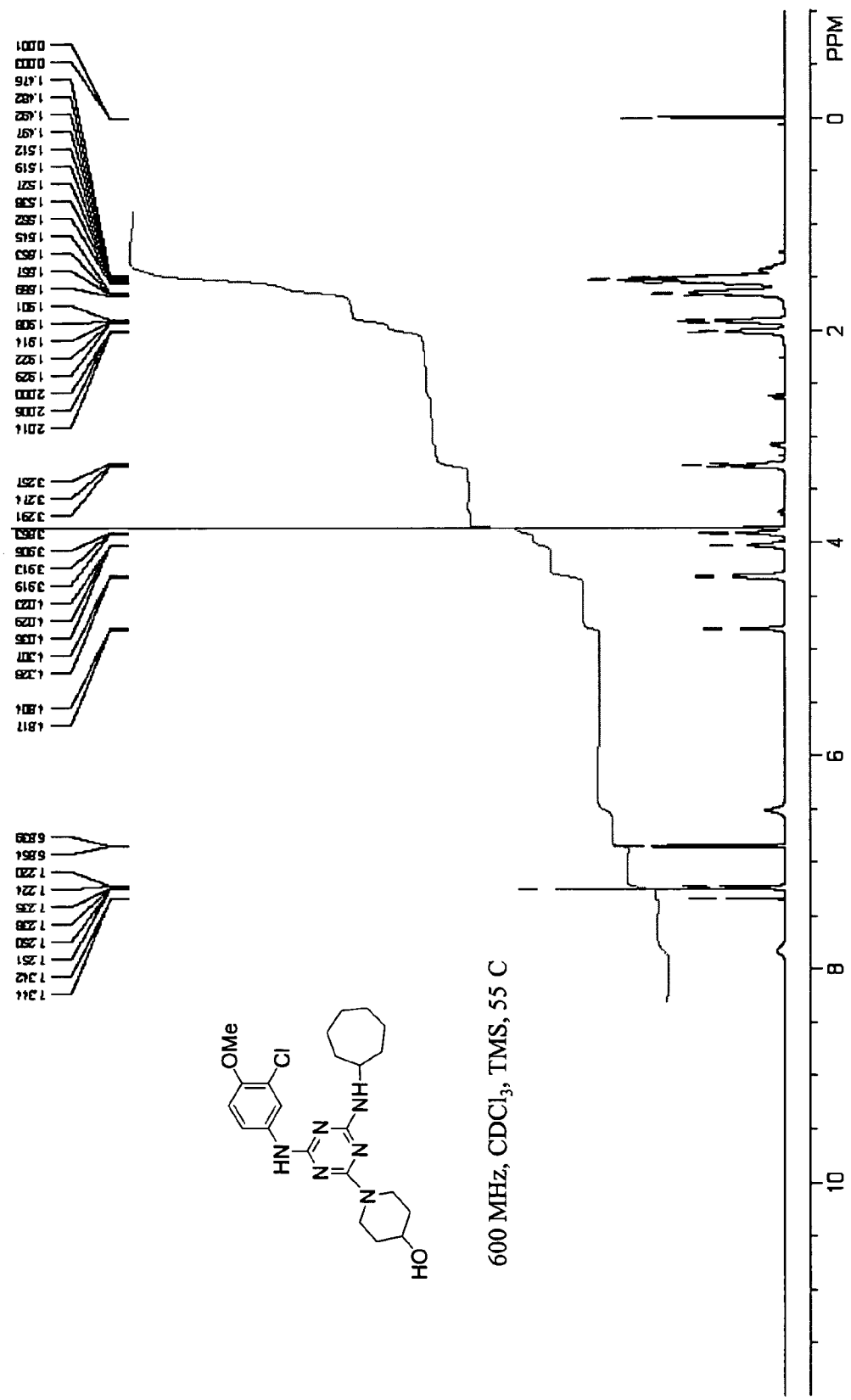
FIG. 76. ¹H NMR of 1-[4-(3-chloro-4-methoxy-phenylamino)-6-cycloheptylamino-[1,3,5]triazine-2-yl]-piperidin-4-ol.
Figure 77:
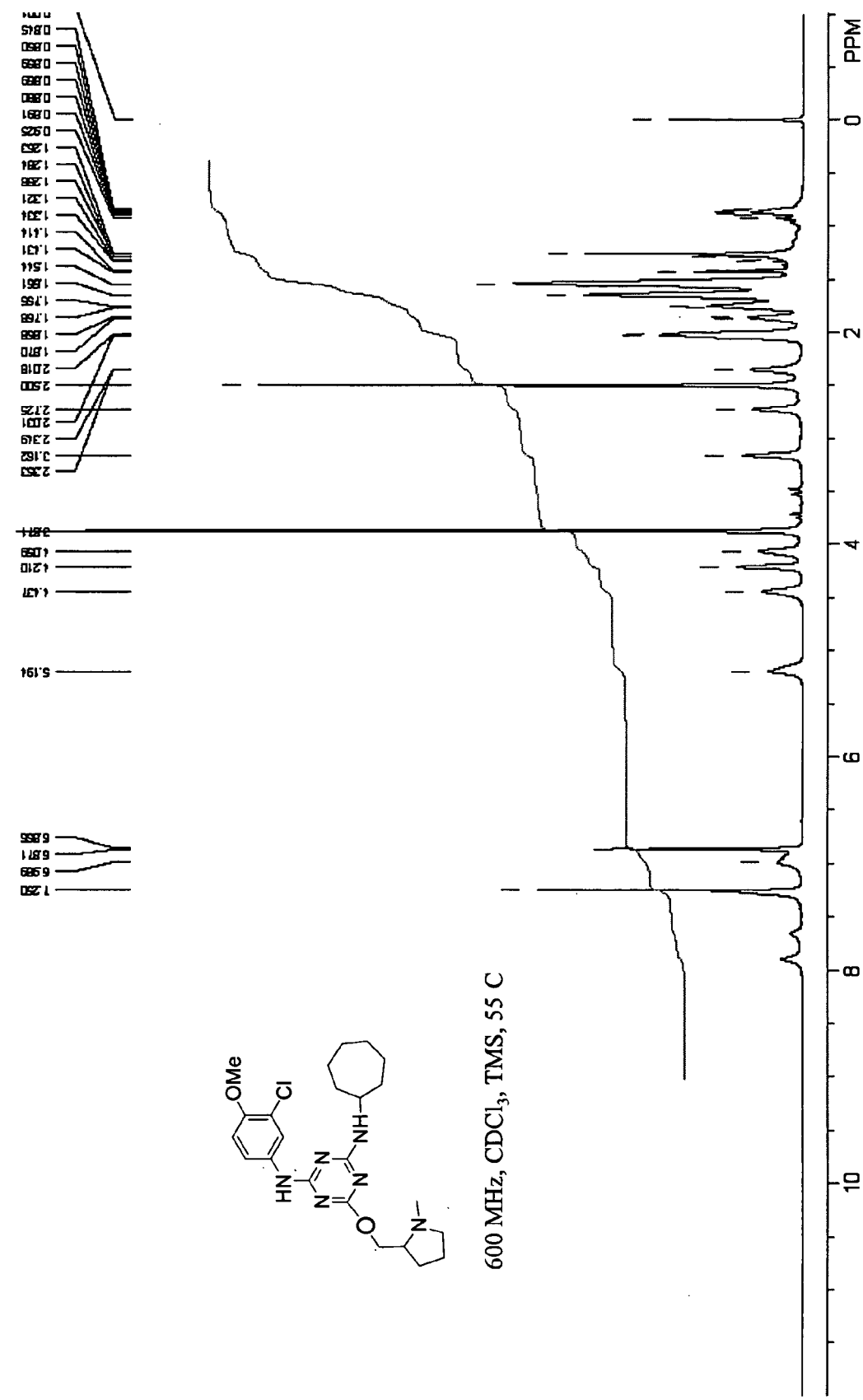
FIG. 77. ¹H NMR of $N^2$-(3-chloro-4-methoxyphenyl)-$N^4$-cycloheptyl-6-(1-methyl-2-azolanylmethoxy)-1,3,5-triazine-2,4-diamine.
Figure 78:
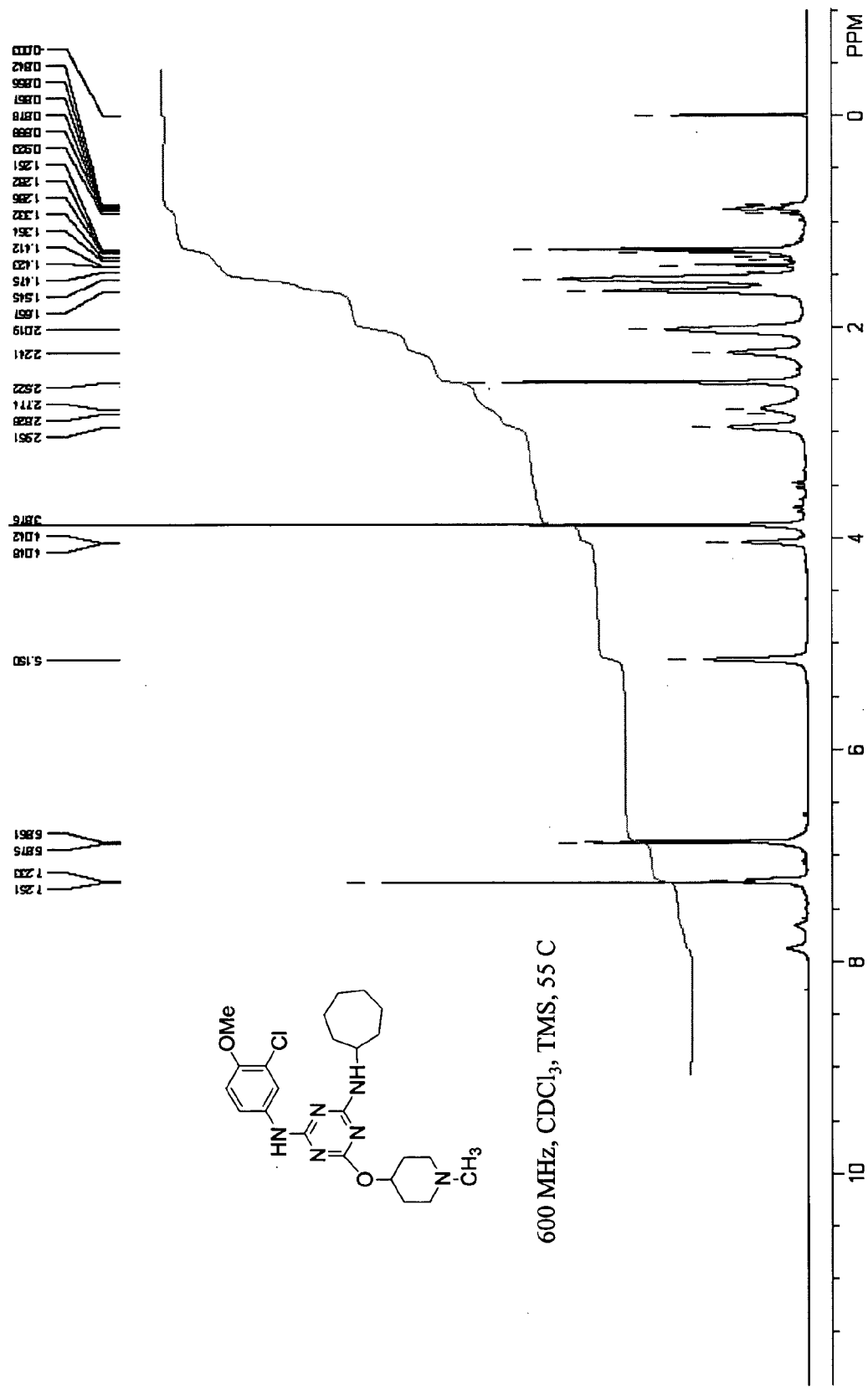
FIG. 78. ¹H NMR of $N^2$-(3-chloro-4-methoxyphenyl)-$N^4$-cycloheptyl-6-(1-methyl-4-piperidyloxy)-1,3,5-triazine-2,4-diamine.
Figure 79:
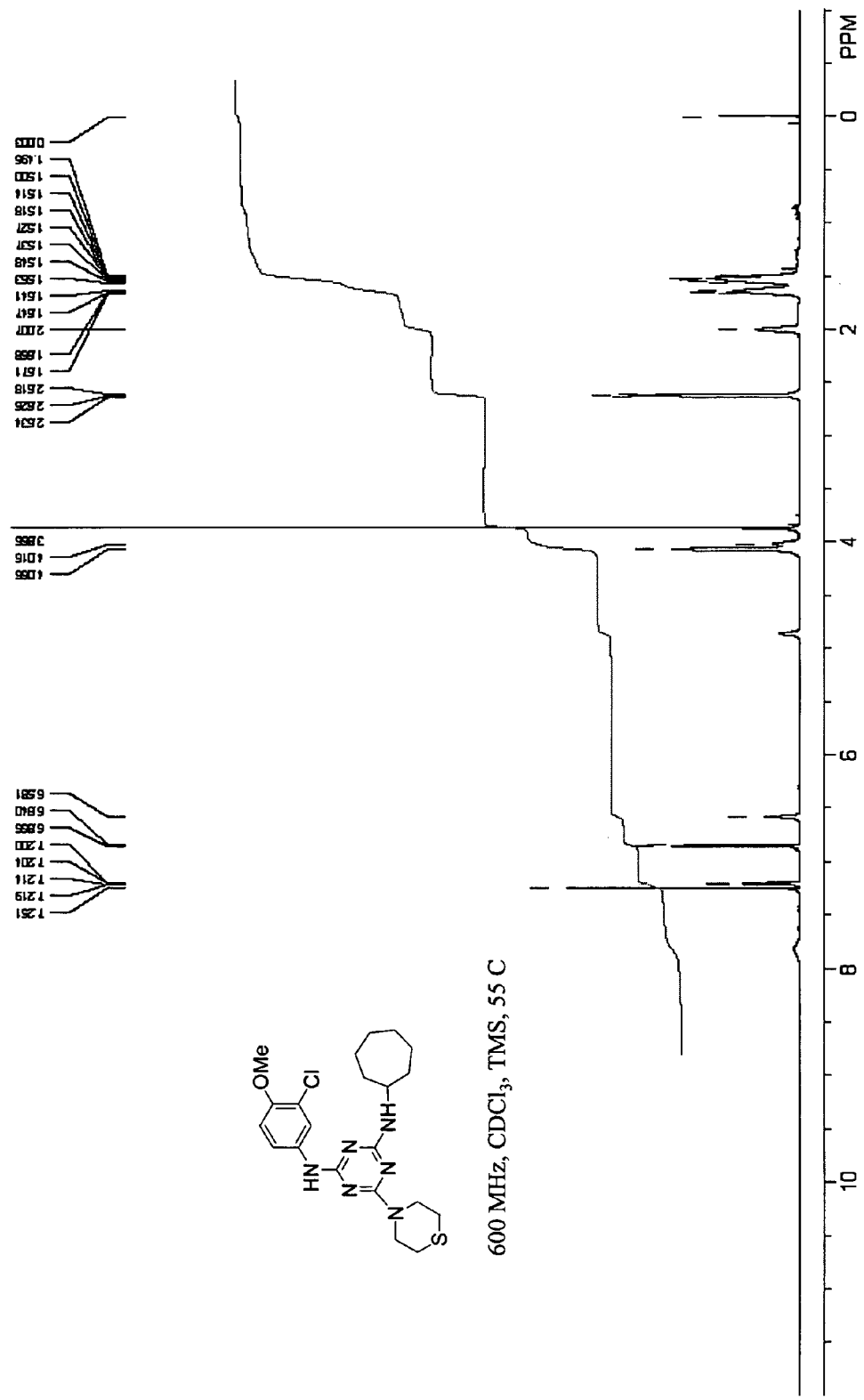
FIG. 79. ¹H NMR of $N^2$-(3-chloro-4-methoxyphenyl)-$N^4$-cycloheptyl-6-(1,4-thiazinan-4-yl)-1,3,5-triazine-4,2-diamine.
Figure 80:
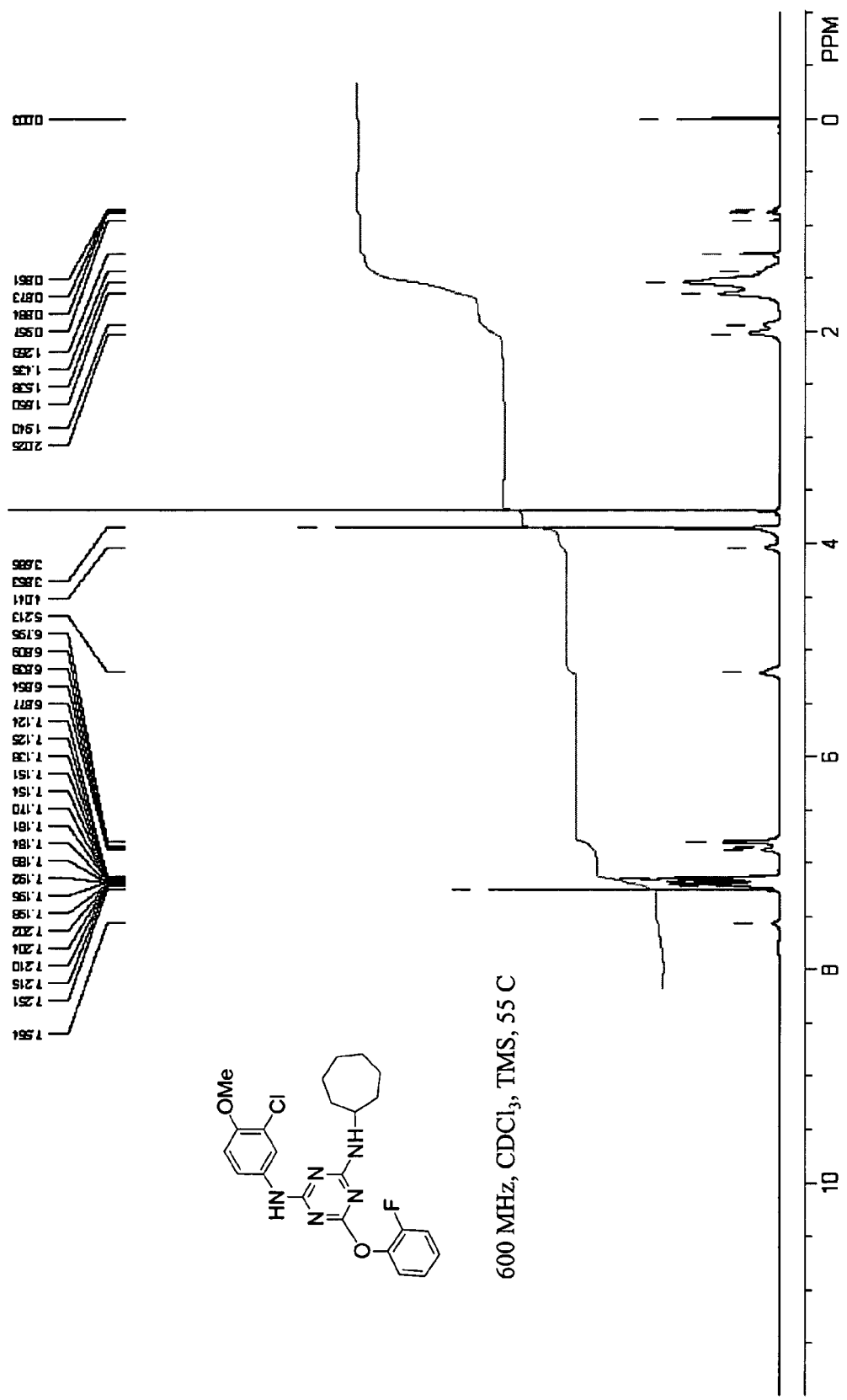
FIG. 80. ¹H NMR of $N^2$-(3-chloro-4-methoxyphenyl)-$N^4$-cycloheptyl-6-(2-fluorophenoxy)-1,3,5-triazine-4,2-diamine.
Figure 81:
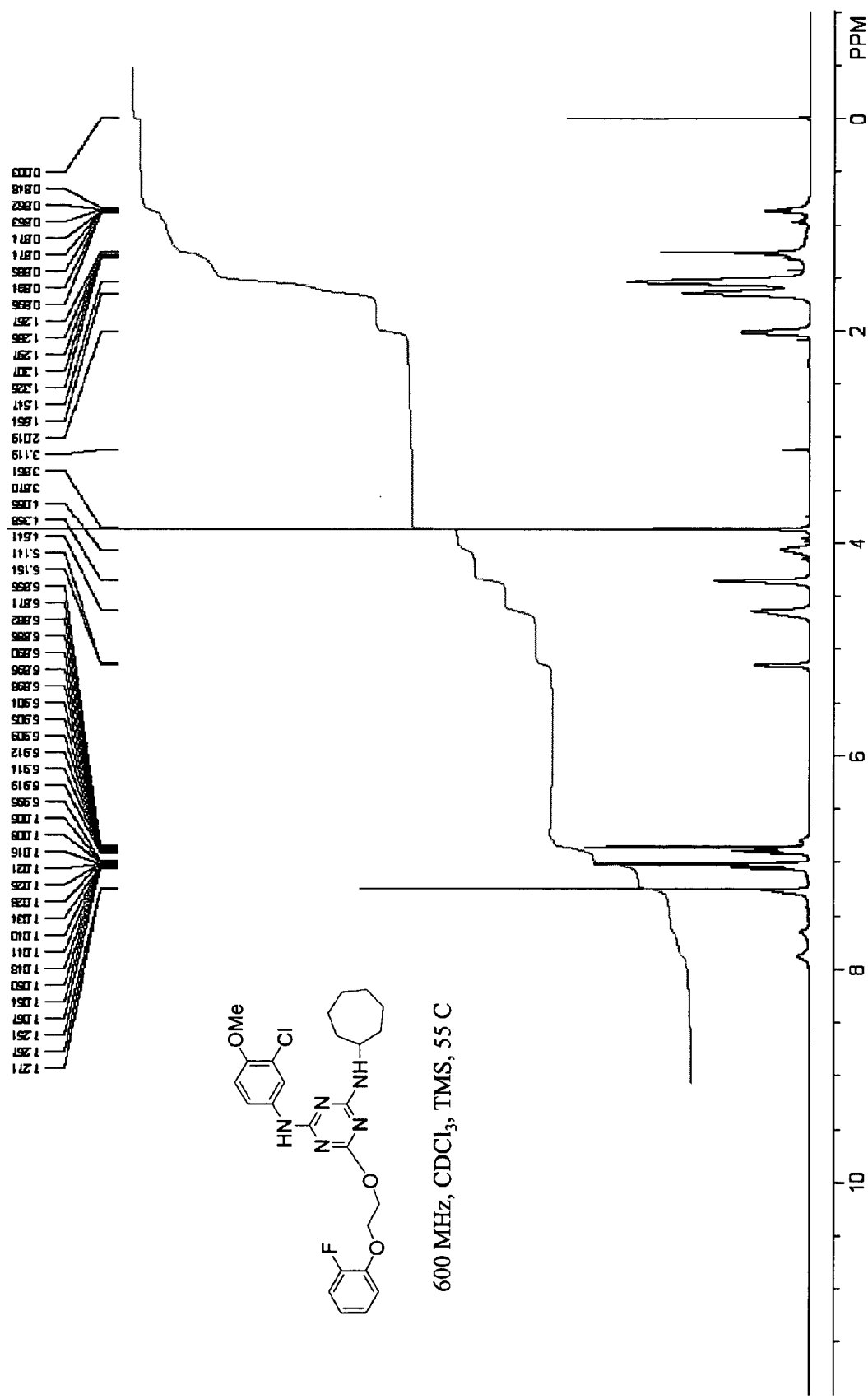
FIG. 81. ¹H NMR of $N^2$-(3-chloro-4-methoxyphenyl)-$N^4$-cycloheptyl-6-[2-(2-fluorophenoxy) ethoxy]-1,3,5-triazine-4,2-diamine.
Figure 82:
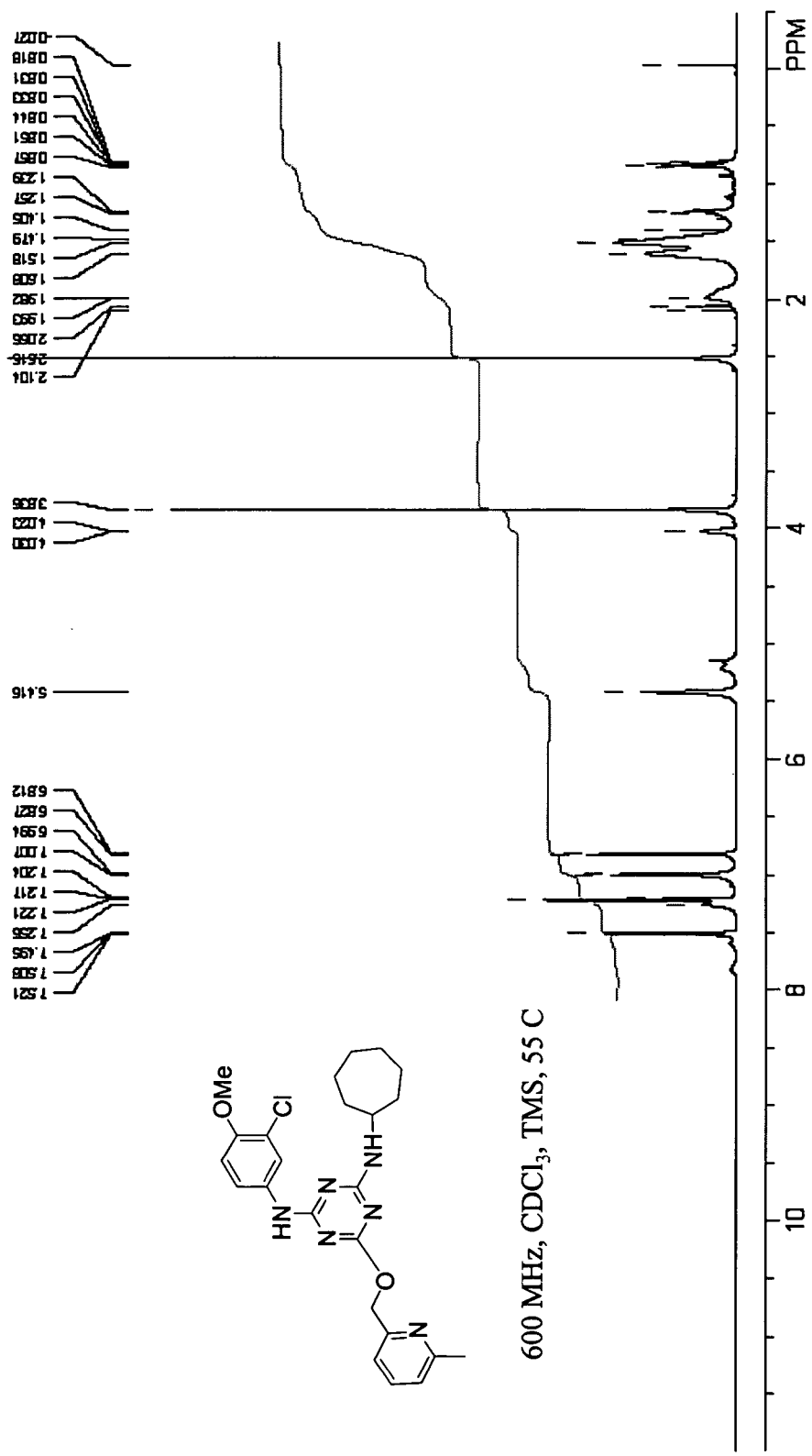
FIG. 82. ¹H NMR of $N^2$-(3-chloro-4-methoxyphenyl)-$N^4$-cycloheptyl-6-(6-methyl-2-pyryl methoxy]-1,3,5-triazine-4,2-diamine.
Figure 83:
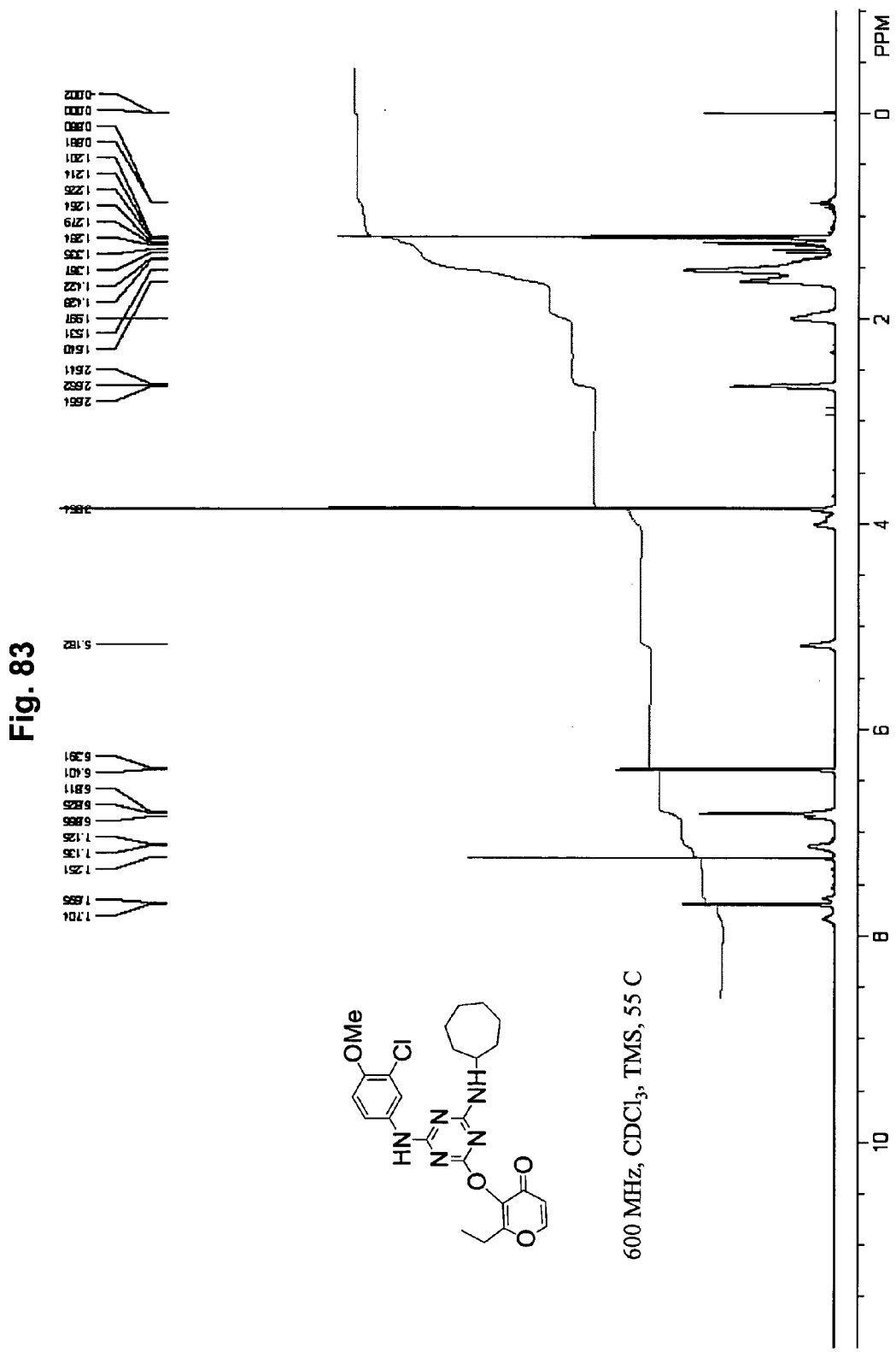
FIG. 83. ¹H NMR of 3-[4-(3-chloro-4-methoxyanilino)-6-cycloheptylamino-1,3,5-triazin-2-yloxy]-2-ethyl-4H-4-pyranone.
Figure 84:
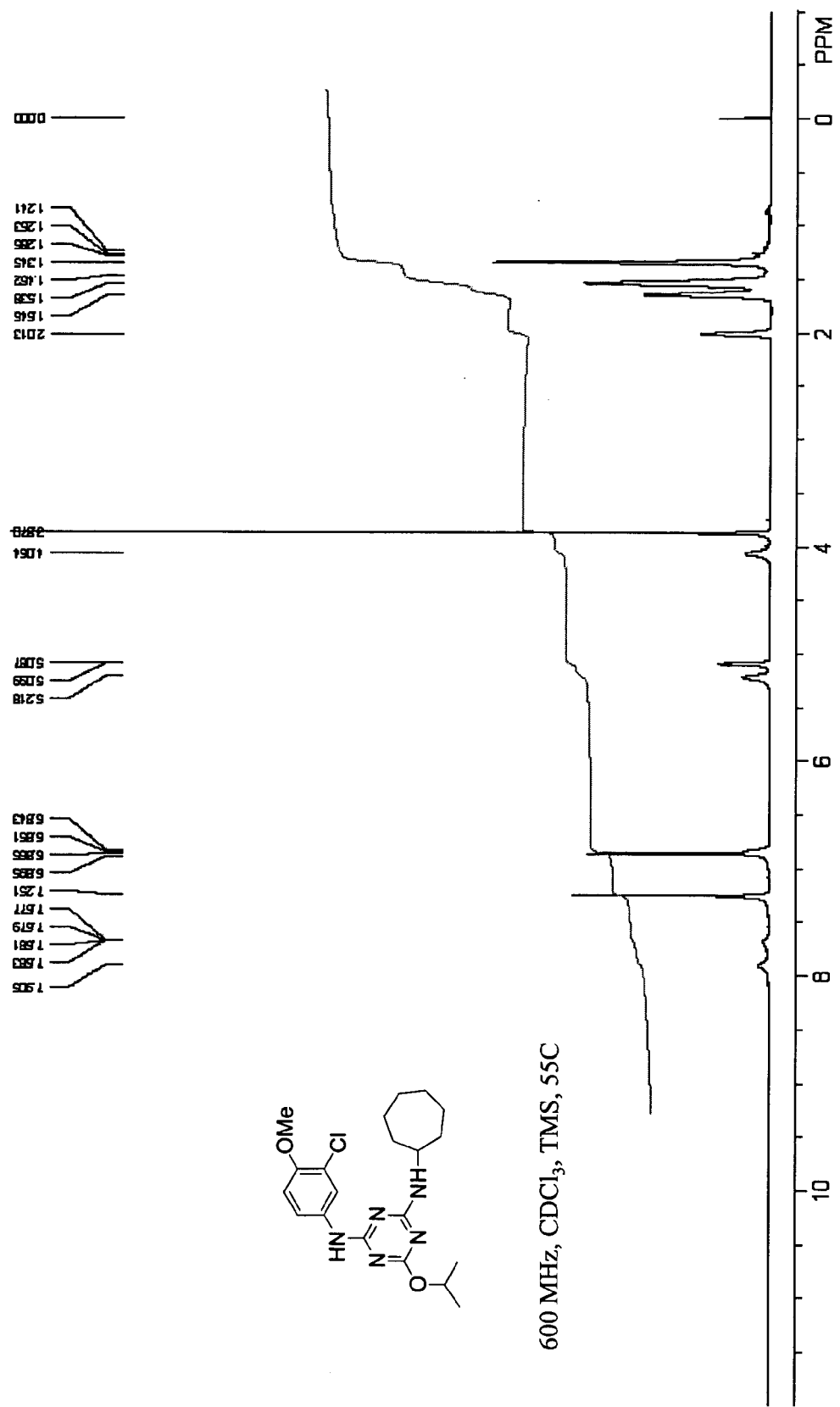
FIG. 84. ¹H NMR of $N^2$-(3-chloro-4-methoxyphenyl)-$N^4$-cycloheptyl-6-isopropoxy-1,3,5-triazine-2,4-diamine.
Figure 85:
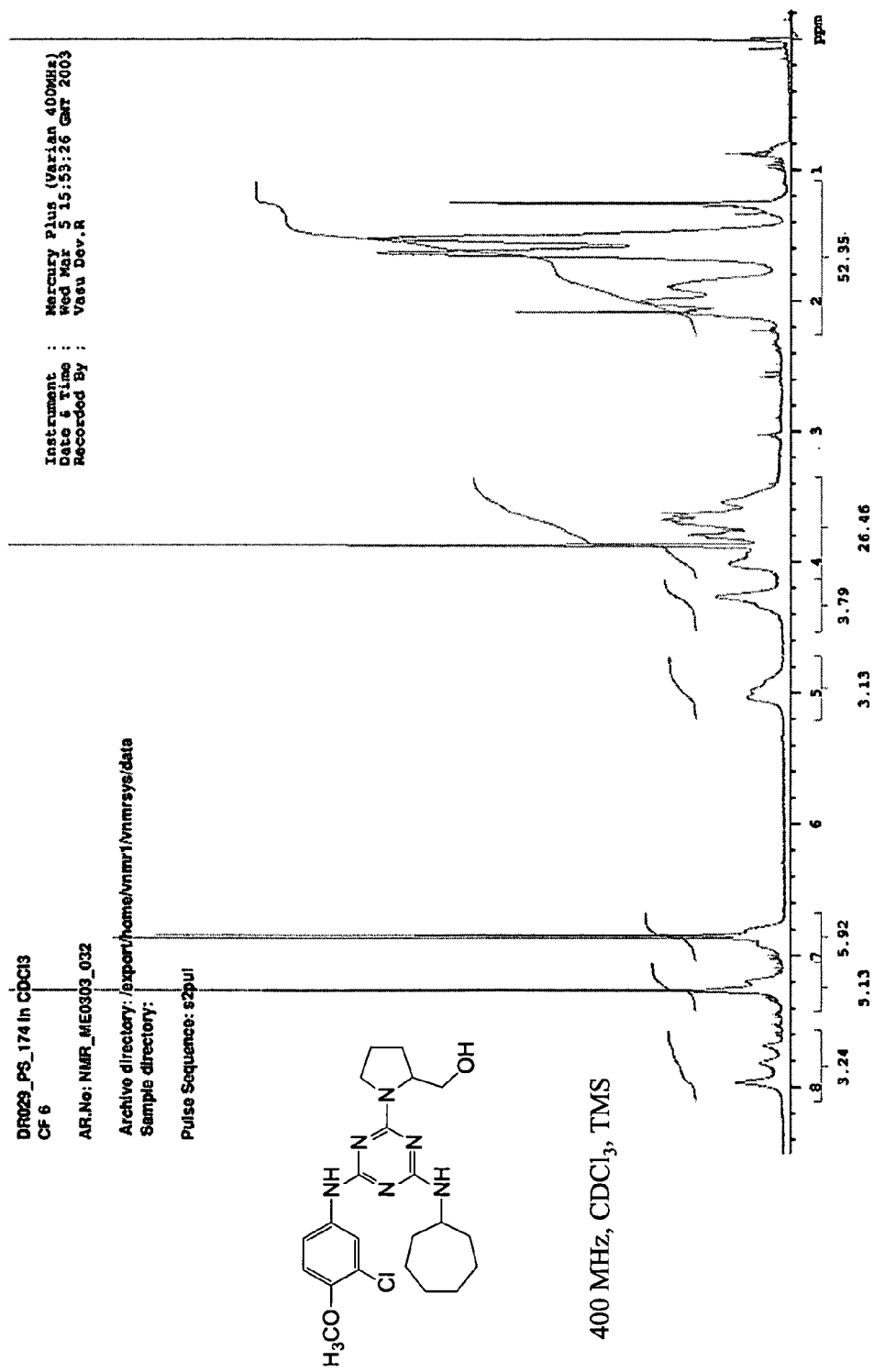
FIG. 85. ¹H NMR of 1-[4-(3-chloro-4-methoxyanilino)-cycloheptyl amino-1,3,5-triazin-2-yl]-2-azoloamymethanol.
Figure 86:
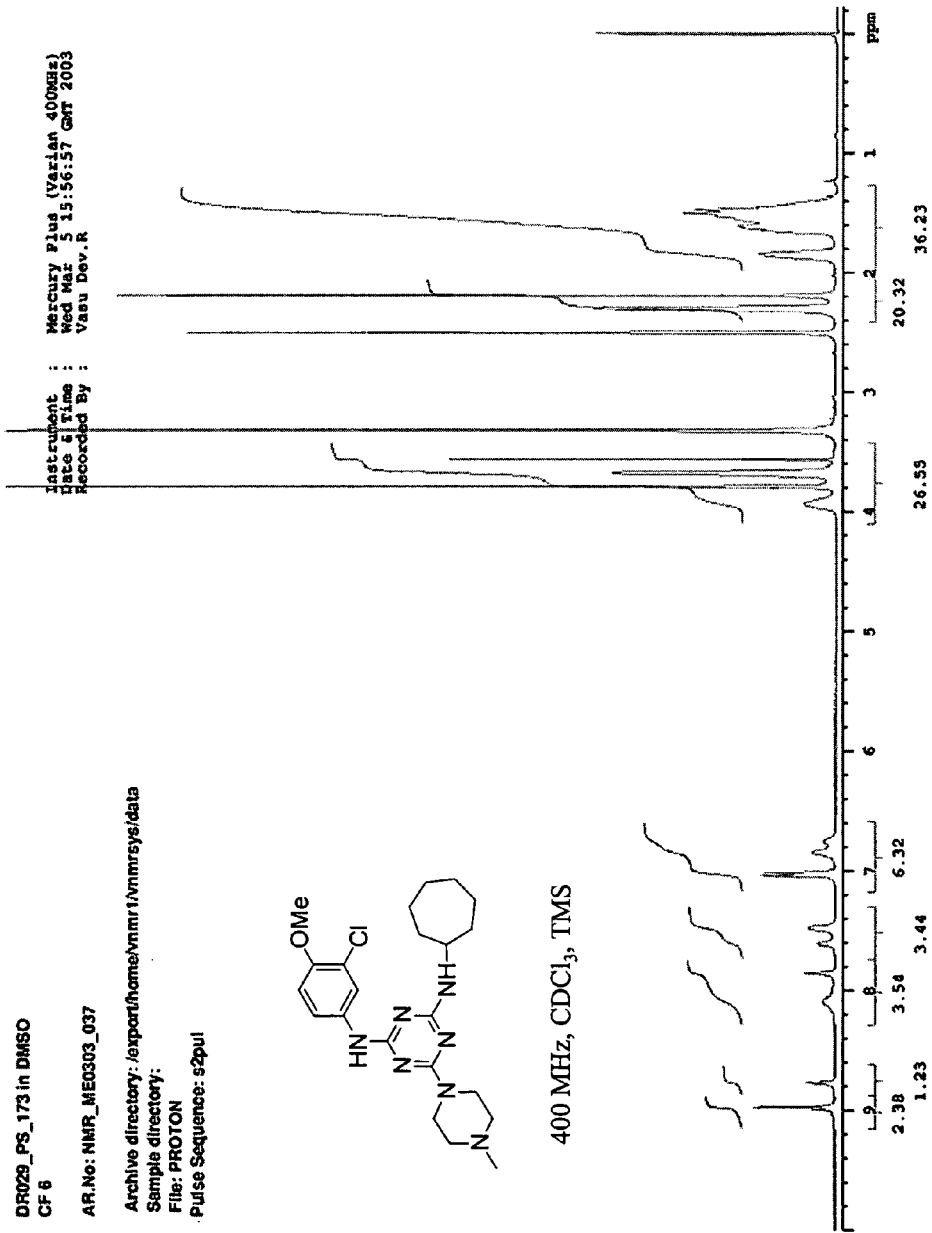
FIG. 86. ¹H NMR of $N^2$-(3-chloro-4-methoxyphenyl)-$N^4$-cycloheptyl-6-(4-methylpiperzino)-1,3,5-triazine-4,2-diamine.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention which will be limited only by the appended claims.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

I. Description of Compounds

In one aspect, the present invention encompasses novel organic compounds that are generally described as $N^2$, $N^4$, $N^6$-tris(amino)-1,3,5-triazines which are represented by the names in Table 1 and the structural formulas in the remaining Tables 2 and following. Representative compounds of this invention can be described by the general structural formula below, where $N^A$, $N^B$ and $N^C$ are pendant substituted amino groups attached to 1,3,5-triazines at the 2, 4 and 6 positions.

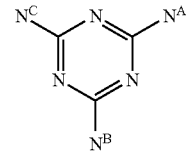

Thus, the typical compound encompassed by the present invention includes triazine compounds comprising the following structure:

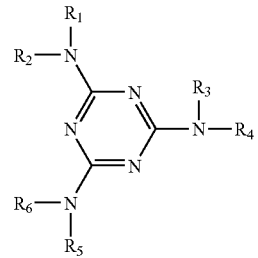

In this typical embodiment, each pendant $NR_1R_2$, $NR_3R_4$, and $NR_5R_6$ amino group can represent a primary, secondary, or tertiary amine when bonded to the triazine core, including a cyclic secondary amide substitutent (for example a pyrrolidin-N-yl group), and a range of other substituents as described herein. Compositions in accordance with the present invention also comprise analogs of the tris(amino) compounds, for example, compounds that are prepared as intermediate compounds in the synthesis of the tris(amino) triazine compounds indicated above, or compounds that represent a partially substituted trizaine core. Many of the syntheses of triazine compounds of this invention typically use cyanuric chloride $C_3N_3Cl_3$ as a starting compound, therefore intermediate species such as bis(amino) chlorotriazine compounds, or amino diclorotriazine compounds shown below, where $N^A$ and $N^B$ are pendant substituted amino groups as described above, are also encompassed by this invention.

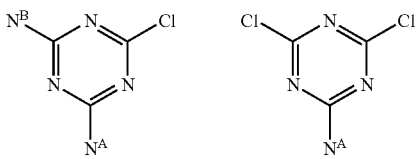

Compositions in accordance with the present invention also comprise analogs of the tris(amino) triazine compounds indicated above, including compounds that are isolated as byproducts in the synthesis of the tris(amino) triazine compounds, a general formula of which is shown below, where E=O or S. An example of such a compound is a bis(amino) alkoxy triazine compound.

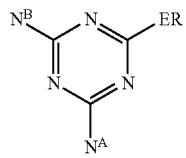

In general terms, the compounds and compositions in accordance with the present invention comprise analogs of the tris(amino) triazine compounds of the following general structure:

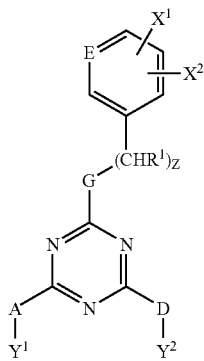

or an ene, a diene, a triene, or an yne derivative thereof; a saturated derivative thereof; a stereoisomer thereof; or a salt thereof;

wherein:

$R^1$ is in each occurrence independently selected from —H; alkyl, cycloalkyl, alkenyl, cycloalkenyl, cycloalkadienyl, alkynyl, aralkyl, aralkenyl, aralkynyl, heteroalkyl, alkoxy, alkylthio, alkylamino, or dialkylamino, each of which having up to 12 carbon atoms and including linear or branched derivatives thereof, cyclic derivatives thereof, substituted derivatives thereof, heteroatom derivatives thereof, or heterocyclic derivatives thereof; aryl; heteroaryl; aryloxy; arylthio; halogen; or amino;

G is selected from $NR^1$ or O;

E is selected from CH or N;

z is an integer from 0 to 3;

$X^1$ is selected from $R^1$, $NR^1_3{}^+$, CN, $NO_2$, $CO_2R^1$, $C(O)NR^1{}_2$, $CH=CR^1{}_2$, $C\equiv CR^1$, $C(O)R^1$, $SO_2R^1$, $SO_2OR^1$, or $NC(O)R^1$, or $X^1$ and $X^2$ together is a fused aryl, pyridine, dioxane, pyrrole, pyrrolidine, furan, or thiophene ring; with the proviso that the $R^1$ moiety of the $C(O)R^1$ substituent in the $X^1$ position excludes amino or dialkylamino when $X^1$ is $C(O)R^1$;

$X^2$ is selected from $R^1$; $CX_xH_{3-x}$, wherein X is a halogen and x is an integer from 0 to 3; $OR^1$; $SR^1$; $NR^1{}_2$; CN; $C(O)OR^1$; $NC(O)R^1$; 4-morpholinyl; 4-methyl-1-piperazinyl; $OR^2$, wherein $R^2$ is selected from $CH_2OCH_3$, $CH_2OCH_2OCH_3$, $CH_2OCH_2CH_2OCH_3$, $CH_2SCH_3$, or $C(O)R^1$; $SR^3$, wherein $R^3$ is selected from $CH_2OCH_3$, $CH_2OCH_2CH_2OCH_3$, $CH_2OCH_2CH(CH_3)_2$, $CH_2NHC(O)CH_3$, or $SR^1$; OM or SM, wherein M is selected from Li, Na, K, Mg, or Ca;

$AY^1$ is halogen, or A is selected from $NR^1$ or O, and $Y^1$ is selected from $R^1$; $CR^4{}_3$; $NR^4{}_2$; $OR^4$; or $SR^4$;

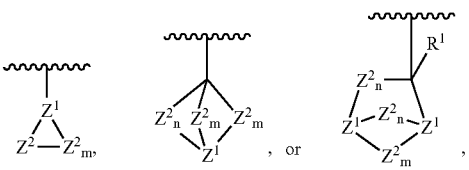

wherein n is an integer from 0 to 8, m is an integer from 1 to 8, $Z^1$ is independently selected from $CR^1$ or N, $Z^2$ is independently selected from $CR^1{}_2$, $NR^1$, O, or S, with the proviso that two O or S atoms are not located adjacent to each other, and the proviso that no more than two $Z^2$ moieties are $NR^1$;

$R^4$ is in each occurrence independently selected from linear or branched alkyl, cycloalkyl, cycloalkenyl, cycloalkadienyl, alkenyl, alkynyl, aralkyl, aralkenyl, aralkynyl, heteroalkyl, alkoxy, alkylthio, alkylamino, or dialkylamino, each of which having up to 10 carbon atoms, —H, aryl, heteroaryl, aryloxy, arylthio, halogen, amino, $NR^1{}_2$-substituted derivatives thereof, $OR^1$-substituted derivatives thereof, $SR^1$-substituted derivatives thereof, or halogen-substituted derivatives thereof; and $DY^2$ is halogen, or D is selected from $NR^1$ or O wherein $R^1$ is defined as above, and $Y^2$ is selected from $R^1$,

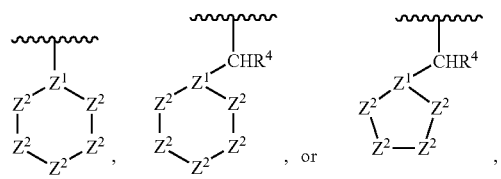

wherein $Z^1$ is independently selected from N or $CR^4$ and $Z^2$ is independently selected as defined above, with the proviso that two O or S atoms are not located adjacent to each other, and with the proviso that no more than two $Z^2$ moieties are $NR^1$. The compounds of the present invention according to this general description do not include those that encompass the unique combination of substituents that would provide the following compounds:

N-Cycloheptyl-N'-methyl-N'-(1-methyl-piperidin-4-yl)-N"-naphthalen-2-yl-[1,3,5]triazine-2,4,6-triamine;

N-Cycloheptyl-N'-(3-fluoro-4-methoxy-phenyl)-N"'-methyl-N"-(1-methyl-piperidin-4-yl)-[1,3,5]triazine-2,4,6-triamine;

[4-(4-Benzyl-piperazin-1-yl)-6-morpholin-4-yl-[1,3,5]triazin-2-yl]-(4-methoxy-phenyl)-amine;

N-Cycloheptyl-6-morpholin-4-yl-N'-naphthalen-2-yl-[1,3,5]triazine-2,4-diamine;

N-Cycloheptyl-N'-(3-fluoro-4-methoxy-phenyl)-6-morpholin-4-yl-[1,3,5]triazine-2,4-diamine;

N-Cycloheptyl-6-morpholin-4-yl-N'-phenyl-[1,3,5]triazine-2,4-diamine;

N-Cycloheptyl-N'-(4-methoxy-phenyl)-6-morpholin-4-yl-[1,3,5]triazine-2,4-diamine;

N-Benzyl-N'-cycloheptyl-N''-(4-methoxy-phenyl)-N-methyl-[1,3,5]triazine-2,4,6-triamine;

N-(2-[1,3]Dioxolan-2-yl-ethyl)-N'-methyl-N'-(1-methyl-piperidin-4-yl)-N''-naphthalen-2-yl-[1,3,5]triazine-2,4,6-triamine; or N-Cyclopropyl-N'-methyl-N'-(1-methyl-piperidin-4-yl)-N''-naphthalen-2-yl-[1,3,5]triazine-2,4,6-triamine.

Because this invention encompass compounds that represent saturated derivatives of the above general structure, and compounds that include various states of unsaturation (for example, -ene, -diene, -triene, and -yne derivatives of the above compounds), then the aryl or pyridyl ring shown in the general formula above can be partially or completed hydrogenated in this invention. As a result, the $C_5E$ ring in the above structure can represent a cylcohexyl or piperidynl ring that is $X^1$ and $X^2$ substituted. In general terms, $X^1$ usually, but not always, represent an electron withdrawing group such as halide or nitro, while $X^2$ usually, but not always, represents an electron donating group such as alkoxide or amino.

As indicated in the general structure above, $AY^1$ and $DY^2$ typically represent an $NR^1$ moiety (where $R^1$ is defined above), in which case these substituents constitute a portion of amino or substituted amino group and therefore, the compound itself constitutes a triazine. In this case, $Y^1$ and $Y^2$ may be selected from a wide range of substituents, including, but not limited to, cycloalkyl with up to 10 carbon atoms;

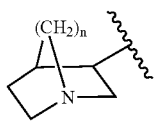

wherein n is from 1 or 2;

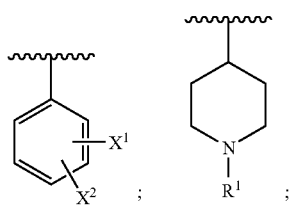

linear or branched alkyl with up to 10 carbon atoms; $CH_2R^1$; $(CHR^1)_xNR^1_2$ wherein x is 1-6; $CH_2R^1$; $(CHR^1)_xOR^1$ wherein x is from 1 to 6;

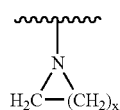

wherein x is from 3 to 5;

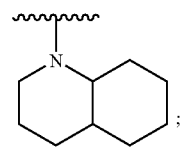

$CH_2CF_3$; $(CHR^1)_xZ^1$ wherein x is from 1 to 6 and $Z^1$ is selected from $NR^1_2$,

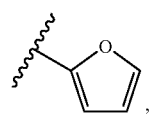 , 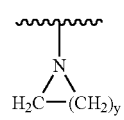

wherein y is from 3 to 5,

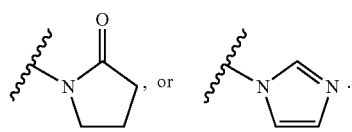

In these examples, $R^1$ is independently selected as defined above. These are merely representative examples of the definitions of the $Y^1$ and $Y^2$ substitutents, and are not intended to be exclusive.

It is also noted that $AY^1$ together, and $DY^2$ together, can also represent a wide range of chemical moieties bonded to the triazine core such as halide or secondary amino groups such as

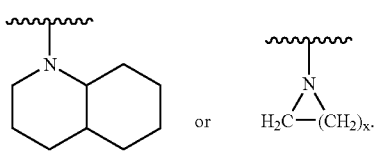

In the latter cases, the amino substituent groups are termed secondary amino groups, however upon bonding to the triazine core, the amino nitrogens become tertiary amine moieties. Examples of $AY^1$ together and $DY^2$ together include, but are not limited to: halide;

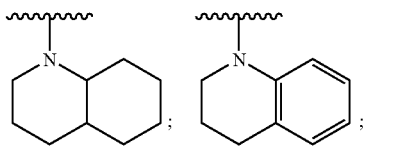 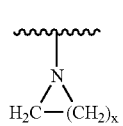 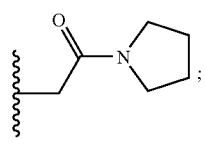

wherein x is from 3 to 5;

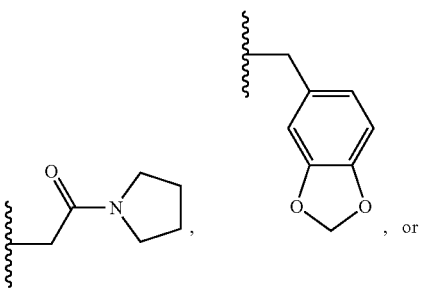

$C(O)R^1$, $C(O)OR^1$, pyridinyl, aryl,

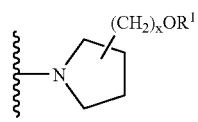

wherein x is from 0 to 6;

wherein $Z^2$ is selected from $R^1$, wherein x is from 0 to 6, and wherein $R^1$ is independently selected as defined above. These are also merely representative examples of the definitions of these substitutents, and are not intended to be exclusive.

Representative compounds in accordance with the present invention are presented in Table 1. This table is not intended to be exclusive of the compounds of the present invention, but rather exemplary of the triazine that are encompassed by this invention.

TABLE 1

| COMPOUND NUMBER | COMPOUND NAME |
|---|---|
| 1 | $N^2$-(4-bromo-1-naphthyl)-$N^4$-cycloheptyl-$N^6$-[(1-ethyl-2-pyrrolidinyl)methyl]-1,3,5-triazine-2,4,6-triamine |
| 2 | $N^2$-(4-chloro-1-naphthyl)-$N^4$-cycloheptyl-$N^6$-[(1-ethyl-2-pyrrolidinyl)methyl]-1,3,5-triazine-2,4,6-triamine |
| 3 | $N^2$-cycloheptyl-$N^4$-[(1-ethyl-2-pyrrolidinyl)methyl]-$N^6$-(3-quinolinyl)-1,3,5-triazine-2,4,6-triamine |
| 4 | $N^2$-cycloheptyl-$N^4$-[(1-ethyl-2-pyrrolidinyl)methyl]-$N^6$-(6-quinolinyl)-1,3,5-triazine-2,4,6-triamine |
| 5 | $N^2$-cycloheptyl-$N^4$-[(1-ethyl-2-pyrrolidinyl)methyl]-$N^6$-(8-quinolinyl)-1,3,5-triazine-2,4,6-triamine |
| 6 | $N^2$-cycloheptyl-$N^4$-[(1-ethyl-2-pyrrolidinyl)methyl]-$N^6$-[1-(2-naphthyl)ethyl]-1,3,5-triazine-2,4,6-triamine |
| 7 | $N^2$-cycloheptyl-$N^4$-(3,4-dichlorophenyl)-$N^6$-[(1-ethyl-2-pyrrolidinyl)methyl]-1,3,5-triazine-2,4,6-triamine |
| 8 | $N^2$-cycloheptyl-$N^4$-(3,4-difluorophenyl)-$N^6$-[(1-ethyl-2-pyrrolidinyl)methyl]-1,3,5-triazine-2,4,6-triamine |
| 9 | $N^2$-cycloheptyl-$N^4$-[(1-ethyl-2-pyrrolidinyl)methyl]-$N^6$-[4-(trifluoromethoxy)phenyl]-1,3,5-triazine-2,4,6-triamine |
| 10 | $N^2$-cycloheptyl-$N^4$-[(1-ethyl-2-pyrrolidinyl)methyl]-$N^6$-(4-fluorophenyl)-1,3,5-triazine-2,4,6-triamine |
| 11 | 4-[(4-(cycloheptylamino)-6-{[(1-ethyl-2-pyrrolidinyl)methyl]amino}-1,3,5-triazin-2-yl)-amino]benzonitrile |
| 12 | $N^2$-(4-chlorophenyl)-$N^4$-cycloheptyl-$N^6$-[(1-ethyl-2-pyrrolidinyl)methyl]-1,3,5-triazine-2,4,6-triamine |
| 13 | $N^2$-(4-bromophenyl)-$N^4$-cycloheptyl-$N^6$-[(1-ethyl-2-pyrrolidinyl)methyl]-1,3,5-triazine-2,4,6-triamine |
| 14 | Ethyl 4-[(4-(cycloheptylamino)-6-{[(1-ethyl-2-pyrrolidinyl)methyl]amino}-1,3,5-triazin-2-yl)-amino]benzoate |

TABLE 1-continued

| COMPOUND NUMBER | COMPOUND NAME |
|---|---|
| 15 | $N^2$-(1,1'-biphenyl-4-yl)-$N^4$-cycloheptyl-$N^6$-[(1-ethyl-2-pyrrolidinyl)methyl]-1,3,5-triazine-2,4,6-triamine |
| 16 | $N^2$-cycloheptyl-$N^4$-[(1-ethyl-2-pyrrolidinyl)methyl]-$N^6$-(3-fluorophenyl)-1,3,5-triazine-2,4,6-triamine |
| 17 | $N^2$-(3-chlorophenyl)-$N^4$-cycloheptyl-$N^6$-[(1-ethyl-2-pyrrolidinyl)methyl]-1,3,5-triazine-2,4,6-triamine |
| 18 | $N^2$-(3-bromophenyl)-$N^4$-cycloheptyl-$N^6$-[(1-ethyl-2-pyrrolidinyl)methyl]-1,3,5-triazine-2,4,6-triamine |
| 19 | Ethyl 3-[(4-(cycloheptylamino)-6-{[(1-ethyl-2-pyrrolidinyl)methyl]amino}-1,3,5-triazin-2-yl)-amino]benzoate |
| 20 | $N^2$-cycloheptyl-$N^4$-[(1-ethyl-2-pyrrolidinyl)methyl]-$N^6$-(2-fluorophenyl)-1,3,5-triazine-2,4,6-triamine |
| 21 | $N^2$-(2-chlorophenyl)-$N^4$-cycloheptyl-$N^6$-[(1-ethyl-2-pyrrolidinyl)methyl]-1,3,5-triazine-2,4,6-triamine |
| 22 | $N^2$-(2-bromophenyl)-$N^4$-cycloheptyl-$N^6$-[(1-ethyl-2-pyrrolidinyl)methyl]-1,3,5-triazine-2,4,6-triamine |
| 23 | $N^2$-(1,3-benzodioxol-5-yl)-$N^4$-cycloheptyl-$N^6$-[(1-ethyl-2-pyrrolidinyl)methyl]-1,3,5-triazine-2,4,6-triamine |
| 24 | $N^2$-cycloheptyl-$N^4$-(2,3-dihydro-1,4-benzodioxin-6-yl)-$N^6$-[(1-ethyl-2-pyrrolidinyl)methyl]-1,3,5-triazine-2,4,6-triamine |
| 25 | $N^2$-cycloheptyl-$N^4$-[4-(dimethylamino)phenyl]-$N^6$-[(1-ethyl-2-pyrrolidinyl)methyl]-1,3,5-triazine-2,4,6-triamine |
| 26 | $N^2$-[3-chloro-4-(diethylamino)phenyl]-$N^4$-cycloheptyl-$N^6$-[(1-ethyl-2-pyrrolidinyl)methyl]-1,3,5-triazine-2,4,6-triamine |
| 27 | $N^2$-cycloheptyl-$N^4$-[(1-ethyl-2-pyrrolidinyl)methyl]-$N^6$-[4-(4-morpholinyl)phenyl]-1,3,5-triazine-2,4,6-triamine |
| 28 | $N^2$-cycloheptyl-$N^4$-[(1-ethyl-2-pyrrolidinyl)methyl]-$N^6$-[4-(4-methyl-1-piperazinyl)phenyl]-1,3,5-triazine-2,4,6-triamine |
| 29 | N-{4-[(4-(cycloheptylamino)-6-{[(1-ethyl-2-pyrrolidinyl)methyl]amino}-1,3,5-triazin-2-yl)-amino]phenyl}acetamide |
| 30 | N-{3-[(4-(cycloheptylamino)-6-{[(1-ethyl-2-pyrrolidinyl)methyl]amino}-1,3,5-triazin-2-yl)-amino]phenyl}acetamide |
| 31 | $N^2$-cycloheptyl-$N^4$-[(1-ethyl-2-pyrrolidinyl)methyl]-$N^6$-(3-methoxyphenyl)-1,3,5-triazine-2,4,6-triamine |
| 32 | $N^2$-cycloheptyl-$N^4$-(4-ethoxyphenyl)-$N^6$-[(1-ethyl-2-pyrrolidinyl)methyl]-1,3,5-triazine-2,4,6-triamine |
| 33 | $N^2$-cycloheptyl-$N^4$-[(1-ethyl-2-pyrrolidinyl)methyl]-$N^6$-[4-(methylthio)phenyl]-1,3,5-triazine-2,4,6-triamine |
| 34 | $N^2$-cycloheptyl-$N^4$-[(1-ethyl-2-pyrrolidinyl)methyl]-$N^6$-(2-pyridinyl)-1,3,5-triazine-2,4,6-triamine |
| 35 | $N^2$-cycloheptyl-$N^4$-[(1-ethyl-2-pyrrolidinyl)methyl]-$N^6$-(2-methylphenyl)-1,3,5-triazine-2,4,6-triamine |
| 36 | $N^2$-cycloheptyl-$N^4$-[(1-ethyl-2-pyrrolidinyl)methyl]-$N^6$-(4-phenoxyphenyl)-1,3,5-triazine-2,4,6-triamine |
| 37 | $N^2$-cycloheptyl-$N^4$-[(1-ethyl-2-pyrrolidinyl)methyl]-$N^6$-(3-methylphenyl)-1,3,5-triazine-2,4,6-triamine |
| 38 | $N^2$-cycloheptyl-$N^4$-[(1-ethyl-2-pyrrolidinyl)methyl]-$N^6$-(4-methylphenyl)-1,3,5-triazine-2,4,6-triamine |
| 39 | 2-[(4-(cycloheptylamino)-6-{[(1-ethyl-2-pyrrolidinyl)methyl]amino}-1,3,5-triazin-2-yl)-amino]-4-methyl-3-thiophenecarboxamide |
| 40 | $N^2$-(4-chlorophenyl)-$N^4$-cycloheptyl-$N^6$-[(1-ethyl-2-pyrrolidinyl)methyl]-$N^2$-methyl-1,3,5-triazine-2,4,6-triamine |
| 41 | 3-[(4-(cycloheptylamino)-6-{[(1-ethyl-2-pyrrolidinyl)methyl]amino}-1,3,5-triazin-2-yl)-(phenyl)amino]propanenitrile |
| 42 | $N^2$-cycloheptyl-$N^4$-[(1-ethyl-2-pyrrolidinyl)methyl]-$N^6$-(4-methoxyphenyl)-$N^6$-methyl-1,3,5-triazine-2,4,6-triamine |
| 43 | $N^2$-cycloheptyl-$N^4$-(2,4-difluorophenyl)-$N^6$-[(1-ethyl-2-pyrrolidinyl)methyl]-$N^4$-methyl-1,3,5-triazine-2,4,6-triamine |
| 44 | [(4-(cycloheptylamino)-6-{[(1-ethyl-2-pyrrolidinyl)methyl]amino}-1,3,5-triazin-2-yl)(phenyl)amino]acetonitrile |
| 45 | $N^2$-(3-chlorophenyl)-$N^4$-cycloheptyl-$N^6$-[(1-ethyl-2-pyrrolidinyl)methyl]-$N^2$-methyl-1,3,5-triazine-2,4,6-triamine |
| 46 | $N^2$-cycloheptyl-$N^4$-[(1-ethyl-2-pyrrolidinyl)methyl]-$N^6$-methyl-$N^6$-[2-(trifluoromethyl)phenyl]-1,3,5-triazine-2,4,6-triamine |
| 47 | $N^2$-cycloheptyl-$N^4$-[(1-ethyl-2-pyrrolidinyl)methyl]-$N^6$-methyl-$N^6$-[4-(trifluoromethoxy)phenyl]-1,3,5-triazine-2,4,6-triamine |
| 48 | $N^2$-(3-chloro-4-methoxyphenyl)-$N^4$-cycloheptyl-$N^6$-[(1-ethyl-2-pyrrolidinyl)methyl]-1,3,5-triazine-2,4,6-triamine |
| 49 | N-benzoyl-4-[(4-(cycloheptylamino)-6-{[(1-ethyl-2-pyrrolidinyl)methyl]amino}-1,3,5-triazin-2-yl)-amino]benzenesulfonamide |
| 50 | $N^2$-cycloheptyl-$N^4$-[(1-ethyl-2-pyrrolidinyl)methyl]-$N^6$-(2-naphthyl)-1,3,5-triazine-2,4,6-triamine |

TABLE 1-continued

| COMPOUND NUMBER | COMPOUND NAME |
|---|---|
| 51 | $N^2$-ethyl-$N^4$-[(1-ethyl-2-pyrrolidinyl)methyl]-$N^6$-(3-fluoro-4-methoxyphenyl)-1,3,5-triazine-2,4,6-triamine |
| 52 | $N^2$-(tert-butyl)-$N^4$-[(1-ethyl-2-pyrrolidinyl)methyl]-$N^6$-(3-fluoro-4-methoxyphenyl)-1,3,5-triazine-2,4,6-triamine |
| 53 | $N^2$-benzyl-$N^4$-[(1-ethyl-2-pyrrolidinyl)methyl]-$N^6$-(3-fluoro-4-methoxyphenyl)-1,3,5-triazine-2,4,6-triamine |
| 54 | $N^2$-cyclooctyl-$N^4$-[(1-ethyl-2-pyrrolidinyl)methyl]-$N^6$-(3-fluoro-4-methoxyphenyl)-1,3,5-triazine-2,4,6-triamine |
| 55 | $N^2$-cyclohexyl-$N^4$-[(1-ethyl-2-pyrrolidinyl)methyl]-$N^6$-(3-fluoro-4-methoxyphenyl)-1,3,5-triazine-2,4,6-triamine |
| 56 | $N^2$-cyclopentyl-$N^4$-[(1-ethyl-2-pyrrolidinyl)methyl]-$N^6$-(3-fluoro-4-methoxyphenyl)-1,3,5-triazine-2,4,6-triamine |
| 57 | $N^2$-[(1-ethyl-2-pyrrolidinyl)methyl]-$N^4$-(3-fluoro-4-methoxyphenyl)-6-(1-pyrrolidinyl)-1,3,5-triazine-2,4-diamine |
| 58 | $N^2$-[(1-ethyl-2-pyrrolidinyl)methyl]-$N^4$-(3-fluoro-4-methoxyphenyl)-$N^6$-hexahydro-1H-azepin-1-yl-1,3,5-triazine-2,4-diamine |
| 59 | $N^2$-[(1-ethyl-2-pyrrolidinyl)methyl]-$N^4$-(3-fluoro-4-methoxyphenyl)-$N^6$-octahydro-1(2H)-quinolinyl-1,3,5-triazine-2,4-diamine |
| 60 | $N^2$-[(1-ethyl-2-pyrrolidinyl)methyl]-$N^4$-(3-fluoro-4-methoxyphenyl)-$N^6$-(4-methylcyclohexyl)-1,3,5-triazine-2,4,6-triamine |
| 61 | $N^2$-(1-ethyl-pyrrolidin-2-ylmethyl]-$N^4$-(3-fluoro-4-methoxyphenyl)-6-((S)-2-methoxymethyl-pyrrolidin-1-yl)-1,3,5-triazine-2,4-diamine |
| 62 | $N^2$-[(1-ethyl-2-pyrrolidinyl)methyl]-$N^4$-(3-fluoro-4-methoxyphenyl)-6-(4-methyl-1-piperazinyl)-1,3,5-triazine-2,4-diamine |
| 63 | 6-(4-acetyl-1-piperazinyl)-$N^2$-[(1-ethyl-2-pyrrolidinyl)methyl]-$N^4$-(3-fluoro-4-methoxyphenyl)-1,3,5-triazine-2,4-diamine |
| 64 | Ethyl 4-{4-{[(1-ethyl-2-pyrrolidinyl)methyl]amino}-$N^6$-[(3-fluoro-4-methoxyphenyl)amino]-1,3,5-triazin-2-yl}-1-piperazinecarboxylate |
| 65 | $N^2$-(cyclohexylmethyl)-$N^4$-[(1-ethyl-2-pyrrolidinyl)methyl]-$N^6$-(3-fluoro-4-methoxyphenyl)-1,3,5-triazine-2,4,6-triamine |
| 66 | $N^2$-[(1-ethyl-2-pyrrolidinyl)methyl]-$N^4$-(3-fluoro-4-methoxyphenyl)-$N^6$-(2-furylmethyl)-1,3,5-triazine-2,4,6-triamine |
| 67 | $N^2$-[(1-ethyl-2-pyrrolidinyl)methyl]-$N^4$-(3-fluoro-4-methoxyphenyl)-$N^6$-(2,2,2-trifluoroethyl)-1,3,5-triazine-2,4,6-triamine |
| 68 | $N^2$-[2-(dimethylamino)ethyl]-$N^4$-[(1-ethyl-2-pyrrolidinyl)methyl]-$N^6$-(3-fluoro-4-methoxyphenyl)-1,3,5-triazine-2,4,6-triamine |
| 69 | $N^2$-[(1-ethyl-2-pyrrolidinyl)methyl]-$N^4$-(3-fluoro-4-methoxyphenyl)-$N^6$-{4-[2-oxo-2-(1-pyrrolidinyl)ethyl]-1-piperazinyl}-1,3,5-triazine-2,4-diamine |
| 70 | $N^2,N^4$-bis[(1-ethyl-2-pyrrolidinyl)methyl]-$N^6$-(3-fluoro-4-methoxyphenyl)-1,3,5-triazine-2,4,6-triamine |
| 71 | $N^2$-[(1-ethyl-2-pyrrolidinyl)methyl]-$N^4$-(3-fluoro-4-methoxyphenyl)-$N^6$-[2-(1-piperidinyl)ethyl]-1,3,5-triazine-2,4,6-triamine |
| 72 | $N^6$-[4-(1,3-benzodioxol-5-ylmethyl)-1-piperazinyl]-$N^2$-[(1-ethyl-2-pyrrolidinyl)methyl]-$N^4$-(3-fluoro-4-methoxyphenyl)-1,3,5-triazine-2,4-diamine |
| 73 | $N^2$-[(1-ethyl-2-pyrrolidinyl)methyl]-$N^4$-(3-fluoro-4-methoxyphenyl)-$N^6$-[4-(2-pyridinyl)-1-piperazinyl]-1,3,5-triazine-2,4-diamine |
| 74 | 1-[3-({4-{[(1-ethyl-2-pyrrolidinyl)methyl]amino}-6-[(3-fluoro-4-methoxyphenyl)amino]-1,3,5-triazin-2-yl}amino)propyl]-2-pyrrolidinone |
| 75 | $N^2$-[(1-ethyl-2-pyrrolidinyl)methyl]-$N^4$-(3-fluoro-4-methoxyphenyl)-$N^6$-[3-(1H-imidazol-1-yl)propyl]-1,3,5-triazine-2,4,6-triamine |
| 76 | $N^2$-cycloheptyl-$N^4$-ethyl-$N^6$-(3-fluoro-4-methoxyphenyl)-1,3,5-triazine-2,4,6-triamine |
| 77 | $N^2$-(tert-butyl)-$N^4$-cycloheptyl-$N^6$-(3-fluoro-4-methoxyphenyl)-1,3,5-triazine-2,4,6-triamine |
| 78 | $N^2$-benzyl-$N^4$-cycloheptyl-$N^6$-(3-fluoro-4-methoxyphenyl)-1,3,5-triazine-2,4,6-triamine |
| 79 | $N^2$-cycloheptyl-$N^4$-cyclooctyl-$N^6$-(3-fluoro-4-methoxyphenyl)-1,3,5-triazine-2,4,6-triamine |
| 80 | $N^2$-cycloheptyl-$N^4$-cyclohexyl-$N^6$-(3-fluoro-4-methoxyphenyl)-1,3,5-triazine-2,4,6-triamine |
| 81 | $N^2$-cycloheptyl-$N^4$-cyclopentyl-$N^6$-(3-fluoro-4-methoxyphenyl)-1,3,5-triazine-2,4,6-triamine |
| 82 | $N^2$-cycloheptyl-$N^4$-(3-fluoro-4-methoxyphenyl)-6-(1-pyrrolidinyl)-1,3,5-triazine-2,4-diamine |
| 83 | $N^2$-cycloheptyl-$N^4$-(3-fluoro-4-methoxyphenyl)-6-hexahydro-1H-azepin-1-yl-1,3,5-triazine-2,4-diamine |
| 84 | $N^2$-cycloheptyl-$N^4$-(3-fluoro-4-methoxyphenyl)-6-octahydro-1(2H)-quinolinyl-1,3,5-triazine-2,4-diamine |
| 85 | $N^2$-cycloheptyl-$N^4$-(3-fluoro-4-methoxyphenyl)-$N^6$-(4-methylcyclohexyl)-1,3,5-triazine-2,4,6-triamine |
| 86 | $N^2$-cycloheptyl-$N^4$-(3-fluoro-4-methoxyphenyl)-6-[(2S)-2-(methoxymethyl)-1-pyrrolidinyl]-1,3,5-triazine-2,4-diamine |
| 87 | $N^2$-cycloheptyl-$N^4$-(3-fluoro-4-methoxyphenyl)-6-(4-methyl-1-piperazinyl)-1,3,5-triazine-2,4-diamine |

TABLE 1-continued

| COMPOUND NUMBER | COMPOUND NAME |
|---|---|
| 88 | 6-(4-acetyl-1-piperazinyl)-$N^2$-cycloheptyl-$N^4$-(3-fluoro-4-methoxyphenyl)-1,3,5-triazine-2,4-diamine |
| 89 | ethyl-4-{4-(cycloheptylamino)-6-[(3-fluoro-4-methoxyphenyl)amino]-1,3,5-triazin-2-yl}-1-piperazinecarboxylate |
| 90 | $N^2$-cycloheptyl-$N^4$-(cyclohexylmethyl)-$N^6$-(3-fluoro-4-methoxyphenyl)-1,3,5-triazine-2,4,6-triamine |
| 91 | $N^2$-cycloheptyl-$N^4$-(3-fluoro-4-methoxyphenyl)-$N^6$-(2-furanylmethyl)-1,3,5-triazine-2,4,6-triamine |
| 92 | $N^2$-cycloheptyl-$N^4$-(3-fluoro-4-methoxyphenyl)-$N^6$-(2,2,2-trifluoroethyl)-1,3,5-triazine-2,4,6-triamine |
| 93 | $N^2$-cycloheptyl-$N^4$-[2-(dimethylamino)ethyl]-$N^6$-(3-fluoro-4-methoxyphenyl)-1,3,5-triazine-2,4,6-triamine |
| 94 | $N^2$-cycloheptyl-$N^4$-(3-fluoro-4-methoxyphenyl)-6-{4-[2-oxo-(1-pyrrolidinyl)ethyl]-1-piperazinyl}-1,3,5-triazine-2,4-diamine |
| 95 | $N^2$-cycloheptyl-$N^4$-[(1-ethyl-2-pyrrolidinyl)methyl]-$N^6$-(3-fluoro-4-methoxyphenyl)-1,3,5-triazine-2,4,6-triamine |
| 96 | $N^2$-cycloheptyl-$N^4$-(3-fluoro-4-methoxyphenyl)-$N^6$-[2-(1-piperidinyl)ethyl]-1,3,5-triazine-2,4,6-triamine |
| 97 | 6-[4-(1,3-benzodioxol-5-ylmethyl)1-piperazinyl]-$N^2$-cycloheptyl-$N^4$-(3-fluoro-4-methoxyphenyl)-1,3,5-triazine-2,4-diamine |
| 98 | $N^2$-cycloheptyl-$N^4$-(3-fluoro-4-methoxyphenyl)-6-[4-(2-pyridinyl)-1-piperazinyl]-1,3,5-triazine-2,4-triamine |
| 99 | 1-[3-({4-(cycloheptylamino)-6-[(3-fluoro-4-methoxyphenyl)amino]-1,3,5-triazin-2-yl}amino)propyl]-2-pyrrolidinone |
| 100 | $N^2$-cycloheptyl-$N^4$-(3-fluoro-4-methoxyphenyl)-$N^6$-[3-(1H-imidazol-1-yl)propyl]-1,3,5-triazine-2,4,6-triamine |
| 101 | (3-Chloro-4-methoxy-phenyl)-(4,6-dichloro-[1,3,5]triazin-2-yl)-amine |
| 102 | 6-Chloro-N-(3-chloro-4-methoxy-phenyl)-N'-cyclohexylmethyl-[1,3,5]triazine-2,4-diamine |
| 103 | N-(3-Chloro-4-methoxy-phenyl)-N'-cyclohexylmethyl-N''-methyl-N''-(1-methyl-piperidin-4-yl)-[1,3,5]triazine-2,4,6-triamine |
| 104 | 6-Chloro-N-(3-chloro-4-methoxy-phenyl)-N'-(1-propyl-butyl)-[1,3,5]triazine-2,4-diamine |
| 105 | N-(3-Chloro-4-methoxy-phenyl)-N'-methyl-N'-(1-methyl-piperidin-4-yl)-N''-(1-propyl-butyl)-[1,3,5]triazine-2,4,6-triamine |
| 106 | N-(3-Chloro-4-methoxy-phenyl)-N'-isopropyl-N''-methyl-N''-(1-methyl-piperidin-4-yl)-[1,3,5]triazine-2,4,6-triamine |
| 107 | $N^2$-(3-chloro-4-methoxy-phenyl)-$N^4$-isopropyl-$N^6$-methyl-$N^6$-piperidin-4-yl-1,3,5-triazine-2,4,6-triamine |
| 108 | 5-{4-(3-Chloro-4-methoxy-phenylamino)-6-[methyl-(1-methyl-piperidin-4-yl)-amino]-[1,3,5]triazin-2-ylamino}-pentan-1-ol |
| 109 | 5-[4-(3-chloro-4-methoxy-phenylamino)-6-(methyl-piperidin-4-yl-amino)-1,3,5-triazin-2-ylamino]-pentan-1-ol |
| 110 | N-Butyl-6-chloro-N'-(3-chloro-4-methoxy-phenyl)-N-propyl-[1,3,5]triazine-2,4-diamine |
| 111 | N-Butyl-N'-(3-chloro-4-methoxy-phenyl)-N''-methyl-N''-(1-methyl-piperidin-4-yl)-N-propyl-[1,3,5]triazine-2,4,6-triamine |
| 112 | $N^2$-Butyl-$N^4$-(3-chloro-4-methoxy-phenyl)-$N^6$-methyl-$N^6$-piperidin-4-yl-$N^2$-propyl-1,3,5-triazine-2,4,6-triamine |
| 113 | 2,4-Dichloro-6-cyclohexylmethoxy-[1,3,5]triazine |
| 114 | (4-Chloro-6-cyclohexylmethoxy-[1,3,5]triazin-2-yl)-(3-fluoro-4-methoxy-phenyl)-amine |
| 115 | 6-Cyclohexylmethoxy-N,N'-bis-(3-fluoro-4-methoxy-phenyl)-1,3,5-triazine-2,4-diamine |
| 116 | 6-Cyclohexylmethoxy-N-(1-ethyl-pyrrolidin-2-ylmethyl)-N'-(3-fluoro-4-methoxy-phenyl)-[1,3,5]triazine-2,4-diamine |
| 117 | (4-Chloro-6-cyclohexylmethoxy-[1,3,5]triazin-2-yl)-(3-chloro-4-methoxy-phenyl)-amine |
| 118 | N,N'-Bis-(3-chloro-4-methoxy-phenyl)-6-cyclohexylmethoxy-1,3,5-triazine-2,4-diamine |
| 119 | N-(3-Chloro-4-methoxy-phenyl)-6-cyclohexylmethoxy-N'-methyl-N'-(1-methyl-piperidin-4-yl)-[1,3,5]triazine-2,4-diamine |
| 120 | 6-Chloro-N,N''-bis-(3-chloro-4-methoxy-phenyl)-[1,3,5]triazine-2,4-diamine |
| 121 | N,N'-Bis-(3-chloro-4-methoxy-phenyl)-N''-methyl-N''-(1-methyl-piperidin-4-yl)-[1,3,5]triazine-2,4,6-triamine |
| 122 | N,N'-Bis-(3-chloro-4-methoxy-phenyl)-N''-cycloheptyl-[1,3,5]triazine-2,4,6-triamine |
| 123 | N-(3-Bromo-4-methoxy-phenyl)-N'-cycloheptyl-N''-methyl-N''-(1-methyl-piperidin-4-yl)-[1,3,5]triazine-2,4,6-triamine |
| 124 | (4,6-Dichloro-[1,3,5]triazin-2-yl)-(3-fluoro-4-methoxy-phenyl)-amine |
| 125 | 6-Chloro-N-cyclohexylmethyl-N'-(3-fluoro-4-methoxy-phenyl)-[1,3,5]triazine-2,4-diamine |
| 126 | N-Cyclohexylmethyl-N'-(1-ethyl-pyrrolidin-2-ylmethyl)-N''-(3-fluoro-4-methoxy-phenyl)-[1,3,5]triazine-2,4,6-triamine |

TABLE 1-continued

| COMPOUND NUMBER | COMPOUND NAME |
|---|---|
| 127 | 6-Chloro-N-cycloheheptyl-N'-(3-fluoro-4-methoxy-phenyl)-[1,3,5]triazine-2,4-diamine |
| 128 | N-Cycloheptyl-N'-(3-fluoro-4-methoxy-phenyl)-6-pyrrolidin-1-yl-[1,3,5]triazine-2,4-diamine |
| 129 | N-Cycloheptyl-N'-ethyl-N''-(3-fluoro-4-methoxy-phenyl)-[1,3,5]triazine-2,4-diamine |
| 130 | N-Cycloheptyl-N'-(1-ethyl-pyrrolidin-2-ylmethyl)-N''-(3-fluoro-4-methoxy-phenyl)-[1,3,5]triazine-2,4,6-triamine |
| 131 | 2-[4-chloro-6-(3-chloro-4-methoxy-phenylamino)-[1,3,5]triazin-2-ylamino]-propane-1,3-diol |
| 132 | 2-{4-(3-chloro-4-methoxy-phenylamino)-6-[methyl-(1-methyl-piperidin-4-yl)-amino]-[1,3,5]triazin-2-ylamino}-propane-1,3-diol |
| 133 | 6-Chloro-N-(3-chloro-4-methoxy-phenyl)-N'-cycloheptyl-[1,3,5]triazine-2,4-diamine |
| 134 | N-(1-benzyl-piperidin-4-yl)-N'-(3-chloro-4-methoxy-phenyl)-N''-cycloheptyl-[1,3,5]-2,4,6-triamine |
| 135 | $N^2$-(3-chloro-4-methoxy-phenyl)-$N^4$-cycloheptyl-$N^6$-piperidin-4-yl-1,3,5-triazine-2,4,6-triamine |
| 136 | $N^2$-(3-chloro-4-methoxy-phenyl)-$N^4$-cycloheptyl-$N^6$-(1-ethyl-pyrrolidin-2-ylmethyl)-1,3,5-triazine-2,4,6-triamine |
| 137 | N-(3-Chloro-4-methoxy-phenyl)-N'-cycloheptyl-N''-methyl-N''-(1-methyl-piperidin-4-yl)-[1,3,5]triazine-2,4,6-triamine |
| 138 | 2-chloro-4-{cycloheptylamino-6-[methyl-(1-methyl-piperidin-4-yl-amino]-1,3,5-triazin-2-ylamino}-phenol |
| 139 | $N^2$-cycloheptyl-$N^4$-((S)-1-ethyl-pyrrolidin-2-ylmethyl)-$N^6$-(3-fluoro-4-methoxyphenyl)-1,3,5-triazine-2,4,6-triamine |
| 140 | $N^2$-cycloheptyl-$N^4$-((R)-1-ethyl-pyrrolidin-2-ylmethyl)-$N^6$-(3-fluoro-4-methoxyphenyl)-1,3,5-triazine-2,4,6-triamine |
| 141 | $N^2$-cyclohexylmethyl-$N^4$-((S)-1-ethyl-pyrrolidin-2-ylmethyl)-$N^6$-(3-fluoro-4-methoxyphenyl)-1,3,5-triazine-2,4,6-triamine |
| 142 | $N^2$-cyclohexylmethyl-$N^4$-((R)-1-ethyl-pyrrolidin-2-ylmethyl)-$N^6$-(3-fluoro-4-methoxyphenyl)-1,3,5-triazine-2,4,6-triamine (42, Scheme 23) |
| 143 | ({4-cycloheptylamino-6-[((S)-1-ethyl-pyrrolidin-2-ylmethyl)-amino]-1,3,5-triazin-2-yl}-phenyl-amino)-acetonitrile (43, Scheme 24) |
| 144 | ({4-cycloheptylamino-6-[((R)-1-ethyl-pyrrolidin-2-ylmethyl)-amino]-1,3,5-triazin-2-yl}-phenyl-amino)-acetonitrile |
| 145 | $N^2$-[(1-ethyl-2-pyrrolidinyl]-$N^4$-(3-fluoro-4-methoxyphenyl)-6-[(S)-2-(methoxymethyl)-1-pyrrolidinyl]-1,3,5-triazine-2,4-diamine |
| 146 | $N^2$-(3-chloro-4-methoxy-phenyl)-$N^4$-cycloheptyl-$N^6$-methyl-$N^6$-piperidin-4-yl-1,3,5-triazine-2,4,6-triamine |
| 147 | 4-(3-Chloro-4-methoxy-phenylamino)-6-cycloheptylamino-1,3,5-triazin-2-ol |
| 148 | N-(1-Aza-bicyclo[2.2.2]oct-3-yl)-N'-(3-chloro-4-methoxy-phenyl)-N''-)1-ethyl-pyrrolidin-2-ylmethyl)-[1,3,5]triazine-2,4,6-triamine |
| 149 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine |
| 150 | $N^2$-cycloheptyl-$N^4$-(2-dimethylamino-ethyl)-$N^6$-(3-fluoro-4-methoxy-phenyl)-1,3,5-triazine-2,4,6-triamine |
| 151 | ({4-cycloheptylamino-6-[1-ethyl-pyrrolidin-2-ylmethyl)-amino]-1,3,5-triazin-2-yl}-phenyl-amino)-acetonitrile |
| 152 | N-Azepan-1-yl-6-chloro-N'-(3-chloro-4-methoxy-phenyl)-[1,3,5]triazine-2,4-diamine |
| 153 | N''-(3-chloro-4-methoxy-phenyl)-N,N'-bis-perhydro-azepin-1-yl-1,3,5-triazine-2,4,6-triamine |
| 154 | N-Azepan-1-yl-N'-(3-chloro-4-methoxy-phenyl)-N''-(1-methyl-piperidin-4-yl)-[1,3,5]triazine-2,4,6-triamine |
| 155 | $N^4$-(3-chloro-4-methoxy-phenyl)-$N^6$-methyl-$N^2$-perhydro-azepin-1-yl-$N^6$-piperidin-4-yl-1,3,5-triazine-2,4,6-triamine |
| 156 | N,N'-di-n-propyl-N''-(3-fluoro-4-methoxy-phenyl)-1,3,5-triazine-2,4,6-triamine |
| 157 | N,N'-dicyclopropyl-N''-(3-fluoro-4-methoxy-phenyl)-1,3,5-triazine-2,4,6-triamine |
| 158 | $N^2$-Cycloheptyl-$N^4$-(3-fluoro-4-methoxy-phenyl)-$N^6$-methyl-$N^6$-(1-methyl-piperidin-4-yl)-1,3,5-triazine-2,4,6-triamine |
| 159 | $N^2$-Cycloheptyl-$N^4$-(3-fluoro-4-methoxy-phenyl)-$N^6$-methyl-$N^6$-piperidin-4-yl-1,3,5-triazine-2,4,6-triamine |
| 160 | $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, hydrogen chloride salt |
| 161 | [N-(3-Chloro-4-methoxy-phenyl)-N'-cycloheptyl-N''-methyl-N''-(1-methyl-piperidin-4-yl)-[1,3,5]trizaine-2,4,6-triamine, hydrogen chloride salt |
| 162 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine |

TABLE 1-continued

| COMPOUND NUMBER | COMPOUND NAME |
|---|---|
| 163 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine hydrogen chloride salt |
| 164 | $N^2$-cycloheptyl-$N^4$-(1-ethyl-pyrrolidin-2-ylmethyl)-$N^6$-(3-fluoro-4-methoxyphenyl)-1,3,5-triazine-2,4,6-triamine hydrogen chloride salt |
| 165 | $N^2$-(cyclohexylmethyl)-$N^4$-[(1-ethyl-2-pyrrolidinyl)methyl]-$N^6$-(4-fluoro-3-methoxyphenyl)-1,3,5-triazine-2,4,6-triamine hydrogen chloride salt |
| 166 | ({4-cycloheptylamino-6-[(1-ethyl-pyrrolidin-2-ylmethyl)-amino]-1,3,5-triazin-2-yl}-phenyl-amino)-acetonitrile hydrogen chloride salt |
| 167 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine maleate salt |
| 168 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine citrate salt |
| 169 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine succinate salt |
| 170 | N-(3-Bromo-4-methoxy-phenyl)-N'-cycloheptyl-N''-methyl-N''-(1-methyl-piperidin-4-yl)-[1,3,5]triazine-2,4,6-triamine hydrogen chloride salt |

In general terms, the compositions in accordance with the present invention also comprise tris(amino) triazine compounds of the following structure:

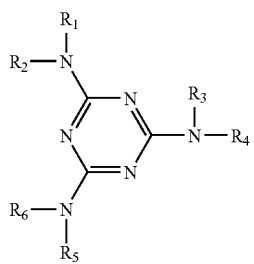

wherein $R_1$ to $R_6$ represent H, alkyl, aryl, alkenyl, alkynyl, aralkyl, aralkenyl, aralkynyl, cycloalkyl, cycloalkenyl, heteroalkyl, heteroaryl, halide, alkoxy, aryloxy, alkylthio, arylthio, silyl, siloxy, amino, alkylamino, dialkylamino and the like, including straight or branched chain derivatives thereof, cyclic derivatives thereof, substituted derivatives thereof, heteroatom derivatives thereof, heterocyclic derivatives thereof, functionalized derivatives thereof, salts thereof, isomers thereof, or combinations thereof.

For example, a typical substituent $R_1$ to $R_6$ is a substituted alkyl, in which the substituent is a heterocyclic derivative. Examples of nitrogen-containing heterocyclic moieties include, but are not limited to groups such as pyridinyl (derived from pyridine, bonded through a ring carbon), piperidinyl (derived from piperidine and bonded through the ring nitrogen atom or a ring carbon), and pyrrolidinyl (derived from pyrrolidine and bonded through the ring nitrogen atom or a ring carbon).

Examples of substituted or functionalized derivatives of $R_1$ to $R_6$ include, but are not limited to, moieties containing substituents such as acyl, formyl, hydroxy, acyl halide, amide, amino, azido, acid, alkoxy, aryloxy, halide, carbonyl, ether, ester, thioether, thioester, nitrile, alkylthio, arylthio, sulfonic acid and salts thereof, thiol, alkenyl, alkynyl, nitro, imine, imide, alkyl, aryl, combinations thereof, and the like. Moreover, in the case of alkylated derivatives of the recited moieties, the alkyl substituent may be pendant to the recited chemical moiety, or used for bonding to the amine nitrogen through the alkyl substituent.

Examples of chemical moieties $R_1$ to $R_6$ of the present invention further include, but are not limited to: H; methyl; ethyl; propyl; butyl; pentyl; hexyl; heptyl; octyl; ethenyl; propenyl; butenyl; ethynyl; propynyl; butynyl; cyclobutyl; cyclopentyl; cyclohexyl; cyclobutenyl; cyclopentenyl; cyclohexenyl; phenyl; tolyl; xylyl; benzyl; naphthyl; pyridinyl; furanyl; tetrahydro-1-napthyl; piperidinyl; indolyl; indolinyl; pyrrolidinyl; 2-(methoxymethyl) pyrrolidinyl; piperazinyl; quinolinyl; quinolyl; alkylated-1,3-dioxolane; triazinyl; morpholinyl; phenyl pyrazolyl; indanyl; indonyl pyrazolyl; thiadiazolyl; rhodaninyl; thiolactonyl; dibenzofuranyl; benzothiazolyl; homopiperidinyl; thiazolyl; quinonuclidinyl; isoxazolidinonyl; any isomers, derivatives, or substituted analogs thereof; or any substituted or unsubstituted chemical groups such as alcohol, ether, thiol, thioether, tertiary amine, secondary amine, primary amine, ester, thioester, carboxylic acid, diol, diester, acrylic acid, acrylic ester, methionine ethyl ester, benzyl-1-cysteine ethyl ester, imine, aldehyde, ketone, amide, or diene.

Further examples of chemical moieties $R_1$ to $R_6$ of this invention include, but are not limited to, the following species or substituted or alkylated derivatives of the following species, covalently bonded to the amine nitrogen: furan; tetrahydrofuran; indole; piperazine; pyrrolidine; pyrrolidinone; pyridine; quinoline; anthracene; tetrahydroquinoline; naphthalene; pyrazole; imidazole; thiophene; pyrrolidine; morpholine; and the like. One feature of the recited species or substituted or alkylated derivatives of these species, is that they may be covalently bonded to the amine nitrogen in any fashion, including through the pendant substituent or alkyl group, through the heteroatom as appropriate, or through a ring atom as appropriate, as understood by one of ordinary skill in the art.

The chemical moieties $R_1$ to $R_6$ of the present invention also include, but are not limited to, cyclic alkanes and alkenes and include bridged and non-bridged rings. Examples of bridged rings include, but are not limited to, groups such as norbornyl; norbonadienyl, adamantyl; 6-azabicyclo[3.2.1]octanyl; 3-azabicyclo[2.2.2]octanyl, and the like.

In one embodiment of the present invention, $NR_1R_2$, $NR_3R_4$, or $NR_5R_6$ are derived from a cyclic secondary amine. Examples of a cyclic amino chemical moiety of the present invention include, but are not limited to piperidine; 4-benzyl-piperidine; 3-piperidinemethanol; morpholine; 4-piperidinopiperidine; 1-(2-amino-methyl)-piperazine; decahydroquinoline; 1,2,3,4-tetrahydro-pyridoindole (either amine moiety); 3-amino-5-phenyl pyrazole; 3-aminopyrazole; histidinol; hexamethyleimine; 4-hydroxypiperidine; 2-piperidinemethanol; 1,3,3-trimethyl-6-azabicyclo[3.2.1]octane; 3-pyrrolidinol; 1-methylpiperazine; 2-ethyl-piperidine; 1,2,3,4-tetrahydroisoquinoline; 3-aminopyrrolidine; 2,6-dimethylmorpholine; 2,3,4-tetrahydroisoquinoline; 1,2,3,4-tetrahydroquinoline; 1-(2-methoxyphenyl) piperazine; 2,6-dimethylpiperazine (either amine moiety); iminodibenzyl; 5-methoxytryptamine; 4,4'-bipiperidine; 1-(2-hydroxyethyl) piperazine; 4-methylpiperidine; and the like.

Importantly, the general structure of the present invention encompasses all states of saturation of the substitutents shown, such as all ene, diene, triene, and yne derivatives of any substitutent. The general structure also encompasses all conformational isomers, regioisomers, and stereoisomers that may arise from a particular set of substitutents. The general structure also encompasses all enantiomers, diastereomers, and other optical isomers whether in enantiomeric or racemic forms, or mixtures of stereoisomers.

Preparation of the Focused Library of Compounds

Many of the compounds of this invention were prepared in a parallel synthetic procedure according to the methods described below. Examples of compounds prepared by the parallel synthesis techniques are provided in Table 2. These preparations involve reacting the individual amine compounds (monomers) with cyanuric chloride, which are also presented in Table 2, along with the chemical structures of compounds prepared by the parallel synthesis methods.

A library of compounds was synthesized according to the present invention to afford substituted $N^2$, $N^4$, $N^6$-tris(amino)-1,3,5-triazines, as follows. The design of the compound library was based primarily on structure 95 shown below. That is, the design of the $N^2$, $N^4$, $N^6$-tris(amino) triazines was focused so that only one of the pendant amino groups ($N^A$, $N^B$, or $N^C$ in the structure above) was changed during each synthesis, while the other two groups were held constant. The combination of the specific amines employed produced a library of compounds of novel composition. Initially, the library was developed using methyl-(1-methyl-piperidin-4-yl)-amine, holding the cycloheptyl and m-fluoroanisidyl groups constant (in structure 95 below). The synthesis of the triazines around methyl-(1-methyl-piperidin-4-yl)-amine was not optimized, and the amine was subsequently replaced with (1-ethyl-pyrrolidin-2-yl)-methylamine which provided a more tractable synthesis.

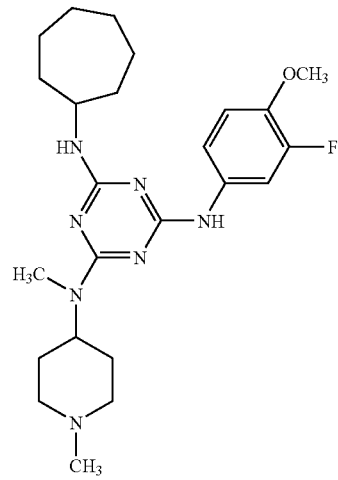

171

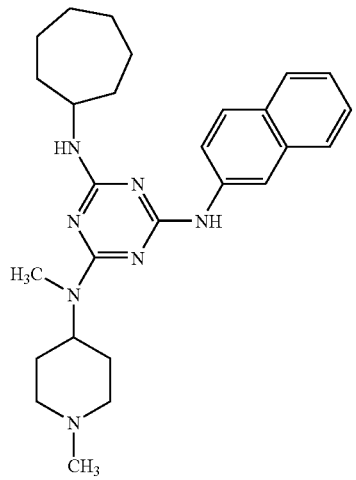

172

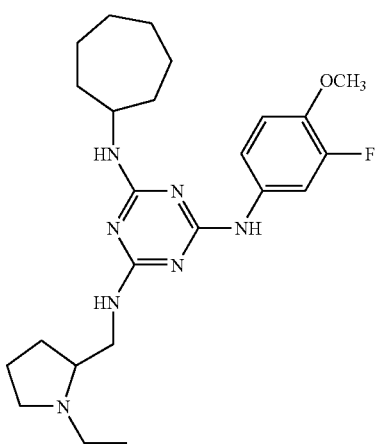

95

The library of $N^2$, $N^4$, $N^6$-tris(amino)-1,3,5-triazines was prepared based on the strategy of changing only one pendant amino group per synthesis, and based on the parent structure 95 shown above. The library was divided into three subgroups: Libraries I, II, and III (shown in Table 2). Library I includes compounds having unchanged $N^B$ and $N^C$ groups but different $N^A$ groups (6). The pendant amino group $N^A$ was changed according to the specific examples listed below. Library II includes compounds having unchanged $N^A$ and $N^C$ groups and different $N^B$ groups (7). Pendant amino group $N^B$ was changed according to the specific examples listed below. Library III includes compounds having unchanged $N^A$ and $N^B$ groups and different $N^C$ groups (8). The pendant amino group $N^C$ was changed according to the specific examples listed below.

The $N^2$, $N^4$, $N^6$-tris(amino)-1,3,5-triazine compound structures that are presented in Tables 2 and following were generated using ISIS-Draw™ version 2.4.0.20, and were generated with the option to display unspecified hydrogen atoms if not shown, however, not all hydrogen atoms were displayed in the structures shown. In all structures presented in any text, table, scheme or figure herein, any hydrogen atoms that are required for any atom to attain its usual valence, whether a carbon atom or a heteroatom, should be inferred if it is not specifically indicated in a structure.

One method of preparation of the compounds is shown in the scheme below. The compounds were prepared by reacting cyanuric chloride sequentially with monomers of primary or secondary amines to afford the desired 1,3,5-triazine derivatives [1,2,3,4]. Thus, the amine starting compounds that are used to react with cyanuric chloride are termed "monomers." The $N^2$, $N^4$, $N^6$-tris(amino-substituted)-1,3,5-triazines were prepared without the need for purification between each step of the synthesis, and the final product was isolated by standard procedures. Purification was accomplished using flash column chromatography as needed. It is within the skill of the art of organic synthesis to prepare, isolate and purify these organic compounds described herein, and to modify the syntheses shown. For example, it is possible to synthesize the compounds of the present invention by using an excess of any monomers of primary or secondary amines in any of the three steps shown in Scheme 1, such that the excess monomer, serves as both substituent for the triazine core, as well as a base, in which case i-Pr$_2$NEt base can be excluded.

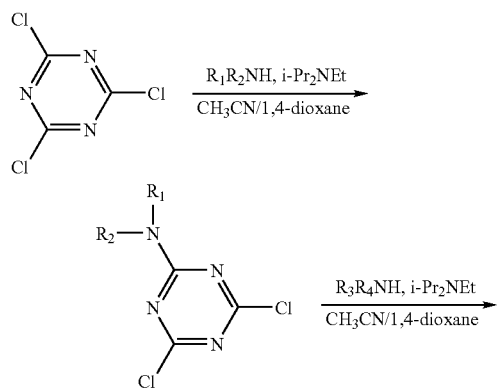

-continued

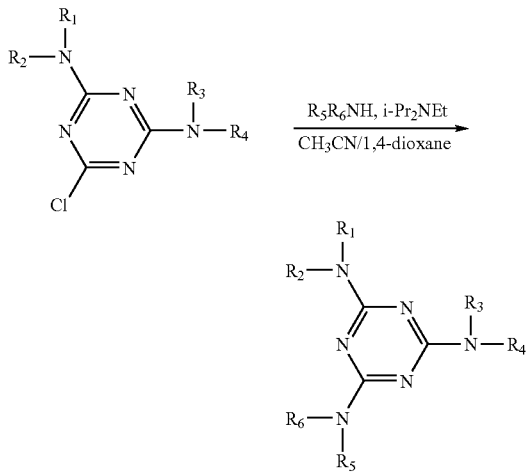

The pendant amino groups can be substituted by functional groups depicted as $R_1$ to $R_6$ groups in Scheme 1. The degree of functionality of a pendant amino group is determined by the structure and complexity of the amine monomer, and will affect the overall molecular diversity of the $N^2$, $N^4$, $N^6$-tris(amino-substituted)-1,3,5-triazines. A wide range of amine monomers may be used in this invention. Once bonded to the triazine core, the pendant amino groups can be described as secondary or tertiary substituted, depending on the degree of substitution at the nitrogen atom.

Table 2 presents charts of $N^2$, $N^4$, $N^6$-tris(amino)-1,3,5-triazine compounds of Libraries I-III of this invention, respectively, along with the amine precursor monomers used in the preparation of the compounds. General procedures and synthetic procedures are detailed in Example 1-5. The sequence in which each monomer is added in Scheme 1 is also presented in Table 2, where Monomer 1 is added first, Monomer 2 added second, and Monomer 3 is added third. While not intending to be bound by the following statement, it is believed that this order of addition is significant, because each synthetic step necessarily involves the reaction of a monomer with a different triazine precursor. That is, monomer 1 reacts with cyanuric chloride, monomer 2 reacts with an amino dichloro(triazine), and monomer 3 reacts with a diamino chloro(triazine), as shown in Scheme 1. Thus, the order in which the monomers are employed is based on the general synthetic principle that the relative nucleophilicity and/or basicity of monomers 1-3 used in the synthetic scheme should generally increase from monomer 1 to monomer 3. This strategy permits the most nucleophilic and/or basic amine monomer to be reacted with the more sterically congested and presumably less-reactive diamino chloro(triazine), where its greater reactivity may assist the reaction proceeding to completion. In some cases, more than one order of monomer addition will provide the desired product, but the reaction sequences provided in Table 2 represents the optimum synthetic methods presently known.

Note that only in a general sense do the substituents indicated as $N^A$, $N^B$, and $N^C$ in the general structures above correspond with the actual $N^2$, $N^4$, $N^6$-nomenclature of the $N^2$, $N^4$, $N^6$-tris(amino)triazines. Because the order in which $N^2$, $N^4$, and $N^6$ substituents are assigned a 2-, 4-, or 6-position on the triazine core is dependent on the name of each amino group in the molecule, it is not always true that one particular amino group always appears as an $N^2$, $N^4$, or $N^6$ substituent, even when only a single substituent is being permuted at one position. For example, many of the compounds of Table 2 contain both cycloheptyl amino and 3-fluoro-4-methoxyphenyl amino groups, yet these groups take on different 2-, 4-, or 6-positions as a function of the name of the third substituent on the triazine core. As a result, the syntheses are discussed in terms of permuting amino groups at one pendant $N^A$, $N^B$, or $N^C$ position (rather than $N^2$, $N^4$, or $N^6$ position) in the structure above, while maintaining the other amino groups constant. Further, note that the compound names used in the Tables, claims and specification were typically generated using Beilstein's Autonom™ 4.01.188, as well as the earlier CD "stand-alone" version of Beilstein's Autonom™, Autonom 2000. Typically, the compound names generated in this fashion were used, regardless of whether the compound name is an IUPAC, CAS, Beilstein, or other nomenclature. In each case however, the names unambiguously identify the compound specified.

A. Amino Groups Derived from Monomer 1

The sequence of monomer reaction with the triazine core, shown in Scheme 1, is Monomer 1, Monomer 2, and Monomer 3, added in that order. Thus, an amino dichloro (triazine) is formed from Monomer 1 and cyanuric chloride. For the first pendant amino group derived from Monomer 1 and cyanuric chloride, the Monomer 1 amine used and proposed included primarily, but not always, aryl amines, specifically phenyl, naphthyl, naphthylalkyl, quinolinyl, heteroaryl derivatives, and the like.

Specific examples of Monomer 1 used to produce the first pendant amino group in $N^2$, $N^4$, $N^6$-tris(amino-substituted)-1,3,5-triazines, and their [Chemical Abstract Registry numbers] include, but are not limited to, 4-chloroaniline [106-47-9], 3,4-ethylenedioxaniline [22013-33-8], 4-bromoanline [106-40-1], ethyl 4-aminobenzoate [94-09-7], 4-fluoro-aniline [371-40-4], 4-aminobiphenyl [92-67-1], 3-fluoroaniline [372-19-0], 2-aminonaphthalene [91-59-8], 3-chloroaniline [108-42-9], 4-morpholinoaniline [2524-67-6], 3-bromoaniline [591-19-5], 4'-aminoacetanilide [122-80-5], ethyl 3-aminobenzoate [582-33-2] m-aminoacetanilide [102-28-3], 2-fluoroaniline [348-54-9], m-anisidine [536-90-3], 2-chloroaniline [[95-51-2], p-phenetidine [156-43-4], 2-bromoaniline [615-36-1], 4-(methylthio)aniline [104-96-1], 3,4-(methylendioxy) aniline [14268-66-7], 2-aminopyridine [504-29-0], o-toluidine [95-53-4], 2,4-difluoro-N-methylaniline [138564-16-6], 4-phenoxyaniline [139-59-3], N-phenylglycinonitrile [3009-97-0], m-toluidine [108-44-1], 3-chloro-N-methylaniline [7006-52-2], p-toluidine 106-49-0], 2-(methylamino)benzotrifluoride, 4-chloro-N-methylaniline [932-96-7], 4-aminobenzonitrile [873-74-5], 3-anilinopropionitrile, [1075-76-9], tetracaine [94-24-6], N-methyl-p-anisidine [5961-59-1], 3-chloro-p-anisidine [5345-54-0], sulfabenzamide [127-71-9], 3-aminoquinoline [580-17-6], 1-amino-4-bromonaphthalene [2298-07-9], 6-aminoquinoline [580-15-4] 1-amino-4-chloronaphthalene, [4684-12-2] 8-aminoquinoline [578-66-5], S-(−)-1-(2-naphthyl)-ethylamine [3082-62-0], 3,4-dichloroaniline [95-76-1], 3,4-difluoroaniline [3863-11-4], N-methyl-4-(trifluoromethoxy)aniline [41419-59-4], 4-(trifluoromethoxy) aniline [461-82-5], 2-amino-4-methylthiophene-3-carboxamide [4651-97-2], N,N-diethyl-N'-phenethylenediamine [1665-59-4],1-(4-amino-phenyl)-4-methylpiperazine hydrochloride [94520-33-9], 2-chloro-N', N'-diethyl-1,4-phenylenediamine monohydrochloride [196938-07-5] 2-(dimethylamino)ethyl 4-aminobenzoate [11012-47-2], N,N-dimethyl-1,4-phenylenediamine [1665-95-4].

B. Amino Groups Derived from Monomer 2

The reaction of Monomer 2 with a preformed amino dichloro(triazine) provides an intermediate diamino chloro (triazine) in the synthesis of $N^2$, $N^4$, $N^6$-tris(amino-substituted)-1,3,5-triazines. Thus, for bonding the second pendant amino group to the triazine core, the Monomer 2 amine used and proposed included amines, specifically alkyl ($C_1$-$C_{12}$, straight chain or branched), cycloalkyl ($C_3$-$C_{10}$ ring size), azacyclo ($C_2$-$C_{10}$), and benzyl amine derivatives. The ring of the cycloalkyl and azacycloamine, and phenyl ring of the benzyl derivatives can be optionally substituted with one or more moieties, or a combination of moieties, such as, alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

In addition, any monomer described that has a stereocenter includes its enantiomers, diastereomers, and optical isomers whether in enantiomeric or racemic forms, or mixtures of stereoisomers. This is to include all of the 1,3,5-triazine derivatives and their stereoisomers presented herein that are formed as a result of using optically active, scalemic or racemic monomers.

Specific examples of Monomer 2 used to attach the second pendant amino group in the synthesis of $N^2$, $N^4$, $N^6$-tris(amino-substituted)-1,3,5-triazines, and their corresponding [Chemical Abstract Registry numbers] include, but are not limited to, ethylamine [75-04-07], cyclohexanemethylamine [3128-02-8] tert-butylamine [75-64-9], furfurylamine [617-89-0], benzylamine [100-46-9], 2,2,2-trifluoroethylamine [753-90-2], cyclooctylamine [5452-37-9N,N-dimethylethylenediamine cyclohexylamine [108-91-8], cyclopentylamine [1003-03-8], 1-(2-aminoethyl)-piperidine [26116-12-1], 1-acetylpiperazine [13096-96-3], pyrrolidine [123-75-1], 1-piperonylpiperazine [32231-06-4], hexamethyleneimine [111-49-9], 1-(2-pyridyl)piperazine [34803-66-2], decahydroquinoline (cis/trans) [2051-28-7], 1-methylpiperazine [109-01-3], 1-(3-aminopropyl)-imidazole [5036-48-6], ethyl 1-piperazine carboxylate [120-43-4], 4-methylcyclohexylamine (cis/trans) [6321-23-9], 1-(3-aminopropyl)-2-pyrrolidine [7663-77-6], 2-(aminomethyl)-ethy-lpyrrolidine [26116-12-1], (+)-S-2-(methoxymethyl) pyrrolidine [631-26-47-6], 1-(pyrrolidineo carbonylmethyl) piperazine [339890-45-4].

C. Amino Groups Derived from Monomer 3

The reaction of Monomer 3 with a preformed diamino chloro(triazine) provides the final step in the synthesis of $N^2$, $N^4$, $N^6$-tris(amino-substituted)-1,3,5-triazines. Thus, for bonding the third pendant amino group to the triazine core, the Monomer 3 used and proposed consisted of amines, specifically alkyl ($C_1$-$C_{12}$, straight chain or branched), cycloalkyl ($C_3$-$C_{10}$ ring size), azacyclo ($C_2$-$C_{10}$), and benzyl amine derivatives. The ring of these cycloalkyl-, azacycloamine, and phenyl ring of the benzyl derivatives can be optionally substituted with one or more moieties, or a combination of moieties such as groups as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like.

In addition, any monomer described that has a stereocenter includes its enantiomers, diastereomers, and optical isomers whether in enantiomeric or racemic forms, or mixtures of stereoisomers. This is to include all of the 1,3,5-triazine derivatives and their stereoisomers presented herein that are formed as a result of using optically active, scalemic or racemic monomers.

Specific examples of Monomer 3 used to attach the third pendant amino group in the synthesis of $N^2$, $N^4$, $N^6$-tris(amino-substituted)-1,3,5-triazines, and their corresponding [Chemical Abstract Registry numbers] used in the synthesis of the $N^2$, $N^4$, $N^6$-tris(amino-substituted)-1,3,5-triazine derivatives include, but are not limited to, ethylamine [75-04-07], cyclohexanemethylamine [3128-02-08], tert-butylamine [75-64-9], furfurylamine [617-89-0], benzylamine [100-46-9], 2,2,2-trifluroethylamine [753-90-2], cyclooctylamine [5452-37-9], N,N-dimethylethylenediamine, cyclohexylamine [108-91-8], cyclopentylamine [1003-03-8], 1-(2-aminoethyl)-piperidine, [26116-12-1], 1-acetylpiperazine [13096-96-3], pyrrolidine [123-75-1], 1-piperonylpiperazine [32231-06-4], hexamethyleneimine [111-49-9], 1-(2-pyridyl)piperazine [34803-66-2], decahydroquinoline (cis/trans) [2051-28-7], 1-methylpiperazine [109-01-3], 1-(3-aminopropyl)-imidazole [5036-48-6], ethyl 1-piperazine carboxylate [120-43-4], 4-methylcyclohexylamine (cis/trans) [6321-23-9], 1-(3-aminopropyl)-2-pyrrolidine [7663-77-6], 2-(aminomethyl)-ethyl-pyrrolidine [26116-12-1], (+)-S-2-(methoxymethyl) pyrrolidine [63126-47-6], 1-(pyrrolidineocarbonylmethyl) piperazine [339890-45-4].

In addition to the parallel synthetic procedures used to prepare the compounds of Table 2, Table 1 also provides other exemplary triazine compounds of the present invention, which were synthesized individually rather than using parallel syntheses. The complete preparation and properties of these compounds are presented in the Examples, where details of the synthetic procedures used are provided. The synthetic procedures for these compounds involve both the substitution of chloride groups on cyanuric chloride, as well as various chemical modifications of these groups once bonded to the trizine core. In particular, this invention also encompasses salts of the neutral triazine compounds, as provided in the Examples and the Tables.

In another aspect of this invention, compounds of the present invention include, but are not limited to, those having the following formula:

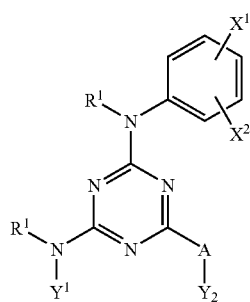

or an ene, a diene, a triene, or an yne derivative thereof; a saturated derivative thereof; a stereoisomer thereof; or a salt thereof; wherein:

$R^1$ is in each occurrence independently selected from —H; linear or branched alkyl with up to 10 carbon atoms; or cycloalkyl with up to 10 carbon atoms;

$X^1$ is selected from m-F, m-Cl, m-Br, m-I, m-CN, m-$NO_2$, m-$SO_2R^1$, or m-$SO_2OR^1$, or $X^1$ and $X^2$ together is a fused benzene, pyridine, or dioxane ring;

$X^2$ is selected from p-$OR^1$, p-$SR^1$, p-$NR^1_2$, p-OM, or p-SM, wherein M is selected from Li, Na, K, Mg, or Ca;

$Y^1$ is selected from cycloalkyl with up to 10 carbon atoms; linear or branched alkyl with up to 10 carbon atoms; $CH_2R^2$, wherein $R^2$ is a cycloalkyl with up to 10 carbon atoms; or

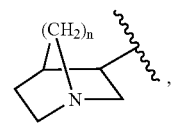

wherein n is 1 or 2;
$AY^2$ is selected from a halogen or $OR^1$, or
A is $NR^1$ and $Y^2$ is selected from $R^1$,

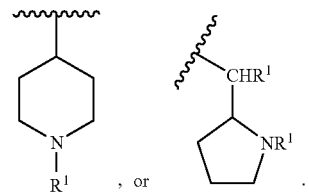

Compositions comprising compounds of this formula are also encompassed by the present invention, as well as mixtures or combinations of compounds of this formula.

In a further aspect of this invention, compounds of the present invention include, but are not limited to, those having the following formula:

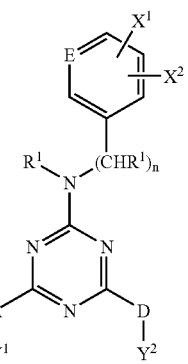

or an ene, a diene, a triene, or an yne derivative thereof; a saturated derivative thereof; a stereoisomer thereof; or a salt thereof; wherein:

$R^1$ is in each occurrence independently selected from —H; linear or branched alkyl with up to 10 carbon atoms; cycloalkyl with up to 10 carbon atoms; or aryl;

E is CH or N;

n is an integer from 0 to 3;

$X^1$ is selected from —H, m-F, m-Cl, m-Br, m-I, m-CN, m-$NO_2$, m-$SO_2R^1$, or m-$SO_2OR^1$, or $X^1$ and $X^2$ together is a fused benzene or pyridine ring;

$X^2$ is selected from —H, o-Cl, o-Br, p-$OR^1$, p-$SR^1$, p-$NR^1_2$, p-F, p-Cl, p-Br, p-$CF_3$, p-C(O)$OR^1$, p-OM, or p-SM, wherein M is selected from Li, Na, K, Mg, or Ca;

A is selected from NR$^1$ or O, wherein Y$^1$ is selected from cycloalkyl with up to 10 carbon atoms, linear or branched alkyl with up to 10 carbon atoms, or

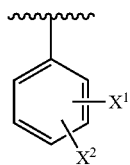

when A is NR$^1$, and wherein Y$^1$ is selected from R$^1$ or CH$^2$R$^1$ when A is O; or AY$^1$ is selected from a halogen,

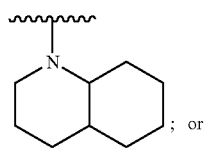 ; or 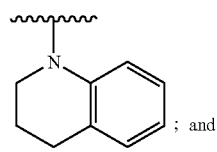 ; and

DY$^2$ is a halogen, or D is NR$^1$ and Y$^2$ is selected from

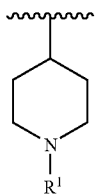 , 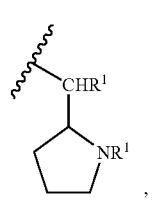 , or (CHR$^1$)$_x$NR$^1{}_2$, wherein x is an integer from 1 to 6.

Compositions comprising compounds of this formula are also encompassed by the present invention, as well as mixtures or combinations of compounds of this formula.

In yet another aspect of this invention, compounds of the present invention include, but are not limited to, those having the following formula:

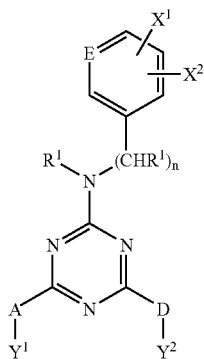

or an ene, a diene, a triene, or an yne derivative thereof, a saturated derivative thereof; a stereoisomer thereof; or a salt thereof; wherein:

R$^1$ is in each occurrence independently selected from —H; linear or branched alkyl with up to 10 carbon atoms; cycloalkyl with up to 10 carbon atoms; aryl; or (CH$_2$)$_x$CN, wherein x is an integer from 0 to 6;

E is CH or N;

n is an integer from 0 to 3;

X$^1$ is selected from —H, m-F, m-Cl, m-Br, m-I, m-CN, m-NO$_2$, m-SO$_2$R$^1$, m-SO$_2$OR$^1$, m-NC(O)R$^1$, or o-F, or X$^1$ and X$^2$ together is a fused benzene, pyridine, or dioxane ring;

X$^2$ is selected from —H, o-Cl, o-Br, o-CF$_3$, o-R$^1$, p-OR$^1$, p-SR$^1$, p-NR$^1{}_2$, p-F, p-Cl, p-Br, p-CF$_3$, p-CN, p-C(O)OR$^1$, p-NC(O)R$^1$, p-(4-morpholinyl), or p-(4-methyl-1-piperazinyl);

AY$^1$ is a halogen, or A is NR$^1$ or 0 and Y$^1$ is selected from cycloalkyl with up to 10 carbon atoms, cycloalkyl with up to 10 carbon atoms substituted with R$^1$, linear or branched alkyl with up to 10 carbon atoms, CH$_2$R$^1$, (CHR$^1$)$_y$OR$^1$, wherein y is an integer from 1 to 6,

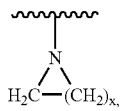

or AY$^1$ together are

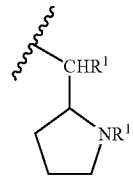

wherein x is an integer from 3 to 5; and

DY$^2$ is a halogen, or D is NR$^1$ and Y$^2$ is selected from

, cycloalkyl with up to 10 carbon atoms, cycloalkyl with up to 10 carbon atoms substituted with R$^1$, linear or branched alkyl with up to 10 carbon atoms, CH$_2$R$^1$,

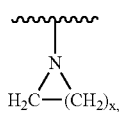

wherein x is an integer from 3 to 5,

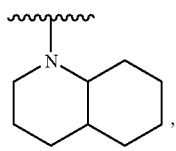

CH$_2$CF$_3$, (CHR$^1$)$_z$Z$^1$, wherein z is an integer from 1 to 6, and Z$^1$ is selected from NR$^1{}_2$,

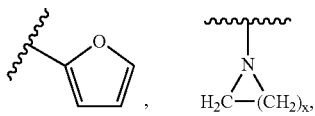

wherein x is an integer from 3 to 5,

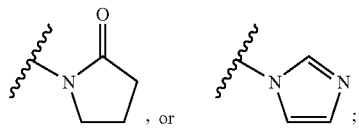

or NY$^2$R$^1$ together is selected from

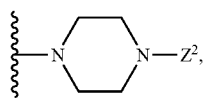

wherein Z$^2$ is selected from R$^1$, C(O)R$^1$, C(O)OR$^1$, pyridinyl, aryl,

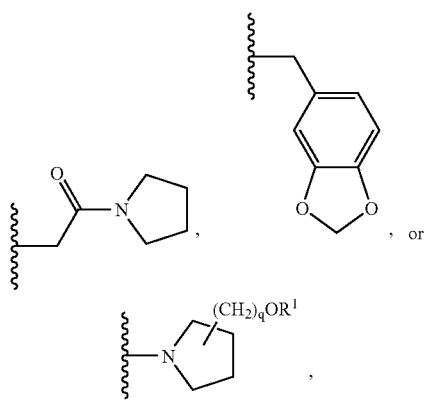

wherein q is an integer from 0 to 6.

Compositions comprising compounds of this formula are also encompassed by the present invention, as well as mixtures or combinations of compounds of this formula.

As an additional aspect of this invention includes compounds of the present invention include, but are not limited to, those having the following formula:

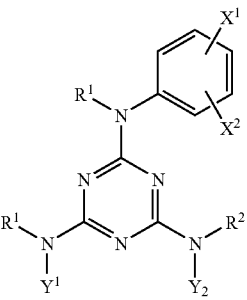

or an ene, a diene, a triene, or an yne derivative thereof; a saturated derivative thereof; a stereoisomer thereof; or a salt thereof;

wherein:

R$^1$ is in each occurrence independently selected from —H; linear or branched alkyl with up to 10 carbon atoms; or cycloalkyl with up to 10 carbon atoms;

X$^1$ is selected from H, m-F, m-Cl, m-Br, m-I, m-CN, m-NO$_2$, m-SO$_2$R$^1$, or m-SO$_2$OR$^1$;

X$^2$ is selected from o-R$^1$, p-OR$^1$, p-SR$^1$, p-NR$^1{}_2$, p-OM, or p-SM, wherein M is selected from Li, Na, K, Mg, or Ca;

Y$^1$ is selected from cycloalkyl with up to 10 carbon atoms or

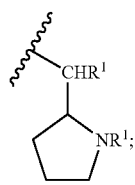

and

Y$^2$ is selected from linear or branched alkyl with up to 10 carbon atoms, cycloalkyl with up to 10 carbon atoms, or

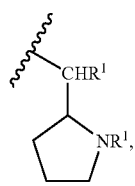

and R$^2$ is —H; or NY$^2$R$^2$ together is selected from

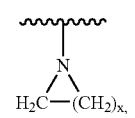

wherein x is an integer from 3 to 5,

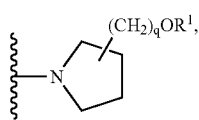

wherein q is an integer from 0 to 6, or

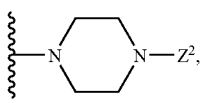

wherein $Z^2$ is selected from $R^1$ or

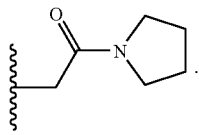

Compositions comprising compounds of this formula are also encompassed by the present invention, as well as mixtures or combinations of compounds of this formula.

In still another aspect of this invention, compounds of the present invention include, but are not limited to, those having the following structural formula:

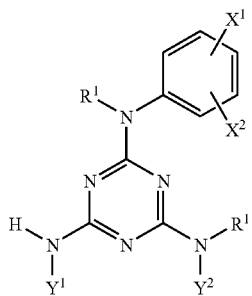

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is in each occurrence independently selected from —H, m-F, m-Cl, m-Br, m-I, m-CN, m-$NO_2$, m-$SO_2R^1$, or m-$SO_2OR^1$;

$X^2$ is in each occurrence independently selected from o-$CH_3$, p-$OR^1$, p-$SR^1$, p-$NR^1_2$, or p-OM or p-SM, wherein M is selected from Li, Na, K, Mg, or Ca;

$Y^1$ is selected from cycloalkyl with up to 10 carbon atoms;

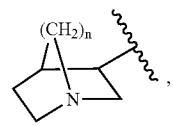

wherein n is 1 or 2; or

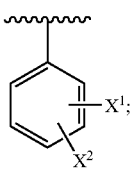

and
$Y^2$ is selected from

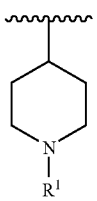 or 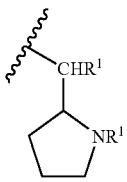

Compositions comprising compounds of this formula are also encompassed by the present invention, as well as mixtures or combinations of compounds of this formula.

These compounds and compositions presented above are not intended to be limiting, but merely representative of the chemical structures and formulas encompassed by the present invention.

Pharmaceutically Acceptable Salts

For the proposed $N^2$, $N^4$, $N^6$-tris(amino-substituted)-1,3,5-triazines, the terms "non-toxic, pharmaceutically acceptable salt" or "pharmaceutically acceptable salt" refer to a salt or complex of the 1,3,5-triazine compounds that retain or enhance the biologically activity of the compounds described in this invention. Examples of salts are those that are derived from the interaction of the 1,3,5-triazine compounds or derivatives and an inorganic (mineral acids) or organic acid, as well as compounds derived from deprotonating an amine nitrogen of the triamine derivatives.

Examples of inorganic acids include, but are not limited to, hydrochloric acid, hydrobromic acid, hydroiodic acid, hydrofluoric acid, nitric acid, nitrous acid, perchloric acid, chloric acid, hypochlorous acid, chlorous acid, phosphoric acid, sulfuric acid, sulfurous acid, and carbonic acid. Examples of organic acids include, but are not limited to acetic acid, benzene sulfonic acid, benzoic acid, butanoic acid, camphorsulfonic acid, citric acid, ethane sulfonic acid, fumaric acid, glutaric acid, 2-hydroxy acetic acid acids (derivatives where alkyl group is c=3-7 and hydroxy group is located accordingly), 2-hydroxy alkyl sulfonic acids (derivatives where alkyl group is c=3-7 and hydroxy group is located accordingly), lactic acid, maleic acid, malic acid malonic, methane sulfonic acid, naphthalene sulfonic acid, oxalic acid, palmitic acid, propanoic acid, phthalic acid, pyruvic acid, salicylic acid, stearic acid, succinic acid, tartaric acid, p-toluene sulfonic acid, and amino acids (e.g., alanine, N-acetylglycine, arginine, aspartic acid, glutamic acid, glycine, lysine, and phenylalanine).

Examples of salts described here include compounds that derive from a deprotonation reaction of an amine nitrogen of the triamine derivatives with a strong base, to form an amido salt, compound or complex. For example, these compounds include those that are derived from the interaction or chemical reaction of the 1,3,5-triazine compounds or derivatives acting as a Bronsted or Lewis acid and an inorganic or organic base to form an ionic and/or complexed species Examples of inorganic bases, include but not limited to, metallic bases or organometallic bases such as alkyllithiums or metal hydrides, where there is a metallic counterion include, but are not limited to, aluminum, barium, calcium, lithium, magnesium, potassium sodium, and zinc.

Examples of organic bases include, but are not limited to, alky and aryl amines as well as ammonia. Included in this description are salts formed from the combination or interaction/reaction of inorganic acids (e.g., Lewis acids) and metallic counterions and the 1,3,4-triazine compounds or derivatives acting as a Bronsted or Lewis base resulting in the formation of ionic and/or complexed species For all salts and complexes as described above, these are to include hydrated or solvated forms of the compounds.

Additionally, this invention also encompasses salts of these triazine derivatives that are non-toxic and pharmaceutically acceptable, such as quaternary ammonium salts, for example [—N+R₂R']X⁻, where the R and R' groups represent hydrogen or an organic group (such as alkyl, alkenyl, alkynyl, aryl, and the like) and the X group is a counter ion (halogen, hydroxide, alkoxide, thioalkoxide, or conjugate base of an organic or inorganic acid). For all salts and complexes as described above, these are to include hydrated or solvated forms of the compounds.

In another aspect of this invention, compounds of the present invention include, but are not limited to, those having the following formula:

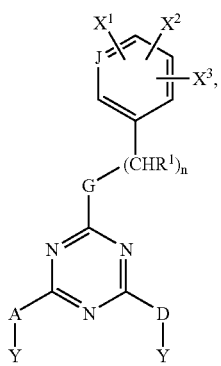

(Ic)

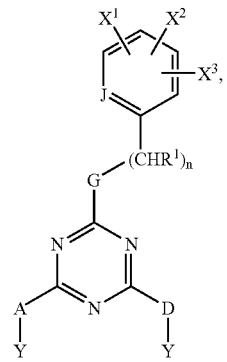

(IIc)

or an ene, a diene, a triene, or an yne derivative thereof; a saturated derivative thereof; a stereoisomer thereof; or a salt thereof;

wherein:

$R^1$ is in each occurrence independently selected from H; linear or branched alkyl with up to 10 carbon atoms; cycloalkyl with up to 10 carbon atoms; cycloalkenyl with up to 10 carbon atoms; benzyl; $O_2CR$, $C(O)R$, or $C(O)OR$ wherein R is H, or linear or branched alkyl with up to 10 carbon atoms; $CH_2NH_2$; $CH_2OH$; or aryl;

G is $NR^1$ or O;

J is CH or N;

n is an integer from 0 to 3;

$X^1$ is selected from o-$R^1$, m-$R^1$, m-$OR^1$, m-$OCF_3$, o-F, o-Cl, m-F, m-Cl, m-Br, m-I, m-$CF_3$, m-CN, m-$NO_2$, m-C(O)$OR^1$, C(O)OLi, C(O)ONa, m-$SO_2R^1$, m-NC(O)$R^1$, or m-$SO_2OR^1$; or $X^1$ and $X^2$ together is a fused benzene, pyridine, dioxane, or tetrahydropyran ring;

$X^2$ is selected from o-$R^1$; p-$R^1$; p-$OR^1$; p-$OCF_3$; o-F; o-Cl; o-Br; o-I; o-$CF_3$; m-F; m-Cl; m-Br; m-I; m-CN; m-$CF_3$; m-$OCF_3$; p-$SR^1$; p-$NR^1_2$; p-F; p-Cl; p-Br; p-$CF_3$; p-$OCF_3$; p-C(O)$OR^1$; p-OC(O)$R^1$; p-CN; p-$NO_2$; p-NC(O)$R^1$; o-C≡CC(CH₃)₂$OR^1$; p-C≡CC(CH₃)₂$OR^1$; p-OM, p-SM, m-C(O)OM, or p-C(O)OM wherein M is selected from Li, Na, K, Mg, or Ca; p-O(CH₂)ₘZ$R^1$ wherein m is an integer from 0 to 3 and Z is selected from O, S, —S(O)—, —SO₂—, —OP(O)(OH)O—, —P(O)(OH)O—, or —C(O)—; p-OC(O)(CH₂CH₂O)ᵣ$R^1$ or p-O(CH₂CH₂O)ᵣ$R^1$ wherein r is from 0 to 6;

$X^3$ is o-$R^1$, m-$R^1$, p-$R^1$, o-$OR^1$, m-$OR^1$, or p-$OR^1$; or $X^2$ and $X^3$ together is a fused benzene, pyridine, dioxane, or tetrahydropyran ring;

AY and DY are independently selected from $OR^1$; F; Cl; Br; I;

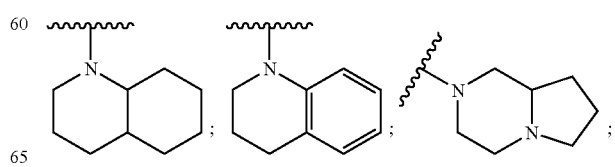

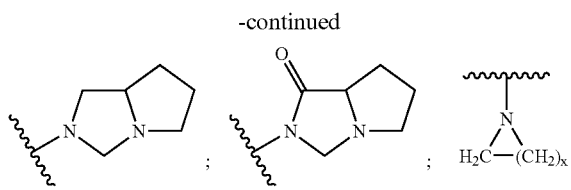
wherein x is an integer from 3 to 5;
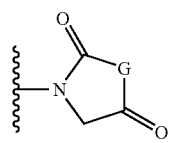
wherein G is selected from NH, CH$_2$ or SH; or
A and D are independently selected from O or NR$^1$; and
Y is in each occurrence independently selected from R$^1$; (CHR$^1$)$_q$R$^1$;
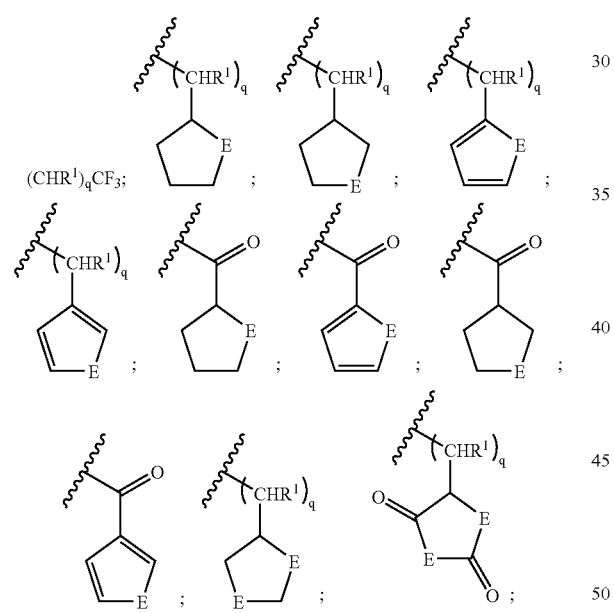
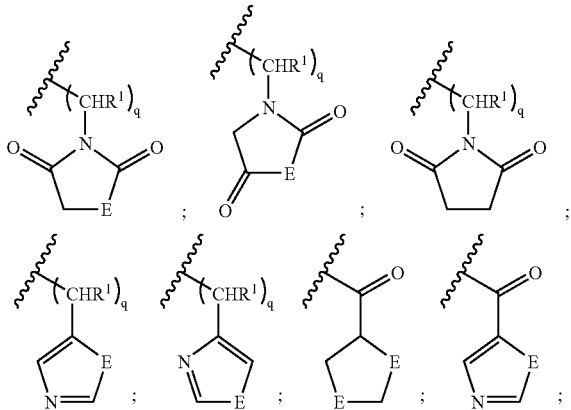
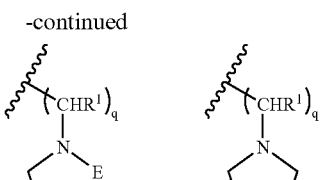
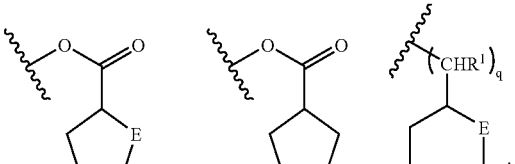
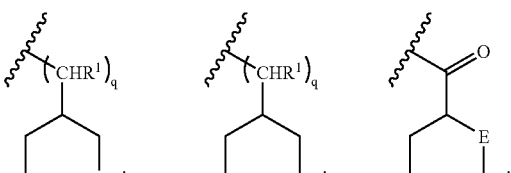
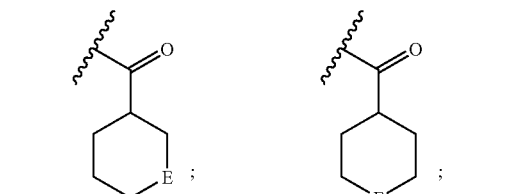
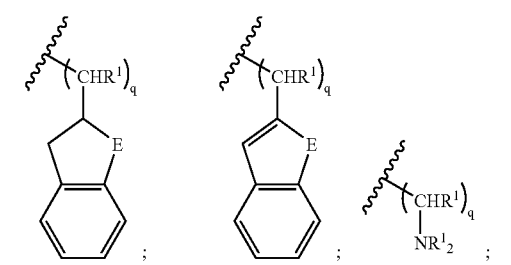
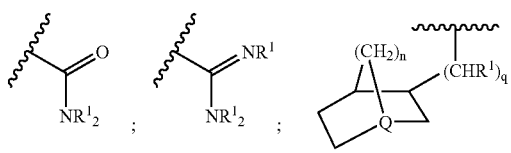
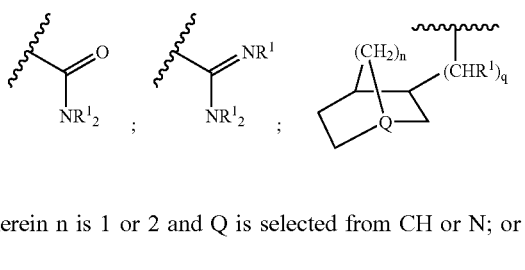
wherein n is 1 or 2 and Q is selected from CH or N; or
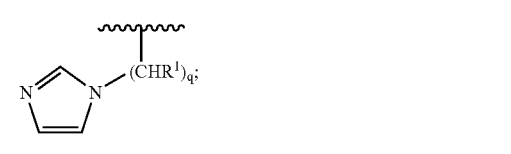

wherein q is an integer from 0 to 3 and E is in each occurrence independently selected from NR$^1$, O, S, C=O, or C=NR$^1$;

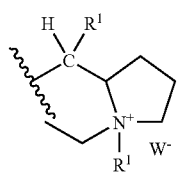 or 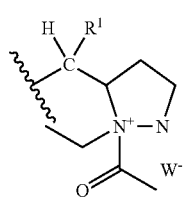

wherein W$^-$ is selected from Cl$^-$, Br$^-$, I$^-$, [O$_2$CCH$_2$CH$_2$CO$_2$R$^1$]$^-$, [O$_2$CCHCHCO$_2$R$^1$]$^-$, or [O$_2$CCF$_3$]$^-$;

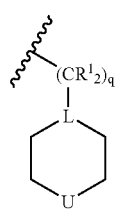

wherein q is an integer from 0 to 3, L is selected from CH or N, and U is selected from O, NR$^1$, S, SO$_2$, CHR$^1$, or CHOH;

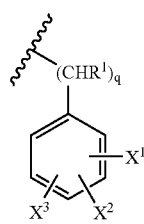

wherein p is an integer from 0 to 3 and X$^1$, X$^2$, and X$^3$ are selected as defined above;

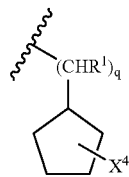

wherein q is an integer from 0 to 3 and X$^4$ is selected from H, 2-R$^1$, 3-R$^1$, 2-OH, 3-OH, 2-NH$_2$, or 3-NH$_2$;

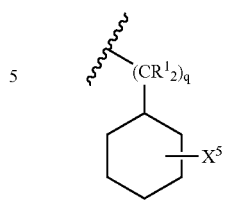

wherein q is an integer from 0 to 3 and X$^5$ is selected from 2-R$^1$, 3-R$^1$, 4-R$^1$, 2-OH, 3-OH, 4-OH, 2-NH$_2$, 3-NH$_2$, or 4-NH$_2$;

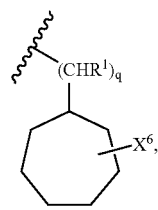

wherein q is an integer from 0 to 3 and X$^6$ is selected from H, 2-R$^1$, 3-R$^1$, 4-R$^1$, 2-OH, 3-OH, 4-OH, 2-NH$_2$, 3-NH$_2$, or 4-NH$_2$;

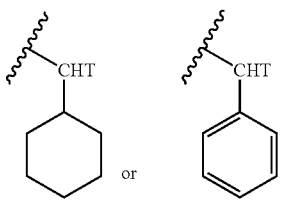

wherein T is selected from CO$_2$H, CH$_2$OH, or (CHR$^1$)$_x$NR$^1$$_2$ wherein x is an integer from 1 to 6;
CH$_2$R$^1$; CH$_2$CF$_3$; C(O)CHR$^1$NH$_2$; CHR$^1$CH$_2$OH; (CHR$^1$)$_x$NR$^1$$_2$ wherein is an integer from 1 to 6;
C(O)Z$^1$ or (CHR$^1$)$_z$Z$^1$ wherein z is an integer from 0 to 6 and Z$^1$ is selected from NR$^1$$_2$;

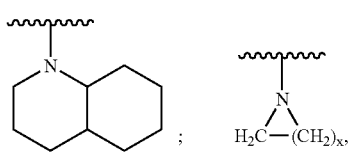

wherein x is an integer from 3 to 5;

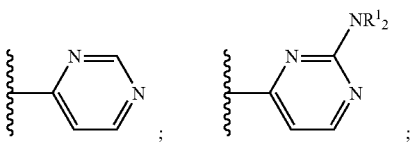

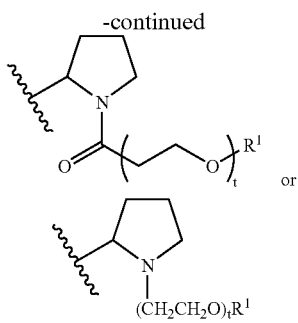

wherein t is from 0 to 6.

In still another aspect of this invention, compounds of the present invention include, but are not limited to, those having the following formula:

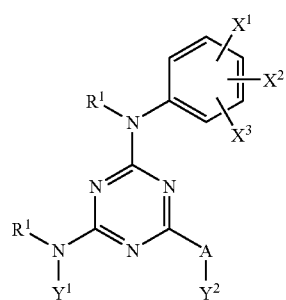
(IIIc)

or an ene, a diene, a triene, or an yne derivative thereof; a saturated derivative thereof; a stereoisomer thereof; or a salt thereof;

wherein:
- $R^1$ is in each occurrence independently selected from —H, linear or branched alkyl with up to 10 carbon atoms, cycloalkyl with up to 10 carbon atoms, aryl, or benzyl;
- $X^1$ and $X^2$ are independently selected from H, m-F, m-Cl, m-Br, m-I, m-CF$_3$, m-CN, m-NO$_2$, m-SO$_2$R$^1$, or m-SO$_2$OR$^1$, or $X^1$ and $X^2$ together is a fused benzene, pyridine, or dioxane ring;
- $X^3$ is selected from p-R$^1$, p-OR$^1$, p-OCF$_3$, p-SR$^1$, p-NR$^{12}$, p-OM or p-SM wherein M is selected from Li, Na, K, Mg, or Ca, p-O(CH$_2$)$_m$ZR$^1$ wherein m is an integer from 0 to 3 and Z is selected from O, S, —S(O)—, —SO$_2$—, —OP(O)(OH)O—, —P(O)(OH)O—, or —C(O)—;
- $Y^1$ is selected from cycloalkyl with up to 10 carbon atoms; linear or branched alkyl with up to 10 carbon atoms; CH$_2$R$^2$, wherein R$^2$ is a cycloalkyl with up to 10 carbon atoms; or

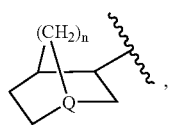

wherein n is 1 or 2 and Q is selected from CH or N;

AY$^2$ is selected from OR$^1$, F, Cl, Br, I,

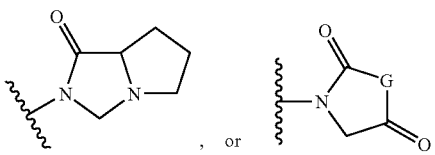
, or wherein G is selected from NH, CH$_2$, or SH, or A is O or NR$^1$ and Y$^2$ is selected from R$^1$;

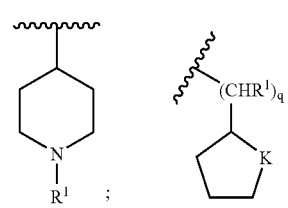

wherein q is an integer from 0 to 3 and K is selected from NR$^1$, O, or S;

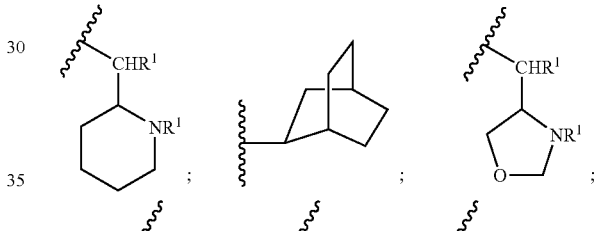

wherein T is selected from O, S, or NR$^1$;

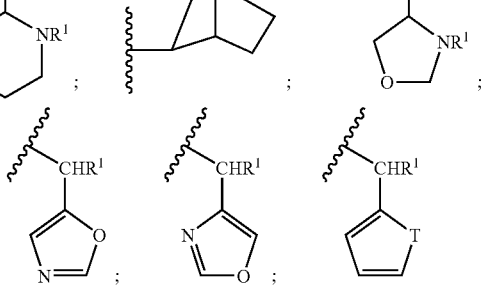

wherein W$^-$ is selected from Cl$^-$, Br$^-$, I$^-$, [O$_2$CCH$_2$CH$_2$CO$_2$R$^1$]$^-$, [O$_2$CCHCHCO$_2$R$^1$]$^-$, [O$_2$CCF$_3$]$^-$;

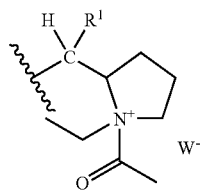

wherein W⁻ is selected from Cl⁻, Br⁻, I⁻, [O₂CCH₂CH₂CO₂R¹]⁻, [O₂CCHCHCO₂R¹]⁻, [O₂CCF₃]⁻; —C(O)CHR¹NH₂; or —CHR¹CH₂OH.

Compositions comprising compounds of this formula are also encompassed by the present invention, as well as mixtures or combinations of compounds of this formula.

In yet another aspect of this invention, compounds of the present invention include, but are not limited to, those having the following formula:

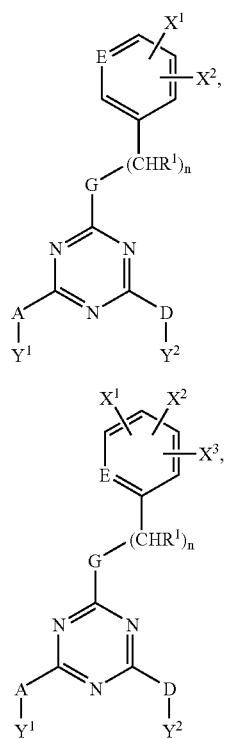

or an ene, a diene, a triene, or an yne derivative thereof; a saturated derivative thereof; a stereoisomer thereof; or a salt thereof;

wherein:
R¹ is in each occurrence independently selected from —H; linear or branched alkyl with up to 10 carbon atoms; cycloalkyl with up to 10 carbon atoms; cycloalkenyl with up to 10 carbon atoms; benzyl; O₂CH; CH₂NH₂; CH₂OH; or aryl;
G is NR¹, O, or S;
E is CH or N;
n is an integer from 0 to 3;
X¹ is selected from —H, o-F, m-F, m-Cl, m-Br, m-I, m-CN, m-NO₂, m-C(O)OR¹, C(O)OLi, C(O)ONa, m-SO₂R¹, or m-SO₂OR¹, or X¹ and X² together is a fused benzene or pyridine ring;
X² is selected from —H, o-Cl, o-Br, p-OR¹, p-SR¹, p-NR¹₂, p-F, p-Cl, p-Br, p-CF₃, p-C(O)OR¹, p-OM, or p-SM, wherein M is selected from Li, Na, K, Mg, or Ca;
X³ is H or X² and X³ together is a fused benzene, pyridine, or tetrahydropyran ring;
A is selected from NR¹ or O, wherein Y¹ is selected from H, cycloalkyl with up to 10 carbon atoms, linear or branched alkyl with up to 10 carbon atoms, or

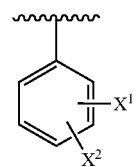

when A is NR¹, and wherein Y¹ is selected from R¹ or CH₂R¹ when A is O; or AY¹ is selected from a halogen,

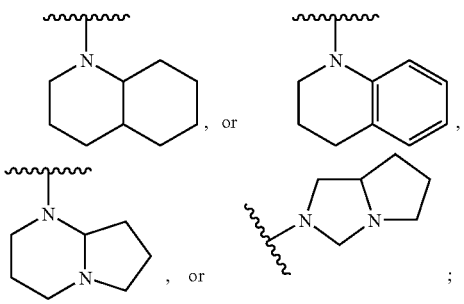

and
DY² is a halogen, or D is NR¹ and Y² is selected from R¹;

wherein m is an integer from 0 to 3, K is selected from CH or N, and Q is selected from O, NR¹, S, SO₂, CHR¹, or CHOH;

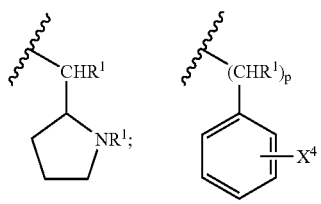

wherein p is an integer from 0 to 3 and $X^4$ is selected from H, p-$OR^1$, p-$NO_2$, or p-F;

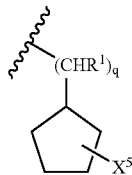

wherein q is an integer from 0 to 3 and $X^5$ is selected from H, 2-OH, 3-OH, 2-$NH_2$, or 3-$NH_2$;

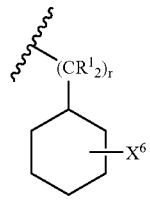

wherein r is an integer from 0 to 3 and $X^6$ is selected from 2-$R^1$, 3-$R^1$, 4-$R^1$, 2-OH, 3-OH, 4-OH, 2-$NH_2$, 3-$NH_2$, or 4-$NH_2$; or

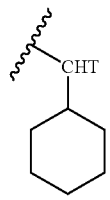

wherein T is selected from $CO_2H$ or $CH_2NH_2$; $(CHR^1)_x$ $NR^1{}_2$ wherein x is an integer from 1 to 6.

Compositions comprising compounds of this formula are also encompassed by the present invention, as well as mixtures or combinations of compounds of this formula.

In another aspect of this invention, compounds of the present invention include, but are not limited to, those having the following formula:

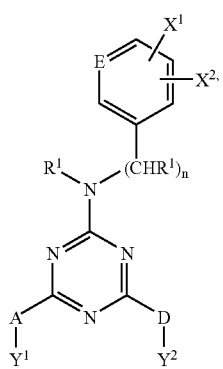

(VIc)

or an ene, a diene, a triene, or an yne derivative thereof; a saturated derivative thereof; a stereoisomer thereof; or a salt thereof;

wherein:
$R^1$ is in each occurrence independently selected from —H; linear or branched alkyl with up to 10 carbon atoms; cycloalkyl with up to 10 carbon atoms; benzyl; aryl; or $(CH_2)_xCN$, wherein x is an integer from 0 to 6;

E is CH or N;

n is an integer from 0 to 3;

$X^1$ is selected from —H, m-F, m-Cl, m-Br, m-I, m-CN, m-$NO_2$, m-$SO_2R^1$, m-$SO_2OR^1$, m-$NC(O)R^1$, or o-F, or $X^1$ and $X^2$ together is a fused benzene, pyridine, or dioxane ring;

$X^2$ is selected from —H, o-Cl, o-Br, o-$CF_3$, o-$R^1$, p-$OR^1$, p-$SR^1$, p-$NR^1{}_2$, p-F, p-Cl, p-Br, p-$CF_3$, p-CN, p-C(O)$OR^1$, p-$NC(O)R^1$, p-(4-morpholinyl), p-(4-methyl-1-piperazinyl), p-$OC(O)(CH_2CH_2O)_rR^1$ wherein r is from 0 to 6, p-$O(CH_2CH_2O)_sR^1$ wherein s is from 0 to 6, or p-OM wherein M is selected from Li, Na, K or Mg;

$AY^1$ is a halogen, or A is $NR^1$ or O and $Y^1$ is selected from cycloalkyl with up to 10 carbon atoms, cycloalkyl with up to 10 carbon atoms substituted with $R^1$, linear or branched alkyl with up to 10 carbon atoms, $CH_2R^1$, $(CHR^1)_yOR^1$, wherein y is an integer from 1 to 6,

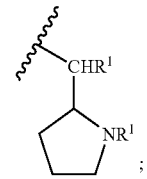

or $AY^1$ together are

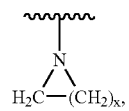

wherein x is an integer from 3 to 5; and $DY^2$ is selected from F; Cl; Br; I; or

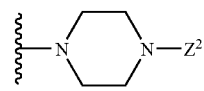

wherein $Z^2$ is selected from $R^1$, $C(O)R^1$, $C(O)OR^1$, pyridinyl, aryl,

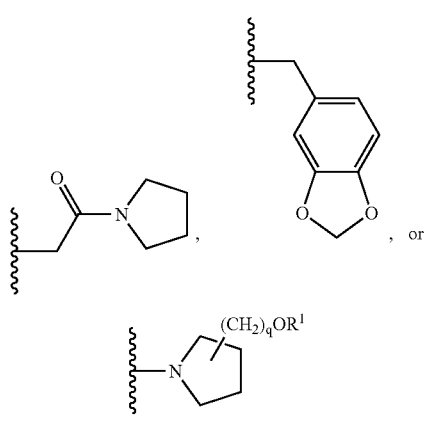

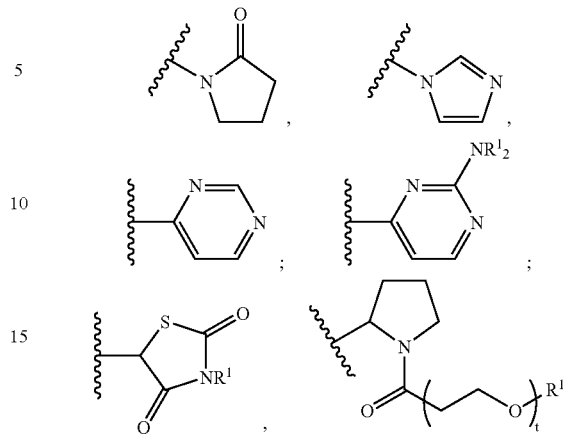

wherein q is an integer from 0 to 6; or

D is $NR^1$ and $Y^2$ is selected from

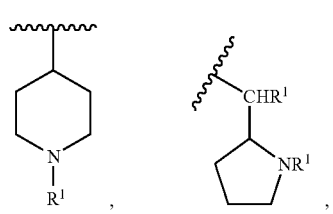

where t is from 0-6, or

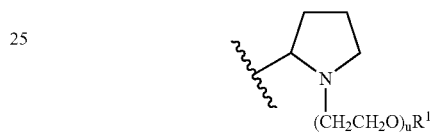

wherein u is from 0 to 6.

Compositions comprising compounds of this formula are also encompassed by the present invention, as well as mixtures or combinations of compounds of this formula.

In still another aspect of this invention, compounds of the present invention include, but are not limited to, those having the following formula:

cycloalkyl with up to 10 carbon atoms, cycloalkyl with up to 10 carbon atoms substituted with $R^1$, linear or branched alkyl with up to 10 carbon atoms, $CH_2R^1$,

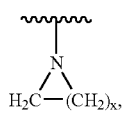

wherein x is an integer from 3 to 5,

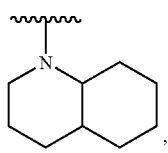

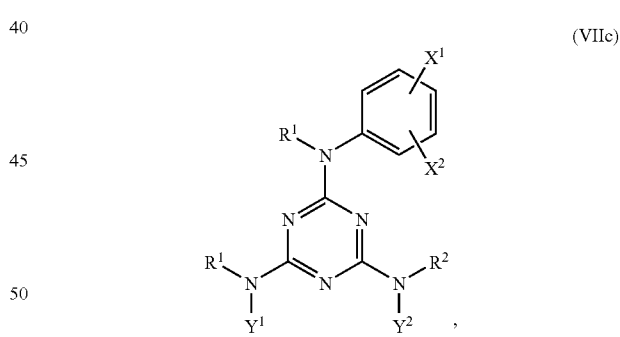

(VIIc)

$CH_2CF_3$, $(CHR^1)_zZ^1$ wherein z is an integer from 0 to 6 and $Z^1$ is selected from $NR^1_2$,

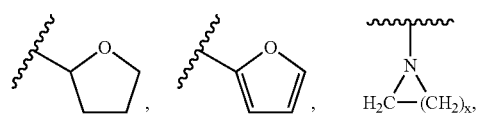

wherein x is an integer from 3 to 5, or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; cycloalkyl with up to 10 carbon atoms; benzyl; or aryl;

$X^1$ is selected from H, m-F, m-Cl, m-Br, m-I, m-CN, m-$NO_2$, m-$SO_2R^1$, or m-$SO_2OR^1$;

$X^2$ is selected from o-$R^1$, p-$OR^1$, p-$SR^1$, p-$NR^1_2$, p-OM, or p-SM, wherein M is selected from Li, Na, K, Mg, or Ca;

Y$^1$ is selected from cycloalkyl with up to 10 carbon atoms or

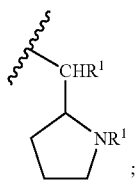

and

Y$^2$ is selected from linear or branched alkyl with up to 10 carbon atoms, cycloalkyl with up to 10 carbon atoms, or

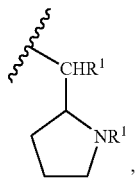

and R$^2$ is —H; or NY$^2$R$^2$ together is selected from

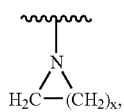

wherein x is an integer from 3 to 5,

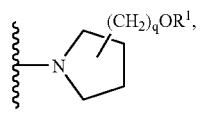

wherein q is an integer from 0 to 6,

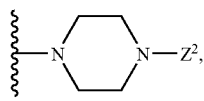

wherein Z$^2$ is selected from R$^1$ or

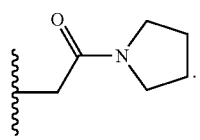

Compositions comprising compounds of this formula are also encompassed by the present invention, as well as mixtures or combinations of compounds of this formula.

In another aspect of this invention, compounds of the present invention include, but are not limited to, those having the following formula:

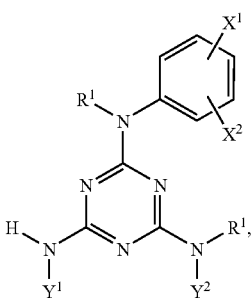

(VIIIc)

or an ene, a diene, a triene, or an yne derivative thereof; a saturated derivative thereof; a stereoisomer thereof; or a salt thereof;

wherein:

R$^1$ is in each occurrence independently selected from —H; linear or branched alkyl with up to 10 carbon atoms; cycloalkyl with up to 10 carbon atoms; benzyl; or aryl;

X$^1$ is in each occurrence independently selected from —H, m-F, m-Cl, m-Br, m-I, m-CN, m-NO$_2$, m-SO$_2$R$^1$, or m-SO$_2$OR$^1$;

X$^2$ is in each occurrence independently selected from o-CH$_3$, p-OR$^1$, p-SR$^1$, p-NR$^1$$_2$, or p-OM or p-SM, wherein M is selected from Li, Na, K, Mg, or Ca;

Y$^1$ is selected from cycloalkyl with up to 10 carbon atoms;

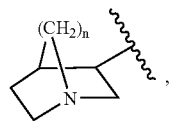

wherein n is 1 or 2; or

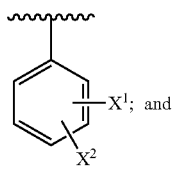

and

Y$^2$ is selected from

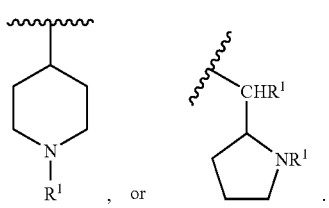

Compositions comprising compounds of this formula are also encompassed by the present invention, as well as mixtures or combinations of compounds of this formula.

In yet another aspect of this invention, compounds of the present invention include, but are not limited to, those having the following formula:

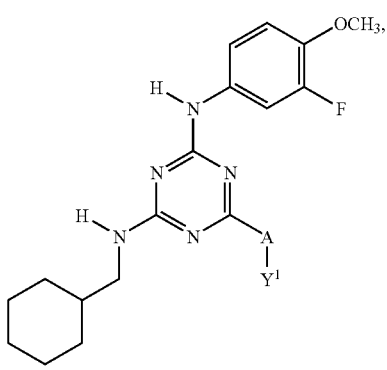

(IXc)

wherein

AY$^1$ is selected from OR$^1$; F; Cl; Br; I;

wherein G is selected from NH, CH$_2$, O, or S;

wherein x is an integer from 3 to 5; or

A is O or NR$^1$ and Y$^1$ is selected from R$^1$;

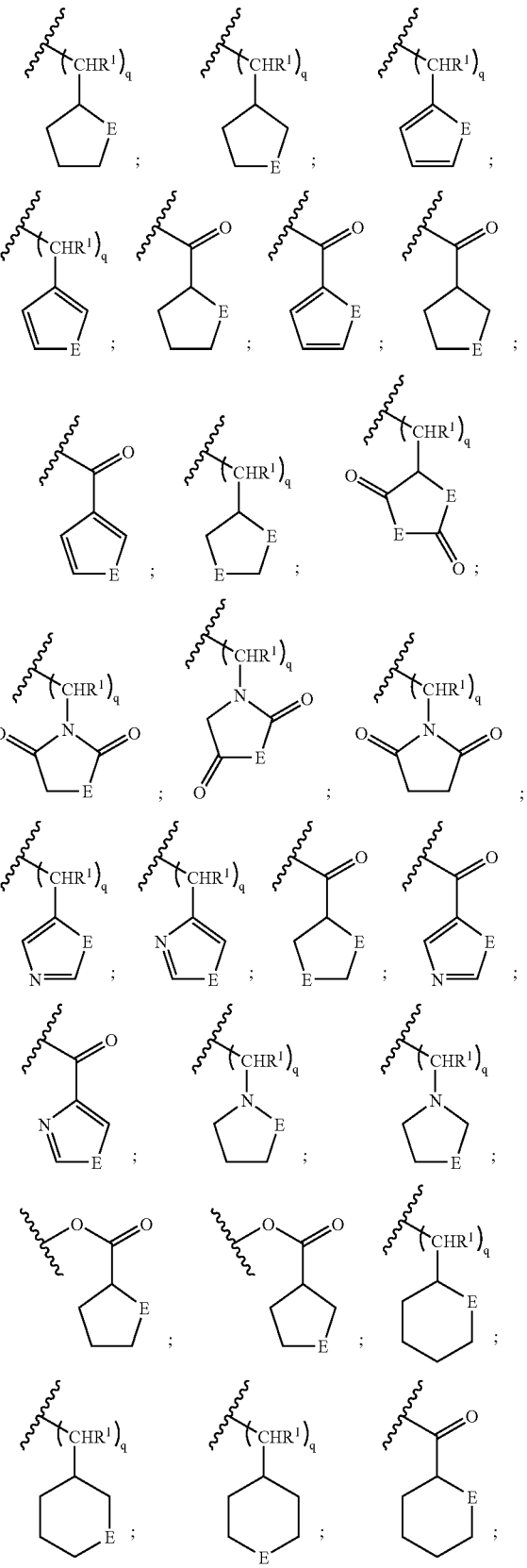

-continued

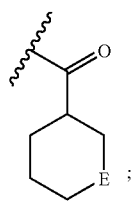 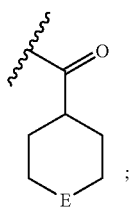 ;

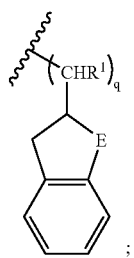 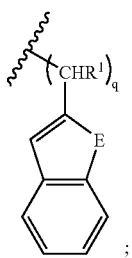 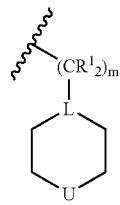 ;

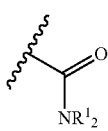 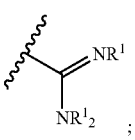 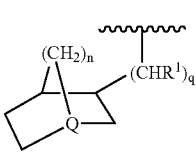

wherein n is 1 or 2 and Q is selected from CH or N; or

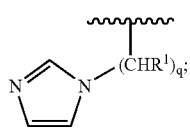

wherein q is an integer from 0 to 3 and E is in each occurrence independently selected from $NR^1$, O, S, C=O, or $C=NR^1$;

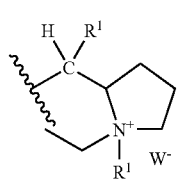 or 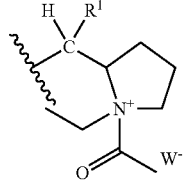

wherein $W^-$ is selected from $Cl^-$, $Br^-$, $I^-$, $[O_2CCH_2CH_2CO_2R^1]^-$, $[O_2CCHCHCO_2R^1]^-$, or $[O_2CCF_3]^-$;

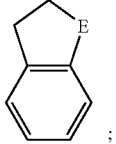

wherein m is an integer from 0 to 3, L is selected from CH or N, and U is selected from O, $NR^1$, S, $SO_2$, $CHR^1$, or CHOH;

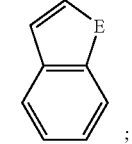

wherein p is an integer from 0 to 3 and $X^4$ is selected from H, p-$OR^1$, p-$NO_2$, or p-F;

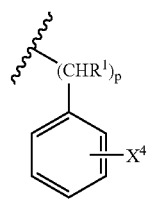

wherein q is an integer from 0 to 3 and $X^5$ is selected from H, 2-$R^1$, 3-$R^1$, 2-OH, 3-OH, 2-$NH_2$, or 3-$NH_2$;

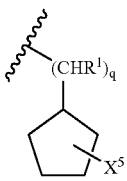

wherein r is an integer from 0 to 3 and $X^6$ is selected from 2-$R^1$, 3-$R^1$, 4-$R^1$, 2-OH, 3-OH, 4-OH, 2-$NH_2$, 3-$NH_2$, or 4-$NH_2$;

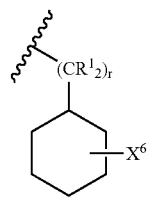

wherein T is selected from $CO_2H$, $CH_2OH$, or $CH_2NH_2$;
$CH_2R^1$; $CH_2CF_3$; $C(O)CHR^1NH_2$; $CHR^1CH_2OH$; $(CHR^1)_xNR^1{}_2$ wherein x is an integer from 1 to 6;
$C(O)Z^1$ or $(CHR^1)_zZ^1$ wherein z is an integer from 0 to 6 and $Z^1$ is selected from $N^1{}_2$;

wherein x is an integer from 3 to 5;

wherein t is from 0 to 6;
wherein $R^1$ is in each occurrence independently selected from —H; linear or branched alkyl with up to 10 carbon atoms; cycloalkyl with up to 10 carbon atoms; cycloalkenyl with up to 10 carbon atoms; benzyl; $O_2CR$, $C(O)R^1$, or $C(O)OR$ wherein R is H, $CH_3$, or $C(CH_3)_3$; $CH_2NH_2$; $CH_2OH$; or aryl.

Compositions comprising compounds of this formula are also encompassed by the present invention, as well as mixtures or combinations of compounds of this formula.

In still another aspect of this invention, compounds of the present invention include, but are not limited to, those having the following formula:

(Xc)

A is selected from or an ene, diene, or saturated derivative thereof;
$R^1$ is in each occurrence independently selected from —H; linear or branched alkyl with up to 10 carbon atoms; cycloalkyl with up to 10 carbon atoms; cycloalkenyl with up to 10 carbon atoms; benzyl; $O_2CH$; $CH_2NH_2$; $CH_2OH$; or aryl;

G is $NR^1$, O, or S;

E is CH or N;

n is an integer from 0 to 3;

$X^1$ is selected from —H; o-F; m-F; m-Cl; m-Br; m-I; m-CN; m-$NO_2$; m-$C(O)OR^1$; C(O)OM wherein M is selected from Li, Na, K, Mg, or Ca; m-$SO_2R^1$; m-NC$(O)R^1$; or m-$SO_2OR^1$; or $X^1$ and $X^2$ together is a fused benzene, pyridine, dioxane, or tetrahydropyran ring;

$X^2$ is selected from —H; o-Cl; o-$CF_3$; o-$R^1$; o-Br; p-$R^1$; p-$OR^1$; p-$SR^1$; p-$NR^{12}$; p-F; p-Cl; p-Br; p-$CF_3$; p-$OCF_3$; p-$C(O)OR^1$; p-CN; p-$NC(O)R^1$; p-(4-morpholinyl); p-(4-methyl-1-piperazinyl); p-OC(O)$(CH^2CH_2O)_rR^1$ wherein r is from 0 to 6; p-O$(CH^2CH_2O)_sR^1$ wherein s is from 0 to 6; p-OM or p-SM wherein M is selected from Li, Na, K, Mg, or Ca; p-O$(CH^2)_mZR^1$ wherein m is an integer from 0 to 3 and Z is selected from O, S, —S(O)—, —$SO_2$—, —OP(O)(OH)O—, —P(O)(OH)O—, or —C(O)—; m-F, m-Cl, m-Br, m-I, m-CN, m-$NO_2$, m-$SO_2R^1$, m-$SO_2OR^1$, m-$NC(O)R^1$, and $X^3$ is H or $X^2$ and $X^3$ together is a fused benzene, pyridine, or tetrahydropyran ring.

Compositions comprising compounds of this formula are also encompassed by the present invention, as well as mixtures or combinations of compounds of this formula.

In another aspect of this invention, compounds of the present invention include, but are not limited to, those having the following formula:

(XIc)

A is O or $NR^1$ and $Y^1$ is selected from $R^1$;

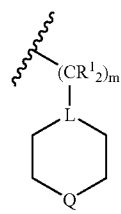

wherein m is an integer from 0 to 3; L is selected from CH or N; and Q is selected from O, $NR^1$, S, $SO_2$, $CHR^1$, or CHOH;

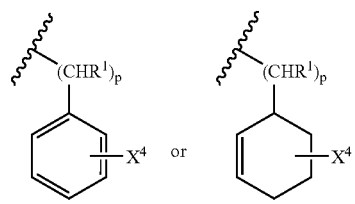

wherein p is an integer from 0 to 3 and $X^4$ is selected from H, $p\text{-}OR^1$, $p\text{-}NO_2$, or p-F;

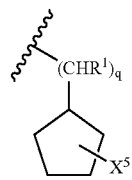

wherein q is an integer from 0 to 3 and $X^5$ is selected from H, $2\text{-}R^1$, $3\text{-}R^1$, 2-OH, 3-OH, $2\text{-}NH_2$, or $3\text{-}NH_2$;

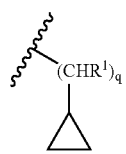

wherein q is an integer from 0 to 3;

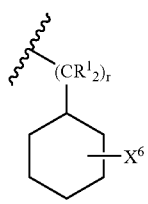

wherein r is an integer from 0 to 3 and $X^6$ is selected from H, $2\text{-}R^1$, $3\text{-}R^1$, $4\text{-}R^1$, 2-OH, 3-OH, 4-OH, $2\text{-}NH_2$, $3\text{-}NH_2$, or $4\text{-}NH_2$;

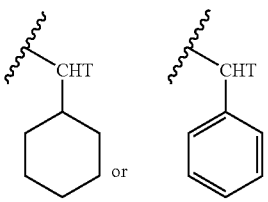

wherein T is selected from $CO_2H$, $CH_2OH$, or $CH_2NH_2$;

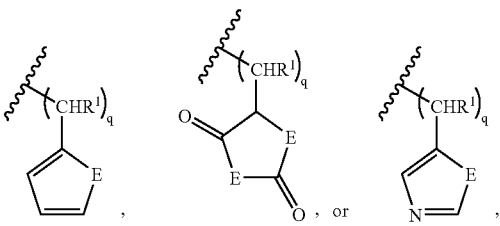

wherein q is an integer from 0 to 3 and E is in each occurrence independently selected from $NR^1$, O, S, C=O, or $C=NR^1$;

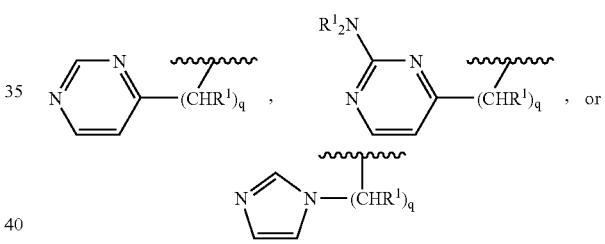

wherein q is an integer from 0 to 3; or

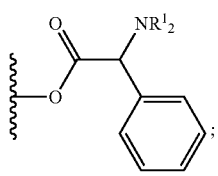

wherein $R^1$ is in each occurrence independently selected from —H; linear or branched alkyl with up to 10 carbon atoms; cycloalkyl with up to 10 carbon atoms; cycloalkenyl with up to 10 carbon atoms; benzyl; $O_2CR$, $C(O)R^1$, or $C(O)OR$ wherein R is H, $CH_3$, or $C(CH_3)_3$; $CH_2NH_2$; $CH_2OH$; or aryl.

Compositions comprising compounds of this formula are also encompassed by the present invention, as well as mixtures or combinations of compounds of this formula.

In yet another aspect of this invention, compounds of the present invention include, but are not limited to, those having the following formula:

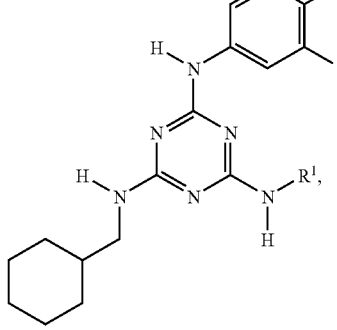
(XIIc)
wherein R¹ is selected from H,
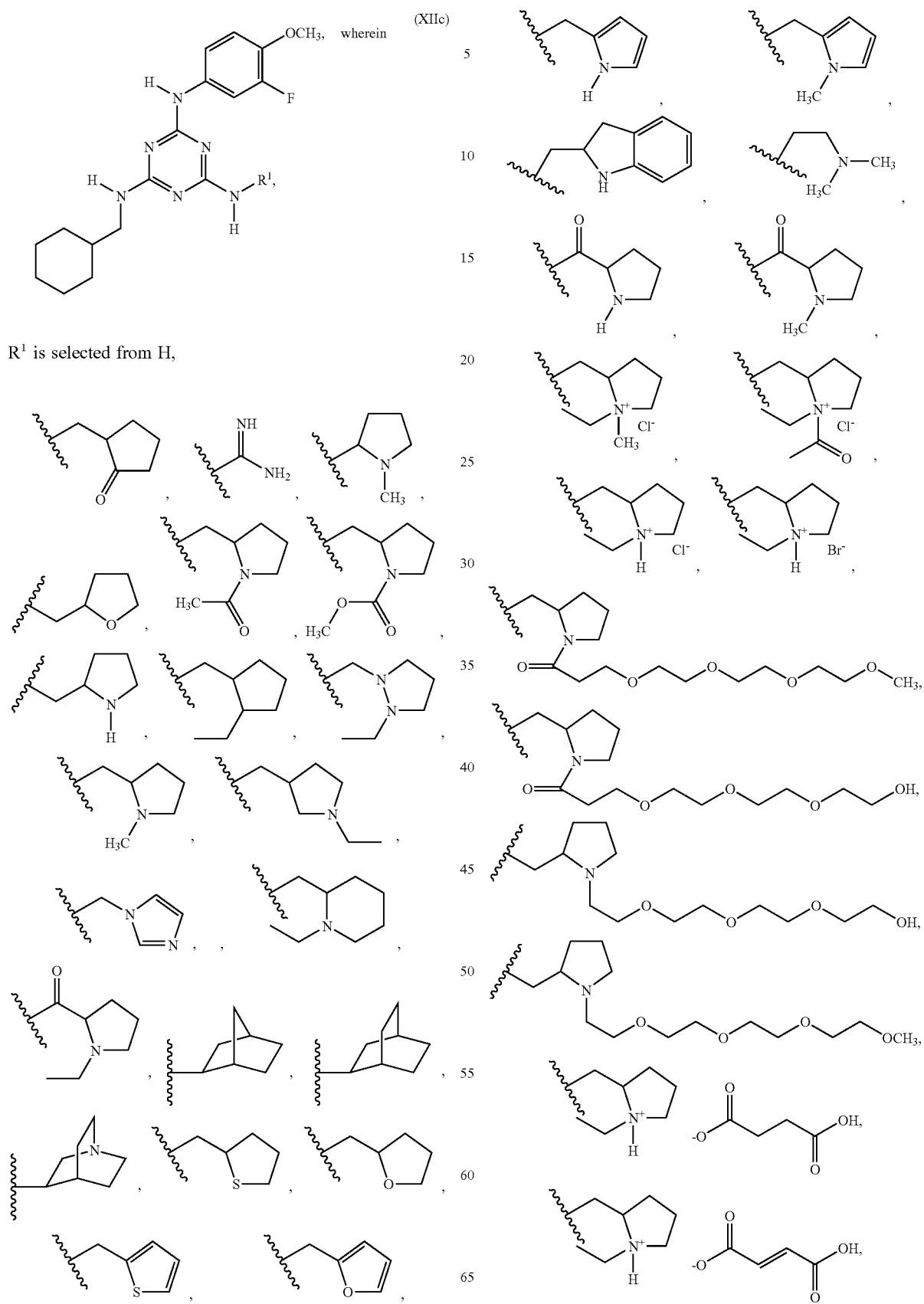

-continued

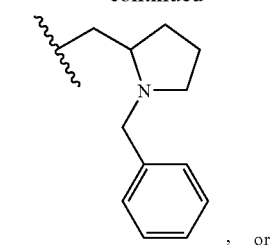
, or

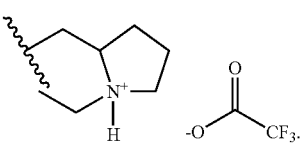

Compositions comprising compounds of this formula are also encompassed by the present invention, as well as mixtures or combinations of compounds of this formula.

In another aspect of this invention, compounds of the present invention include, but are not limited to, those having the following formula:

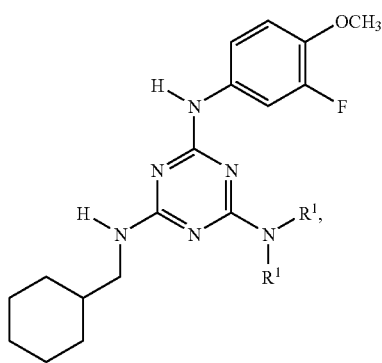 (XIIIc)

wherein $R^1$ is

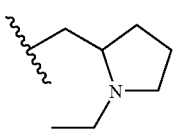

and wherein $R^2$ is selected from H or $CH_3$.

Compositions comprising compounds of this formula are also encompassed by the present invention, as well as mixtures or combinations of compounds of this formula.

In others aspect of this invention, compounds of the present invention include, but are not limited to, those having the following formula:

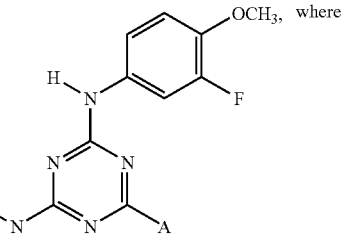 (XIVc)

wherein:

A is selected from

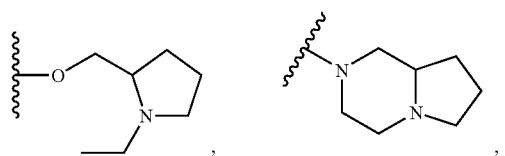

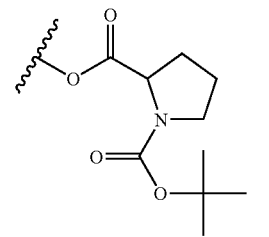

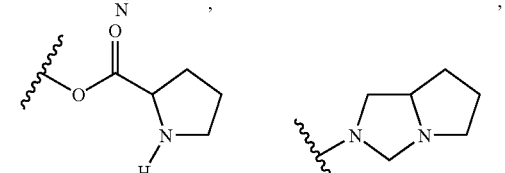

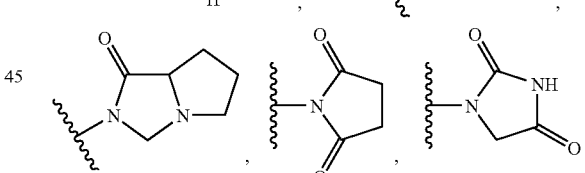

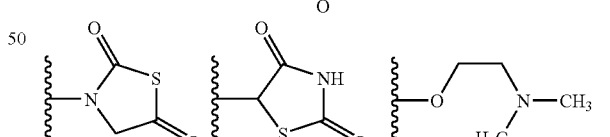

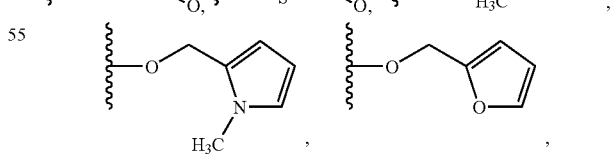

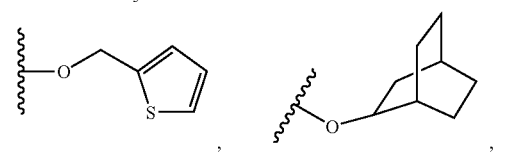

-continued
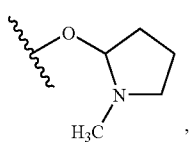
Compositions comprising compounds of this formula are also encompassed by the present invention, as well as mixtures or combinations of compounds of this formula.
In another aspect of this invention, compounds of the present invention include, but are not limited to, those having the following formula:
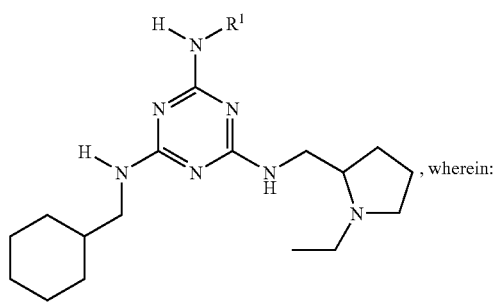
(XVc)
, wherein:
R¹ is selected from
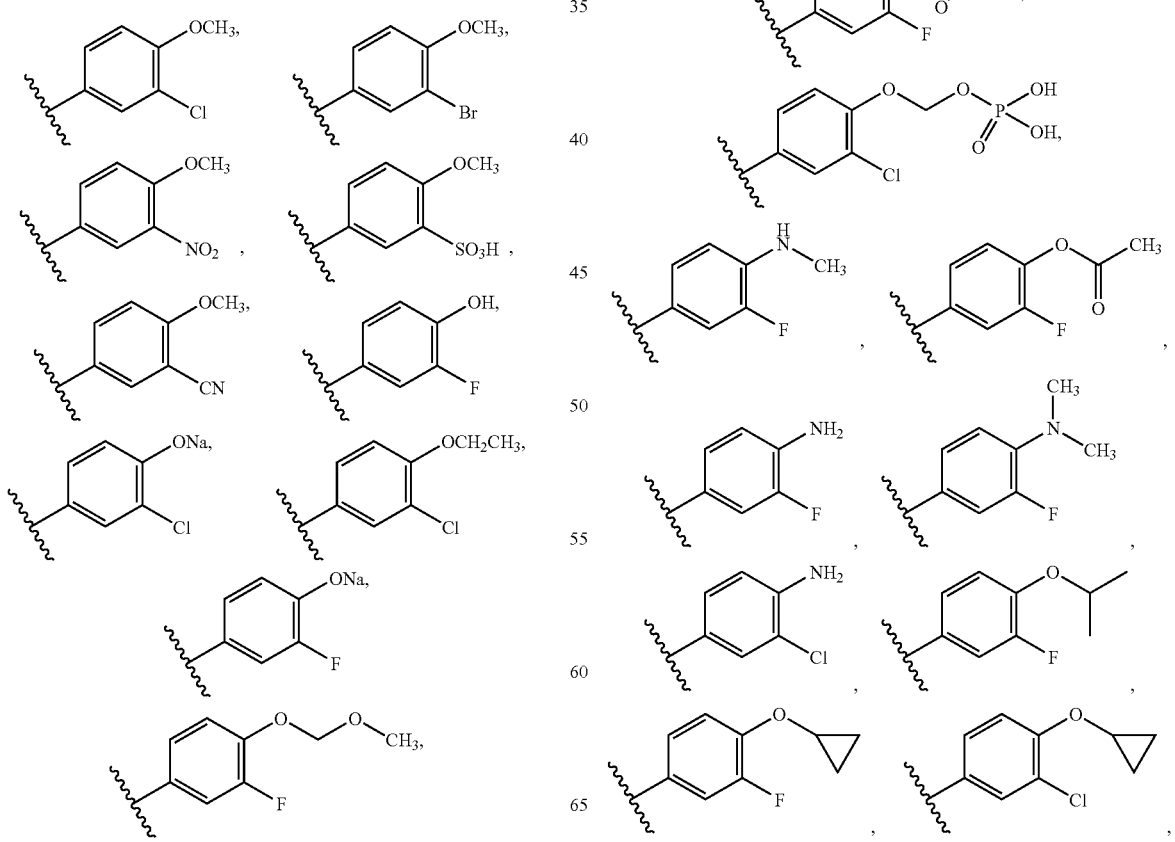
-continued
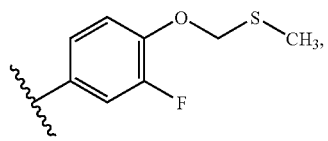
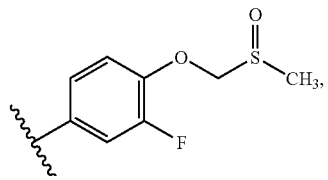
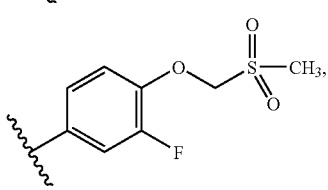
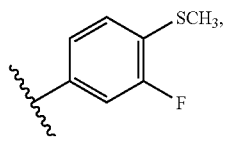
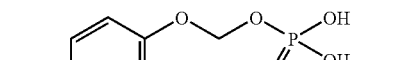
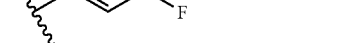
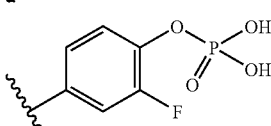
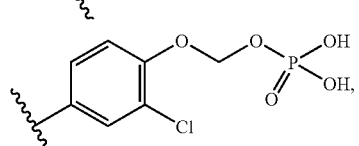
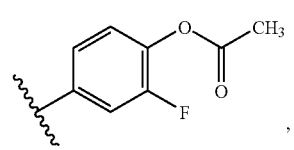
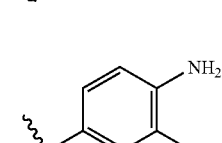
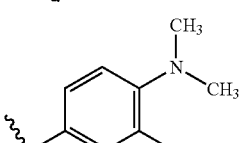
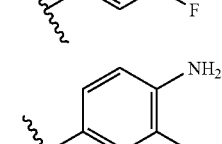
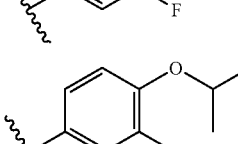
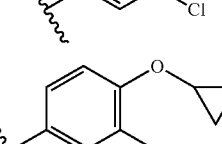
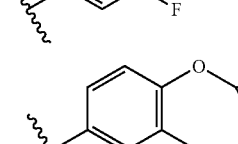

-continued

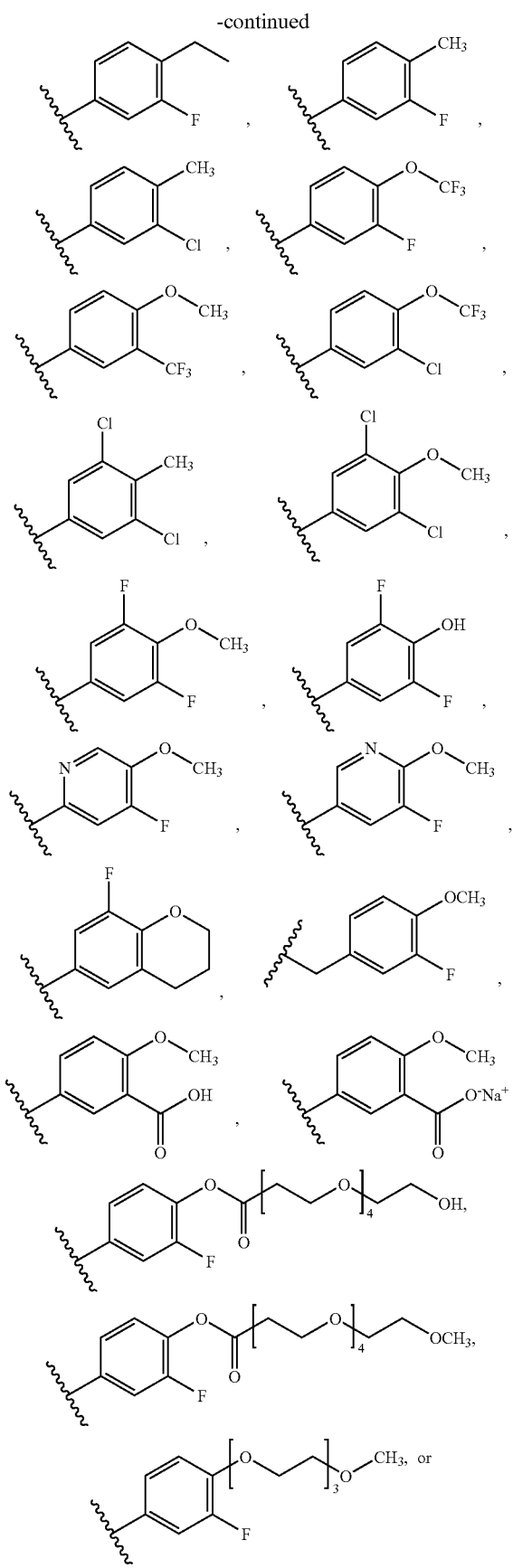

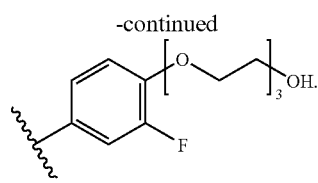

Compositions comprising compounds of this formula are also encompassed by the present invention, as well as mixtures or combinations of compounds of this formula.

In another aspect of this invention, compounds of the present invention include, but are not limited to, those having the following formula:

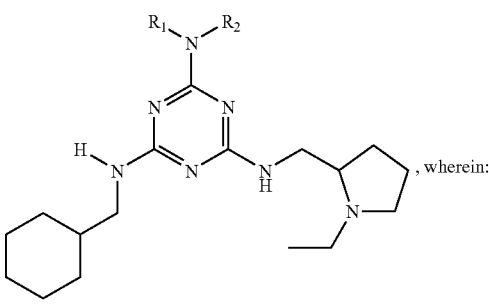

(XVIc)

wherein:
$R^1$ is

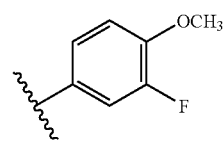

and wherein $R^2$ is selected from H or Me.

Compositions comprising compounds of this formula are also encompassed by the present invention, as well as mixtures or combinations of compounds of this formula.

In yet another aspect of this invention, compounds of the present invention include, but are not limited to, those having the following formula:

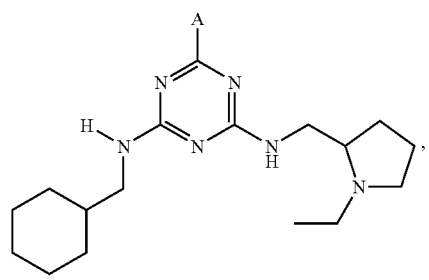

(XVIIc)

wherein A is selected from

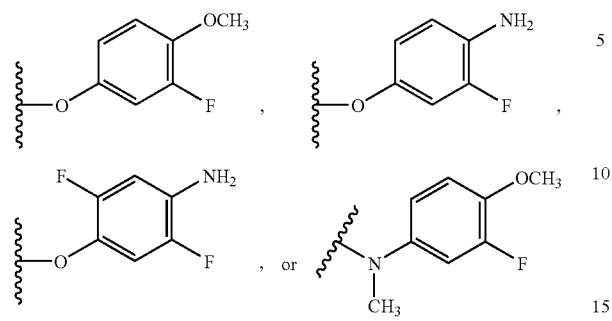

Compositions comprising compounds of this formula are also encompassed by the present invention, as well as mixtures or combinations of compounds of this formula.

In still another aspect of this invention, compounds of the present invention include, but are not limited to, those having the following formula:

(XVIIIc)

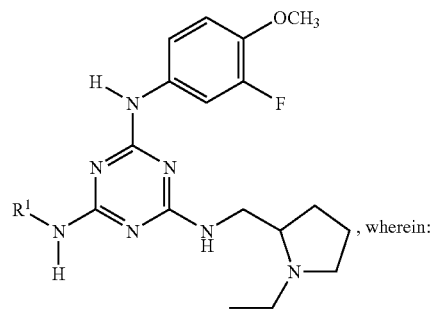

wherein:
R¹ is selected from

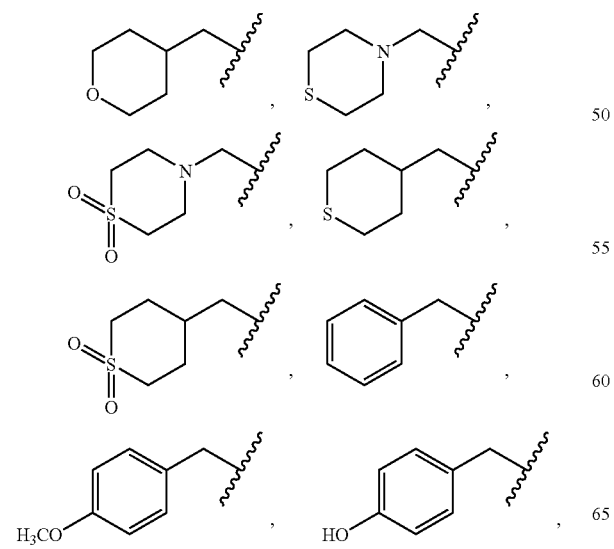

-continued

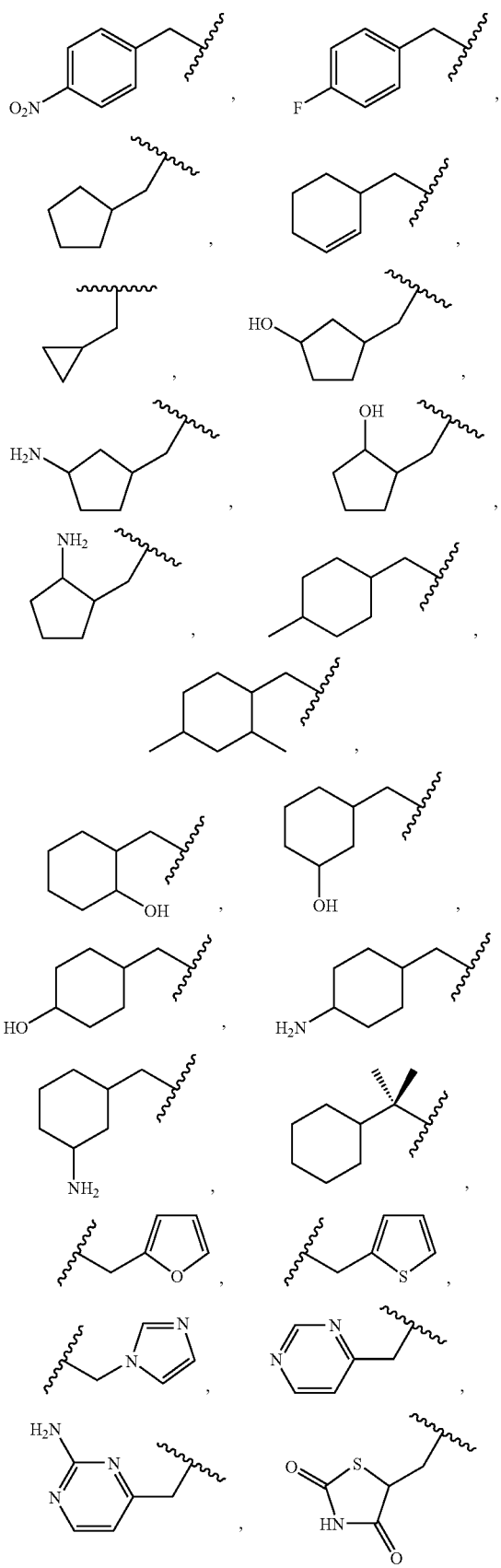

-continued

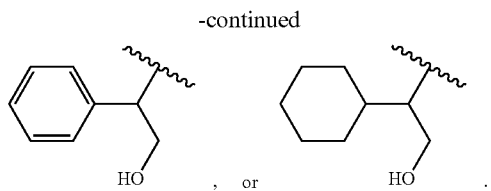

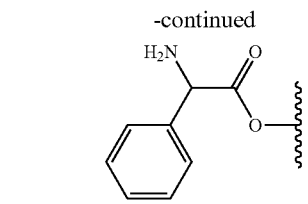

Compositions comprising compounds of this formula are also encompassed by the present invention, as well as mixtures or combinations of compounds of this formula.

In another aspect of this invention, compounds of the present invention include, but are not limited to, those having the following formula:

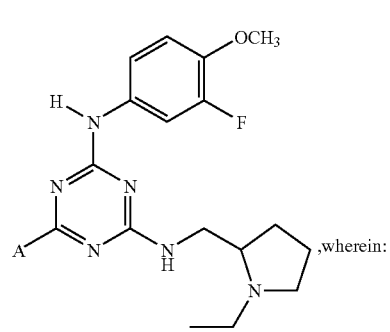

(XIXc)

A is selected from

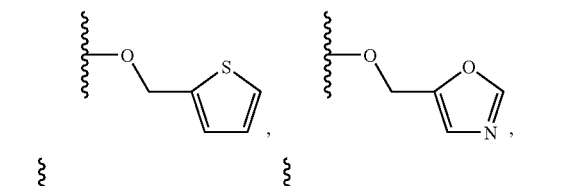

Compositions comprising compounds of this formula are also encompassed by the present invention, as well as mixtures or combinations of compounds of this formula.

In another aspect of this invention, compounds of the present invention include, but are not limited to, those having the following formula:

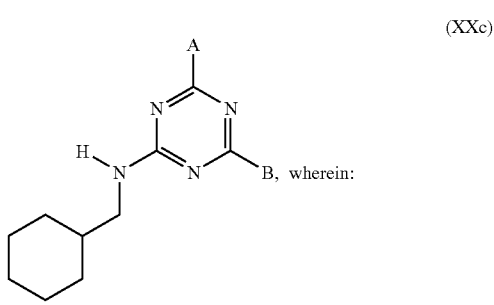

(XXc)

A is

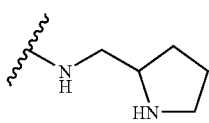

and B is

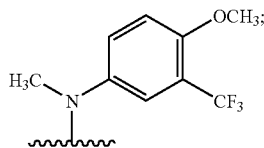

A is

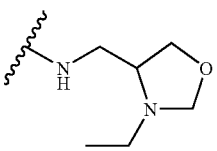

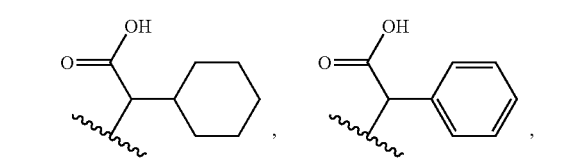

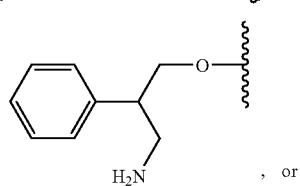

, or and B is

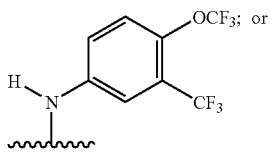

A is

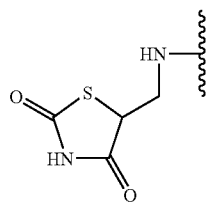

and B is selected from

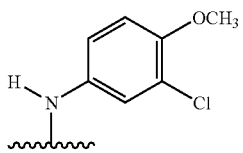 , 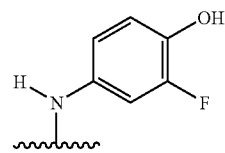 ,

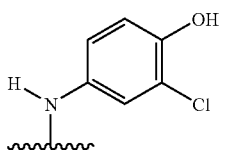 , or 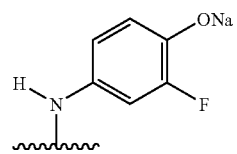 .

Compositions comprising compounds of this formula are also encompassed by the present invention, as well as mixtures or combinations of compounds of this formula.

In another aspect of this invention, compounds of the present invention include, but are not limited to, those having the following formula:

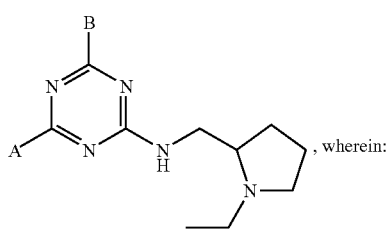 , wherein:

(XXIc)

A is

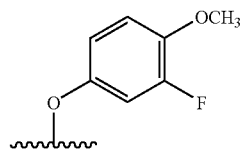

and B is

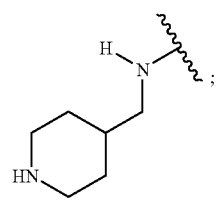

or
A is

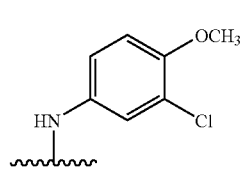

and B is selected from

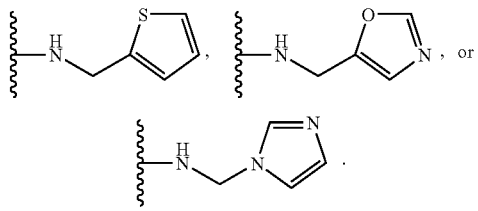

Compositions comprising compounds of this formula are also encompassed by the present invention, as well as mixtures or combinations of compounds of this formula.

Table 1C presents further exemplary compounds of the present invention. The inclusion of compounds in this table is not to be seen as limiting, rather compounds are provided in this table by way of example.

Additionally, compounds in accordance with the present invention include the compounds listed in Table 1E. Again, these compounds, which are discussed in the Examples provided herein, are to be considered as exemplary.

TABLE 1E

Representative Compounds According to the Present Invention

| COMPOUND NUMBER | COMPOUND NAME |
|---|---|
| E1 | 4-Benzyloxy-3-chloro-phenylamine, |
| E2 | N-(4-Benzyloxy-3-chloro-phenyl)-N'-cycloheptyl-N''-(1-methyl-piperidin-4-yl)-[1,3,5]triazine-2,4,6-triamine, |
| E3 | N-(4-benzyloxy-3-chloro-phenyl)-N'-cycloheptyl-N''-methyl-N''-piperidin-4-yl-[1,3,5]triazine-2,4,6-triamine, |
| E4 | 4-[4-Cycloheptylamino-6-(methyl-piperidin-4-yl-amino)-[1,3,5]triazin-2-ylamino]-phenol, |
| E5 | 4-{4-Cycloheptylamino-6-[methyl-(1-methyl-piperidin-4-yl)-amino]-1,3,5]triazin-2-ylamino}-phenol, |
| E6 | 2-Chloro-4-(4,6-dichloro-[1,3,5]triazin-2-ylamino)-phenol, |
| E7 | 2-Chloro-4-(4-chloro-6-cycloheptylamino-[1,3,5]triazin-2-ylamino)-phenol, |
| E8 | N-(1-Benzyl-piperidin-4-yl)-N'-(3-fluoro-4-methoxy-phenyl)-N''-cycloheptyl-[1,3,5]triazine-2,4,6-diamine, |
| E9 | N-Cycloheptyl-N'-(4-methoxy-phenyl)-N''-piperidin-4-yl-[1,3,5]triazine-2,4,6-triamine, |
| E10 | 6-Chloro-N-cyclopropyl-N'-(3-fluoro-4-methoxy-phenyl)-[1,3,5]triazine-2,4-diamine, |
| E11 | N-Cyclopropyl-N'-(3-flouro-4-methoxy-phenyl)-N''-methyl-N''-(1-methyl-piperidin-4-yl)-[1,3,5]triazine-2,4,6-triamine, |
| E12 | N-Cyclopropyl-N'-(1-ethyl-pyrrolidin-2-ylmethyl)-N''-(3-fluoro-4-methoxy-phenyl)-[1,3,5]triazine-2,4,6-triamine, |
| E13 | 6-Chloro-N-(3-chloro-4-methoxy-phenyl)-N'-cyclopropyl-[1,3,5]triazine-2,4-diamine |
| E14 | N-Cyclopropyl-N'-(3-chloro-4-methoxy-phenyl)-N''-methyl-N''-(1-methyl-piperidin-4-yl)-[1,3,5]triazine-2,4,6-triamine, |
| E15 | 6-Chloro-N,N'-bis-(3-fluoro-4-methoxy-phenyl)-[1,3,5]triazine-2,4-diamine, |
| E16 | N-(1-Ethyl-pyrrolidin-2-ylmethyl)-N',N''-bis-(3-fluoro-4-methoxy-phenyl)-[1,3,5]triazine-2,4,6-triamine, |
| E17 | 1-[4-(3-chloro-4-methoxyanilino)-cycloheptyl amino-1,3,5-triazin-2-yl]-2-azoloamymethanol, |
| E18 | $N^2$-(3-chloro-4-methoxyphenyl)-$N^4$-cycloheptyl-6-(4-methylpiperzino)-1,3,5-triazine-4,2-diamine, |
| E19 | 3-[4-(3-chloro-4-methoxyanilmo)-6-cycloheptylamino-1,3,5-triazin-2-yloxy]-2-ethyl-4H-4-pyranone, |
| E20 | 1-[3-{4-(3-chloro-4-methoxyanilino)-6-cycloheptylamino-1,3,5-triazine-2-yloxy}piperidino]-1-ethanone, |
| E21 | $N^2$-(3-chloro-4-methoxyphenyl)-$N^4$-cycloheptyl-6-isopropoxy-1,3,5-triazine-2,4-diamine, |
| E22 | $N^2$-(3-chloro-4-methoxyphenyl)-$N^4$-cycloheptyl-6-(2-azolanylmethoxy)-1,3,5-triazine-2,4-diamine, |
| E23 | 1-[4-(3-chloro-4-methoxy-phenylamino)-6-cycloheptylamino-[1,3,5]triazine-2-yl]-piperidin-3-ol], |
| E24 | 1-[4-(3-chloro-4-methoxy-phenylamino)-6-cycloheptylamino-[1,3,5]triazine-2-yl]-piperidin-4-ol], |
| E25 | $N^2$-(3-chloro-4-methoxyphenyl)-$N^4$-cycloheptyl-6-(1-methyl-2-azolanylmethoxy)-1,3,5-triazine-2,4-diamine, |
| E26 | $N^2$-(3-chloro-4-methoxyphenyl)-$N^4$-cycloheptyl-6-(1-methyl-4-piperidyloxy)-1,3,5-triazine-2,4-diamine, |
| E27 | $N^2$-(3-chloro-4-methoxyphenyl)-$N^4$-cycloheptyl-6-(1,4-thiazinan-4-yl)-1,3,5-triazine-4,2-diamine, |
| E28 | $N^2$-(3-chloro-4-methoxyphenyl)-$N^4$-cycloheptyl-6-(2-fluorophenoxy)-1,3,5-triazine-4,2-diamine, |
| E29 | $N^2$-(3-chloro-4-methoxyphenyl)-$N^4$-cycloheptyl-6-[2-(2-fluorophenoxy) ethoxy]-1,3,5-triazine-4,2-diamine, |
| E30 | $N^2$-(3-chloro-4-methoxyphenyl)-$N^4$-cycloheptyl-6-(6-methyl-2-pyryl methoxy]-1,3,5-triazine-4,2-diamine, |
| E31 | N-(3-chloro-4-methoxyphenyl)-N'-cycloheptyl-N''-methyl-N''-(1-methyl piperidin-4-yl)[1,3,5]triazine-2,4,6-triamine, HCl salt, |
| E32 | 6-methoxy-N-(3-Chloro-4-methoxy phenyl)-N'-cyclo heptyl-[1,3,5] triazine-2,4 diamine, |
| E33 | 6-ethoxy-N-(3-Chloro-4-methoxy phenyl)-N'-cyclo heptyl-[1,3,5] triazine-2,4 diamine, |
| E34 | 6-isopropoxy-N-(3-Chloro-4-methoxy phenyl)-N'-cyclo heptyl-[1,3,5] triazine-2,4 diamine. |

III. Antiproliferative Activities

One embodiment of the present invention comprises methods and compositions comprising the compounds of the present invention for the treatment and prevention of conditions or diseases that have as an aspect of the disease or condition, unwanted cellular proliferation occurring or are the result of cellular proliferation. For example, many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation. Smooth muscle cell (SMC) hyperplasia is a major event in the development of atherosclerosis and is also responsible for the significant number of failure rates following vascular procedures such as angioplasty and coronary artery bypass surgery, particularly due to restenosis. Proliferation of arterial wall SMC in response to local injury is a major feature of many vascular proliferative disorders. Neointimal hyperplasia is commonly seen after various forms of vascular injury and a major component of the vein graft's response to harvest and surgical implantation into high-pressure arterial circulation. Proliferation of SMC in response to local injury is a major feature of vascular proliferative disorders such as atherosclerosis and restenosis after angioplasty.

One aspect of the present invention relates to methods and compositions for the treatment and prevention of smooth muscle cell (SMC) proliferation, preferably comprising compositions and compounds having cellular antiproliferative activity. These compounds and compositions comprising such compounds are referred to as antiproliferative compounds or compositions. At least one activity of one or more of these compounds is that the compound has the activity of effecting the synthesis of proteoglycans including induction and synthesis of proteoglycans and active fragments of proteoglycans. Thus, one aspect of the activity of one or more of the compounds and compositions of the present invention comprise molecules that induce HSPG production and that regulate SMC (smooth muscle cell) proliferation.

Compounds of the present invention that have at least the activity of effecting cellular proliferation are shown in TABLE 3. The compounds shown in this Table have the activity of effecting cellular proliferation as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following structure:

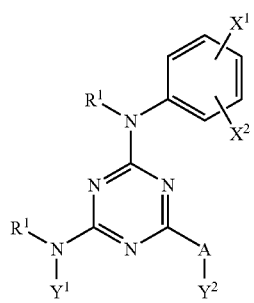

or an ene, a diene, a triene, or an yne derivative thereof; a saturated derivative thereof; a stereoisomer thereof; or a salt thereof;

wherein:
R$^1$ is in each occurrence independently selected from —H; linear or branched alkyl with up to 10 carbon atoms; or cycloalkyl with up to 10 carbon atoms;
X$^1$ is selected from m-F, m-Cl, m-Br, m-I, m-CN, m-NO$_2$, m-SO$_2$R$^1$, or m-SO$_2$OR$^1$, or X$^1$ and X$^2$ together is a fused benzene, pyridine, or dioxane ring;
X$^2$ is selected from p-OR$^1$, p-SR$^1$, p-NR$^1{}_2$, p-OM, or p-SM, wherein M is selected from Li, Na, K, Mg, or Ca;
Y$^1$ is selected from cycloalkyl with up to 10 carbon atoms; linear or branched alkyl with up to 10 carbon atoms; CH$_2$R$^2$, wherein R$^2$ is a cycloalkyl with up to 10 carbon atoms; or

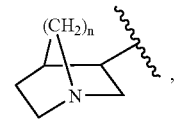

wherein n is 1 or 2;
AY$^2$ is selected from a halogen or OR$^1$, or
A is NR$^1$ and Y$^2$ is selected from R$^1$, or

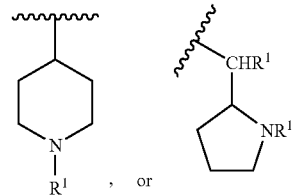

Further examples of compounds that show at least this activity and utility are presented in Table 3, where compound activity is also presented. The activity scale used in Table 3 as follows (numbers are inclusive): "+++" represents IC$_{50}$ of less than about 3 µM; "++" represents IC$_{50}$ of between about 3 and about 7 µM; and "+" represents IC$_{50}$ of greater than about 7 µM. In addition, compounds, to include compositions thereof, encompassed within the scope of structures Ic-XXIc, respectively, or listed in Tables 1C and 1E may be likewise employed in this embodiment and/or aspect of the present invention. Further, any hydrogen atoms that are required for any atom to attain its usual valence in a structure presented in Table 3, whether a carbon atom or a heteroatom, should be inferred if it is not specifically indicated.

In addition to the above compounds, the following compounds and compositions comprising these compounds are active in an anti-proliferation assay (Perlecan). These compounds and compositions comprising these compounds are, among other things, generally useful for treating cardiovascular disorders associated with proliferative activity. Specifically, these compounds include N$^2$-cycloheptyl-N$^4$-(3-fluoro-4-methoxyphenyl)-N$^6$-methyl-N$^6$-(1-methyl-piperidin-4-yl)-1,3,5-triazine-2,4,6-triamine, and N$^2$-cycloheptyl-N$^4$-methyl-N$^4$-(1-methyl-piperidin-4-yl)-N$^6$-naphthalen-2-yl-1,3,5-triazine-2,4,6-triamine. Using the same activity scale used in Table 3, and discussed above, the first compound, $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, is characterized as a compound exhibiting medium or moderate activity, while the second compound, $N^2$-cycloheptyl-$N^4$-methyl-$N^4$-(1-methyl-piperidin-4-yl)-$N^6$-naphthalen-2-yl-1,3,5-triazine-2,4,6-triamine, is characterized as a compound exhibiting high activity.

As used herein, when a proteoglycan is referred to, the entire molecule or fragments are included therein. For example, perlecan refers to the entire perlecan molecule or fragments thereof. Different fragments of perlecan may have the same or different effects on cells and the effects may be the same as or different from the effects that the entire perlecan molecule has on cells. These fragments and activities are contemplated in the present invention and compounds included in the present invention may have at least one activity that modulates or effects the fragements' activities or the entire molecule's activities. Although the discussion herein refers specifically to perlecans it is important to note that the compositions, methods, and assays described herein are equally applicable in the context of other proteoglycans, including HSPGs, and including but not limited to, chondroitan sulfates (e.g., A, B, and C), dermatan sulfates, syndecans and glypicans.

Methods for identifying the activity and screening for one or more of these compounds or molecules that induce synthesis of proteoglycans such as HSPG (heparan sulfate proteoglycan) are taught in U.S. patent application Ser. No. 10/091,357, which is incorporated herein in its entirety. Assays of effects of compounds in vivo are also taught in the incorporated references and are known to those skilled in the art. In general, methods comprise the addition of such compounds to assays and measurement of HSPG synthesis including, but not limited to, the production of syndecans, glypicans and perlecans, for example, syndecans 1, 2 and 4; and glypican-1. Other assays that can be used to determine the activity of the compounds of the present invention include other methods for measuring the induction of perlecan synthesis. For example, in one assay, perlecan is induced in cells by certain inducers, and the response is measured. Compounds of the present invention are then added to a replicate assay and the effect on perlecan induction is determined. Using such methods, compounds are determined that can either inhibit perlecan, elevate induction of perlecan, or that have no effect at all. Those compounds that are effective as therapeutic agents can then be used in animals, humans or patients with cellular proliferation disease aspects, such as vascular-associated diseases or SMC proliferation pathologies.

Another assay for determining compounds having SMC effects comprises adding a composition suspected of effecting SMC proliferation to smooth muscle cells in growth medium or serum-free medium. The change in cell proliferation can be measured by methods known to those skilled in the art, such as incorporation of labeled nucleotides into dividing cells' DNA, and compared to the proliferation of cells which are not treated with the compound. Other measurements include directly determining levels of HSPG synthesis by measuring the amount or change in amount of HSPG such as with ELISA for HSPGs, and compared to the amount of HSPG synthesis in untreated cells. Other indirect or direct measurement are contemplated by the present invention and are known to those skilled in the art. For example, such methods include, but are not limited to, measurement of RNA levels, RT-PCR, Northern blotting, Western blotting promoter-based assays to identify compounds that affect one or more proteoglycans and assays for proteoglycan biological activity shown by recombinant proteins, partially purified proteins, or lysates from cells expressing proteoglycans in the presence or absence of compounds of interest.

An assay for identifying and determining an activity of one or more of the compounds of the present invention comprises identifying compounds that interact with the promoter regions of a gene, or interact and effect proteins that interact with the promoter region, and are important in the transcriptional regulation of the protein's expression. For example, if perlecan were the protein, in general, the method comprises a vector comprising regulatory sequences of the perlecan gene and an indicator region controlled by the regulatory sequences, such as an enzyme, in a promoter-reporter construct. The protein product of the indicator region is referred to herein as a reporter enzyme or reporter protein. The regulatory region of the sequence of perlecan comprises a range of nucleotides from approximately −4000 to +2000 wherein the transcription initiation site is +1, more preferably, from −2500 to +1200, most preferably, from −1500 to +800 relative to the transcription initiation site.

Cells are transfected with a vector comprising the promoter-reporter construct and then treated with one or more compositions comprising at least one compound of the present invention. For example, the transfected cells are treated with a composition comprising a compound suspected of effecting the transcription of perlecan and the level of activity of the perlecan regulatory sequences are compared to the level of activity in cells that were not treated with the compound. The level of activity of the perlecan regulatory sequences are determined by measuring the amount of the reporter protein or determining the activity of the reporter enzyme controlled by the regulatory sequences. An increase in the amount of the reporter protein or the reporter enzyme activity shows a stimulatory effect on perlecan, by positively effecting the promoter, whereas a decrease in the amount or the reporter protein or the reporter enzyme activity shows a negative effect on the promoter and thus, on perlecan.

Additionally, the present invention comprises methods and compositions that can be used with gene therapy methods and composition, such as those gene therapy methods comprising administering compositions comprising nucleic acids that effect the synthesis or expression of HSPGs, particularly perlecan. Such methods and compositions are taught in U.S. patent application Ser. No. 10/091,357, incorporated herein by reference.

The present invention comprises methods and compositions for mediating proteoglycan synthesis, expression and for the maintenance of SMC in a quiescent state. Methods and compositions of the present invention comprise treatment and prevention of vascular diseases and pathologies related to celluar proliferation, such as SMC proliferation. Such methods and compositions comprise methods for inhibition of smooth muscle cell (SMC) growth and proliferation, and for induction of quiescence in smooth muscle cells. Embodiments of the present invention comprise methods and compositions for inducing proteoglycan synthesis, particularly HSPG synthesis and expression including, but not limited to, the induction of HSPGs such as syndecans, glypicans and perlecans, and preferably perlecan synthesis and gene expression. Perlecan is a major extracellular HSPG in the blood vessel matrix. It interacts with extracellular matrix proteins, growth factors and receptors. Perlecan is also present in basement membranes other than blood vessels and in other extracellular matrix structures.

The activities of the compounds included in the present invention effect cells or tissues to increase the synthesis of proteoglycans by those cells or tissues or may act directly upon one or more proteoglycans to modulate the biological activity or to increase the biological stability of the proteoglycan itself, for example, of the protein perlecan. Activities also included herein are ones that increase the biosynthesis of one or more proteoglycans by increasing the transcription of the poteoglycan gene, increasing the biological stability of the proteoglycan mRNA or increasing the translation of proteoglycan mRNA into protein. Further activites include activities of compounds that can block or decrease the effects of agents or proteins that inhibit the activity of proteoglycans.

The present invention comprises methods and compositions for the treatment and prevention of smooth muscle cell proliferation, including vascular occlusive pathologies. Such methods comprise administration of compositions comprising compounds capable of inhibiting SMC proliferation, such as compositions comprising compounds disclosed herein that inhibit SMC proliferation. Administration of such compounds that are effective in inhibiting SMC proliferation are administered to humans and animals suspected of having or who have, for example, vasculopathy or who have undergone angioplasty or other procedures damaging to the endothelium. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

The compounds of the present invention are useful in the treatment or prophylaxis of at least one cardiovascular disease in a cell, tissue, organ, animal, or patient including, but not limited to, vascular occlusive lesions including atherosclerosis, transplant vasculopathy, cardiac allograft vasculopathy, restenosis, graft atherosclerosis after coronary transplantation, cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such methods can optionally comprise administering an effective amount of a composition or pharmaceutical composition comprising at least one compound to a cell, tissue, organ, animal or patient in need of such modulation, treatment or therapy.

Proteoglycan-associated diseases that are treatable with the compounds of the present invention include, but are not limited to, hereditary multiple exostosis, mucopolysaccharidosis types I-III and VII, commonly known as Hurler's Syndrome, Hunter's Syndrome, Sanfilippo's Syndrome and Sly's Syndrome respectively, Alzheimer's disease, Simpson-Golabi-Behmel syndrome, fibroblast growth factor related disorders, herpes simplex virus, dengue fever, Parkinson's disease, renal disease, muscular dystrophy, Schwarts-Jampel syndrome, proteinuric glomerulopathies, myotonia and skeletal dysplasia, kyphoscoliosis, dyssegmental dysplasia, Silverman-Handmaker type, chondrodysplasia, periodontitis, rheumatoid and osteoarthritis, Gerstmann-Straussler syndrome, Creutzfeldt-Jakob disease, scrapie, carcinomas, Happle syndrome, macular dystrophy, bone diseases, corneal diseases, leukocyte-mediated disease, collagen fibril assembly disorder and coronary heart disease and other vascular disorders.

IV. Glycosidase Modulation Activity

The present invention also comprises methods and compositions comprising compounds described herein that have an activity associated with modulation of glycosidase enzymes and thus, effecting the substrates for such enzymes. Glycosidase enzymes and their activity with their substrates, such as proteoglycans or glycated proteins, are aspects of a variety of diseases such as vascular conditions, including those conditions discussed supra, proteoglycan-associated diseases, supra, associated diseases with vascular components, including but not limited to, kidney disease, ischemic heart disease, cardiovascular disease, generalized vascular disease, proliferative retinopathy, and macroangeopathy, inflammatory diseases and metastatic diseases such as cancer, cellular proliferative conditions, and solid and blood borne tumors or other oncological conditions. Compounds described herein that have an activity that effects the concentrations of substrates of glycosidase enzymes are used in methods of treatment of such vascular, inflammatory, metastatic and systemic diseases.

An aspect of the present invention comprises methods and compositions for the modulation of enzymes, such as glycosaminoglycan degrading enzymes, which effect or are effected by proteoglycan levels, amount or activity. For example, the present invention comprises methods and compositions comprising compounds that modulate enzymes including but not limited to, heparanase, chondroitanase, heparan sulfate endoglycosidase, heparan sulfate exoglycosidase, polysaccharide lyases, keratinase, hyauronidase, glucanase, amylase, glycosidases, or other proteoglycan degrading enzymes are useful for the treatment of conditions such as diabetic vasculopathy, cancer, inflammatory diseases, autoimmune diseases and cardiovascular diseases. For example, the present invention comprises methods and compositions of compounds that inhibit, impair or down-regulate the activity of proteoglycan degrading enzymes.

Proteoglycans such as HSPG are important components of the subendothelial extracellular matrix and the basement membrane of blood vessels. Rosenberg et al., 99 J. CLIN. INVEST. 2062-70 (1997). Basement membranes are continuous sheets of extracellular matrix composed of collagenous and noncollagenous proteins and proteoglycans that separate parenchymal cells from underlying interstitial connective tissue. They have characteristic permeabilities and play a role in maintaining tissue architecture.

In addition to HSPGs, the basal lamina consists predominantly of a complex network of adhesion proteins, fibronectin, laminin, collagen and vitronectin. Wight et al., 6 CURR. OPIN. LIPIDOL. 326-334 (1995). Heparan sulfate (HS) is an important structural component of the basal lamina. Each of the adhesion proteins interacts with HS side chains of HSPGs within the matrix. Thus, HSPGs function as a barrier to the extravasation of metastatic and inflammatory cells. Cleavage of HS by the endoglycosidase heparanase produced by metastatic tumor cells and inflammatory cells destroys the filtering properties of the lamina. In addition, the degradation of the HS may assist in the disassembly of the extracellular matrix and thereby facilitate cell migration by allowing blood borne cells to escape into the bloodstream. Vlodavsky et al., 12 INVASION METASTASIS 112-127 (1992).

Heparanase activity has been described in a number of tissues and cell types including liver, placenta, platelets, fibroblasts, neutrophils, activated T and B-lymphocytes, monocytes, and endothelial cells (7-16). Nakajima et al., (31) CANCER LETT. 277-283 (1986); Nakajima et al., 36 J. CELL. BIOCHEM. 157-167 (1988); Ricoveri et al., 46 CANCER RES. 3855-3861 (1986); Gallagher et al., 250 BIOCHEM. J. 719-726 (1988); Dempsey et al., 10 GLYCOBIOLOGY 467 (2000); Goshen et al., 2 MOL. HUM. REPROD. 679 (1996); Parish et al., 76 IMMUNOL CELL BIOL. 104-113 (1998); Gilat et al., 181 J. EXP. MED. 1929-1934 (1995); Graham, et al., 39 BIOCHEM. MOL. BIOL. INT. 56371 (1996); Pillarisetti et al., 270 J.BIOL.CHEM. 29760-29765 (1995). An important process in tissue invasion by blood-borne tumor cells and white cells involves their passage through the vascular endothelial cell layer and subsequent degradation of the underlying basal lamina or basement membranes and extracellular matrix with a battery of secreted proteases and glycosidases. Nakajinia et al., 220 SCIENCE 611-613 (1983); Vlodavsky et al., 12 INVASION METASTASIS 112-127 (1992).

Heparanase activity was shown to correlate with the metastatic potential of animal and human tumor cell lines. Nakajima et al., 31 CANCER LETT. 277-283 (1986); Nakajima et al., 212 PROG CLIN BIOL RES. 113-122 (1986); Freeman et al., 325 BIOCHEM. J. 229-237 (1997); Vlodavsky et al., 5 NAT. MED. 793-802 (1999); Hulett et al., 5 NAT MED. 803-809 (1999). It is also known to regulate growth factor activity. Many growth factors remain bound to heparan sulfate in storage form and are disassociated by heparanase during angiogenesis, improving the survival rate of cancer cells.

Serum heparanase levels in rats were higher by more than an order of magnitude after injection of the rats with highly metastatic mammary adenocarcinoma cells. In addition, heparanase activity in the sera of rats bearing MTLn3 tumors correlated well with the extent of the metastases. Moreover, serum/urine heparanase activity in cancer patients was shown to be 2-4 fold increased in particular where tissue metastases were present. Because the cleavage of HS appears to be essential for the passage of metastatic tumor cells and leukocytes through basement membranes, studies of heparanase inhibitors provides the potential of developing a novel and highly selective class of anti-metastatic and anti-inflammatory drugs.

The present invention comprises methods and compositions comprising compounds that modulate heparanase activity or the activity of other glycosidases, including, but not limited to enzymes with glycosaminoglycan activity such as chondroitinase, heparan sulfate endoglycosidase, heparan sulfate exoglycosidase, polysaccharide lyases, keratinase, hyaluranidase, glucanase, and amylase. Compounds of the present invention that have at least the activity of modulating glycosidase enzyme activity are shown in TABLE 6. The compounds shown in this Table have the activity of modulating glycosidase enzyme activity as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

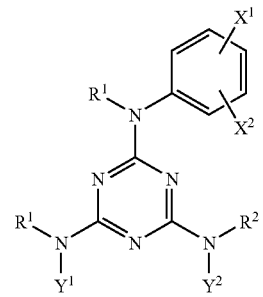

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is selected from H, m-F, m-Cl, m-Br, m-I, m-CN, m-$NO_2$, m-$SO_2R^1$, or m-$SO_2OR^1$;

$X^2$ is selected from o-$R^1$, p-$OR^1$, p-$SR^1$, P—$NR^1{}_2$, p-OM, orp-SM, wherein M is selected from Li, Na, K, Mg, or Ca;

$Y^1$ is selected from cycloalkyl with up to 10 carbon atoms or

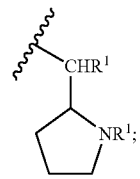

and $Y^2$ is selected from linear or branched alkyl with up to 10 carbon atoms, cycloalkyl with up to 10 carbon atoms, or

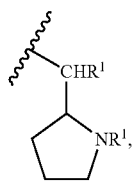

and R² is —H; or NY²R² together is selected from

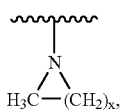

wherein x is an integer from 3 to 5,

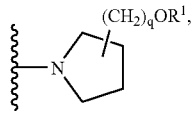

wherein q is an integer from 0 to 6, or

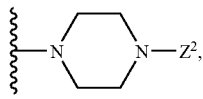

wherein Z² is selected from R¹ or

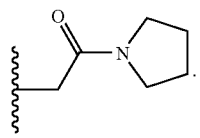

Further examples of compounds that show at least this activity and utility are presented in Table 6, where compound activity is also shown. The activity scale used in Table 6 is as follows (numbers are inclusive): "+++" represents between about 70 and about 100% inhibition; "++" represents between about 30 and about 40% inhibition; and "+" indicates between 0 and about 30% inhibition, all at 5 µM compound concentration. In addition, compounds, to include compositions thereof, encompassed within the scope of structures Ic-XXIc, respectively, or listed in Tables 1C and 1E may be likewise employed in this embodiment and/or aspect of the present invention. Also note that any hydrogen atoms that are required for any atom to attain its usual valence in a structure presented in Table 6, whether a carbon atom or a heteroatom, should be inferred if it is not specifically indicated.

Compounds or compositions comprising such compounds that are effective in modulating glycosidase enzyme activity are useful in treating and/or preventing cancer including, but not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

In another aspect of the present invention, the compounds disclosed herein are useful in modulating heparanase activity or the activity of other glycosidases as a means for treating and preventing autoimmune diseases. Generally autoimmune disease results when (1) the immune system mistakenly identifies a cell surface molecule on normal tissue as a foreign molecule (2) the synthesis and secretion of chemokines, cytokines and lymphokines is not shut down after the eradication of the disease or (3) the immune system overreacts to the apparent infection and destroys vast quantities of surrounding normal tissue.

To be effective in an immune response, the immune effector cells must bind to the luminal/apical surface of the blood vessel walls. This is accomplished through the interaction of adhesion molecules on the immune effector cells with their locally upregulated cognate receptors on the endothelial cells lining the vasculature near the site of infection. After binding to the apical surface and before entering the inflamed tissue, the immune effector cells must breach the basement membrane (BM) and extracellular matrix (ECM) that surround the basal portion of the blood vessels and give the vessels their shape and strength. The BM and ECM consists of structural proteins embedded in a fiber meshwork consisting mainly of complex carbohydrate containing structures (glycosaminoglycans), of which the main constituent is heparin sulfate proteoglycan (HSPG). In order to breach this barrier the immune effector cell must weaken or destroy it, which is accomplished through the local secretion of proteases and heparanase(s).

Thus, the inhibition of heparanase or the activity of other glycosidases using the compounds of the present invention finds utitlity in treating arthritis and other autoimmune diseases. More specifically, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, -meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, anti-phospholipid syndrome, pemphigus, scleroderma, mixed connective tissue disease, idiopathic Addison's disease, autoimmune hemolytic anemia, autoimmune hepatitis, idiopathic pulmonary fibrosis, scleroderma, diabetes mellitus, chronic active hepatitis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barré, Hashimoto's thyroiditis, idiopathic thrombocytopenia purpura (ITP), IgA nephropathy, insulin dependent diabetes, juvenile arthritis, lichen planus, ménière's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjögren's syndrome, stiff-man syndrome, Takayasu arteritis, temporal arteritis/giant cell arteritis, Wegener's granulomatosis; okt3 therapy, anti-cd3 therapy, cytokine therapy, chemotherapy, radiation therapy (e.g., including but not limited toasthenia, anemia, cachexia, and the like), chronic salicylate intoxication, and the like.

Compounds having heparanase activity inhibition, that are effective for example, in treatment of cancer and autoimmune disease, can be determined using assays such as those disclosed in U.S. patent application Ser. No. 09/952,648, which is incorporated herein in its entirety. Such assays, which are used for measurement of cellular and enzymatic activities, both qualitatively and quantitatively, and in methods for diagnosing metastases, metastatic potential and inflammatory states, are performed with and without the addition of at least one of the compounds of the present invention to determine the activity of the compound. Existing heparanase assays are taught in Goshen et al., 2 MOL. HUM. REPROD. 679-84 (1996); Nakajima et al., 31 CANCER LETT. 277-83 (1986); and Vlodasky et al., 12 INVASION METASTASIS 112-27 (1992); Freeman and Parish, 325 BIOCHEM. J. 229-37 (1997); Kahn and Newman, 196 ANAL. BIOCHEM. 373-76 (1991). Solid-phase heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is entirely expressly herein incorporated by reference.

In general, a preferred assay comprises attaching one of a binding partner to a substrate for the enzyme to be measured, forming the substrate-binding partner. Incubation with a sample comprising the enzyme to be measured allows for activity by the enzyme to be measured in a reaction mixture. A portion or the whole reaction mixture, depending on the amount needed, is then mixed with the complementary binding partner, so that the binding partners are bound together. This is the first binding reaction. After incubating to allow for binding, washings are performed. A complementary binding partner, complementary to the first binding partner attached to the substrate, is added. This complementary binding partner may or may not be the same as the first complementary binding partner. This is the second binding reaction. The complementary binding partner in the second binding reaction is labeled in a manner that is detectable. For example, the complementary binding partner is labeled with an enzyme that causes a detectable color change when the appropriate reaction conditions exist. The difference between the activity of the enzyme in the presence of a compound and the absence of compound is used to determine the activity of the compound.

An example of a heparanase assay comprises the following steps. A composition comprising biotin-HS (heparan sulfate) is mixed with a biological sample such as a tumor sample, bodily fluid, or other fluid suspected of having heparanase activity, to form a reaction mixture. This sample may be pretreated to remove contaminating or reactive substances such as endogenous biotin. A control portion for this reaction mixture does not contain a compound of the present invention, whereas a test portion contains one or more compounds disclosed herein. After incubation, an aliquot or portion of the reaction mixture portions is removed and placed in a biotin-binding plate. The biotin-binding plate comprises any means for binding biotin, preferably to a solid surface. See WO 02/23197, which is entirely expressly incorporated herein by reference. After washing with buffers, a streptavidin-enzyme conjugate is added to the biotin-binding plate. Reagents for the enzyme are added to form a detectable color product. For example, a decrease in color formation, from a known standard, indicates there was heparanase activity in the sample. The difference between the activity of the enzyme in the presence of a compound and the absence of compound is used to determine the activity of the compound.

Using the above assays or those taught in the Examples herein, the amount of enzyme activity in a sample can be determined and the activities of compounds of the present invention can be determined. For example, a composition comprising a compound of the present invention is added to a known amount of heparanase either before or during the incubation of the heparanase and its substrate-binding partner. If the compound alters the activity of the heparanase, the assay methods of the present invention will show a change in the amount of detectable label. Such assays are used for high throughput determination of the activity of compounds. See WO 02/23197, which is entirely expressly incorporated herein by reference.

The activities of the compounds included in the present invention modulate the activity of glycosidases, either positively or negatively, include effects on the glycosidases either directly or indirectly. The compounds may modulate the synthesis of glycosidases by cells or tissues or may act directly upon one or more glycosidases to modulate the biological activity or the biological stability of the enzyme itself, for example, heparanase. Activities also included herein are ones that increase the biosynthesis of one or more glycosidases by increasing the transcription of the glycosidase gene, increasing the biological stability of the glycosidase mRNA or increasing the translation of glycosidase mRNA into protein. Further activites include activities of compounds that can block or decrease the effects of agents or proteins that inhibit the activity of glycosidases. Additionally, acitivities are included that effect the substrates for the glycosidases, such as those discussed supra in relation to proteoglycans, or effect the binding parameters of the enzyme with its substrate, cofactors or stimulatory or inhibitory factors.

The present invention comprises methods and compositions for the treatment and prevention of diseases or conditions that present or result from glycosidase activity. Such methods comprise administration of compositions comprising compounds capable of modulating heparanase activity, such as compositions comprising compounds disclosed herein that inhibit heparanase activity. Administration of such compounds that are effective in modulating heparanase activity are administered to humans and animals suspected of having or who have, for example, inflammatory conditions, autoimmune disease or diabetic vasculopathy. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities.

V. Inflammation Modulation

An embodiment of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. The activity of modulating inflammation includes, but is not limited to, inhibiting inflammation and/or its associated cell activation by glycated proteins or AGE, blocking the glycation of proteins, blocking AGE interactions with receptors, blocking AGE-induced signaling or signaling-associated inflammatory responses, cytokine induction, synthesis or release, AGE formation or AGE cross-linking.

The present invention also provides compositions for and methods of treatment of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. Other inflammatory related diseases include, but are not limited to, inflammatory diseases of the joint such as rheumatoid arthritis, osteoarthritis, autoimmune diseases such as those taught supra, streptococcal cell-wall induced arthritis, adjuvant-induced arthritis, bursitis; inflammatory diseases of the thyroid such as acute, subacute and chronic thyroiditis, pelvic inflammatory disease, hepatitis; inflammatory bowel diseases such as Crohn's disease and colitis; neuroinflammatory diseases such as multiple sclerosis, abscess, meningitis, encephalitis, and vasculitis; inflammatory diseases of the heart such as myocarditis, chronic obstructive pulmonary disease, atherosclerosis, pericarditis; inflammatory diseases of the skin such as acute inflammatory dermatoses (urticaria (hives), spongiotic dermatitis, erythema multiforme (em minor), Stevens-Johnson syndrome (sjs, em major), toxic epidermal necrolysis (ten) and chronic inflammatory dermatoses (psoriasis, lichen planus, discoid lupus erythematosus, acne vulgaris); inflammatory diseases of the eye such as uveitis, allergic conjunctivitis, corneal inflammation, intraocular inflammation, iritis; laryngitis and asthma.

The compounds of the present invention have utility in inhibiting inflammation and/or its associated cell activation by glycated proteins or AGE. Pharmacological inhibition of AGE-induced cell activation provides the basis for therapeutic intervention in many diseases, notably in diabetic complications and Alzheimer's disease. Therapeutic approaches for inhibition of AGE-induced inflammation include, but are not limited to, blocking the glycation of proteins, blocking AGE interactions with receptors and blocking AGE-induced signaling or signaling-associated inflammatory responses.

At least one activity of some of the compounds of the present invention is to block AGE effects by inhibiting AGE-induced signaling. The sequence of these signaling events leading to inflammation are not clear, but inhibition of these signaling events leads to reduced or no inflammatory results. Compounds that block AGE-induced up-regulation of inflammatory molecules were determined using screening assays. Other aspects of the present invention comprise methods and compositions comprising compounds that block glycated protein-induced inflammation. Some compounds may effect AGE formation or AGE cross-linking.

At least one activity of some of the compounds of the present invention is to block AGE effects by inhibiting reactions with receptors of AGE and such activities are also contemplated by the methods of the present invention for treatment of related pathologies. For example, RAGE, a known receptor for AGE, is a therapeutic target. Blocking RAGE inhibited AGE-induced inflammation. Prior to use of the compounds of the present invention, the multiple functions of RAGE and possible long term side effects of accumulated AGE in plasma, have prevented this method of treatment from being implemented. However, using the methods and compositions of the present invention, more specific inhibitory compounds can be used for treatments and overcome the current problems with treatments that target receptors.

Compounds of the present invention that have at least the activity of modulating inflammation activity are shown in TABLE 5. The compounds shown in this Table have the activity of modulating inflammation activity as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

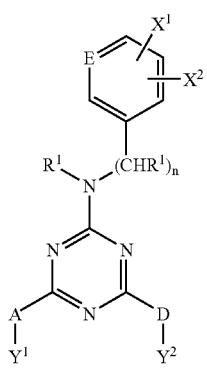

or an ene, a diene, a triene, or an yne derivative thereof; a saturated derivative thereof; a stereoisomer thereof; or a salt thereof, wherein:
- $R^1$ is in each occurrence independently selected from —H; linear or branched alkyl with up to 10 carbon atoms; cycloalkyl with up to 10 carbon atoms; aryl; or $(CH_2)_xCN$, wherein x is an integer from 0 to 6;
- E is CH or N;
- n is an integer from 0 to 3;
- $X^1$ is selected from —H, m-F, m-Cl, m-Br, m-I, m-CN, m-NO$_2$, m-SO$_2$R$^1$, m-SO$_2$OR$^1$, m-NC(O)R$^1$, or o-F, or $X^1$ and $X^2$ together is a fused benzene, pyridine, or dioxane ring;
- $X^2$ is selected from —H, o-Cl, o-Br, o-CF$_3$, o-R$^1$, p-OR$^1$, p-SR$^1$, p-NR$^1{}_2$, p-F, p-Cl, p-Br, p-CF$_3$, p-CN, p-C(O)OR$^1$, p-NC(O)R$^1$, p-(4-morpholinyl), or p-(4-methyl-1-piperizinyl);
- $AY^1$ is a halogen, or A is NR$^1$ or O and Y$^1$ is selected from cycloalkyl with up to 10 carbon atoms, cycloalkyl with up to 10 carbon atoms substituted with R$^1$, linear or branched alkyl with up to 10 carbon atoms, CH$_2$R$^1$, (CHR$^1$)$_y$OR$^1$, wherein y is an integer from 1 to 6,

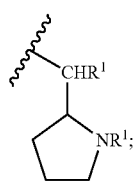

or $AY^1$ together are

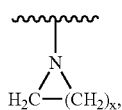

wherein x is an integer from 3 to 5; and
$DY^2$ is a halogen, or D is NR$^1$ and Y$^2$ is selected from

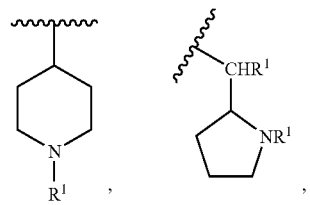

cycloalkyl with up to 10 carbon atoms, cycloalkyl with up to 10 carbon atoms substituted with R$^1$, linear or branched alkyl with up to 10 carbon atoms, CH$_2$R$^1$,

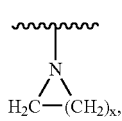

wherein x is an integer from 3 to 5,

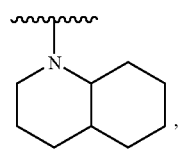

CH$_2$CF$_3$, (CHR$^1$)$_z$Z$^1$, wherein z is an integer from 1 to 6, and Z$^1$ is selected from NR$^1{}_2$,

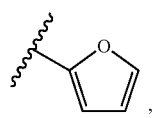 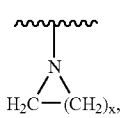

wherein x is an integer from 3 to 5,

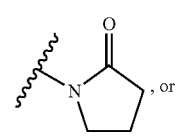, or

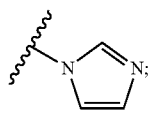

or $NY^2R^1$ together is selected from

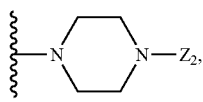

wherein $Z^2$ is selected from $R^1$, $C(O)R^1$, $C(O)OR^1$, pyridinyl, aryl,

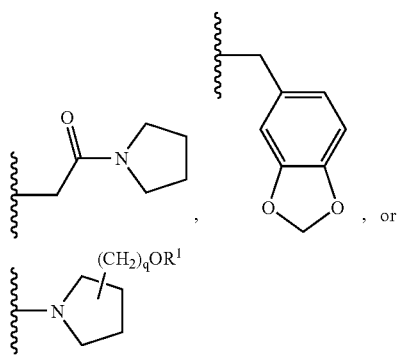

wherein q is an integer from 0 to 6.

Further examples of compounds that show at least this activity and utility are presented in Table 5, where compound activity is also shown. The activity scale used in Table 5 is as follows (numbers are inclusive): "++++" represents between 0 and about 25% of IL6 production compared to cells that did not receive compound (or percent of control IL6 production); "+++" represents between about 25 and about 50% of control IL6 production; "++" represents between about 50 and about 75% of control IL6 production; and "+" represents between about 75 and 100% of control IL6 production. The note "n.d." indicates that the activity of the compound was not determined in the given assay. Further note that any hydrogen atoms that are required for any atom to attain its usual valence in a structure presented in Table 5, whether a carbon atom or a heteroatom, should be inferred if it is not specifically indicated.

In addition to the above compounds, the compounds shown in Table 7, and compositions comprising these compounds, also exhibit the activity of modulating inflammation activity as measured by the assays taught herein. The activity scale used in Table 7 is as follows (numbers are inclusive): "+++" represents between about 85 to 100% inhibition of IL6 production in the presence of AGE or TNF, as compared to cells that did not receive any compound; "++" represents between about 65 and about 85% inhibition of IL6 production in the presence of AGE or TNF; and "+" represents between about 50 and about 65% inhibition of IL6 production in the presence of AGE or TNF. In addition, compounds, to include compositions thereof, encompassed within the scope of structures Ic-XXIc, respectively, or listed in Tables 1C and 1E may be likewise employed in this embodiment and/or aspect of the present invention. As before, the inclusion of compounds in the categories of the Tables disclosed herein are not to be seen as limiting, in that compounds included in such Tables have at least the activity shown for inclusion in the Tables and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Enhanced formation and accumulation of glycated proteins and AGE are thought to play a major role in the pathogenesis of diabetic complications, and atherosclerosis, leading to the development of a range of diabetic complications including nephropathy, retinopathy and neuropathy. There is ample in vivo evidence that suggests that diabetes-related complications can be reduced by 1) preventing glycation of proteins, 2) by breaking the cross-links in glycated proteins or 3) by blocking glycated protein interaction with receptors. Despite the importance of AGE in the pathogenesis of diabetic microangiopathies, there are no currently available medications known to block AGE formation.

Endothelium is the target organ of damage in diabetes. See Laight et al., 15 DIABETES METAB. RES. REV. 274-82 (1999); Stehouwer et al., 34 CARDIOVASC. 55-68 (1997). Up-regulation of molecules involved in endothelial inflammation, such as IL-6 and monocyte chemoattractant protein-I (MCP-1) leads to endothelial dysfunction and vasculopathy. See Stehouwer et al., 34 CARDIOVASC. 55-68 (1997); Libby, 247 J. INTERN. MED. 349-58 (2000); Van Lente, 293 CLINICA. CHIMICA. ACTA. 31-52 (2000).

IL-6 is a pro-inflammatory cytokine that is known to play a key role in the pathogenesis of diabetes and atherosclerosis. See Horii et al., 39 KIDNEY INT. SUPPL. 71-5 (1993); Huber et al., 19 ARTERIOSCLERTHROMB. VASC. BIOL. 2364-67 (1999); Shikano et al., 85 NEPHRON 81-5 (2000); Pickup et al., 8(67) LIFE SCI. 291-300 (2000). IL-6 also promotes the growth of renal mesangial cells thus contributing to nephropathy. See Kado et al., 36 ACTA. DIABETOL. 67-72 (1999). The serum IL-6 level in diabetic subjects was significantly higher than in normal healthy controls (3.48+/-3.29 pg/ml vs 0.784+/-0.90 pg/ml, mean+/-SD). In addition the urinary IL-6 level is a good indicator of diabetic nephropathy. Serum IL-6 is useful in the evaluation of atherosclerosis and nephropathy.

MCP-1, another pro-inflammatory cytokine is found highly expressed in human atherosclerotic lesions and postulated to play a central in monocyte recruitment into the arterial wall and developing lesions. See Libby, 247 J. INTERN. MED. 349-58 (2000). Recent results show that MCP-1 is also a key pathogenic molecule in diabetic nephropathy. See Eitner et al., 51 KIDNEY INT. 69-78 (1997); Banba et al. 58 KIDNEY INT. 684-90 (2000). Glycated albumin stimulates endothelial production of IL-6 and MCP-1. The effects of glycated albumin on IL-6 production are comparable to that of TNFα, a known inducer of IL-6. These cytokines are known to be factors in vascular diseases.

The activity of the compounds of the present invention in inhibiting glycated protein- and AGE-induced inflammation can be determined using the assays described herein and in U.S. patent application Ser. No. 10/026,335, which is herein incorporated in its entirety. Such assays comprise measurement of the specific activity of biological components involved in a known cellular response. The assays provide a measurable response in which the activity of the compounds is determined. One assay comprises measurement of the effects of compounds on an inflammatory response by cells to the presence of a stimulating agent. Yet another assay comprises endothelial cells that are stimulated by the addition of a glycated protein, the stimulating agent. The endothelial cells respond by producing specific cytokines. The amount of cytokines produced are determined by measurement protocols known to those skilled in the art. The compounds of the present invention are then added to the assay and the production of cytokines is measured. From the comparison of the assay without the compound with the assay with the compound, the biological effect of the compound can be determined. The compound may have an inhibitory effect, a stimulatory effect, or no effect at all.

The amount and type of cytokine produced can be determined using immunological methods, such as ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

An aspect of the present invention comprises methods and compositions for the treatment of diseases, preconditions or pathologies associated with inflammatory cytokines and other inflammation related molecules including, but not limited to IL-6, VCAm-1, AGE-induced MCP-1, (monocyte chemoattractant protein 1), heme oxygenase, insulin-like growth factor, selectins, IP-10, MIG and I-TAC, NF-κB, IL-1β (interleukin 1p), IL-11 (interleukin 11), m-CSF (macrophage colony stimulating factor), fibrinogen, TNF-α (tumor necrosis factor α), adhesion molecules, selectins, VCAm-1 (Vascular Cell Adhesion Molecule-1), CRP(C-reactive protein), and PAI-1 (plasminogen activator inhibitor-1). Examples of such diseases include the pathogenesis of atherosclerosis and the development of diabetic vasculopathy in type II diabetes. For example, affecting the activity or level of TNFα is a key mediator of tissue damage following acute or chronic inflammatory reactions. The present invention contemplates providing compositions and methods that modulate the effects of cytokines and inflammatory molecules such as TNFα, IL-6, VCAm-1, IP-10, MIG, I-TAC and AGE-induced MCP-1, and treat the associated diseases, acute or chronic conditions, preconditions and pathologies.

Assays for determining the activity of compounds capable of modulating inflammation include those taught in U.S. patent application Ser. No. 10/026,335 and 09/969,013, which are both expressly incorporated by reference. In general, once the baseline response to the stimulating agent for the production of cytokines by the endothelial cells is established, thus comprising the control levels for the screening assay, the methods comprise addition of compounds of the present invention. The effect of the compound on the baseline response is determined by comparing the amount of cytokine produced in the presence of the stimulating agent and the amount of cytokine produced in the presence of the stimulating agent and the compound of the present invention. In a preferred method, compounds that have inhibitory effects on the inflammation of the cells in the presence of glycated albumin are then used as therapeutic agents. One or more compounds may be added to the screening assay. Combinations or mixtures of compounds can be added. Different amounts and formulations of the compounds are added to determine the effects on the screening assay. The screening assay may also be used to determine stimulatory compounds or compounds that have no effects in the assay.

The present invention comprises methods and compositions for the treatment and prevention of disease, conditions and pathologies associated with inflammation. Such methods comprise administration of compositions comprising compounds capable of modulating the activity of molecules associated with inflammation such as AGE or cytokines or other cellular factors, including release rates or activity, and include compositions comprising compounds disclosed herein with inflammation modulating activity. Administration of such compounds that are effective in modulating inflammation are administered to humans and animals suspected of having or who have inflammatory diseases, for example, diabetic-induced vasculopathies, autoimmune diseases, renal insufficiency, Alzheimer's syndrome, and inflammation-induced diseases such as atherosclerosis. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

VI. Cytotoxic Activity

An embodiment of the present invention comprises methods and compositions comprising compounds that have at least the activity of causing cellular death or a cessation of cellular activity, referred to herein as cytotoxic activity. This activity can be used in methods for in vitro or in vivo cytotoxicity. For example, compounds having this activity can be selectively delivered to an area within a living organism to selectively kill cells in that area. Such methods are using in treating hyperproliferative cells, such as cancers, or other unwanted cellular growth or cellular activities. One aspect of the invention provides compositions comprising compounds that nonselectively kill cells. Another aspect of the invention provides compounds that selectively kill cells, for example, cells that have a particular cellular marker or other identifying characteristic such as metabolic rate or uptake of a particular compound, such as sodium, calcium or thymidine.

The present invention also provides compositions for and methods of treatment of biological conditions including, but not limited to, conditions for which cytotoxic activity is a treatment. For example, the compositions and methods for providing compounds that have at least the activity of cytotoxicity are useful in the treatment or prophylaxis of at least one hyperproliferative disease in a cell, tissue, organ, animal, or patient including, but not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

Compounds of the present invention that have at least the activity of cytotoxicity are shown in TABLE 4A and B. The compounds shown in this Table have the activity of cytotoxicty as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

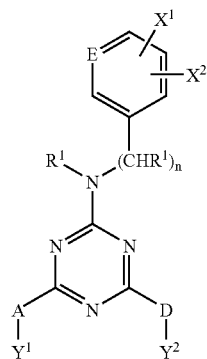

or an ene, a diene, a triene, or an yne derivative thereof; a saturated derivative thereof; a stereoisomer thereof; or a salt thereof;

wherein:
  $R^1$ is in each occurrence independently selected from —H; linear or branched alkyl with up to 10 carbon atoms; cycloalkyl with up to 10 carbon atoms; or aryl;
  E is CH or N;
  n is an integer from 0 to 3;
  $X^1$ is selected from —H, m-F, m-Cl, m-Br, m-I, m-CN, m-$NO_2$, m-$SO_2R^1$, or m-$SO_2OR^1$, or $X^1$ and $X^2$ together is a fused benzene or pyridine ring;
  $X^2$ is selected from —H, o-Cl, o-Br, p-$OR^1$, p-$SR^1$, p-$NR^1_2$, p-F, p-Cl, p-Br, p-$CF_3$, p-C(O)$OR^1$, p-OM, or p-SM, wherein M is selected from Li, Na, K, Mg, or Ca;
  A is selected from $NR^1$ or O, wherein $Y^1$ is selected from cycloalkyl with up to 10 carbon atoms, linear or branched alkyl with up to 10 carbon atoms, or

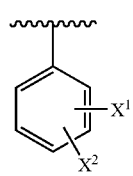

when A is $NR^1$, and wherein $Y^1$ is selected from $R^1$ or $CH^2R^1$ when A is O; or $AY^1$ is selected from a halogen,

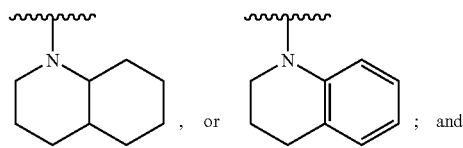

and
  $DY^2$ is a halogen, or D is $NR^1$ and $Y^2$ is selected from

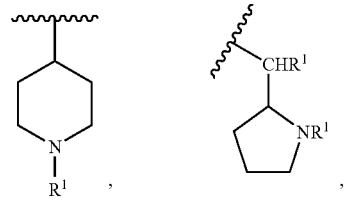

or (CHR$^1$)$_x$NR$^1_2$, wherein x is an integer from 1 to 6.

Additional examples of compounds that show at least this activity and utility are shown in the following formula:

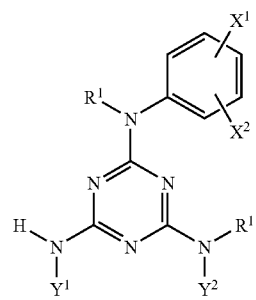

or an ene, a diene, a triene, or an yne derivative thereof; a saturated derivative thereof; a stereoisomer thereof; or a salt thereof;

wherein:
  $R^1$ is in each occurrence independently selected from —H; linear or branched alkyl with up to 10 carbon atoms; or cycloalkyl with up to 10 carbon atoms;
  $X^1$ is in each occurrence independently selected from —H, m-F, m-Cl, m-Br, m-I, m-CN, m-$NO_2$, m-$SO_2R^1$, or m-$SO_2OR^1$;
  $X^2$ is in each occurrence independently selected from o-$CH_3$, p-$OR^1$, p-$SR^1$, p-$NR^1_2$, or p-OM or p-SM, wherein M is selected from Li, Na, K, Mg, or Ca;
  $Y^1$ is selected from cycloalkyl with up to 10 carbon atoms;

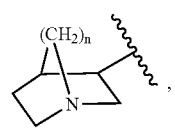

wherein n is 1 or 2; or

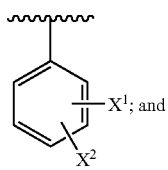

$Y^2$ is selected from

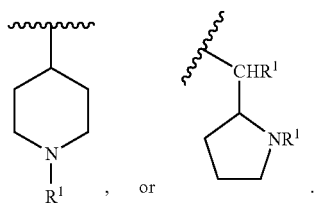

Further examples of compounds that show at least this activity and utility are presented in Tables 4A and 4B. The compound nomenclature of Tables 4A and 4B, as in the other tables presented herein, was generated using Autonom, where the name provided may be the Beilstein or CAS version of the chemical name. Note that any hydrogen atoms that are required for any atom to attain its usual valence in a structure presented in Tables 4A and 4B, whether a carbon atom or a heteroatom, should be inferred if it is not specifically indicated. In addition, compounds, to include compositions thereof, encompassed within the scope of structures Ic-XXIc, respectively, or listed in Tables 1C and 1E may be likewise employed in this embodiment and/or aspect of the present invention.

Assays for determining the activity of compounds capable of cytotoxic activity include those taught in herein and others that are well known in the art. In general, to determine if there is cytotoxic activity associated with a compound, cells of a particular type, in a growing stage or a quiescent stage, are treated with the compound of interest. Various parameters of cell death or cessation are used to measure the effects of the compound. For example, the amount of nucleic acid or protein synthesis can be measured or visual observation of the state of the cells, such as release from the substrate, can be used to measure the state of the cells.

The present invention comprises methods and compositions for the treatment and prevention of diseases or conditions that present or result from cellular proliferation or unwanted cellular growth or cellular activity. Such methods comprise administration of compositions comprising compounds capable of modulating cellular activity or causing cellular death or cessation of growth such as compositions comprising compounds disclosed herein that have cytotoxic activity. Administration of such compounds that are effective in cytotoxic activity are administered to humans and animals suspected of having or who have, for example, cancer, overactive tissues such as thyroid or hypothalamus, or cellular conditions where factors are released in unwanted amounts. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities.

Compound/Composition-Coated Medical Devices

The compounds of the present invention may be used alone or in combination with other agents along with delivery devices to effectively prevent and treat the diseases described herein, though particular applications are found in vascular disease, and in particular, vascular disease caused by injury and/or by transplantation. Though this example focuses on vascular disease, provision of the compounds of the present invention with medical devices for treatment of the diseases and conditions capable of being treated with the compounds is contemplated by the present invention.

Various medical treatment devices utilized in the treatment of vascular disease may ultimately induce further complications. For example, balloon angioplasty is a procedure utilized to increase blood flow through an artery and is the predominant treatment for coronary vessel stenosis. However, the procedure typically causes a certain degree of damage to the vessel wall, thereby creating new problems or exacerbating the original problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits in other organs or sites of the body, such as the liver, lung, bladder, kidney, brain, prostate, neck and legs.

The local delivery of a compound of the present invention and, in some embodiments, along with other therapeutic agents, from a stent prevents vessel recoil and remodeling through the scaffolding action of the stent. The activity of compound provided, with or without other therapeutic agents, helps determine for which application, to treat which disease, the coated medical device is being administered. For example, compound-coated stents can prevent multiple components of neointimal hyperplasia or restenosis as well as reduce inflammation and thrombosis. Local administration of a compound of the present invention and other therapeutic agents to stented coronary arteries may also have additional therapeutic benefit. For example, higher tissue concentrations of the compounds of the present invention and other therapeutic agents may be achieved utilizing local delivery rather than systemic administration. In addition, reduced systemic toxicity may be achieved utilizing local delivery rather than systemic administration while maintaining higher tissue concentrations. In utilizing local delivery from a stent rather than systemic administration, a single procedure may suffice with better patient compliance. An additional benefit of combination therapeutic agent and/or compound therapy may be to reduce the dose of each of the therapeutic agents, thereby limiting toxicity, while still achieving a reduction in restenosis, inflammation and thrombosis. Local stent-based therapy is therefore a means of improving the therapeutic ratio (efficacy/toxicity) of anti-restenosis, anti-inflammatory, and anti-thrombotic therapeutic agents.

Although exemplary embodiments of the invention will be described with respect to the treatment of restenosis and other related complications, it is important to note that the local delivery of a compound of the present invention, alone or as part of a therapeutic agent combination, may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining one or more compounds of the present invention having activity that is effecting in preventing unwanted cellular growth with the device. Other medical devices that often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the combinations of the compounds of the present invention, possibly other pharmaceutical agents, and the devices. Other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this compound-device combination approach. Essentially, any type of medical device may be coated in some fashion with at least one compound of the present invention, alone or as part of a therapeutic agent combination, which enhances treatment over the use of the device or therapeutic agent without combination with the compound.

As disclosed supra, the compounds of the present invention can be administered in combinational therapies with other therapeutic agents, and are not limited to only the other therapeutic agents disclosed herein. Thus, the present invention also contemplates, in addition to various medical devices, the coatings on these devices may be used to deliver a compound of the present invention in combination with other therapeutic agents. This illustrative list of therapeutic agents can be administered through pharmeutical means or in association with medical devices and such therapeutic agents include, but are not limited to, antiproliferative/antimitotic agents including natural products such as vinca alkaloids (e.g., vinblastine, vincristine, and vinorelbine), paclitaxel, epipodophyllotoxins (e.g., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (brevelidin); anti-inflammatory agents such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenyl derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives. (Cyclosporine, tacrolimus (FK-506), sirolimus (rapamycin), azathioprine, mycophenylate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor signal transduction kinase inhibitors.

Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized. For example, though stents are described, sleeves outside the vessels are also contemplated, as are other medical devices that can provide a substrate for administration for at least one of the compounds of the present invention.

A stent is commonly used as a tubular structure left inside the lumen of a duct to relieve an obstruction. Typically, stents are inserted into the lumen in a non-expanded form and are then expanded autonomously, or with the aid of a second device in situ. A common method of expansion occurs through the use of a catheter-mounted, angioplasty balloon that is inflated within the stenosed vessel or body passageway in order to shear and disrupt the obstructions associated with the wall components of the vessel and to obtain an enlarged lumen.

A stent may resemble an expandable cylinder and may comprise a fenestrated structure for placement in a blood vessel, duct or lumen to hold the vessel, duct or lumen open, more particularly for protecting a segment of artery from restenosis after angioplasty. The stent may be expanded circumferentially and maintained in an expanded configuration that is circumferentially or radially rigid. The stent may be axially flexible and when flexed at a band, for example, the stent avoids any externally protruding component parts.

The stent may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one embodiment, expansion may be effected in a blood vessel by a balloon catheter, where the final diameter of the stent is a function of the diameter of the balloon catheter used. It should be appreciated that a stent in accordance with the present invention may be embodied in a shape-memory material including, for example, an appropriate alloy of nickel and titanium or stainless steel.

Structures formed from stainless steel may be made self-expanding by configuring the stainless steel in a predetermined manner, for example, by twisting it into a braided configuration. In this embodiment, after the stent has been formed it may be compressed so as to occupy a space sufficiently small as to permit its insertion in a blood vessel or other tissue by insertion means, wherein the insertion means include a suitable catheter, or flexible rod. Upon emerging from the catheter, the stent may be configured to expand into the desired configuration where the expansion is automatic or triggered by a change in pressure, temperature or electrical stimulation.

Furthermore, a stent may be modified to comprise one or more reservoirs. Each of the reservoirs may be opened or closed as desired. These reservoirs may be specifically designed to hold the compound or compound/therapeutic agent combination to be delivered. Regardless of the design of the stent, it is preferable to have the compound or compound/therapeutic agent combination dosage applied with enough specificity and a sufficient concentration to provide an effective dosage in the affected area. In this regard, the reservoir size in the bands is preferably sized to adequately apply the compound or compound/therapeutic agent combination dosage at the desired location and in the desired amount.

In an alternative embodiment, the entire inner and outer surface of the stent may be coated with the compound or compound/therapeutic agent combination in therapeutic dosage amounts. The coating techniques may vary depending on the compound or compound/therapeutic agent combination. Also, the coating techniques may vary depending on the material comprising the stent or other intraluminal medical device.

One or more compounds of the present invention and, in some instances, other therapeutic agents as a combination, may be incorporated onto or affixed to the stent in a number of ways. In one embodiment, the compound is directly incorporated into a polymeric matrix and sprayed onto the outer surface of the stent. The compound elutes from the polymeric matrix over time and enters the surrounding tissue. The compound preferably remains on the stent for at least three days up to approximately six months, and more preferably between seven and thirty days.

Any number of non-erodible polymers may be utilized in conjunction with the compound, and such polyermic compositions are well known in the art. In one embodiment, the polymeric matrix comprises two layers. The base layer comprises a solution of poly(ethylene-covinylacetate) and polybutylmethacrylate. The compound is incorporated into this base layer. The outer layer comprises only polybutylmethacrylate and acts as a diffusion barrier to prevent the compound from eluting too quickly. The thickness of the outer layer or topcoat determines the rate at which the compound elutes from the matrix. Essentially, the compound elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate and compound solution may be incorporated into or onto the stent in a number of ways. For example, the solution may be sprayed onto the stent or the stent may be dipped into the solution. Other methods include spin coating and plasma polymerization. In one embodiment, the solution is sprayed onto the stent and then allowed to dry. In another embodiment, the solution may be electrically charged to one polarity and the stent electrically charged to the opposite polarity. In this manner, the solution and stent will be attracted to one another. In using this type of spraying process, waste may be reduced and more precise control over the thickness of the coat may be achieved.

Drug-coated stents are manufactured by a number of companies including Johnson & Johnson, Inc. (New Brunswick, N.J.), Guidant Corp. (Santa Clara, Calif.), Medtronic, Inc. (Minneapolis, Minn.), Cook Group Incorporated (Bloomington, Ind.), Abbott Labs., Inc. (Abbott Park, Ill.), and Boston Scientific Corp. (Natick, Mass.). See e.g., U.S. Pat. No. 6,273,913; U.S. Patent Application No. 20020051730; WO 02/26271; and WO 02/26139, each expressly entirely incorporated herein by reference.

Expression Profiles and Microarray Methods of Use

Other aspects of the present invention comprise compositions and methods for microarray devices. Such microarray devices and methods comprise a variety of microarrays that may be used, for example, to study and monitor gene expression in response to treatment with the compounds of the present invention. The microarrays may comprise nucleic acid sequences, carbohydrates or proteins that are determinative for specific cells, tissues, species, disease states, prognoses, disease progression, or any other combination of molecules that can be used to determine an effect of one or more of the compounds of the present invention.

For example, the microarrays of the present invention may be derived from, or representative of, for example, a specific organism or cell type, including human microarrays, vascular microarrays, inflammation microarrays, cancer microarrays, apoptosis microarrays, oncogene and tumor suppressor microarrays, cell-cell interaction microarrays, cytokine and cytokine receptor microarrays, blood microarrays, cell cycle microarrays, neuroarrays, mouse microarrays, and rat microarrays, or combinations thereof. In further embodiments, the microarrays may represent diseases including cardiovascular diseases, vasculopathic conditions, inflammatory diseases, autoimmune diseases, neurological diseases, immunological diseases, various cancers, infectious diseases, endocrine disorders, and genetic diseases.

Alternatively, the microarrays useful in assessing the efficacy of the compounds of the present invention may represent a particular tissue type including, but not limited to, heart, liver, prostate, lung, nerve, muscle, or connective tissue; preferably coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, prostate stromal cells, or combinations thereof.

The present invention further contemplates microarrays comprising a gene expression profile comprising one or more polynucleotide sequences including complementary and homologous sequences, wherein said gene expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

The present invention contemplates microarrays comprising one or more protein-binding agents, wherein a protein expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

More specifically, the present invention contemplates methods for the reproducible measurement and assessment of the expression of specific mRNAs or proteins in, for example, a specific set of cells. One method combines and utilizes the techniques of laser capture microdissection, T7-based RNA amplification, production of cDNA from amplified RNA, and DNA microarrays containing immobilized DNA molecules for a wide variety of specific genes, including HSPGs such as perlecan, to produce a profile of gene expression analysis for very small numbers of specific cells. The desired cells are individually identified and attached to a substrate by the laser capture technique, and the captured cells are then separated from the remaining cells. RNA is then extracted from the captured cells and amplified about one million-fold using the T7-based amplification technique, and cDNA may be prepared from the amplified RNA. A wide variety of specific DNA molecules are prepared that hybridize with specific polynucleotides of the microarray, and the DNA molecules are immobilized on a suitable substrate. The cDNA made from the captured cells is applied to the microarray under conditions that allow hybridization of the cDNA to the immobilized DNA on the microarray. The expression profile of the captured cells is obtained from the analysis of the hybridization results using the amplified RNA or cDNA made from the amplified RNA of the captured cells, and the specific immobilized DNA molecules on the microarray. The hybridization results demonstrate, for example, which genes of those represented on the microarray as probes are hybridized to cDNA from the captured cells, and/or the amount of specific gene expression. The hybridization results represent the gene expression profile of the captured cells. The gene expression profile of the captured cells can be used to compare the gene expression profile of a different set of captured cells. For example, gene expression profiles may be generated from cells treated (and not treated) with a compound of the present invention. The similarities and differences provide useful information for determining the differences between the same cell type under different conditions, more specifically, the change in gene expression in response to treatment with a compound of the present invention.

The techniques used for gene expression analysis are likewise applicable in the context of protein expression profiles. Total protein may be isolated from a cell sample and hybridized to a microarray comprising a plurality of protein-binding agents, which may include antibodies, receptor proteins, small molecules, and the like. Using any of several assays known in the art, hybridization may be detected and analyzed as described above. In the case of fluorescent detection, algorithms may be used to extract a protein expression profile representative of the particular cell type. In this regard, the change in protein expression in response to treatment of cells with a compound of the present invention may be evaluated.

Thus, in one aspect, the present invention comprises at least one microarray corresponding to a population of genes isolated from a particular tissue or cell type in methods that is used to detect changes in gene transcription levels that result from exposing the selected tissue or cells to at least one compound of the present invention. In this embodiment, a biological sample derived from an organism, or an established cell line, may be exposed to at least one compound of the present invention in vivo or ex vivo. Thereafter, the gene transcripts, primarily mRNA, of the tissue or cells are isolated by methods well-known in the art. SAMBROOK ET AL., MOLECULAR CLONING: A LAB. MANUAL (2001). The isolated transcripts are then contacted with a microarray under conditions where the transcripts hybridize with a corresponding probe to form hybridization pairs. Thus, the microarray provides a model of the transcriptional responsiveness following exposure to at least one compound of the present invention. Such information can be used to determine therapeutic candidates. A hybridization signal may then be detected at each hybridization pair to obtain a gene expression profile.

Gene and/or protein expression profiles and microarrays may also be used to identify activating or non-activating compounds of a particular gene such as perlecan or other HSPG. Compounds that increase transcription rates or stimulate, maintain, or stabilize the activity of a protein are considered activating, and compounds that decrease rates or inhibit the activity of a protein are non-activating. Moreover, the biological effects of a compound may be reflected in the biological state of a cell. This state is characterized by the cellular constituents. One aspect of the biological state of a cell is its transcriptional state. The transcriptional state of a cell includes the identities and amounts of the constituent RNA species, especially mRNAs, in the cell under a given set of conditions. Thus, the gene expression profiles, microarrays, and algorithms discussed herein may be used to analyze and characterize the transcriptional state of a given cell or tissue following exposure to an activating or non-activating compound, specifically, a compound of the present invention.

Microarray techniques and methods for analyzing results are well known in the art. See U.S. Pat. Nos. 6,263,287; 6,239,209; 6,218,122; 6,197,599; 6,156,501; 5,874,219; 5,837,832; 5,700,637; 5,445,934; U.S. Patent Application Nos. 2001/0014461 A1; 2001/0039016 A1; 2001/0034023 A1; WO 01/94946; and WO 01/77668. See also, Haab et al., 2 GENOME BIOLOGY 1-12 (2001); Brown et al., 97 PROC. NATL. ACAD. SCI. USA 262-7 (2000); Getz et al., 97 PROC. NATL. ACAD. SCI. USA 12079-84 (2000); Harrington et al., 3

CURRENT OPINION MICROBIOL. 285-91 (2000); Holter et al., 97 PROC. NATL. ACAD. SCI. USA 8409-14 (2000); MacBeath et al., 289 SCIENCE 1760-63 (2000); Duggan et al., 21 NATURE GENET. 10-14 (1999); Lipshutz et al., 21 NATURE GENET. 5-9 (1999); Eisen et al., 95 PROC. NATL. ACAD. SCI. USA 14863-68 (1998); Ermolaeva et al., 20 NATURE GENET. 19-23 (1998); Hacia et al., 26 NUCLEIC ACIDS RES. 3865-66 (1998); Lockhart et al., NUCLEIC ACIDS SYMP. SER. 11-12 (1998); Schena et al., 16 TRENDS BIOTECHNOL. 301-6 (1998); Shalon, 46 PATHOL. BIOL. 107-9 (1998); Welford et al., 26 NUCLEIC ACID RES. 3059-65 (1998); Blanchard et al., 11 BIOSENSORS BIOELECTRONICS 687-90 (1996); Lockhart et al., 14 NATURE BIOTECHNOL. 1675-80 (1996); Schena et al., 93 PROC. NATL. ACAD. SCI. USA 10614-19 (1996); Tomayo et al., 96 PROC. NATL. ACAD. SCI. USA 2907-12 (1996); Schena et al., 270 SCIENCE 467-70 (1995)

Database Creation, Database Access and Associated Methods of Use

Another embodiment of the present invention comprises a variety of methods for managing or using data related to the compounds, methods of making the compounds, methods of using and administering the compounds, and diagnosing, prognosing and following the outcomes associated with diseases in which the compounds are effective in treating. For example, methods for providing diagnostics and predictors relating to biomolecules including HSPGS, particularly, perlecan, are contemplated by the present invention. Also within the scope of this invention are methods providing diagnostics and predictors relating to the efficacy of the compounds of the present invention. The present invention further contemplates methods of providing expression profile databases, and methods for producing such databases, for normal and diseased tissues.

The expression profile database may be an internal database designed to include annotation information about the expression profiles generated to assess the effect of the compounds of the present invention and through other sources and methods. Such information may include, for example, the databases in which a given biomolecule was found, patient information associated with the expression profile, including age, cancer or tumor type or progression, information related to a compound of the present invention such as dosage and administration information, descriptive information about related cDNAs associated with the sequence, tissue or cell source, sequence data obtained from external sources, expression profiles for a given gene and the related disease state or course of disease, for example whether the expression profile relates to or signifies a particular disease state, and preparation methods. The expression profiles may be based on protein and/or polynucleotide microarray data obtained from publicly available or proprietary sources. The database may be divided into two sections: one for storing the sequences and related expression profiles and the other for storing the associated information. This database may be maintained as a private database with a firewall within the central computer facility. However, this invention is not so limited and the expression profile database may be made available to the public.

The database may be a network system connecting the network server with clients. The network may be any one of a number of conventional network systems, including a local area network (LAN) or a wide area network (WAN), as is known in the art (e.g., Ethernet). The server may include software to access database information for processing user requests, and to provide an interface for serving information to client machines. The server may support the World Wide Web and maintain a website and Web browser for client use. Client/server environments, database servers, and networks are well documented in the technical, trade, and patent literature.

Through the Web browser, clients may construct search requests for retrieving data from, for example, a microarray database and an expression profile database. For example, the user may "point and click" to user interface elements such as buttons, pull down menus, and scroll bars. The client requests may be transmitted to a Web application that formats them to produce a query that may be used to gather information from the system database, based, for example, on microarray or expression data obtained by the client, and/or other phenotypic or genotypic information. Specifically, the client may submit expression data based on microarray expression profiles obtained from a patient treated with a compound of the present invention and use the system to obtain a diagnosis based on that information based on a comparison by the system of the client expression data with the expression data contained in the database. By way of example, the system compares the expression profiles submitted by the client with expression profiles contained in the database and then provides the client with diagnostic information based on the best match of the client expression profiles with the database profiles. Thus, in one aspect, the comparison of expression profiles aids the clinician in determining the effectiveness of treatment with a compound of the present invention. Based on such a comparison, the clinician may alter or adjust the treatment regimen.

In addition, the website may provide hypertext links to public databases such as GenBank and associated databases maintained by the National Center for Biotechnology Information (NCBI), part of the National Library of Medicine as well as, any links providing relevant information for gene expression analysis, genetic disorders, scientific literature, and the like. Information including, but not limited to, identifiers, identifier types, biomolecular sequences, common cluster identifiers (GenBank, Unigene, Incyte template identifiers, and so forth) and species names associated with each gene, is contemplated.

The present invention also provides a system for accessing and comparing bioinformation, specifically expression profiles and other information which is useful in the context of the compositions and methods of the present invention. In one embodiment, the computer system may comprise a computer processor, suitable memory that is operatively coupled to the computer processor, and a computer process stored in the memory that executes in the computer processor and which comprises a means for matching an expression profile of a biomolecular sequence from a patient with expression profile and sequence identification information of biomolecular sequences in a database. More specifically, the computer system is used to match an expression profile generated from a biological sample treated with a compound of the present invention with expression profile and other information in a database.

Furthermore, the system for accessing and comparing information contained in biomolecular databases comprises a computer program comprising computer code providing an algorithm for matching an expression profile generated from a patient, for example, treated with a compound of the present invention, with expression profile and sequence identification information of biomolecular sequences in a biomolecular database.

The present invention contemplates, in one embodiment, the use of a Graphical User Interface ("GUI") for the access of expression profile information stored in a biomolecular database. In a specific embodiment, the GUI may be composed of two frames. A first frame may contain a selectable list of biomolecular databases accessible by the user. When a biomolecular database is selected in the first frame, a second frame may display information resulting from the pair-wise comparison of the expression profile database with the client-supplied expression profile as described above, along with any other phenotypic or genotypic information.

The second frame of the GUI may contain a listing of biomolecular sequence expression information and profiles contained in the selected database. Furthermore, the second frame may allow the user to select a subset, including all of the biomolecular sequences, and to perform an operation on the list of biomolecular sequences. In one embodiment, the user may select the subset of biomolecular sequences by selecting a selection box associated with each biomolecular sequence. In another embodiment, the operations that may be performed include, but are not limited to, downloading all listed biomolecular sequences to a database spreadsheet with classification information, saving the selected subset of biomolecular sequences to a user file, downloading all listed biomolecular sequences to a database spreadsheet without classification information, and displaying classification information on a selected subset of biomolecular sequences.

If the user chooses to display classification information on a selected subset of biomolecular sequences, a second GUI may be presented to the user. In one embodiment, the second GUI may contain a listing of one or more external databases used to create the expression profile databases as described above. Furthermore, for each external database, the GUI may display a list of one or more fields associated with each external database. In yet another embodiment, the GUI may allow the user to select or deselect each of the one or more fields displayed in the second GUI. In yet another embodiment, the GUI may allow the user to select or deselect each of the one or more external databases.

The methods of the present application futher relate to the commercial and other uses of the compositions and methodologies of the present invention. In one aspect, the methods include the marketing, sale, or licensing of the compositions and methodologies of the present invention in the context of providing consumers, i.e., patients, medical practitioners, medical service providers, researchers, and pharmaceutical distributors and manufacturers, with expression profile databases including, in particular, databases produced in accordance with the use of the compounds of the present invention.

In another embodiment, the methods of the present invention include establishing a distribution system for distributing the pharmaceutical compositions of the present invention for sale, and may optionally include establishing a sales group for marketing the pharmaceutical composition. Yet another aspect of the present invention provides a method of conducting target discovery comprising identifying, by one or more of the above drug discovery methods, a test compound, as described above, which modulates the level of expression of a gene or the activity of a gene product such as perlecan; conducting therapeutic profiling of agents identified, or further analogs thereof, for efficacy and toxicity in animals; and optionally formulating a pharmaceutical composition including one or more of the agents identified as having an acceptable therapeutic profile; and optionally licensing or selling, the rights for further drug development of said identified agents.

Pharmaceutical Compositions

In addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical excipients and additives useful in the present invention include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

The pharmaceutical compositions comprising the compounds of the present invention can also include a buffer or a pH adjusting agent. Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, pharmaceutical compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, anti-microbial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA). These and additional known pharmaceutical excipients and/or additives suitable for use in the present invention are known in the art, e.g., as listed in REMINGTON: THE SCIENCE & PRACTICE OF PHARMACY ($19^{th}$ ed., Williams & Williams (1995)) and PHYSICIAN'S DESK REFERENCE ($52^{nd}$ ed., Medical Economics (1998)), the disclosures of which are expressly entirely incorporated herein by reference.

Pharmaceutical Compositions for Oral Administration

For oral administration in the form of a tablet or capsule, a compound may be combined with an oral, non-toxic pharmaceutically acceptable inert carrier such as ethanol, glycerol, water and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

In addition, the combinations may be incorporated into biodegradable polymers allowing for sustained release of the compound, the polymers being implanted in the vicinity of where drug delivery is desired, for example, at the site of restenosis. The biodegradable polymers and their uses are described, for example, in detail in Brem et al., 74 J. Neurosurg. 441-46 (1991). Suitable examples of sustained-release compositions include semipermeable matrices of solid hydrophobic polymers containing a compound of the present invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(-)-3-hydroxybutyric acid.

Pharmaceutical Compositions for Parenteral Administration

Formulations suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous administration is desired. The pharmaceutical compositions may be administered parenterally via injection of a formulation consisting of the active ingredient dissolved in an inert liquid carrier. The term "parenteral," as used herein, includes, but is not limited to, subcutaneous injections, intravenous, intramuscular, intraperitoneal injections, or infusion techniques. Acceptable liquid carriers include, for example, vegetable oils such as peanut oil, cotton seed oil, sesame oil and the like, as well as organic solvents such as solketal, glycerol formal and the like. The formulations may be prepared by dissolving or suspending the active ingredient in the liquid carrier such that the final formulation contains from about 0.005% to 30% by weight of the active ingredient, i.e., a compound of the present invention.

Pharmaceutical Compositions for Other Routes of Administration

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the compound to be administered in a suitable liquid carrier. The liquid forms may include suitably flavored suspending or dispersing agents such as the synthetic and natural gums, for example, tragacanth, acacia, methyl-cellulose and the like.

Formulations for rectal administration may be presented as a suppository with a suitable base comprising, for example, cocoa butter or a salicylate.

Formulations suitable for vaginal administration may be presented as pessaries, tamports, creams, gels, pastes, foams or spray formulations containing in addition to the active ingredient such carriers as are known in the art to be appropriate.

The compounds may also be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions. Remington's Pharmaceutical Sciences (A. Osol ed., 16th ed. (1980)).

In a specific embodiment, the compounds disclosed herein are formulated as liposomes. Liposomes containing a compound of the present invention are prepared by methods known in the art. See, e.g., U.S. Pat. Nos. 5,013,556; 4,485,045; 4,544,545; WO 97/38731; Epstein et al., 82 Proc. Natl. Acad. Sci. USA 3688 (1985); and Hwang et al., 77 Proc. Natl. Acad. Sci. USA 4030 (1980). The compounds of the present invention can also be administered in the form of liposome delivery systems such as small unilamellar vesicles, large unilamellar vesicles, and multilamellar vesicles. Liposomes can be formed from a variety of phospholipids such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue.

Pharmaceutically Acceptable Preservatives

The present invention provides stable formulations as well as preserved solutions and formulations containing a preservative as well as multi-use preserved formulations suitable for pharmaceutical or veterinary use, comprising at least one compound disclosed herein in a pharmaceutically acceptable formulation. Formulations in accordance with the present invention may optionally contain at least one known preservative. Preservatives include, but are not limited to, phenyl, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein. Non-limiting examples include, no preservative, 0.1-2% m-cresol, 0.1-3% benzyl alcohol, 0.001-0.5% thimerosal, 0.001-2.0% pheno, 0.0005-1.0% alkylparaben(s), and the like.

Other excipients, e.g., isotonicity agents, buffers, antioxidants, preservative enhancers, can be optionally added to the diluent. An isotonicity agent such as glycerin, is commonly used at known concentrations. A physiologically tolerated buffer is preferably added to provide improved pH control. The formulations can cover a wide range of pHs, such as from about pH 4 to about pH 10, specifically, a range from about pH 5 to about pH 9, and more specifically, a range of about 6.0 to about 8.0. In one aspect, the formulations of the present invention have pH between about 6.8 and about 7.8. Suitable buffers include phosphate buffers, for example, sodium phosphate and phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the pharmaceutical compositions to reduce aggregation. These additives are particularly useful if a pump or plastic container is used to administer the pharmacuetical composition. The presence of pharmaceutically acceptable surfactant mitigates the propensity for the composition to aggregate.

During any of the processes for preparation of the compounds of the present invention, it may be necessary and/or desirable to protect sensitive or reactive groups on any of the molecules concerned. This may be achieved by means of conventional protecting groups, such as those described in PROTECTIVE GROUPS IN ORGANIC CHEMISTRY (1973); and GREENE AND WUTS, PROTECTIVE GROUPS IN ORGANIC SYNTHESIS (1991). The protecting groups may be removed at a convenient subsequent stage using methods known from the art.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Pulmonary/Nasal Administration

There are a several desirable features of an inhalation device for administering a compound of the present invention. For example, delivery by the inhalation device is reliable, reproducible, and accurate. For pulmonary administration, at least one pharmaceutical composition is delivered in a particle size effective for reaching the lower airways of the lung or sinuses. The inhalation device can optionally deliver small dry particles, e.g. less than about 10 µm, preferably about 1-5 µm, for good respirability.

According to the invention, at least one pharmaceutical composition can be delivered by any of a variety of inhalation or nasal devices known in the art for administration of a therapeutic agent by inhalation. Devices capable of depositing aerosolized formulations in the sinus cavity or alveoli of a patient include metered dose inhalers, nebulizers, dry powder generators, sprayers, and the like. Other devices suitable for directing pulmonary or nasal administration are also known in the art.

All such devices can be used for the administration of a pharmaceutical composition in an aerosol. Such aerosols may comprise either solutions (both aqueous and non aqueous) or solid particles. Metered dose inhalers like the Ventolin® metered dose inhaler, typically use a propellent gas and require actuation during inspiration. See, e.g., WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each entirely expressly incorporated herein by reference. Nebulizers like AERx®, Aradigm, the Ultravent® nebulizer (Mallinckrodt), and the Acorn II® nebulizer (Marquest Medical Products), the above references entirely expressly incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of the invention, and are not intended as limiting the scope of the invention.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

A spray comprising a pharmaceutical composition of the present invention can be produced by forcing a suspension or solution of a compound disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one compound delivered by a sprayer have a particle size in a range of about less than 1 μm to less than about 20 μm.

Pharmaceutical compositions of at least one of the compounds of the present invention suitable for use with a sprayer typically include a compound disclosed herein in an aqueous solution at a concentration of about 0.1 mg to about 100 mg of a compound disclosed herein per ml of solution or mg/gm, or any range or value therein, including, but not limited to, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The pharmaceutical composition can include agents such as an excipient, a buffer, an isotonicity agent, a preservative, a surfactant, or other known agents of pharmaceutical compositions.

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of composition protein either directly or through a coupling fluid, creating an aerosol including the composition protein. Advantageously, particles of the pharmaceutical composition delivered by a nebulizer have a particle size range of from about less than 1 μm to less than about 20 μm.

Pharmaceutical compositions comprising a compound of the present invention suitable for use with a nebulizer, either jet or ultrasonic, typically include a concentration of about 0.1 mg to about 100 mg of a compound disclosed herein per ml of solution or mg/gm, or any range or value therein including, but not limited to, the individual amounts disclosed for spray compositions. The pharmaceutical composition can include other pharmaceutical agents such as an excipient, a buffer, an isotonicity agent, a preservative, a surfactant, and those known in the art for use in nebulizer administration.

In a metered dose inhaler (MDI), a propellant, a compound of the present invention, and any excipients or other additives are contained in a cannister as a mixture including a liquefied, compressed gas. Actuation of the metering valve releases the mixture as an aerosol, preferably containing a particle size range of from about less than 1 μm to less than about 20 μm.

The desired aerosol particle size can be obtained by employing a formulation of a compound of the present invention produced by various methods known to those of skill in the art including, but not limited to, jet-milling, spray drying, critical point condensation, and the like. Suitable metered dose inhalers include those manufactured by 3M or Glaxo and employing a hydrofluorocarbon propellant.

Pharmaceutical compositions for use with a metered-dose inhaler device will generally include a finely divided powder containing a compound disclosed herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. In one embodiment, the propellant is a hydrofluorocarbon. The surfactant can be chosen to stabilize the compound of the present invention as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. One of ordinary skill in the art will recognize that the methods of the present invention can be achieved by pulmonary administration of a compound disclosed herein via devices not described herein.

For absorption through mucosal surfaces, the compositions and methods of the present invention for administering a compound disclosed herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles. See, e.g., U.S. Pat. No. 5,514,670. Mucous surfaces suitable for application of the emulsions of the present invention can include corneal, conjunctival, buccal, sublingual, nasal, vaginal, pulmonary, abdominal, intestinal, and rectal routes of administration. Pharmaceutical compositions for vaginal or rectal administration such as suppositories, can contain as excipients, for example, polyalkyleneglycols, vaseline, cocoa butter, and the like. Pharmaceutical composition s for intranasal administration can be solid and contain excipients, for example, lactose or can be aqueous or oily solutions of nasal drops. For buccal administration, excipients include sugars, calcium stearate, magnesium stearate, pregelinatined starch, and the like. See, e.g., U.S. Pat. No. 5,849,695.

In another embodiment, the pharmaceutical compositions of the present invention may be administered via transdermal routes using forms of transdermal skin patches well known to those of ordinary skill in that art. For transdermal administration, a compound of the present invention is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. See, e.g., U.S. Pat. No. 5,814,599. To be administered in the form of a transdermal delivery system, the dosage administration may be, for example, continuous rather than intermittent throughout the dosage regimen.

Formulations suitable for topical administration to the skin may be presented as ointments, creams, gels and pastes comprising the ingredient to be administered in a pharmaceutical acceptable carrier. A preferred topical delivery system is a transdermal patch comprising a compound of the present invention.

Topical compositions containing a compound of the present invention may be admixed with a variety of carrier materials well known in the art including alcohols, aloe vera gel, allantoin, glycerine, vitamin A and E olis, mineral oil, PPG2 myristyl propionate and the like to form, for example, alcoholic solutions, topical cleansers, cleansing creams, skin gels, skin lotions, and shampoos in cream or gel formulations. Examples of such carriers and methods of formulation may be found in REMINGTON'S PHARMACEUTICAL SCIENCES (1990). Pharmaceutical formulations may contain from about 0.005% to about 10% by weight of the active ingredient. In one embodiment, the pharmaceutical formulations contain from about 0.01% to 5% by weight of the compound of the present invention.

It can be sometimes desirable to deliver the compounds of the present invention to the subject over prolonged periods of time, for example, for periods of one week to one year from a single administration. Certain medical devices may be employed to provide a continuous intermittent or on demand dosing of a patient. The devices may be a pump of diffusion apparatus, or other device containing a reservoir of drug and optionally diagnostic or monitoring components to regulate the delivery of the drug. Various slow-release, depot or implant dosage forms can be utilized. For example, a dosage form can contain a pharmaceutically acceptable non-toxic salt of compound disclosed herein that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or, preferably, a relatively insoluble salt such as those just described, can be formulated in a gel, for example, an aluminum monostearate gel with, e.g., sesame oil, suitable for injection. Exemplary salts include, but are not limited to, zinc salts, zinc tannate salts, pamoate salts, and the like. Another type of slow-release depot formulation for injection would contain the compound or salt dispersed or encapsulated in a slow degrading, non-toxic, non-antigenic polymer such as a polylactic acid/polyglycolic acid polymer, for example, as described in U.S. Pat. No. 3,773,919. The compounds or relatively insoluble salts thereof such as those described above can also be formulated in cholesterol matrix silastic pellets, particularly for use in animals. Additional slow-release, depot or implant formulations, e.g., gas or liquid liposomes are known in the literature. See, e.g., U.S. Pat. No. 5,770,222; SUSTAINED AND CONTROLLED RELEASE DRUG DELIVERY SYSTEMS (1978).

Other examples include provision of the compounds of the present invention to be administered by sustained release delivery system containing a biodegradable composition. The biodegradable composition may be composed of a biodegradable, water-coagulable, non-polymeric material and a biocompatible, non-toxic organic solvent that is miscible to dispersible in an aqueous medium. The delivery system may be implanted at an implant site causing the solvent to dissipate, disperse or leach from the composition into surrounding tissue fluid through a resulting microporous matrix.

As used herein, the term "implant site" is meant to include a site, in or on which the non-polymeric composition is applied. Implantation or implant site can also include the incorporation of the pharmaceutical composition comprising at least one compound of the present invention with a solid device. For example, the pharmaceutical composition is incorporated into a coating on a stent that is implanted into a subject. Additionally, other solid or biodegradeable materials can be used as a substrate on which the pharmaceutical composition is applied. The coated material, comprising the pharmaceutical composition is then implanted, inserted or is adjacent to the subject or patient. The term "biodegradable" means that the non-polymeric material and/or matrix of the implant will degrade over time by the action of enzymes, by simple or enzymatically catalyzed hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, for example, by a cell, a tissue, and the like.

Non-polymeric materials that can be used in the composition generally are those that are biocompatible, substantially insoluble in water and body fluids, and biodegradable and/or bioerodible. The non-polymeric material is capable of being at least partially solubilized in a water-soluble organic solvent. The non-polymeric materials are also capable of coagulating or solidifying to form a solid implant matrix. The non-polymeric material is combined with a compatible and suitable organic solvent to form a composition that has the desired consistency ranging from watery to viscous to a spreadable putty or paste.

Suitable organic solvents are those that are biocompatible, pharmaceutically-acceptable, and will at least partially dissolve the non-polymeric material. The organic solvent has a solubility in water ranging from miscible to dispersible. Optionally, a pore-forming agent can be included in the composition to generate additional pores in the implant matrix. The pore-forming agent can be any organic or inorganic, pharmaceutically-acceptable substance that is substantially soluble in water or body fluid, and will dissipate from the coagulating non-polymeric material and/or the solid matrix of the implant into surrounding body fluid at the implant site.

The compounds of the present invention are capable of providing a local or systemic biological, physiological or therapeutic effect in the body of an animal. In formulating some pharmaceutical compositions described herein, the compound is preferably soluble or dispersible in the non-polymeric composition to form a homogeneous mixture, and upon implantation, becomes incorporated into the implant matrix. As the solid matrix degrades over time, the compound is capable of being released from the matrix into the adjacent tissue fluid, and to the pertinent body tissue or organ, either adjacent to or distant from the implant site, preferably at a controlled rate. The release of the compound from the matrix may be varied, for example, by the solubility of the compound in an aqueous medium, the distribution of the compound within the matrix, the size, shape, porosity, and solubility and biodegradability of the solid matrix. See e.g. U.S. Pat. No. 5,888,533. The amounts and concentrations of ingredients in the composition administered to the patient will generally be effective to accomplish the task intended.

Compounds of the present invention may be administered by bioactive agent delivery systems containing microparticles suspended in a polymer matrix. The microparticles may be microcapsules, microspheres or nanospheres currently known in the art. The microparticles should be capable of being entrained intact within a polymer that is or becomes a gel once inside a biological environment. The microparticles can be biodegradable or non-biodegradable. Many microencapsulation techniques used to incorporate a bioactive agent into a microparticle carrier are taught in the art. See e.g. U.S. Pat. Nos. 4,652,441; 5,100,669; 4,438,253; and 5,665,428.

A preferred polymeric matrix will be biodegradable and exhibit water solubility at low temperature and will undergo reversible thermal gelation at physiological mammalian body temperatures. The polymeric matrix is capable of releasing the substance entrained within its matrix over time and in a controlled manner. The polymers are gradually degraded by enzymatic or non-enzymatic hydrolysis in aqueous or physiological environments. See e.g. U.S. Pat. No. 6,287,588.

Compounds of the present invention may be administered by a drug delivery composition comprising microparticles containing at least one chemotherapeutic agent and at least one chemosensitizer suspended in a polymer matrix. The microparticles may be microcapsules, microspheres or nanospheres currently known in the art. The microparticles should be biodegradable and stable in physiological environments. The microparticles also permit diffusion of the chemotherapeutic agent and chemosensitizer from the core through the matrix at a predetermined release rate. Ionic chemotherapeutic agents are suitable for use in the delivery composition of the invention. Ionic chemosensitizers are suitable for use in the delivery composition of the invention. The drug delivery compositions may be delivered to a target site through a variety of known routes of administration. Dosages of the chemotherapeutic agent and chemosensiti The drug delivery compositions may be delivered to a target site through a variety of known routes of administration. Dosages of the chemotherapeutic agent and chemosensitizer incorporated in the drug delivery composition will depend on individual needs, the desired effect and on the chosen route of administration. See e.g. WO 98/50018.

Dosage Determinations

In general, the compounds disclosed herein may be used alone or in concert with other therapeutic agents at appropriate dosages defined by routine testing in order to obtain optimal efficacy while minimizing any potential toxicity. The dosage regimen utilizing a compound of the present invention may be selected in accordance with a variety of factors including type, species, age, weight, sex, medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the compound's availability to one or more target sites. Distribution, equilibrium, and elimination of a drug may be considered when determining the optimal concentration for a treatment regimen. The dosages of a compound disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a compound disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compounds exhibiting large therapeutic indices are preferred except when cytotoxicity of the compound is the activity or therapeutic outcome that is desired. Although compounds that exhibit toxic side effects may be used, a delivery system can target such compounds to the site of affected tissue in order to minimize potential damage to uninfected cells and, thereby, reduce side effects. Generally, the compounds of the present invention may be administered in a manner that maximizes efficacy and minimizes toxicity.

Data obtained from cell culture assays and animal studies may be used in formulating a range of dosages for use in humans. The dosages of such compounds lies preferably within a range of circulating concentrations that include the $ED_{50}$ with little or no toxicity. The dosage may vary within this range depending upon the dosage form employed and the route of administration utilized. For any compound used in the methods of the invention, the therapeutically effective dose may be estimated initially from cell culture assays. A dose may be formulated in animal models to achieve a circulating plasma concentration range that includes the $IC_{50}$ (the concentration of the test compound that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the pharmaceutical compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount," as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician. Thus, the present invention provides combinations of two or more therapeutic agents wherein, for example, (a) each therapeutic agent is administered in an independently therapeutically or prophylactically effective amount; (b) at least one therapeutic agent in the combination is administered in an amount that is subtherapeutic or subprophylactic if administered alone, but is therapeutic or prophylactic when administered in combination with the second or additional therapeutic agents according to the invention; or (c) both therapeutic agents are administered in an amount that is subtherapeutic or subprophylactic if administered alone, but are therapeutic or prophylactic when administered together. Combinations of three or more therapeutic agents are analogously possible. Methods of combination therapy include coadministration of a single formulation containing all active agents; essentially contemporaneous administration of more than one formulation; and administration of two or more active agents separately formulated.

Dosages

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg).

The daily dosage of the pharmaceutical compositions may be varied over a wide range from about 0.01 to about 1000 mg per adult human per day. For oral administration, the pharmaceutical compositions are preferably provided in the form of tablets containing from about 0.1 mg to about 1000 mg of the compound or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the active compound for the symptomatic adjustment of the dosage to the patient to be treated. An effective amount of the drug is ordinarily supplied at a dosage level of from about 0.1 mg/kg to about 20 mg/kg of body weight per day. In one embodiment, the range is from about 0.2 mg/kg to about 10 mg/kg of body weight per day. In another embodiment, the range is from about 0.5 mg/kg to about 10 mg/kg of body weight per day. The compounds may be administered on a regimen of about 1 to about 10 times per day.

In the case of injections, it is usually convenient to give by an intravenous route in an amount of about 0.01-30 mg, about 0.1-20 mg or about 0.1-10 mg per day to adults (at about 60 kg). In the case of other animals, the dose calculated for 60 kg may be administered as well.

Doses of a compound of the present invention can optionally include 0.0001 to 1,000 mg/kg/administration, or 0.001 to 100.0 mg/kg/administration, from 0.01 to 10 mg/kg/administration, from 0.1 to 10 mg/kg/administration, including 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of humans or animals can be provided as a one-time or periodic dosage of a compound of the present invention 0.1 to 100 mg/kg such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

Combination Therapy

In addition, co-administration or sequential administration of the compounds of the present invention and other therapeutic agents may be desirable, such as chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

The compounds of this invention may be administered in combination with at least one selected from the group consisting of an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an anti-cancer, an antimicrobial (e.g., aminoglycoside, an anti-fungal, an antiparasitic, an antiviral, a carbapenem, cephalosporin, a flurorquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (e.g., epoetin alpha), a filgrastim (e.g., G-CSF, Neupogen), a sargramostim (Gm-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), or a cytokine.

Such anti-cancer or antimicrobial compounds can also include toxin molecules that are associated, bound, co-formulated, co-administered or sequentially administered, in either order, with at least one of the compounds of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal* enterotoxin A (SEA), B (SEB), or C (SEC), *Streptococcal* enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios*

*cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

More specifically, the compound of the present invention may be administered in combination with at least one immunosuppressive agent for use in, for example, treating or preventing a vascular occlusive conditions such as transplant vasculopathy. Suitable immunosuppressive agents include, but are not limited to, CellCept (Roche Labs.), Gengraf (Abbott Labs., Inc.), Micrhogam (Ortho-Clinical), Neoral (Novartis), Orthoclone OKT3 (Ortho-Biotech), Prograf (Fujisawa), Rapamune (Wyeth-Ayerst), Sandimmune (Novartis), Thymoglobulin (SangStat), Zenapax (Roche).

In one embodiment, the therapeutic agent administered simultaneously or sequentially, in either order and at various times with a compound of the present invention, comprises a chemotherapeutic agent. A "chemotherapeutic agent" is a compound useful in the treatment of cancer. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembiehin, phenesterine, prednimustine, trofosfamide, uracil mustard; nitroureas such as cannustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenylic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, rnepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofrran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

In another embodiment, the therapeutic agent comprises a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (m-CSF); granulocyte-macrophage-CSF (Gm-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

In another embodiment, the compounds of the present invention may be administered in combination with an anti-inflammatory agent including, but not limited to, adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenyl derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate). Commercially available nonsteroidal anti-inflammatory drugs include, but are not limited to, Anaprox (Roche Labs.), Arthrotec (Searle), Cataflam (Novartis), Celebrex (Pfizer), Clinoril (Merck), Dolobid (Merck), Feldene (Pfizer), Indocin (Merck), Lodine (Wyeth-Ayerst), Mobic (Boehringer Ingelheim), Motrin (McNeil Consumer), Naprosyn (Roche Labs.), Orudis (Wyeth-Ayerst), Oruvail (Wyeth-Ayerst), Ponstel (First Horizon), Relafen (GlaxoSmithKline), Tolectin (Ortho-McNeil), Toradol (Roche Labs., Inc.), Vioxx (Merck), Voltaren (Novartis), Advair (GlaxoSmithKline), Flovent (GlaxoSmithKline), Pulmicort (AstranZeneca), and Vanceril (Schering), Asacol (Procter & Gamble), Colazal (Salix), Dipentum (Pharmacia & Upjohn), and Rowasa (Solvay).

In yet another embodiment, the compounds of the present invention may be admistered in combination with an antirheumatic agent. Commercially available antirheumatic agents include, but are not limited to, Anaprox (Roche Labs.), Arava (Aventic), Arthrotec (Searle), Azulfidine (Pharmacia & Upjohn), Cataflam (Novartis), Celebrex (Pfizer), Celestone (Schering), Cuprimine (Merck), Enbrel (Immunex), Feldene (Pfizer), Gengraf (Abbott), Indocin (Merck), Lodine (Wyeth-Ayerst), Naprosyn (Roche Labs.), Neoral (Novartis), Pediapred (Celltech), Prednisone (Roxanne), Remicade (Centocor), Solu-Medrol (Pharmacia & Upjohn), Triliate (Purdue Frederick), and Voltaren (Novartis).

Moreover, the compounds of the present invention may be used in combination with any cardiovascular agent including, but not limited to, adrenergic blockers such as Cardura (Pfizer), Dibenzyline (WellSpring), Hytrin (Abbott), Minipress (Pfizer), and Minizide (Pfizer); adrenergic stimulants such as Aldoclor (Merck), Aldomet (Merck), Aldoril (Merck), Catapres (Boehringer Ingelheim), Clorpres (Bertek), and Tenex (Robins); alpha/beta adrenergic blockers such as Coreg (GlaxoSmithKline), and Normodyne (Schering); angiotensin converting enzyme inhibitors such as Accupril (Parke-Davis), Aceon (Solvay), Altace (Monarch), Captopril (Mylan), Enalaprilat (Baxter Anesthesia), Lotensin (Novartis), Mavik (Abbott), Monopril (Bristol-Myers Squibb), Prinivil (Merck), Univasc (Schwarz), Vaotec (Merck), and Zestril (AstraZeneca); angiotenisin converting enzyme inhibitors such as Lexxel (AstraZeneca), Lotrel (Novartis), Tarka (Abbott), Accuretic (Parke-Davis), Lotensin (Novartis), Prinzide (Merck), Uniretic (Schwarz), Vaeretic (Merck), and Zestoretic (AstraZeneca); angiotensin II receptor antagonists such as Atacand (AstraZeneca), Avapro (Briston-Myers Squibb), Cozaar (Merck), Diovan (Novartis), Micardis (Boehringer Ingelheim), and Teveten (Unimed); antiarrhythmics (Groups I-IV), antilipemic agents such as bile acid sequestrants, fibric acid derivatives, HMG-CoA reductase inhibitors, and nicotinic acid; Beta adrenergic blocking agents; calcium channel blockers; inotropic agents; vasodilators including coronoary vasodilators, natriuretic peptides, and peripheral vasodilators; and vasopressors.

In another aspect of the present invention, the therapeutic agent comprises a small molecule toxin, including maytansine, calicheamicin, trichothene, and CC 1065. In a specific embodiment, the therapeutic agent may comprise one more calicheamicin molecules. The calicheamicin family of antibiotics are capable of producing double-stranded DNA breaks at sub-picomolar concentrations. Structured analogues of calicheamicin are also known. See Hinman et al., 53 CANCER RESEARCH 333642 (1993); Lode et al., 58 CANCER RESEARCH 2925-28 (1998).

In yet another aspect of the present invention, the therapeutic agent may comprise one or more enzymatically active toxins and fragments thereof. Examples of such toxins include nonbinding active fragments of diphtheria toxin, diphtheria A chain, exotoxin A chain (from *Pseudomonas aeruginosa*), ricin A chain, abrin A chain, modeccin A chain, alpha-sarcin, dianthin proteins, *Phytolaca americana* proteins (PAPI, PAPAII, and PAP-S), *momordica charantia* inhibitor, curcin, crotin *sapaonaria officinalis* inhibitor, gelonin, mitogellin, restrictoein, phenomycin, enomycin and the tricothecenes. See, e.g., WO 93/21232.

The present invention further contemplates therapeutic agents that have nucleolytic activity such as a ribonuclease and a deoxyribonuclease. In addition, a variety of radioactive isotopes are available for the production of radioconjugated binding partners. Examples include $Y^{90}$, $At^{222}$, $Ret^{86}$, $Re^{186}$, $Sm^{153}$, $Bi^{212}$, $P^{32}$ and radioactive isotopes of Lu.

In yet another aspect of the present invention, the at least one compound may be conjugated to a receptor, such as streptavidin, for utilization in tumor pretargeting. Briefly, the compound-receptor conjugate is administered to the patient and unbound conjugate is removed from circulation with a clearing agent. A ligand, such as biotin, which is conjugated to a cytotoxic agent is then administered.

Timing of Administration

In several embodiments of the present invention, a compound described herein is administered before or after administration of a second therapeutic agent. The administration of a compound may occur anytime from several minutes to several hours before the administration of the second therapeutic agent. The compound may alternatively be administered anytime from several hours to several days, possibly several weeks, and up to several months before the second therapeutic agent.

More specifically, a compound of the present invention may be administered at least about 1 minute, at least about minutes, at least about minutes, at least about minutes, at least about minutes, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 21 minutes, at least about 22 minutes, at least about 23 minutes, at least about 24 minutes, at least about 25 minutes, at least about 26 minutes, at least about 27 minutes, at least about 28 minutes, at least about 29 minutes, at least about 30 minutes, at least about 31 minutes, at least about 32 minutes, at least about 33 minutes, at least about 34 minutes, at least about 35 minutes, at least about 36 minutes, at least about 37 minutes, at least about 38 minutes, at least about 39 minutes, at least about 40 minutes, at least about 41 minutes, at least about 42 minutes, at least about 43 minutes, at least about 44 minutes, at least about 45 minutes, at least about 46 minutes, at least about 47 minutes, at least about 48 minutes, at least about 49 minutes, at least about 50 minutes, at least about 51 minutes, at least about 52 minutes, at least about 53 minutes, at least about 54 minutes, at least about 55 minutes, at least about 56 minutes, at least about 57 minutes, at least about 58 minutes, at least about 59 minutes, or at least about 60 minutes before or after the second therapeutic agent. Furthermore, a compound of the present invention may be administered at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours before or after the second therapeutic agent.

Moreover, a compound of the present invention may be administered at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or at least about 31 days before or after the administration of the second therapeutic agent.

In yet another aspect of the present invention, a compound of the present invention may be administered at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, or at least about 20 weeks before or after the second therapeutic agent.

In a further aspect of the present invention, a compound of the present invention may be administered at least about one month, at least about two months, at least about three months, at least about four months, at least about five months, at least about six months, at least about seven months, at least about eight months, at least about nine months, at least about ten months, at least about eleven months, or at least about twelve months before or after the second therapeutic agent.

For convenience, the meaning of certain terms and phrases employed in the specification, examples, and appended claims are provided below.

DEFINITIONS

As used herein, the term "compound" includes both the singular and the plural, and includes any single entity or combined entities that have at least the activity disclosed herein and combinations, fragments, analogs or derivatives of such entities. Such entities include, but are not limited to, chemical elements, molecules, compounds, mixtures, emulsions, chemotherapeutic agents, pharmacological agents, hormones, antibodies, growth factors, cellular factors, nucleic acids, proteins, peptides, peptidomimetics, nucleotides, carbohydrates, and combinations, fragments, analogs or derivatives of such entities.

The term "phenylamine" refers to a primary or secondary benzeneamine, more commonly known as an aniline. The amino group on the aniline can be substituted with hydrogen, alkyl ($C_1$-$C_{12}$, straight chain or branched), cycloalkyl ($C_3$-$C_{10}$), or aryl substituted aryl groups. The phenyl ring of this aniline derivative can be optionally substituted with one or more functional groups, or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, piperazinyl, pyridyl, thienyl, furanyl, pyrroyl, pyrazoyl, phosphate, phosphonic acid, or phosphonate. If applicable, these groups can be represented in protected or unprotected forms used in standard organic synthesis.

The term "naphthylamine" refers to a primary or secondary α- or β-naphthylamine. The ring substructure in the naphthylamine can be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

The term "naphthylalkyl amine" refers to a primary or secondary α- and β-naphthylalkyl amine (for example, 2-α-naphthylethyl amine). The term "benzalkyl amine" refers to a primary or secondary benzylalkyl amine (for example, phenylethyl amine). These aryl alkyl substructures or compounds can be optically active or optically inactive. The aryl (ring) substructures of the naphthylalkyl and benzalkyl amines can be optionally subsituted with one or a combination of functional groups, such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carbolyl, amido, sulfonamido, sulfonyl, sulfate, sulfonic acid, morpholino, piperazinyl, pyridyl, thienyl, furanyl, pyrroyl, pyrazoyl, phosphate, phosphonic acid, phosphonate and the like. If applicable these groups can be represented in protected or unprotected forms used in standard organic synthesis.

The term "quinolinyl amine" refers to primary or secondary quinolyl amines. These amines can be in optically active or inactive forms. The aryl (ring) substructure of the quinolyl amine can be optionally substituted with one a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

The term "heteroaryl amines" refers to pyrroles, pyrazoles, imidazoles, and indoles. The aryl (ring) substructure of the heteroaryl amine can be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, phosphate, phosphonic acid, or phosphonate. These groups can be represented in protected or unprotected forms used in standard organic synthesis.

The term "glycated protein," as used herein, includes proteins linked to glucose, either enzymatically or non-enzymatically, primarily by condensation of free epsilon-amino groups in the protein with glucose, forming Amadori adducts. Furthermore, glycated protein, as used herein, includes not only proteins containing these initial glycation products, but also glycation products resulting from further reactions such as rearrangements, dehydration, and condensations that form irreversible advanced glycation end products (AGE).

The term "polynucleotide" refers generally to polymeric forms of nucleotides of any length, either ribonucleotides or deoxynucleotides. Thus, this term includes, but is not limited to, single-stranded, double-stranded, or multi-stranded DNA or RNA. Polynucleotides may further comprise genomic DNA, cDNA, or DNA-RNA hybrids. Moreover, the polynucleotides of the present invention may be synthetically produced.

Polynucleotides may comprise chemically modified, biochemically modified, or derivatized nucleotides. For example, a polynucleotide may comprise, in part, modified nucleotides such as methylated nucleotides or nucleotide analogs. In other embodiments, polynucleotides may comprise sugars, caps, nucleotide branches, and linking groups such as fluororibose and thioate. In addition, the sequence of nucleotides may be interrupted by non-nucleotide components. Furthermore, a polynucleotide may be modified after polymerization to facilitate its attachment to other polynucleotides, proteins, metal ions, labeling components, or a solid support.

The backbone of the polynucleotide may comprise modified or substituted sugar and/or phosphate groups. Alternatively, the backbone of the polynucleotide may comprise a polymer of synthetic subunits such as phosphoramidites and thus may be an oligodeoxynucleoside phosphoramidate or a mixed phosphoramidate-phosphodiester oligomer. See Peyrottes et al., NUCL. ACIDS RES. (1996) 24:1841-1848, and Chaturvedi et al., NUCL. ACIDS RES. (1996) 24:2318-2323.

The term "homology", as used herein, refers to a degree of complementarity. There may be partial homology or complete homology (i.e., identity). A partially complementary sequence is one that at least partially inhibits an identical sequence from hybridizing to a target polynucleotide; it is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

The term "gene" refers to a polynucleotide sequence that comprises coding sequences necessary for the production of a polypeptide or precursor, and may also include expression control sequences or other control or regulatory sequences. The polypeptide can be encoded by a full length coding sequence or by any portion of the coding sequence. The gene may be derived in whole or in part from any source known to those of ordinary skill in the art including a plant, a fungus, an animal, a bacterial genome or episome, eukaryotic, nuclear or plasmid DNA, cDNA, viral DNA, or chemically synthesized DNA. A gene may constitute an uninterrupted coding sequence or it may include one or more introns, bound by the appropriate splice junctions. Moreover, a gene may contain one or more modifications in either the coding or the untranslated regions that could affect certain properties of the polynucleotide or polypeptide, such as the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as variants of the native gene.

"Gene expression" refers to the process by which a polynucleotide sequence undergoes successful transcription and translation such that detectable levels of the nucleotide sequence are expressed as proteins or the polynucleotide sequence undergoes transcription, if RNA is copied from DNA, or replication if DNA is copied from DNA, such that the resulting nucleotide copies are detectable.

The term "gene expression profile" refers to a group of genes representing a particular cell or tissue type (e.g., neuron, coronary artery endothelium, or disease tissue) in any activation state. In one aspect, a gene expression profile is generated from cells exposed to a compound of the present invention. This profile may be compared to a gene expression profile generated from the same type of cell or tissue type prior to treatment with a compound of the present invention. Furthermore, a series of gene expression profiles may be generated from cells or tissues treated with a compound of the present invention, specifically, at different doses or a time-course to assess the effects of the compound. A gene expression profile is also known as a gene expression signature.

The term "differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue or cell type that is detectable in either control or disease conditions, but is not detectable in both. "Differentially expressed polynucleotide," as used herein, refers to a polynucleotide sequence that uniquely identifies a differentially expressed gene so that detection of the differentially expressed polynucleotide in a sample is correlated with the presence of a differentially expressed gene in a sample.

Similarly, a differentially expressed protein may have its expression activated or completely inactivated in normal versus disease conditions. Such a qualitatively regulated protein may exhibit an expression pattern within a given tissue or cell type that is detectable in either control or disease conditions, but is not detectable in both. A "differentially expressed protein," as used herein, refers to an amino acid sequence that uniquely identifies a differentially expressed protein so that detection of the differentially expressed protein in a sample is correlated with the presence of a differentially expressed protein in a sample.

"Cell type," as used herein, refers to a cell from a given source (e.g., tissue or organ), a cell in a given state of differentiation, or a cell associated with a given pathology or genetic makeup.

The term "polypeptide" refers to a polymeric form of amino acids of any length, which may include translated, untranslated, chemically modified, biochemically modified, and derivatized amino acids. A polypeptide may be naturally occurring, recombinant, or synthetic, or any combination of these. Moreover, the term "polypeptide," as used herein, refers to proteins, polypeptides, and peptides of any size, structure, or function. For example, a polypeptide may comprise a string of amino acids held together by peptide bonds. A polypeptide may alternatively comprise a long chain of amino acids held together by peptide bonds. Moreover, a polypeptide may also comprise a fragment of a naturally occurring protein or peptide. A polypeptide may be a single molecule or may be a multi-molecular complex. In addition, such polypeptides may have modified peptide backbones as well.

The term "polypeptide" further comprises immunologically tagged proteins and fusion proteins, including, but not limited to, fusion proteins with a heterologous amino acid sequence, fusion proteins with heterologous and homologous leader sequences, and fusion proteins with or without N-terminal methionine residues.

The term "protein expression" refers to the process by which a polynucleotide sequence undergoes successful transcription and translation such that detectable levels of the amino acid sequence or protein are expressed.

The term "protein expression profile" refers to a group of proteins representing a particular cell or tissue type (e.g., neuron, coronary artery endothelium, or disease tissue). In one aspect, a protein expression profile is generated from cells or tissues exposed to a compound of the present invention. This profile may be compared to a protein expression profile generated from the same type of cell or tissue prior to treatment with a compound of the present invention. Furthermore, a series of protein expression profiles may be generated from cells or tissues treated with a compound of the present invention, specifically, at different doses or a time-course to assess the effects of the compound. A protein expression profile is also known as a "protein expression signature."

As used herein, a "biomolecule" includes polynucleotides and polypeptides. Moreover, a "biomolecular sequence," as used herein, is a term that refers to all or a portion of a polynucleotide sequence. A biomolecular sequence may also refer to all or a portion of a polypeptide sequence. In the context of biomolecule, for example, perlecan, the term "functional equivalent" refers to a protein or polynucleotide molecule that possesses functional or structural characteristics that are substantially similar to all or part of the native perlecan protein or native perlecan-encoding polynucleotides. A functional equivalent of a native perlecan protein may contain modifications depending on the necessity of such modifications for a specific structure or the performance of a specific function. The term "functional equivalent" is intended to include the "fragments," "mutants," "derivatives," "alleles," "hybrids," "variants," "analogs," or "chemical derivatives" of native perlecan.

A "host cell," as used herein, refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. It is understood that the progeny of a single cell may not necessarily be completely identical in morphology or in genomic or total DNA complement as the original parent due to natural, accidental, or deliberate mutation.

In the context of immunoglobulins, the term "functional equivalent" refers to immunoglobulin molecules that exhibit immunological binding properties that are substantially similar to the parent immunoglobulin. As used herein, the term "immunological binding properties" refers to non-covalent interactions of the type which occur between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise $F(ab')_2$ fragments, F(ab) molecules, Fv fragments, single chain fragment variable displayed on phage (scFv), single domain antibodies, chimeric antibodies, or the like so long as the immunoglobulin exhibits the characteristics of the parent immunoglobulin.

As used herein, the term "isolated" refers to a polynucleotide, a polypeptide, an antibody, or a host cell that is in an environment different from that in which the polynucleotide, the polypeptide, the antibody, or the host cell naturally occurs. An isolated polynucleotide, polypeptide, antibody, or host cell is generally substantially purified.

As used herein, the term "substantially purified" refers to a compound that is removed from its natural environment and is at least about 60% to 99.9% free from other components, or is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% free from other components with which it is naturally associated. For example, a composition containing A is "substantially free of" B when at least about 85% by weight of the total A+B in the composition is A. Alternatively, A comprises at least about 90% by weight of the total of A+B in the composition, further still, at least about 95% or even 99% by weight.

"Diagnosis," as used herein, generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

The term "biological sample" encompasses a variety of sample types obtained from or originating from an organism which may be used in diagnostic, monitoring, or other assays. The term encompasses blood, serum, plasma, cells, proteins, carbohydrates, nucleic acids, urine, nasal secretions, mucosal secretions, cellular fluid, cellular exudate and other liquid samples of biological origin, solid tissue samples such as a biopsy specimen, or tissue cultures or cells derived therefrom and the progeny thereof. The term specifically encompasses a clinical sample, and further includes cells in cell culture, cell supernatants, cell lysates, amniotic fluid, biological fluids, and tissue samples. The term also encompasses samples that have been manipulated in any way after procurement such as treatment with reagents, solubilization, or enrichment for certain components. The biological sample can be derived from the organism directly or can be collected from the environment.

The terms "individual," "subject," "host," and "patient" refer to any subject for whom diagnosis, treatment, or therapy is desired. In one embodiment, the individual, subject, host, or patient is a human. Other subjects may include, but are not limited to, animals including but not limited to, cattle, sheep, horses, dogs, cats, guinea pigs, rabbits, rats, primates, opossums and mice. Other subjects include species of bacteria, phages, cell cultures, viruses, plants and other eucaryotes, prokaryotes and unclassified organisms.

The terms "treatment," "treating," "treat," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The expression "therapeutically effective amount" refers to an amount of, for example, a compound disclosed herein, that is effective for preventing, ameliorating, treating or delaying the onset of a disease or condition.

A "prophylactically effective amount" refers to an amount of, for example, a compound disclosed herein that is effective for preventing a disease or condition.

A "liposome" is a small vesicle composed of various types of lipids, phospholipids and/or surfactant, which is useful for delivery of a drug to a subject, such as a mammal or other animal. The compounds of the present invention may be delivered by a liposome. The components of the liposome are commonly arranged in a bilayer formation, similar to the lipid arrangement of biological membranes. Liposome formulations, loading of liposomes and administration and delivery of liposomes are known in the art.

"Hybridization," broadly defined, refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency. Hybridization may also refer to the binding of a protein-capture agent to a target protein under certain conditions, such as normal physiological conditions.

As understood herein, the term "activation" refers to any alteration of a signaling pathway or biological response including, for example, increases above basal levels, restoration to basal levels from an inhibited state, and stimulation of the pathway above basal levels.

The term "biological activity" refers to the biological behavior and effects of a protein or peptide. The biological activity of a protein may be affected at the cellular level and the molecular level. For example, an antisense oligonucleotide may prevent translation of a particular mRNA, thereby inhibiting the biological activity of the protein encoded by the mRNA. In addition, an antibody may bind to a particular protein and inhibit that protein's biological activity.

The term "oligonucleotide" as used herein refers to a polynucleotide sequence comprising, for example, from about 4 nucleotides (nt) to about 1000 nt. Oligonucleotides for use in the present invention are preferably from about 15 nt to about 150 nt, more preferably from about 150 nt to about 1000 nt in length. The oligonucleotide may be a naturally occurring oligonucleotide or a synthetic oligonucleotide. Oligonucleotides may be prepared by the phosphoramidite method (Beaucage and Carruthers, TETRAHE-DRON LETT. (1981) 22:1859-1862), or by the triester method (Matteucci et al., J. AM. CHEM. SOC. (1981) 103:3185), or by other chemical methods known in the art.

The term "microarray" refers generally to the type of genes or proteins represented on a microarray by oligonucleotides (polynucleotide sequences) or protein-binding agents, and where the type of genes or proteins represented on the microarray is dependent on the intended purpose of the microarray (e.g., to monitor expression of human genes or proteins). The oligonucleotides or protein-binding agents on a given microarray may correspond to the same type, category, or group of genes or proteins. Genes or proteins may be considered to be of the same type if they share some common characteristics such as species of origin (e.g., human, mouse, rat); disease state (e.g., cancer); function (e.g., protein kinases, tumor suppressors); same biological process (e.g., apoptosis, signal transduction, cell cycle regulation, proliferation, differentiation). For example, one microarray type may be a "cancer microarray" in which each of the microarray oligonucleotides or protein-binding agents correspond to a gene or protein associated with a cancer. An "epithelial microarray" may be a microarray of oligonucleotides or protein-binding agents corresponding to unique epithelial genes or proteins. Similarly, a "cell cycle microarray" may be an microarray type in which the oligonucleotides or protein-binding agents correspond to unique genes or proteins associated with the cell cycle.

The term "detectable", one in sense, refers to a polynucleotide expression pattern which is detectable via the standard techniques of polymerase chain reaction (PCR), reverse transcriptase (RT)-PCR (RT-PCR), differential display, and Northern analyses, which are well known to those of skill in the art. Similarly, polypeptide expression patterns may be "detected" via standard techniques including immunoassays such as Western blots. In general, the term "detectable is used when a result of an action, such as addition of a compound in an assay step, is observable, particularly by physical means, such as a color change.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to an polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e.g., gene or mRNA) whose expression level it is desired to detect.

The term "complementary" refers to the topological compatibility or matching together of the interacting surfaces of a probe molecule and its target. The target and its probe can be described as complementary, and furthermore, the contact surface characteristics are complementary to each other.

Hybridization or base pairing between nucleotides or nucleic acids, such as, for example, between the two strands of a double-stranded DNA molecule or between an oligonucleotide probe and a target are complementary.

The term "background" refers to non-specific binding or other interactions between, for example, polynucleotides, polypeptides, small molecules and polypeptides, or small molecules and polynucleotides. "Background" may also refer to the non-specific binding or other interactions in the context of assays including immunoassays.

In the context of microarrays, the term "background" refers to hybridization signals resulting from non-specific binding, or other interactions, between the labeled target polynucleotides and components of the oligonucleotide microarray (e.g., the oligonucleotide probes, control probes, the microarray support) or between target proteins and the protein-binding agents of a protein microarray. Background signals may also be produced by intrinsic fluorescence of the microarray components themselves. A single background signal may be calculated for the entire microarray, or a different background signal may be calculated for each target polynucleotide or target protein. The background may be calculated as the average hybridization signal intensity, or where a different background signal is calculated for each target gene or target protein. Alternatively, background may be calculated as the average hybridization signal intensity produced by hybridization to probes that are not complementary to any sequence found in the sample (e.g., probes directed to polynucleotides of the opposite sense or to genes not found in the sample such as bacterial genes where the sample is mammalian polynucleotides). The background can also be calculated as the average signal intensity produced by regions of the microarray which lack any probes or protein-binding agents at all.

A "small molecule" comprises a compound or molecular complex, either synthetic, naturally derived, or partially synthetic, composed of carbon, hydrogen, oxygen, and nitrogen, which may also contain other elements, and which may have a molecular weight of less than about 100 to about 15,000 Daltons, or less than about 15,000, less than about 14,000, less than about 13,000, less than about 12,000, less than about 11,000, less than about 10,000, less than about 9,000, less than about 8,000, less than about 7,000, less than about 6,000, less than about 5,000, less than about 4,000, less than about 3,000, less than about 2,000, less than about 1,000, less than about 900, less than about 800, less than about 700, less than about 600, less than about 500, less than about 400, less than about 300, less than about 200, or less than about 100.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

The term "cluster" refers to a group of clones or biomolecular sequences related to one another by sequence homology. In one example, clusters are formed based upon a specified degree of homology and/or overlap (e.g., stringency). "Clustering" may be performed with the sequence data. For instance, a biomolecular sequence thought to be associated with a particular molecular or biological activity in one tissue might be compared against another library or database of sequences. This type of search is useful to look for homologous, and presumably functionally related, sequences in other tissues or samples, and may be used to streamline the methods of the present invention in that clustering may be used within one or more of the databases to cluster biomolecular sequences prior to performing a method of the invention. The sequences showing sufficient homology with the representative sequence are considered part of a "cluster." Such "sufficient" homology may vary within the needs of one skilled in the art.

As used herein, the term "internal database" refers to a database maintained within a local computer network. It contains, for example, biomolecular sequences associated with a project. It may also contain information associated with sequences including, but not limited to, a library in which a given sequence is found and descriptive information about a likely gene associated with the sequence. The internal database may typically be maintained as a private database behind a firewall within an enterprise network. However, the invention is not limited to only this embodiment and an internal database could be made available to the public. The internal database may include sequence data generated by the same enterprise that maintains the database, and may also include sequence data obtained from external sources.

The term "external database," as understood herein, refers to a database located outside all internal databases. Typically, an enterprise network differing from the enterprise network maintaining the internal database will maintain an external database. The external database may be used, for example, to provide some descriptive information on biomolecular sequences stored in the internal database. In one embodiment, the external database is GenBank and associated databases maintained by the National Center for Biotechnology Information (NCBI), part of the National Library of Medicine.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention which will be limited only by the appended claims.

Additional bioactivity data for compounds of the present invention are presented in Table 8, where compounds that have at least the activity of effecting cellular proliferation or at least the activity of modulating inflammation activity, as measured by the assays taught herein, are provided. The inclusion of compounds in the categories of the Tables disclosed herein, including this Table, are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

TABLE 1C

Representative Compounds of the Present Invention

| Cmpd No. | Structure | Name |
|---|---|---|
| | 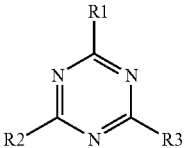 | |
| C1 | 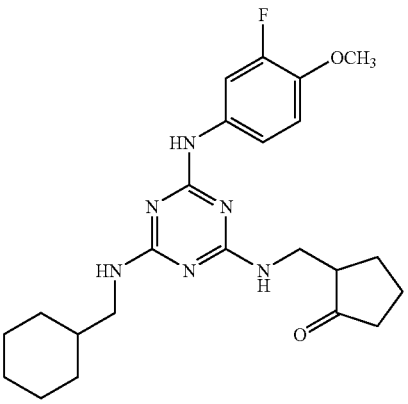 | 2-{[4-(Cyclohexylmethyl-amino)-6-(3-fluoro-4-methoxy-phenylamino)-[1,3,5]triazin-2-ylamino]-methyl}-cyclopentanone |
| C2 | 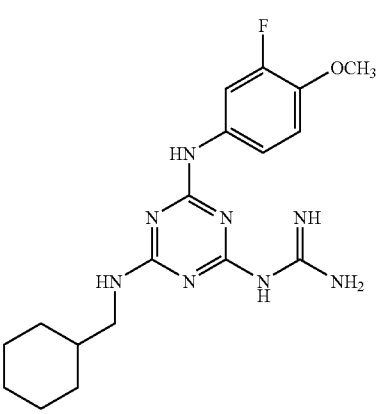 | N-[4-(Cyclohexylmethyl-amino)-6-(3-fluoro-4-methoxy-phenylamino)-[1,3,5]triazin-2-yl]-guanidine |

TABLE 1C-continued

Representative Compounds of the Present Invention

| Cmpd No. | Structure | Name |
|---|---|---|
| C3 | 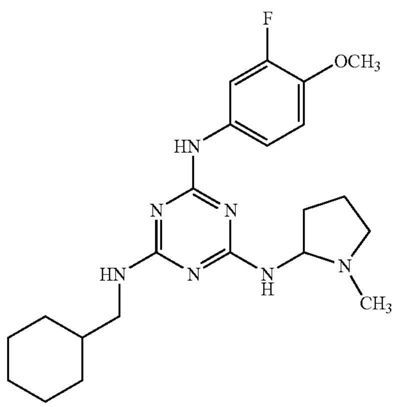 | N-Cyclohexylmethyl-N'-(3-fluoro-4-methoxy-phenyl)-N''-(1-methyl-pyrrolidin-2-yl)-[1,3,5]triazine-2,4,6-triamine |
| C4 | 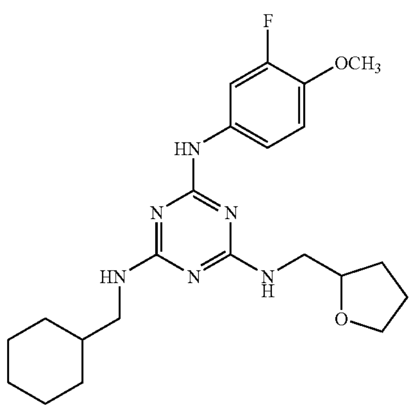 | N-Cyclohexylmethyl-N'-(3-fluoro-4-methoxy-phenyl)-N''-(tetrahydro-furan-2-ylmethyl)-[1,3,5]triazine-2,4,6-triamine |
| C5 | 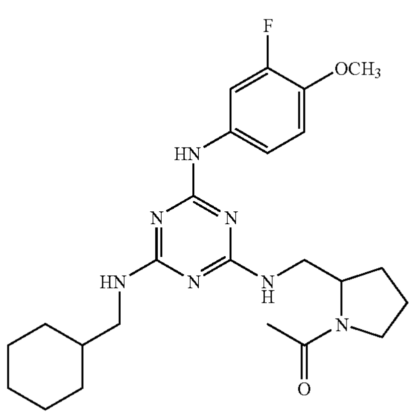 | 1-(2-{[4-(Cyclohexylmethyl-amino)-6-(3-fluoro-4-methoxy-phenylamino)-[1,3,5]triazin-2-ylamino]-methyl}-pyrrolidin-1-yl)-ethanone |

TABLE 1C-continued

Representative Compounds of the Present Invention

| Cmpd No. | Structure | Name |
|---|---|---|
| C6 | 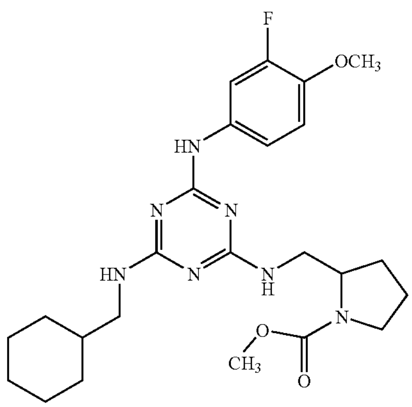 | 2-{[4-(Cyclohexylmethyl-amino)-6-(3-fluoro-4-methoxy-phenylamino)-[1,3,5]triazin-2-ylamino]-methyl}-pyrrolidine-1-carboxylic acid methyl ester |
| C7 | 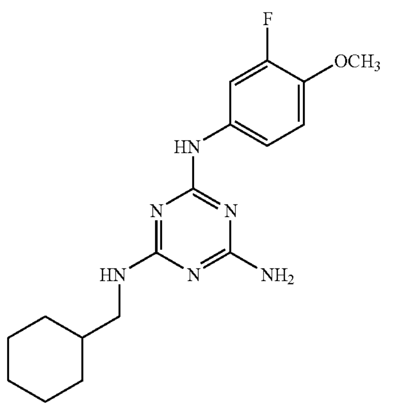 | N-Cyclohexylmethyl-N'-(3-fluoro-4-methoxy-phenyl)-[1,3,5]triazine-2,4,6-triamine |
| C8 | 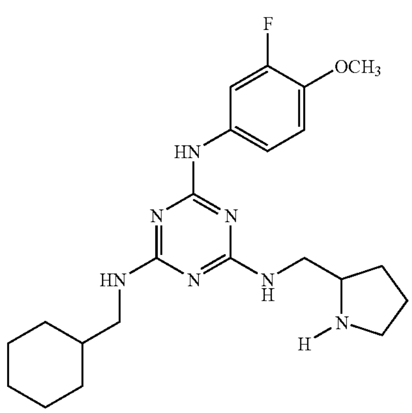 | N-Cyclohexylmethyl-N'-(3-fluoro-4-methoxy-phenyl)-N''-pyrrolidin-2-ylmethyl-[1,3,5]triazine-2,4,6-triamine |

TABLE 1C-continued

Representative Compounds of the Present Invention

| Cmpd No. | Structure | Name |
|---|---|---|
| C9 | 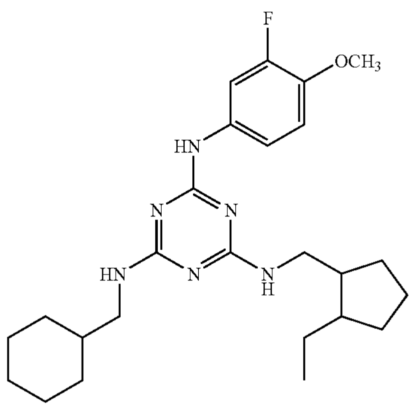 | N-Cyclohexylmethyl-N'-(2-ethyl-cyclopentylmethyl)-N''-(3-fluoro-4-methoxy-phenyl)-[1,3,5]triazine-2,4,6-triamine |
| C10 | 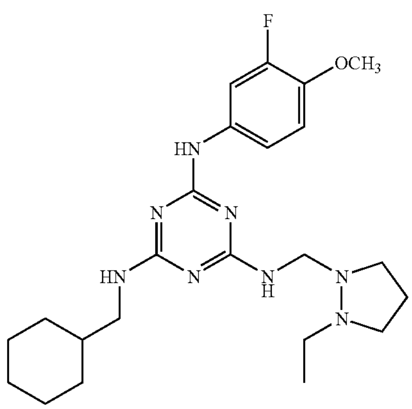 | N-Cyclohexylmethyl-N'-(2-ethyl-pyrazolidin-1-ylmethyl)-N''-(3-fluoro-4-methoxy-phenyl)-[1,3,5]triazine-2,4,6-triamine |
| C11 | 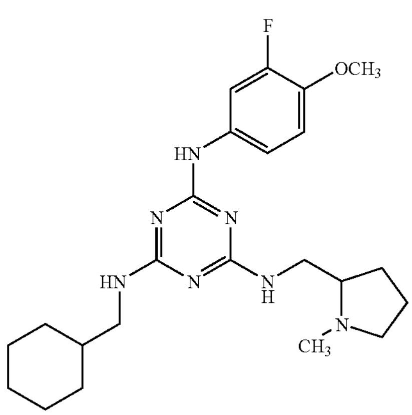 | N-Cyclohexylmethyl-N'-(3-fluoro-4-methoxy-phenyl)-N''-(1-methyl-pyrrolidin-2-ylmethyl)-[1,3,5]triazine-2,4,6-triamine |

TABLE 1C-continued

Representative Compounds of the Present Invention

| Cmpd No. | Structure | Name |
|---|---|---|
| C12 | 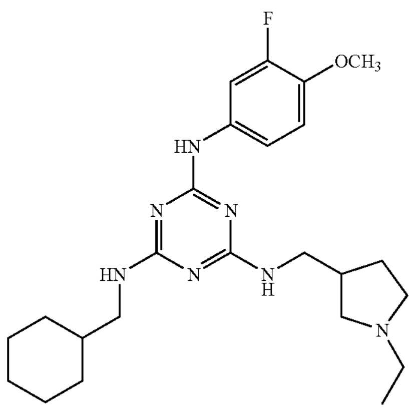 | N-Cyclohexylmethyl-N'-(1-ethyl-pyrrolidin-3-ylmethyl)-N''-(3-fluoro-4-methoxy-phenyl)-[1,3,5]triazine-2,4,6-triamine |
| C13 | 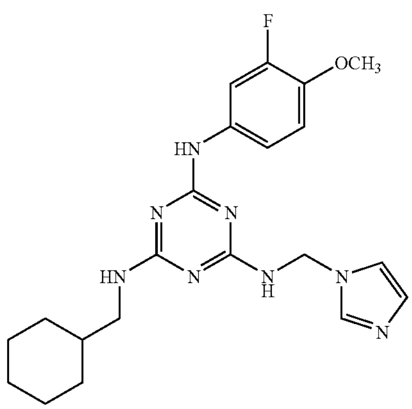 | N-Cyclohexylmethyl-N'-(3-fluoro-4-methoxy-phenyl)-N''-imidazol-1-ylmethyl-[1,3,5]triazine-2,4,6-triamine |
| C14 | 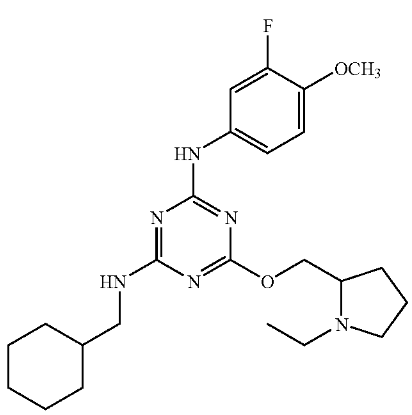 | N-Cyclohexylmethyl-6-(1-ethyl-pyrrolidin-2-ylmethoxy)-N'-(3-fluoro-4-methoxy-phenyl)-[1,3,5]triazine-2,4-diamine |

TABLE 1C-continued

Representative Compounds of the Present Invention

| Cmpd No. | Structure | Name |
|---|---|---|
| C15 | 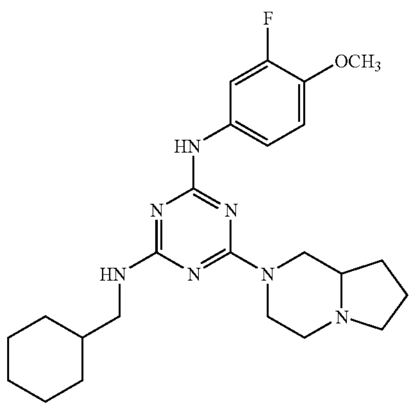 | N-Cyclohexylmethyl-N'-(3-fluoro-4-methoxy-phenyl)-6-(hexahydro-pyrrolo[1,2-a]pyrazin-2-yl)-[1,3,5]triazine-2,4-diamine |
| C16 | 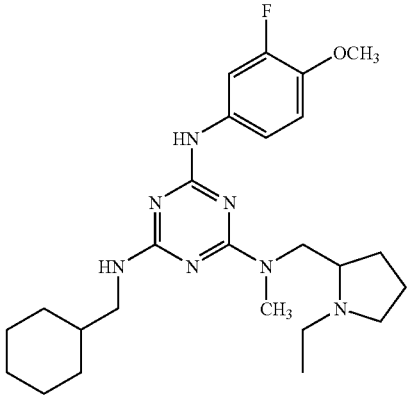 | N-Cyclohexylmethyl-N'-(1-ethyl-pyrrolidin-2-ylmethyl)-N''-(3-fluoro-4-methoxy-phenyl)-N'-methyl-[1,3,5]-triazine-2,4,6-triamine |
| C17 | 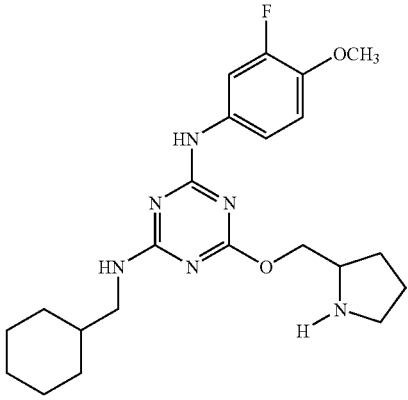 | N-Cyclohexylmethyl-N'-(3-fluoro-4-methoxy-phenyl)-6-(pyrrolidin-2-ylmethoxy)-[1,3,5]triazine-2,4-diamine |

TABLE 1C-continued

Representative Compounds of the Present Invention

| Cmpd No. | Structure | Name |
|---|---|---|
| C18 | 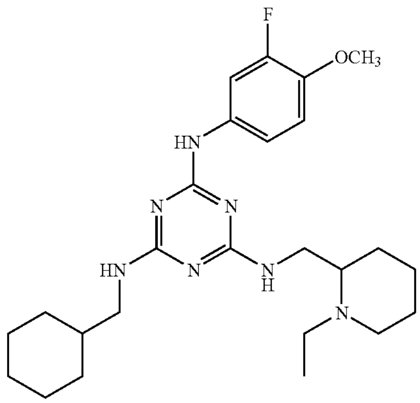 | N-Cyclohexylmethyl-N'-(1-ethyl-piperidin-2-ylmethyl)-N''-(3-fluoro-4-methoxy-phenyl)-[1,3,5]triazine-2,4,6-triamine |
| C19 | 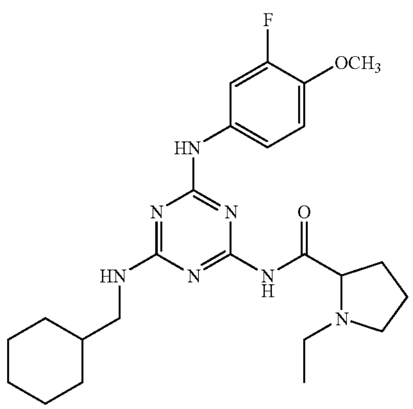 | 1-Ethyl-pyrrolidine-2-carboxylic acid [4-(cyclohexylmethyl-amino)-6-(3-fluoro-4-methoxy-phenylamino)-[1,3,5]triazin-2-yl]-amide |
| C20 | 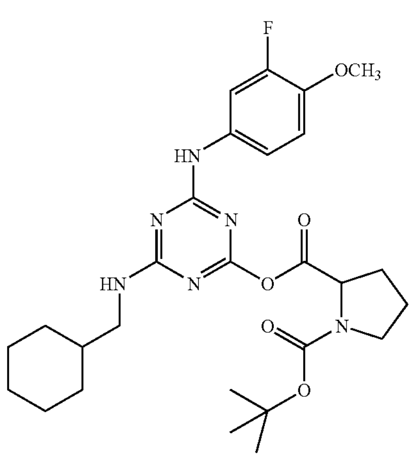 | Pyrrolidine-1,2-dicarboxylic acid 1-tert-butyl ester 2-[4-(cyclohexylmethyl-amino)-6-(3-fluoro-4-methoxy-phenylamino)-[1,3,5]triazin-2-yl] ester |

TABLE 1C-continued

Representative Compounds of the Present Invention

| Cmpd No. | Structure | Name |
|---|---|---|
| C21 | 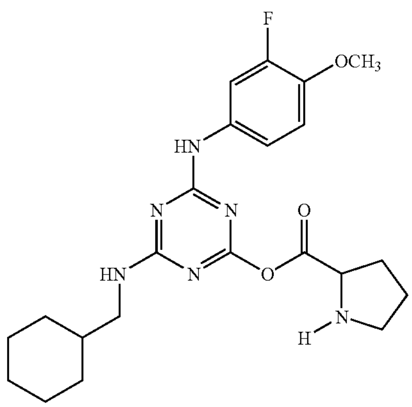 | Pyrrolidine-2-carboxylic acid 4-(cyclohexylmethyl-amino)-6-(3-fluoro-4-methoxy-phenylamino)-[1,3,5]-triazin-2-yl ester |
| C22 | 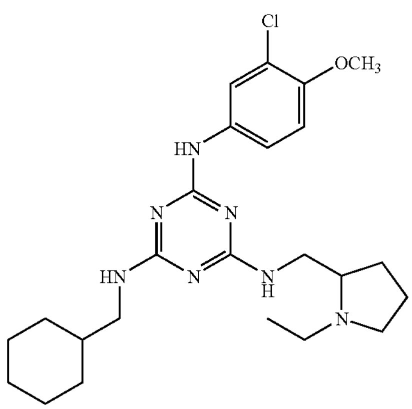 | N-(3-Chloro-4-methoxy-phenyl)-N'-cyclohexylmethyl-N''-(1-ethyl-pyrrolidin-2-ylmethyl)-[1,3,5]-triazine-2,4,6-triamine |
| C23 | 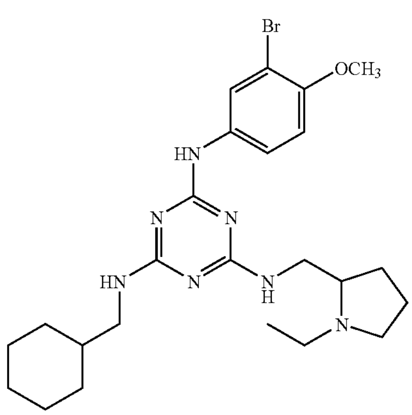 | N-(3-Bromo-4-methoxy-phenyl)-N'-cyclohexylmethyl-N''-(1-ethyl-pyrrolidin-2-ylmethyl)-[1,3,5]-triazine-2,4,6-triamine |

TABLE 1C-continued

Representative Compounds of the Present Invention

| Cmpd No. | Structure | Name |
|---|---|---|
| C24 | 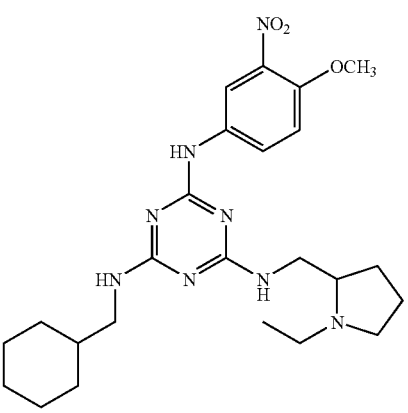 | N-Cyclohexylmethyl-N'-(1-ethyl-pyrrolidin-2-ylmethyl)-N''-(4-methoxy-3-nitro-phenyl)-[1,3,5]-triazine-2,4,6-triamine |
| C25 | 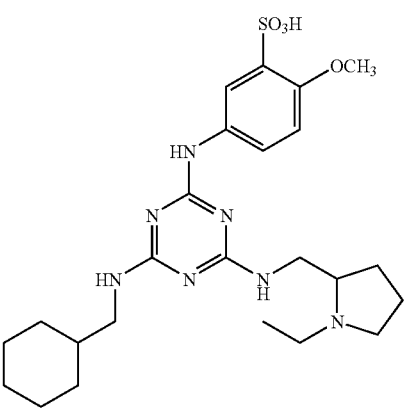 | 5-[4-[(1-Ethyl-pyrrolidin-2-ylmethyl)-amino]-6-(2-methyl-pentylamino)-[1,3,5]triazin-2-ylamino]-2-methoxy-benzenesulfonic acid |
| C26 | 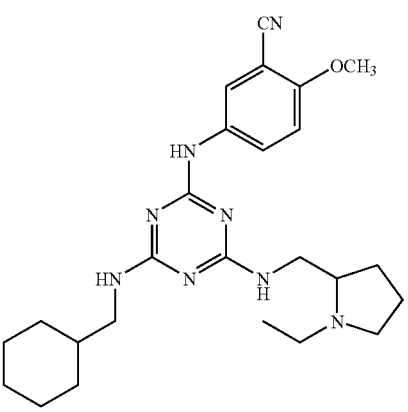 | 5-{4-(Cyclohexylmethyl-amino)-6-[(1-ethyl-pyrrolidin-2-ylmethyl)-amino]-[1,3,5]triazin-2-ylamino}-2-methoxy-benzonitrile |

TABLE 1C-continued

Representative Compounds of the Present Invention

| Cmpd No. | Structure | Name |
|---|---|---|
| C27 | 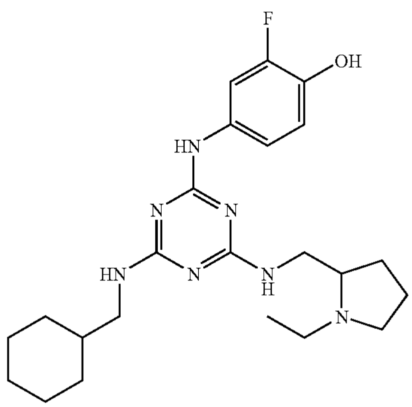 | 4-{4-(Cyclohexylmethyl-amino)-6-[(1-ethyl-pyrrolidin-2-ylmethyl)-amino]-[1,3,5]triazin-2-ylamino}-2-fluoro-phenol |
| C28 | 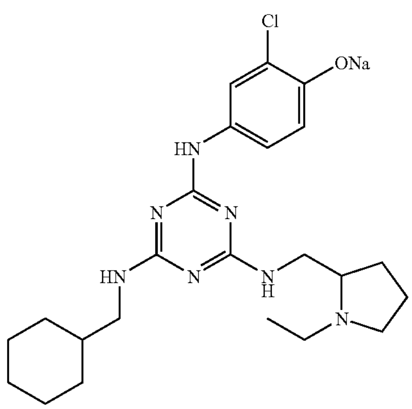 | Sodium; 2-chloro-4-{4-(cyclohexyl-methyl-amino)-6-[(1-ethyl-pyrrolidin-2-ylmethyl)-amino]-[1,3,5]triazin-2-ylamino}-phenolate |
| C29 | 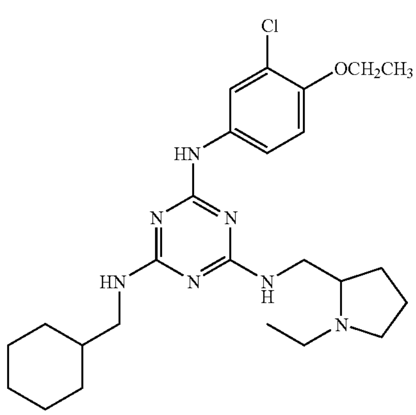 | N-(3-Chloro-4-ethoxy-phenyl)-N'-(1-ethyl-pyrrolidin-2-ylmethyl)-N''-(2-methyl-pentyl)-[1,3,5]triazine-2,4,6-triamine |

TABLE 1C-continued

Representative Compounds of the Present Invention

| Cmpd No. | Structure | Name |
|---|---|---|
| C30 | 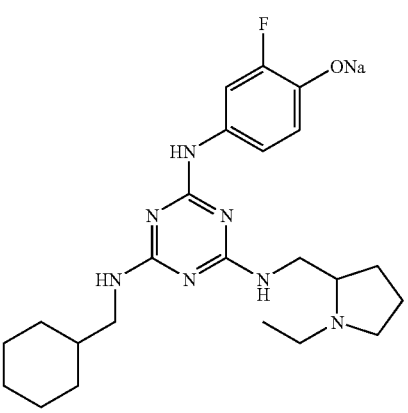 | Sodium; 4-{4-(cyclohexylmethyl-amino)-6-[(1-ethyl-pyrrolidin-2-ylmethyl)-amino]-[1,3,5]triazin-2-ylamino}-2-fluoro-phenolate |
| C31 | 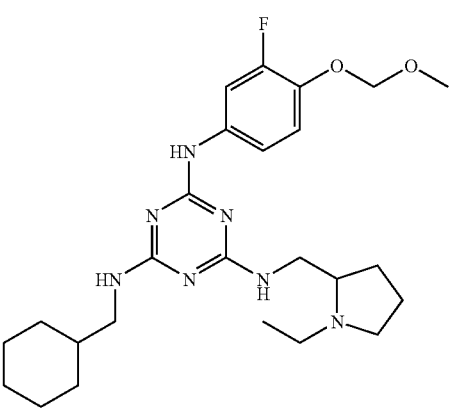 | N-Cyclohexylmethyl-N'-(1-ethyl-pyrrolidin-2-ylmethyl)-N''-(3-fluoro-4-methoxymethoxy-phenyl)-[1,3,5]triazine-2,4,6-triamine |
| C32 | 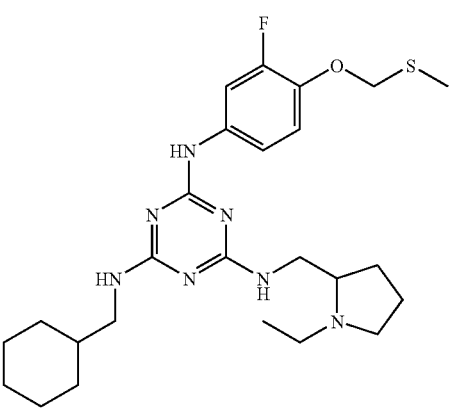 | N-Cyclohexylmethyl-N'-(1-ethyl-pyrrolidin-2-ylmethyl)-N''-(3-fluoro-4-methylsulfanylmethoxy-phenyl)-[1,3,5]triazine-2,4,6-triamine |

TABLE 1C-continued

Representative Compounds of the Present Invention

| Cmpd No. | Structure | Name |
|---|---|---|
| C33 | 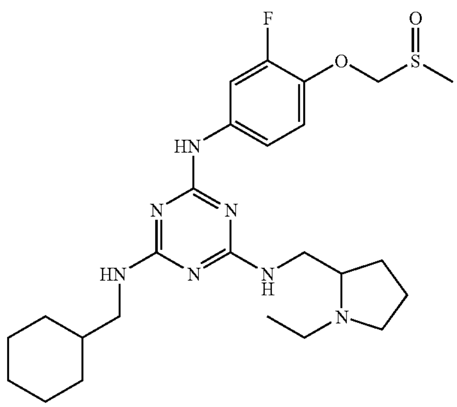 | N-Cyclohexylmethyl-N'-(1-ethyl-pyrrolidin-2-ylmethyl)-N''-(3-fluoro-4-methanesulfinylmethoxy-phenyl)-[1,3,5]triazine-2,4,6-triamine |
| C34 | 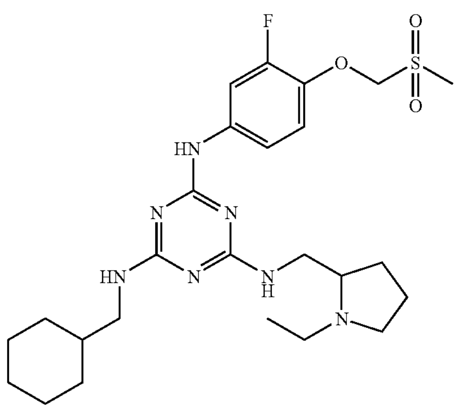 | N-Cyclohexylmethyl-N'-(1-ethyl-pyrrolidin-2-ylmethyl)-N''-(3-fluoro-4-methanesulfonylmethoxy-phenyl)-[1,3,5]triazine-2,4,6-triamine |
| C35 | 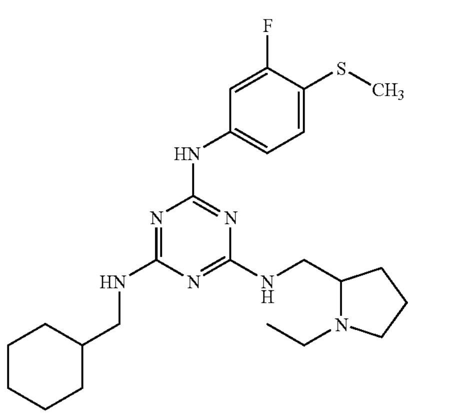 | N-Cyclohexylmethyl-N'-(1-ethyl-pyrrolidin-2-ylmethyl)-N''-(3-fluoro-4-methylsulfanyl-phenyl)-[1,3,5]triazine-2,4,6-triamine |

TABLE 1C-continued

Representative Compounds of the Present Invention

| Cmpd No. | Structure | Name |
| --- | --- | --- |
| C36 | 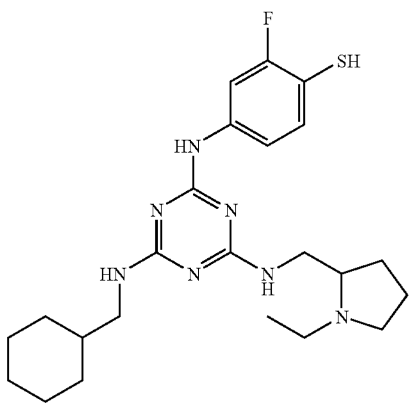 | 4-{4-(Cyclohexylmethyl-amino)-6-[(1-ethyl-pyrrolidin-2-ylmethyl)-amino-]-[1,3,5]triazin-2-ylamino}-2-fluoro-benzenethiol |
| C37 | 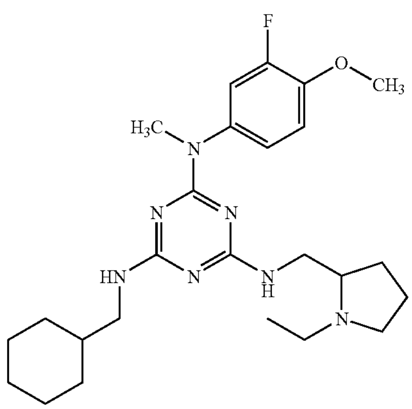 | N-Cyclohexylmethyl-N'-(1-ethyl-pyrrolidin-2-ylmethyl)-N''-(3-fluoro-4-methoxy-phenyl)-N''-methyl-[1,3,5]-triazine-2,4,6-triamine |
| C38 | 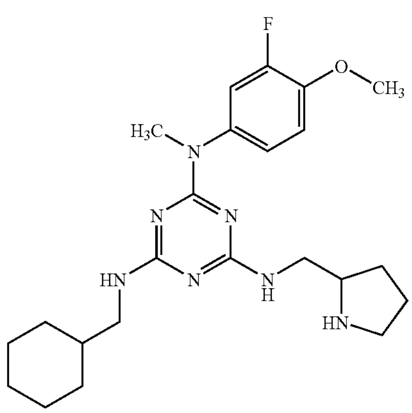 | N-Cyclohexylmethyl-N'-(3-fluoro-4-methoxy-phenyl)-N'-methyl-N''-pyrrolidin-2-ylmethyl-[1,3,5]triazine-2,4,6-triamine |

TABLE 1C-continued

Representative Compounds of the Present Invention

| Cmpd No. | Structure | Name |
|---|---|---|
| C39 | 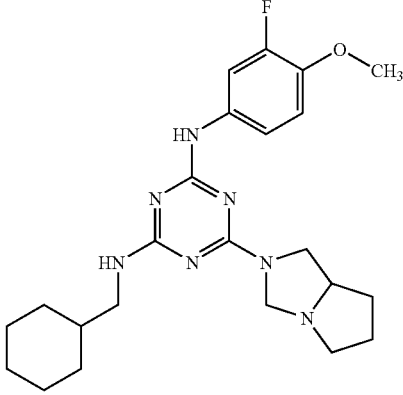 | N-Cyclohexylmethyl-N'-(3-fluoro-4-methoxy-phenyl)-6-(tetrahydro-pyrrolo[1,2-c]imidazol-2-yl)-[1,3,5]triazine-2,4-diamine |
| C40 | 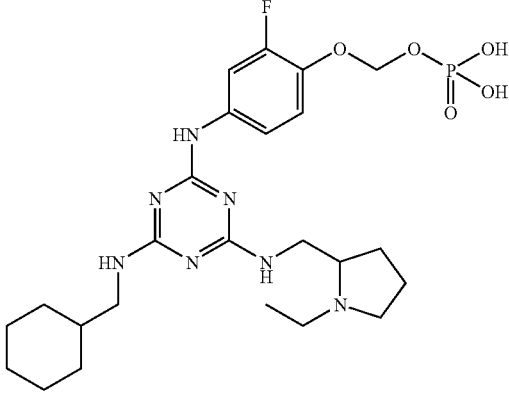 | Phosphoric acid mono-(4-{4-(cyclohexylmethyl-amino)-6-[(1-ethyl-pyrrolidin-2-ylmethyl)-amino]-[1,3,5]-triazin-2-ylamino}-2-fluoro-phenoxymethyl) ester |
| C41 | 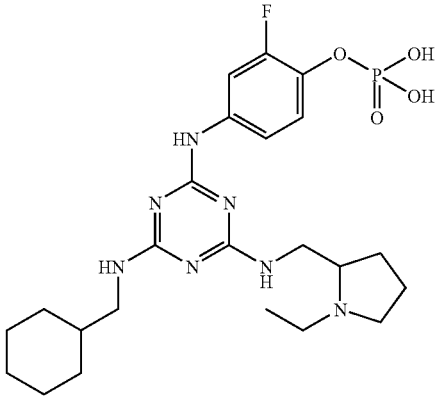 | Phosphoric acid mono-(4-{4-(cyclohexylmethyl-amino)-6-[(1-ethyl-pyrrolidin-2-ylmethyl)-amino]-[1,3,5]-triazin-2-ylamino}-2-fluoro-phenyl) ester |

TABLE 1C-continued

Representative Compounds of the Present Invention

| Cmpd No. | Structure | Name |
|---|---|---|
| C42 | 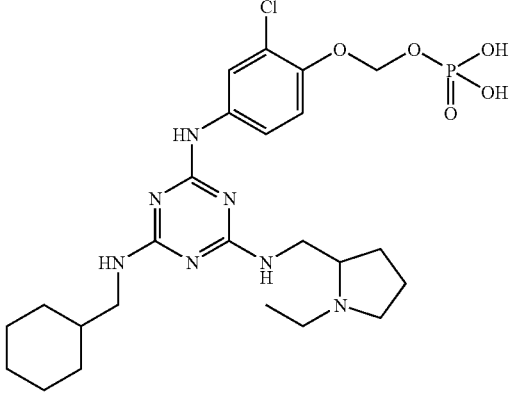 | Phosphoric acid mono-(2-chloro-4-{4-(cyclohexylmethyl-amino)-6-[(1-ethyl-pyrrolidin-2-ylmethyl)-amino]-[1,3,5]triazin-2-ylamino}-phenoxymethyl) ester |
| C43 | 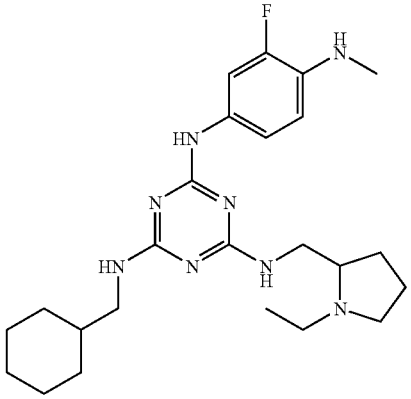 | N-Cyclohexylmethyl-N'-(1-ethyl-pyrrolidin-2-ylmethyl)-N''-(3-fluoro-4-methylamino-phenyl)-[1,3,5]triazine-2,4,6-triamine |
| C44 | 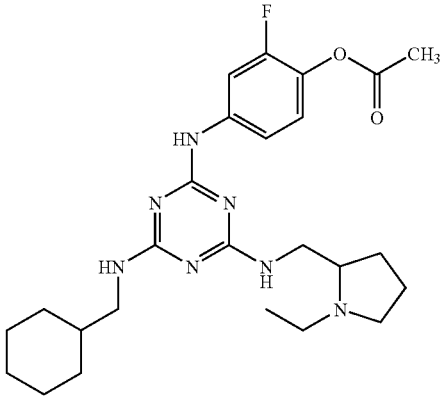 | Acetic acid 4-{4-(cyclohexylmethyl-amino)-6-[(1-ethyl-pyrrolidin-2-ylmethyl)-amino]-[1,3,5]triazin-2-ylamino}-2-fluoro-phenyl ester |

TABLE 1C-continued

Representative Compounds of the Present Invention

| Cmpd No. | Structure | Name |
|---|---|---|
| C45 | 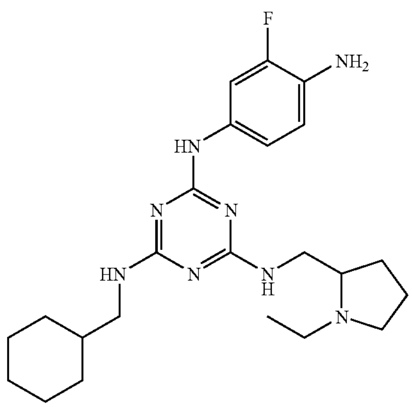 | N-(4-Amino-3-fluoro-phenyl)-N'-cyclohexylmethyl-N''-(1-ethyl-pyrrolidin-2-ylmethyl)-[1,3,5]-triazine-2,4,6-triamine |
| C46 | 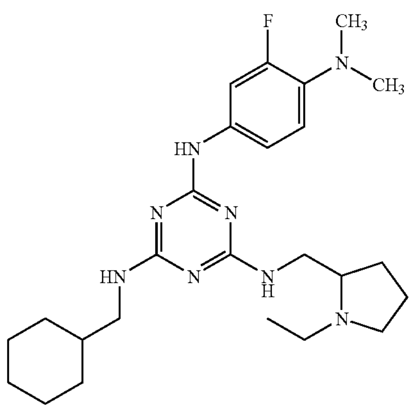 | N-Cyclohexylmethyl-N'-(4-dimethylamino-3-fluoro-phenyl)-N''-(1-ethyl-pyrrolidin-2-ylmethyl)-[1,3,5]triazine-2,4,6-triamine |
| C47 | 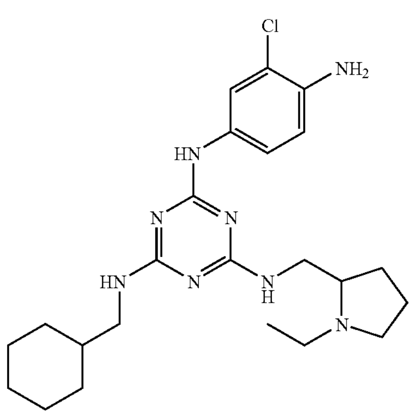 | N-(4-Amino-3-chloro-phenyl)-N'-cyclohexylmethyl-N''-(1-ethyl-pyrrolidin-2-ylmethyl)-[1,3,5]triazine-2,4,6-triamine |

TABLE 1C-continued

Representative Compounds of the Present Invention

| Cmpd No. | Structure | Name |
|---|---|---|
| C48 | 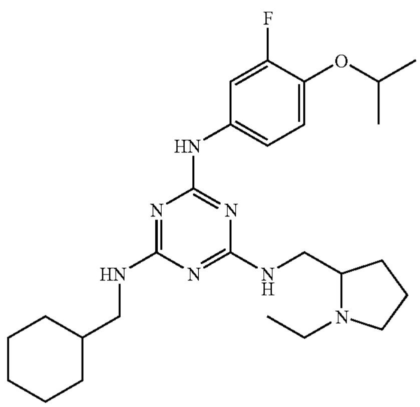 | N-Cyclohexylmethyl-N'-(1-ethyl-pyrrolidin-2-ylmethyl)-N''-(3-fluoro-4-isopropoxy-phenyl)-[1,3,5]triazine-2,4,6-triamine |
| C49 | 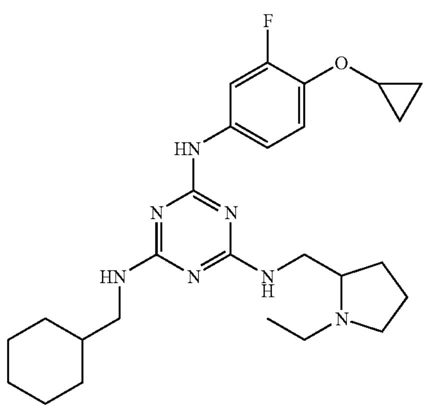 | N-Cyclohexylmethyl-N'-(4-cyclopropoxy-3-fluoro-phenyl)-N''-(1-ethyl-pyrrolidin-2-ylmethyl)-[1,3,5]triazine-2,4,6-triamine |
| C50 | 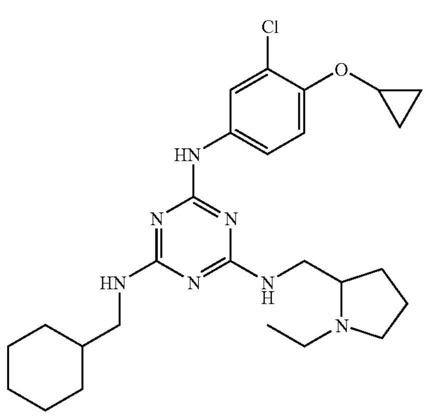 | N-(3-Chloro-4-cyclopropoxy-phenyl)-N'-cyclohexylmethyl-N''-(1-ethyl-pyrrolidin-2-ylmethyl)-[1,3,5]-triazine-2,4,6-triamine |

TABLE 1C-continued

Representative Compounds of the Present Invention

| Cmpd No. | Structure | Name |
|---|---|---|
| C51 | 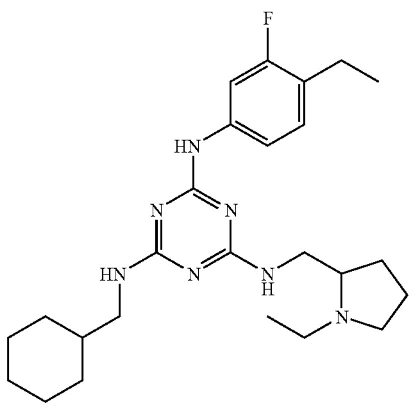 | N-Cyclohexylmethyl-N'-(4-ethyl-3-fluoro-phenyl)-N''-(1-ethyl-pyrrolidin-2-ylmethyl)-[1,3,5]triazine-2,4,6-triamine |
| C52 | 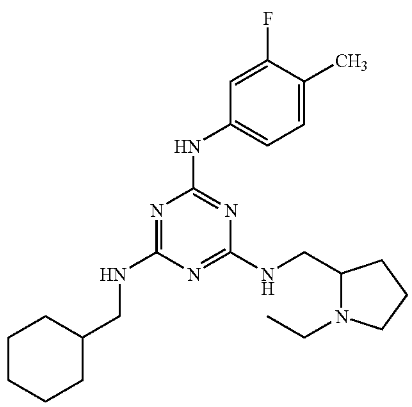 | N-Cyclohexylmethyl-N'-(1-ethyl-pyrrolidin-2-ylmethyl)-N''-(3-fluoro-4-methyl-phenyl)-[1,3,5]triazine-2,4,6-triamine |
| C53 | 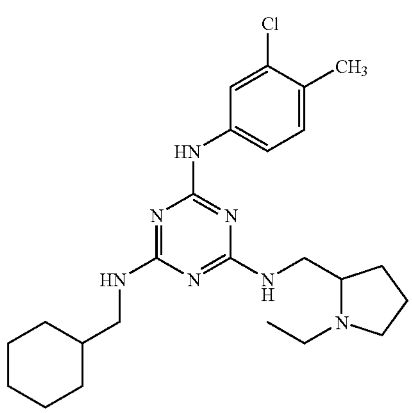 | N-(3-Chloro-4-methyl-phenyl)-N'-cyclohexylmethyl-N''-(1-ethyl-pyrrolidin-2-ylmethyl)-[1,3,5]triazine-2,4,6-triamine |

TABLE 1C-continued

Representative Compounds of the Present Invention

| Cmpd No. | Structure | Name |
|---|---|---|
| C54 | 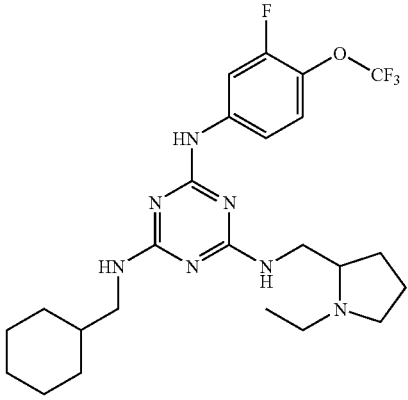 | N-Cyclohexylmethyl-N'-(1-ethyl-pyrrolidin-2-ylmethyl)-N''-(3-fluoro-4-trifluoromethoxy-phenyl)-[1,3,5]triazine-2,4,6-triamine |
| C55 | 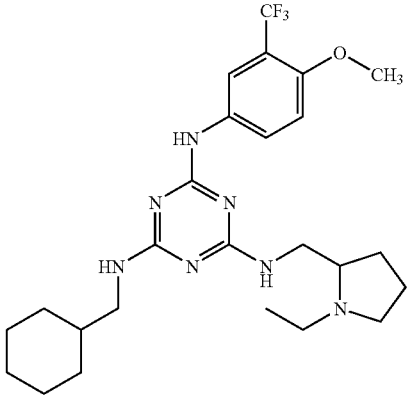 | N-Cyclohexylmethyl-N'-(1-ethyl-pyrrolidin-2-ylmethyl)-N''-(4-methoxy-3-trifluoromethyl-phenyl)-[1,3,5]triazine-2,4,6-triamine |
| C56 | 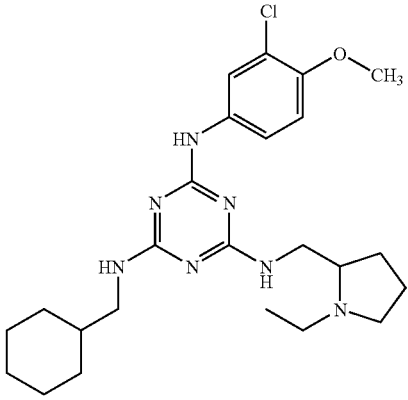 | N-(3-Chloro-4-trifluoromethoxy-phenyl)-N'-cyclohexylmethyl-N''-(1-ethyl-pyrrolidin-2-ylmethyl)-[1,3,5]triazine-2,4,6-triamine |

TABLE 1C-continued

Representative Compounds of the Present Invention

| Cmpd No. | Structure | Name |
|---|---|---|
| C57 | 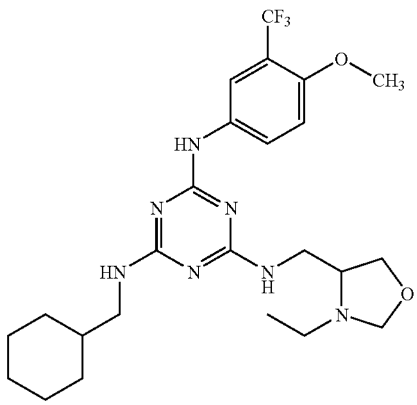 | N-Cyclohexylmethyl-N'-(3-ethyl-oxazolidin-4-ylmethyl)-N''-(4-trifluoromethoxy-3-trifluoromethyl-phenyl)-[1,3,5]triazine-2,4,6-triamine |
| C58 | 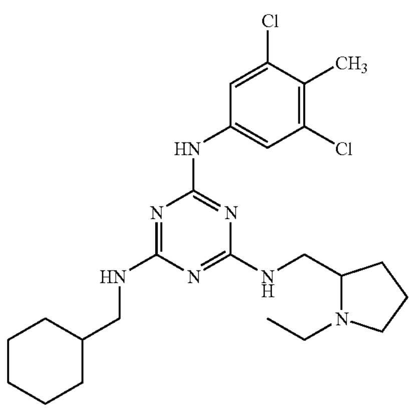 | N-Cyclohexylmethyl-N'-(3,5-dichloro-4-methyl-phenyl)-N''-(1-ethyl-pyrrolidin-2-ylmethyl)-[1,3,5]-triazine-2,4,6-triamine |
| C59 | 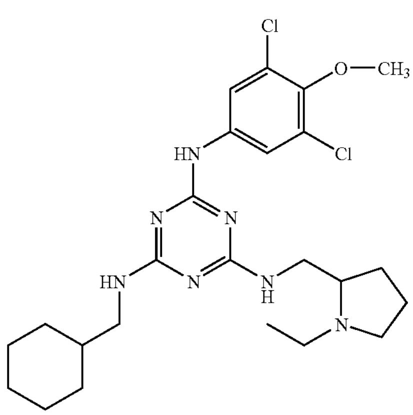 | N-Cyclohexylmethyl-N'-(3,5-dichloro-4-methoxy-phenyl)-N''-(1-ethyl-pyrrolidin-2-ylmethyl)-[1,3,5]-triazine-2,4,6-triamine |

TABLE 1C-continued

Representative Compounds of the Present Invention

| Cmpd No. | Structure | Name |
|---|---|---|
| C60 | 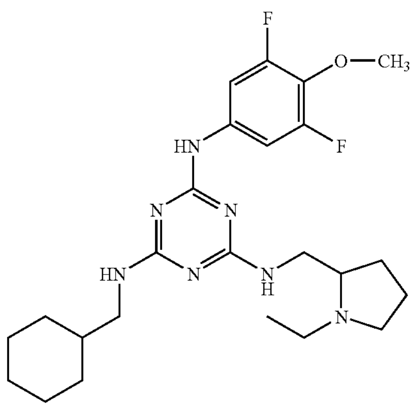 | N-Cyclohexylmethyl-N'-(3,5-difluoro-4-methoxy-phenyl)-N''-(1-ethyl-pyrrolidin-2-ylmethyl)-[1,3,5]-triazine-2,4,6-triamine |
| C61 | 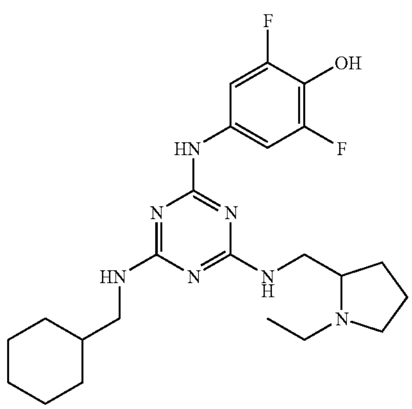 | 4-{4-(Cyclohexylmethyl-amino)-6-[(1-ethyl-pyrrolidin-2-ylmethyl)-amino]-[1,3,5]triazin-2-ylamino}-2,6-difluoro-phenol |
| C62 | 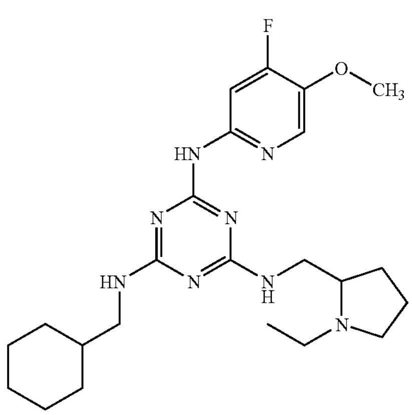 | N-Cyclohexylmethyl-N'-(1-ethyl-pyrrolidin-2-ylmethyl)-N''-(4-fluoro-5-methoxy-pyridin-2-yl)-[1,3,5]-triazine-2,4,6-triamine |

TABLE 1C-continued

Representative Compounds of the Present Invention

| Cmpd No. | Structure | Name |
| --- | --- | --- |
| C63 | 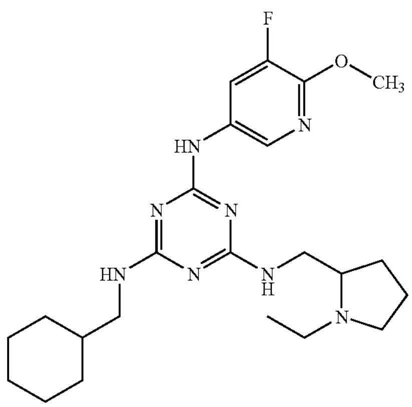 | N-Cyclohexylmethyl-N'-(1-ethyl-pyrrolidin-2-ylmethyl)-N''-(5-fluoro-6-methoxy-pyridin-3-yl)-[1,3,5]-triazine-2,4,6-triamine |
| C64 | 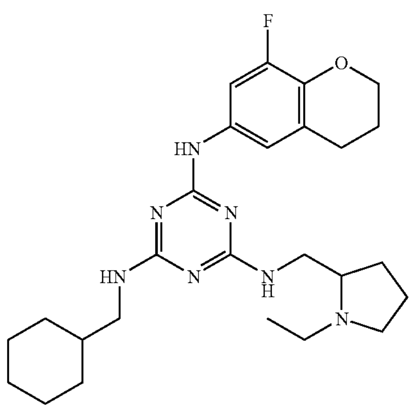 | N-Cyclohexylmethyl-N'-(1-ethyl-pyrrolidin-2-ylmethyl)-N''-(8-fluoro-chroman-6-yl)-[1,3,5]triazine-2,4,6-triamine |
| C65 | 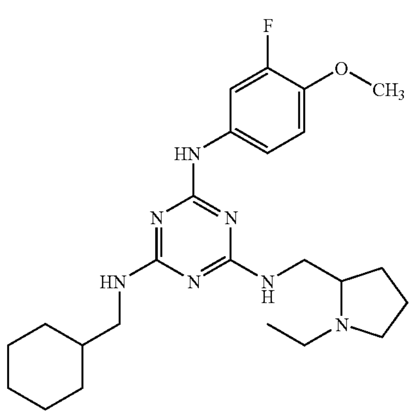 | N-Cyclohexylmethyl-N'-(1-ethyl-pyrrolidin-2-ylmethyl)-6-(3-fluoro-4-methoxy-phenoxy)-[1,3,5]-triazine-2,4-diamine |

TABLE 1C-continued

Representative Compounds of the Present Invention

| Cmpd No. | Structure | Name |
|---|---|---|
| C66 | 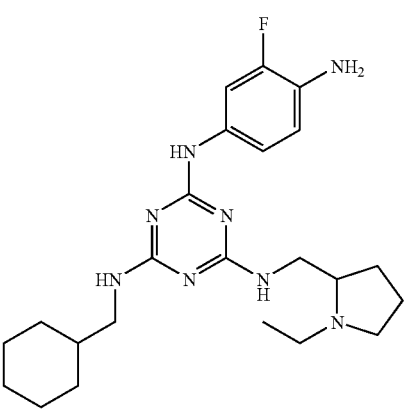 | 6-(4-Amino-3-fluoro-phenoxy)-N-cyclohexylmethyl-N'-(1-ethyl-pyrrolidin-2-ylmethyl)-[1,3,5]-triazine-2,4-diamine |
| C67 | 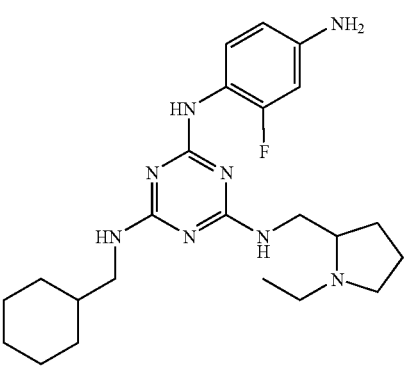 | 6-(4-Amino-2-fluoro-phenoxy)-N-cyclohexylmethyl-N'-(1-ethyl-pyrroiidin-2-ylmethyl)-[1,3,5]-triazine-2,4-diamine |
| C68 | 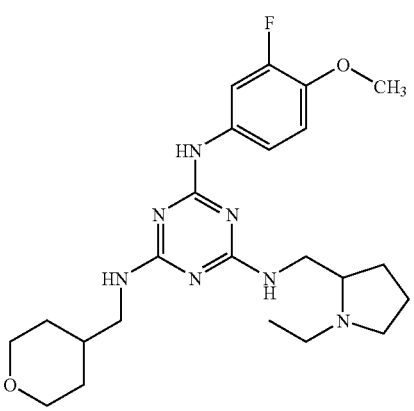 | N-(1-Ethyl-pyrrolidin-2-ylmethyl)-N'-(3-fluoro-4-methoxy-phenyl)-N'-(tetrahydro-pyran-4-ylmethyl)-[1,3,5]triazine-2,4,6-triamine |

TABLE 1C-continued

Representative Compounds of the Present Invention

| Cmpd No. | Structure | Name |
|---|---|---|
| C69 | 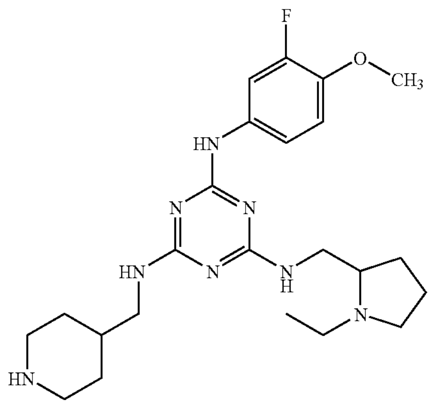 | N-(1-Ethyl-pyrrolidin-2-ylmethyl)-6-(3-fluoro-4-methoxy-phenoxy)-N'-piperidin-4-ylmethyl-(1,3,5]triazine-2,4-diamine |
| C70 | 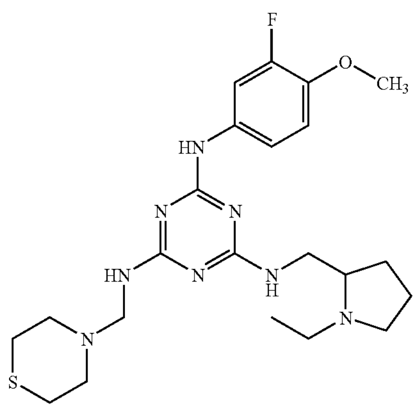 | N-(1-Ethyl-pyrrolidin-2-ylmethyl)-N'-(3-fluoro-4-methoxy-phenyl)-N''-thiomorpholin-4-ylmethyl-[1,3,5]-triazine-2,4,6-triamine |
| C71 | 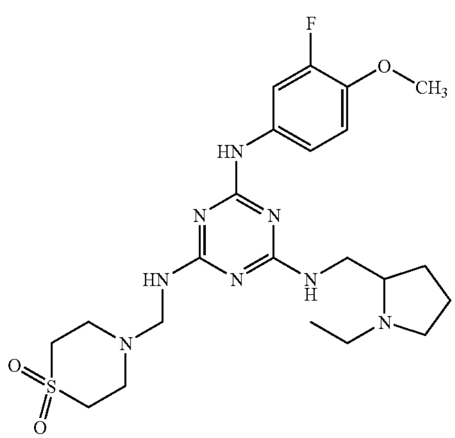 | N-(1,1-Dioxo-1lambda*6*-thiomorpholin-4-ylmethyl)-N'-(1-ethyl-pyrrolidin-2-ylmethyl)-N''-(3-fluoro-4-methoxy-phenyl)-[1,3,5]triazine-2,4,6-triamine |

TABLE 1C-continued

Representative Compounds of the Present Invention

| Cmpd No. | Structure | Name |
| --- | --- | --- |
| C72 | 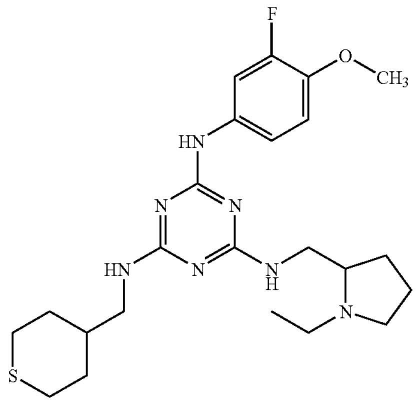 | N-(1-Ethyl-pyrrolidin-2-ylmethyl)-N'-(3-fluoro-4-methoxy-phenyl)-N''-(tetrahydro-thiopyran-4-ylmethyl)-[1,3,5]triazine-2,4,6-triamine |
| C73 | 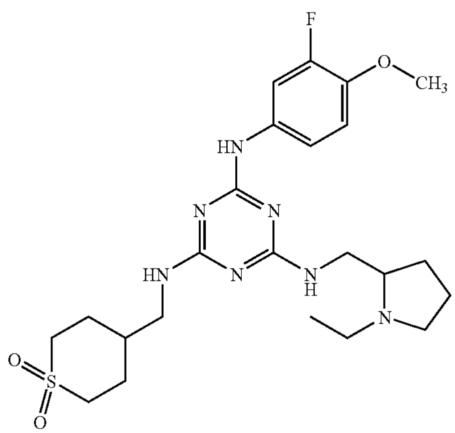 | N-(1,1-Dioxo-hexahydro-1lambda*6*-thiopyran-4-ylmethyl)-N'-(1-ethyl-pyrrolidin-2-ylmethyl)-N''-(3-fluoro-4-methoxy-phenyl)-[1,3,5]-triazine-2,4,6-triamine |
| C74 | 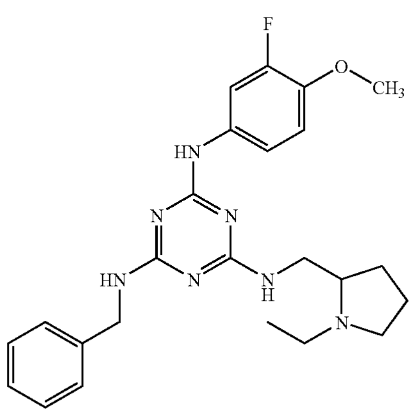 | N-Benzyl-N'-(1-ethyl-pyrrolidin-2-ylmethyl)-N''-(3-fluoro-4-methoxy-phenyl)-[1,3,5]triazine-2,4,6-triamine |

TABLE 1C-continued

Representative Compounds of the Present Invention

| Cmpd No. | Structure | Name |
|---|---|---|
| C75 | 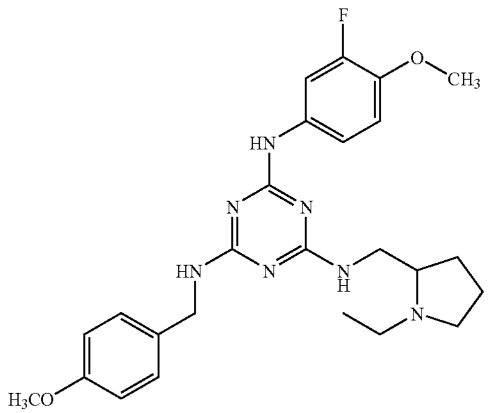 | N-(1-Ethyl-pyrrolidin-2-ylmethyl)-N'-(3-fluoro-4-methoxy-phenyl)-N''-(4-methoxy-benzyl)-[1,3,5]triazine-2,4,6-triamine |
| C76 | 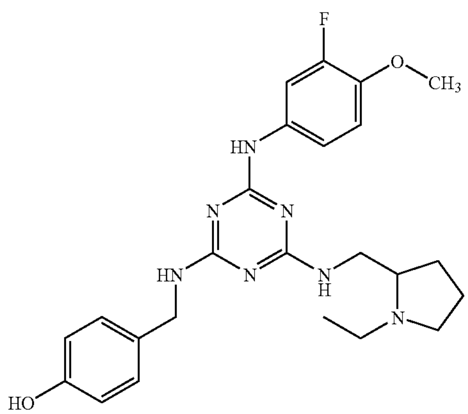 | N-(1-Ethyl-pyrrolidin-2-ylmethyl)-N'-(3-fluoro-4-methoxy-phenyl)-N''-(4-hydroxy-benzyl)-[1,3,5]triazine-2,4,6-triamine, |
| C77 | 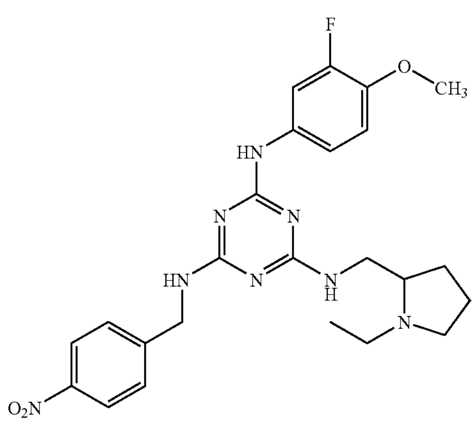 | N-(1-Ethyl-pyrrolidin-2-ylmethyl)-N'-(3-fluoro-4-methoxy-phenyl)-N''-(4-nitro-benzyl)-[1,3,5]triazine-2,4,6-triamine |

TABLE 1C-continued

Representative Compounds of the Present Invention

| Cmpd No. | Structure | Name |
|---|---|---|
| C78 | 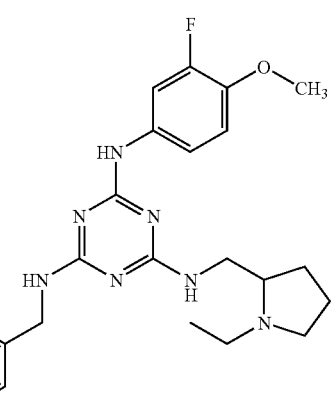 | N-(1-Ethyl-pyrrolidin-2-ylmethyl)-N'-(4-fluoro-benzyl)-N''-(3-fluoro-4-methoxy-phenyl)-[1,3,5]triazine-2,4,6-triamine |
| C79 | 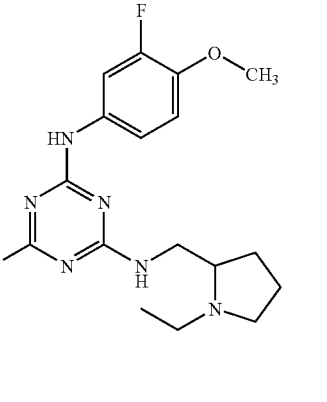 | N-Cyclopentylmethyl-N'-(1-ethyl-pyrrolidin-2-ylmethyl)-N'-(3-fluoro-4-methoxy-phenyl)-[1,3,5]triazine-2,4,6-triamine |
| C80 | 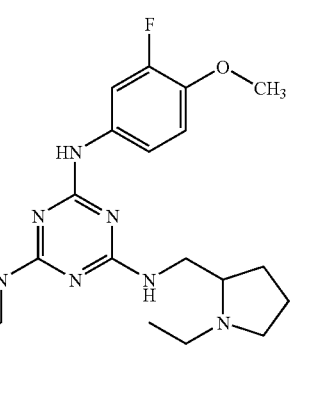 | N-Cyclohex-2-enylmethyl-N'-(1-ethyl-pyrrolidin-2-ylmethyl)-N''-(3-fluoro-4-methoxy-phenyl)-[1,3,5]-triazine-2,4,6-triamine |

TABLE 1C-continued

Representative Compounds of the Present Invention

| Cmpd No. | Structure | Name |
| --- | --- | --- |
| C81 | 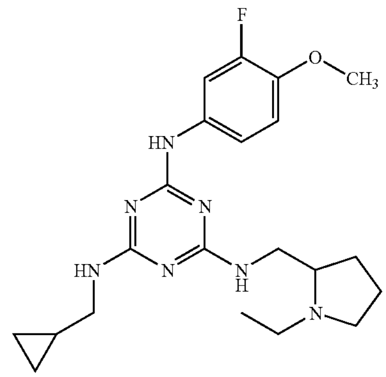 | N-Cyclopropylmethyl-N'-(1-ethyl-pyrrolidin-2-ylmethyl)-N'-(3-fluoro-4-methoxy-phenyl)-[1,3,5]-triazine-2,4,6-triamine |
| C82 | 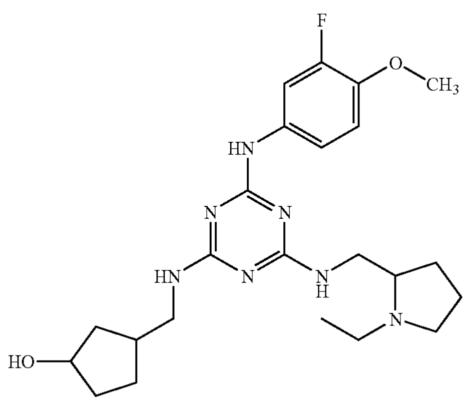 | 3-{(4-[(1-Ethyl-pyrrolidin-2-ylmethyl)-amino]-6-(3-fluoro-4-methoxy-phenylamino)-[1,3,5]triazin-2-ylamino]-methyl}-cyclopentanol |
| C83 | 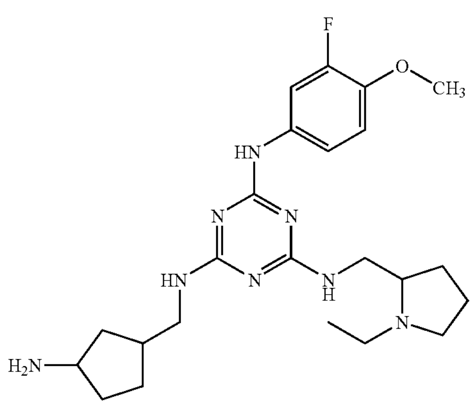 | N-(3-Amino-cyclopentylmethyl)-N'-(1-ethyl-pyrrolidin-2-ylmethyl)-N''-(3-fluoro-4-methoxy-phenyl)-[1,3,5]-triazine-2,4,6-triamine |

TABLE 1C-continued

Representative Compounds of the Present Invention

| Cmpd No. | Structure | Name |
|---|---|---|
| C84 | 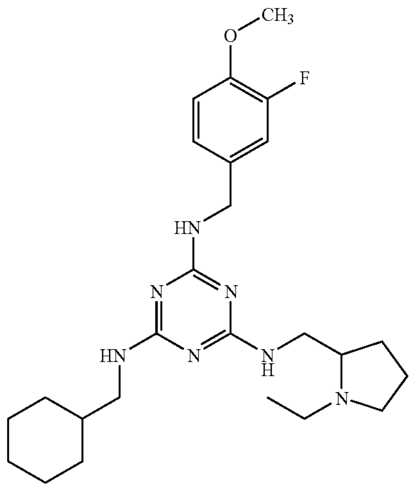 | N-Cyclohexylmethyl-N'-(1-ethyl-pyrrolidin-2-ylmethyl)-N''-(3-fluoro-4-methoxy-benzyl)-[1,3,5]-triazine-2,4,6-triamine |
| C85 | 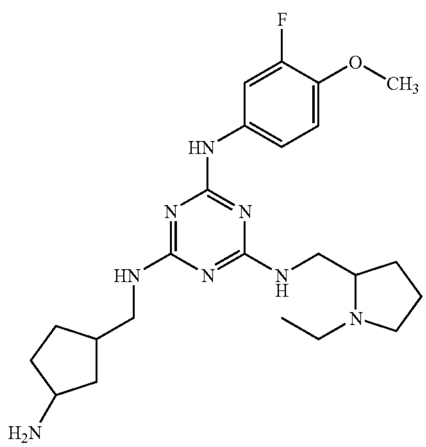 | N-(3-Amino-cyclopentylmethyl)-N'-(1-ethyl-pyrrolidin-2-ylmethyl)-N''-(3-fluoro-4-methoxy-phenyl)-[1,3,5]triazine-2,4,6-triamine |
| C86 | 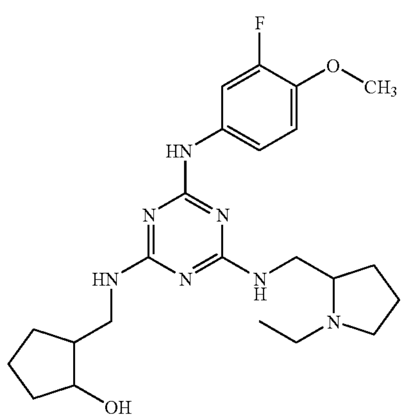 | 2-{[4-[(1-Ethyl-pyrrolidin-2-ylmethyl)-amino]-6-(3-fluoro-4-methoxy-phenylamino)-[1,3,5]-triazin-2-ylamino]-methyl}-cyclopentanol |

TABLE 1C-continued

Representative Compounds of the Present Invention

| Cmpd No. | Structure | Name |
|---|---|---|
| C87 | 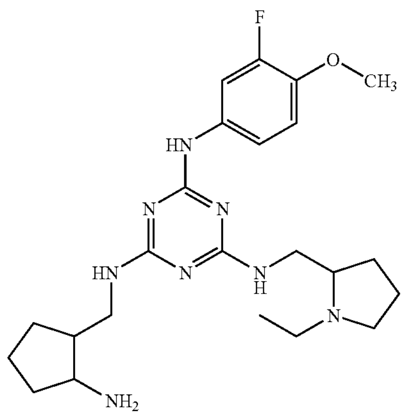 | N-(2-Amino-cyclopentylmethyl)-N'-(1-ethyl-pyrrolidin-2-ylmethyl)-N''-(3-fluoro-4-methoxy-phenyl)-[1,3,5]-triazine-2,4,6-triamine |
| C88 | 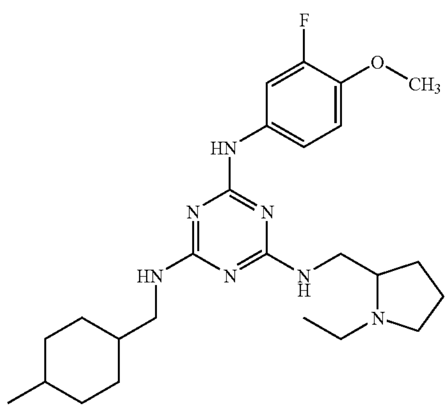 | N-(1-Ethyl-pyrrolidin-2-ylmethyl)-N'-(3-fluoro-4-methoxy-phenyl)-N''-(4-methyl-cyclohexylmethyl)-[1,3,5]-triazine-2,4,6-triamine |
| C89 | 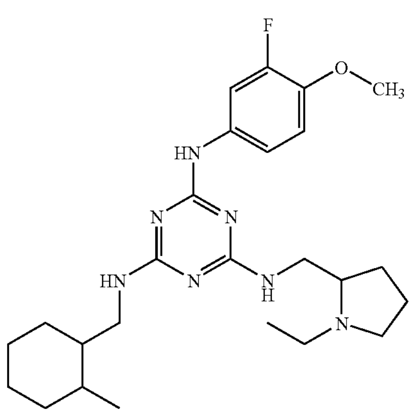 | N-(1-Ethyl-pyrrolidin-2-ylmethyl)-N'-(3-fluoro-4-methoxy-phenyl)-N''-(2-methyl-cyclohexylmethyl)-[1,3,5]-triazine-2,4,6-triamine |

TABLE 1C-continued

Representative Compounds of the Present Invention

| Cmpd No. | Structure | Name |
|---|---|---|
| C90 | 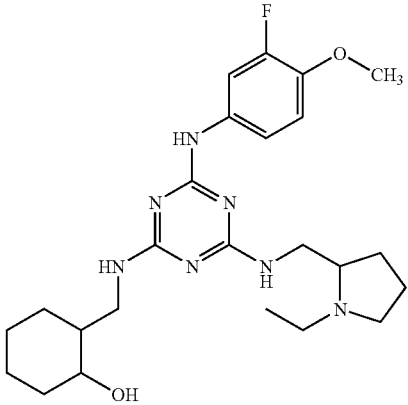 | 2-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol |
| C91 | 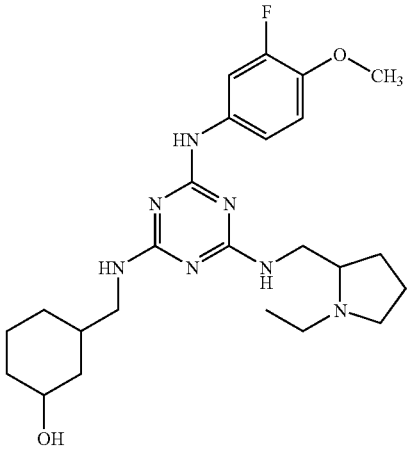 | 3-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol |
| C92 | 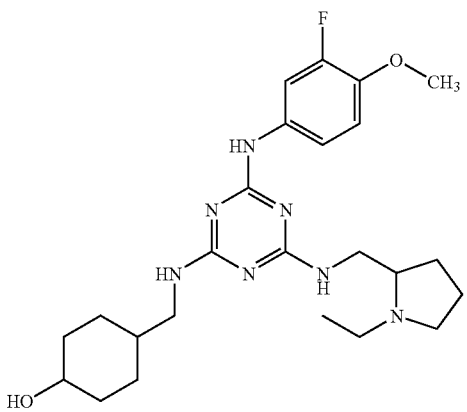 | 4-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol |

TABLE 1C-continued

Representative Compounds of the Present Invention

| Cmpd No. | Structure | Name |
|---|---|---|
| C93 | 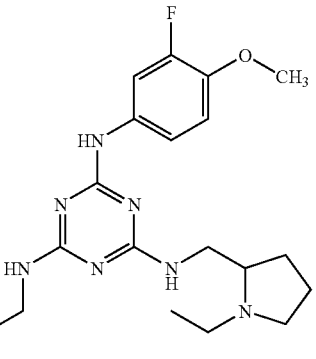 | N-(4-Amino-cyclohexylmethyl)-N'-(1-ethyl-pyrrolidin-2-ylmethyl)-N''-(3-fluoro-4-methoxy-phenyl)-[1,3,5]-triazine-2,4,6-triamine |
| C94 | 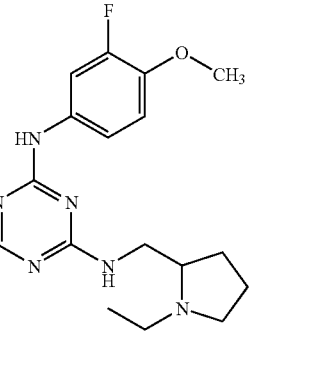 | N-(3-Amino-cyclohexylmethyl)-N'-(1-ethyl-pyrrolidin-2-ylmethyl)-N''-(3-fluoro-4-methoxy-phenyl)-[1,3,5]-triazine-2,4,6-triamine |
| C95 | 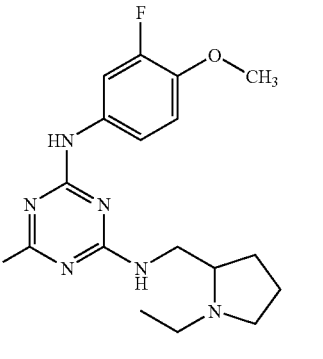 | N-Cycloheptylmethyl-N'-(1-ethyl-pyrrolidin-2-ylmethyl)-N''-(3-fluoro-4-methoxy-phenyl)-[1,3,5]triazine-2,4,6-triamine |

TABLE 1C-continued
Representative Compounds of the Present Invention
| Cmpd No. | Structure | Name |
|---|---|---|
| C96 | 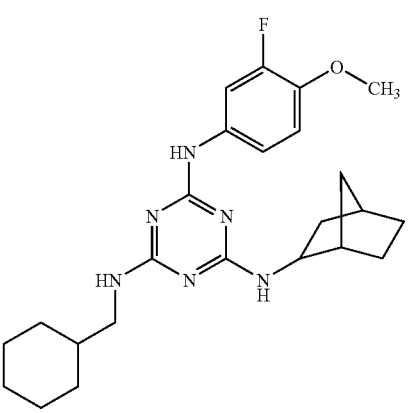 | N-Bicyclo[2.2.1]hept-2-yl-N'-cyclohexylmethyl-N''-(3-fluoro-4-methoxy-phenyl)-[1,3,5]triazine-2,4,6-triamine |
| C97 | 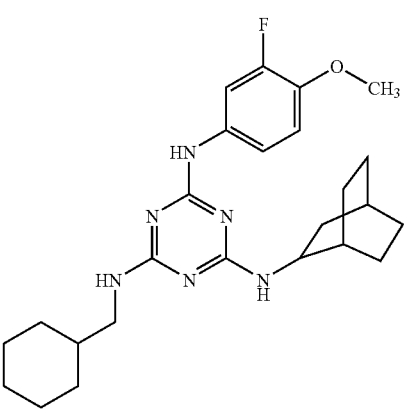 | N-Bicyclo[2.2.2]oct-2-yl-N'-cyclohexylmethyl-N''-(3-fluoro-4-methoxy-phenyl)-[1,3,5]triazine-2,4,6-triamine |
| C98 | 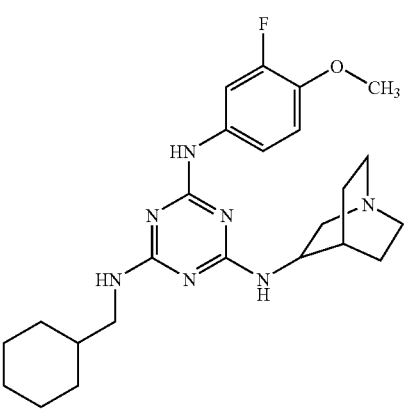 | N-(1-Aza-bicyclo[2.2.2]oct-3-yl)-N'-cyclohexylmethyl-N''-(3-fluoro-4-methoxy-phenyl)-[1,3,5]-triazine-2,4,6-triamine |

TABLE 1C-continued

Representative Compounds of the Present Invention

| Cmpd No. | Structure | Name |
|---|---|---|
| C99 | 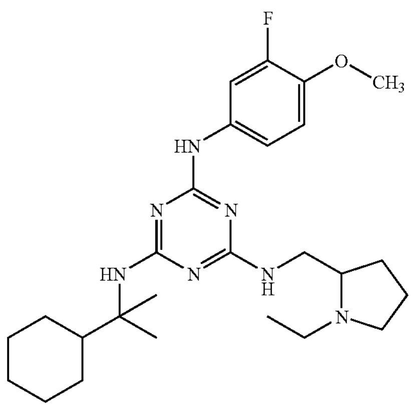 | N-(1-Cyclohexyl-1-methyl-ethyl)-N'-(1-ethyl-pyrrolidin-2-ylmethyl)-N''-(3-fluoro-4-methoxy-phenyl)-[1,3,5]triazine-2,4,6-triamine |
| C100 | 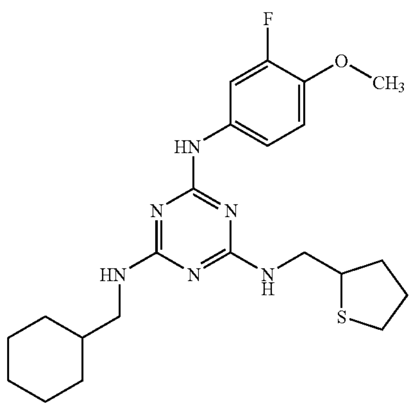 | N-Cyclohexylmethyl-N'-(3-fluoro-4-methoxy-phenyl)-N''-(tetrahydro-thiophen-2-ylmethyl)-[1,3,5]-triazine-2,4,6-triamine |
| C101 | 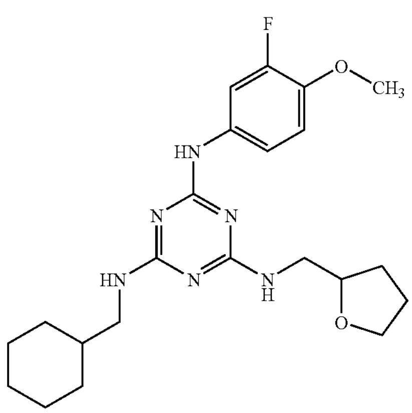 | N-Cyclohexylmethyl-N'-(3-fluoro-4-methoxy-phenyl)-N''-(tetrahydro-furan-2-ylmethyl)-[1,3,5]triazine-2,4,6-triamine |

TABLE 1C-continued
Representative Compounds of the Present Invention
| Cmpd No. | Structure | Name |
|---|---|---|
| C102 | 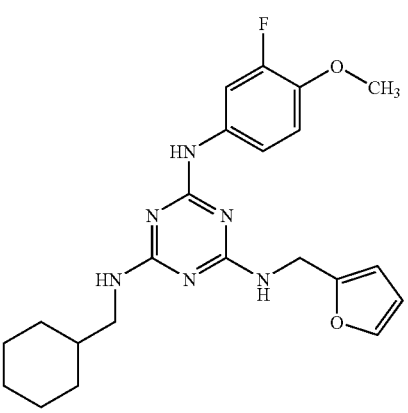 | N-Cyclohexylmethyl-N'-(3-fluoro-4-methoxy-phenyl)-N''-furan-2-ylmethyl-[1,3,5]triazine-2,4,6-triamine |
| C103 | 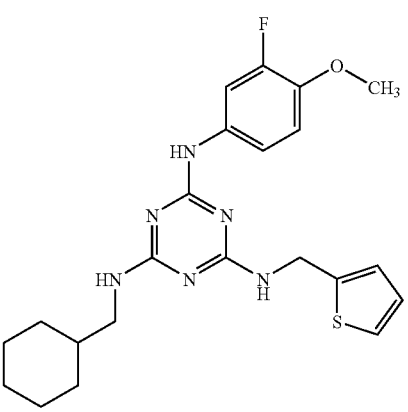 | N-Cyclohexylmethyl-N'-(3-fluoro-4-methoxy-phenyl)-N''-thiophen-2-ylmethyl-[1,3,5]triazine-2,4,6-triamine |
| C104 | 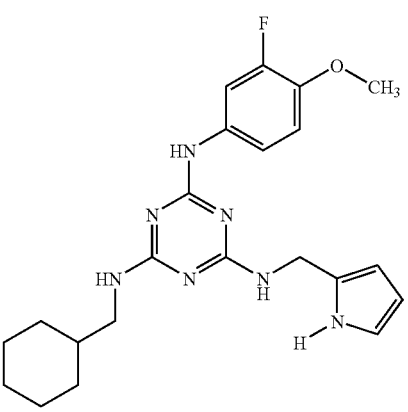 | N-Cyclohexylmethyl-N'-(3-fluoro-4-methoxy-phenyl)-N''-(1H-pyrrol-2-ylmmethyl)-[1,3,5]triazine-2,4,6-triamine |

TABLE 1C-continued

Representative Compounds of the Present Invention

| Cmpd No. | Structure | Name |
|---|---|---|
| C105 | 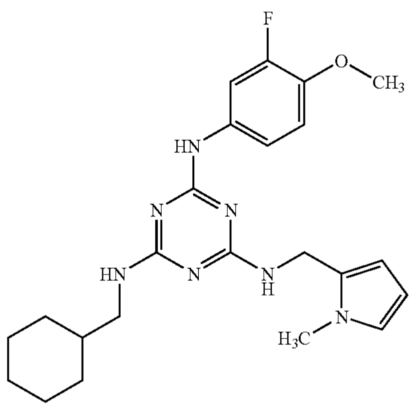 | N-Cyclohexylmethyl-N'-(3-fluoro-4-methoxy-phenyl)-N''-(1-methyl-1H-pyrrol-2-ylmethyl)-[1,3,5]-triazine-2,4,6-triamine |
| C106 | 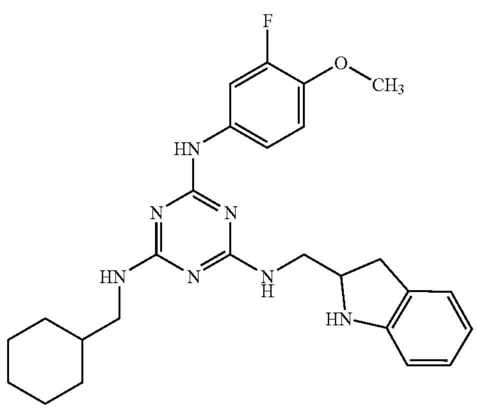 | N-Cyclohexylmethyl-N'-(2,3-dihydro-1H-indol-2-ylmethyl)-N''-(3-fluoro-4-methoxy-phenyl)-[1,3,5]triazine-2,4,6-triamine |
| C107 | 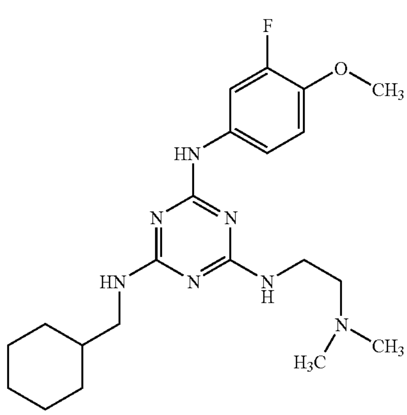 | N-Cyclohexylmethyl-N'-(2-dimethylamino-ethyl)-N''-(3-fluoro-4-methoxy-phenyl)-[1,3,5]triazine-2,4,6-triamine |

TABLE 1C-continued

Representative Compounds of the Present Invention

| Cmpd No. | Structure | Name |
|---|---|---|
| C108 | 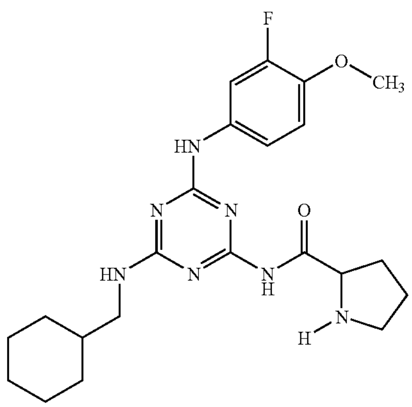 | Pyrrolidine-2-carboxylic acid [4-(cyclohexylmethyl-amino)-6-(3-fluoro-4-methoxy-phenylamino)-[1,3,5]triazin-2-yl]-amine |
| C109 | 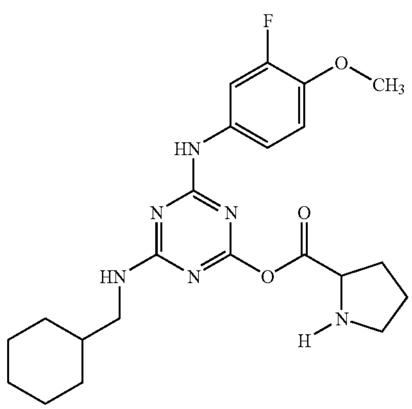 | Pyrrolidine-2-carboxylic acid 4-(cyclohexylmethyl-amino)-6-(3-fluoro-4-methoxy-phenylamino)-[1,3,5]triazin-2-yl ester |
| C110 | 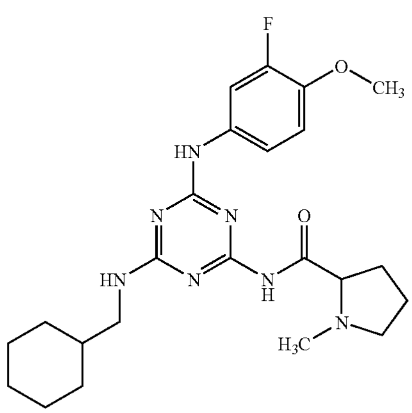 | 1-Methyl-pyrrolidine-2-carboxylic acid [4-(cyclohexylmethyl-amino)-6-(3-fluoro-4-methoxy-phenylamino)-[1,3,5]triazin-2-yl]-amide |

TABLE 1C-continued

Representative Compounds of the Present Invention

| Cmpd No. | Structure | Name |
|---|---|---|
| C111 | 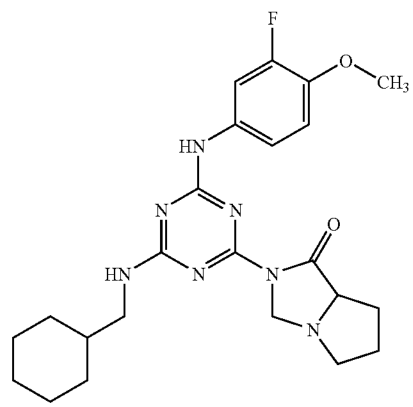 | 2-[4-(Cyclohexylmethyl-amino)-6-(3-fluoro-4-methoxy-phenylamino)-[1,3,5]triazin-2-yl]-hexahydro-pyrrolo[1,2-c]imidazol-1-one |
| C112 | 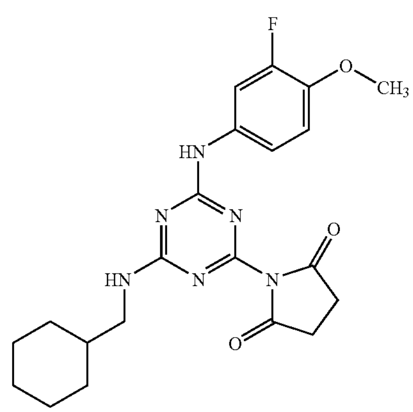 | 1-[4-(Cyclohexylmethyl-amino)-6-(3-fluoro-4-methoxy-phenylamino)-[1,3,5]triazin-2-yl]-pyrrolidine-2,5-dione |
| C113 | 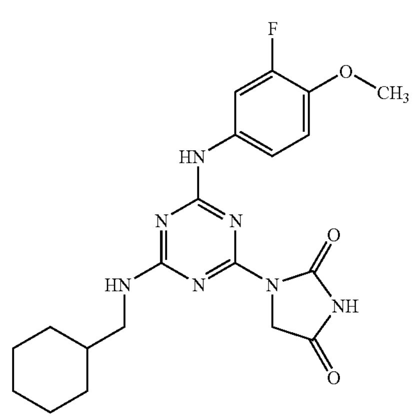 | 1-[4-(Cyclohexylmethyl-amino)-6-(3-fluoro-4-methoxy-phenylamino)-[1,3,5]triazin-2-yl]-imidazolidine-2,4-dione |

TABLE 1C-continued

Representative Compounds of the Present Invention

| Cmpd No. | Structure | Name |
|---|---|---|
| C114 | 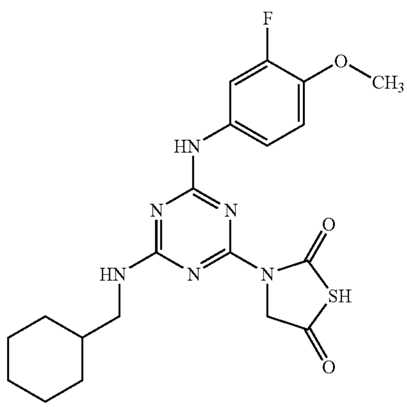 | 3-[4-(Cyclohexylmethyl-amino)-6-(3-fluoro-4-methoxy-phenylamino)-[1,3,5]triazin-2-yl]-thiazolidine-2,5-dione |
| C115 | 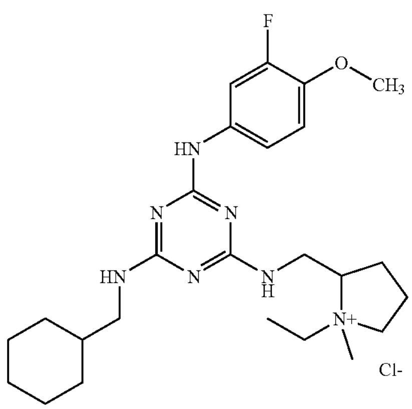 | 2-{[4-(Cyclohexylmethyl-amino)-6-(3-fluoro-4-methoxy-phenylamino)-[1,3,5]triazin-2-ylamino]-methyl}-1-ethyl-1-methyl-pyrrolidinium; chloride |
| C116 | 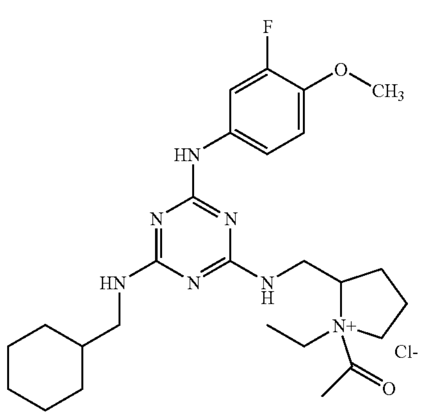 | 1-Acetyl-2-{[4-(cyclohexylmethyl-amino)-6-(3-fluoro-4-methoxy-phenylamino)-[1,3,5]triazin-2-ylamino]-methyl}-1-ethyl-pyrrolidinium; chloride |

TABLE 1C-continued

Representative Compounds of the Present Invention

| Cmpd No. | Structure | Name |
|---|---|---|
| C117 | 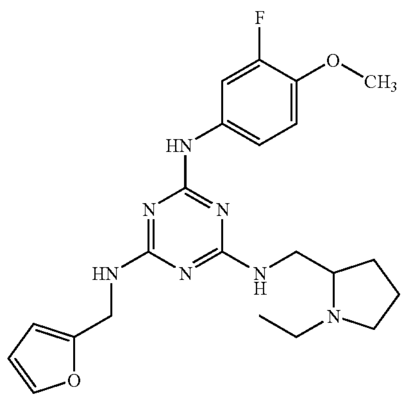 | N-(1-Ethyl-pyrrolidin-2-ylmethyl)-N'-(3-fluoro-4-methoxy-phenyl)-N''-furan-2-ylmethyl-[1,3,5]triazine-2,4,6-triamine |
| C118 | 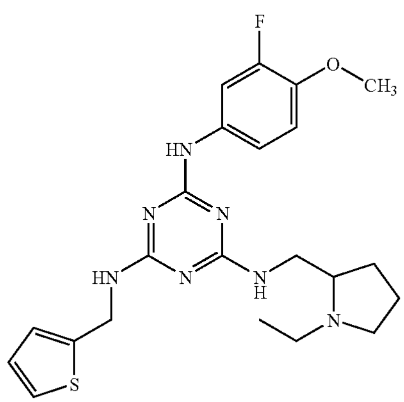 | N-(1-Ethyl-pyrrolidin-2-ylmethyl)-N'-(3-fluoro-4-methoxy-phenyl)-N''-thiophen-2-ylmethyl-[1,3,5]triazine-2,4,6-triamine |
| C119 | 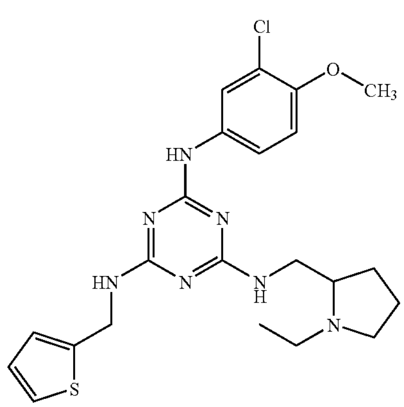 | N-(3-Chloro-4-methoxy-phenyl)-N'-(1-ethyl-pyrrolidin-2-ylmethyl)-N''-thiophen-2-ylmethyl-[1,3,5]triazine-2,4,6-triamine |

TABLE 1C-continued

Representative Compounds of the Present Invention

| Cmpd No. | Structure | Name |
|---|---|---|
| C120 | 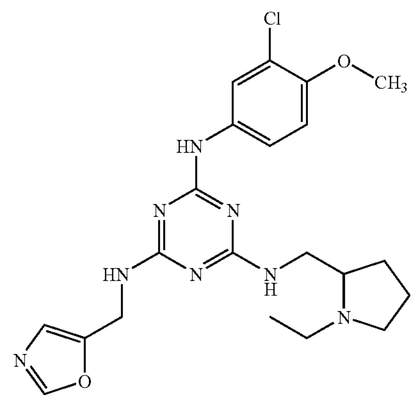 | N-(3-Chloro-4-methoxy-phenyl)-N'-(1-ethyl-pyrrolidin-2-ylmethyl)-N''-oxazol-5-ylmethyl-[1,3,5]triazine-2,4,6-triamine |
| C121 | 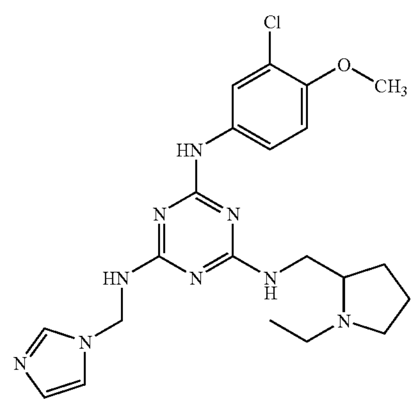 | N-(3-Chloro-4-methoxy-phenyl)-N'-(1-ethyl-pyrrolidin-2-ylmethyl)-N''-imidazol-1-ylmethyl-[1,3,5]triazine-2,4,6-triamine |
| C122 | 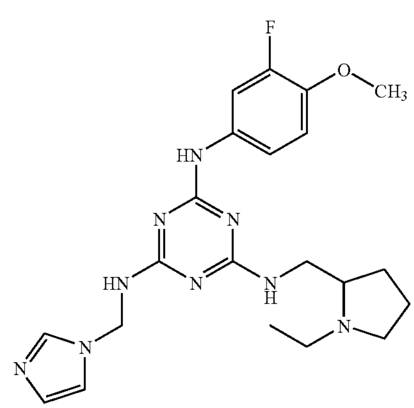 | N-(1-Ethyl-pyrrolidin-2-ylmethyl)-N'-(3-fluoro-4-methoxy-phenyl)-N''-imidazol-1-ylmethyl-[1,3,5]triazine-2,4,6-triamine |

TABLE 1C-continued

Representative Compounds of the Present Invention

| Cmpd No. | Structure | Name |
|---|---|---|
| C123 | 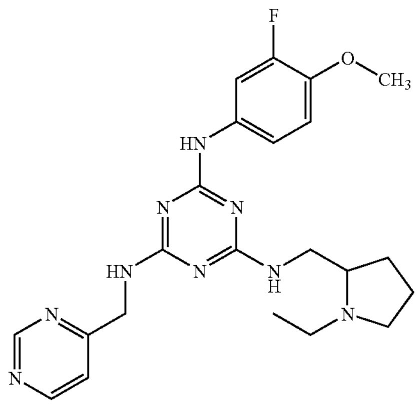 | N-(1-Ethyl-pyrrolidin-2-ylmethyl)-N'-(3-fluoro-4-methoxy-phenyl)-N''-pyrimidin-4-ylmethyl-[1,3,5]triazine-2,4,6-triamine |
| C124 | 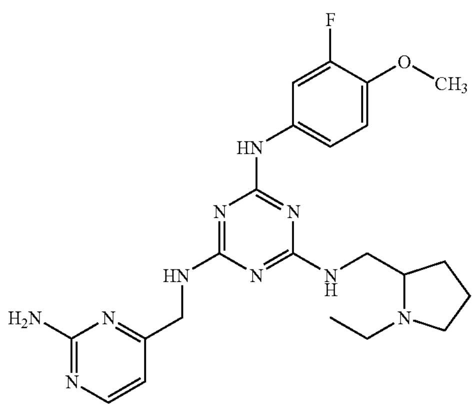 | N-(2-Amino-pyrimidin-4-ylmethyl)-N'-(1-ethyl-pyrrolidin-2-ylmethyl)-N''-(3-fluoro-4-methoxy-phenyl)-[1,3,5]triazine-2,4,6-triamine |
| C125 | 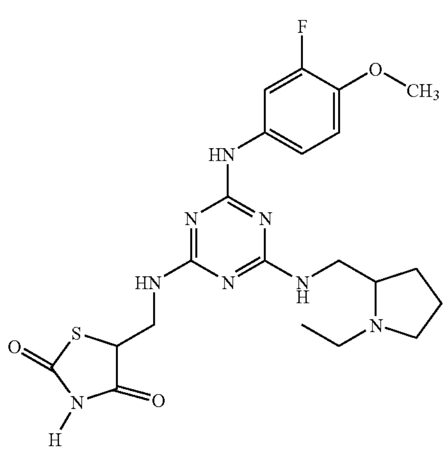 | 5-{[4-[(1-Ethyl-pyrrolidin-2-ylmethyl)-amino]-6-(3-fluoro-4-methoxy-phenylamino)-[1,3,5]triazin-2-ylamino]-methyl}-thiazolidine-2,4-dione |

TABLE 1C-continued

Representative Compounds of the Present Invention

| Cmpd No. | Structure | Name |
|---|---|---|
| C126 | 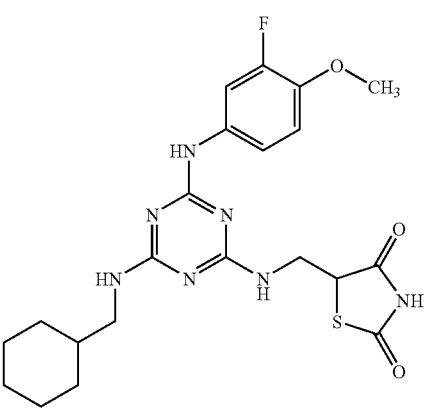 | 5-{[4-(Cyclohexylmethyl-amino)-6-(3-fluoro-4-methoxy-phenylamino)-[1,3,5]triazin-2-ylamino]-methyl}-thiazolidine-2,4-dione |
| C127 | 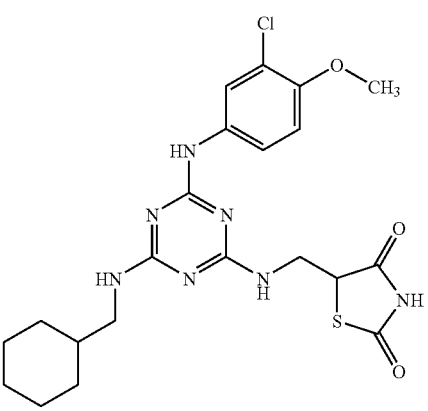 | 5-{[4-(3-Chloro-4-methoxy-phenylamino)-6-(cyclohexylmethyl-amino)-[1,3,5]triazin-2-ylamino]-methyl}-thiazolidine-2,4-dione |
| C128 | 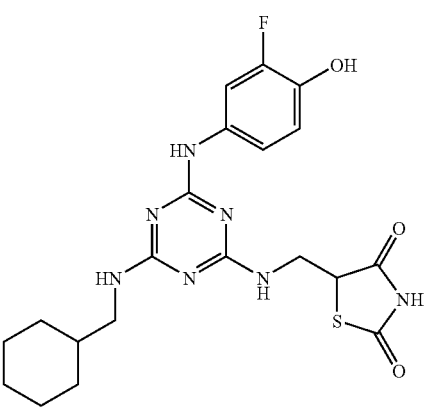 | 5-{[4-(Cyclohexylmethyl-amino)-6-(3-fluoro-4-hydroxy-phenylamino)-[1,3,5]triazin-2-ylamino]-methyl}-thiazolidine-2,4-dione |

TABLE 1C-continued

Representative Compounds of the Present Invention

| Cmpd No. | Structure | Name |
|---|---|---|
| C129 | 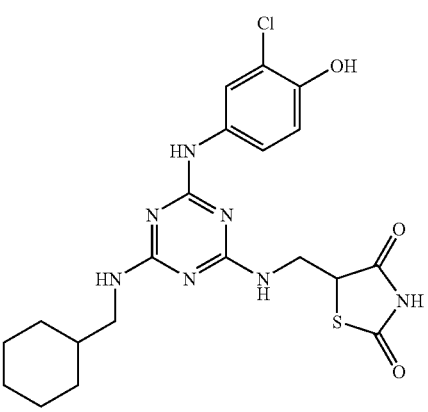 | 5-{[4-(3-Chloro-4-hydroxy-phenyl-amino)-6-(cyclohexylmethyl-amino)-[1,3,5]triazin-2-ylamino]-methyl}-thiazolidine-2,4-dione |
| C130 | 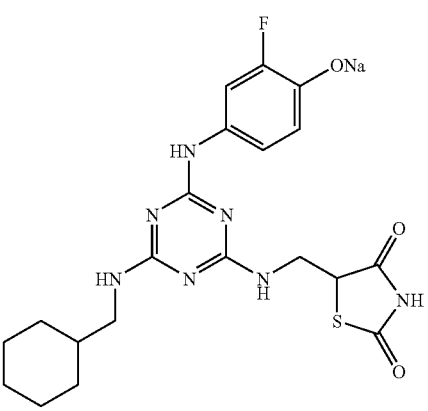 | Sodium; 4-{4-(cyclohexylmethyl-amino)-6-[(2,4-dioxo-thiazolidin-5-ylmethyl)-amino]-[1,3,5]triazin-2-ylamino}-2-fluoro-phenolate |
| C131 | 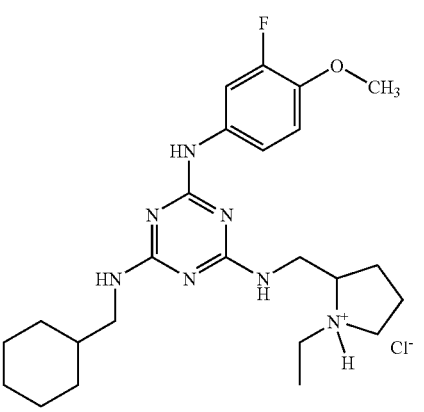 | 2-{[4-(Cyclohexylmethyl-amino)-6-(3-fluoro-4-methoxy-phenylamino)-[1,3,5]triazin-2-ylamino]-methyl}-1-ethyl-pyrrolidinium; chloride |

TABLE 1C-continued

Representative Compounds of the Present Invention

| Cmpd No. | Structure | Name |
|---|---|---|
| C132 | 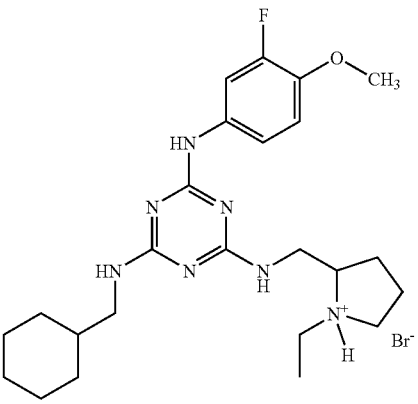 | 2-{[4-(Cyclohexylmethyl-amino)-6-(3-fluoro-4-methoxy-phenylamino)-[1,3,5]triazin-2-ylamino]-methyl}-1-ethyl-pyrrolidinium; bromide |
| C133 | 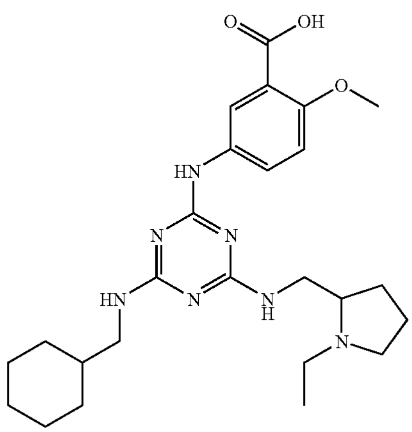 | 5-{4-(Cyclohexylmethyl-amino)-6-[(1-ethyl-pyrrolidin-2-ylmethyl)-amino]-[1,3,5]triazin-2-ylamino}-2-methoxy-benzoic acid |
| C134 | 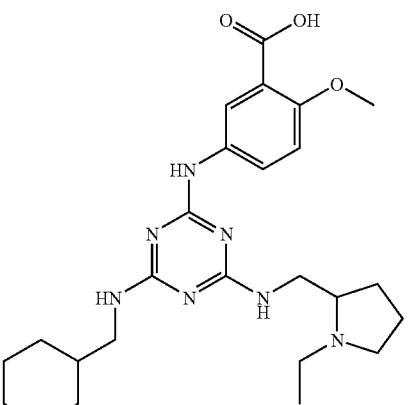 | Sodium; 5-{4-(cyclohexylmethyl-amino)-6-[(1-ethyl-pyrrolidin-2-ylmethyl)-amino]-[1,3,5]triazin-2-ylamino}-2-methoxy-benzoate |

TABLE 1C-continued

Representative Compounds of the Present Invention

| Cmpd No. | Structure | Name |
|---|---|---|
| C135 | 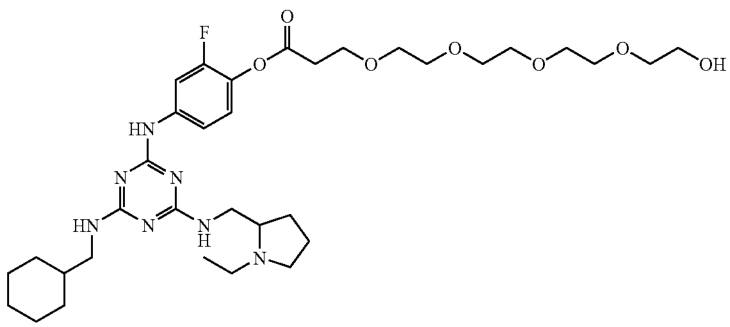 | 3-(2-{2-[2-(2-Hydroxy-ethoxy]-ethoxy}-ethoxy)-propionic acid 4-{4-(cyclohexylmethyl-amino)-6-[(1-ethyl-pyrrolidin-2-ylmethyl)-amino]-[1,3,5]triazin-2-ylamino}-2-fluoro-phenyl ester |
| C136 | 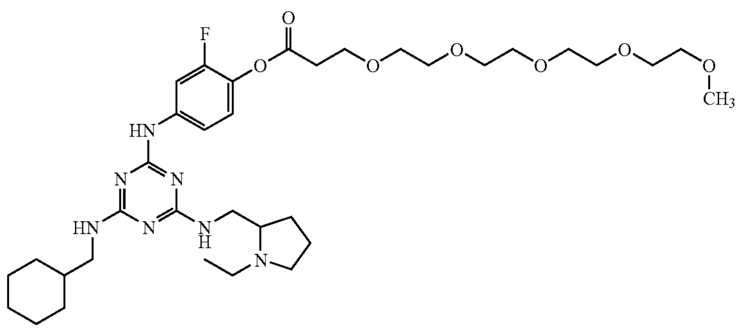 | 3-(2-{2-[2-(2-Methoxy-ethoxy]-ethoxy}-ethoxy)-propionic acid 4-{4-(cyclohexylmethyl-amino)-6-[(1-ethyl-pyrrolidin-2-ylmethyl)-amino]-[1,3,5]triazin-2-ylamino}-2-fluoro-phenyl ester |
| C137 | 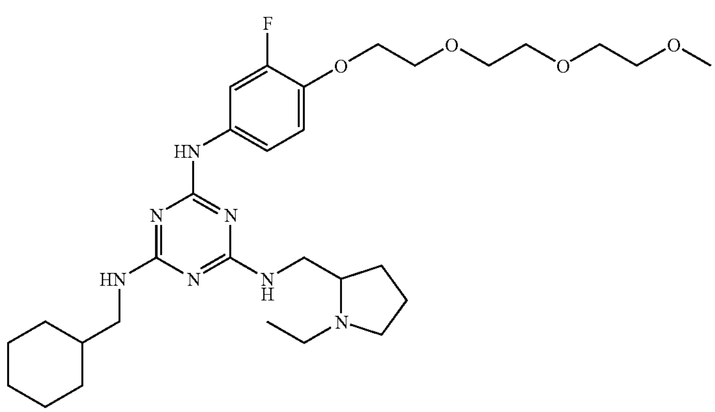 | N-Cyclohexylmethyl-N'-(1-ethyl-pyrrolidin-2-ylmethyl)-N''-(3-fluoro-4-{2-[2-(2-methoxy-ethoxy)-ethoxy]-ethoxy}-phenyl)-[1,3,5]triazine-2,4,6-triamine |
| C138 | 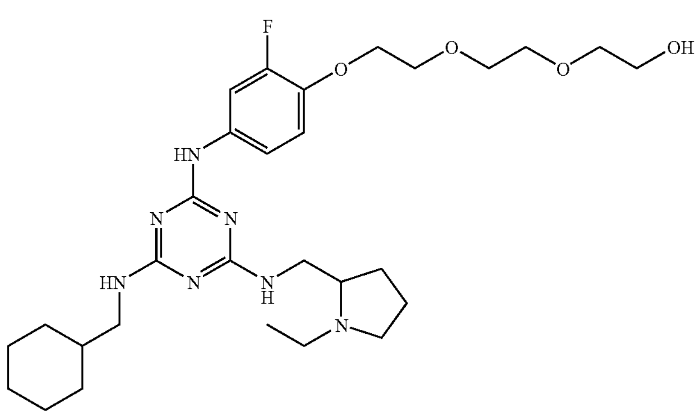 | 2-{2-[2-(4-{4-(Cyclohexylmethyl-amino)-6-[(1-ethyl-pyrrolidin-2-ylmethyl)-amino]-[1,3,5]-triazin-2-ylamino}-2-fluoro-phenoxy)-ethoxy]-ethoxy}-ethanol |

TABLE 1C-continued

Representative Compounds of the Present Invention

| Cmpd No. | Structure | Name |
|---|---|---|
| C139 | 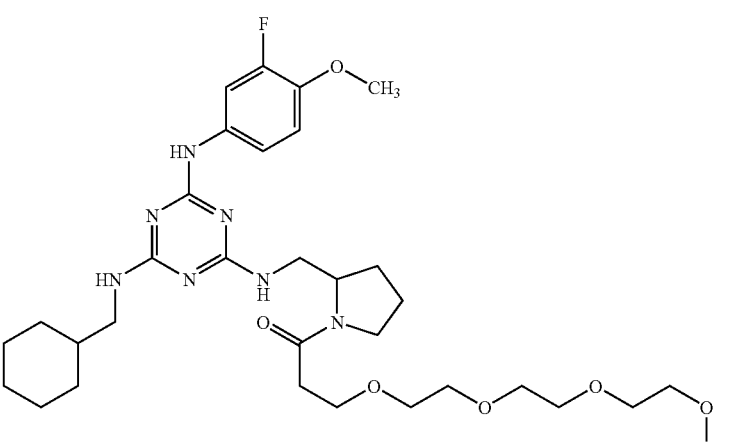 | 1-(2-{[4-(Cyclohexylmethyl-amino)-6-(3-fluoro-4-methoxy-phenylamino)-[1,3,5]triazin-2-ylamino]-methyl}-pyrrolidin-1-yl)-3-{2-[2-(2-methoxy-ethoxy)-ethoxy]-ethoxy}-propan-1-one |
| C140 | 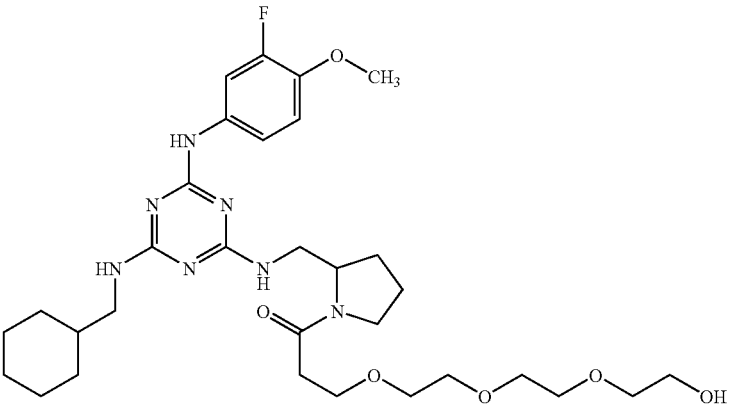 | 1-(2-{[4-(Cyclohexylmethyl-amino)-6-(3-fluoro-4-methoxy-phenylamino)-[1,3,5]triazin-2-ylamino]-methyl}-pyrrolidin-1-yl)-3-{2-[2-(2-hydroxy-ethoxy)-ethoxy]-ethoxy}-propan-1-one |
| C141 | 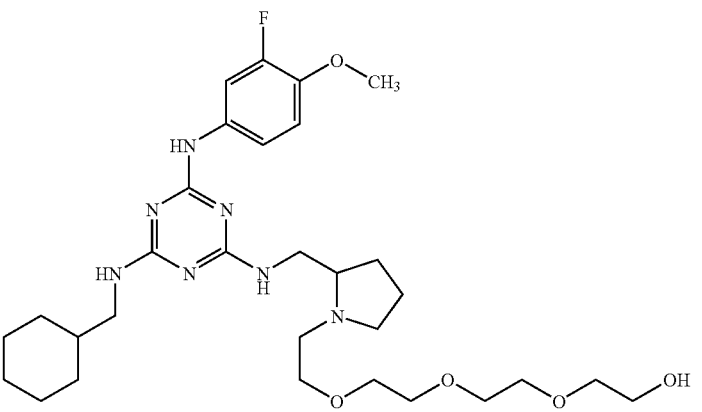 | 2-(2-{2-[2-(2-{[4-(Cyclohexylmethyl-amino)-6-(3-fluoro-4-methoxy-phenylamino)-[1,3,5]triazin-2-ylamino]-methyl}-pyrrolidin-1-yl)-ethoxy]-ethoxy}-ethoxy)-ethanol |

TABLE 1C-continued

Representative Compounds of the Present Invention

| Cmpd No. | Structure | Name |
|---|---|---|
| C142 | 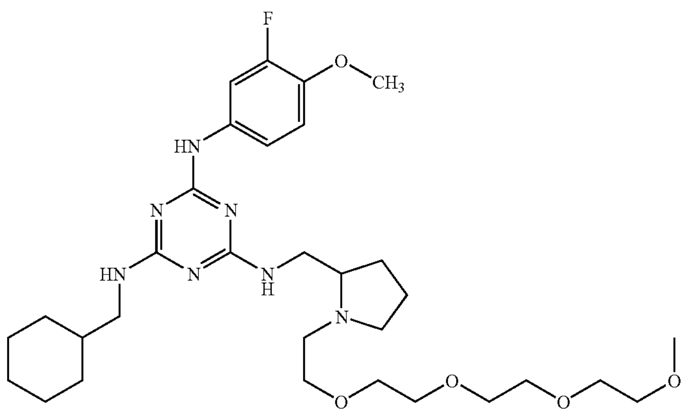 | N-Cyclohexylmethyl-N'-(3-fluoro-4-methoxy-phenyl)-N''-[1-(2-{2-[2-(2-methoxy-ethoxy)-ethoxy]-ethoxy}-ethyl)-pyrrolidin-2-ylmethyl]-[1,3,5]triazine-2,4,6-triamine |
| C143 | 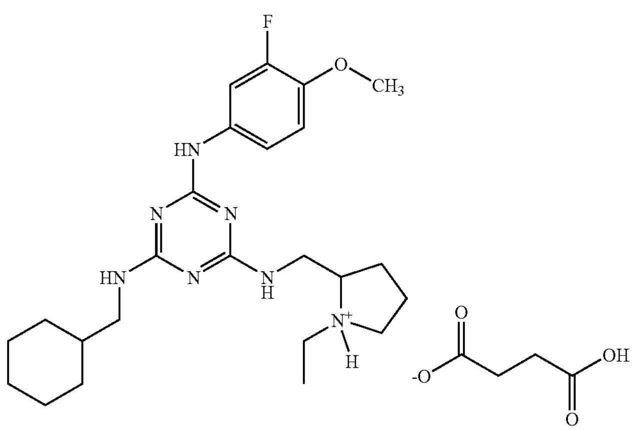 | 3-Carboxy-propionate2-{[4-(cyclo-hexylmethyl-amino)-6-(3-fluoro-4-methoxy-phenylamino)-[1,3,5]-triazin-2-ylamino]-methyl}-1-ethyl-pyrrolidinium; |
| C144 | 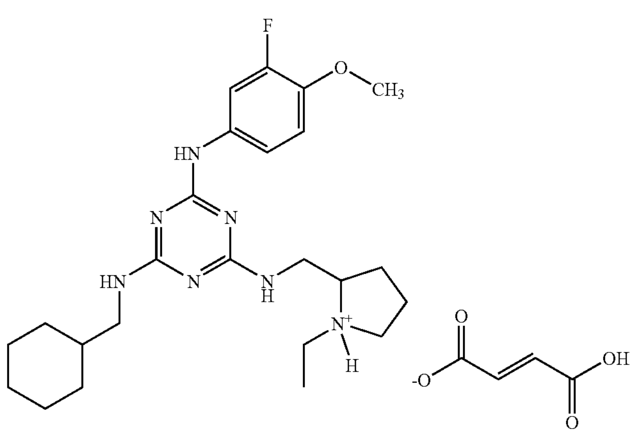 | 3-Carboxy-acrylate2-{[4-(cyclo-hexylmethyl-amino)-6-(3-fluoro-4-methoxy-phenylamino)-[1,3,5]-triazin-2-ylamino]-methyl}-1-ethyl-pyrrolidinium; |

TABLE 1C-continued

Representative Compounds of the Present Invention

| Cmpd No. | Structure | Name |
|---|---|---|
| C145 | 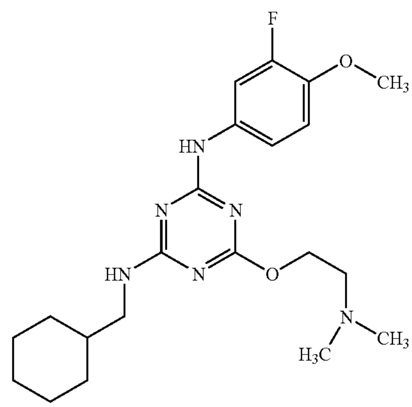 | N-Cyclohexylmethyl-6-(2-dimethyl-amino-ethoxy)-N'-(3-fluoro-4-methoxy-phenyl)-[1,3,5]triazine-2,4-diamine |
| C146 | 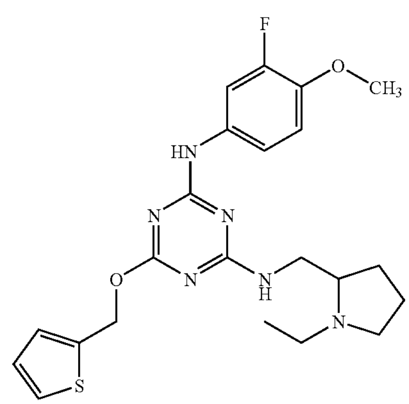 | N-(1-Ethyl-pyrrolidin-2-ylmethyl)-N'-(3-fluoro-4-methoxy-phenyl)-6-(thiophen-2-ylmethoxy)-[1,3,5]-triazine-2,4-diamine |
| C147 | 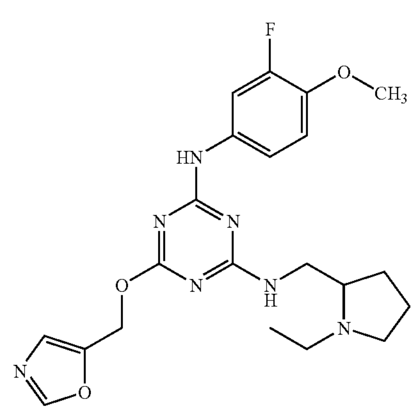 | N-(1-Ethyl-pyrrolidin-2-ylmethyl)-N'-(3-fluoro-4-methoxy-phenyl)-6-(oxazol-5-ylmethoxy)-[1,3,5]-triazine-2,4-diamine |

TABLE 1C-continued
Representative Compounds of the Present Invention
| Cmpd No. | Structure | Name |
|---|---|---|
| C148 | 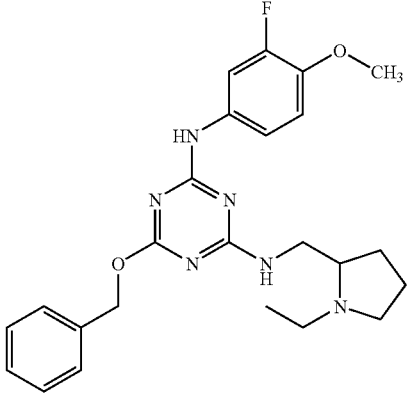 | 6-Benzyloxy-N-(1-ethyl-pyrrolidin-2-ylmethyl)-N'-(3-fluoro-4-methoxy-phenyl)-[1,3,5]triazine-2,4-diamine |
| C149 | 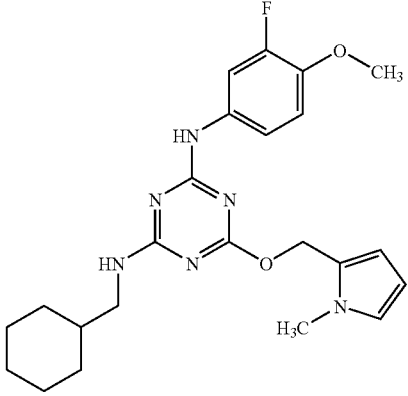 | N-Cyclohexylmethyl-N'-(3-fluoro-4-methoxy-phenyl)-6-(1-methyl-1H-pyrrol-2-ylmethoxy)-[1,3,5]-triazine-2,4-diamine |
| C150 | 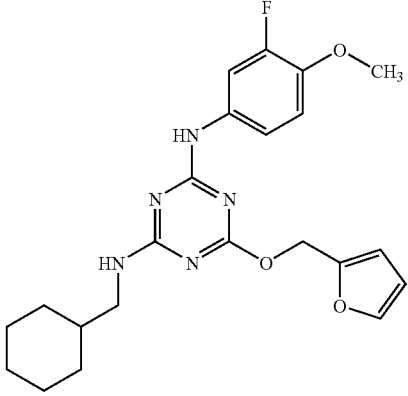 | N-Cyclohexylmethyl-N'-(3-fluoro-4-methoxy-phenyl)-6-(furan-2-ylmethoxy)-[1,3,5]triazine-2,4-diamine |

TABLE 1C-continued

Representative Compounds of the Present Invention

| Cmpd No. | Structure | Name |
|---|---|---|
| C151 | 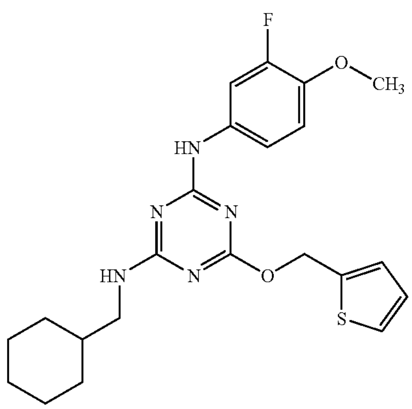 | N-Cyclohexylmethyl-N'-(3-fluoro-4-methoxy-phenyl)-6-(thiophen-2-ylmethoxy)-[1,3,5]-triazine-2,4-diamine |
| C152 | 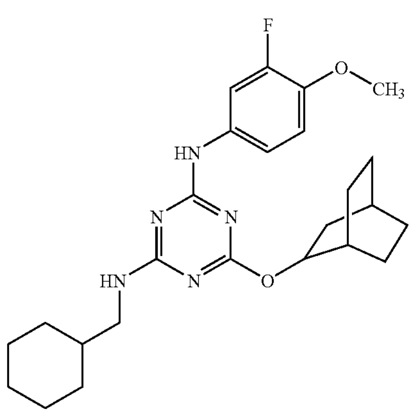 | 6-(Bicycio[2.2.2]oct-2-yloxy)-N-cyclohexylmethyl-N'-(3-fluoro-4-methoxy-phenyl)-[1,3,5]-triazine-2,4-diamine |
| C153 | 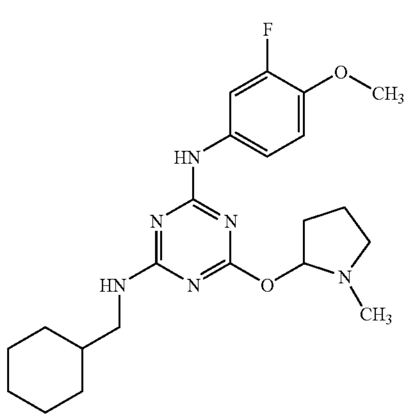 | N-Cyclohexylmethyl-N'-(3-fluoro-4-methoxy-phenyl)-6-(1-methyl-pyrrolidin-2-yloxy)-[1,3,5]-triazine-2,4-diamine |

TABLE 1C-continued

Representative Compounds of the Present Invention

| Cmpd No. | Structure | Name |
|---|---|---|
| C154 | 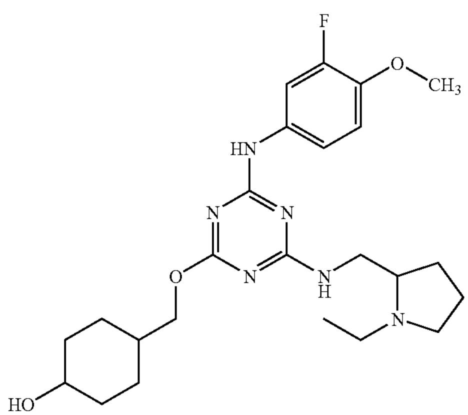 | 4-[4-[(1-Ethyl-pyrrolidin-2-ylmethyl)-amino]-6-(3-fluoro-4-methoxy-phenylamino)-[1,3,5]-triazin-2-yloxymethyl]-cyclohexanol |
| C155 | 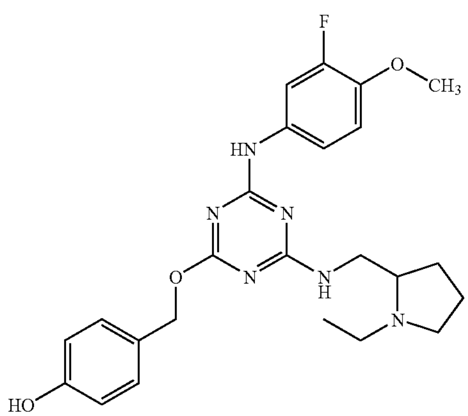 | 4-[4-[(1-Ethyl-pyrrolidin-2-ylmethyl)-amino]-6-(3-fluoro-4-methoxy-phenylamino)-[1,3,5]-triazin-2-yloxymethyl]-phenol |
| C156 | 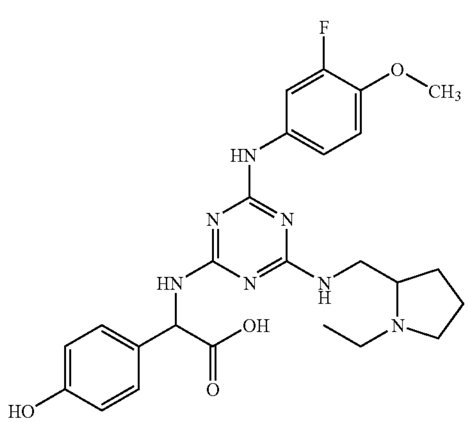 | [4-[(1-Ethyl-pyrrolidin-2-ylmethyl)-amino]-6-(3-fluoro-4-methoxy-phenylamino)-[1,3,5]triazin-2-ylamino]-(4-hydroxy-phenyl)-acetic acid |

TABLE 1C-continued

Representative Compounds of the Present Invention

| Cmpd No. | Structure | Name |
|---|---|---|
| C157 | 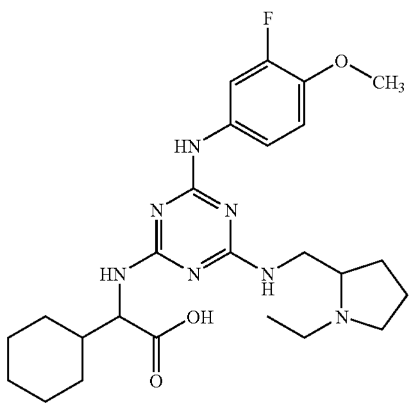 | Cyclohexyl-[4-[(1-ethyl-pyrrolidin-2-ylmethyl)-amino]-6-(3-fluoro-4-methoxy-phenylamino)-[1,3,5]-triazin-2-ylamino]-acetic acid |
| C158 | 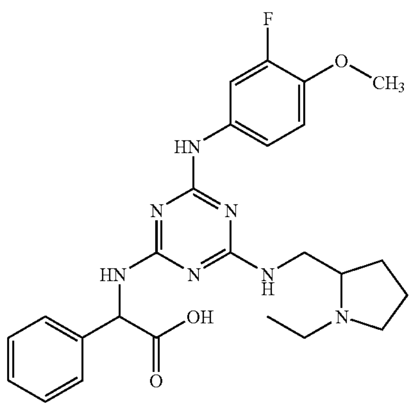 | [4-[(1-Ethyl-pyrrolidin-2-ylmethyl)-amino]-6-(3-fluoro-4-methoxy-phenylamino)-[1,3,5]triazin-2-ylamino]-phenyl-acetic acid |
| C159 | 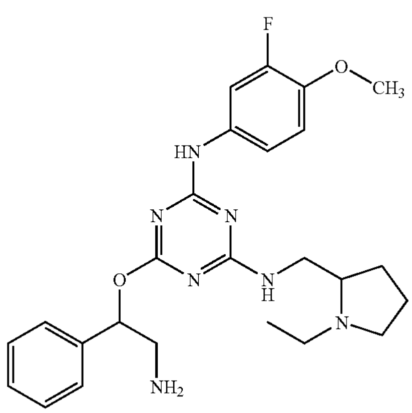 | 6-(2-Amino-1-phenyl-ethoxy)-N-(1-ethyl-pyrrolidin-2-ylmethyl)-N'-(3-fluoro-4-methoxy-phenyl)-[1,3,5]-triazine-2,4-diamine |

TABLE 1C-continued

Representative Compounds of the Present Invention

| Cmpd No. | Structure | Name |
|---|---|---|
| C160 | 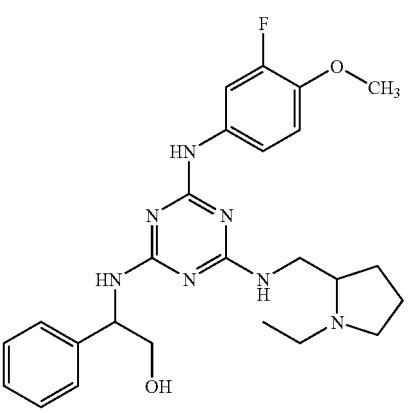 | 2-[4-[(1-Ethyl-pyrrolidin-2-ylmethyl)-amino]-6-(3-fluoro-4-methoxy-phenylamino)-[1,3,5]-triazin-2-ylamino]-2-phenyl-ethanol |
| C161 | 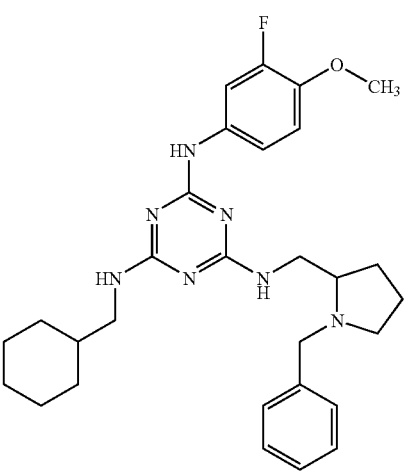 | N-(1-Benzyl-pyrrolidin-2-ylmethyl)-N'-cyclohexylmethyl-N''-(3-fluoro-4-methoxy-phenyl)-[1,3,5]-triazine-2,4,6-triamine |
| C162 | 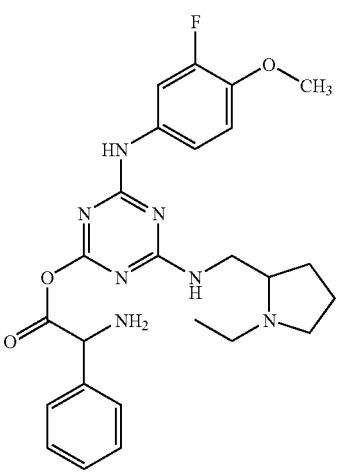 | Amino-phenyl-acetic acid 4-[(1-ethyl-pyrrolidin-2-ylmethyl)-amino]-6-(3-fluoro-4-methoxy-phenylamino)-[1,3,5]triazin-2-yl ester |

TABLE 1C-continued
Representative Compounds of the Present Invention
| Cmpd No. | Structure | Name |
|---|---|---|
| C163 | 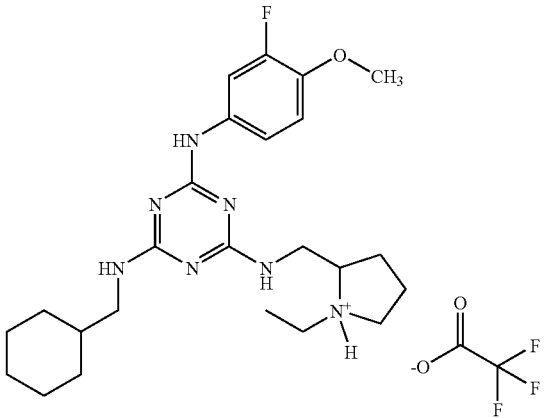 | Trifluoro-acetate2-{[4-(cyclo-hexylmethyl-amino)-6-(3-fluoro-4-methoxy-phenylamino)-[1,3,5]-triazin-2-ylamino]-methyl}-1-ethyl-pyrrolidinium; |
| C164 | 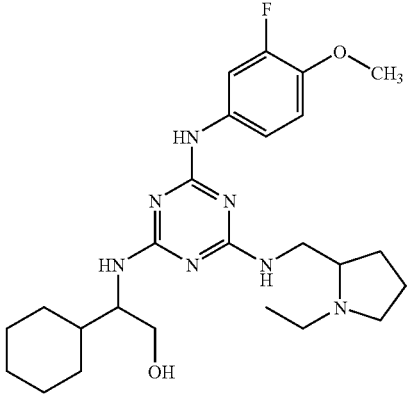 | 2-Cyclohexyl-2-[4-[(1-ethyl-pyrrolidin-2-ylmethyl)-amino]-6-(3-fluoro-4-methoxy-phenylamino)-[1,3,5]-triazin-2-ylaminol-ethanol |

TABLE 2

Representative compounds of the present invention prepared by parallel synthesis reactions, including amine monomers, products, and characterization data

| Cmpd No. | R1(Monomer 1) | R2(Monomer 2) | R3(Monomer 3) | Product(Structure) |
|---|---|---|---|---|
| 1 | 4-bromo-1-naphthylamine | cycloheptylamine | 1-ethyl-2-(aminomethyl)pyrrolidine | triazine product with 4-bromonaphthyl, cycloheptyl, and (1-ethylpyrrolidin-2-yl)methyl substituents |
| 2 | 4-chloro-1-naphthylamine | cycloheptylamine | 1-ethyl-2-(aminomethyl)pyrrolidine | triazine product with 4-chloronaphthyl, cycloheptyl, and (1-ethylpyrrolidin-2-yl)methyl substituents |

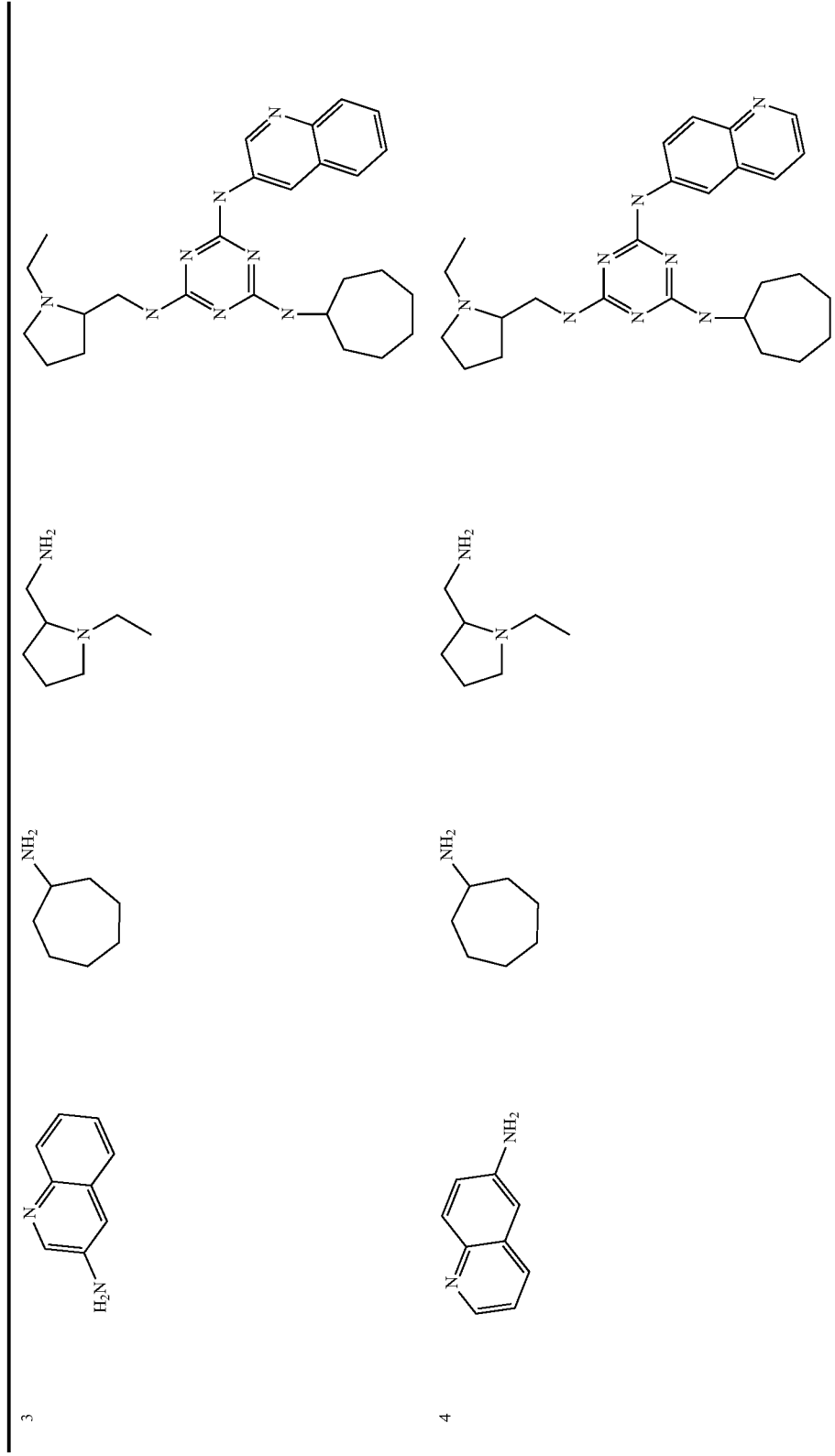

TABLE 2-continued
Representative compounds of the present invention prepared by parallel synthesis reactions, including amine monomers, products, and characterization data
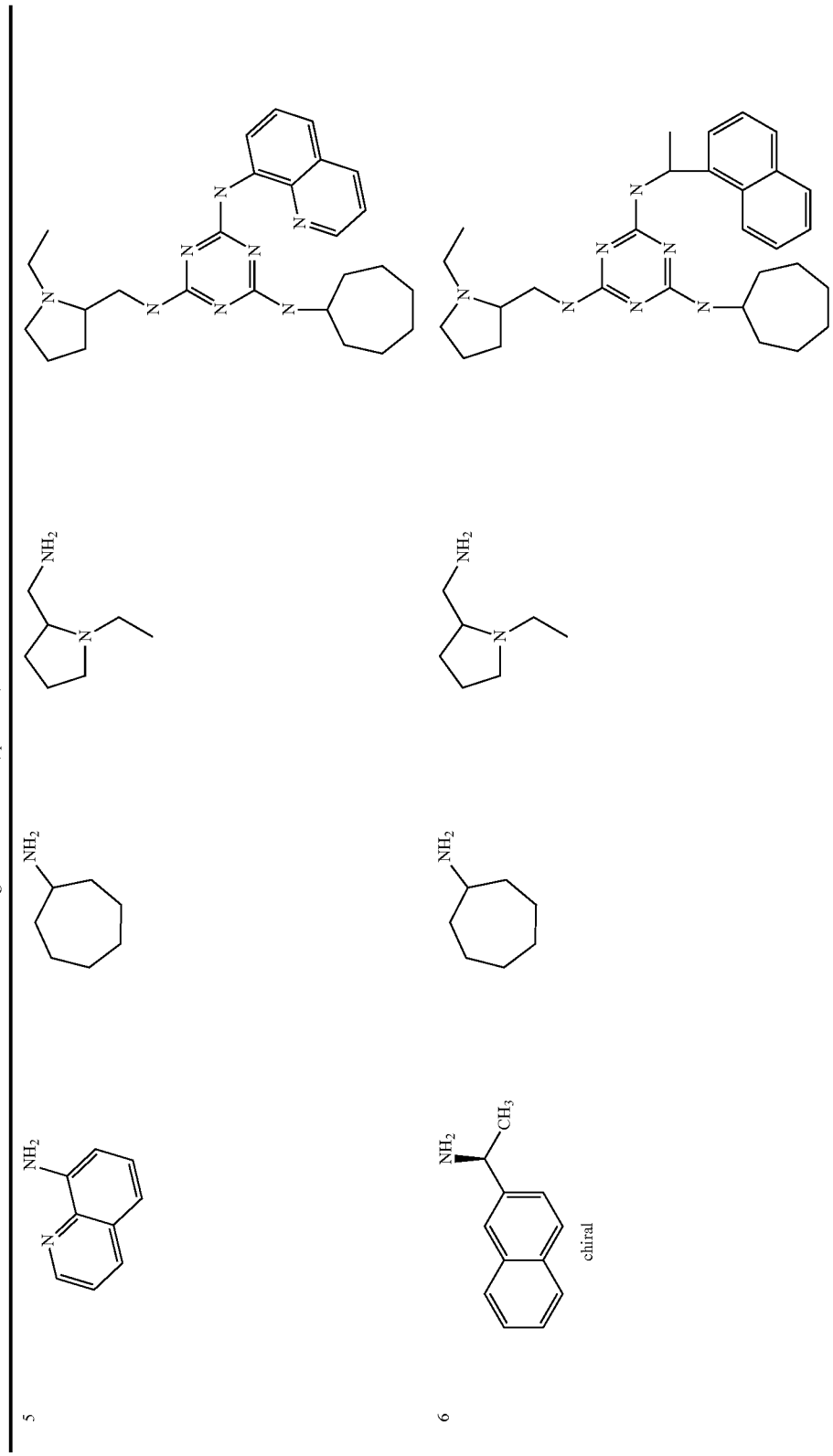

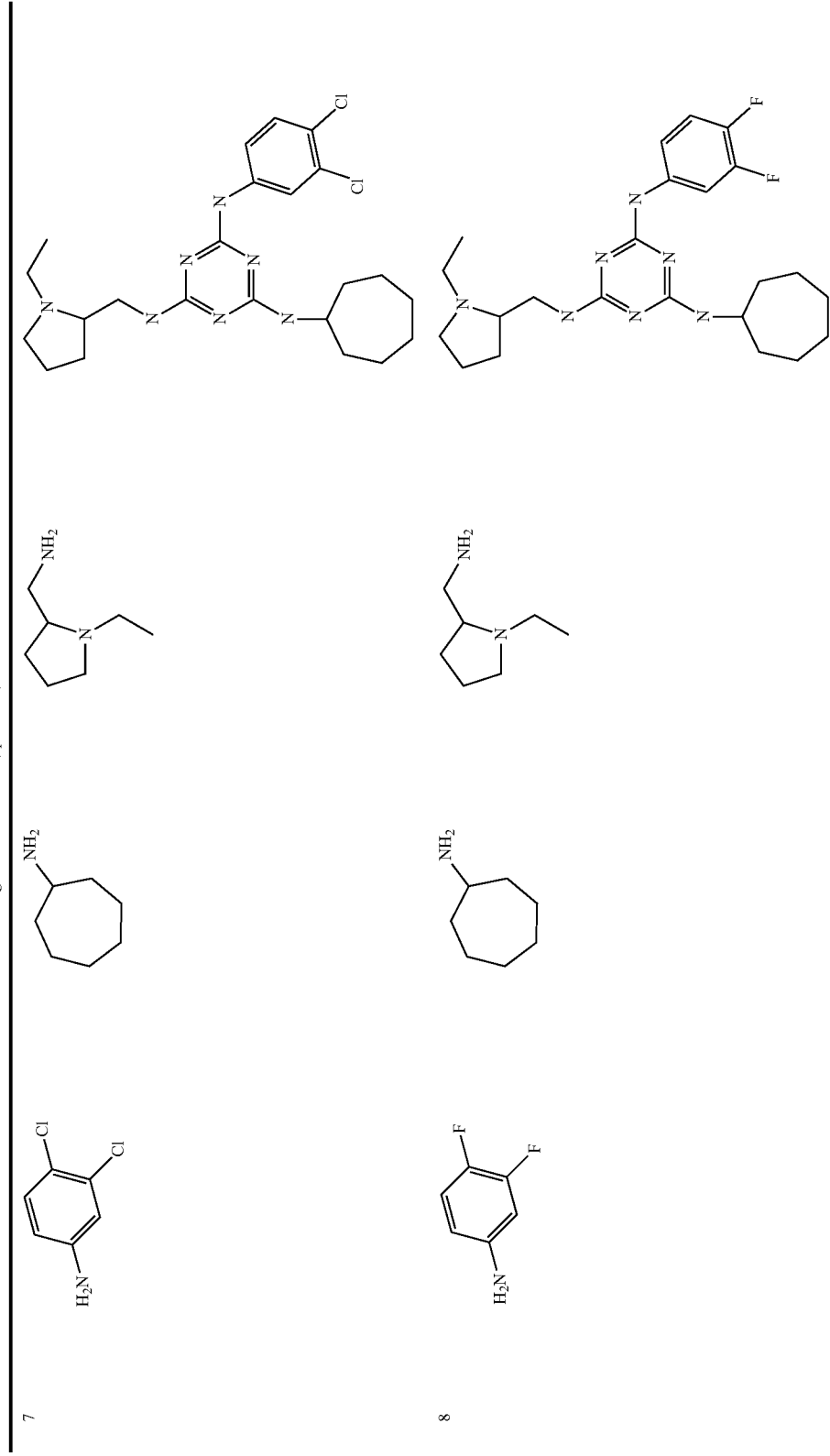

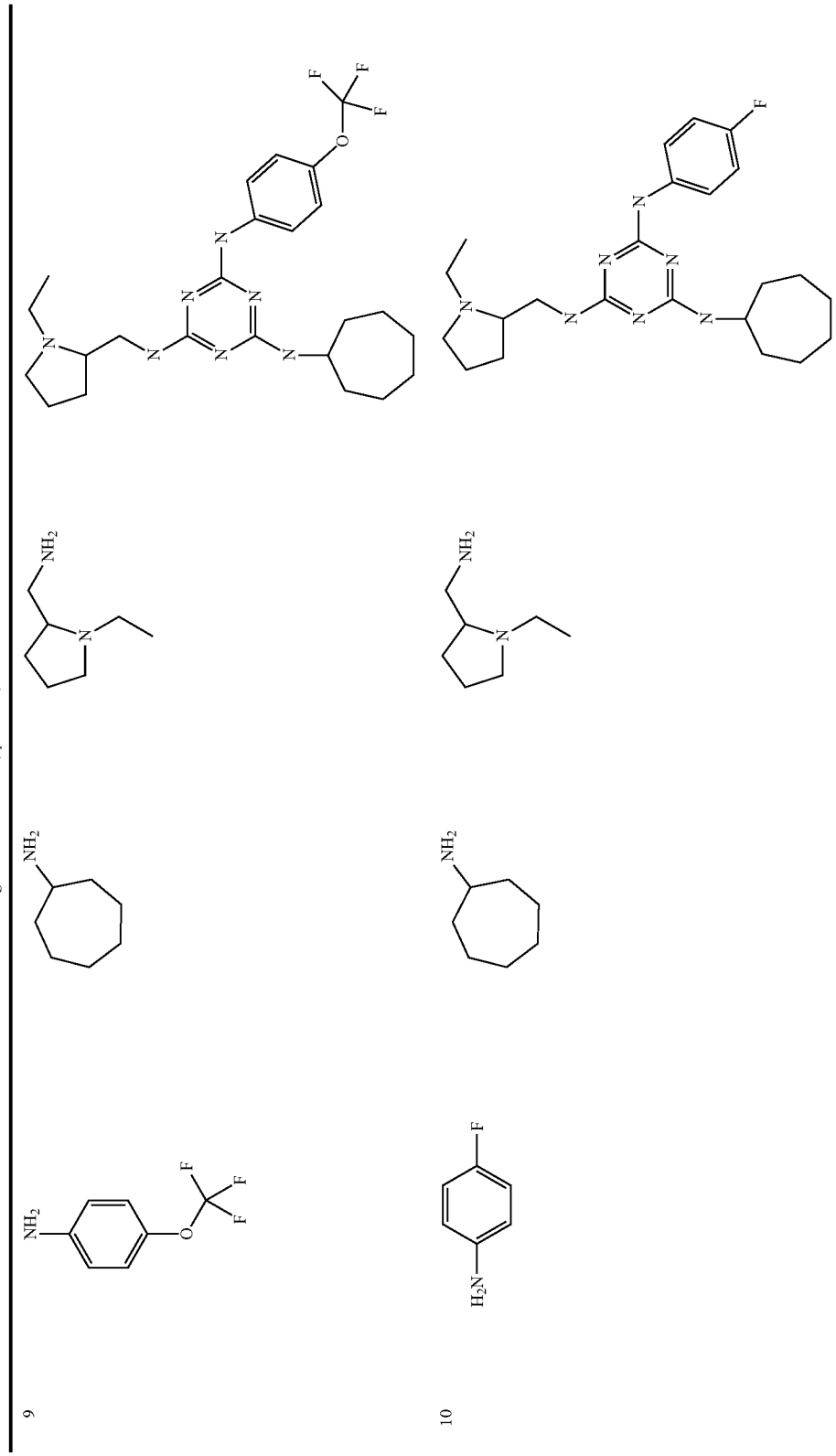

TABLE 2-continued
Representative compounds of the present invention prepared by parallel synthesis reactions, including amine monomers, products, and characterization data
| | | | |
|---|---|---|---|
| 11 | 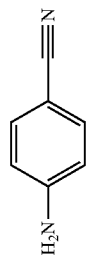 | 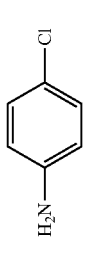 | 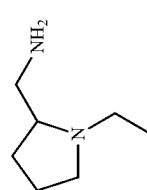 |
| 12 | 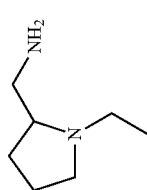 | 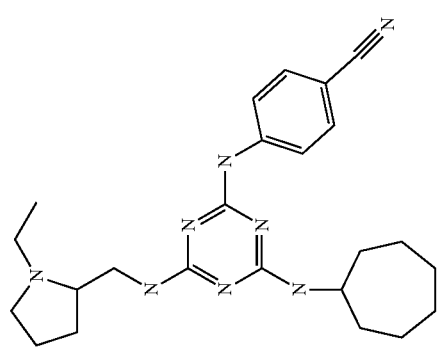 | 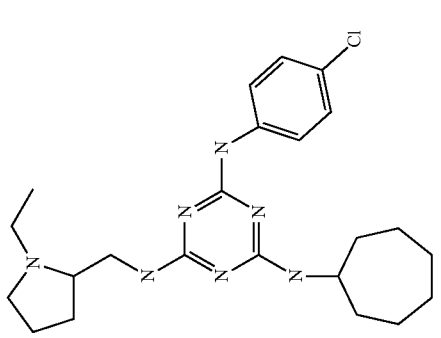 |

TABLE 2-continued

Representative compounds of the present invention prepared by parallel synthesis reactions, including amine monomers, products, and characterization data

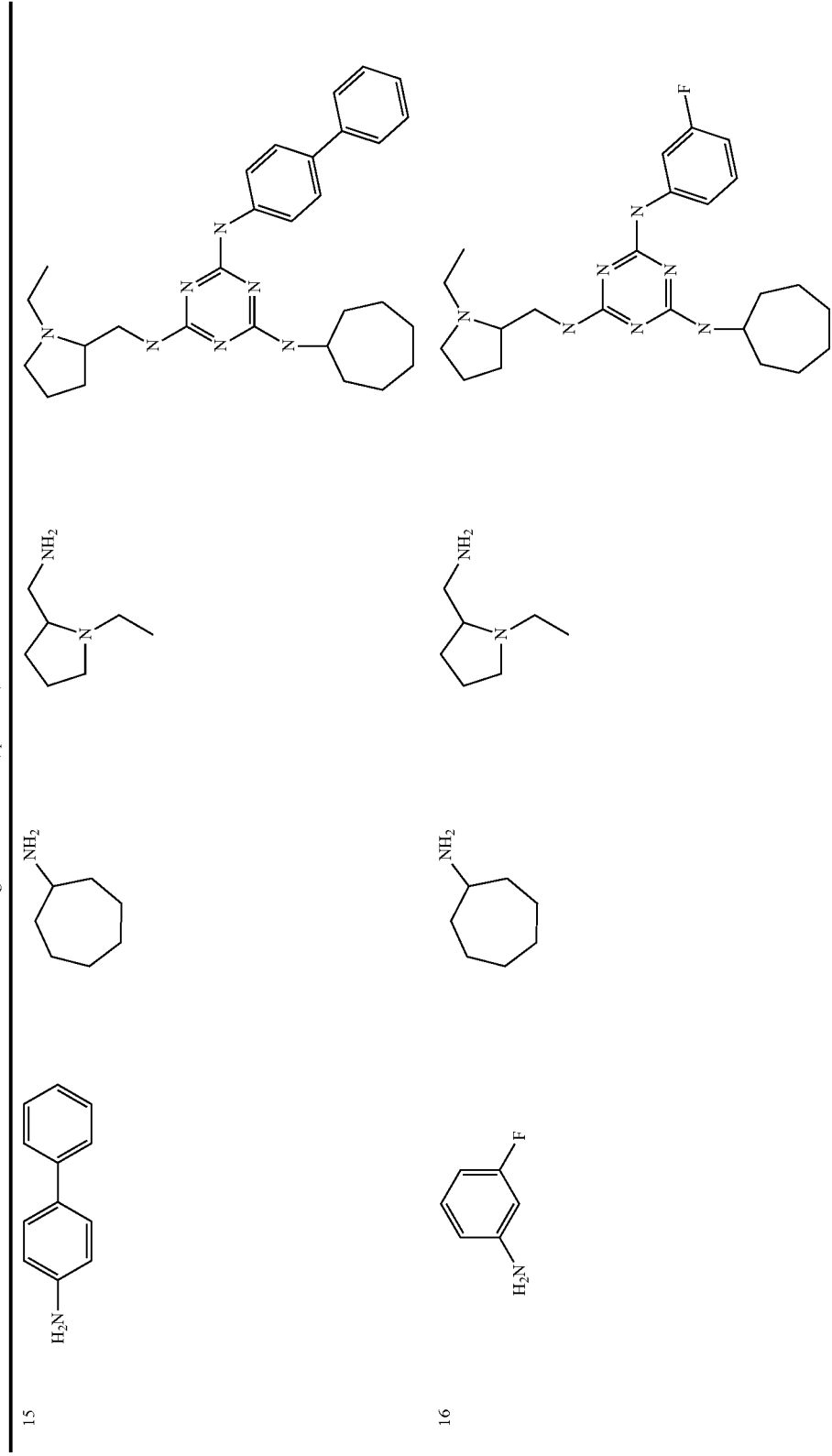

TABLE 2-continued
Representative compounds of the present invention prepared by parallel synthesis reactions, including amine monomers, products, and characterization data
| 17 | 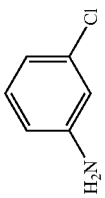 | 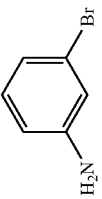 | 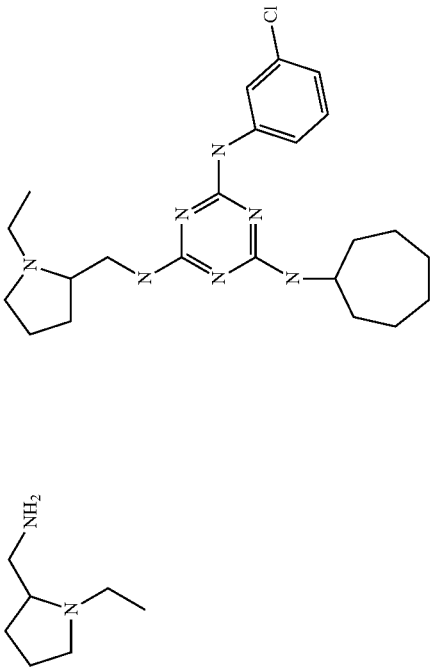 |
| --- | --- | --- | --- |
| 18 | | | 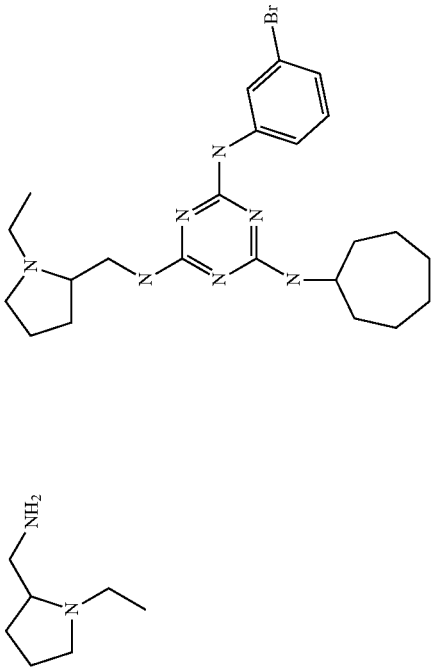 |

TABLE 2-continued
Representative compounds of the present invention prepared by parallel synthesis reactions, including amine monomers, products, and characterization data
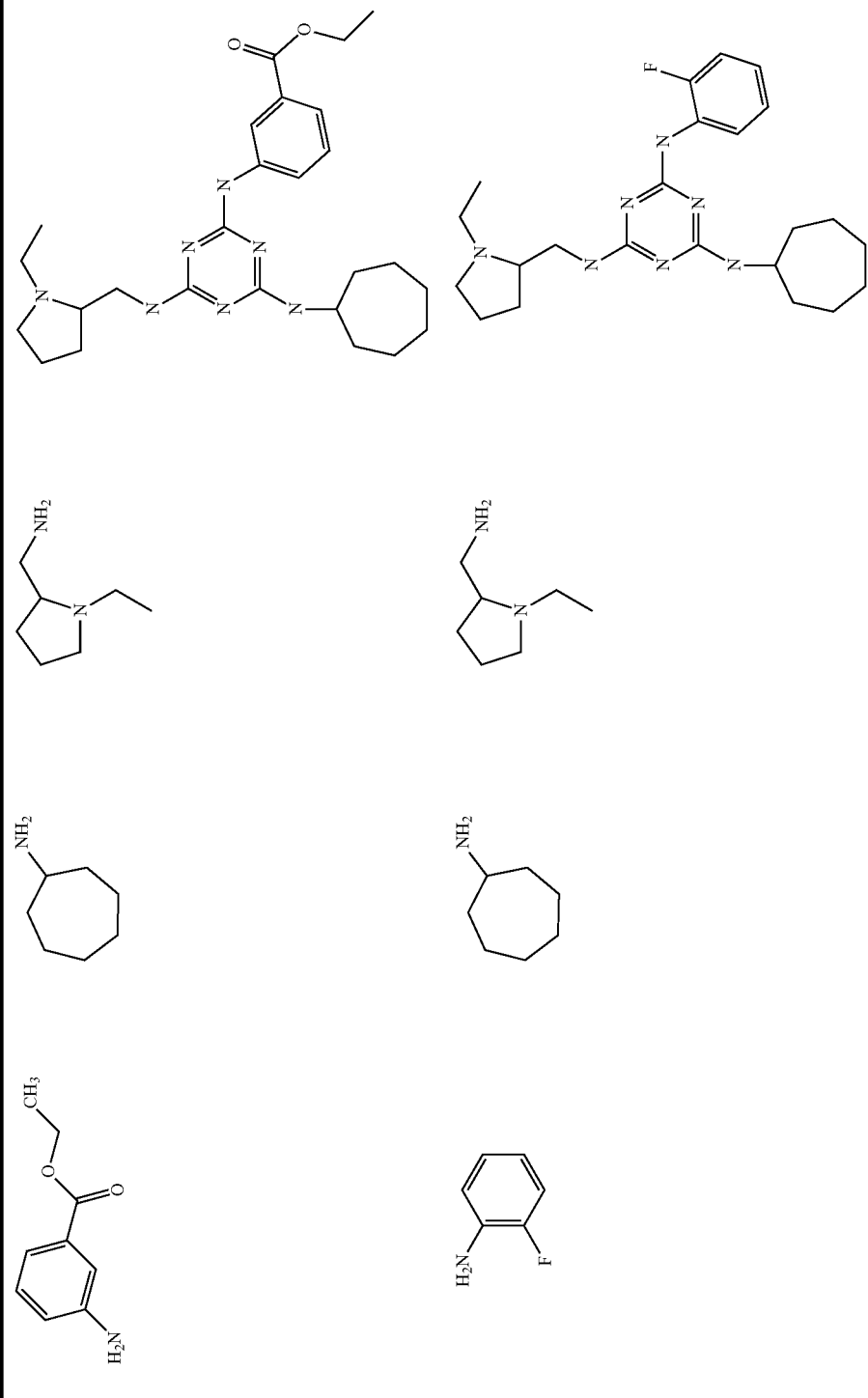

TABLE 2-continued
Representative compounds of the present invention prepared by parallel synthesis reactions, including amine monomers, products, and characterization data
| 21 | 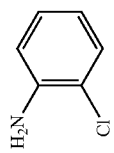 | 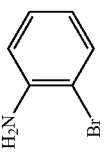 | 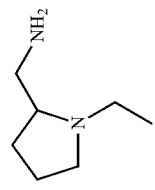 |
| 22 | 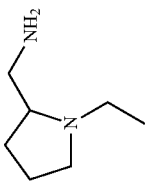 | 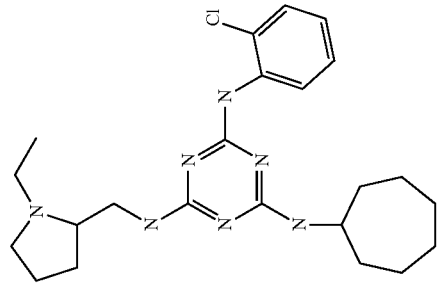 | 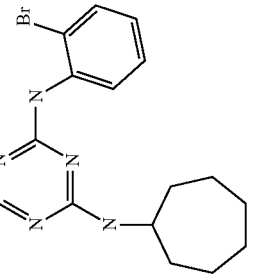 |

TABLE 2-continued
Representative compounds of the present invention prepared by parallel synthesis reactions, including amine monomers, products, and characterization data
| | | | | |
|---|---|---|---|---|
| 23 | 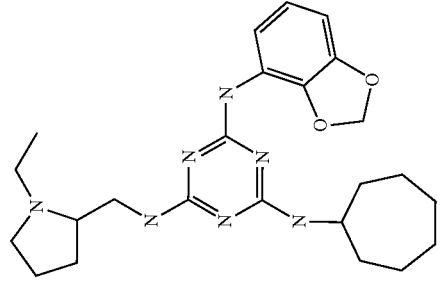 | 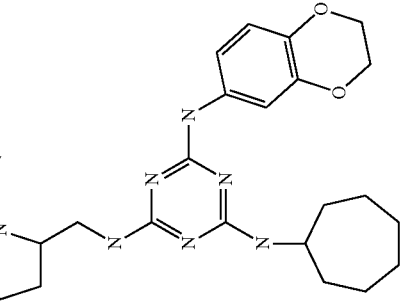 | 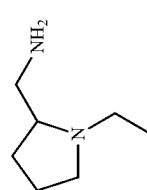 | 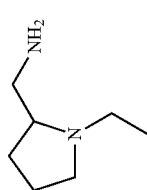 |
| 24 | 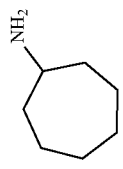 | 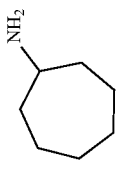 | 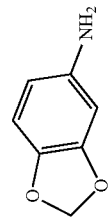 | 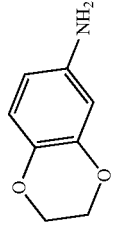 |

TABLE 2-continued

Representative compounds of the present invention prepared by parallel synthesis reactions, including amine monomers, products, and characterization data

| 25 | | | |
| 26 | | | | .HCl

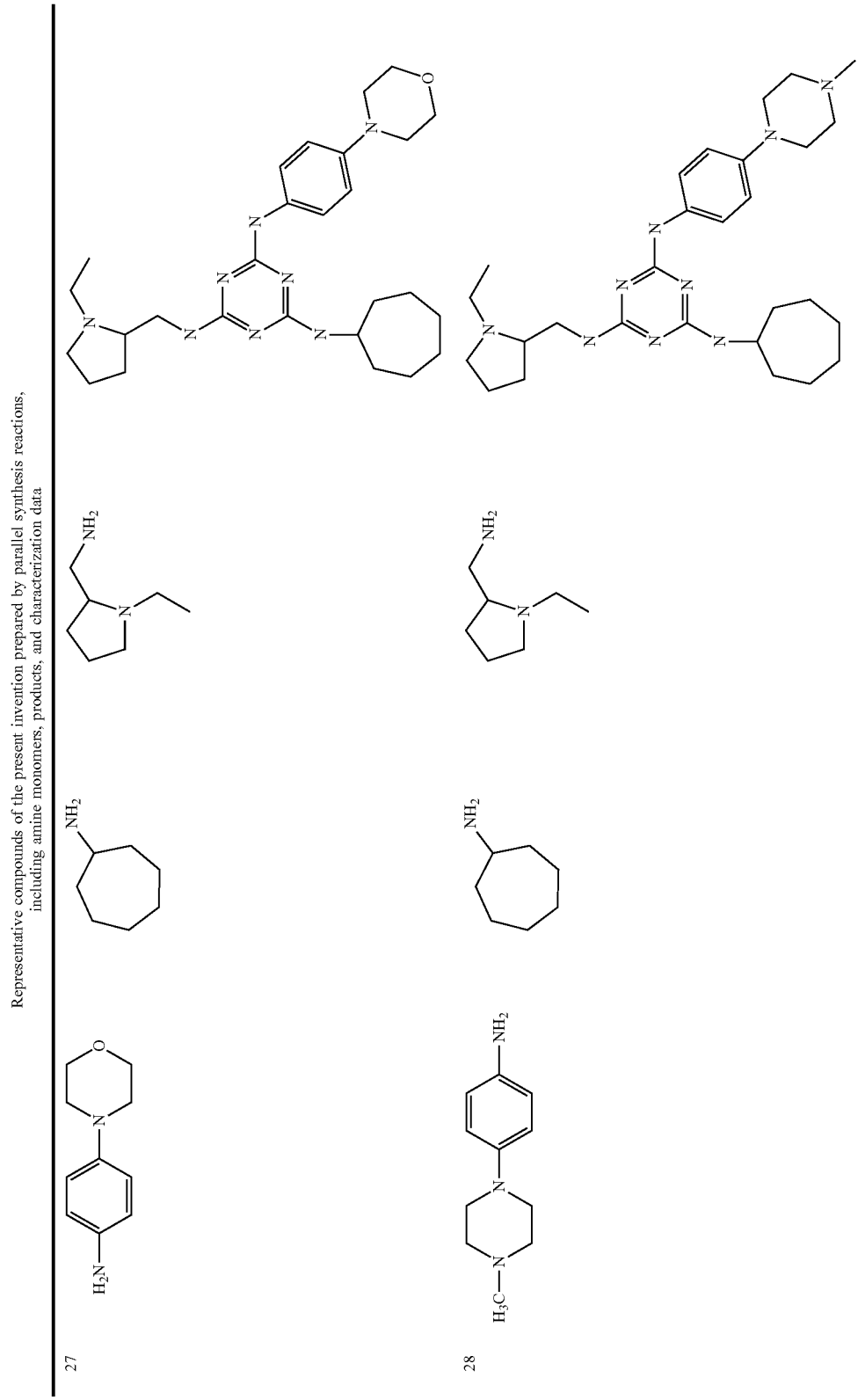

TABLE 2-continued

Representative compounds of the present invention prepared by parallel synthesis reactions, including amine monomers, products, and characterization data TABLE 2-continued
Representative compounds of the present invention prepared by parallel synthesis reactions, including amine monomers, products, and characterization data
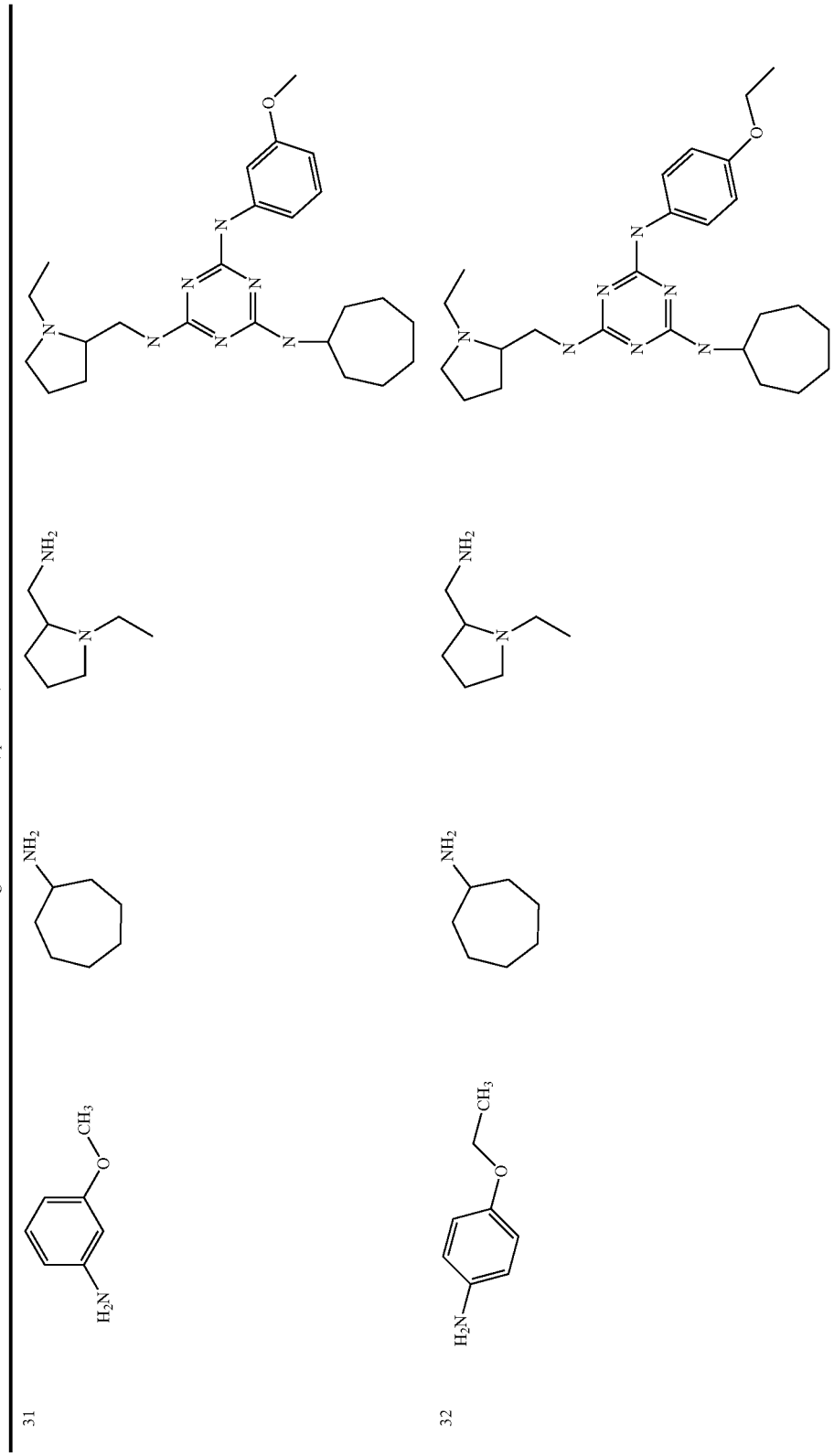

TABLE 2-continued
Representative compounds of the present invention prepared by parallel synthesis reactions, including amine monomers, products, and characterization data
| | | | |
|---|---|---|---|
| 33 | 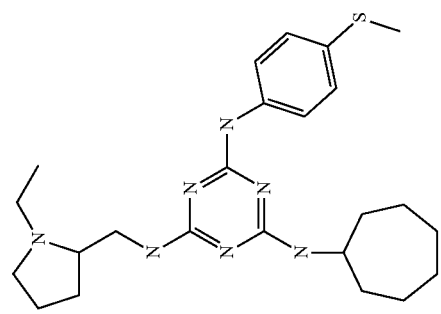 | 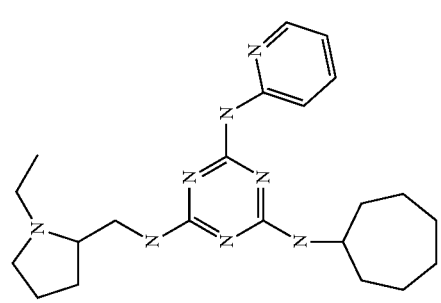 | 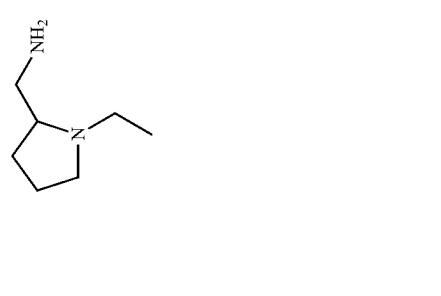 |
| 34 | 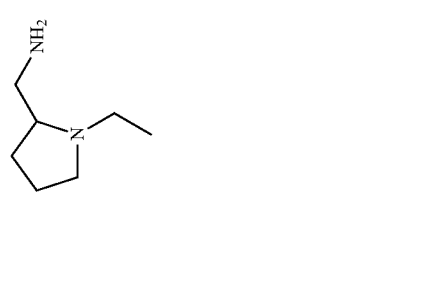 | | |

TABLE 2-continued
Representative compounds of the present invention prepared by parallel synthesis reactions, including amine monomers, products, and characterization data
| | | | |
|---|---|---|---|
| 35 | 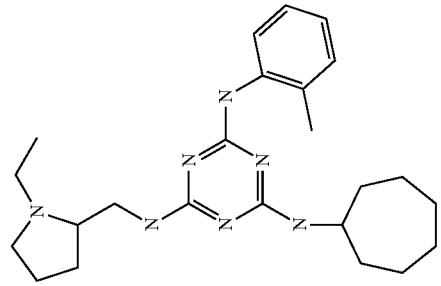 | 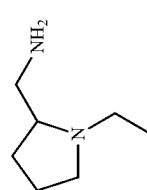 | |
| 36 | | | |

TABLE 2-continued
Representative compounds of the present invention prepared by parallel synthesis reactions, including amine monomers, products, and characterization data
| | | | |
|---|---|---|---|
| 37 | 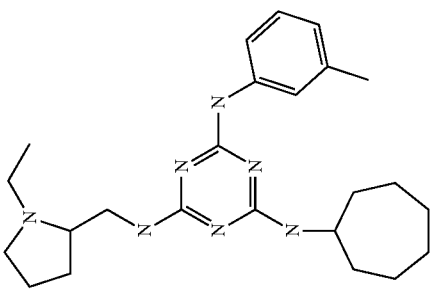 | 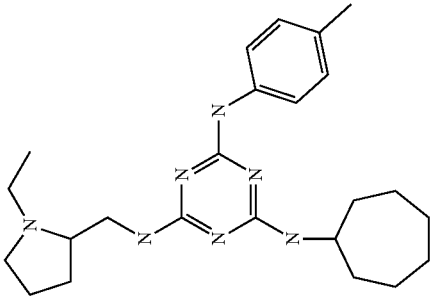 | 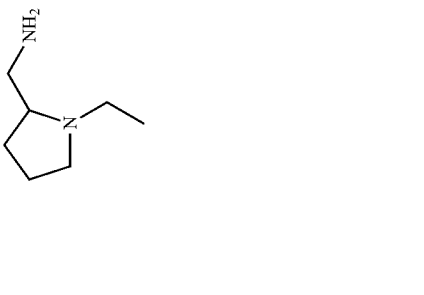 |
| 38 | 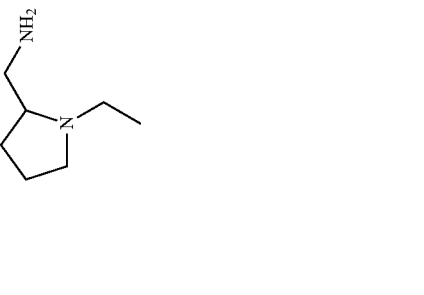 | 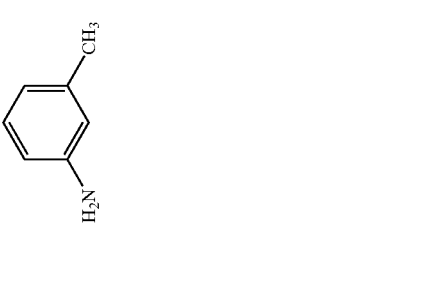 | 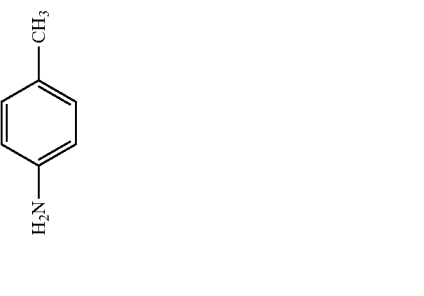 |

TABLE 2-continued
Representative compounds of the present invention prepared by parallel synthesis reactions, including amine monomers, products, and characterization data
| 39 | 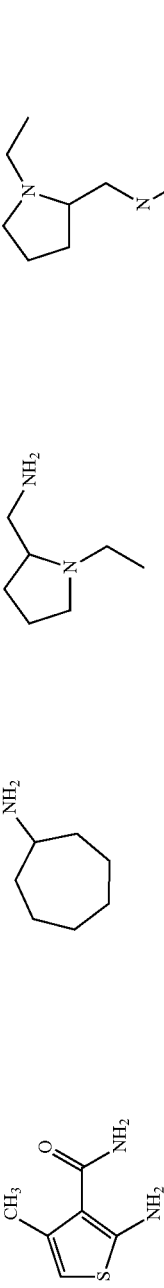 | 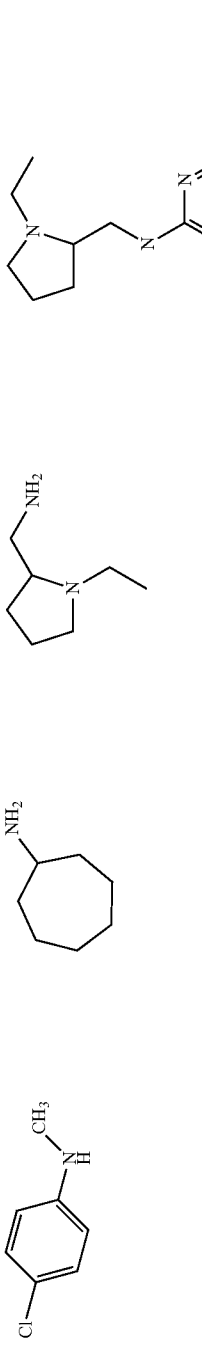 | 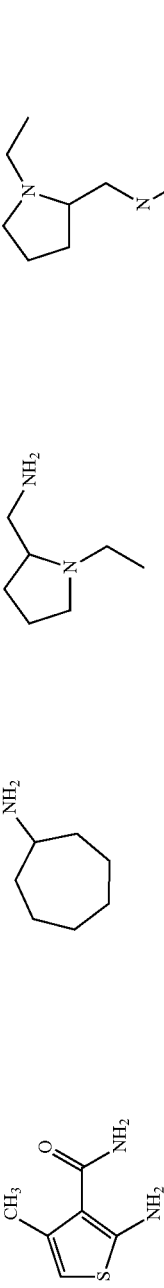 | 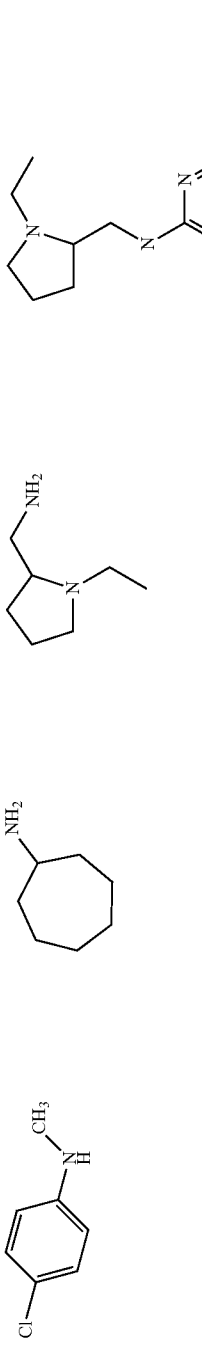 |
| 40 | 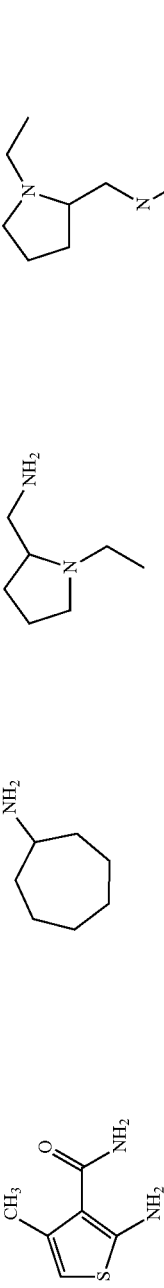 | 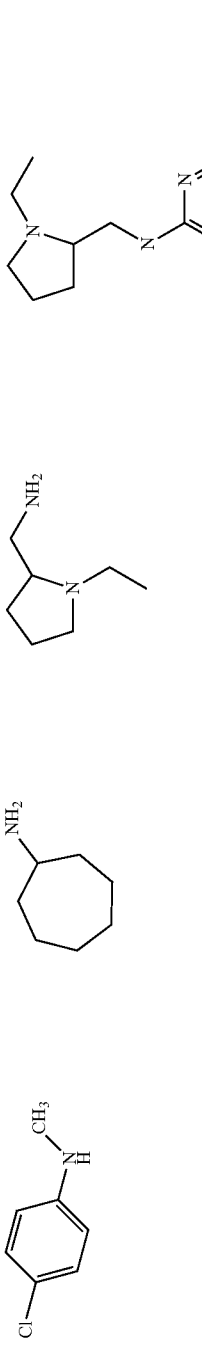 | 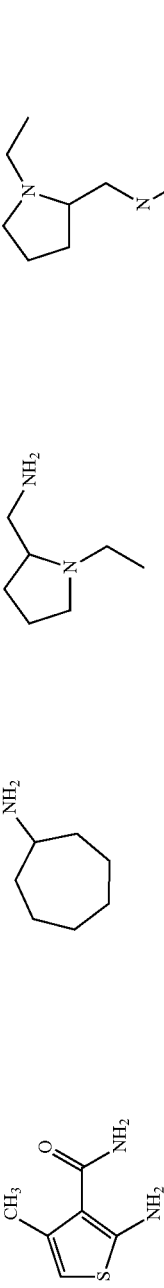 | 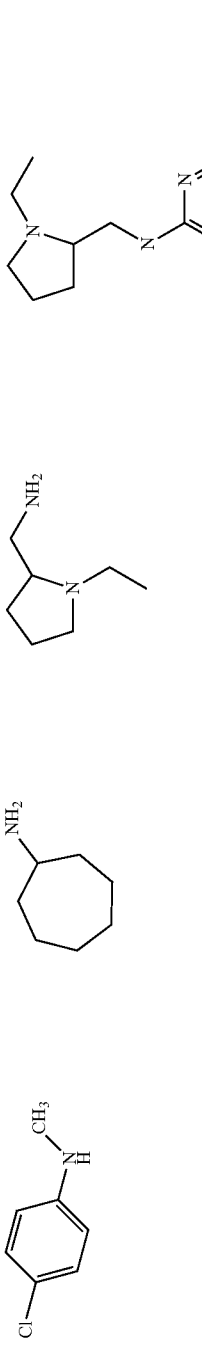 |

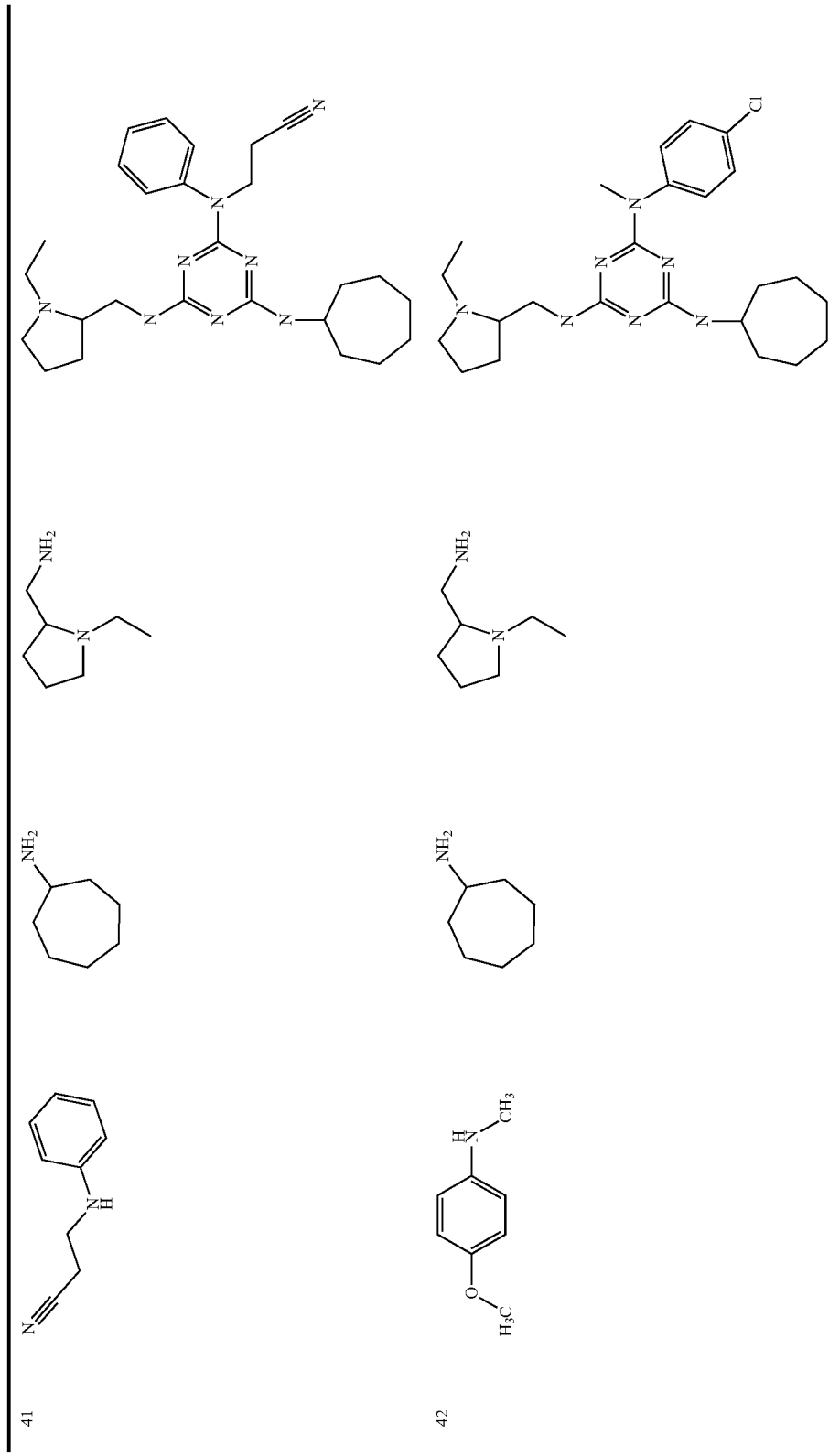

TABLE 2-continued
Representative compounds of the present invention prepared by parallel synthesis reactions, including amine monomers, products, and characterization data
| 43 | 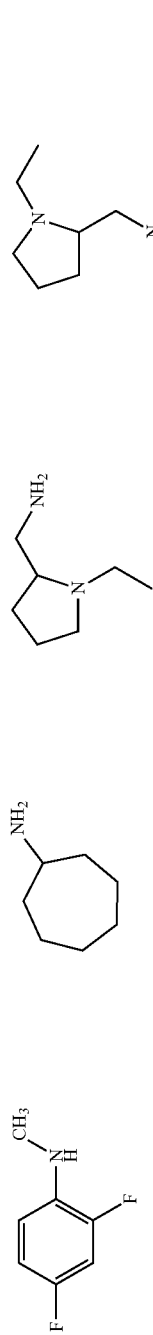 |  | 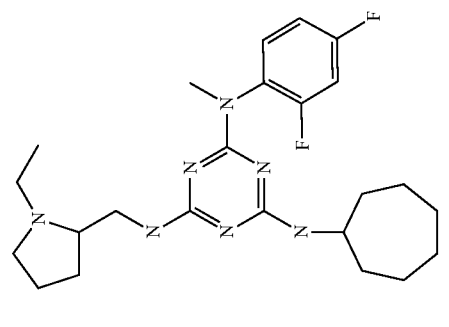 |
| 44 | 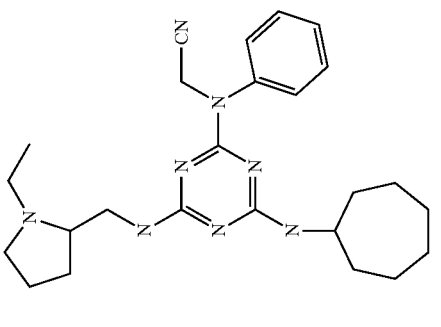 | | |

TABLE 2-continued
Representative compounds of the present invention prepared by parallel synthesis reactions, including amine monomers, products, and characterization data
| 45 | 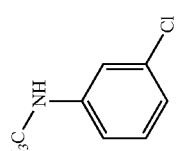 | 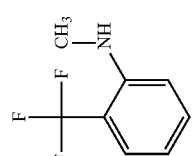 | 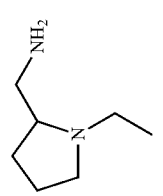 |
| 46 | 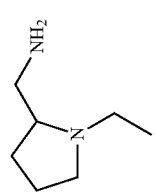 | 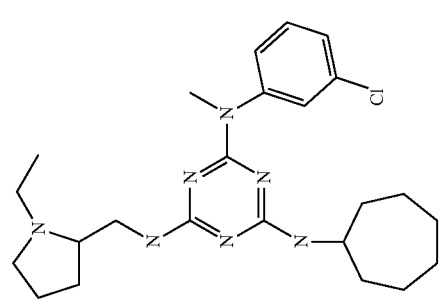 | 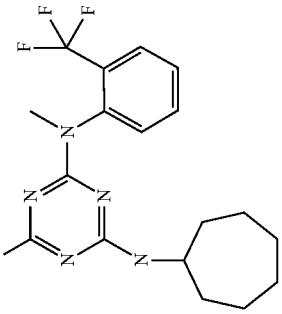 |

TABLE 2-continued
Representative compounds of the present invention prepared by parallel synthesis reactions, including amine monomers, products, and characterization data
| 47 | 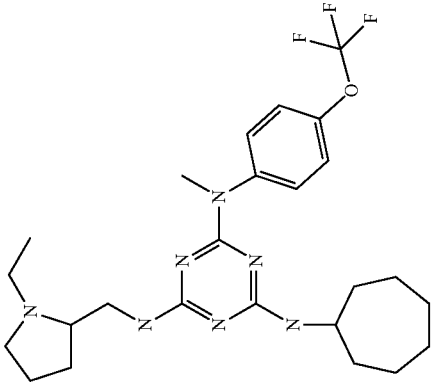 | 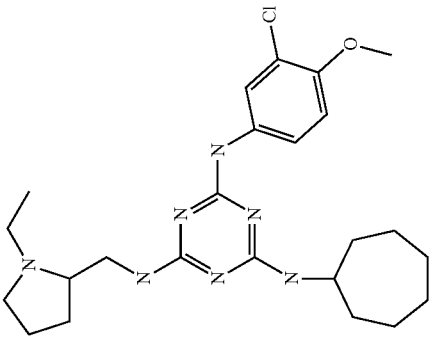 | 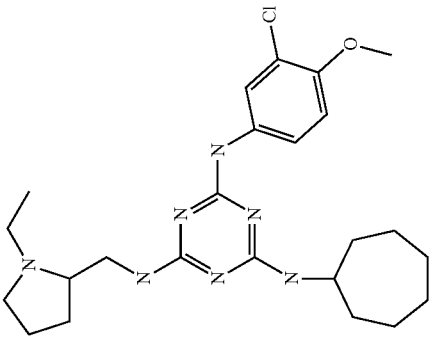 |
| 48 | 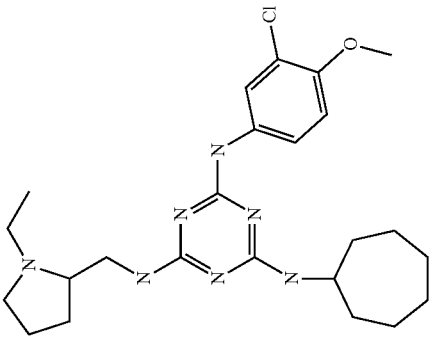 | | |

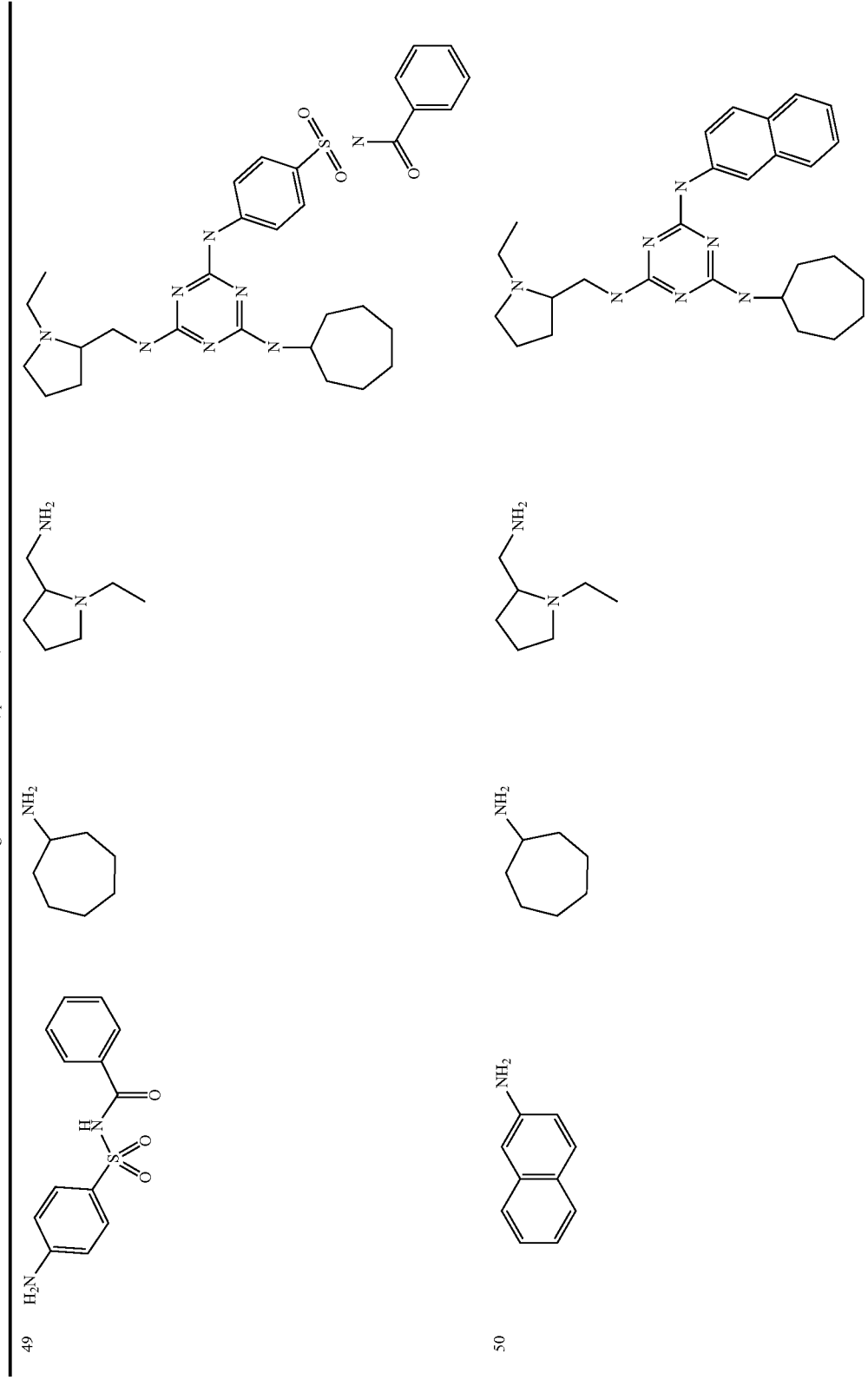

TABLE 2-continued
Representative compounds of the present invention prepared by parallel synthesis reactions, including amine monomers, products, and characterization data
| | | | |
|---|---|---|---|
| 51 | 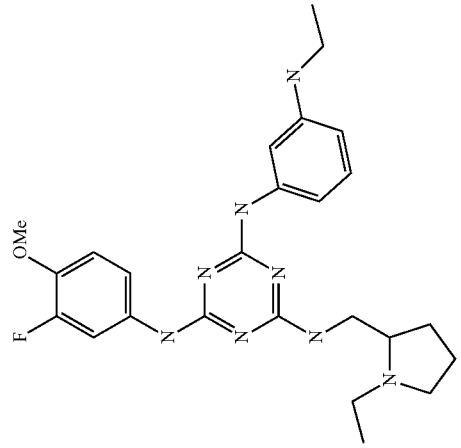 | 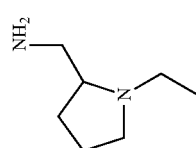 | 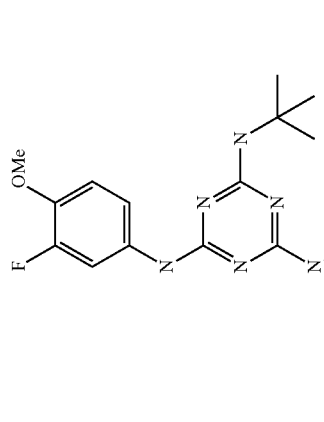 |
| 52 | 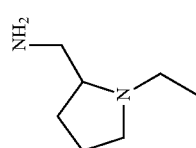 | 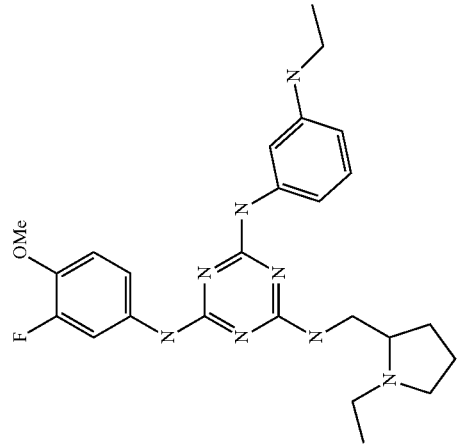 | 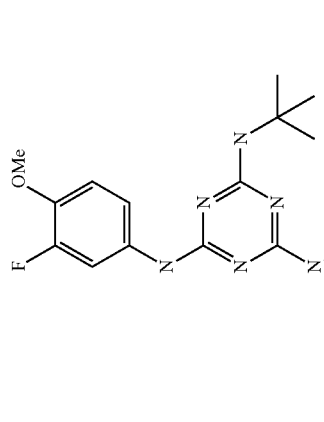 |

TABLE 2-continued
Representative compounds of the present invention prepared by parallel synthesis reactions, including amine monomers, products, and characterization data
| | | | |
|---|---|---|---|
| 53 | 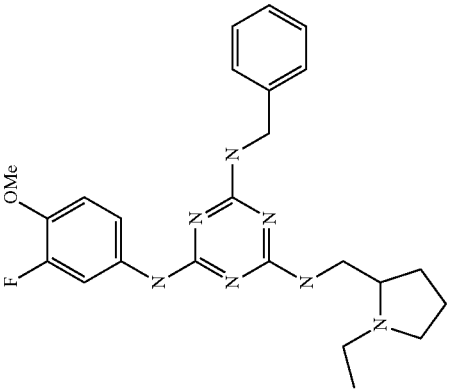 | 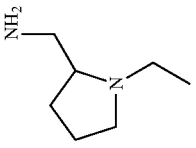 | |
| 54 | | | |

TABLE 2-continued
Representative compounds of the present invention prepared by parallel synthesis reactions, including amine monomers, products, and characterization data
| | | | | |
|---|---|---|---|---|
| 55 | 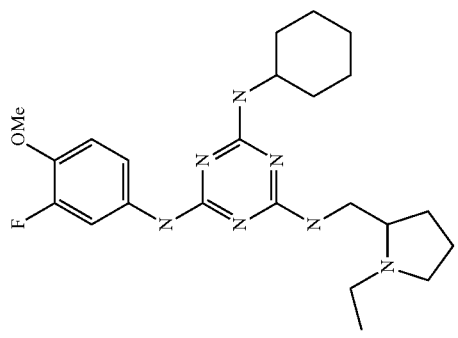 | 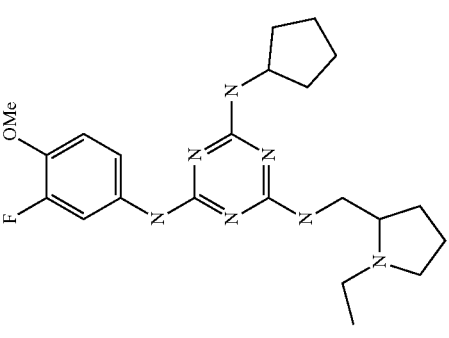 | 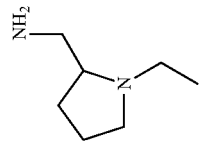 | 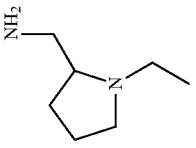 |
| 56 | | | | |

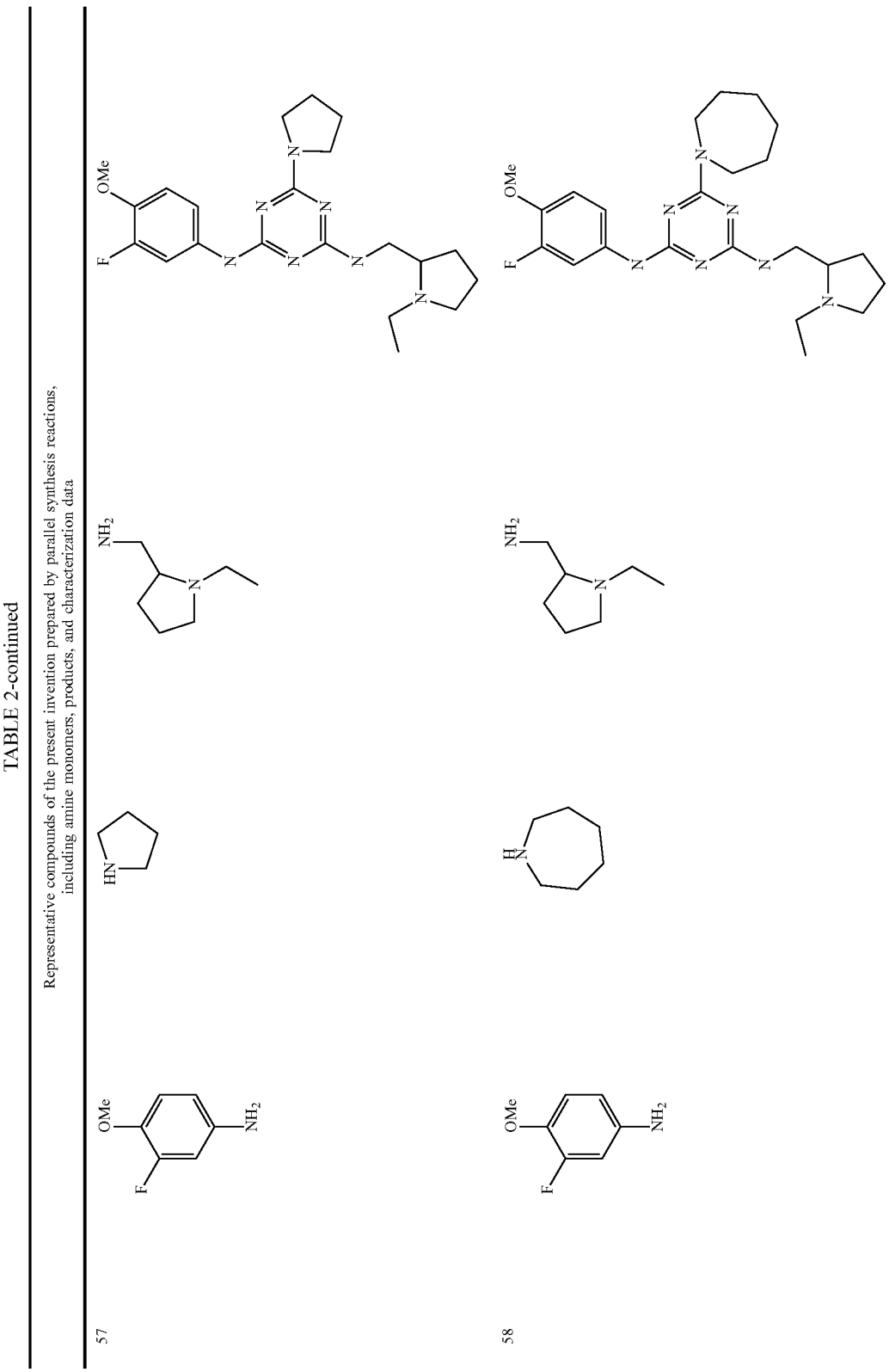

TABLE 2-continued
Representative compounds of the present invention prepared by parallel synthesis reactions, including amine monomers, products, and characterization data
| 59 |  | 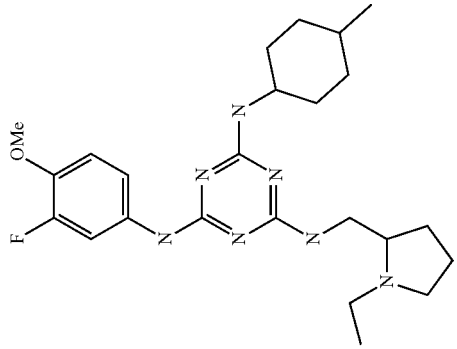 | 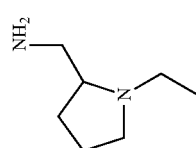 |
| 60 | 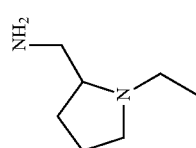 | 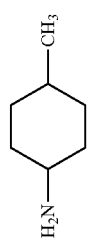 | 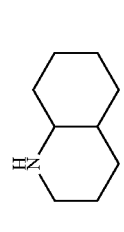 |

TABLE 2-continued

Representative compounds of the present invention prepared by parallel synthesis reactions, including amine monomers, products, and characterization data TABLE 2-continued
Representative compounds of the present invention prepared by parallel synthesis reactions, including amine monomers, products, and characterization data
| 63 | 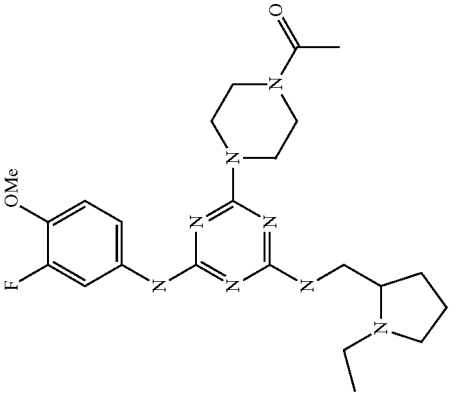 | 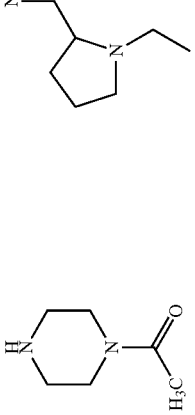 | | |
| 64 | | | | |

TABLE 2-continued
Representative compounds of the present invention prepared by parallel synthesis reactions, including amine monomers, products, and characterization data
| 65 | 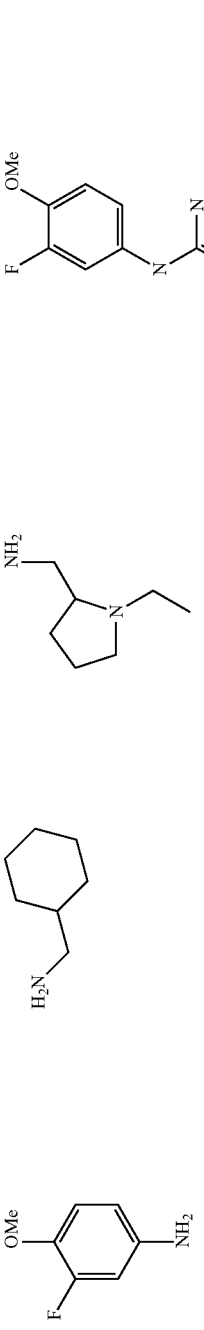 | 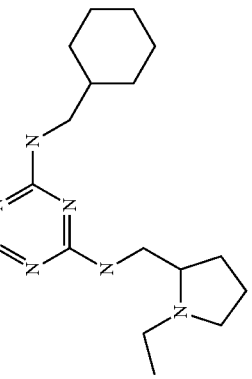 | 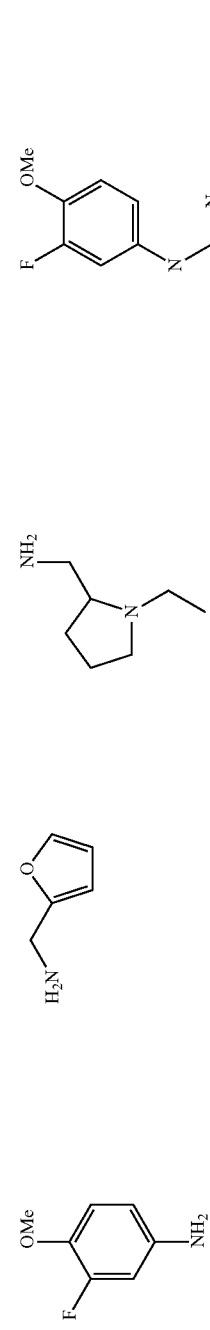 |
| 66 | 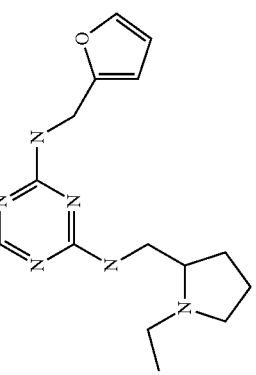 | 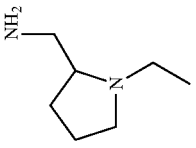 | 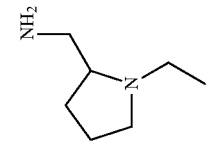 |

TABLE 2-continued
Representative compounds of the present invention prepared by parallel synthesis reactions, including amine monomers, products, and characterization data
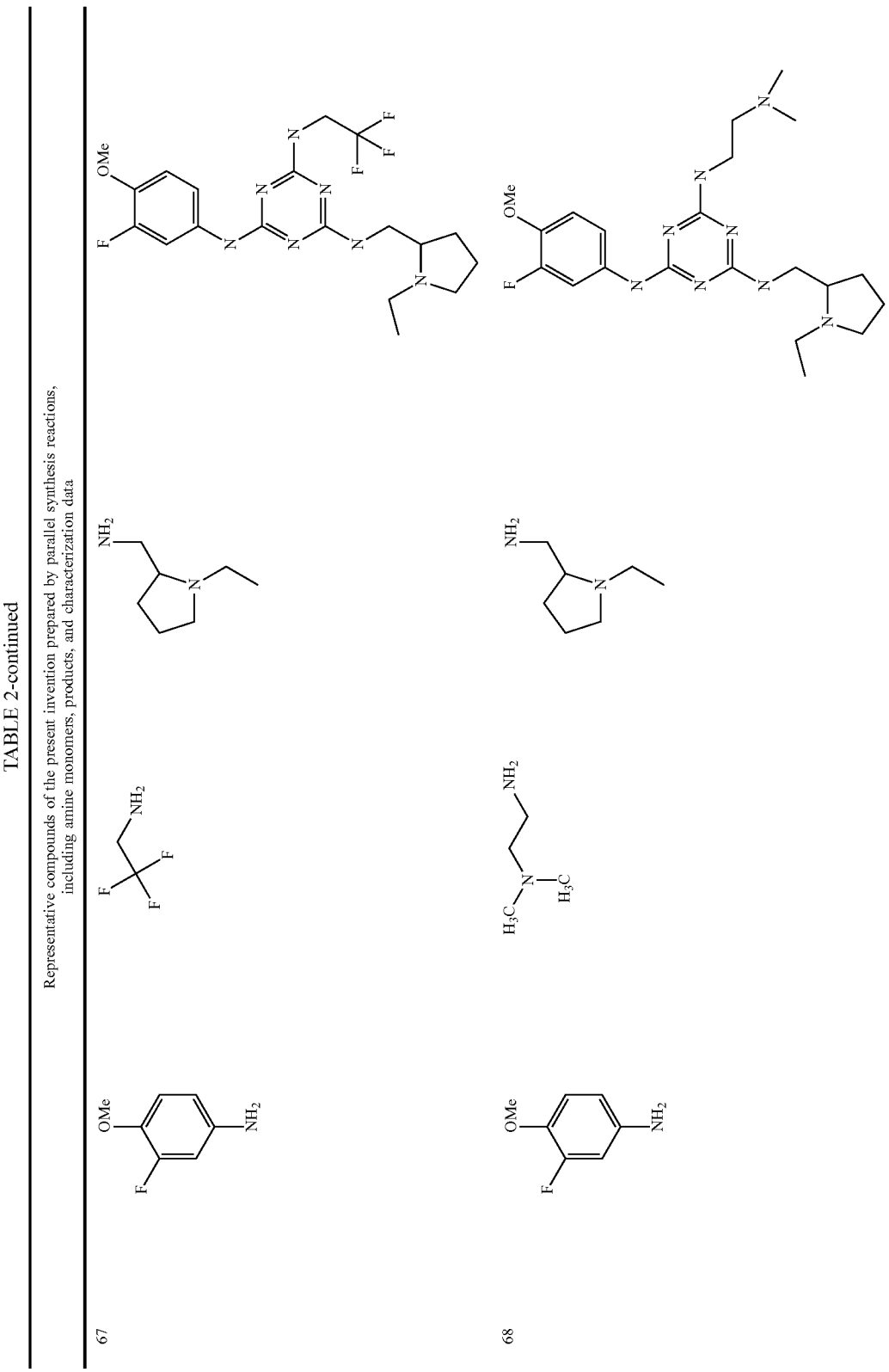

TABLE 2-continued
Representative compounds of the present invention prepared by parallel synthesis reactions, including amine monomers, products, and characterization data
| | | | |
|---|---|---|---|
| 69 | 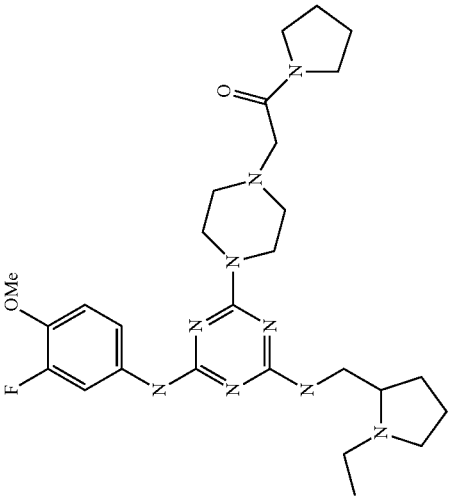 | 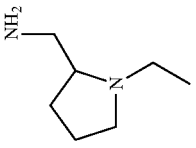 | |
| 70 | 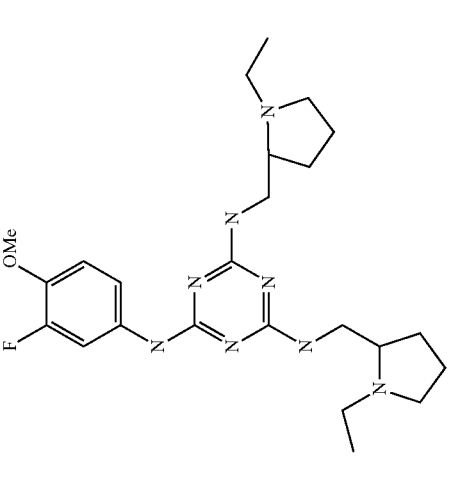 | 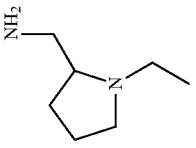 | |

TABLE 2-continued
Representative compounds of the present invention prepared by parallel synthesis reactions, including amine monomers, products, and characterization data
| 71 | 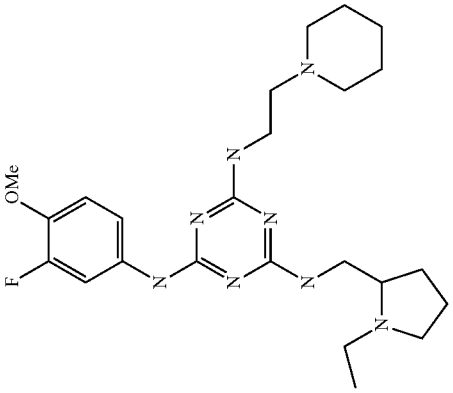 | 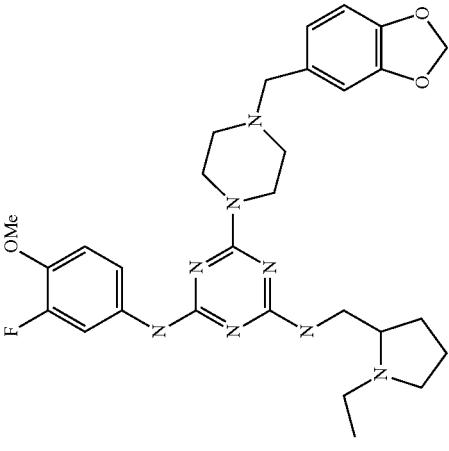 | 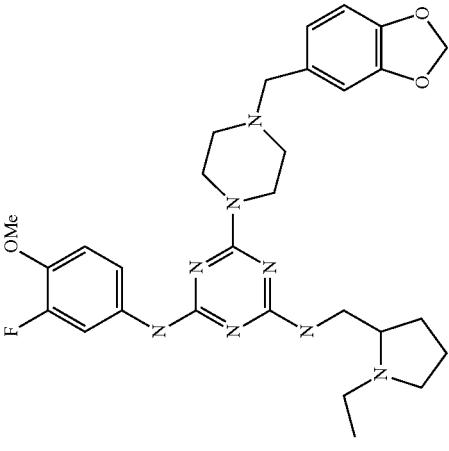 | 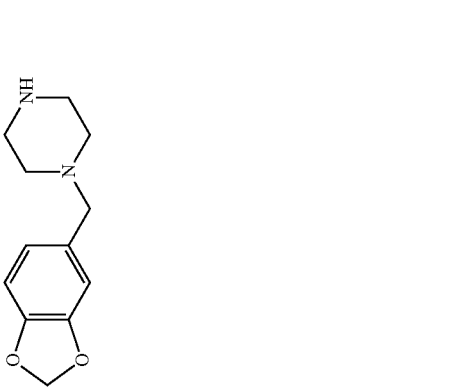 |
| 72 | 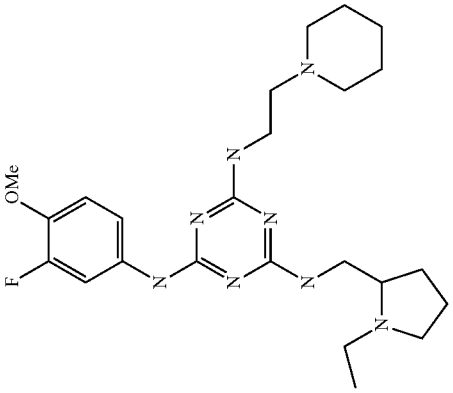 | 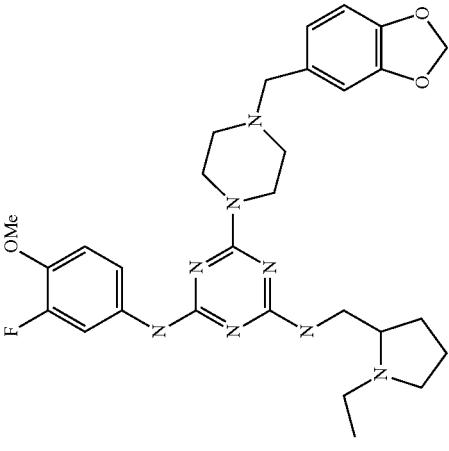 | 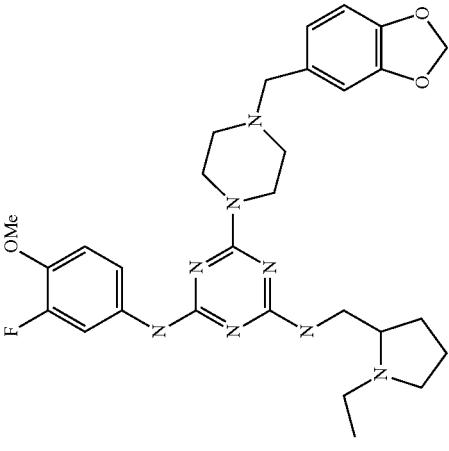 | 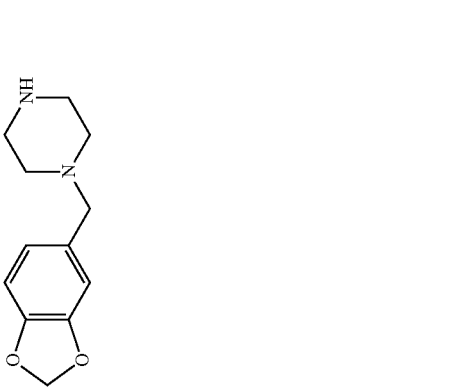 |

TABLE 2-continued
Representative compounds of the present invention prepared by parallel synthesis reactions, including amine monomers, products, and characterization data
| 73 | 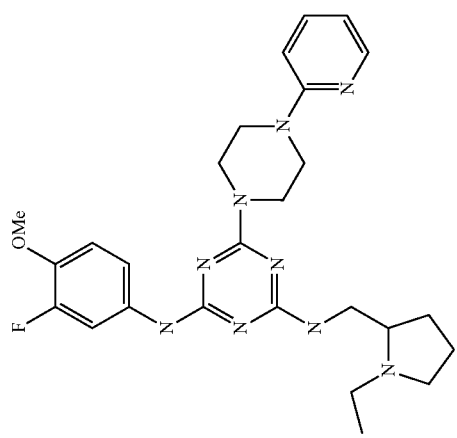 | 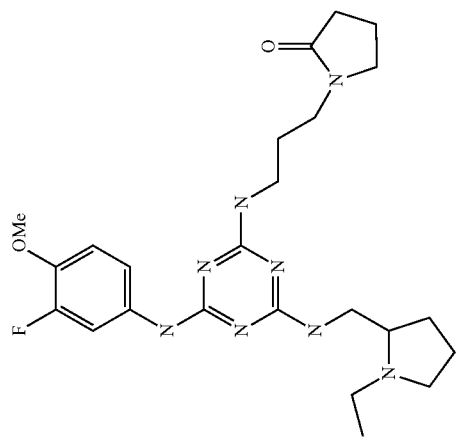 | 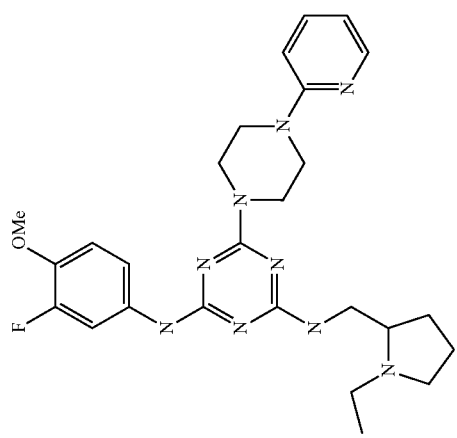 |
| 74 | | | 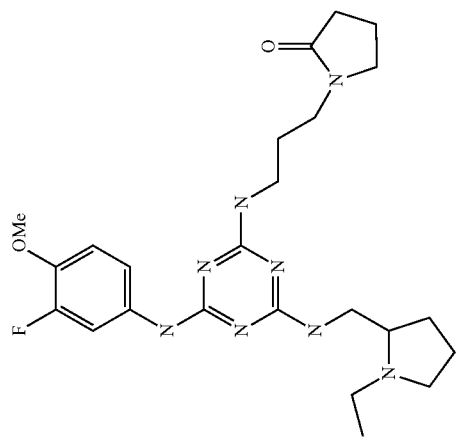 |

TABLE 2-continued
Representative compounds of the present invention prepared by parallel synthesis reactions, including amine monomers, products, and characterization data
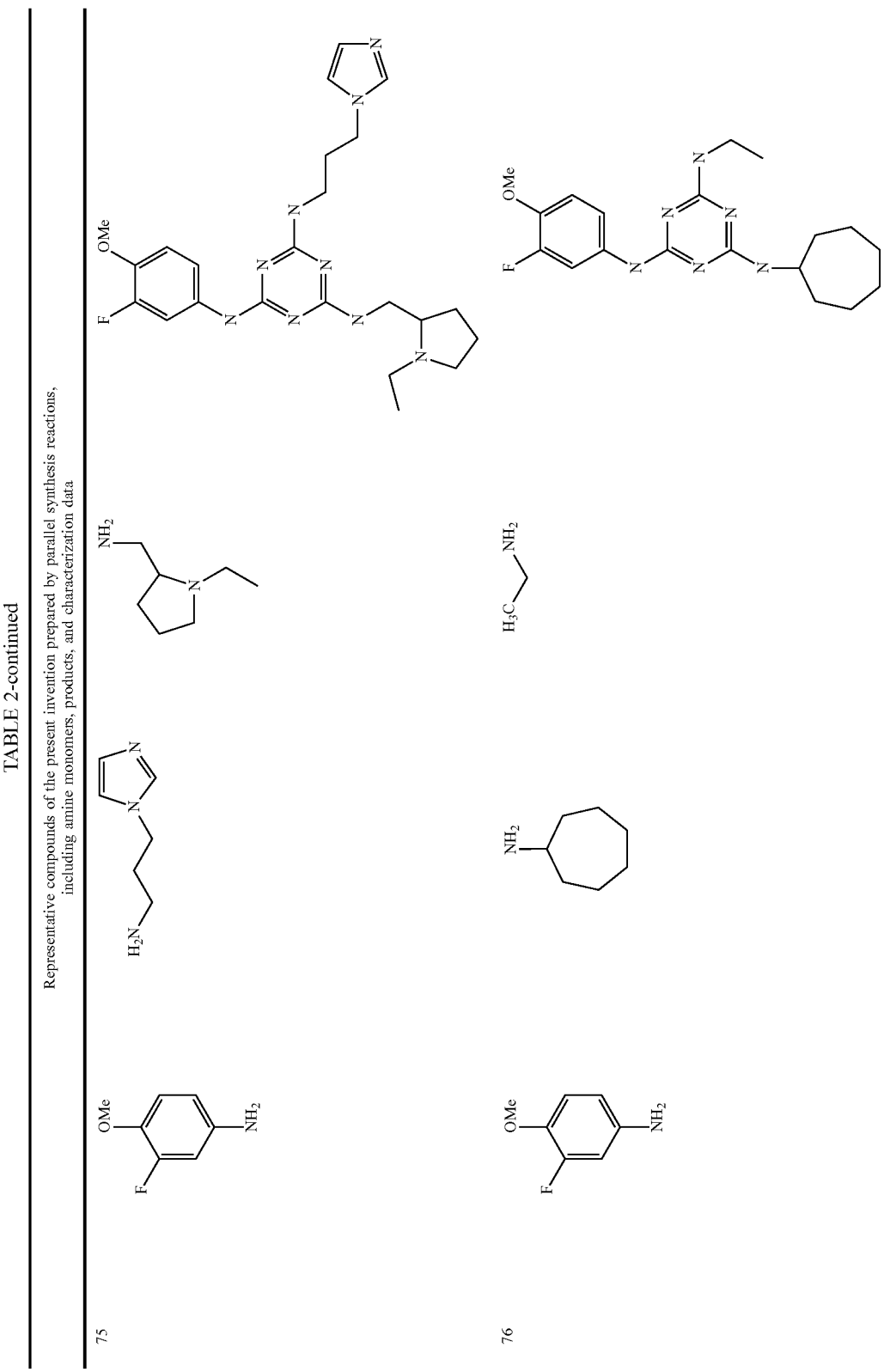

TABLE 2-continued

Representative compounds of the present invention prepared by parallel synthesis reactions, including amine monomers, products, and characterization data

| 77 | | | |
| 78 | | | |

TABLE 2-continued
Representative compounds of the present invention prepared by parallel synthesis reactions, including amine monomers, products, and characterization data
| 79 | 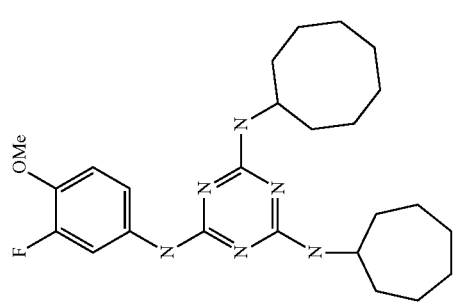 | 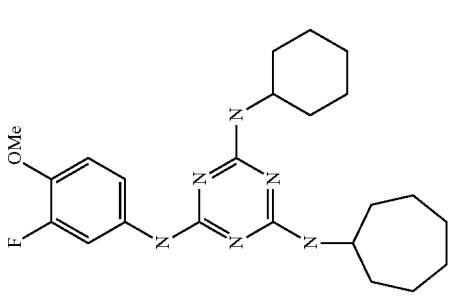 | 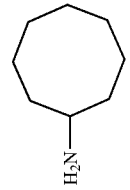 | 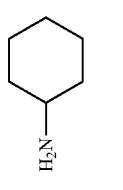 |
| 80 | 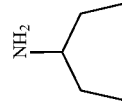 | 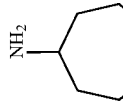 | | |

TABLE 2-continued
Representative compounds of the present invention prepared by parallel synthesis reactions, including amine monomers, products, and characterization data
| 81 | 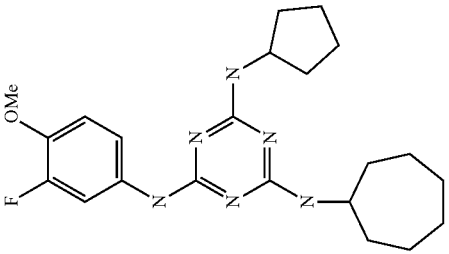 | 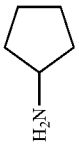 | | 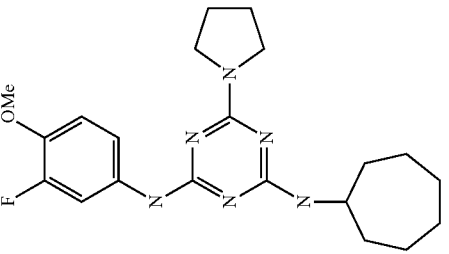 |
| 82 | | | 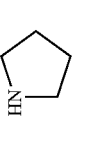 | |

TABLE 2-continued
Representative compounds of the present invention prepared by parallel synthesis reactions, including amine monomers, products, and characterization data
| 83 | 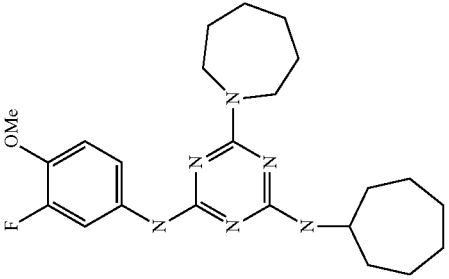 | 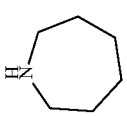 | 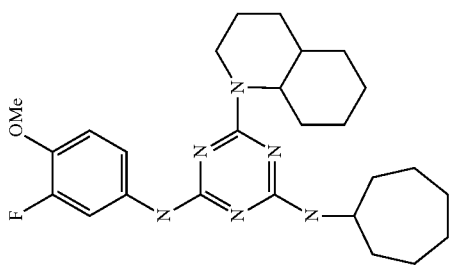 |  |
| 84 | | | | |

TABLE 2-continued
Representative compounds of the present invention prepared by parallel synthesis reactions, including amine monomers, products, and characterization data
| 85 | 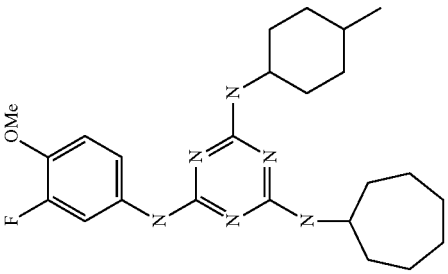 | 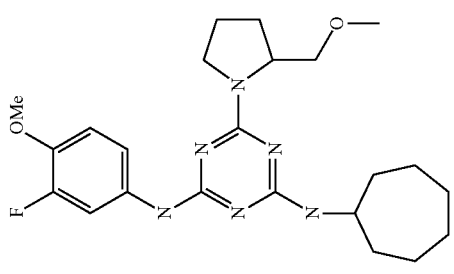 | | 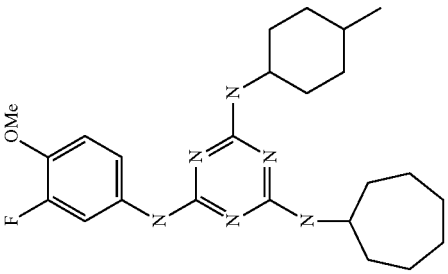 |
| 86 | | | | 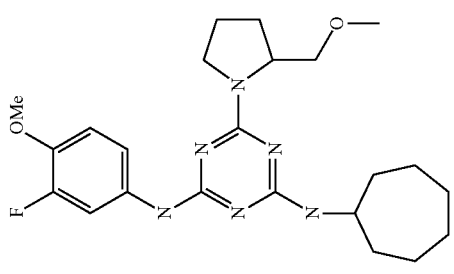 |

TABLE 2-continued
Representative compounds of the present invention prepared by parallel synthesis reactions, including amine monomers, products, and characterization data
| | | | |
|---|---|---|---|
| 87 | 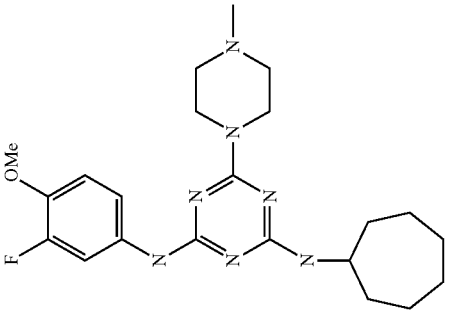 | 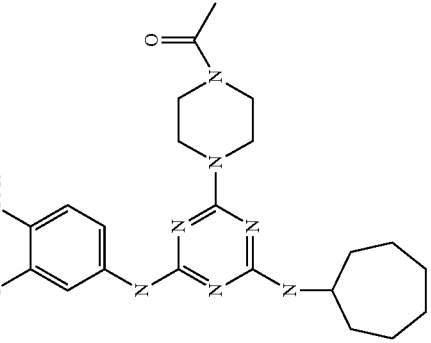 |  |
| 88 | 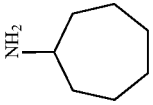 | 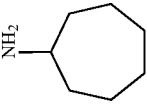 | 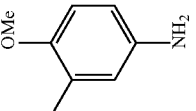 |

TABLE 2-continued
Representative compounds of the present invention prepared by parallel synthesis reactions, including amine monomers, products, and characterization data
| 89 | 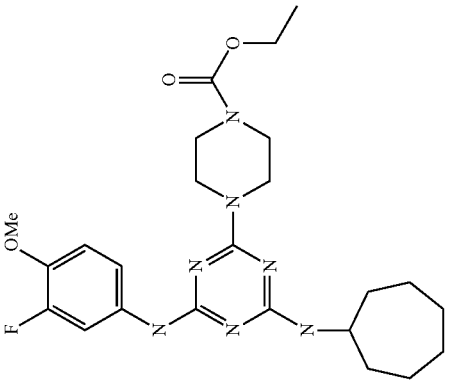 | 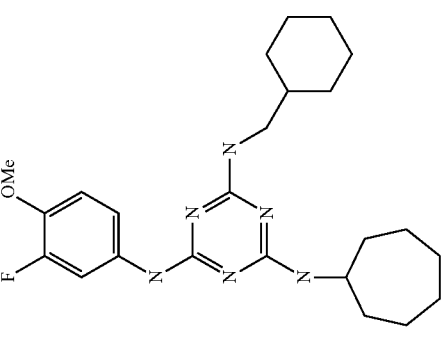 | 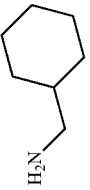 |
| 90 | 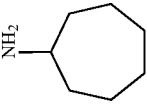 | | 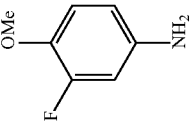 |

TABLE 2-continued
Representative compounds of the present invention prepared by parallel synthesis reactions, including amine monomers, products, and characterization data
| 91 | 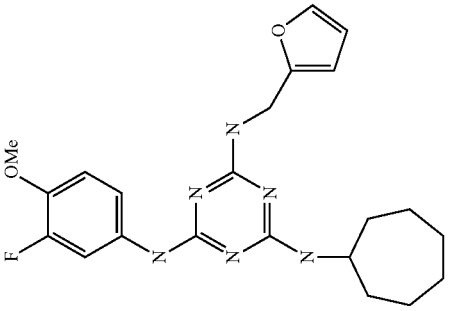 | 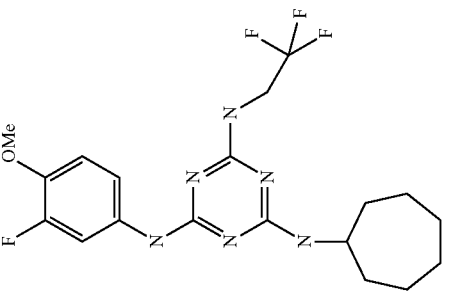 | | |
| 92 | | | | |

TABLE 2-continued
Representative compounds of the present invention prepared by parallel synthesis reactions, including amine monomers, products, and characterization data
| | | | | |
|---|---|---|---|---|
| 93 | 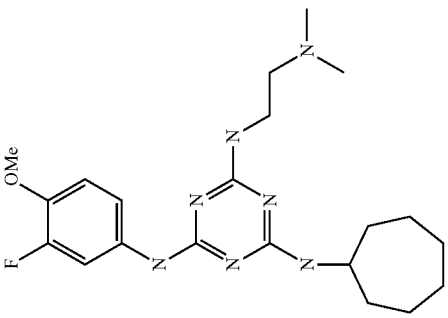 | 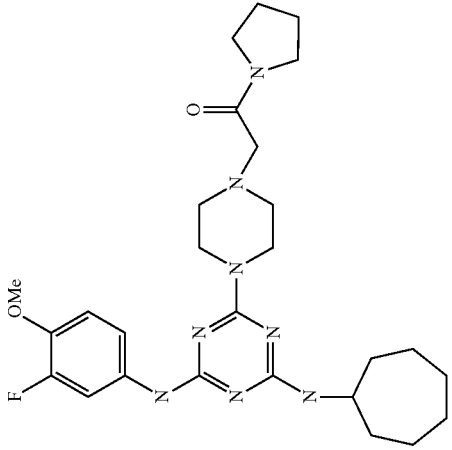 | 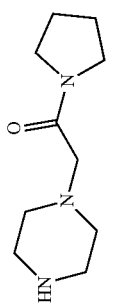 | 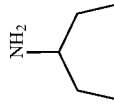 |
| 94 | | | | |

TABLE 2-continued
Representative compounds of the present invention prepared by parallel synthesis reactions, including amine monomers, products, and characterization data
| 95 | 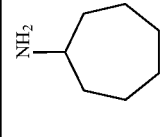 | 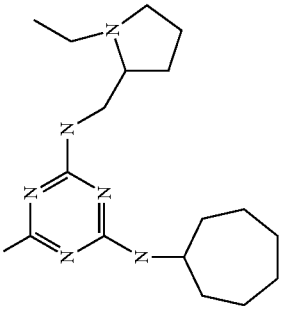 | 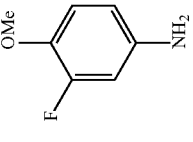 |
| 96 | 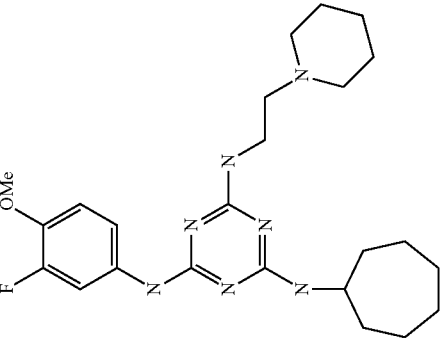 |  | 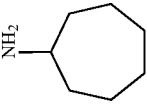 |

TABLE 2-continued
Representative compounds of the present invention prepared by parallel synthesis reactions, including amine monomers, products, and characterization data
| | | | |
|---|---|---|---|
| 97 | 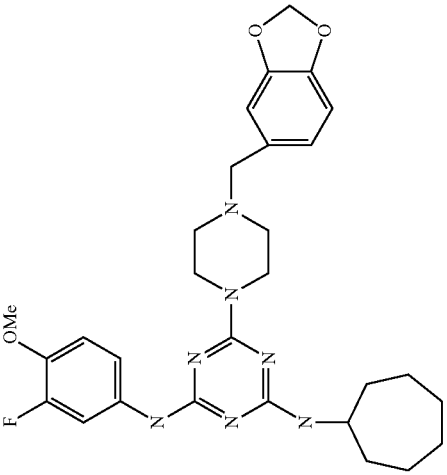 | 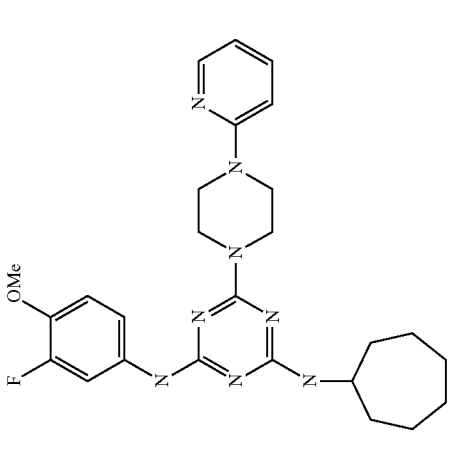 | 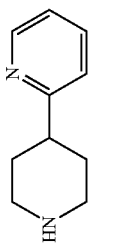 |
| 98 | 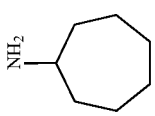 | | |

TABLE 2-continued

Representative compounds of the present invention prepared by parallel synthesis reactions, including amine monomers, products, and characterization data

| Cmpd No. | Product Name | | | Synthetic Procedure | LC-MS (Calc'd MW) Observed MW (M + H) | LCPurity | YieldBasedon Purity | Purification method |
|---|---|---|---|---|---|---|---|---|
| 99 | | | | | | | | |
| 100 | | | | | | | | |

TABLE 2-continued

Representative compounds of the present invention prepared by parallel synthesis reactions, including amine monomers, products, and characterization data

| | | | | | | |
|---|---|---|---|---|---|---|
| 1 | N2-(4-bromo-1-naphthyl)-N4-cycloheptyl-N6-[(1-ethyl-2-pyrrolidinyl)methyl]-1,3,5-triazine-2,4,6-triamine | Parallel synthesis method A | (538)540.4 | 62 | 23 | ISCO |
| 2 | N2-(4-chloro-1-naphthyl)-N4-cycloheptyl-N6-[(1-ethyl-2-pyrrolidinyl)methyl]-1,3,5-triazine-2,4,6-triamine | Parellel synthesis method A | (493)494.3 | 54 | 18 | ISCO |
| 3 | N2-cycloheptyl-N4-[(1-ethyl-2-pyrrolidinyl)methyl]-N6-(3-quinolinyl)-1,3,5-triazine-2,4,6-triamine | Parallel synthesis method A | (460)461.5 | 95 | 25 | ISCO |
| 4 | N2-cycloheptyl-N4-[(1-ethyl-2-pyrrolidinyl)methyl]-N6-(6-quinolinyl)-1,3,5-triazine-2,4,6-triamine | Parallel synthesis method A | (460)461.4 | 97 | 26 | ISCO |
| 5 | N2-cycloheptyl-N4-[(1-ethyl-2-pyrrolidinyl)methyl]-N6-(8-quinolinyl)-1,3,5-triazine-2,4,6-triamine | Parallel synthesis method A | (460)461.4 | 98 | 61 | ISCO |
| 6 | N2-cycloheptyl-N4-[(1-ethyl-2-pyrrolidinyl)methyl]-N6-[1-(2-naphthyl)ethyl]-1,3,5-triazine-2,4,6-triamine | Parallel synthesis method A | (487)488.5 | 94 | 39 | ISCO |
| 7 | N2-cycloheptyl-N4-(3,4-dichlorophenyl)-N6-[(1-ethyl-2-pyrrolidinyl)methyl]-1,3,5-triazine-2,4,6-triamine | Parallel synthesis method A | (478)478.3 | 94 | 53 | ISCO |
| 8 | N2-cycloheptyl-N4-(3,4-difluorophenyl)-N6-[(1-ethyl-2-pyrrolidinyl)methyl]-1,3,5-triazine-2,4,6-triamine | Parallel synthesis method A | 445(446.3) | 98 | 55 | ISCO |
| 9 | N2-cycloheptyl-N4-[(1-ethyl-2-pyrrolidinyl)methyl]-N6-[4-(triflouromethoxy)phenyl]-1,3,5-triazine-2,4,6-triamine | Parallel synthesis method A | (493)494.3 | 96 | 40 | ISCO |
| 10 | N2-cycloheptyl-N4-[(1-ethyl-2-pyrrolidinyl)methyl]-N6-(4-fluorophenyl)-1,3,5-triazine-2,4,6-triamine | Parallel synthesis method A | (493)428.4 | 90 | 37 | ISCO |
| 11 | 4-[(4-(cycloheptylamino)-6-{[(1-ethyl-2-pyrrolidinyl)methyl]amino}-1,3,5-triazin-2-yl)amino]benzonitrile | Parallel synthesis method A | (434)435.4 | 76 | 64 | none |
| 12 | N2-(4-chlorophenyl)-N4-cycloheptyl-N6-[(1-ethyl-2-pyrrolidinyl)methyl]-1,3,5- | Parallel synthesis method A | (444)444.3 | 76 | 69 | none |

TABLE 2-continued

Representative compounds of the present invention prepared by parallel synthesis reactions, including amine monomers, products, and characterization data

| | | | | | |
|---|---|---|---|---|---|
| 13 | triazine-2,4,6-triamine N2-(4-bromophenyl)-N4-cycloheptyl-N6-[(1-ethyl-2-pyrrolidinyl)methyl]-1,3,5-triazine-2,4,6-triamine | Parallel synthesis method A | (488)488.4 | 77 | 70 | none |
| 14 | 4-[(4-(cycloheptylamino)-6-{[(1-ethyl-2-pyrrolidinyl)methyl]amino}-1,3,5-triazine-2-yl)amino]benzoate | Parallel synthesis method A | (461)482.5 | 96 | 46 | ISCO |
| 15 | N2-(1,1'-biphenyl-4-yl)-N4-cycloheptyl-N6-[(1-ethyl-2-pyrrolidinyl)methyl]-1,3,5-triazine-2,4,6-triamine | Parallel synthesis method A | (485)486.5 | 75 | 69 | none |
| 16 | N2-cycloheptyl-N4-[(1-ethyl-2-pyrrolidinyl)methyl]-N6-(3-fluorophenyl)-1,3,5-triazine-2,4,6-triamine | Parallel synthesis method A | (427)428.3 | 78 | 75 | none |
| 17 | N2-(3-chlorophenyl)-N4-cycloheptyl-N6-[(1-ethyl-2-pyrrolidinyl)methyl]-1,3,5-triazine-2,4,6-triamine | Parallel synthesis method A | (444)444.3 | 77 | 74 | none |
| 18 | N2-(3-bromophenyl)-N4-cycloheptyl-N6-[(1-ethyl-2-pyrrolidinyl)methyl]-1,3,5-triazine-2,4,6-triamine | Parallel synthesis method A | (488)488.4 | 82 | 75 | none |
| 19 | 3-[(4-(cycloheptylamino)-8-{[(1-ethyl-2-pyrrolidinyl)methyl]amino}-1,3,5-triazin-2-yl)amino]benzoate | Parallel synthesis method A | (481)482.4 | 98 | 45 | ISCO |
| 20 | N2-cycloheptyl-N4-[(1-ethyl-2-pyrrolidinyl)methyl]-N6-(2-fluorophenyl)-1,3,5-triazine-2,4,6-triamine | Parallel synthesis method A | (427)428.4 | 80 | 23 | ISCO |
| 21 | N2-(2-chlorophenyl)-N4-cycloheptyl-N6-[(1-ethyl-2-pyrrolidinyl)methyl]-1,3,5-triazine-2,4,6-triamine | Parallel synthesis method A | (444)444.3 | 53 | 26 | ISCO |
| 22 | N2-(2-bromophenyl)-N4-cycloheptyl-N6-[(1-ethyl-2-pyrrolidinyl)methyl]-1,3,5-triazine-2,4,6-triamine | Parallel synthesis method A | (488)490.3 | 51 | 17 | ISCO |
| 23 | N2-(1,3-benzodioxol-5-yl)-N4-cycloheptyl-N6-[(1-ethyl-2-pyrrolidinyl)methyl]-1,3,5-triazine-2,4,6-triamine | Parallel synthesis method A | (453)454.4 | 16 | 4 | ISCO |
| 24 | N2-cycloheptyl-N4-(2,3-dihydro-1,4-benzodioxin-6-yl)-N6-[(1-ethyl-2-pyrrolidinyl)methyl]-1,3,5-triazine-2,4,6-triamine | Parallel synthesis method A | (467)454.4 | 91 | 30 | ISCO |

TABLE 2-continued

Representative compounds of the present invention prepared by parallel synthesis reactions, including amine monomers, products, and characterization data

| | | | | | |
|---|---|---|---|---|---|
| 25 | N2-cycloheptyl-N4-[4-(dimethylamino)phenyl]-N6-[(1-ethyl-2-pyrrolidinyl)methyl]-1,3,5-triazine-2,4,6-triamine | Parallel synthesis method A | (452)453.5 | 67 | 17 | ISCO |
| 26 | N2-[3-chloro-4-(diethylamino)phenyl-N4-cycloheptyl-N6-[1-ethyl-2-pyrrolidinyl)methyl]1,3,5-triazine-2,4,6-triamine | Parallel synthesis method A | (515)515.5 | 91 | 45 | ISCO |
| 27 | N2-cycloheptyl-N4-[(1-ethyl-2-pyrrolidinyl)methyl]-N6-[4-(4-morpholinyl)phenyl]-1 3,5-triazine-2,4,6-triamine | Parallel synthesis method A | (494)495.4 | 92 | 41 | ISCO |
| 28 | N2-cycloheptyl-N4-[(1-ethyl-2-pyrrolidinyl)methyl]-N6-[4-(4-methyl-1-piperazinyl)phenyl]-1,3,5-triazine-2,4,6-triamine | Parallel synthesis method A | (507)508.5 | 4 | 0.004 | none |
| 29 | N-{4-((4-(cycloheptylamino)-6-{[(1-ethyl-2-pyrrolidinyl)methyl]amino}-1,3,5-triazin-2-yl)-amino]phenyl}acetamide | Parallel synthesis method A | (466)467.3 | 91 | 26 | ISCO |
| 30 | N-(3-[(4-(cycloheptylamino)-6-{[(1-ethyl-2-pyrrolidinyl)methyl]amino}-1,3,5-triazin-2-yl)-amino]phenyl}acetamide | Parallel synthesis method A | (468)467.4 | 100 | 38 | ISCO |
| 31 | N2-cycloheptyl-N4-[(1-ethyl-2-pyrrolidinyl)methyl]-N6-(3-methoxyphenyl)-1,3,5-triazine-2,4,6-triamine | Parallel synthesis method A | (439)440.4 | 96 | 42 | ISCO |
| 32 | N2-cycloheptyl-N4-(4-ethoxyphenyl)-N6-[(1-ethyl-2-pyrrolidinyl)methyl]-1,3,5-triazine-2,4,6-triamine | Parallel synthesis method A | (453)454.2 | 97 | 47 | ISCO |
| 33 | N2-cycloheptyl-N4-[(1-ethyl-2-pyrrolidinyl)methyl]-N6-(4-(methylthio)phenyl]1,3,5-triazine-2,4,6-triamine | Parallel synthesis method A | (455)456.4 | 93 | 49 | ISCO |
| 34 | N2-cycloheptyl-N4-[(1-ethyl-2-pyrrolidinyl)methyl]-N6-(2-pyridinyl)-1,3,5-triazine-2,4,6-triamine | Parallel synthesis method A | (410)411.3 | 27 | 7 | ISCO |
| 35 | N2-cycloheptyl-N4-[(1-ethyl-2-pyrrolidinyl)methyl]-N6-(2-methylphenyl)-1,3,5-triazine-2,4,6-triamine | Parallel synthesis method A | (423) | 72 | 76 | none |
| 36 | N2-cycloheptyl-N4-[(1-ethyl-2-pyrrolidinyl)methyl]-N6-(4- | Parallel synthesis method A | (501)502.3 | 100 | 46 | ISCO |

TABLE 2-continued

Representative compounds of the present invention prepared by parallel synthesis reactions, including amine monomers, products, and characterization data

| | | | | | |
|---|---|---|---|---|---|
| 37 | phenoxyphenyl)-1,3,5-triazine-2,4,6-triamine | | | | |
| | N2-cycloheptyl-N4-[(1-ethyl-2-pyrrolidinyl)methyl]-N6-(3-methylphenyl)-1,3,5-triazine-2,4,6-triamine | Parallel synthesis method A | (423)424.4 | 86 | 46 | ISCO |
| 38 | N2-cycloheptyl-N4-[(1-ethyl-2-pyrrolidinyl)methyl]-N6-(4-methylphenyl)-1,3,5-triazine-2,4,6-triamine | Parallel synthesis method A | (423)424.3 | 98 | 44 | ISCO |
| 39 | 2-[(4-(cycloheptylamino)-6-{[(1-ethyl-2-pyrrolidinyl)methyl]amino}-1,3,5-triazin-2-yl)-amino]-4-methyl-3-thiophenecarboxamide | Parallel synthesis method A | (472)473.3 | 63 | 16 | ISCO |
| 40 | N2-(4-chlorophenyl)-N4-cycloheptyl-N6-[(1-ethyl-2-pyrrolidinyl)methyl]-N2-methyl-1,3,5-triazine-2,4,6-triamine | Parallel synthesis method A | (458)458.5 | 98 | 42 | ISCO |
| 41 | 3-[(4-(cycloheptylamino)-6-{[(1-ethyl-2-pyrrolidinyl)methyl]amino}-1,3,5-triazin-2-yl)-(phenyl)amino]propanenitrile | Parallel synthesis method A | (462)463.4 | 97 | 45 | ISCO |
| 42 | N2-cycloheptyl-N4-[(1-ethyl-2-pyrrolidinyl)methyl]-N6-(4-methoxyphenyl)-N6-methyl-1,3,5-triazine-2,4,6-triamine | Parallel synthesis method A | (543)454.4 | 89 | 36 | ISCO |
| 43 | N2-cycloheptyl-N4-(2,4-difluorophenyl)-N6-[(1-ethyl-2-pyrrolidinyl)methyl]-N4-methyl-1,3,5-triazine-2,4,6-triamine | Parallel synthesis method A | (459)460.3 | 73 | 74 | none |
| 44 | [(4-(cycloheptylamino)-6-{[(1-ethyl-2-pyrrolidinyl)methyl]amino}-1,3,5-triazin-2-yl)(phenyl)amino]acetonitrile | Parallel synthesis method A | (448)449.3 | 85 | 76 | none |
| 45 | Parallel synthesis cycloheptyl-N6-[(1-ethyl-2-pyrrolidinyl)methyl]-N2-methyl-1,3,5-triazine-2,4,6-triamine | (458)458.5 method A | 98 | 37 | ISCO | |
| 46 | N2-cycloheptyl-N4-[(1-ethyl-2-pyrrolidinyl)methyl]-N6-methyl-N6-[2-(trifluoromethyl)phenyl]-1,3,5-triazine-2,4,6-triamine | Parallel synthesis method A | (491)492.3 | 82 | 21 | ISCO |
| 47 | N2-cycloheptyl-N4-[(1-ethyl-2-pyrrolidinyl)methyl]-N6-methyl-N6-[2-(trifluoromethoxy)phenyl]-1,3,5-triazine-2,4,6-triamine | Parallel synthesis method A | (507)508.3 | 100 | 41 | ISCO |

TABLE 2-continued

Representative compounds of the present invention prepared by parallel synthesis reactions, including amine monomers, products, and characterization data

| # | Compound | Method | MS (calc) found | % | % | Purif. |
|---|---|---|---|---|---|---|
| 48 | N2-(3-chloro-4-methoxyphenyl)-N4-cycloheptyl-N6-[(1-ethyl-2-pyrrolidinyl)methyl]-1,3,5-triazine-2,4,6-triamine | Parallel synthesis method A | (474)474.3 | 93 | 51 | ISCO |
| 49 | N-benzoyl-4-[(4-(cycloheptylamino)-6-{[(1-ethyl-2-pyrrolidinyl)methyl]amino}-1,3,5-triazin-2-yl)amino]benzenesulfonamide | Parallel synthesis method A | (592)593.4 | 14 | 2 | none |
| 50 | N2-cycloheptyl-N4-[(1-ethyl-2-pyrrolidinyl)methyl]-N6-(2-naphthyl)-1,3,5-triazine-2,4,6-triamine | Parallel synthesis method A | (459)480.4 | 83 | 36 | ISCO |
| 51 | N2-ethyl-N4-[(1-ethyl-2-pyrrolidinyl)methyl]-N6-(3-fluoro-4-methoxyphenyl)-1,3,5-triazine-2,4,6-triamine | Parallel synthesis method B | (389)390.2 | 48 | 36 | none |
| 52 | N2-(tert-butyl)-N4-[(1-ethyl-2-pyrrolidinyl)methyl]-N6-(3-fluoro-4-methoxyphenyl)-1,3,5-triazine-2,4,6-triamine | Parallel synthesis method B | (417)418.4 | 38 | 28 | none |
| 53 | N2-benzyl-N4-[(1-ethyl-2-pyrrolidinyl)methyl]-N6-(3-fluoro-4-methoxyphenyl)-1,3,5-triazine-2,4,6-triamine | Parallel synthesis method B | (451)452.3 | 87 | 75 | none |
| 54 | N2-cyclooctyl-N4-[(1-ethyl-2-pyrrolidinyl)methyl]-N6-(3-fluoro-4-methoxyphenyl)-1,3,5-triazine-2,4,6-triamine | Parallel synthesis method B | (471)472.4 | 83 | 66 | none |
| 55 | N2-cyclohexyl-N4-[(1-ethyl-2-pyrrolidinyl)methyl]-N6-(3-fluoro-4-methoxyphenyl)-1,3,5-triazine-2,4,6-triamine | Parallel synthesis method B | (443)444.3 | 75 | 80 | none |
| 56 | N2-cyclopentyl-N4-[(1-ethyl-2-pyrrolidinyl)methyl]-N6-(3-fluoro-4-methoxyphenyl)-1,3,5-triazine | Parallel synthesis method B | (429)430.3 | 79 | 75 | none |
| 57 | N2-[(1-ethyl-2-pyrrolidinyl)methyl]-N4-(3-fluoro-4-methoxyphenyl)-6-(1-pyrrolidinyl)-1,3,5-triazine-2,4-diamine | Parallel synthesis method B | (415)416.3 | 84 | 45 | ISCO |
| 58 | N2-[(1-ethyl-2-pyrrolidinyl)methyl]-N4-(3-fluoro-4-methoxyphenyl)-6-hexahydro-1H-azepin-1-yl-1,3,5-triazine-2,4-diamine | Parallel synthesis method B | (443)444.4 | 90 | 51 | ISCO |
| 59 | N2-[(1-ethyl-2-pyrrolidinyl)methyl]-N4-(3-fluoro- | Parallel synthesis method B | (483)484.5 | 86 | 47 | ISCO |

TABLE 2-continued

Representative compounds of the present invention prepared by parallel synthesis reactions, including amine monomers, products, and characterization data

| | | | | | |
|---|---|---|---|---|---|
| 60 | 4-methoxyphenyl)-6-octahydro-1(2H)-quinolinyl-1,3,5-triazine-2,4-diamine | Parallel synthesis method B | 457(458.4) | 88 | 50 | ISCO |
| 61 | N²-[(1-ethyl-2-pyrrolidinyl)methyl]-N⁴-(3-fluoro-4-methoxyphenyl)-N⁶-(4-methylcyclohexyl)-1,3,5-triazine-2,4,6-triamine | Parallel synthesis method B | (459)460.4 | 81 | 36 | ISCO |
| 62 | N²-(1-ethyl-pyrrolidin-2-ylmethyl)-N⁴-(3-fluoro-4-methoxyphenyl)-6-[(S)-2-methoxymethyl-pyrrolidin-1-yl)-1,3,5-triazine-2,4-diamine | Parallel synthesis method B | (444)445.3 | 30 | 10 | none |
| 63 | N²-[(1-ethyl-2-pyrrolidinyl)methyl]-N⁴-(3-fluoro-4-methoxyphenyl)-6-(4-methyl-1-piperazinyl)-1,3,5-triazine-2,4-diamine | Parallel synthesis method B | 472(473.3) | 83 | 43 | ISCO |
| 64 | 6-(4-acetyl-1-piperazinyl)-N²-[(1-ethyl-2-pyrrolidinyl)methyl]-N⁴-(3-fluoro-4-methoxyphenyl)-1,3,5-triazine-2,4-diamine | Parallel synthesis method B | (502)503.2 | 75 | 74 | none |
| 65 | Ethyl 4-(4-{[(1-ethyl-2-pyrrolidinyl)methyl]amino}-N⁶-[(3-fluoro-4-methoxyphenyl)-amino]-1,3,5-triazin-2-yl)-1-piperazinecarboxylate | Parallel synthesis method B | | | | |
| 65 | N²-(cyclohexylmethyl)-N²-[(1-ethyl-2-pyrrolidinyl)methyl]-N⁶-(3-fluoro-4-methoxyphenyl)-1,3,5-triazine-2,4,6-triamine | Parallel synthesis method B | (457)458.4 | 76 | 77 | none |
| 66 | N²-[(1-ethyl-2-pyrrolidinyl)methyl]-N⁴-(3-fluoro-4-methoxyphenyl)-N⁶-(2-furylmethyl)-1,3,5-triazine-2,4,6-triamine | Parallel synthesis method B | (441)442.2 | 77 | 70 | none |
| 67 | N²-[(1-ethyl-2-pyrrolidinyl)methyl]-N⁴-(3-fluoro-4-methoxyphenyl)-N⁶-(2,2,2-trifluoroethyl)-1,3,5-triazine-2,4,6-triamine | Parallel synthesis method B | (443)444.1 | 77 | 69 | none |
| 68 | N²-[2-(dimethylamino)ethyl]-N⁴-[(1-ethyl-2-pyrrolidinyl)methyl]-N⁶-(3-fluoro-4-methoxyphenyl)-1,3,5-triazine-2,4,6-triamine | Parallel synthesis method B | (432)433.5 | 6 | 2 | none |
| 69 | N²-[(1-ethyl-2-pyrrolidinyl)methyl]-N⁴-(3-fluoro-4-methoxyphenyl)-N⁶-{4-[2-oxo- | Parallel synthesis method B | (541)542.4 | 78 | 39 | ISCO |

TABLE 2-continued

Representative compounds of the present invention prepared by parallel synthesis reactions, including amine monomers, products, and characterization data

| | | | | | |
|---|---|---|---|---|---|
| 70 | 2-(1-pyrrolidinyl)ethyl]-1-piperazinyl}-1,3,5-triazine-2,4-diamine | | | | |
| 70 | N²,N⁴-bis[(1-ethyl-2-pyrrolidinyl)methyl]-N⁶-(3-fluoro-4-methoxyphenyl)-1,3,5-triazine-2,4,6-triamine | Parallel synthesis method B | (472)473.3 | 63 | 20 | ISCO |
| 71 | N²-[(1-ethyl-2-pyrrolidinyl)methyl]-N⁴-(3-fluoro-4-methoxyphenyl)-N⁶-[2-(1-piperidinyl)ethyl]-1,3,5-triazine-2,4,6-triamine | Parallel synthesis method B | (472)473.3 | 67 | 28 | ISCO |
| 72 | N⁶-(4-(1,3-benzodioxol-5-ylmethyl)-1-piperazinyl]-N²-[(1-ethyl-2-pyrrolidinyl)methyl]-N⁴-(3-fluoro-4-methoxyphenyl)-1,3,5-triazine-2,4-diamine | Parallel synthesis method B | (564)565.4 | 87 | 83 | none |
| 73 | N²-[(1-ethyl-2-pyrrolidinyl)methyl]-N⁴-(3-fluoro-4-methoxyphenyl)-N⁶-[4-(2-pyridinyl)-1-piperazinyl]-1,3,5-triazine-2,4-diamine | Parallel synthesis method B | (507)508.3 | 86 | 41 | ISCO |
| 74 | 1-[3-[(4-{[(1-ethyl-2-pyrrolidinyl)methyl]amino}-6-[(3-fluoro-4-methoxyphenyl)amino]-1,3,5-triazin-2-yl)amino]propyl]-2-pyrrolidinone | Parallel synthesis method B | (486)487.5 | 85 | 31 | ISCO |
| 75 | N²-[(1-ethyl-2-pyrrolidinyl)methyl]-N⁴-(3-fluoro-4-methoxyphenyl)-N⁶-[3-(1H-imidazol-1-yl)propyl]-1,3,5-triazine-2,4,6-triamine | Parallel synthesis method B | (469)470.3 | 90 | 38 | ISCO |
| 76 | N2-cycloheptyl-N⁴-ethyl-N6-(3-fluoro-4-methoxyphenyl)-1,3,5-triazine-2,4,6-triamine | Parallel synthesis method C | (374)375.3 | 85 | 18 | preparative HPLC |
| 77 | N2-(tert-butyl)-N4-cycloheptyl-N6-(3-fluoro-4-methoxyphenyl)-1,3,5-triazine-2,4,6-triamine | Parallel synthesis method C | (402)403.4 | 81 | 3 | preparative HPLC |
| 78 | N2-benzyl-N4-cycloheptyl-N6-(3-fluoro-4-methoxyphenyl)-1,3,5-triazine-2,4,6-triamine | Parallel synthesis method C | (436)438.9 | 96 | 15 | preparative HPLC |
| 79 | N2-cycloheptyl-N4-cyclooctyl-N6-(3-fluoro-4-methoxyphenyl)-1,3,5-triazine-2,4,6-triamine | Parallel synthesis method C | (456)457.3 | 96 | 5 | preparative HPLC |
| 80 | N2-cycloheptyl-N4-cyclohexyl-N6-(3-fluoro-4-methoxyphenyl)-1,3,5-triazine-2,4,6-triamine | Parallel synthesis method C | (428)429.3 | 100 | 10 | preparative HPLC |
| 81 | N2-cycloheptyl-N4-cyclopentyl-N6-(3-fluoro-4-methoxyphenyl)- | Parallel synthesis method C | (414)415.2 | 89 | 26 | preparative HPLC |

TABLE 2-continued

Representative compounds of the present invention prepared by parallel synthesis reactions, including amine monomers, products, and characterization data

| | | | | | |
|---|---|---|---|---|---|
| 82 | 1,3,5-triazine-2,4,6-triamine N2-cycloheptyl-N4-(3-fluoro-4-methoxyphenyl)-6-(1-pyrrolidinyl)-1,3,5-triazine-2,4-diamine | Parallel synthesis method C | (400)400.9 | 98 | 22 | preparative HPLC |
| 83 | N2-cycloheptyl-N4-(3-fluoro-4-methoxyphenyl)-6-hexahydro-1H-azepin-1-yl-1,3,5-triazine-2,4-diamine | Parallel synthesis method C | (428)429 | 96 | 5 | preparative HPLC |
| 84 | N2-cycloheptyl-N4-(3-fluoro-4-methoxyphenyl)-6-octahydro-1(2H)-quinolinyl-1,3,5-triazine-2,4-diamine | Parallel synthesis method C | (468)469.3 | 67 | 21 | preparative HPLC |
| 85 | N2-cycloheptyl-N4-(3-fluoro-4-methoxyphenyl)-N6-(4-methylcyclohexyl)-1,3,5-triazine-2,4,6-triamine | Parallel synthesis method C | (442)443.3 | 64 | 4 | preparative HPLC |
| 86 | N2-cycloheptyl-N4-(3-fluoro-4-methoxyphenyl)-6-[(2S)-2-(methoxymethyl)-1-pyrrolidinyl]-1,3,5-triazine-2,4-diamine | Parallel synthesis method C | (444)444.9 | 100 | 17 | preparative HPLC |
| 87 | N2-cycloheptyl-N4-(3-fluoro-4-methoxyphenyl)-6-(4-methyl-1-piperazinyl)-1,3,5-triazine-2,4-diamine | Parallel synthesis method C | (429)430.3 | 94 | 13 | preparative HPLC |
| 88 | 6-(4-acetyl-1-piperazinyl)-N2-cycloheptyl-N4-(3-fluoro-4-methoxyphenyl)-1,3,5-triazine-2,4-diamine | Parallel synthesis method C | (457)Wrong MW observed | 100 | compound not observed after prep HPLC | preparative HPLC |
| 89 | ethyl-4-(4-(cycloheptylamino)-6-[(3-fluoro-4-methoxyphenyl]amino]-1,3,5-triazin-2-yl)-1-piperazinecarboxylate | Parallel synthesis method C | (487)488.3 | 97 | 4 | preparative HPLC |
| 90 | N2-cycloheptyl-N4-(cyclohexylmethyl)-N6-(3-fluoro-4-methoxyphenyl)-1,3,5-triazine-2,4,6-triamine | Parallel synthesis method C | (442) | 100 | 16 | preparative HPLC |
| 91 | N2-cycloheptyl-N4-(3-fluoro-4-methoxyphenyl)-N6-(2-furanylmethyl)-1,3,5-triazine-2,4,6-triamine | Parallel synthesis method C | (426)426.9 | 59 | 31 | preparative HPLC |
| 92 | N2-cycloheptyl-N4-(3-fluoro-4-methoxyphenyl)-N6-(2,2,2-trifluoroethyl)-1,3,5-triazine-2,4,6-triamine | Parallel synthesis method C | (428)352.1 | 93 | 1 | preparative HPLC |
| 93 | N2-cycloheptyl-N4-[2-(dimethylamino)ethyl]-N6-(3-fluoro-4-methoxyphenyl)-1,3,5-triazine-2,4,6-triamine | Parallel synthesis method C | (417)418.3 | 76 | 11 | preparative HPLC |

TABLE 2-continued

Representative compounds of the present invention prepared by parallel synthesis reactions, including amine monomers, products, and characterization data

| | | | | | |
|---|---|---|---|---|---|
| 94 | N2-cycloheptyl-N4-(3-fluoro-4-methoxyphenyl)-6-{4-[2-oxo-(1-pyrrolidinyl)ethyl]-1-piperazinyl]-1,3,5-triazine-2,4-diamine | Parallel synthesis method C | (526)527.3 | 27 | 15 | preparative HPLC |
| 95 | N2-cycloheptyl-N4-[(1-ethyl-2-pyrrolidinyl)methyl]-N6-(3-fluoro-4-methoxyphenyl)-1,3,5-triazine-2,4,6-triamine | Parallel synthesis method C | (457)458.4 | 80 | 24 | preparative HPLC |
| 96 | N2-cycloheptyl-N4-(3-fluoro-4-methoxyphenyl)-N6-[2-(1-piperidinyl)ethyl]-1,3,5-triazine-2,4,6-triamine | Parallel synthesis method C | (457)458.4 | 86 | 21 | preparative HPLC |
| 97 | 6-[4-(1,3-benzodioxol-5-ylmethyl)1-piperazinyl]-N2-cycloheptyl-N4-(3-fluoro-4-methoxyphenyl)-1,3,5-triazine-2,4-diamine | Parallel synthesis method C | (549)493.2 | 94 | 21 | preparative HPLC |
| 98 | N2-cycloheptyl-N4-(3-fluoro-4-methoxyphenyl)-6-[4-(2-pyridinyl)-1-piperazinyl)-1,3,5-triazine-2,4-triamine | Parallel synthesis method C | (492)incorrect MW observed | 70 | compound not observed after prep HPLC | preparative HPLC |
| 99 | 1-[3-((4-(cycloheptylamino)-6-[3-fluoro-4-methoxyphenyl)amino)-1,3,5-triazin-2-yl)amino)propyl]-2-pyrrolidinone | Parallel synthesis method C | (471)472.3 | 96 | 29 | preparative HPLC |
| 100 | N2-cycloheptyl-N4-(3-fluoro-4-methoxyphenyl)-N6-[3-(1H-imidazol-1-yl)propyl]-1,3,5-triazine-2,4,6-triamine | Parallel synthesis method C | (454)455.3 | 94 | 24 | preparative HPLC |

TABLE 3

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 160 | 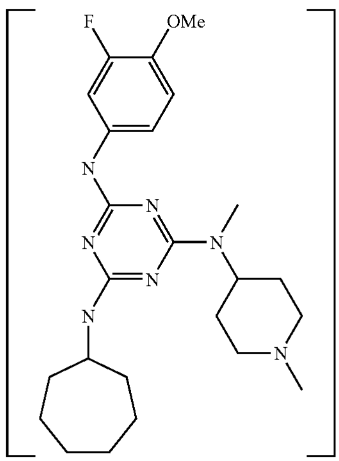 | HCl N2-cycloheptyl-N4-(3-fluoro-4-methoxy-phenyl)-N6-methyl-N6-(1-methyl-piperidin-4-yl)-1,3,5-triazine-2,4,6-triamine hydrogen chloride | ++ | 4–5 |
| 95 | 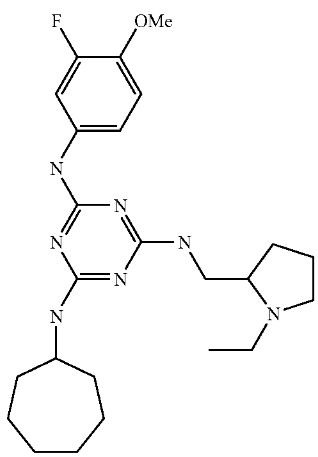 | N2-cycloheptyl-N4-(1-ethyl-pyrrolidin-2-ylmethyl)-N6-(3-fluoro-4-methoxy-phenyl)-1,3,5-triazine-2,4,6-triamine | + | 7.3 |
| 26 | 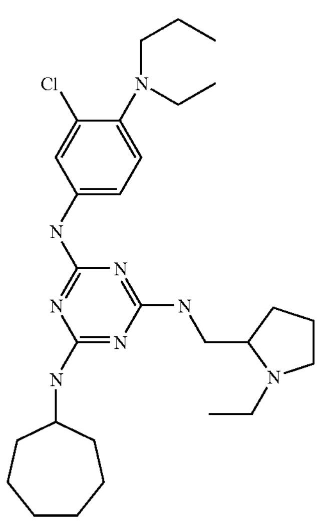 | N2-(3-chloro-4-diethylamino-phenyl)-N4-cycloheptyl-N6-(1-ethyl-pyrrolidin-2-ylmethyl)-1,3,5-triazine-2,4,6-triamine | + | 7.73 |

TABLE 3-continued

*Triazine compounds active in anti-proliferation assay (perlecan), generally useful in treating cardiovascular disorders associated with*

| Patent # | STRUCTURE | CAS NAME | Activity (note 1) | Avg IC-50 |
|---|---|---|---|---|
| 139 | 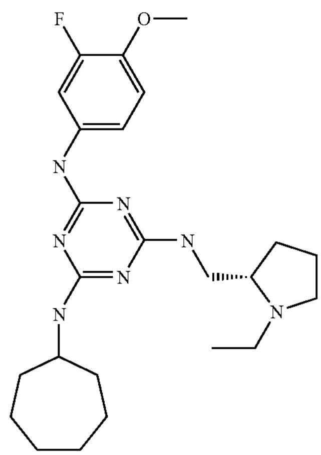 | N2-cycloheptyl-N4-((S)-1-ethyl-pyrrolidin-2-ylmethyl)-N6-(3-fluoro-4-methoxy-phenyl)-1,3,5-triazine-2,4,6-triamine | ++ | 4–5 |
| 140 | 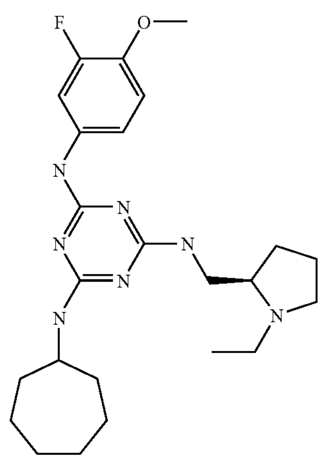 | N2-cycloheptyl-N4-((R)-1-ethyl-pyrrolidin-2-ylmethyl)-N6-(3-fluoro-4-methoxy-phenyl)-1,3,5-triazine-2,4,6-triamine | ++ | 4–5 |
| 163 | 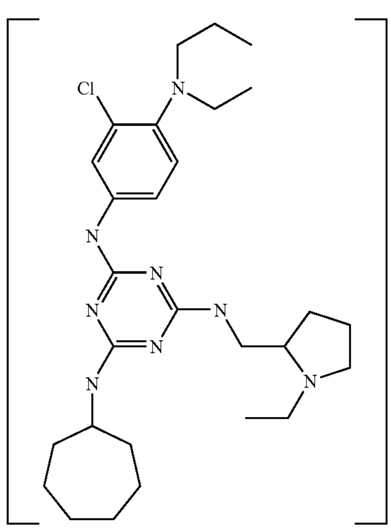 | HCl N2-(3-chloro-4-diethylamino-phenyl)-N4-cycloheptyl-N6-(1-ethyl-pyrrolidin-2-ylmethyl)-1,3,5-triazine-2,4,6-triamine hydrogen chloride | + | 8–10 |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 123 | 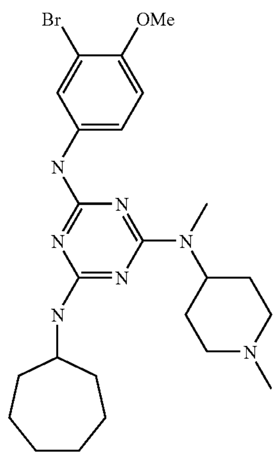 | N2-(3-bromo-methoxy-phenyl)-N4-cycloheptyl-N6-methyl-N6-(1-methyl-piperidin-4-yl)-1,3,5-triazine-2,4,6-triamine | + | |
| 170 | 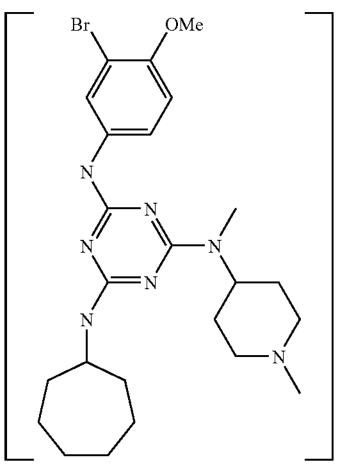 | HCl N2-(3-bromo-methoxy-phenyl)-N4-cycloheptyl-N6-methyl-N6-(1-methyl-piperidin-4-yl)-1,3,5-triazine-2,4,6-triamine hydrogen chloride | + | 8–9 |
| 137 | 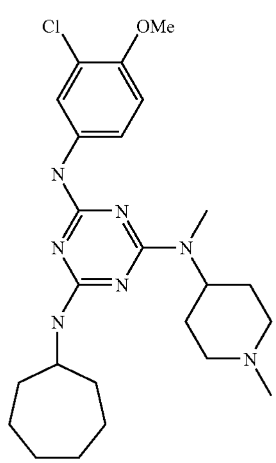 | N2-(3-chloro-methoxy-phenyl)-N4-cycloheptyl-N6-methyl-N6-(1-methyl-piperidin-4-yl)-1,3,5-triazine-2,4,6-triamine | ++ | 4–5 |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 103 | 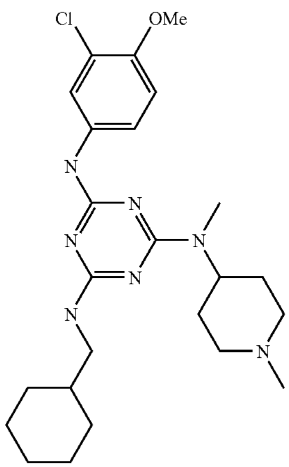 | N2-(3-chloro-4-methoxy-phenyl)-N4-cyclohexylmethyl-N6-methyl-N6-(1-methyl-piperidin-4-yl)-1,3,5-triazine-2,4,6-triamine | + | ~7 uM |
| 105 | 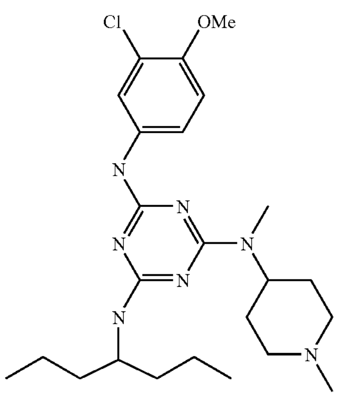 | N2-(3-chloro-4-methoxy-phenyl)-N4-methyl-N4-(1-methyl-piperidin-4-yl)-N6-(1-propyl-butyl)-1,3,5-triazine-2,4,6-triamine | + | ~7 uM |
| 148 | 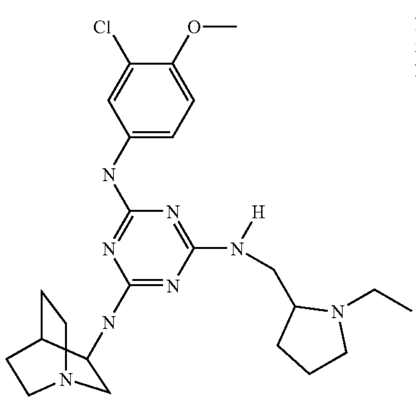 | N2-(1-aza-bicyclo[2.2.2]oct-3-yl)-N4-(3-chloro-4-methoxy-phenyl)-N6-(1-ethyl-pyrrolidin-2-ylmethyl)-1,3,5-triazine-2,4,6-triamine | ++ | less than 5 uM |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 146 | 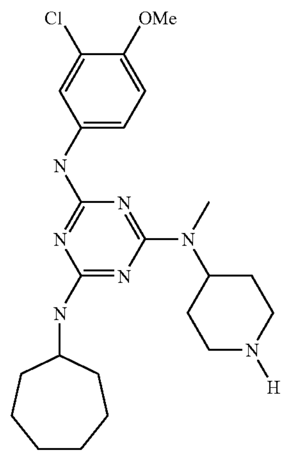 | $N^2$-(3-chloro-4-methoxy-phenyl)-$N^4$-cycloheptyl-$N^6$-methyl-$N^6$-piperidin-4-yl-1,3,5-triazine-2,4,6-triamine | +++ | ~2.2 |
| 138 | 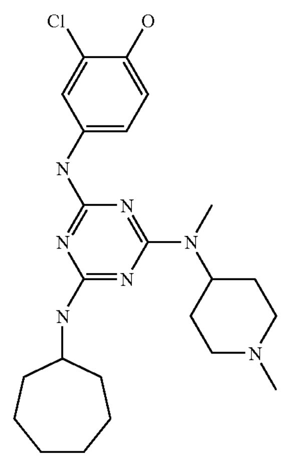 | 2-chloro-4-{4-cycloheptylamino-6-[methyl-(1-methyl-piperidin-4-yl-amino]-1,3,5-triazin-2-ylamino}-phenol | ++ | 4.03 uM |
| 135 | 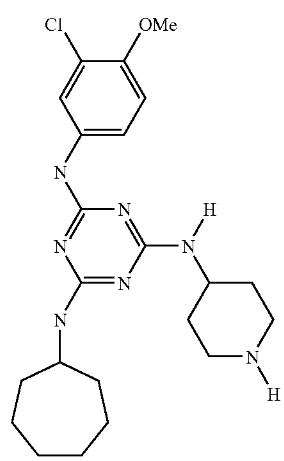 | N2-(3-chloro-4-methoxy-phenyl)-N4-cyclohepty-N6-piperidin-4-yl-1,3,5-triazine-2,4,6-triamine | ++ | 5.83 uM |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 169 | 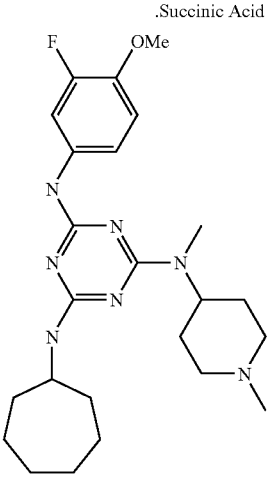 .Succinic Acid | N2-cycloheptyl-N4-(3-fluoro-4-methoxy-phenyl)-N6-methyl-N6-(1-methyl-piperidin-4-yl)-1,3,5-triazine-2,4,6-triamine succinate | + | 7.2 uM |
| 167 | 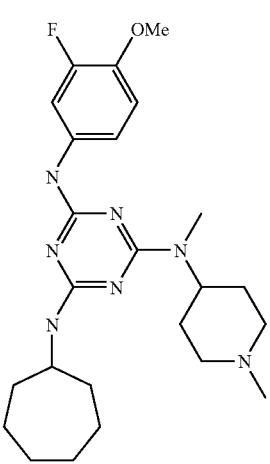 .Maleic Acid | N2-cycloheptyl-N4-(3-fluoro-4-methoxy-phenyl)-N6-methyl-N6-(1-methyl-piperidin-4-yl)-1,3,5-triazine-2,4,6-triamine maleate | + | 6.8 uM |
| 159 | 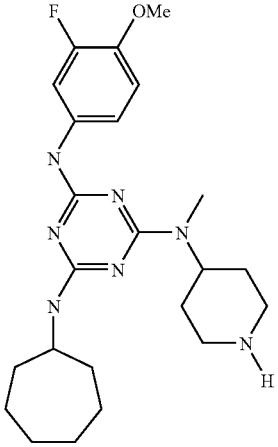 | $N^2$-Cycloheptyl-$N^4$-(3-fluoro-4-methoxy-phenyl)-$N^6$-methyl-$N^6$-piperidin-4-yl-1,3,5-tnazine-2,4,6-triamine | ++ | 5.7–6.9 uM |

TABLE 3-continued

Triazine compounds active in anti-proliferation assay (perlecan), generally useful in treating cardiovascular disorders associated with

| Patent # | STRUCTURE | CAS NAME | Activity (note 1) | Avg IC-50 |
|---|---|---|---|---|
| 125 | (structure) | 6-chloro-N-cyclohexylmethyl-N'-(3-fluoro-4-methoxy-phenyl)-[1,3,5]triazine-2,4-diamine | + | 10 uM |
| 127 | (structure) | 6-Chloro-N-cycloheheptyl-N'-(3-fluoro-4-methoxy-phenyl)-[1,3,5]triazine-2,4-diamine | + | 10 uM |

NOTE 1:
The activity scale is as follows (inclusive): (1) "+++" = IC50 < 3 uM; (2) "++" = IC50 is 3–7 uM; and (3) "+" = IC50 is > 7 uM.

TABLE 4A

Triazine compounds that are toxic or cause cell death
for use in oncology applications

| Patent Number | STRUCTURE | Name Generated Name by Autonom™ | Toxicity |
|---|---|---|---|
| 93 | 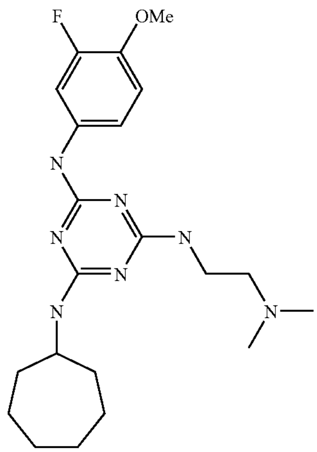 | N2-cycloheptyl-N4-[2-(dimethylamino)ethyl]-N6-(3-fluoro-4-methoxyphenyl)-1,3,5-triazine-2,4,6-triamine | toxic |
| 3 | 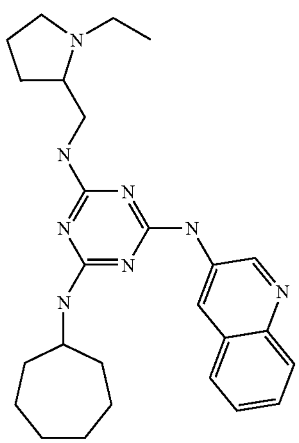 | N2-cycloheptyl-N4-[(1-ethyl-2-pyrrolidinyl)methyl]-N6-(3-quinolinyl)-1,3,5-triazine-2,4,6-triamine | toxic |
| 5 | 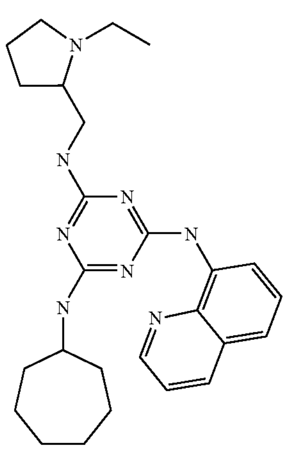 | N2-cycloheptyl-N4-[(1-ethyl-2-pyrrolidinyl)methyl]-N6-(8-quinolinyl)-1,3,5-triazine-2,4,6-triamine | toxic |

TABLE 4A-continued

Triazine compounds that are toxic or cause cell death for use in oncology applications

| Patent Number | STRUCTURE | Name Generated Name by Autonom™ | Toxicity |
|---|---|---|---|
| 6 | 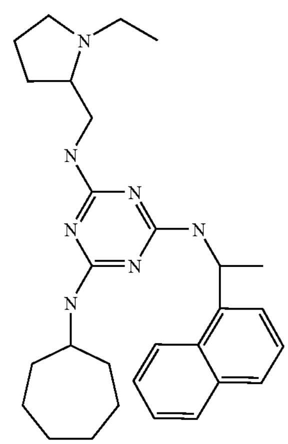 | N2-cycloheptyl-N4-[(1-ethyl-2-pyrrolidinyl)methyl]-N6-[1-(2-naphthyl)ethyl]-1,3,5-triazine-2,4,6-triamine | toxic |
| 7 | 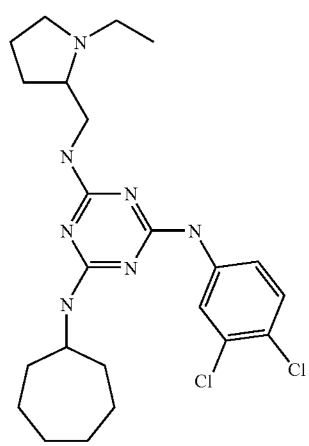 | N2-cycloheptyl-N4-(3,4-dichlorophenyl)-N6-[(1-ethyl-2-pyrrolidinyl)methyl]-1,3,5-triazine-2,4,6-triamine | toxic |
| 8 | 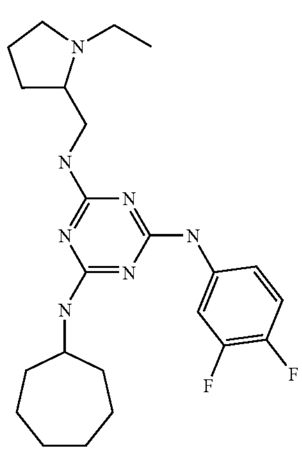 | N2-cycloheptyl-N4-(3,4-difluorophenyl) N6-[(1-ethyl-2-pyrrolidinyl)methyl]-1,3,5-triazine-2,4,6-triamine | toxic |

TABLE 4A-continued

Triazine compounds that are toxic or cause cell death for use in oncology applications

| Patent Number | STRUCTURE | Name Generated Name by Autonom™ | Toxicity |
|---|---|---|---|
| 9 | 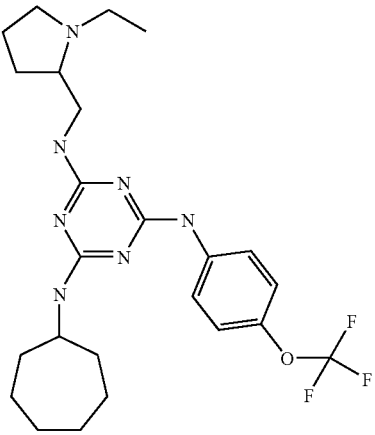 | N2-cycloheptyl-N4-[(1-ethyl-2-pyrrolidinyl)methyl]-N6-[4-(triflouromethoxy)phenyl]-1,3,5-triazine-2,4,6-triamine | toxic |
| 12 | 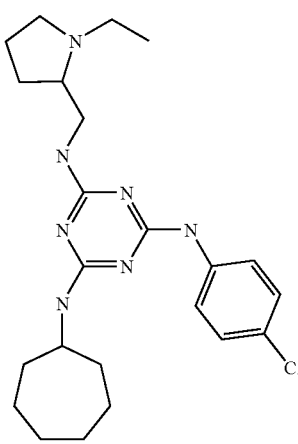 | N2-(4-chlorophenyl)-N4-cycloheptyl-N6-[(1-ethyl-2-pyrrolidinyl)methyl]-1,3,5-triazine-2,4,6-triamine | toxic |
| 13 | 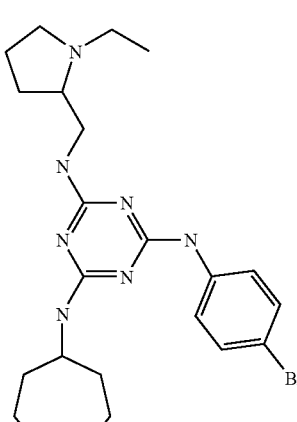 | N2-(4-bromophenyl)-N4-cycloheptyl-N6-[(1-ethyl-2-pyrrolidinyl)methyl]-1,3,5-triazine-2,4,6-triamine | toxic |

TABLE 4A-continued

Triazine compounds that are toxic or cause cell death
for use in oncology applications

| Patent Number | STRUCTURE | Name Generated Name by Autonom™ | Toxicity |
|---|---|---|---|
| 14 | 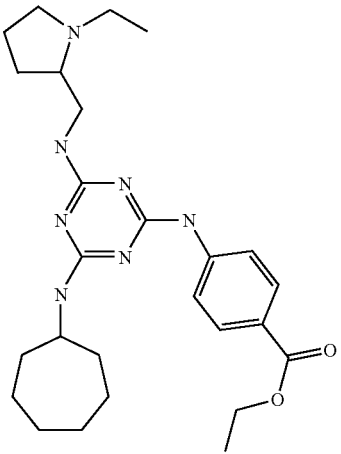 | 4-[(4-(cycloheptylamino)-6-{[(1-ethyl-2-pyrrolidinyl)methyl]amino}-1,3,5-triazin-2-yl)-amino]benzoate | toxic |
| 16 | 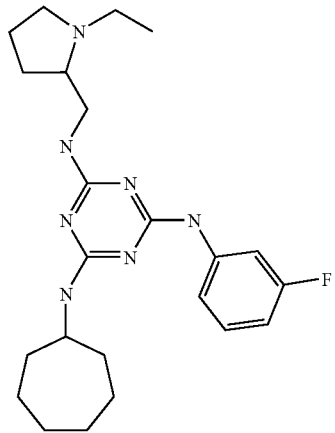 | N2-cycloheptyl-N4-[(1-ethyl-2-pyrrolidinyl)methyl]-N6-(3-fluorophenyl)-1,3,5-triazine-2,4,6-triamine | toxic |
| 21 | 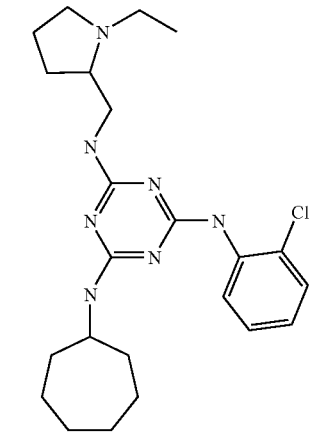 | N2-(2-chlorophenyl)-N4-cycloheptyl-N6-[(1-ethyl-2-pyrrolidinyl)methyl]-1,3,5-triazine-2,4,6-triamine | toxic |

TABLE 4A-continued

Triazine compounds that are toxic or cause cell death for use in oncology applications

| Patent Number | STRUCTURE | Name Generated Name by Autonom™ | Toxicity |
|---|---|---|---|
| 22 | 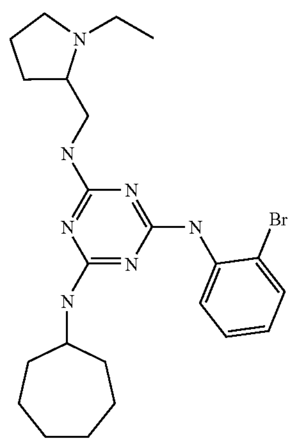 | N2-(2-bromophenyl)-N4-cycloheptyl-N6-[(1-ethyl-2-pyrrolidinyl)methyl]-1,3,5-triazine-2,4,6-triamine | toxic |
| 36 | 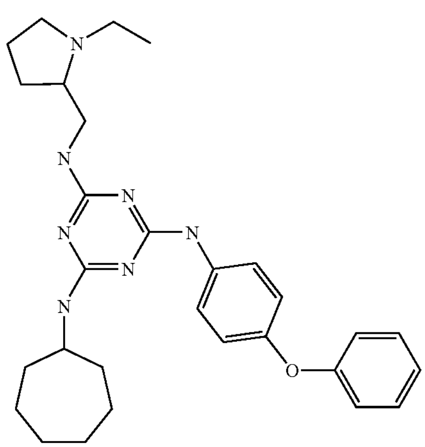 | N2-cycloheptyl-N4-[(1-ethyl-2-pyrrolidinyl)methyl]-N6-(4-phenoxyphenyl)-1,3,5-triazine-2,4,6-triamine | toxic |
| 47 | 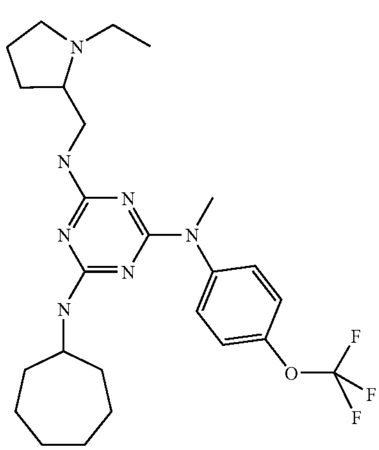 | N2-cycloheptyl-N4-[(1-ethyl-2-pyrrolidinyl)methyl]-N6-methyl-N6-[2-(trifluoromethoxy)phenyl]-1,3,5-triazine-2,4,6-triamine | toxic |

TABLE 4A-continued

Triazine compounds that are toxic or cause cell death for use in oncology applications

| Patent Number | STRUCTURE | Name Generated Name by Autonom™ | Toxicity |
|---|---|---|---|
| 54 | 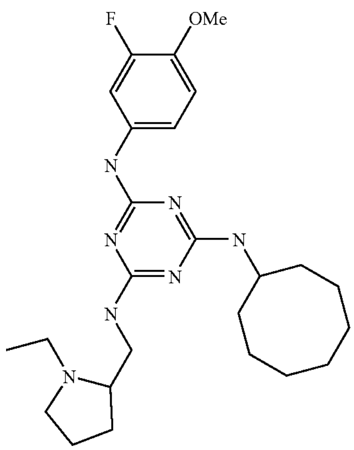 | N2-cyclooctyl-N4-[(1-ethyl-2-pyrrolidinyl)methyl]-N6-(4-fluoro-3-methoxyphenyl)-1,3,5-triazine-2,4,6-triamine | toxic |
| 59 | 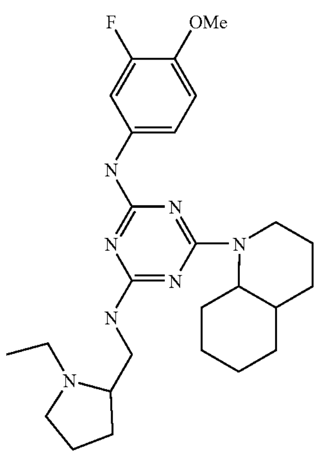 | N2-[(1-ethyl-2-pyrrolidinyl)methyl]-N4-(4-fluoro-3-methoxyphenyl)-6-octahydro-1(2H)-quinolinyl-1,3,5-triazine-2,4-diamine | toxic |
| 121 | 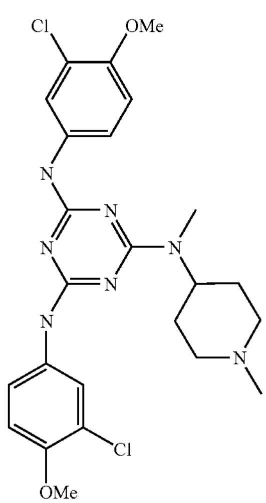 | N,N'-Bis-(3-chloro-4-methoxy-phenyl)-N''-methyl-N''-(1-methyl-piperidin-4-yl)-[1,3,5]triazine-2,4,6-triamine | Toxic by toxicity assay at 0.75 uM. Starts blunting by 1 uM and rounding by 5 uM |

TABLE 4A-continued

Triazine compounds that are toxic or cause cell death
for use in oncology applications

| Patent Number | STRUCTURE | Name Generated Name by Autonom™ | Toxicity |
|---|---|---|---|
| 111 | 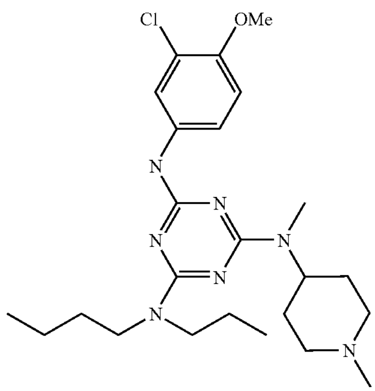 | N-Butyl-N'-(3-chloro-4-methoxy-phenyl)-N''-methyl-N''-(1-methyl-piperin-4-yl)-N-propyl-[1,3,5]triazine-2,4,6-triamine | Toxic by eye at 50 and 10 uM no blunt/round just death |
| 112 | 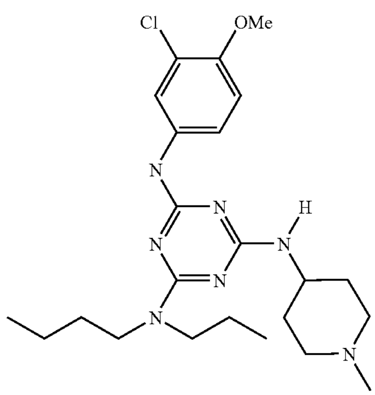 | N2-Butyl-N4-(3-chloro-4-methoxy-phenyl)-N6-methyl-N6-piperidin-4-yl-N2-propyl-1,3,5-triazine-2,4,6-triamine | Toxic by eye at 50 and 10 uM no blunt/round just death |
| 136 | 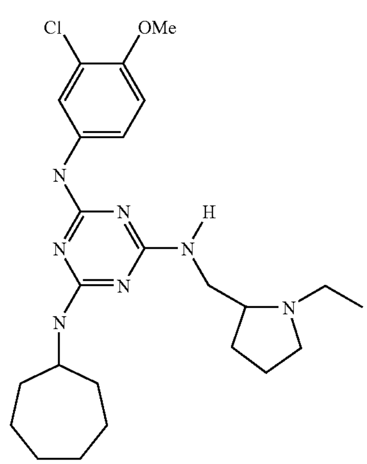 | N-(3-Chloro-4-methoxy-phenyl)-N'-cycloheptyl-N''-(1-ethyl-pyrrolidin-2-ylmethyl)-[1,3,5]triazine-2,4,6-triamine | Nothing but cell debris at 3 uM very toxic |

TABLE 4A-continued
Triazine compounds that are toxic or cause cell death for use in oncology applications
| Patent Number | STRUCTURE | Name Generated Name by Autonom™ | Toxicity |
|---|---|---|---|
| 119 | 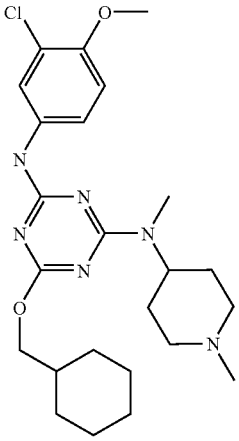 | N2-(3-chloro-4-methoxyphenyl)-6-cyclohexylmethoxy-N4-methyl-N4-(1-methyl-piperidin-4-yl)-1,3,5-triazine-2,4-diamine | toxic |

TABLE 4B

Triazine compounds toxic to endothelial cells when AGE stimulated

| Compound Number | STRUCTURE | Name Generated by Autonom™ | Toxic (AGE-treated) | Toxic (TNF-treated) | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 121 | [structure] | N,N'-Bis-(3-chloro-4-methoxy-phenyl)-N''-methyl-N''-(4-methyl-cyclohexyl)-[1,3,5]triazine-2,4,6-triamine | toxic | n.d. | total cell death @ 10 uM [50 @ 5 uM, but some toxicity (~20%)] | n.d. |

TABLE 4B-continued

Triazine compounds toxic to endothelial cells when AGE stimulated

| Compound Number | STRUCTURE | Name Generated by Autonom™ | Toxic (AGE-treated) | Toxic (TNF-treated) | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 168 | 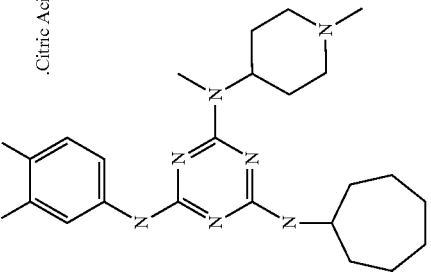 | N2-cycloheptyl-N4-(3-fluoro-4-methoxy-phenyl)-N6-methyl-N6-(1-methyl-piperidin-4-yl)-1,3,5-triazine-2,4,6-triamine citrate salt | toxic | n.d. | total cell death @ 10 uM [40 @ 5 uM] | n.d. |
| 159 | 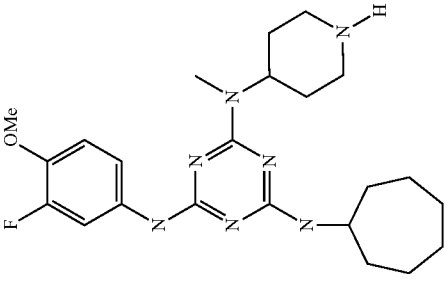 | N2-Cycloheptyl-N4-(3-fluoro-4-methoxy-phenyl)-N6-methyl-N6-piperidin-4-yl-1,3,5-triazine-2,4,6-triamine | toxic | n.d. | total cell death @ 5 and 10 uM | n.d. |

TABLE 4B-continued

Triazine compounds toxic to endothelial cells when AGE stimulated

| Compound Number | STRUCTURE | Name Generated by Autonom™ | Toxic (AGE-treated) | Toxic (TNF-treated) | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 167 | .Maleic Acid | N2-cycloheptyl-N4-(3-fluoro-4-methoxy-phenyl)-N6-methyl-N6-(1-methyl-piperidin-4-yl)-1,3,5-triazine-2,4,6-triamine maleate salt | toxic | n.d. | total cell death @ 10 uM [25 @ 5 uM] | n.d. |
| 169 | .Succinic Acid | N2-cycloheptyl-N4-(3-fluoro-4-methoxy-phenyl)-N6-methyl-N6-(1-methyl-piperidin-4-yl)-1,3,5-triazine-2,4,6-triamine succinate salt | toxic | n.d. | total cell death @ 10 uM [45 @ 5 uM] | n.d. |

TABLE 4B-continued

Triazine compounds toxic to endothelial cells when AGE stimulated

| Compound Number | STRUCTURE | Name Generated by Autonom™ | Toxic (AGE-treated) | Toxic (TNF-treated) | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 148 | 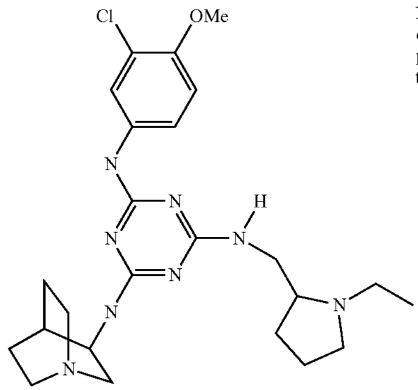 | N-(1-Aza-bicyclo[2.2.2]oct-3-yl)-N'-(3-chloro-4-methoxy-phenyl)-N''-(1-ethyl-pyrrolidin-2-ylmethyl)-[1,3,5]triazine-2,4,6-triamine | toxic | n.d. | total cell death @ 10 uM [60 @ 5 uM] | n.d. |
| 134 | 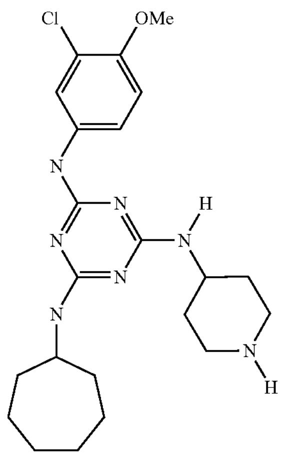 | N-(1-benzyl-piperidin-4-yl)-N'-(3-chloro-4-methoxy-phenyl)-N''-cycloheptyl-[1,3,5]-2,4,6-triamine | toxic | n.d. | total cell death @ 10 uM [55 @ 5 uM] | n.d. |

TABLE 4B-continued

Triazine compounds toxic to endothelial cells when AGE stimulated

| Compound Number | STRUCTURE | Name Generated by Autonom™ | Toxic (AGE-treated) | Toxic (TNF-treated) | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 135 | 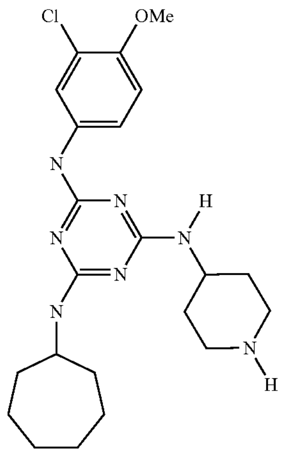 | N2-(3-chloro-4-methoxy-phenyl)-N4-cycloheptyl-N6-piperidin-4-yl-1,3,5-triazine-2,4,6-triamine | toxic | n.d. | total cell death @ 10 uM [60 @ 5 uM] | n.d. |
| 138 | 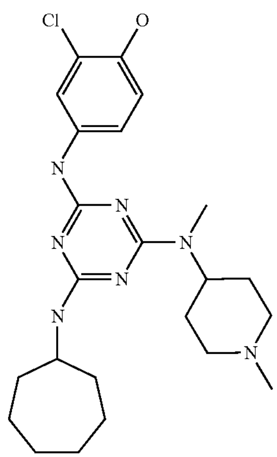 | 2-chloro-4-[4-cycloheptylamino-6-[methyl-(1-methyl-piperidin-4-yl-amino]-1,3,5-triazin-2-ylamino]-phenol | toxic | n.d. | toxic | n.d. |

TABLE 5

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 76 | [structure] | N2-cycloheptyl-N4-ethyl-N6-(3-fluoro-4-methoxyphenyl)-1,3,5-triazine-2,4,6-triamine | ++++ | n.d. | 18 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 77 | 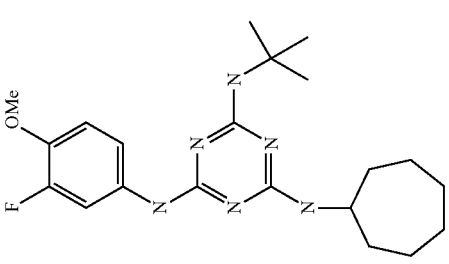 | N2-(tert-butyl)-N4-cycloheptyl-N6-(3-fluoro-4-methoxyphenyl)-1,3,5-triazine-2,4,6-triamine | ++++ | n.d. | 21 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 78 | 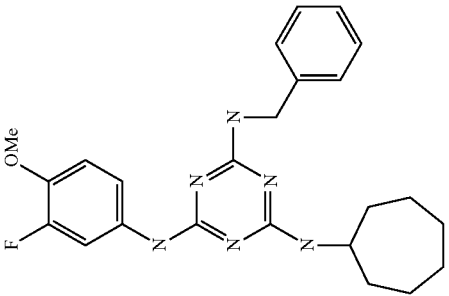 | N2-benzyl-N4-cycloheptyl-N6-(3-fluoro-4-methoxyphenyl)-1,3,5-triazine-2,4,6-triamine | +++ | n.d. | 47 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 82 | [structure] | N2-cycloheptyl-N4-(3-fluoro-4-methoxyphenyl)-6-(1-pyrrolidinyl)-1,3,5-triazine-2,4-diamine | +++ | n.d. | 34 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 83 | 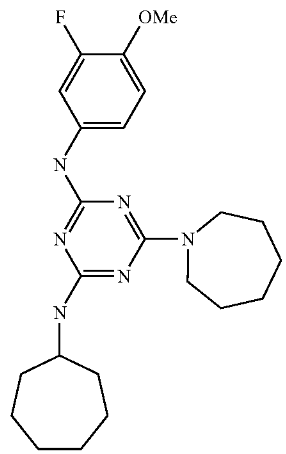 | N2-cycloheptyl-N4-(3-fluoro-4-methoxyphenyl)-6-hexahydro-1H-azepin-1-yl-1,3,5-triazine-2,4-diamine | ++++ | n.d. | 18 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 84 | 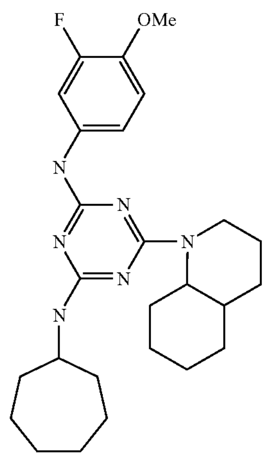 | N2-cycloheptyl-N4-(3-fluoro-4-methoxyphenyl)-6-octahydro-1(2H)-quinolinyl-1,3,5-triazine-2,4-diamine | +++ | n.d. | 33 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 85 | 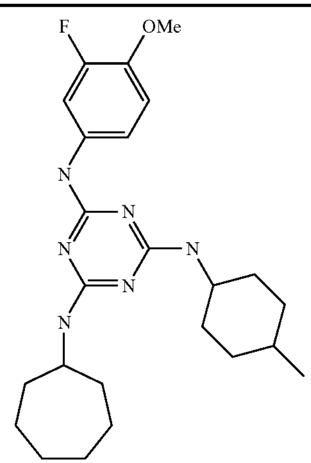 | N2-cycloheptyl-N4-(3-fluoro-4-methoxyphenyl)-N6-(4-methylcyclohexyl)-1,3,5-triazine-2,4,6-triamine | +++ | n.d. | | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 86 | 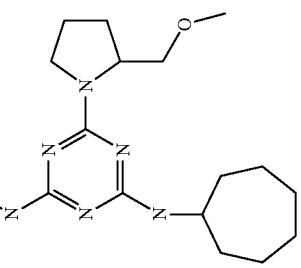 | N2-cycloheptyl-N4-(3-fluoro-4-methoxyphenyl)-6-[(2S)-2-(methoxymethyl)-1-pyrrolidinyl]-1,3,5-triazine-2,4-diamine | ++++ | n.d. | 19 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 87 | 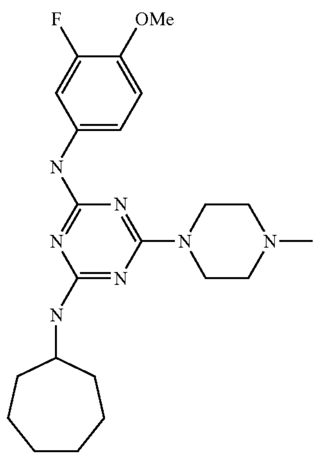 | N2-cycloheptyl-N4-(3-fluoro-4-methoxyphenyl)-6-(4-methyl-1-piperazinyl)-1,3,5-triazine-2,4-diamine | n.d. | ++++ | n.d. | 5 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 88 | 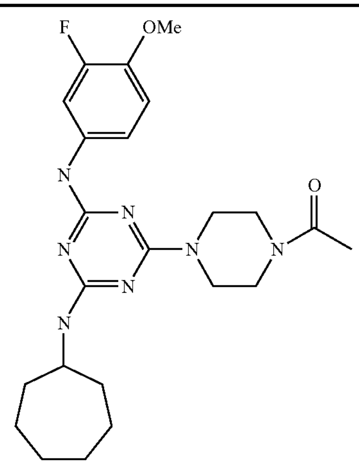 | 6-(4-acetyl-1-piperazinyl)-N2-cycloheptyl-N4-(3-fluoro-4-methoxyphenyl)-1,3,5-triazine-2,4-diamine | ++++ | n.d. | 19 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 91 | 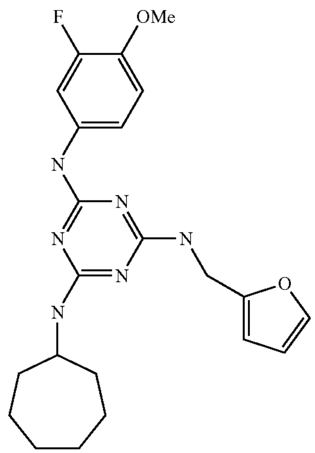 | N2-cycloheptyl-N4-(3-fluoro-4-methoxyphenyl)-N6-(2-furanylmethyl)-1,3,5-triazine-2,4,6-triamine | +++ | n.d. | 28 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 93 | 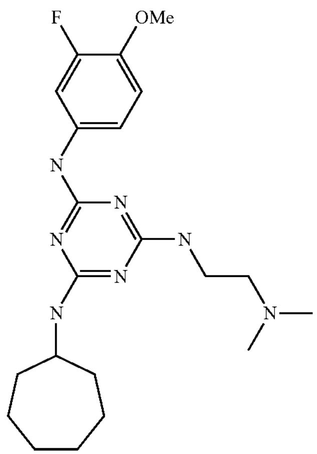 | N2-cycloheptyl-N4-[2-(dimethylamino)ethyl]-N6-(3-fluoro-4-methoxyphenyl)-1,3,5-triazine-2,4,6-triamine | ++++ | ++++ | 13 | 6 (IC50 = 3.36) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 94 | 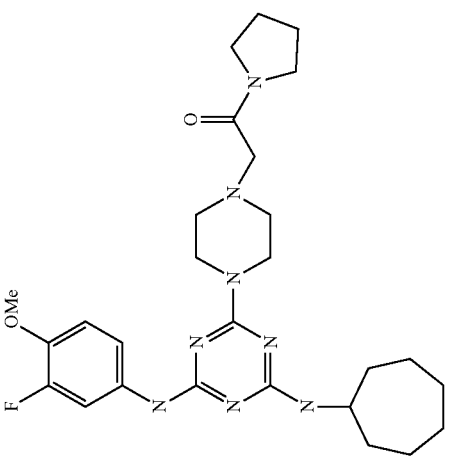 | N2-cycloheptyl-N4-(3-fluoro-4-methoxyphenyl)-6-{4-[2-oxo-(1-pyrrolidinyl)ethyl]-1-piperazinyl}-1,3,5-triazine-2,4-diamine | +++ | ++++ | 32 | 10 (IC50 = 5.8) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 95 | (structure) | N-Cycloheptyl-N'-(1-ethyl-pyrrolidin-2-ylmethyl)-N''-(3-fluoro-4-methoxy-phenyl)-[1,3,5]triazine-2,4,6-triamine | ++++ | ++++ | 5 (IC50 = 28) | 1 (IC50 = 6.6) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 96 | 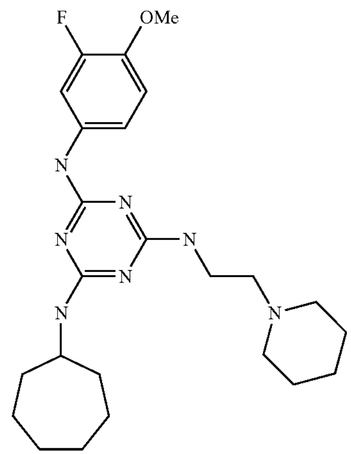 | N2-cycloheptyl-N4-(3-fluoro-4-methoxyphenyl)-N6-[2-(1-piperidinyl)ethyl]-1,3,5-triazine-2,4,6-triamine | ++++ | n.d. | 6 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 99 | 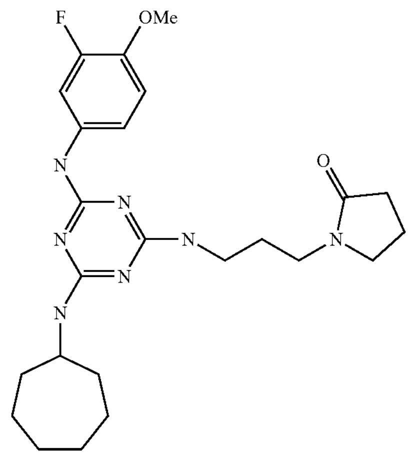 | 1-[3-({4-(cycloheptylamino)-6-[(3-fluoro-4-methoxyphenyl)amino]-1,3,5-triazin-2-yl}aminopropyl]-2-pyrrolidinone | +++ | ++++ | 39 | 8 (IC50 = 6.04) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 100 | 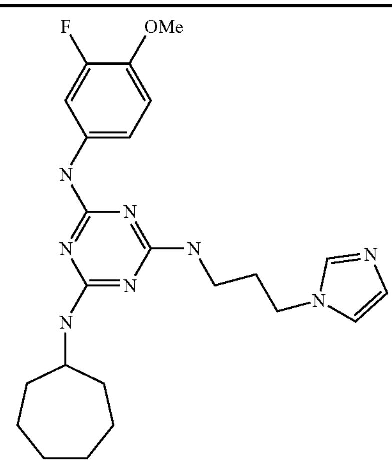 | N2-cycloheptyl-N4-(3-fluoro-4-methoxyphenyl)-N6-[3-(1H-imidazol-1-yl)propyl]-1,3,5-triazine-2,4,6-triamine | n.d. | ++++ | n.d. | 1 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 3 | N2-cycloheptyl-N4-[(1-ethyl-2-pyrrolidinyl)methyl]-N6-(3-quinolinyl)-1,3,5-triazine-2,4,6-triamine | 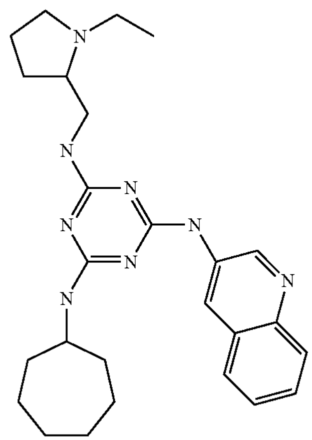 | n.d. | ++++ | n.d. | 1 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 4 | N2-cycloheptyl-N4-[(1-ethyl-2-pyrrolidinyl)methyl]-N6-(6-quinolinyl)-1,3,5-triazine-2,4,6-triamine | 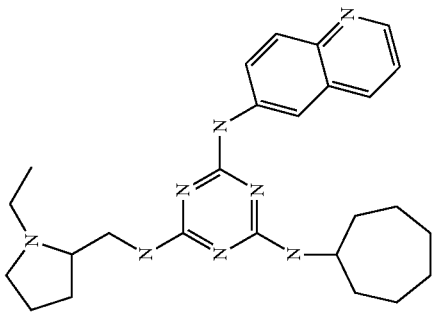 | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 10 | 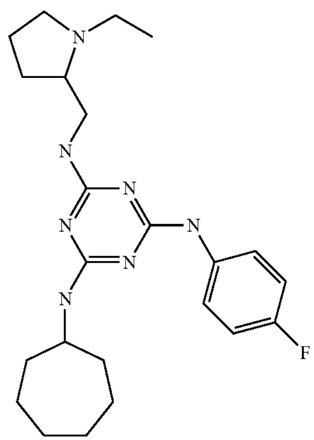 | N2-cycloheptyl-N4-[(1-ethyl-2-pyrrolidinyl)methyl]-N6-(4-fluorophenyl)-1,3,5-triazine-2,4,6-triamine | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 11 | 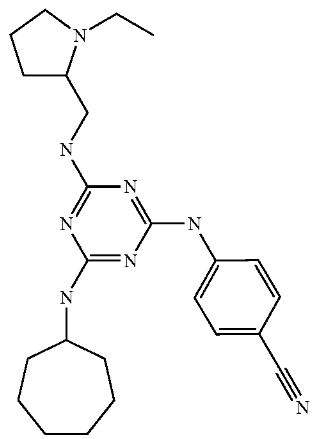 | 4-[(4-(cycloheptyl)amino)-6-[[(1-ethyl-2-pyrrolidinyl)methyl]amino}-1,3,5-triazin-2-yl)-amino]benzonitrile | n.d. | ++++ | n.d. | 1 (IC50 = 8.87) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 24 | 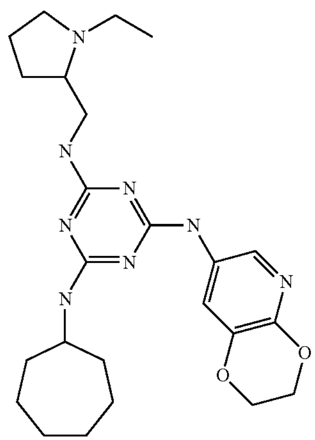 | N2-cycloheptyl-N4-(2,3-dihydro-1,4-benzodioxin-6-yl)-N6-[(1-ethy-2-pyrrolidinyl)methyl]-1,3,5-triazine-2,4,6-triamine | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 25 | 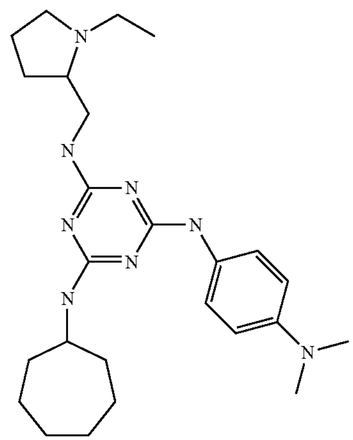 | N2-cycloheptyl-N4-[4-(dimethylamino)phenyl]-N6-[(1-ethyl-2-pyrrolidinyl)methyl]-1,3,5-triazine-2,4,6-triamine | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 26 | 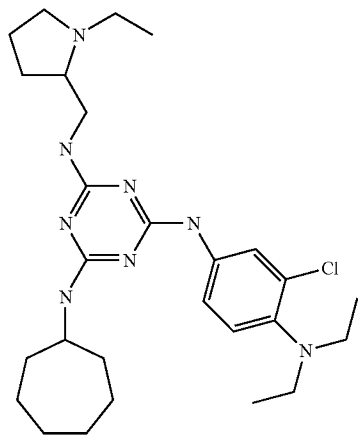 | N²-(3-chloro-4-diethylamino-phenyl)-N⁴-cycloheptyl-N⁶-(1-ethyl-pyrrolidin-2-ylmethyl)-1,3,5-triazine-2,4,6-triamine | ++++ | n.d. | 1 (over 50% of cells were floating) | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 27 | 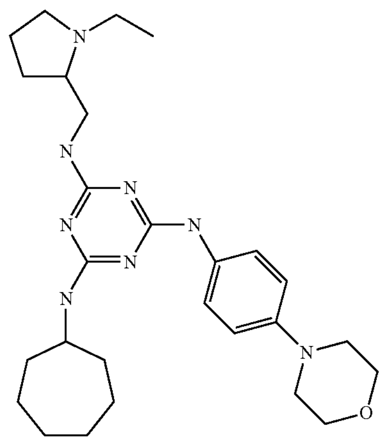 | N2-cycloheptyl-N4-[(1-ethyl-2-pyrrolidinyl)methyl]-N6-[4-(4-morpholinyl)phenyl]-1,3,5-triazine-2,4,6-triamine | ++++ | ++++ | 3 | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 28 | 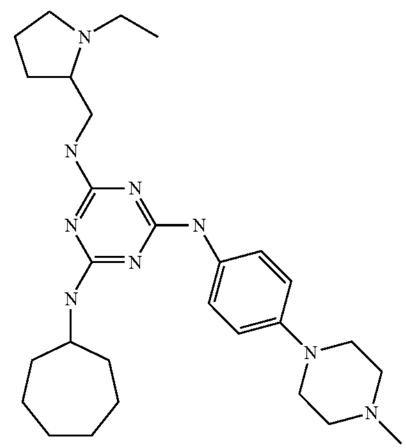 | N2-cycloheptyl-N4-[(1-ethyl-2-pyrrolidinyl)methyl]-N6-[4-(4-methyl-1-piperazinyl)phenyl]-1,3,5-triazine-2,4,6-triamine | ++++ | n.d. | 23 | n.d. |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 29 | N-{4-[(4-(cycloheptylamino)-6-{[(1-ethyl-2-pyrrolidinyl)methyl]amino}-1,3,5-triazin-2-yl-amino]phenyl}acetamide | 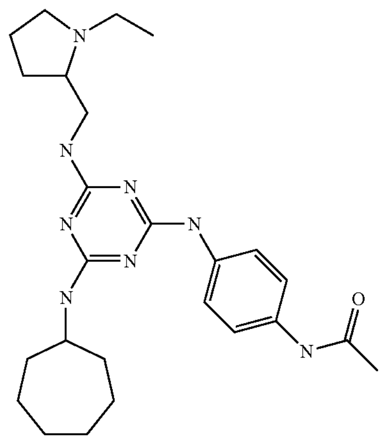 | ++++ | ++++ | 13 | 7 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 30 | N-{3-[(4-(cycloheptylamino)-6-{[(1-ethyl-2-pyrrolidinyl)methyl]amino}-1,3,5-triazin-2-yl)-amino]phenyl}acetamide | 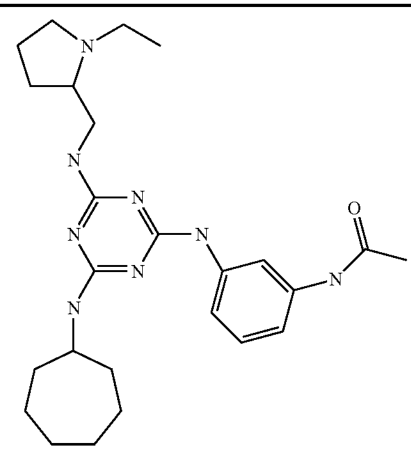 | ++++ | ++++ | 9 | 17 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 32 | N2-cycloheptyl-N4-(4-ethoxyphenyl)-N6-[(1-ethyl-2-pyrrolidinyl)methyl]-1,3,5-triazine-2,4,6-triamine) | 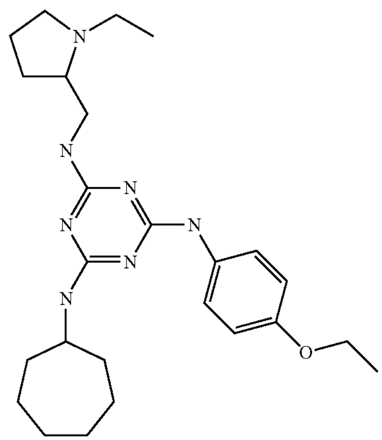 | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 34 | 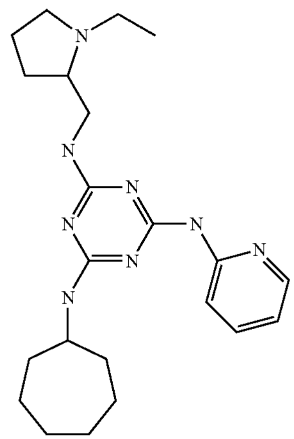 | N2-cycloheptyl-N4-[(1-ethyl-2-pyrrolidinyl)methyl]-N6-(2-pyridinyl)-1,3,5-triazine-2,4,6-triamine | ++++ | ++++ | 3 | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 35 | 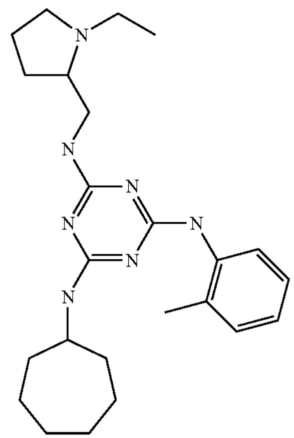 | N2-cycloheptyl-N4-[(1-ethyl-2-pyrrolidinyl)methyl]-N6-(2-methylphenyl)-1,3,5-triazine-2,4,6-triamine | +++ | ++++ | 34 | 4 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 39 | 2-[(4-(cycloheptylamino)-6-[[(1-ethyl-2-pyrrolidinyl)methyl]amino]-1,3,5-triazin-2-yl)-amino]-4-methyl-3-thiophenecarboxamide | 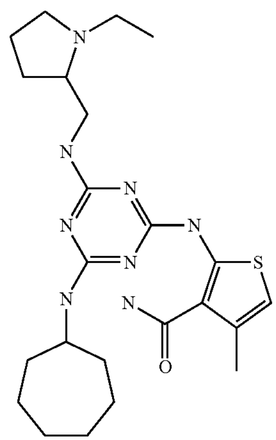 | n.d. | +++ | n.d. | 28 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 40 | 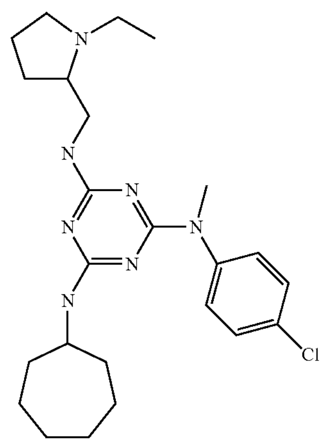 | N2-(4-chlorophenyl)-N4-cycloheptyl-N6-[(1-ethyl-2-pyrrolidinyl)methyl]-N2-methyl-1,3,5-triazine-2,4,6-triamine | n.d. | ++++ | n.d. | 19 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 41 | 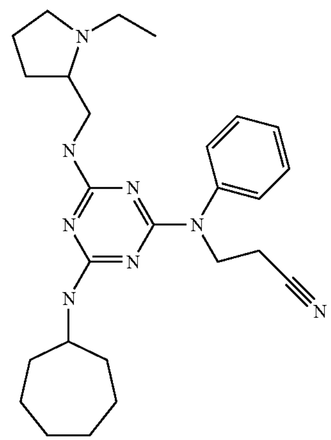 | 3-[(4-(cycloheptyl)amino)-6-[[(1-ethyl-2-pyrrolidinyl)methyl]amino]-1,3,5-triazin-2-yl)-(phenyl)amino]propanenitrile | n.d. | ++++ | n.d. | 18 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 42 | 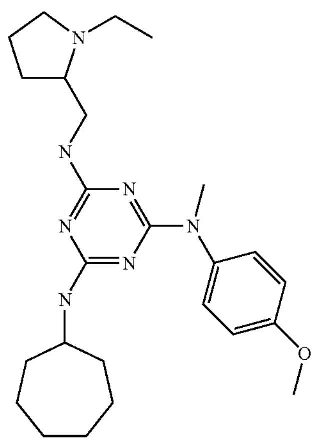 | N2-cycloheptyl-N4-[(1-ethyl-2-pyrrolidinyl)methyl]-N6-(4-methoxyphenyl)-N6-methyl-1,3,5-triazine-2,4,6-triamine | ++++ | ++++ | 1 | 1 |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 43 | N2-cycloheptyl-N4-(2,4-difluorophenyl)-N6-[(1-ethyl-2-pyrrolidinyl)methyl]-N4-methyl-1,3,5-triazine-2,4,6-triamine | 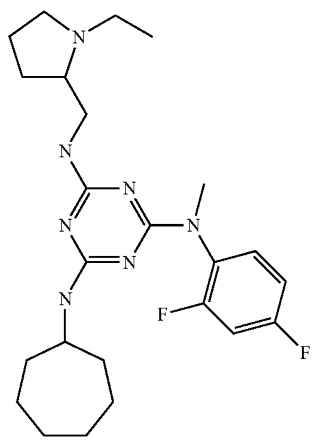 | n.d. | ++++ | n.d. | 4 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 44 | 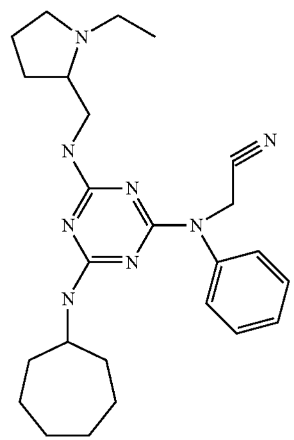 | [(4-(cycloheptylamino)-6-{[(1-ethyl-2-pyrrolidinyl)methyl]amino}-1,3,5-triazin-2-yl)(phenyl)amino]acetonitrile | n.d. | ++++ | n.d. | 1 (IC50 = 7.1) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 45 | 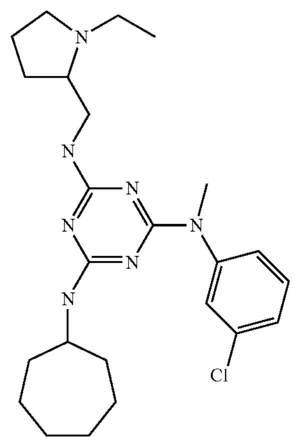 | N2-(3-chlorophenyl)-N4-cycloheptyl-N6-[(1-ethyl-2-pyrrolidinyl)methyl]-N2-methyl-1,3,5-triazine-2,4,6-triamine | n.d. | ++++ | n.d. | 1 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 46 | 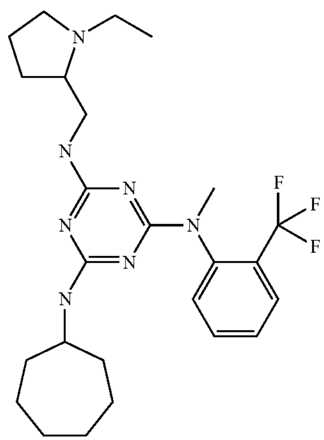 | N2-cycloheptyl-N4-[(1-ethyl-2-pyrrolidinyl)methyl]-N6-methyl-N6-[2-(trifluoromethyl)phenyl]-1,3,5-triazine-2,4,6-triamine | n.d. | ++++ | n.d. | 3 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 48 | 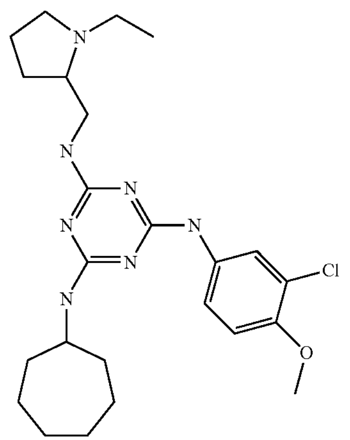 | N2-(3-chloro-4-methoxyphenyl)-N4-cycloheptyl-N6-[(1-ethyl-2-pyrrolidinyl)methyl]-1,3,5-triazine-2,4,6-triamine | +++ | n.d. | 3074 (IC50 = 4.3) | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 51 | (structure) | N2-ethyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |

TABLE 5-continued

Triazine compounds useful in treating inflammatory disorders generally, and all diseases related to inhibition of IL6.

| Patent Number | Name Generated by Autonom(TM) | STRUCTURE | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 52 | N2-(tert-butyl)-N4-[(1-ethyl-2-pyrrolidinyl)methyl]-N6-(3-fluoro-4-methoxyphenyl)-1,3,5-triazine-2,4,6-triazmine | 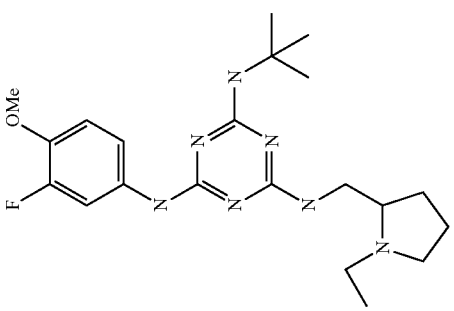 | ++++ | +++ | 1 | 35 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 53 | 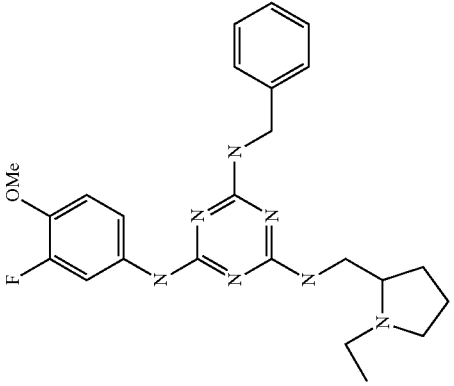 | N2-benzyl-N4-[(1-ethyl-2-pyrrolidinyl)methyl]-N6-(3-fluoro-4-methoxyphenyl)-1,3,5-triazine-2,4,6-triamine | ++++ | +++ | 1 | 32 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 55 | 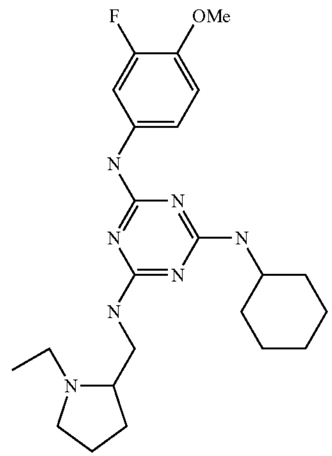 | N2-cyclohexyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 56 | 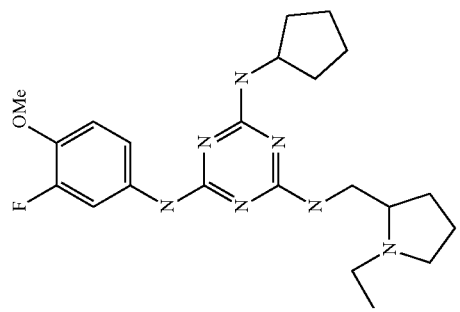 | N2-cyclohexyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 57 | 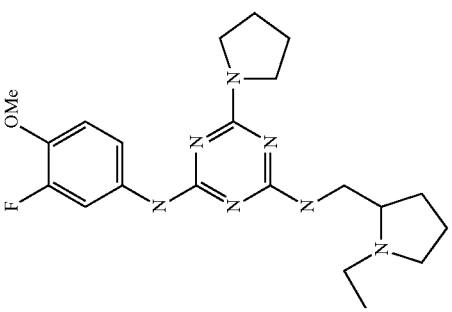 | N2-[(1-ethyl-2-pyrrolidinyl)methyl]-N4-(3-fluoro-4-methoxyphenyl)-6-(1-pyrrolidinyl)-1,3,5-triazine-2,4-diamine | ++++ | +++ | 1 | 25 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 58 | 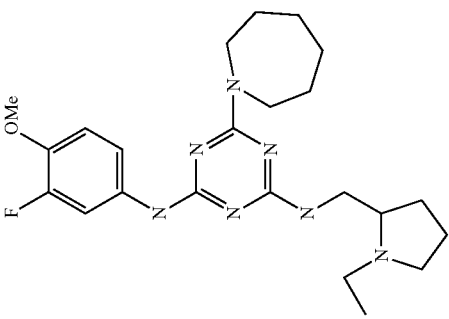 | N2-[(1-ethyl-2-pyrrolidinyl)methyl]-N4-(3-fluoro-4-methoxyphenyl)-6-hexahydro-1H-azepin-1-yl-1,3,5-triazine-2,4-diamine | ++++ | +++ | 1 | 30 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 60 | [structure] | N2-[(1-ethyl-2-pyrrolidinyl)methyl]-N3-(3-fluoro-4-meethoxyphenyl)-N6-(4-methylcyclohexyl)-1,3,5-triazine-2,4,6-triamine | ++++ | n.d. | 1 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 61 | 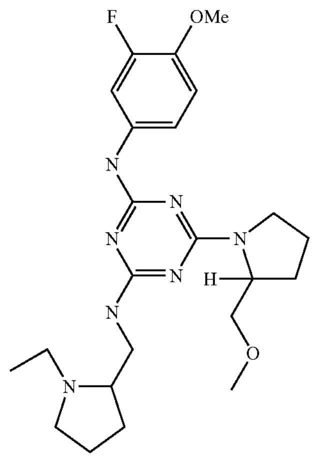 | N2-[(1-ethyl-2-pyrrolidinyl)methyl]-N4-(4-fluoro-3-methoxyphenyl)-6-[2-(methoxyphenyl)-1-pyrrolidinyl]-1,3,5-triazine-2,4-diamine | ++++ | +++ | 2 | 38 (IC50 = 6.47) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 62 | 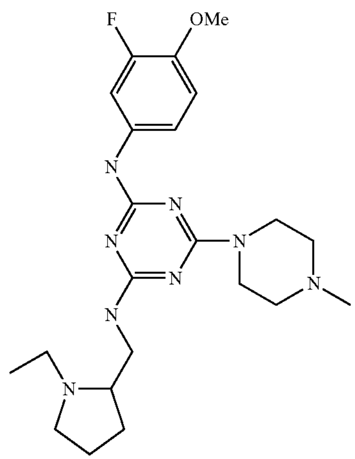 | N2-[(1-ethyl-2-pyrrolidinyl)methyl]-N4-(3-fluoro-4-methoxyphenyl)-6-(4-methyl-1-piperazinyl)-1,3,5-triazine-2,4-diamine | n.d. | +++ | n.d. | 42 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 63 | 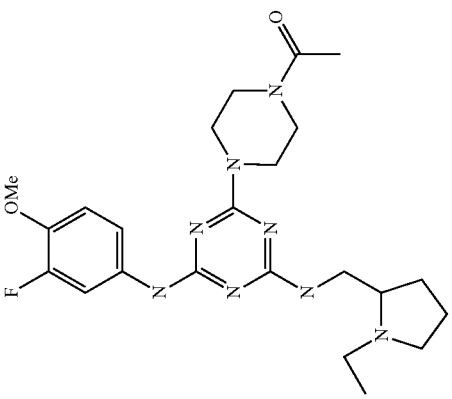 | 6-(4-acetyl-1-piperazinyl)-N2-[(1-ethyl-2-pyrrolidinyl)methyl]-N4-(3-fluoro-4-methoxyphenyl)-1,3,5-triazine-2,4-diamine | +++ | n.d. | 26 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 64 | 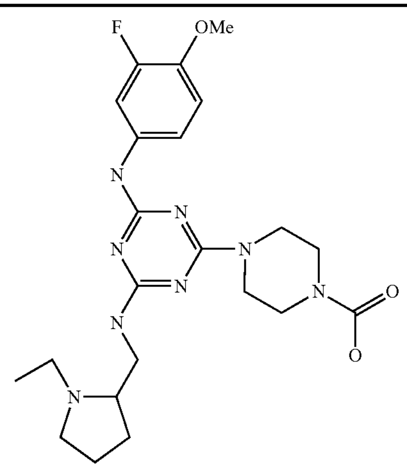 | 4-(4-{[(1-ethyl-2-pyrrolidinyl)methyl]amino}-6-[(3-fluoro-4-methoxyphenyl)amino]-1,3,5-triazin-2-yl]-1-piperazinylcarboxylate | +++ | n.d. | 23 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 65 | 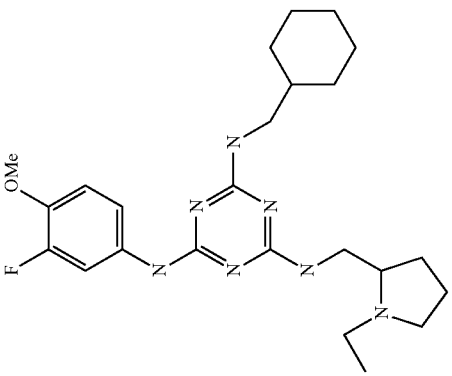 | N2-(cyclohexylmethyl)-N4-[(1-ethyl-2-pyrrolidinyl)methyl]-N6-(3-fluoro-4-methoxyphenyl)-1,3,5-triazine-2,4,6-triamine | ++++ | +++ | 1 (IC50 = 6.7) | 45 (IC50 = 3.24) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 66 | 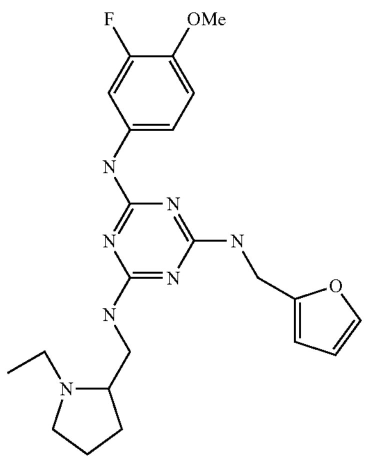 | N2-[(1-ethyl-2-purrolidinyl)methyl]-N4-[3-fluoro-4-methoxyphenyl]-N6-(2-furylmethyl)-1,3,5-triazine-2,4,6-triamine | ++++ | ++++ | 1 | 23 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 67 | [structure] | N2-[(1-ethyl-2-pyrrolidinyl)methyl]-N4-(3-fluoro-4-methoxyphenyl)-N6-(2,2,2-trifluoromethyl)-1,3,5-triazine-2,4,6-triamine | n.d. | +++ | n.d. | 39 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 68 | [structure] | N2-[2-(dimethylamino)ethyl]-N4-[(1-ethyl-2-pyrrolidinyl-methyl]-N6-(3-fluoro-4-methoxyphenyl)-1,3,5-triazine-2,4,6-triamine | ++++ | +++ | 1 | 40 (IC50 = 7.7) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 69 | 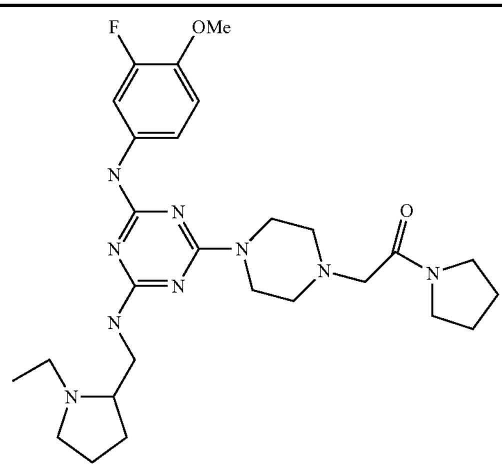 | N2-[(1-ethyl-2-pyrrolidinyl)methyl]-N4-(3-fluoro-4-methoxyphenyl)-6-{4-[2-oxo-2-(1-pyrrolidinyl)ethyl]-1-piperazinyl}-1,3,5-triazine-2,4-diamine | ++++ | ++++ | 1 | 5 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 70 | 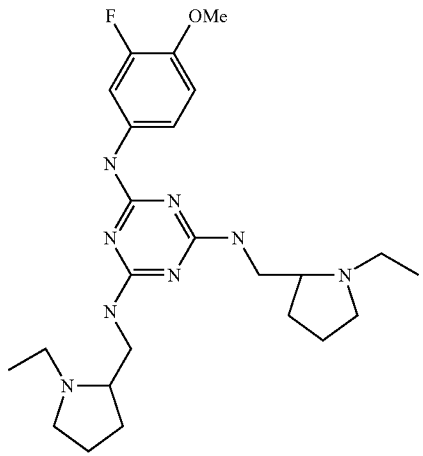 | N2,N4-bis[(1-ethyl-2-pyrrolidinyl)methyl]-N6-(3-fluoro-4-methoxyphenyl)-1,3,5-triazine-2,4,6-triamine | ++++ | +++ | 1 | 35 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 71 | 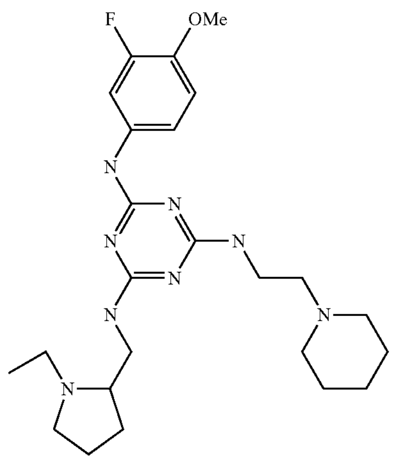 | N2-[(1-ethyl-2-pyrrolidinyl)methyl]-N3-(3-fluoro-4-methoxyphenyl)-N6-[2-(1-piperidinyl)ethyl]-1,3,5-triazine-2,4,6-triamine | ++++ | +++ | 1 | 29 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 72 | 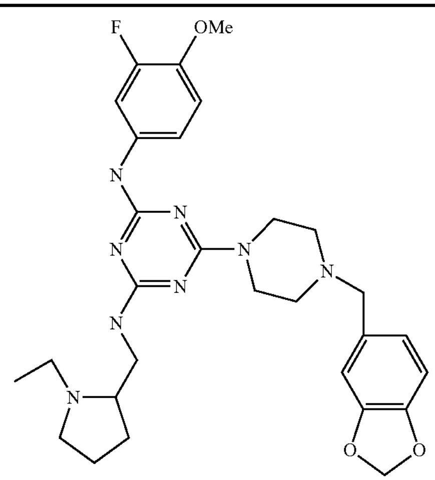 | 6-[4-(1,3-benzodioxol-5-ylmethyl)-1-piperazinyl]-N2-[(1-ethyl-2-pyrrolidinyl)methyl]-N4-(3-fluoro-4-methoxyphenyl)-1,3,5-triazine-2,4-diamine | ++++ | +++ | 5 | 31 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 73 | 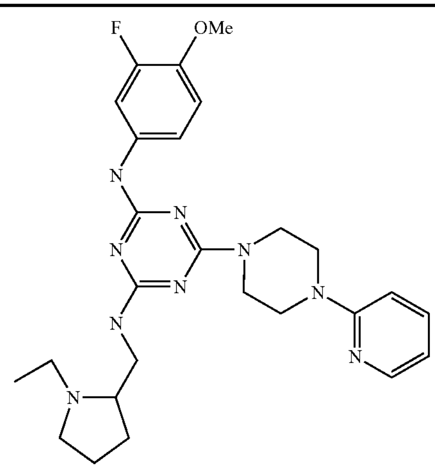 | N2-[(1-ethyl-2-pyrrolidinyl)methyl]-N4-(3-fluoro-4-methoxyphenyl)-6-[4-(2-pyridinyl)-1-piperazinyl]-1,3,5-triazine-2,4-diamine | ++++ | ++++ | 1 (IC50 = 8.7) | 20 (IC50 = 7.5) |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 74 | 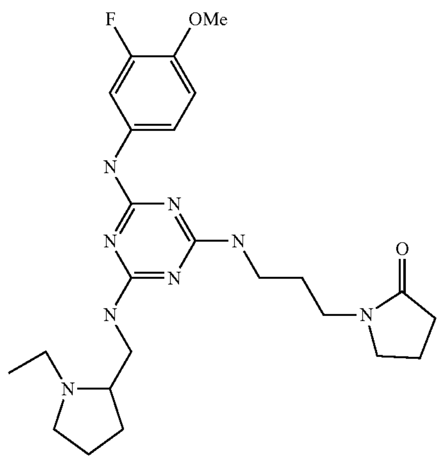 | 1-[3-((4-{[(1-ethyl-2-pyrrolidinyl)methyl]amino)-6-[(3-fluoro-4-methoxyphenyl)amino]-1,3,5-triazin-2-yl}amino)propyl]-2-pyrrolidinone | n.d. | +++ | n.d. | 49 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 75 | 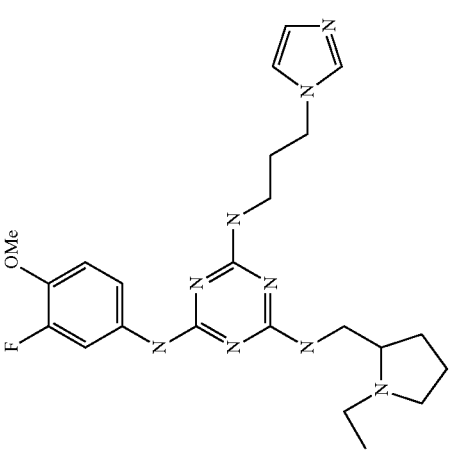 | N2-[(1-ethyl-2-pyrrolidinyl)methyl]-N4-(3-fluoro-4-meethoxyphenyl)-N6-[3-(1H-imidazol-1-yl)propyl]-1,3,5-triazine-2,4,6-triamine | +++ | +++ | 43 | 46 |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 140 | 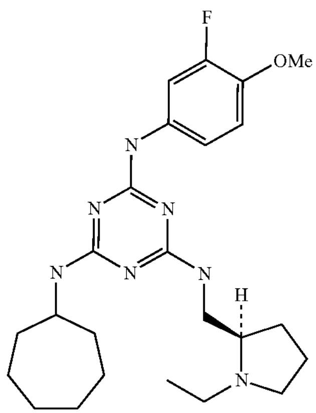 | N²-cycloheptyl-N⁴-((R)-1-ethyl-pyrrolidin-2-ylmethyl)-N⁶-(3-fluoro-4-methoxyphenyl)-1,3,5-triazine-2,4,6-triamine | ++++ | n.d. | 12.57 | n.d. |
| 139 | 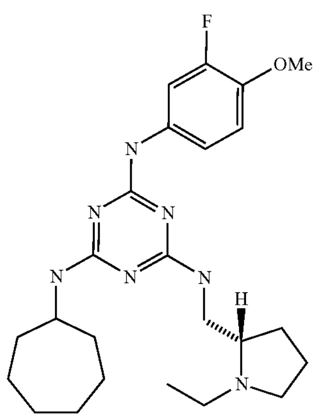 | N²-cycloheptyl-N⁴-((S)-1-ethyl-pyrrolidin-2-ylmethyl)-N⁶-(3-fluoro-4-methoxyphenyl)-1,3,5-triazine-2,4,6-triamine | ++++ | n.d. | 16.08 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 127 | 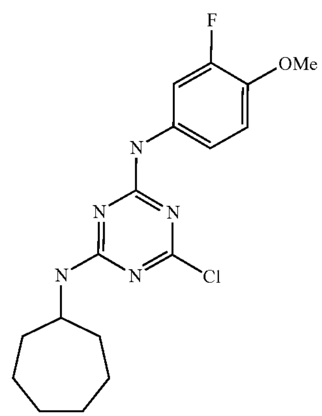 | 6-Chloro-N-cycloheptyl-N'-(3-fluoro-4-meethoxy-phenyl)-[1,3,5]triazine-2,4-diamine | +++ | n.d. | 48 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 141 | 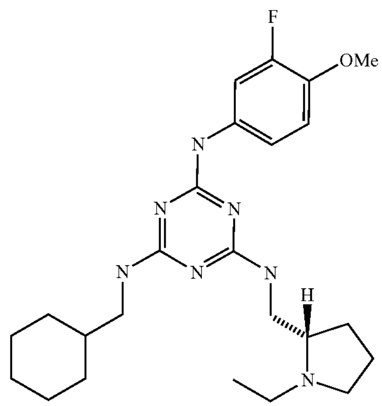 | $N^2$-cyclohexylmethyl-$N^4$-((S)-1-ethyl-pyrrolidin-2-ylmethyl)-$N^6$-(3-fluoro-4-methoxyphenyl)-1,3,5-triazine-2,4,6-triamine | ++++ | n.d. | 23.44 | n.d. |
| 142 | 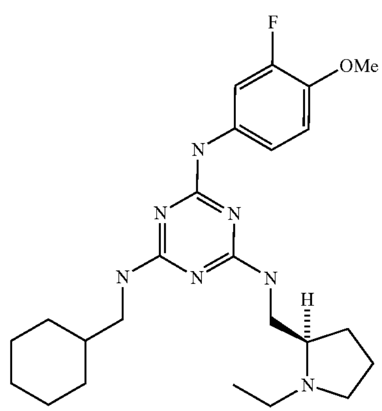 | $N^2$-cyclohexylmethyl-$N^4$-((R)-1-ethyl-pyrrolidin-2-ylmethyl)-$N^6$-(3-fluoro-4-methoxyphenyl)-1,3,5-triazine-2,4,6-triamine | ++++ | n.d. | 21.62 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 143 | 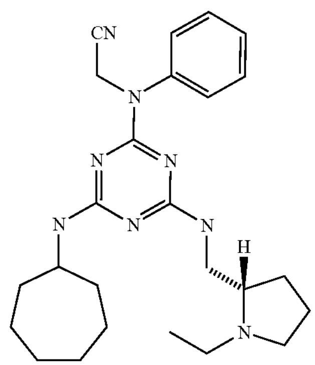 | ({4-cycloheptylamino-6-[((S)-1-ethyl-pyrrolidin-2-ylmethyl)-amino]-1,3,5-triazin-2-yl}-phenyl-amino)-acetonitrile | ++++ | n.d. | 18.88 | n.d. |
| 144 | 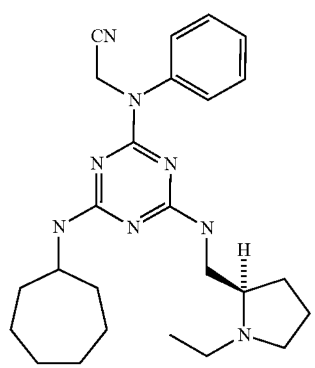 | ({4-cycloheptylamino-6-(((R)-1-ethyl-pyrrolidin-2-ylmethyl)-amino]-1,3,5-triazin-2-yl}-phenyl-amino)-acetonitrile | ++++ | n.d. | | |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 157 | 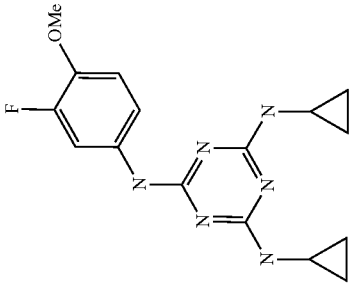 | N,N'-dicyclopropyl-N''-(3-fluoro-4-methoxy-phenyl)-1,3,5-triazine-2,4,6-diamine | ++ | n.d. | 60.48 | n.d. |

TABLE 5-continued

Triazine compounds useful in treating inflammatory disorders generally, and all diseases related to inhibition of IL6.

| Patent Number | STRUCTURE | | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|---|
| 160 | 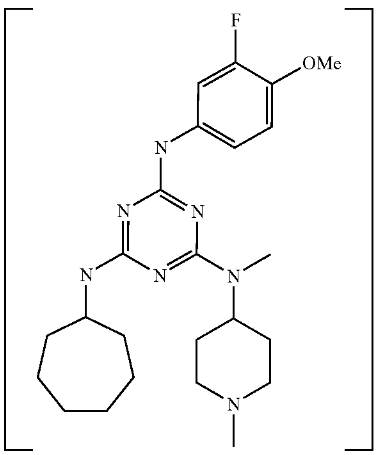 | HCl | N²-cycloheptyl-N⁴-(3-fluoro-4-methoxyphenyl)-N⁶-methyl-N⁶-(1-methyl-piperidin-4-yl)-1,3,5-triazine-2,4,6-triamine, hydrogen chloride salt | ++++ | n.d. | 1 | n.d. |
| 101 | 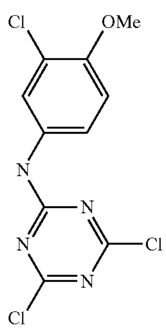 | | (3-Chloro-4-methoxy-phenyl)-(4,6-dichloro-[1,3,5]triazin-2-yl)-amine | n.d. | n.d. | n.d. | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 107 | 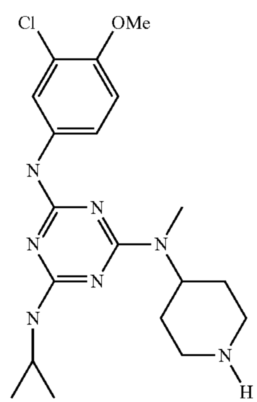 | $N^2$-(3-chloro-4-methoxy-phenyl)-$N^4$-isopropyl-$N^6$-methyl-$N^8$-piperidin-4-yl-1,3,5-triazine-2,4,6-triamine | ++ | n.d. | 60 @ 5 uM | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 108 | 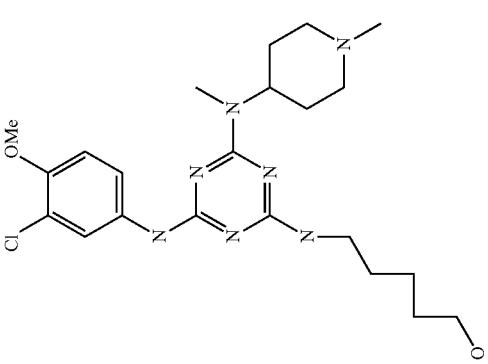 | 5-[4-(3-Chloro-4-methoxy-phenylamino)-6-[methyl-(1-methyl-piperidin-4-yl)-amino]-[1,3,5]triazin-2-ylamino)-pentan-1-ol | +++ | n.d. | 25 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 109 | 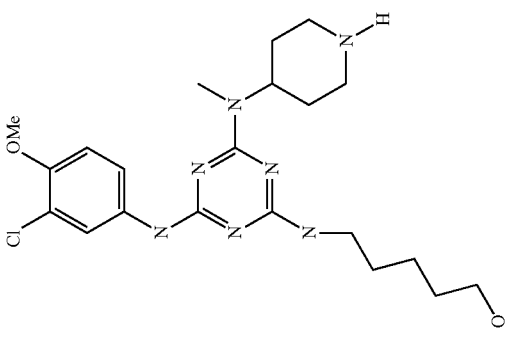 | 5-[4-(3-chloro-4-methoxy-phenylamino)-6-(methyl-piperidin-4-yl-amino)-1,3,5-triazin-2-ylamino]-pentan-1-ol | +++ | n.d. | 40 | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 111 | 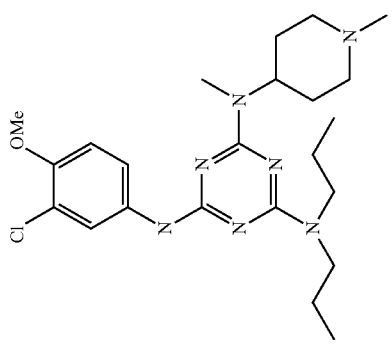 | N-Butyl-N'-(3-chloro-4-methoxy-phenyl)-N''-(1-methyl-piperidin-4-yl)-N-propyl-[1,3,5]triazine-2,4,6-triamine | + | n.d. | >90 [46 @ 5 uM] did not see toxicity | n.d. |

TABLE 5-continued

Triazine compounds useful in treating inflammatory disorders generally, and all diseases related to inhibition of IL6.

| Patent Number | STRUCTURE | Name Generated by Autonom(TM) | Inhibition of TNF-induced IL6 production (See NOTE) | Inhibition of TNF-induced IL6 production | % IL6 production compare to TNF stimulation of IL6(100%). Compds tested @ 10 uM HAEC, IL6 | % IL6 production compare to AGE stimulation of IL6(100%). Compds tested @ 10 uM HAEC, IL6 |
|---|---|---|---|---|---|---|
| 112 | [structure] | $N^2$-Butyl-$N^4$-(3-chloro-4-methoxy-phenyl)-$N^6$-methyl-$N^6$-piperidin-4-yl-$N^2$-propyl-1,3,5-triazine-2,4,6-triamine | + | n.d. | 90 @ 5 uM did not see toxicity | n.d. |

NOTE: The scale is as follows:
(1) "++++" = 0–25% of IL6 production compared to cells that did not receive compound (or per cent of control IL6 production);
(2) "+++" = >25–50% of control IL6 production; and
(3) "++" = >50–75% of control IL6 production; and
(4) "+" = >75–100% of control IL6 production.
"n.d." means that the activity of the compound was not determined in the given assay.

TABLE 6

Inhibition of TNF-induced heparanase secretion

| Patent # | STRUCTURE | Name Generated by Autonom ™ | Relative Activity | Activity |
|---|---|---|---|---|
| 76 | 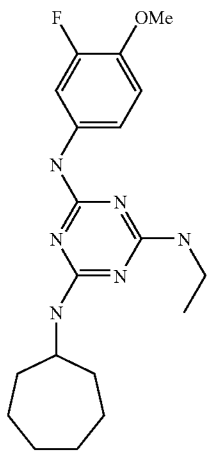 | N2-cycloheptyl-N4-ethyl-N6-(3-fluoro-4-methoxyphenyl)-1,3,5-triazine-2,4,6-triamine | ++ | 50% inhibition @ 5 uM |
| 82 | 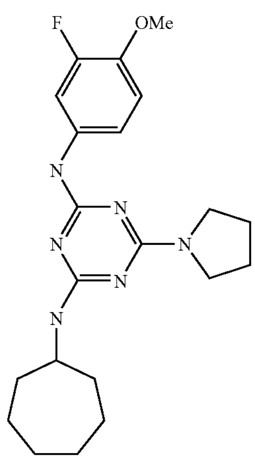 | N2-cycloheptyl-N4-(3-fluoro-4-methoxyphenyl)-6-(1-pyrrolidinyl)-1,3,5-triazine-2,4-diamine | +++ | 73% inhibition @ 5 uM |
| 87 | 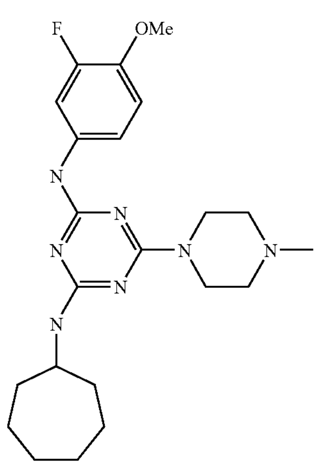 | N2-cycloheptyl-N4-(3-fluoro-4-methoxyphenyl)-6-(4-methyl-1-piperazinyl)-1,3,5-triazine-2,4-diamine | + | 40–60% inhibition @ 10 uM |

TABLE 6-continued

Inhibition of TNF-induced heparanase secretion

| Patent # | STRUCTURE | Name Generated by Autonom ™ | Relative Activity | Activity |
|---|---|---|---|---|
| 94 | 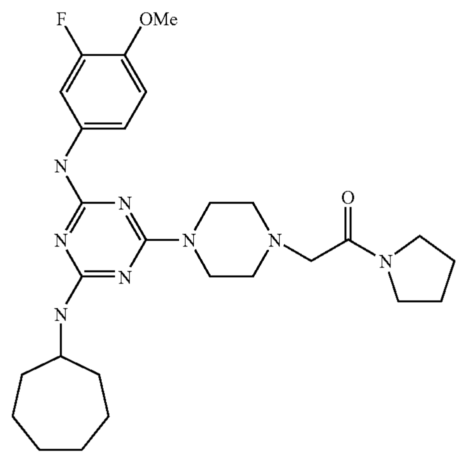 | N2-cycloheptyl-N4-(3-fluoro-4-methoxyphenyl)-6-{4-[2-oxo-(1-pyrrolidinyl)ethyl]-1-piperazinyl}-1,3,5-triazine-2,4-diamine | + | 40–60% inhibition @ 10 uM |
| 35 | 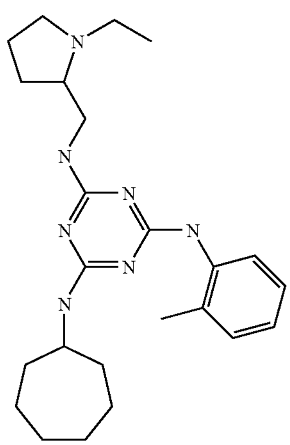 | N2-cycloheptyl-N4-[(1-ethyl-2-pyrrolidinyl)methyl]-N6-(2-methylphenyl)-1,3,5-triazine-2,4,6-triamine | ++ | 53% inhibition @ 5 uM |
| 52 | 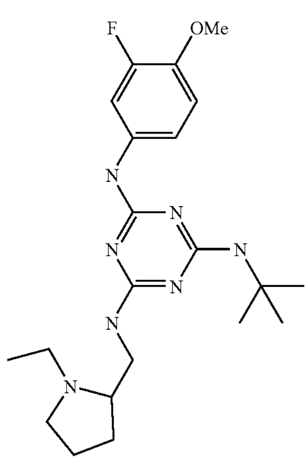 | N2-(tert-butyl)-N4-[(1-ethyl-2-pyrrolidinyl)methyl]-N6-(3-fluoro-4-methoxyphenyl)-1,3,5-triazine-2,4,6-triamine | + | 40–60% inhibition @ 10 uM |

TABLE 6-continued

Inhibition of TNF-induced heparanase secretion

| Patent # | STRUCTURE | Name Generated by Autonom ™ | Relative Activity | Activity |
|---|---|---|---|---|
| 58 | 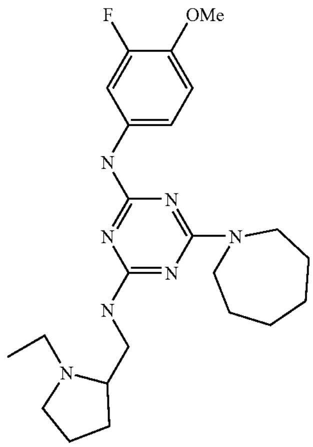 | N2-[(1-ethyl-2-pyrrolidinyl)methyl]-N4-(3-fluoro-4-methoxyphenyl)-6-hexahydro-1H-azepin-1-yl-1,3,5-triazine-2,4-diamine | + | 40–60% inhibition @ 10 uM |
| 61 | 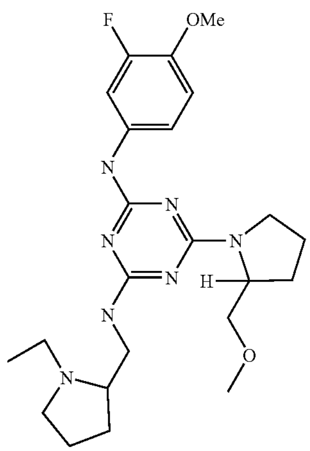 | N2-[(1-ethyl-2-pyrrolidinyl)methyl]-N4-(3-fluoro-4-methoxyphenyl)-6-[(2-(methoxymethyl)-1-pyrrolidinyl]-1,3,5-triazine-2,4-diamine | + | 40–60% inhibition @ 10 uM |

NOTE: The scale is as follows:
(1) "+++" = 70–100% inhibition;
(2) "++" = 30–40% inhibition; and
(3) "+" = 0–30% inhibition all at 5 uM compound concentration.

TABLE 7

Triazine compounds useful in treating inflammatory disorders generally, and all diseases related to inhibition of IL6.

| Compound Number | STRUCTURE | Name (IUPAC- Generated by Autonom) | Inhibition of TNF- induced IL6 production | Inhibition of TNF- induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 172 | 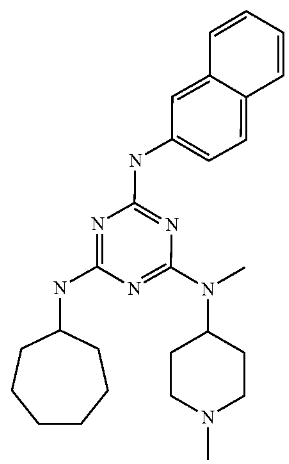 | N-Cycloheptyl-N'-methyl-N'-(1-methyl-piperidin-4-yl)-N''-naphthalen-2-yl-[1,3,5]triazine-2,4,6-triamine | +++ | ++ | 18 | n.d. |
| 171 | 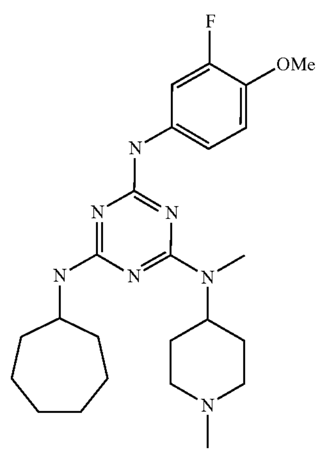 | N-Cycloheptyl-N'-(3-fluoro-4-methoxy-phenyl)-N'',methyl-N''-(1-methyl-piperidin-4-yl)-[1,3,5]triazine-2,4,6-triazmine | +++ | ++ | 21 | n.d. |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|
| 173 | 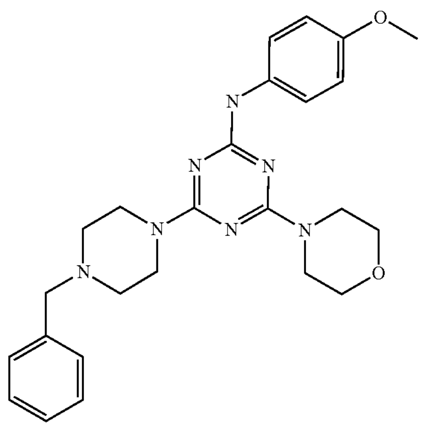 | [4-(4-Benzyl-piperazin-1-yl)-6-morpholin-4-yl-[1,3,5]triazin-2-yl]-(4-methoxy-phenyl)-amine | ++ | 47 | n.d. |
| 174 | 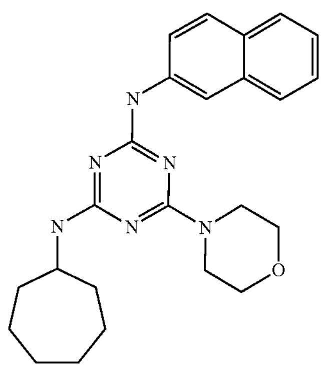 | N-Cycloheptyl-6-morpholin-4-yl-N'-naphthalen-2-yl-[1,3,5]triazine-2,4-diamine | +++ | 34 | n.d. |

TABLE 7-continued

Triazine compounds useful in treating inflammatory disorders generally, and all diseases related to inhibition of IL6.

| Compound Number | STRUCTURE | Name (IUPAC- Generated by Autonom) | Inhibition of TNF- induced IL6 production | Inhibition of TNF- induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 175 | 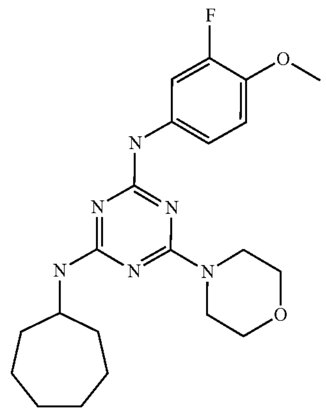 | N-Cycloheptyl-N'-(3-fluoro-4-methoxy-phenyl)-6-morpholin-4-yl-[1,3,5]triazine-2,4-diamine | +++ | | 18 | n.d. |
| 176 | 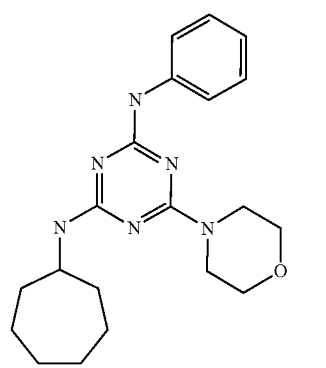 | N-Cycloheptyl-6-morpholin-4-yl-N'-phenyl-[1,3,5]triazine-2,4-diamine | +++ | | 33 | n.d. |

TABLE 7-continued

Triazine compounds useful in treating inflammatory disorders generally, and all diseases related to inhibition of IL6.

| Compound Number | STRUCTURE | Name (IUPAC-Generated by Automon) | Inhibition of TNF-induced IL6 production | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 177 | 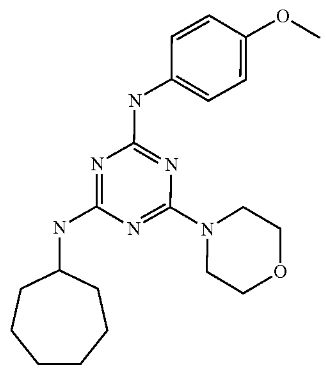 | N-Cycloheptyl-N'-(4-methoxy-phenyl)-6-morpholin-4-yl-[1,3,5]triazine-2,4-diamine | +++ | ++ | | n.d |
| 178 | 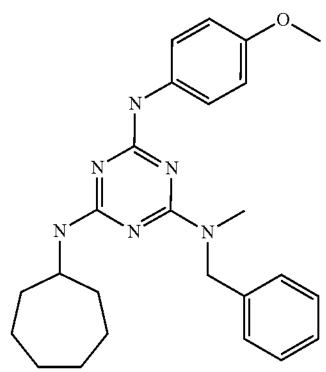 | N-Benzyl-N'-cycloheptyl-N''-(4-methoxy-phenyl)-N-methyl-[1,3,5]triazine-2,4,6-triamine | ++ | | 19 | n.d. |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 179 | 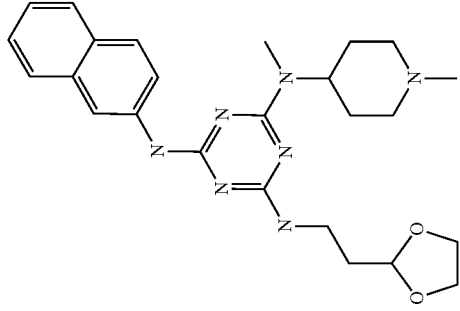 | N-(2-[1,3]Dioxolan-2-yl-ethyl)-N'-methyl-N'-(1-methyl-piperidin-4-yl)-N''-naphthalen-2-yl-[1,3,5]triazine-2,4,6-triamine | ++ | + | | |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 180 | 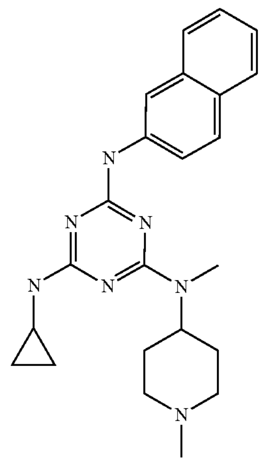 | N-Cyclopropyl-N'-methyl-N'-(1-methyl-piperidin-4-yl)-N''-naphthalen-2-yl-[1,3,5]triazine-2,4,6-triamine | +++ | + | n.d. | 5 |

NOTE:
"+++" represents between about 85 to 100% inhibition of IL6 production in the presence of AGE or TNF, as compared to cells that did not receive any compound;
"++" represents between about 65 and about 85% inhibition of IL6 production in the presence of AGE or TNF; and
"+" represents between about 50 and about 65% inhibition of IL6 production in the presence of AGE or TNF.

TABLE 8

Bioactivity Data for Representative Compounds

| Cmpd No. | Structure | Proliferation Data | Inflammation Data |
| --- | --- | --- | --- |
|  | [structure: triazine with 3-chloro-4-methoxyanilino, cycloheptylamino, and 2-(hydroxymethyl)pyrrolidinyl substituents] | Did not pass 5 & 10 uM screens; rounding | Not Active |
|  | [structure: triazine with 3-chloro-4-methoxyanilino, cycloheptylamino, and 4-methylpiperazinyl substituents] | Did not pass 5 & 10 uM screens; blunting and rounding | total cell death at 10 uM (75% inhibition); 25% cell death at 5 uM (not active) |
|  | [structure: triazine with 3-chloro-4-methoxyanilino, cycloheptylamino, and (2-ethyl-4-oxo-4H-pyran-3-yl)oxy substituents] | Not active at 5 & 10 uM | 48% inhibition at 10 uM with 20% cell death |
|  | [structure: triazine with 3-chloro-4-methoxyanilino, cycloheptylamino, and (1-acetylpiperidin-3-yl)oxy substituents] | Not active at 5 & 10 uM | complete inhibition at 10 uM |

TABLE 8-continued

Bioactivity Data for Representative Compounds

| Cmpd No. | Structure | Proliferation Data | Inflammation Data |
|---|---|---|---|
| | (structure: triazine with 3-Cl-4-OMe-anilino, cycloheptylamino, and isopropoxy substituents) | Not active | <25% inhibition at 10 uM |
| | (structure: triazine with 3-Cl-4-OMe-anilino, cycloheptylamino, and pyrrolidin-2-ylmethoxy substituents) | Not active at 5 & 10 uM | 75% inhibition at 10 uM |
| | (structure: triazine with 3-Cl-4-OMe-anilino, cycloheptylamino, and piperidin-3-yloxy substituents) | 4.9 uM average IC50 | 60% inhibition at 10 uM with 20% cell death |
| | (structure: triazine with 3-Cl-4-OMe-anilino, cycloheptylamino, and piperidin-4-yloxy substituents) | 1.85 uM average IC50 | 85% inhibition at 10 uM with 20% cell death |

TABLE 8-continued
Bioactivity Data for Representative Compounds
| Cmpd No. | Structure | Proliferation Data | Inflammation Data |
|---|---|---|---|
| | 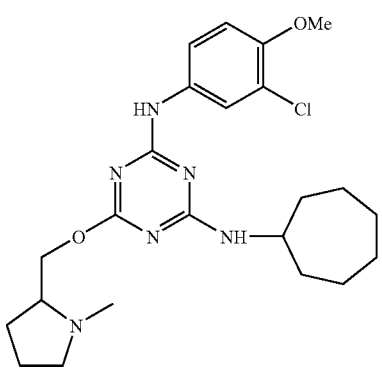 | 5.25 uM average IC50 | total cell death at 10 uM (complete inhibition) |
| | 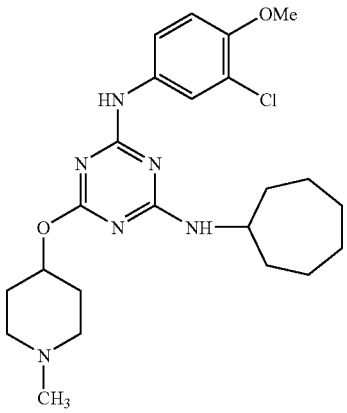 | rounding at 5 & 10 uM | total cell death at 10 uM (95% inhibition) |
| | 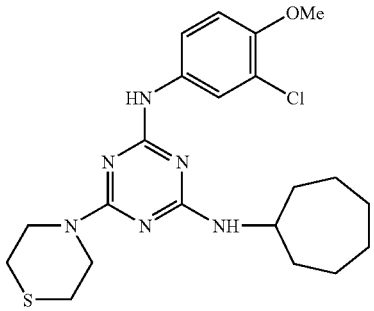 | Not active | Not Active |
| | 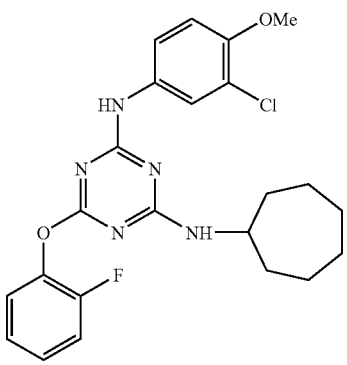 | Not active | Not Active |

TABLE 8-continued
Bioactivity Data for Representative Compounds
| Cmpd No. | Structure | Proliferation Data | Inflammation Data |
|---|---|---|---|
| | 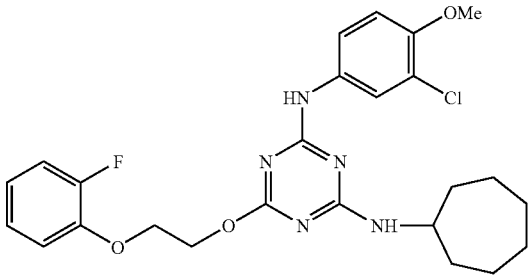 | Not active | Not Active |
| | 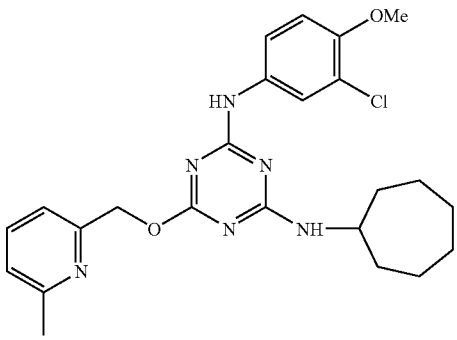 | Not active | 60% inhibition at 10 uM |
| | 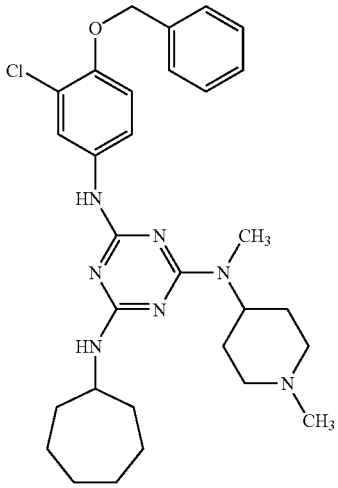 | 6.37 uM; cell morphology change at 5 & 10 uM; no cell death | Not active at 1 or 5 uM; 30% cell death at 5 uM and total death at 10 uM |

TABLE 8-continued

Bioactivity Data for Representative Compounds

| Cmpd No. | Structure | Proliferation Data | Inflammation Data |
|---|---|---|---|
| | [structure: 4-benzyloxy-3-chloroanilino triazine with cycloheptylamino and N-methyl-piperidin-4-yl-amino] | 6.1 uM; cell morphology change at 7.5 uM and cell death at 10 uM | total cell death at 10 uM; 58% inhibition at 5 uM, but may be due to cell death (50% death), not active at 1 uM |
| | [structure: 4-hydroxyanilino triazine with cycloheptylamino and N-methyl group on (1-methylpiperidin-4-yl)amino] | 5.5 uM | total cell death at 10 uM; 50% inhibition at 5 uM with 20% cell death |
| | [structure: 3-chloro-4-hydroxyanilino-4,6-dichloro-1,3,5-triazine] | Not active | 35% inhibition at 10 uM |

TABLE 8-continued

Bioactivity Data for Representative Compounds

| Cmpd No. | Structure | Proliferation Data | Inflammation Data |
|---|---|---|---|
| | [Structure: 2-chloro-4-(4-chloro-6-(cycloheptylamino)-1,3,5-triazin-2-ylamino)phenol] | Not active | 25% inhibition at 5 uM and 10 uM |
| | [Structure: 2-chloro-4-(4-(cycloheptylamino)-6-(methyl(1-methylpiperidin-4-yl)amino)-1,3,5-triazin-2-ylamino)phenol] | 3.3 uM; 4.5 uM; cell blunting at 3 to 10 uM | total cell death at 10 uM (84% inhibition); 64% inhibition at 5 uM |
| | [Structure: N2-(1-benzylpiperidin-4-yl)-N4-cycloheptyl-N6-(3-fluoro-4-methoxyphenyl)-1,3,5-triazine-2,4,6-triamine] | 1.5 uM; 4.2 uM; cell blunting at 3 uM and rounding at 5 uM | total cell death at 10 uM (97% inhibition); 43% inhibition at 5 uM with 25% cell death |

TABLE 8-continued

Bioactivity Data for Representative Compounds

| Cmpd No. | Structure | Proliferation Data | Inflammation Data |
|---|---|---|---|
| | (structure: 3-fluoro-4-methoxyphenyl-NH / cycloheptyl-NH / 1-benzylpiperidin-4-yl-NH triazine) | 1.9 uM; cell blunting at 1 uM and rounding at 5 uM | 41% inhibition at 10 uM with >50% cell death; 37% inhibition at 5 uM with 20% cell death |
| | (structure: 4-methoxyphenyl-NH / cycloheptyl-NH / piperidin-4-yl-NH triazine) | 6.6 uM | 88% inhibition at 10 uM with >50% cell death; 69% inhibition at 5 uM with 20% cell death |
| | (structure: 3-fluoro-4-methoxyphenyl-NH / cyclopropyl-NH / Cl triazine) | Not active | 36% inhibition at 10 uM |

TABLE 8-continued

Bioactivity Data for Representative Compounds

| Cmpd No. | Structure | Proliferation Data | Inflammation Data |
|---|---|---|---|
| | [Structure: triazine with 3-fluoro-4-methoxyphenylamino, cyclopropylamino, and N-methyl-N-(1-methylpiperidin-4-yl)amino substituents] | Not active | 25% inhibition at 10 uM |
| | [Structure: triazine with 3-fluoro-4-methoxyphenylamino, cyclopropylamino, and (1-ethylpyrrolidin-2-yl)methylamino substituents] | Not active | 23% inhibition at 10 uM |
| | [Structure: triazine with 3-chloro-4-methoxyphenylamino, cyclopropylamino, and chloro substituents] | Not tested | Not tested |

TABLE 8-continued
Bioactivity Data for Representative Compounds
| Cmpd No. | Structure | Proliferation Data | Inflammation Data |
|---|---|---|---|
| | 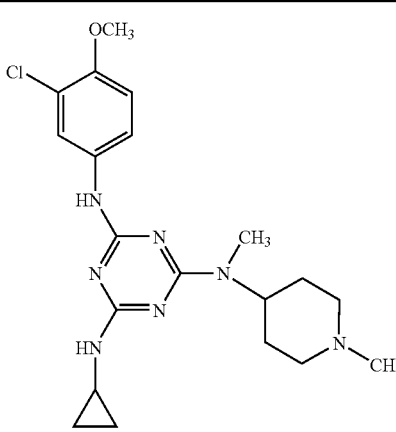 | 4.1 uM | Not active with 15% cell death at 10 uM |
| | 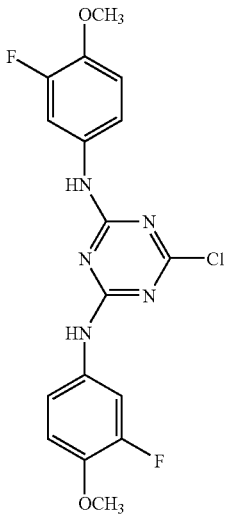 | Not active | 20% inhibition at 10 uM, no effect at 5 uM |
| | 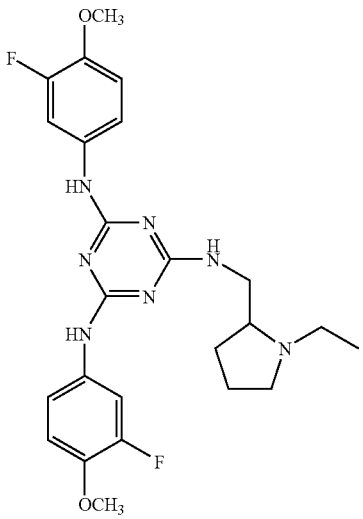 | 7.8 uM; 5.3 uM | 35% inhibition at 10 uM, 25% inhibition at 5 uM |

We claim:
1. A stent comprising a compound disposed on or within the stent, wherein the compound is:
2-{[4-(Cyclohexylmethyl-amino)-6-(3-fluoro-4-methoxy-phenylamino)-[1,35]triazin-2-ylamino]-methyl}-cyclopentanone,
N-[4-(Cyclohexylmethyl-amino)-6-(3-fluoro-4-methoxy-phenylamino)-[1,3,5]triazin-2-yl]-guanidine,
N-Cyclohexylmethyl-N'-(3-fluoro-4-methoxy-phenyl)-N"-(1-methyl-pyrrolidin-2-yl)-[1,3,5]triazine-2,4,6-triamine,
N-Cyclohexylmethyl-N'-(3-fluoro-4-methoxy-phenyl)-N"-(tetrahydro-furan-2-ylmethyl)-[1,3,5]triazine-2,4,6-triamine,
1-(2-{[4-(Cyclohexylmethyl-amino)-6-(3-fluoro-4-methoxy-phenylamino)-[1,3,5]triazin-2-ylamino]-methyl}-pyrrolidin-1-yl)-ethanone,
2-{[4-(Cyclohexylmethyl-amino)-6-(3-fluoro-4-methoxy-phenylamino)-[1,3,5]triazin-2-ylamino]-methyl}-pyrrolidine-1-carboxylic acid methyl ester,
N-Cyclohexylmethyl-N'-(3-fluoro-4-methoxy-phenyl)-[1,3,5]triazine-2,4,6-triamine,
N-Cyclohexylmethyl-N'-(3-fluoro-4-methoxy-phenyl)-N"-pyrrolidin-2-ylmethyl-[1,3,5]triazine-2,4,6-triamine,
N-Cyclohexylmethyl-N'-(2-ethyl-cyclopentylmethyl)-N"-(3-fluoro-4-methoxy-phenyl)-[1,3,5]triazine-2,4,6-triamine,
N-Cyclohexylmethyl-N'-(2-ethyl-pyrazolidin-1-ylmethyl)-N"-(3-fluoro-4-methoxy-phenyl)-[1,3,5]triazine-2,4,6-triamine,
N-Cyclohexylmethyl-N'-(3-fluoro-4-methoxy-phenyl)-N"-(1-methyl-pyrrolidin-2-ylmethyl)-[1,3,5]triazine-2,4,6-triamine,
N-Cyclohexylmethyl-N'-(1-ethyl-pyrrolidin-3-ylmethyl)-N"-(3-fluoro-4-methoxy-phenyl)-[1,3,5]triazine-2,4,6-triamine,
N-Cyclohexylmethyl-N'-(3-fluoro-4-methoxy-phenyl)-N"-imidazol-1-ylmethyl-[1,3,5]triazine-2,4,6-triamine,
N-Cyclohexylmethyl-6-(1-ethyl-pyrrolidin-2-ylmethoxy)-N'-(3-fluoro-4-methoxy-phenyl)-[1,3,5]triazine-2,4-diamine,
N-Cyclohexylmethyl-N'-(3-fluoro-4-methoxy-phenyl)-6-(hexahydro-pyrrolo[1,2-a]pyrazin-2-yl)-[1,3,5]triazine-2,4-diamine,
N-Cyclohexylmethyl-N'-(1-ethyl-pyrrolidin-2-ylmethyl)-N"-(3-fluoro-4-methoxy-phenyl)-N'-methyl-[1,3,5]triazine-2,4,6-triamine,
N-Cyclohexylmethyl-N'-(3-fluoro-4-methoxy-phenyl)-6-(pyrrolidin-2-ylmethoxy)-[1,3,5]triazine-2,4-diamine,
N-Cyclohexylmethyl-N-(1-ethyl-piperidin-2-ylmethyl)-N"-(3-fluoro-4-methoxy-phenyl)-[1,3,5]triazine-2,4,6-triamine,
1-Ethyl-pyrrolidine-2-carboxylic acid [4-(cyclohexylmethyl-amino)-6-(3-fluoro-4-methoxy-phenylamino)-[1,3,5]triazin-2-yl]-amide,
Pyrrolidine-1,2-dicarboxylic acid 1-tert-butyl ester 2-[4-(cyclohexylmethyl-amino)-6-(3-fluoro-4-methoxyphenylamino)-[1,3,5]triazin-2-yl] ester,
Pyrrolidine-2-carboxylic acid 4-(cyclohexylmethylamino)-6-(3-fluoro-4-methoxy-phenylamino)-[1,3,5]triazin-2-yl ester,
N-(3-Chloro-4-methoxy-phenyl)-N'-cyclohexylmethyl-N"-(1-ethyl-pyrrolidin-2-ylmethyl)-[1,3,5]triazine-2,4,6-triamine,
N-(3-Bromo-4-methoxy-phenyl)-N'-cyclohexylmethyl-N"-(1-ethyl-pyrrolidin-2-ylmethyl)-[1,3,5]triazine-2,4,6-triamine,
N-Cyclohexylmethyl-N'-(1-ethyl-pyrrolidin-2-ylmethyl)-N"-(4-methoxy-3-nitro-phenyl)-[1,3,5]triazine-2,4,6-triamine,
5-[4-[(1-Ethyl-pyrrolidin-2-ylmethyl)-amino]-6-(2-methyl-pentylamino)[1,3,5]triazin-2-ylamino]-2-methoxy-benzenesulfonic acid,
5-{4-(Cyclohexylmethyl-amino)-6-[(1-ethyl-pyrrolidin-2-ylmethyl)-amino]-[1,3,5]triazin-2-ylamino)-2-methoxy-benzonitrile,
4-{4-(Cyclohexylmethyl-amino)-6-[(1-ethyl-pyrrolidin-2-ylmethyl)-amino]-[1,3,5]triazin-2-ylamino)-2-fluoro-phenol,
Sodium; 2-chloro-4-{4-(cyclohexylmethyl-amino)-6-[(1-ethyl-pyrrolidin-2-ylmethyl)-amino]-[1,3,5]triazin-2-ylamino}-phenylate,
N-(3-Chloro-4-ethoxy-phenyl)-N'-(1-ethyl-pyrrolidin-2-ylmethyl)-N"-(2-methyl-phenyl)-[1,3,5]triazine-2,4,6-triamine,
Sodium; 4-{4-(cyclohexylmethyl-amino)-6-[(1-ethyl-pyrrolidin-2-yl methyl)-amino]-[1,3,5]triazin-2-ylamino}-2-fluoro-phenolate,
N-Cyclohexylmethyl-N'-(1-ethyl-pyrrolidin-2-ylmethyl)-N"-(3-fluoro-4-methoxymethoxy-phenyl)-[1,3,5]triazine-2,4,6-triamine,
N-Cyclohexylmethyl-N'-(1-ethyl-pyrrolidin-2-ylmethyl)-N"-(3-fluoro-4-methylsulfanylethoxy-phenyl)-[1,3,5]triazine-2,4,6-triamine,
N-Cyclohexylmethyl-N'-(1-ethyl-pyrrolidin-2-ylmethyl)-N"-(3-fluoro-4-methanesulfanylmethoxy-phenyl)-[1,3,5]triazine-2,4,6-triamine,
N-Cyclohexylmethyl-N'-(1-ethyl-pyrrolidin-2-ylmethyl)-N"-(3-fluoro-4-methanesulfonylmethoxy-phenyl)-[1,3,5]triazine-2,4,6-triamine,
N-Cyclohexylmethyl-N'-(1-ethyl-pyrrolidin-2-ylmethyl)-N"-(3-fluoro-4-methylsulfanyl-phenyl)-[1,3,5]triazine-2,4,6-triamine,
4-{4-(Cyclohexylmethyl-amino)-6-[(1-ethyl-pyrrolidin-2-ylmethyl)-amino]-[1,3,5]triazin-2-ylamino}-2-fluoro-benzenethiol,
N-Cyclohexylmethyl-N'-(1-ethyl-pyrrolidin-2-ylmethyl)-N"-(3-fluoro-4-methoxy-phenyl)-N"-methyl-[1,3,5]triazine-2,4,6-triamine,
N-Cyclohexylmethyl-N'-(3-fluoro-4-methoxy-phenyl)-N'-Methyl-N"-pyrrolidin-2-ylmethyl-[1,3,5]triazine-2,4,6-triamine,
N-Cyclohexylmethyl-N'-(3-fluoro-4-methoxy-phenyl)-6-(tetrahydro-pyrrolo[1,2-c]imidazol-2-yl)-[1,3,5]triazine-2,4-diamine,
Phosphoric acid mono-(4-{4-(cyclohexylmethyl-amino)-6-[(1-ethyl-pyrrolidin-2-ylmethyl)-amino]-[1,3,5]triazin-2-ylamino}-2-fluoro-phenoxymethyl) ester,
Phosphoric acid mono-(4-{4-(cyclohexylmethyl-amino)-6-[(1-ethyl-pyrrolidin-2-ylmethyl)-amino]-[1,3,5]triazin-2-ylamino}-2-fluoro-phenyl) ester,
Phosphoric acid mono-(2-chloro-4-{4-(cyclohexylmethyl-amino)-6-[(1-ethyl-pyrrolidin-2-ylmethyl)-amino]-[1,3,5]triazin-2-ylamino}-phenoxymethyl) ester,
N-Cyclohexy[methyl-N'-(1-ethyl-pyrrolidin-2-ylmethyl)-N"-(3-fluoro-4-methylamino-phenyl)-[1,3,5]triazine-2,4,6-triamine,
Acetic acid 4-{4-(cyclohexylmethylamino)-6-[(1-ethyl-pyrrolidin-2-ylmethyl)-amino]-[1,3,5]triazin-2-ylamino}-2-fluoro-phenyl ester,

N-(4-Amino-3-fluoro-phenyl)-N'-cyclohexylmethyl-N"-(1-ethyl-pyrrolidin-2-ylmethyl)-[1,3,5]triazine-2,4,6-triamine, N-Cyclohexylmethyl-N'-(4-dimethylamino-3-fluoro-phenyl)-N"-(1-ethyl-pyrrolidin-2-ylmethyl)-[1,3,5]triazine-2,4,6-triamine, N-(4-Amino-3-chloro-phenyl)-N'-cyclohexylmethyl-N"-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N"-(3-fluoro-4-isopropoxy-phenyl)-[1,3,5]triazine-2,4,6-triamine, N-Cyclohexylmethyl-N'-(4-cyclopropoxy-3-fluoro-phenyl)-N"-(1-ethyl-pyrrolidin-2-ylmethyl)-[1,3,5]triazine-2,4,6-triamine, N-(3-Chloro-4-cyclopropoxy-phenyl)N'-Cyclohexylmethyl-N"-(1-ethyl-pyrrolidin-2-ylmethyl)-[1,3,5]triazine-2,4,6-triamine, N-Cyclohexylmethyl-N'-(4-ethyl-3-fluoro-phenyl)-N"-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N"-(3-fluoro-4-methyl-phenyl)-[1,3,5]triazine-2,4,6-triamine, N-(3-Chloro-4-methyl-phenyl)-N'-cyclohexylmethyl-N"-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N"-(3-fluoro-4trifluoromethoxy-phenyl)-[1,3,5]triazine-2,4,6-triamine, N-Cyclohexylmethyl-N'-(1-ethyl-pyrrolidin-2-ylmethyl)-N"-(4-methoxy-3-trifluoromethyl-phenyl)-[1,3,5]triazine-2,4,6-triamine, N-(3-Chloro-4-trifluoromethoxy-phenyl)-N'-cyclohexylmethyl-N"-(1-ethyl-pyrrolidin-2-ylmethyl)-[1,3,5]triazine-2,4,6-triamine, N-Cyclohexylmethyl-N'-(3-ethyl-oxazolidin-4-ylmethyl)-N"-(4-trifluoromethoxy-3-trifluoromethyl-phenyl)-[1,3,5]triazine-2,4,6-triamine, N-Cyclohexylmethyl-N'-(3,5-dichloro-4-methyl-phenyl)-N"-(1-ethyl-pyrrolidin-2-ylmethyl)-[1,3,5]triazine-2,4,6-triamine, N-Cyclohexylmethyl-N'-(3,5-dichloro-4-methoxy-phenyl)-N"-(1-ethyl-pyrrolidin-2-ylmethyl)-[1,3,5]triazine-2,4,6-triamine, N-Cyclohexylmethyl-N'-(3,5-difluoro-4-methoxy-phenyl)-N"-(1-ethyl-pyrrolidin-2-ylmethyl)-[1,3,5]triazine-2,4,6-triamine, 4-{4-(Cyclohexylmethyl-amino)-6-[(1-ethyl-pyrrolidin-2-ylmethyl)-amino]-[1,3,5]triazin-2-ylamino}-2,6-difluoro-phenyl, N-Cyclohexylmethyl-N'-(1-ethyl-pyrrolidin-2-ylmethyl)-N"-(4-fluoro-5methoxy-pyridin-2-yl)-[1,3,5]triazine-2,4,6-triamine, N-Cyclohexylmethyl-N'-(1-ethyl-pyrrolidin-2-ylmethyl)-N"-(5-fluoro-6methoxy-pyridin-3-yl)-[1,3,5]triazine-2,4,6-triamine, N-Cyclohexylmethyl-N'-(1-ethyl-pyrrolidin-2-ylmethyl)-N"-(8-fluoro-chroman-6-yl)-[1,3,5]triazine-2,4,6-triamine, N-Cyclohexylmethyl-N'-(1-ethyl-pyrrolidin-2-ylmethyl)-6-(3-fluoro-4-methoxy-phenoxy)-[1,3,5]triazine-2,4-diamine, 6-(4-Amino-3-fluoro-phenoxy)-N-cyclohexylmethyl-N'-(1-ethyl-pyrrolidin-2-ylmethyl)-[1,3,5]triazine-2,4-diamine, 6-(4-Amino-2-fluoro-phenoxy)-N-cyclohexylmethyl-N'-(1-ethyl-pyrrolidin-2-ylmethyl)-[1,3,5]triazine-2,4-diamine, N-(1-Ethyl-pyrrolidin-2-ylmethyl)-N-(3-fluoro-4-methoxy-phenyl)-N"-(tetrahydro-pyran-4-ylmethyl)-[1,3,5]triazine-2,4,6-triamine, N-(1-Ethyl-pyrrolidin-2-ylmethyl)-6-(3-fluoro-4-methoxy-phenoxy)-N'-piperidin-4-ylmethyl-[1,3,5]triazine-2,4-diamine, N-(1-Ethyl-pyrrolidin-2-ylmethyl)-N'-(3-fluoro-4-methoxy-phenyl)-N"-thiomorpholin-4-ylmethyl-[1,3,5]triazine-2,4,6-triamine, N-(1,1-Dioxo-1 lambda*6*-thiomorpholin-4-ylmethyl)-N'-1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N'-(3-fluoro-4-methoxy-phenyl)-N"-(tetrahydro-thiopyran-4-ylmethyl)-[1,3,5]triazine-2,4,6-triamine, N-(1,1-Dioxo-hexahydro-1 lambda*6*-thiopyran-4-ylmethyl)-N'-(1-ethyl-pyrrolidin-2-ylmethyl)-N"-(3-fluoro-4-methoxy-phenyl)-[1,3,5]triazine-2,4,6-triamine, N-Benzyl-N'-(1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N'-(3-fluoro-4-methoxy-phenyl)-N"-(4-methoxy-benzyl)-[1,3,5]triazine-2,4,6-triamine, N-(1-Ethyl-pyrrolidin-2-ylmethyl)-N'-(3-fluoro-4-methoxy-phenyl)-N"-(4-methyl-benzyl)-[1,3,5]triazine-2,4,6-triamine, N-(1-Ethyl-pyrrolidin-2-ylmethyl)-N'-(3-fluoro-4-methoxy-phenyl)-N"-(4-nitro-benzyl)-[1,3,5]triazine-2,4,6-triamine, N-(1-Ethyl-pyrrolidin-2-ylmethyl)-N'-(4-fluoro-benzyl)-N"-(3-fluoro-4-methoxy-phenyl)-[1,3,5]triazine-2,4,6-triamine, N-Cyclopenty[methyl-N'-(1-ethyl-pyrrolidin-2-ylmethyl)-N"-(3-fluoro-4-methoxy-phenyl)-[1,3,5]triazine-2,4,6-triamine, N-Cyclohex-2-enylmethyl-N'-(1-ethyl-pyrrolidin-2-ylmethyl)-N"-(3-fluoro-4-methoxy-phenyl)-[1,3,5]triazine-2,4,6-triamine, N-Cyclopropylmethyl-N'-(1-ethyl-pyrrolidin-2-ylmethyl)-N"-(3-fluoro-4-methoxy-phenyl)-[1,3,5]triazine-2,4,6-triamine, '3-{[4-[(1-Ethyl-pyrrolidin-2-ylmethyl)-amino]-6-(3-fluoro-4-methoxy-phenylamino)-[1,3,5]triazin-2-ylamino]-methyl}-cyclopentanol, N-(3-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, N-Cyclohexylmethyl-N'-(1-ethyl-pyrrolidin-2-ylmethyl)-N"-(3-fluoro-4-methoxy-benzyl)-[1,3,5]triazine-2,4,6-triamine, N-(3-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, 2-{[4-[(1-Ethyl-pyrrolidin-2-ylmethyl)-amino]-6-(3-fluoro-4-methoxy-phenylamino)-[1,3,5]triazin-2-ylamino]-methyl}-cyclopentanol, N-(2-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N'-(3-fluoro-4-methoxy-phenyl)-N"-(4-methyl-cyclohexylmethyl)-[1,3,5]triazine-2,4,6-triamine, N-(1-Ethyl-pyrrolidin-2-ylmethyl)-N'-(3-fluoro-4-methoxy-phenyl)-N''-(2-methyl-cyclohexylmethyl)-[1,3,5]triazine-2,4,6-triamine, 2-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, 3-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, 4-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, N-(4-Amino-cyclohexylmethyl)-N'-(1-ethyl-pyrrolidin-2-ylmethyl)-N''-(3-fluoro-4-methoxy-phenyl)-[1,3,5]triazine-2,4,6-triamine, N-(3-Amino-cyclohexylmethyl)-N'-(1-ethyl-pyrrolidin-2-ylmethyl)-N''-(3-fluoro-4-methoxy-phenyl)-[1,3,5]triazine-2,4,6-triamine, N-Cycloheptylmethyl-N'-(1-ethyl-pyrrolidin-2-ylmethyl)-N''-(3-fluoro-4-methoxy-phenyl)-[1,3,5]triazine-2,4,6-triamine, N-Bicyclo[2.2.1]hept-2-yl-N'-cyclohexylmethyl-N''-(3-fluoro-4-methoxyphenyl)-[1,3,5]triazine-2,4,6-triamine, N-Bicyclo[2.2.2]oct-2-yl-N'-cyclohexylmethyl-N''-(3-fluoro-4-methoxy-phenyl)-[1,3,5]triazine-2,4,6-triamine, N-(1-Aza-bicyclo[2.2.2]oct-3-yl)-N'-cyclohexylmethyl-N''-(3-fluoro-4-methoxy-phenyl)-[1,3,5]triazine-2,4,6-triamine, N-(1-Cyclohexyl-1-methyl-ethyl)-N'-(1-ethyl-pyrrolidin-2-ylmethyl)-N''-(3-fluoro-4-methoxy-phenyl)-[1,3,5]triazine-2,4,6-triamine, N-Cyclohexylmethyl-N'-(3-fluoro-4-methoxy-phenyl)-N''-(tetrahydro-thiophen-2-ylmethyl)-[1,3,5]triazine-2,4,6-triamine, N-Cyclohexylmethyl-N'-(3-fluoro-4-methoxy-phenyl)-N''-(tetrahydro-furan-2-ylmethyl)-[1,3,5]triazine-2,4,6-triamine, N-Cyclohexylmethyl-N'-(3-fluoro-4-methoxy-phenyl)-N''-furan-2-ylmethyl-[1,3,5]triazine-2,4,6-triamine, N-Cyclohexylmethyl-N'-(3-fluoro-4-methoxy-phenyl)-N''-thiophen-2-ylmethyl-[1,3,5]triazine-2,4,6-triamine, N-Cyclohexylmethyl-N'-(3-fluoro-4-ethoxy-phenyl)-N''-(1H-pyrrol-2-ylmethyl)-[1,3,5]triazine-2,4,6-triamine, N-Cyclohexylmethyl-N'-(3-fluoro-4-nethoxy-phenyl)-N''-(1-methyl-1H-pyrrol-2-ylmethyl)-[1,3,5]triazine-2,4,6-triamine, N-Cyclohexylmethyl-N'-(2,3-dihydro-1H-indol-2-ylmethyl)-N''-(3-fluoro-4-methoxy-phenyl)-[1,3,5]triazine-2,4,6-triamine, N-Cyclohexylmethyl-N'-(2-dimethylamino-ethyl)-N''-(3-fluoro-4-methoxyphenyl)-[1,3,5]triazine-2,4,6-triamine, Pyrrolidine-2-carboxylic acid [4-(cyclohexylmethyl-amino)-6-(3-fluoro-4-methoxy-phenylamino)-[1,3,5]triazin-2-yl]-amide, Pyrrolidine-2-carboxylic acid 4-(cyclohexylmethyl-amino)-6-(3-fluoro-4-methoxy-phenylamino)-[1,3,5]triazin-2-yl ester, 1-Methyl-pyrrolidine-2-carboxylic acid [4-(cyclohexylmethyl-amino)-6-(3-fluoro-4-methoxy-phenylamino)-[1,3,5]triazin-2-yl]-amide, 2-[4-(Cyclohexylmethyl-amino)-6-(3-fluoro-4-methoxy-phenylamino)-[1,3,5]triazin-2-yl]-hexahydro-pyrrolo[1,2-c]imidazol-1-one, 1-[4-(Cyclohexylmethyl-amino)-6-(3-fluoro-4-methoxy-phenylamino)-[1,3,5]triazin-2-yl]-pyrrolidine-2,5-dione, 1-[4-(Cyclohexylmethyl-amino)-6-(3-fluoro-4-methoxy-phenylamino)-[1,3,5]triazin-2-yl]-imidazolidine-2,4-dione, 3-[4-(Cyclohexylmethyl-amino)-6-(3-fluoro-4-methoxy-phenylamino)-[1,3,5]triazin-2-yl]-thiazolidine-2,5-dione, 2-{[4-(Cyclohexylmethyl-amino)-6-(3-fluoro-4-methoxy-phenylamino)-[1,3,5]triazin-2-ylamino]-methyl}-1-ethyl-1-methyl-pyrrolidinium; chloride, 1-Acetyl-2-{[4-(cyclohexylmethyl-amino)-6-(3-fluoro-4-methoxy-phenylamino)-[1,3,5]triazin-2-ylamino]-methyl}-1-ethyl-pyrrolidinium; chloride, N-(1-Ethyl-pyrrolidin-2-ylmethyl)-N'-(3-fluoro-4-methoxy-phenyl)-N''-furan-2-ylmethyl-[1,3,5]triazine-2,4,6-triamine, N-(1-Ethyl-pyrrolidin-2-ylmethyl)-N'-(3-fluoro-4-methoxy-phenyl)-N''-thiophen-2-ylmethyl-[1,3,5]triazine-2,4,6-triamine, N-(3-Chloro-4-methoxy-phenyl)-N'-(1-ethyl-pyrrolidin-2-ylmethyl)-N''-thiophen-2-ylmethyl-[1,3,5]triazine-2,4,6-triamine, N-(3-Chloro-4-methoxy-phenyl)-N'-(1-ethyl-pyrrolidin-2-ylmethyl)-N''-oxazol-5-ylmethyl-[1,3,5]triazine-2,4,6-triamine, N-(3-Chloro-4-methoxy-phenyl)-N'-(1-ethyl-pyrrolidin-2-ylmethyl)-N''-imidazol-1-ylmethyl-[1,3,5]triazine-2,4,6-triamine, N-(1-Ethyl-pyrrolidin-2-ylmethyl)-N'-(3-fluoro-4-methoxy-phenyl)-N''-imidazol-1-ylmethyl-[1,3,5]triazine-2,4,6-triamine, N-(1-Ethyl-pyrrolidin-2-ylmethyl)-N'-(3-fluoro-4-methoxy-phenyl)-N''-pyrimidin-4-ylmethyl-[1,3,5]triazine-2,4,6-triamine, N-(2-Amino-pyrimidin-4-ylmethyl)-N'-(1-ethyl-pyrrolidin-2-ylmethyl)-N''-(3-fluoro-4-methoxy-phenyl)-[1,3,5]triazine-2,4,6-triamine, 5-{[4-[(1-Ethyl-pyrrolidin-2-ylmethyl)-amino]-6-(3-fluoro-4-methoxy-phenylamino)-[1,3,5]triazin-2-ylamino]-methyl}-thiazolidine-2,4-dione, 5-{[4-(Cyclohexylmethyl-amino)-6-(3-fluoro-4-methoxy-phenylamino)-[1,3,5]triazin-2-ylamino]-methyl}-thiazolidine-2,4-dione, 5-{[4-(3-Chloro-4-methoxy-phenylamino)-6-(cyclohexylmethyl-amino)-[1,3,5]triazin-2-ylamino]-methyl}-thiazolidine-2,4-dione, 5-{[4-(Cyclohexylmethyl-amino)-6-(3-fluoro-4-hydroxy-phenylamino)-[1,3,5]triazin-2-ylamino]-methyl}-thiazolidine-2,4-dione, 5-{[4-(3-Chloro-4-hydroxy-phenylamino)-6-(cyclohexylmethyl-amino)-[1,3,5]triazin-2-ylamino]-methyl}-thiazolidine-2,4-dione, Sodium; 4-{4-(cyclohexylmethyl-amino)-6-[(2,4-dioxo-thiazolidin-5-ylmethyl)-amino]-[1,3,5]triazin-2-ylamino}-2-fluoro-phenylate, 2-{[4-(Cyclohexylmethyl-amino)-6-(3-fluoro-4-methoxy-phenylamino)-[1,3,5]triazin-2-ylamino]-methyl}-1-ethyl-pyrrolidinium; chloride, 2-{[4-(Cyclohexylmethyl-amino)-6-(3-fluoro-4-methoxy-phenylamino)-[1,3,5]triazin-2-ylamino]-methyl}-1-ethyl-pyrrolidinium; bromide, 5-{4-(Cyclohexylmethyl-amino)-6-[(1-ethyl-pyrrolidin-2-ylmethyl)-amino]-[1,3,5]triazin-2-ylamino}-2-methoxy-benzoic acid, Sodium; 5-{4-(cyclohexylmethyl-amino)-6-[(1-ethyl-pyrrolidin-2-ylmethyl)-amino]-[1,3,5]triazin-2-ylamino}-2-methoxy-benzoate, 3-(2-{2-[2-(2-Hydroxy-ethoxy)-ethoxy]-ethoxy}-ethoxy)-propionic acid-{4-(cyclohexylmethyl-amino)-6-[(1 ethyl-pyrrolidin-2-ylmethyl)-amino]-[1,3,5]triazin-2-ylamino}-2-fluoro-phenyl ester, 3-(2-{2-[2-(2-Methoxy-ethoxy)-ethoxy]-ethoxy}-ethoxy)-propionic acid 4-{4-(cyclohexylmethyl-amino)-6-[(1-ethyl-pyrrolidin-2-ylmethyl)-amino]-[1,3,5]triazin-2-ylamino)-2-fluoro-phenyl ester, N-Cyclohexylmethyl-N'-(1-ethyl-pyrrolidin-2-ylmethyl)-N''-(3-fluoro-4{2-[2-(2-methoxy-ethoxy)-ethoxy]-ethoxy)-phenyl)-[1,3,5]triazine-2,4,6-triamine, .OH2-{2-[2-(4-{4-(Cyclohexylmethyl-amino)-6-[(1-ethyl-pyrrolidin-2-ylmethyl)-amino]-[1,3,5]triazin-2-ylamino}-2-fluoro-phenoxy)-ethoxy]-ethoxy)-ethanol, 1-(2-{[4-(Cyclohexylmethyl-amino)-6-(3-fluoro-4-methoxy-phenylamino)-[1,3,5]triazin-2-ylamino]-methyl)-pyrrolidin-1-yl)-3-{2-[2-(2-methoxy-ethoxy)-ethoxy]-ethoxy}-propan-1-one, 1-(2-{[4-(Cyclohexylmethyl-amino)-6-(3-fluoro-4-methoxy-phenylamino)-[1,3,5]triazin-2-ylamino]-methyl}-pyrrolidin-1-yl)-3-{2-[2-(2-hydroxy-ethoxy)-ethoxy]-ethoxy}-propan-1-one, 2-(2-{2-[2-(2-{[4-(Cyclohexylmethyl-amino)-6-(3-fluoro-4-methoxy-phenylamino)-[1,3,5]triazin-2-ylamino]-methyl}-pyrrolidin-1-yl)-ethoxy]-ethoxy}-ethoxy)-ethanol, N-Cyclohexylmethyl-N'-(3-fluoro-4-methoxy-phenyl)-N''-[1-(2-{2-[2-(2-methoxy-ethoxy)-ethoxy]-ethoxy}-ethyl)-pyrrolidin-2-ylmethyl]-[1,3,5]triazine-2,4,6-triamine, 3-Carboxy-propionate 2-{[4-(cyclohexylmethyl-amino)-6-(3-fluoro-4-methoxy-phenylamino)-[1,3,5]triazin-2-ylamino]-methyl)-1-ethyl-pyrrolidinium, 3-Carboxy-acrylate 2-{[4-(cyclohexylmethyl-amino)-6-(3-fluoro-4-methoxy-phenylamino)-[1,3,5]triazin-2-ylamino]-methyl}-1-ethyl-pyrrolidinium, N-Cyclohexylmethyl-6-(2-dimethylamino-ethoxy)-N'-(3-fluoro-4-methoxy-phenyl)-[1,3,5]triazine-2,4-diamine, N-(1-Ethyl-pyrrolidin-2-ylmethyl)-N'-(3-fluoro-4-methoxy-phenyl)-6-(thiophen-2-ylmethoxy)-[1,3,5]triazine-2,4-diamine, N-(1-Ethyl-pyrrolidin-2-ylmethyl)-N'-(3-fluoro-4-methoxy-phenyl)-6-(oxazol-5-ylmethoxy)-[1,3,5]triazine-2,4-diamine, 6-Benzyloxy-N-(1-ethyl-pyrrolidin-2-ylmethyl)-N'-(3-fluoro-4-methoxy-phenyl)-[1,3,5]triazine-2,4-diamine, N-Cyclohexylmethyl-N'-(3-fluoro-4-methoxy-phenyl)-6-(1-methyl-1H-pyrrol-2-ylmethoxy)-[1,3,5]triazine-2,4-diamine, N-Cyclohexylmethyl-N'-(3-fluoro-4-methoxy-phenyl)-6-(furan-2-ylmethoxy-[1,3,5]triazine-2,4-diamine, N-Cyclohexylmethyl-N'-(3-fluoro-4-methoxy-phenyl)-6-(thiophen-2-ylmethoxy)-[1,3,5]triazine-2,4-diamine, 6-(Bicyclo[2.2.2]oct-2-yloxy)-N-cyclohexylmethyl-N'-(3-fluoro-4-methoxy-phenyl)-[1,3,5]triazine-2,4-diamine, N-Cyclohexylmethyl-N'-(3-fluoro-4-methoxy-phenyl)-6-(1-methyl-pyrrolidin-2-yloxy)-[1,3,5]triazine-2,4-diamine, 4-[4-[(1-Ethyl-pyrrolidin-2-yl methyl)-amino]-6-(3-fluoro-4-methoxy-phenylamino)-[1,3,5]triazin-2-yloxymethyl]-cyclohexanol, 4-[4-[(1-Ethyl-pyrrolidin-2-ylmethyl)-amino]-6-(3-fluoro-4-methoxy-phenylamino)-[1,3,5]triazin-2-yloxymethyl]-phenyl,

[4-[(1-Ethyl-pyrrolidin-2-ylmethyl)-amino]-6-(3-fluoro-4-methoxy-phenylamino)-[1,3,5]triazin-2-ylamino]-(4-hydroxy-phenyl)-acetic acid, Cyclohexyl-[4-[(1-ethyl-pyrrolidin-2-ylmethyl)-amino]-6-(3-fluoro-4-methoxy-phenylamino)-[1,3,5]triazin-2-ylamino]-acetic acid,

[4-[(1-Ethyl-pyrrolidin-2-ylmethyl)-amino]-6-(3-fluoro-4-methoxy-phenylamino)-[1,3,5]triazin-2-ylamino]-phenyl-acetic acid, 6-(2-Amino-1-phenyl-ethoxy)-N1-ethyl-pyrrolidin-2-yl-methyl)-N'-(3-fluoro-4-methoxy-phenyl)-[1,3,5]triazine-2,4-diamine, 2-[4-[(1-Ethyl-pyrrolidin-2-ylmethyl)-amino]-6-(3-fluoro-4-methoxy-phenylamino)-[1,3,5]triazin-2-ylamino]-2-phenyl-ethanol, N-(1-Benzyl-pyrrolidin-2-ylmethyl)N'-cyclohexylmethyl-N''-(3-fluoro-4-methoxy-phenyl)-[1,3,5]triazine-2,4,6-triamine, Amino-phenyl-acetic acid 4-[(1-ethyl-pyrrolidin-2-ylmethyl)-amino]-6-(3-fluoro-4-methoxy-phenylamino)-[1,3,5]triazin-2-yl ester, Trifluoro-acetate 2-{[4-(cyclohexylmethyl-amino)-6-(3-fluoro-4-methoxyphenylamino)-[1,3,5]triazin-2-ylamino]-methyl)-1-ethyl-pyrrolidinium, or 2-Cyclohexyl-2-[4-[(1-ethyl-pyrrolidin-2-ylmethyl)-amino]-6-(3-fluoro-4-methoxy-phenylamino)-[1,3,5] triazin-2-ylamino]-ethanol, or a stereoisomer, and enantiomer, a diastereomer, a racemic mixture, a salt, or a combination thereof.

2. A stent comprising a composition disposed on or within the stent, the composition comprising a pharmaceutically acceptable carrier and a compound, wherein the compound is selected from:

{[4-(Cyclohexylmethyl-amino)-6-(3-fluoro-4-methoxy-phenylamino)-[1,3,5]triazin-2-ylamino]-methyl}-cyclopentanone, N-[4-(Cyclohexylmethyl-amino)-6-(3fluoro-4-methoxy-phenylamino)-[1,3,5]triazin-2-yl]-guanidine, N-Cyclohexylmethyl-N'-(3-fluoro-4-methoxy-phenyl)-N''-(1-methyl-pyrrolidin-2-yl)-[1,3,5]triazine-2,4,6-triamine, N-Cyclohexylmethyl-N'-(3-fluoro-4-methoxy-phenyl)-N''-(tetrahydro-furan-2-ylmethyl)-[1,3,5]triazine-2,4,6-triamine, 1-(2-{[4-(Cyclohexylmethyl-amino)-6-(3-fluoro-4-methoxy-phenylamino)-[1,3,5]triazin-2-ylamino]-methyl}-pyrrolidin-1-yl)-ethanone, 2-{[4-(Cyclohexylmethyl-amino)-6-(3-fluoro-4-methoxy-phenylamino)-[1,3,5]triazin-2-ylamino]-methyl}-pyrrolidine-1-carboxylic acid methyl ester, N-Cyclohexylmethyl-N'-(3-fluoro-4-methoxy-phenyl)-[1,3,5]triazine-2,4,6-triamine, N-Cyclohexylmethyl-N'-(3-fluoro-4-methoxy-phenyl)-N''-pyrrolidin-2-ylmethyl-[1,3,5]triazine-2,4,6-triamine, N-Cyclohexylmethyl-N'-(2-ethyl-cyclopentylmethyl)-N''-(3-fluoro-4-methoxy-phenyl)-[1,3,5]triazine-2,4,6-triamine, N-Cyclohexylmethyl-N'-(2-ethyl-pyrazolidin-1-ylmethyl)-N''-(3-fluoro-4-methoxy-phenyl)-[1,3,5]triazine-2,4,6-triamine, N-Cyclohexylmethyl-N'-(3-fluoro-4-methoxy-phenyl)-N''-(1-methyl-pyrrolidin-2-ylmethyl)-[1,3,5]triazine-2,4,6-triamine, N-Cyclohexylmethyl-N'-(1-ethyl-pyrrolidin-3-ylmethyl)-N''-(3-fluoro-4-methoxy-phenyl)-[1,3,5]triazine-2,4,6-triamine, N-Cyclohexylmethyl-N'-(3-fluoromethoxy-phenyl)-N''-imidazol-1-ylmethyl-[1,3,5]triazine-2,4,6-triamine, N-Cyclohexylmethyl-6-(1-ethyl-pyrolidin-2-ylmethoxy)-N'-(3-fluoromethoxy-phenyl)-[1,3,5]triazine-2,4diamine, N-Cyclohexylmethyl-N'-(3-fluoromethoxy-phenyl)-6-(hexahydro-pyrrolo[1,2-a]pyrazin-2-yl)-[1,3,5]triazine-2,4-diamine, N-Cyclohexylmethyl-N'-(1-ethyl-pyrrolidin-2-ylmethyl)-N''-(3-fluoro-4-methoxy-phenyl)-N'-methyl-[1,3,5]triazine-2,4,6-triamine, N-Cyclohexylmethyl-N'-(3-fluoro-4-methoxy-phenyl)-6-(pyrrolidin-2-ylmethoxy)-[1,3,5]triazine-2,4-diamine, N-Cyclohexylmethyl-N'-(1-ethyl-piperidin-2-ylmethyl)-N''-(3-fluoro-4-methoxy-phenyl)-[1,3,5]triazine-2,4,6-triamine, 1-Ethyl-pyrrolidine-2-carboxylic acid [4-(cyclohexylmethyl-amino)-6-(3-fluoro-4-methoxy-phenylamino)-[1,3,5]triazin-2-yl]-amide, Pyrrolidine-1,2-dicarboxylic acid 1-tert-butyl ester 2-[4-(cyclohexylmethyl-amino)-6-(3-fluoro-4-methoxyphenylamino)-[1,3,5]triazin-2-yl]ester, Pyrrolidine-2-carboxylic acid 4-(cyclohexylmethyl-amino)-6-(3-fluoro-4-methoxy-phenylamino)-[1,3,5]triazin-2-yl ester, N-(3-Chloro-4-methoxy-phenyl)-N'-cyclohexylmethyl-N''-(1-ethyl-pyrrolidin-2-ylmethyl)-[1,3,5]triazine-2,4,6-triamine, N-(3-Bromo-4-methoxy-phenyl)-N'-cyclohexylmethyl-N''-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N''-(4-methoxy-3-nitro-phenyl)-[1,3,5]triazine-2,4,6-triamine, 5-[4-[(1-Ethyl-pyrrolidin-2-ylmethyl)-amino]-6-(2-methyl-pentylamino)[1,3,5]triazin-2-ylamino]-2-methoxy-benzenesulfonic acid, 5-{4-(Cyclohexylmethyl-amino)-6-[(1-ethyl-pyrrolidin-2-ylmethyl)-amino]-[1,3,5]triazin-2-ylamino)-2-methoxy-benzonitrile, 4-{4-(Cyclohexylmethyl-amino)-6-[(1-ethyl-pyrrolidin-2-ylmethyl)-amino]-[1,3,5]triazin-2-ylamino)-2-fluoro-phenyl, Sodium; 2-chloro-4-{4-(cyclohexylmethyl-amino)-6-[(1-ethyl-pyrrolidin2-ylmethyl)-amino]-[1,3,5]triazin-2-ylamino}-phenylate, N-(3-chloro-4-ethoxy-phenyl)-N'-(1-ethyl-pyrrolidin-2-ylmethyl)-N''-(2-methyl-phenyl)-[1,3,5]triazine-2,4,6-triamine, Sodium; 4-{4-(cyclohexylmethyl-amino)-6-[(1-ethyl-pyrrolidin-2-ylmethyl)-amino]-[1,3,5]triazin-2-ylamino}-2-fluoro-phenylate, N-Cyclohexylmethyl-N'-(1-ethyl-pyrrolidin-2-ylmethyl)-N''-(3-fluoro-4-methoxymethoxy-phenyl)-[1,3,5]triazine-2,4,6-triamine, N-Cyclohexylmethyl-N'-(1-ethyl-pyrrolidin-2-ylmethyl)-N''-(3-fluoro-4-methylsulfanylmethoxy-phenyl)-[1,3,5]triazine-2,4,6-triamine, N-Cyclohexylmethyl-N'-(1-ethyl-pyrrolidin-2-ylmethyl)-N''-(3-fluoro-4-methanesulfinylmethoxy-phenyl)-[1,3,5]triazine-2,4,6-triamine, N-Cyclohexylmethyl-N'-(1-ethyl-pyrrolidin-2-ylmethyl)-N''-(3-fluoro-4-methanesulfonylmethoxy-phenyl)-[1,3,5]triazine-2,4,6-triamine, N-Cyclohexylmethyl-N'-(1-ethyl-pyrrolidin-2-ylmethyl)-N''-(3-fluoro-4-methylsulfanyl-phenyl)-[1,3,5]triazine-2,4,6-triamine, 4-{4-(Cyclohexylmethyl-amino)-6-[(1-ethyl-pyrrolidin-2-ylmethyl)-amino]-[1,3,5]triazin-2-ylamino}-2-fluoro-benzenethiol, N-Cyclohexylmethyl-N'-(1-ethyl-pyrrolidin-2-ylmethyl)-N''-(3-fluoro-4-methoxy-phenyl)-N''-methyl-[1,3,5]triazine-2,4,6-triamine, N-Cyclohexylmethyl-N'-(3-fluoro-4-methoxy-phenyl)-N'-methyl-N''-pyrrolidin-2-ylmethyl-[1,3,5]triazine-2,4,6-triamine, N-Cyclohexylmethyl-N'-(3-fluoro-4-methoxy-phenyl)-6-(tetrahydro-pyrrolo[1,2-c]imidazol-2-yl)-[1,3,5]triazine-2,4-diamine, Phosphoric acid mono-(4-{4-(cyclohexylmethyl-amino)-6-[(1-ethyl-pyrrolidin-2-ylmethyl)-amino]-[1,3,5]triazin-2-ylamino}-2-fluoro-phenoxymethyl) ester, Phosphoric acid mono-(4-{4-(cyclohexylmethyl-amino)-6-[(1-ethyl-pyrrolidin-2-ylmethyl)-amino]-[1,3,5]triazin-2-ylamino}-2-fluoro-phenyl) ester, Phosphoric acid mono-(2-chloro-4-{4-(cyclohexylmethyl-amino)-6-[(1-ethyl-pyrrolidin-2-ylmethyl)-amino]-[13,5]triazin-2-ylamino}-phenoxymethyl) ester, N-Cyclohexy[methyl-N'-(1-ethyl-pyrrolidin-2-ylmethyl)-N''-(3-fluoro-4methylamino-phenyl)-[1,3,5]triazine-2,4,6-triamine, Acetic acid 4-{4-(cyclohexylmethylamino)-6-[(1-ethyl-pyrrolidin-2-ylmethyl)-amino]-[1,3,5]triazin-2-ylamino}-2-fluoro-phenyl ester, N-(4-Amino-3-fluoro-phenyl)-N'-cyclohexylmethyl-N''-(1-ethyl-pyrrolidin-2-ylmethyl)-[1,3,5]triazine-2,4,6-triamine, N-Cyclohexylmethyl-N'-(4-dimethylamino-3-fluoro-phenyl)-N''-(1-ethyl-pyrrolidin-2-ylmethyl)-[1,3,5]triazine-2,4,6-triamine, N-(4-Amino-3-chloro-phenyl)-N'-cyclohexylmethyl-N''-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N''-(3-fluoro-4-isopropoxy-phenyl)-[1,3,5]triazine-2,4,6-triamine, N-Cyclohexylmethyl-N-(4-cyclopropoxy-3-fluoro-phenyl)-N''-1-ethyl-pyrrolidin-2-ylmethyl)-[1,3,5]triazine-2,4,6-triamine, N-(3-Chloro-4-cyclopropoxy-phenyl)N'-Cyclohexylmethyl-N''-(1-ethyl-pyrrolidin-2-ylmethyl)-[1,3,5]triazine-2,4,6-triamine, N-Cyclohexylmethyl-N'-(4-ethyl-3-fluoro-phenyl)-N''-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N''-(3-fluoro-4methyl-phenyl)-[1,3,5]triazine-2,4,6-triamine, N-(3-Chloro-4-methyl-phenyl)-N'-cyclohexylmethyl-N''-(1-ethyl-pyrrolidin-2-ylmethyl)-[1,3,5]triazine-2,4,6-triamine, N-Cyclohexylmethyl-N'-(1-ethyl-pyrrolidin-2-ylmethyl)-N''-(3-fluoro-4trifluoromethoxy-phenyl)-[1,3,5]triazine-2,4,6-triamine, N-Cyclohexylmethyl-N'-(1-ethyl-pyrrolidin-2-ylmethyl)-N''-(4-methoxy-3-trifluoromethyl-phenyl)-[1,3,5]triazine-2,4,6-triamine, N-(3-Chloro-4-trifluoromethoxy-phenyl)-N'-cyclohexylmethyl-N''-(1-ethyl-pyrrolidin-2-ylmethyl)-[1,3,5]triazine-2,4,6-triamine, N-Cyclohexylmethyl-N'-(3-ethyl-oxazolidin-4-ylmethyl)-N"-(4-trifluoromethoxy-3-trifluoromethyl-phenyl)-[1,3,5]triazine-2,4,6-triamine, N-Cyclohexylmethyl-N'-(3,5-dichloro-4-methyl-phenyl)-N"-(1-ethyl-pyrrolidin-2-ylmethyl)-[1,3,5]triazine-2,4,6-triamine, N-Cyclohexylmethyl-N'-(3,5-dichloro-4-methoxy-phenyl)-N"-(1-ethyl-pyrrolidin-2-ylmethyl)-[1,3,5]triazine-2,4,6-triamine, N-Cyclohexylmethyl-N'-(3,5-difluoro-4-methoxy-phenyl)-N"-(1-ethyl-pyrrolidin-2-ylmethyl)-[1,3,5]triazine-2,4,6-triamine, 4-{4-(Cyclohexylmethyl-amino)-6-[(1-ethyl-pyrrolidin-2-ylmethyl)-amino]-[1,3,5]triazin-2-ylamino}-2,6-difluoro-phenyl, N-Cyclohexylmethyl-N'-(1-ethyl-pyrrolidin-2-ylmethyl)-N"-(4-fluoro-5methoxy-pyridin-2-yl)-[1,3,5]triazine-2,4,6-triamine, N-Cyclohexylmethyl-N'-(1-ethyl-pyrrolidin-2-ylmethyl)-N"-(5-fluoro-6methoxy-pyridin-3-yl)-[1,3,5]triazine-2,4,6-triamine, N-Cyclohexylmethyl-N'-(1-ethyl-pyrrolidin-2-ylmethyl)-N"-(8-fluoro-chroman-6-yl)-[1,3,5]triazine-2,4,6-triamine, N-Cyclohexylmethyl-N'-(1-ethyl-pyrrolidin-2-ylmethyl)-6-(3-fluoro-4-methoxy-phenoxy)-[1,3,5]triazine-2,4-diamine, 6-(4-Amino-3-fluoro-phenoxy)-N-cyclohexylmethyl-N'-(1-ethyl-pyrrolidin-2-ylmethyl)-[1,3,5]triazine-2,4-diamine, 6-(4-Amino-2-fluoro-phenoxy)-N-cyclohexylmethyl-N'-(1-ethyl-pyrrolidin-2-ylmethyl)-[1,3,5]triazine-2,4-diamine, N-(1-Ethyl-pyrrolidin-2-ylmethyl)-N-(3-fluoromethoxy-phenyl)-N"-(tetrahydro-pyran-4-ylmethyl)-[1,3,5]triazine-2,4,6-triamine, N-(1-Ethyl-pyrrolidin-2-ylmethyl)-6-(3-fluoro-4-methoxy-phenoxy)-N-piperidin-4-ylmethyl-[1,3,5]triazine-2,4-diamine, N-(1-Ethyl-pyrrolidin-2-ylmethyl)-N'-(3-fluoro-4-methoxy-phenyl)-N"-thiomorpholin-4-ylmethyl-[1,3,5]triazine-2,4,6-triamine, N-(1,1-Dioxo-1 lambda*6*-thiomorpholin-4-ylmethyl)-N'-(1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N-(3-fluoro-4-methoxy-phenyl)-N"-(tetrahydro-thiopyran-4-ylmethyl)-[1,3,5]triazine-2,4,6-triamine, N-(1,1-Dioxo-hexahydro-1 lambda*6*-thiopyran-4-ylmethyl)-N'-1-ethyl-pyrrolidin-2-ylmethyl)-N"-(3-fluoro-4-methoxy-phenyl)-[1,3,5]triazine-2,4,6-triamine, N-Benzyl-N'-(1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N'-(3-fluoro-4-methoxy-phenyl)-N"-(4-methoxy-benzyl)-[1,3,5]triazine-2,4,6-triamine, N-(1-Ethyl-pyrrolidin-2-ylmethyl)-N'-(3-fluoro-4-methoxy-phenyl)-N"-(4-methyl-benzyl)-[1,3,5]triazine-2,4,6-triamine, N-(1-Ethyl-pyrrolidin-2-ylmethyl)-N'-(3-fluoro-4-methoxy-phenyl)-N"-(4-nitro-benzyl)-[1,3,5]triazine-2,4,6-triamine, N-(1-Ethyl-pyrrolidin-2-ylmethyl)-N'-(4-fluoro-benzyl)-N"-(3-fluoro-4-methoxy-phenyl)-[1,3,5]triazine-2,4,6-triamine, N-Cyclopenty[methyl-N'-(1-ethyl-pyrrolidin-2-ylmethyl)-N"-(3-fluoro-4-methoxy-phenyl)-[1,3,5]triazine-2,4,6-triamine, N-Cyclohex-2-enylmethyl-N'-(1-ethyl-pyrrolidin-2-ylmethyl)-N"-(3-fluoro-4-methoxy-phenyl)-[1,3,5]triazine-2,4,6-triamine, N-Cyclopropylmethyl-N'-(1-ethyl-pyrrolidin-2-ylmethyl)-N"-(3-fluoro-4-methoxy-phenyl)-[1,3,5]triazine-2,4,6-triamine, '3-{[4-[(1-Ethyl-pyrrolidin-2-ylmethyl)-amino]-6-(3-fluoro-4-methoxy-phenylamino)-[1,3,5]triazin-2-ylamino]-methyl}-cyclopentanol, N-(3-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, N-Cyclohexylmethyl-N'-(1-ethyl-pyrrolidin-2-ylmethyl)-N"-(3-fluoro-4-methoxy-benzyl)-[1,3,5]triazine-2,4,6-triamine, N-(3-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, 2-{[4-[(1-Ethyl-pyrrolidin-2-ylmethyl)-amino]-6-(3-fluoro-4-methoxy-phenylamino)-[1,3,5]triazin-2-ylamino]-methyl}-cyclopentanol, N-(2-Amino-cyclopentylmethyl)-N'-(1-ethyl-pyrrolidin-2-ylmethyl)-N"-(3-fluoro-4-methoxy-phenyl)-[1,3,5]triazine-2,4,6-triamine, N-(1-Ethyl-pyrrolidin-2-ylmethyl)-N'-(3-fluoro-4-methoxy-phenyl)-N"-(4-methyl-cyclohexylmethyl)-[1,3,5]triazine-2,4,6-triamine, N-(1-Ethyl-pyrrolidin-2-ylmethyl)-N'-(3-fluoro-4-methoxy-phenyl)-N"-(2-methyl-cyclohexylmethyl)-[1,3,5]triazine-2,4,6-triamine, 2-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, 3-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, 4-{[4-[(1-Ethyl-pyrrolidin-2-ylmethyl)-amino]-6-(3-fluoro-4-methoxy-phenylamino)-[1,3,5]triazin-2-ylamino]-methyl}-cyclohexanol, N-(4-Amino-cyclohexylmethyl)-N'-(1-ethyl-pyrrolidin-2-ylmethyl)-N"-(3-fluoro-4-methoxy-phenyl)-[1,3,5]triazine-2,4,6-triamine, N-(3-Amino-cyclohexylmethyl)-N'-(1 ethyl-pyrrolidin-2-ylmethyl)-N"-(3-fluoro-4-methoxy-phenyl)-[1,3,5]triazine-2,4,6-triamine, N-Cycloheptylmethyl-N'-(1-ethyl-pyrrolidin-2-ylmethyl)-N"-(3-fluoro-4-methoxy-phenyl)-[1,3,5]triazine-2,4,6-triamine, N-Bicyclo[2.2.1]hept-2-yl-N'-cyclohexylmethyl-N"-(3-fluoro-4-methoxyphenyl)-[1,3,5]triazine-2,4,6-triamine, N-Bicyclo[2.2.2]oct-2-yl-N'-cyclohexylmethyl-N"-(3-fluoro-4-methoxy-phenyl)-[1,3,5]triazine-2,4,6-triamine, N-(1-Aza-bicyclo[2.2.2]oct-3-yl)-N'-cyclohexylmethyl-N"-(3-fluoro-4-methoxy-phenyl)-[1,3,5]triazine-2,4,6-triamine, N-(1-Cyclohexyl-1-methyl-ethyl)-N'-(1-ethyl-pyrrolidin-2-ylmethyl)-N"-(3-fluoro-4-methoxy-phenyl)-[1,3,5]triazine-2,4,6-triamine, N-Cyclohexylmethyl-N'-(3-fluoro-4-methoxy-phenyl)-N"-(tetrahydro-thiophen-2-ylmethyl)-[1,3,5]triazine-2,4,6-triamine, N-Cyclohexylmethyl-N'-(3-fluoro-4-methoxy-phenyl)-N"-(tetrahydro-furan-2-ylmethyl)-[1,3,5]triazine-2,4,6-triamine, N-Cyclohexylmethyl-N'-(3-fluoro-4-methoxy-phenyl)-N"-furan-2-ylmethyl-[1,3,5]triazine-2,4,6-triamine, N-Cyclohexylmethyl-N'-(3-fluoro-4-methoxy-phenyl)-N"-thiophen-2-ylmethyl-[1,3,5]triazine-2,4,6-triamine, N-Cyclohexylmethyl-N'-(3-fluoro-4-ethoxy-phenyl)-N"-(1H-pyrrol-2-ylmethyl)-[1,3,5]triazine-2,4,6-triamine, N-Cyclohexylmethyl-N'-(3-fluoro-4-nethoxy-phenyl)-N"-(1-methyl-1H-pyrrol-2-ylmethyl)-[1,3,5]triazine-2,4,6-triamine, N-Cyclohexylmethyl-N'-(3-fluoro-4-methoxy-phenyl)-N"-(1-methyl-1H-pyrrol-2-ylmethyl)-[1,3,5]triazine-2,4,6-triamine, N-Cyclohexylmethyl-N'-(2,3-dihydro-1H-indol-2-ylmethyl)-N"-(3-fluoro-4-methoxy-phenyl)-[1,3,5]triazine-2,4,6-triamine, N-Cyclohexylmethyl-N'-(2-dimethylamino-ethyl)-N"-(3-fluoro-4-methoxyphenyl)-[1,3,5]triazine-2,4,6-triamine, Pyrrolidine-2-carboxylic acid [4-(cyclohexylmethyl-amino)-6-(3-fluoro-4-methoxy-phenylamino)-[1,3,5]triazin-2-yl]-amide, Pyrrolidine-2-carboxylic acid 4-(cyclohexylmethyl-amino)-6-(3-fluoro-4-methoxy-phenylamino)-[1,3,5]triazin-2-yl ester, 1-Methyl-pyrrolidine-2-carboxylic acid [4-(cyclohexylmethyl-amino)-6-(3-fluoro-4-methoxy-phenylamino)-[1,3,5]triazin-2-yl]-amide, 2-[4-(Cyclohexylmethyl-amino)-6-(3-fluoro-4-methoxy-phenylamino)-[1,3,5]triazin-2-yl]-hexahydro-pyrrolo[1,2-c]imidazol-1-one, 1-[4-(Cyclohexylmethyl-amino)-6-(3-fluoro-4-methoxy-phenylamino)-[1,3,5]triazin-2-yl]-pyrrolidine-2,5-dione, 1-[4-(Cyclohexylmethyl-amino)-6-(3-fluoro-4-methoxy-phenylamino)-[1,3,5]triazin-2-yl]-imidazolidine-2,4-dione, 3-[4-(Cyclohexylmethyl-amino)-6-(3-fluoro-4-methoxy-phenylamino)-[1,3,5]triazin-2-yl]-thiazolidine-2,5-dione, 2-{[4-(Cyclohexylmethyl-amino)-6-(3-fluoro-4-methoxy-phenylamino)-[1,3,5]triazin-2-ylamino]-methyl}-1-ethyl-1-methyl-pyrrolidinium; chloride, 1-Acetyl-2-{[4-(cyclohexylmethyl-amino)-6-(3-fluoro-4-methoxy-phenylamino)-[1,3,5]triazin-2-ylamino]-methyl}-1-ethyl-pyrrolidinium; chloride, N-(1-Ethyl-pyrrolidin-2-ylmethyl)-N'-(3-fluoro-4-methoxy-phenyl)-N"-furan-2-ylmethyl-[1,3,5]triazine-2,4,6-triamine, N-(1-Ethyl-pyrrolidin-2-ylmethyl)-N'-(3-fluoro-4-methoxy-phenyl)-N"-thiophen-2-ylmethyl-[1,3,5]triazine-2,4,6-triamine, N-(3-Chloro-4-methoxy-phenyl)-N'-(1-ethyl-pyrrolidin-2-ylmethyl)-N"-thiophen-2-ylmethyl-[1,3,5]triazine-2,4,6-triamine, N-(3-Chloro-4-methoxy-phenyl)-N'-(1-ethyl-pyrrolidin-2-ylmethyl)-N"-oxazol-5-ylmethyl-[1,3,5]triazine-2,4,6-triamine, N-(3-Chloro-4-methoxy-phenyl)-N'-(1-ethyl-pyrrolidin-2-ylmethyl)-N"-imidazol-1-ylmethyl-[1,3,5]triazine-2,4,6-triamine, N-(1-Ethyl-pyrrolidin-2-ylmethyl)-N'-(3-fluoro-4-methoxy-phenyl)-N"-imidazol-1-ylmethyl-[1,3,5]triazine-2,4,6-triamine, N-(1-Ethyl-pyrrolidin-2-ylmethyl)-N-(3-fluoro-4-methoxy-phenyl)-N"-pyrimidin-4-ylmethyl-[1,3,5]triazine-2,4,6-triamine, N-(2-Amino-pyrimidin-4-ylmethyl)-N'-(1-ethyl-pyrrolidin-2-ylmethyl)-N"-(3-fluoro-4-methoxy-phenyl)-[1,3,5]triazine-2,4,6-triamine, 5-{[4-[(1-Ethyl-pyrrolidin-2-ylmethyl)-amino]-6-(3-fluoro-4-methoxy-phenylamino)-[1,3,5]triazin-2-ylamino]-methyl}-thiazolidine-2,4-dione, 5-{[4-(Cyclohexylmethyl-amino)-6-(3-fluoro-4-methoxy-phenylamino)-[1,3,5]triazin-2-ylamino]-methyl}-thiazolidine-2,4-dione, 5-{[4-(3-Chloro-4-methoxy-phenylamino)-6-(cyclohexylmethyl-amino)-[1,3,5]triazin-2-ylamino]-methyl}-thiazolidine-2,4-dione, 5-{[4-(Cyclohexylmethyl-amino)-6-(3-fluoro-4-hydroxy-phenylamino)-[1,3,5]triazin-2-ylamino]-methyl}-thiazolidine-2,4-dione, 5-{[4-(3-Chloro-4-hydroxy-phenylamino)-6-(cyclohexylmethyl-amino)-[1,3,5]triazin-2-ylamino]-methyl}-thiazolidine-2,4-dione, Sodium; 4-{4-(cyclohexylmethyl-amino)-6-[(2,4-dioxo-thiazolidin-5-ylmethyl)-amino]-[1,3,5]triazin-2-ylamino}-2-fluoro-phenylate, 2-{[4-(Cyclohexylmethyl-amino)-6-(3-fluoro-4-methoxy-phenylamino)-[1,3,5]triazin-2-ylamino]-methyl}-1-ethyl-pyrrolidinium; chloride, 2-{[4-(Cyclohexylmethyl-amino)-6-(3-fluoro-4-methoxy-phenylamino)-[1,3,5]triazin-2-ylamino]-methyl}-1-ethyl-pyrrolidinium; bromide, 5-{4-(Cyclohexylmethyl-amino)-6-[(1-ethyl-pyrrolidin-2-ylmethyl)-amino]-[1,3,5]triazin-2-ylamino}-2-methoxy-benzoic acid, Sodium; 5-{4-(cyclohexylmethyl-amino)-6-[(1-ethyl-pyrrolidin-2-ylmethyl)-amino]-[1,3,5]triazin-2-ylamino}-2-methoxy-benzoate, 3-(2-{2-[2-(2-Hydroxy-ethoxy)-ethoxy]-ethoxy}-ethoxy)-propionic acid-{4-(cyclohexylmethyl-amino)-6-[(1 ethyl-pyrrolidin-2-ylmethyl)-amino]-[1,3,5]triazin-2-ylamino}-2-fluoro-phenyl ester, 3-(2-{2-[2-(2-Methoxy-ethoxy)-ethoxy]-ethoxy)-ethoxy)-propionic acid 4-{4-(cyclohexylmethyl-amino)-6-[(1-ethyl-pyrrolidin-2-ylmethyl)-amino]-[1,3,5]triazin-2-ylamino)-2-fluoro-phenyl ester, N-Cyclohexylmethyl-N'-(1-ethyl-pyrrolidin-2-ylmethyl)-N"-(3-fluoro-4 {2-[2-(2-methoxy-ethoxy)-ethoxy]-ethoxy)-phenyl)-[1,3,5]triazine-2,4,6-triamine, .OH2-{2-[2-(4-{4-(Cyclohexylmethyl-amino)-6-[(1-ethyl-pyrrolidin-2-ylmethyl)-amino]-[1,3,5]triazin-2-ylamino}-2-fluoro-phenoxy)-ethoxy]-ethoxy)-ethanol, 1-(2-{[4-(Cyclohexylmethyl-amino)-6-(3-fluoro-4-methoxy-phenylamino)-[1,3,5]triazin-2-ylamino]-methyl)-pyrrolidin-1-yl)-3-{2-[2-(2-methoxy-ethoxy)-ethoxy]-ethoxy)-propan-1-one, 1-(2-{[4-(Cyclohexylmethyl-amino)-6-(3-fluoromethoxy-phenylamino)-[1,3,5]triazin-2-ylamino]-methyl}-pyrrolidin-1-yl)-3-{2-[2-(2-hydroxy-ethoxy)-ethoxy]-ethoxy)-propan-1-one, 2-(2-{2-[2-(2-{[4-(Cyclohexylmethyl-amino)-6-(3-fluoro-4-methoxy-phenylamino)-[1,3,5]triazin-2-ylamino]-methyl}-pyrrolidin-1-yl)-ethoxy]-ethoxy}-ethoxy)-ethanol, N-Cyclohexylmethyl-N'-(3-fluoro-4-methoxy-phenyl)-N"-[1-(2-{2-[2-(2-methoxy-ethoxy)-ethoxy]-ethoxy}-ethyl)-pyrrolidin-2-ylmethyl]-[1,3,5]triazine-2,4,6-triamine, 3-Carboxy-propionate 2-{[4-(cyclohexylmethyl-amino)-6-(3-fluoro-4-methoxy-phenylamino)-[1,3,5]triazin-2-ylamino]-methyl)-1-ethyl-pyrrolidinium, 3-Carboxy-acrylate 2-{[4-(cyclohexylmethyl-amino)-6-(3-fluoro-4-methoxy-phenylamino)-[1,3,5]triazin-2-ylamino]-methyl}-1-ethyl-pyrrolidinium, N-Cyclohexylmethyl-6-(2-dimethylamino-ethoxy)-N'-(3fluoro-4-methoxy-phenyl)-[1,3,5]triazine-2,4-diamine, N-(1-Ethyl-pyrrolidin-2-ylmethyl)-N'-(3-fluoro-4-methoxy-phenyl)-6-(thiophen-2-ylmethoxy)-[1,3,5]triazine-2,4-diamine, N-(1-Ethyl-pyrrolidin-2-ylmethyl)-N'-(3-fluoro-4-methoxy-phenyl)-6-(oxazol-5-ylmethoxy)-[1,3,5]triazine-2,4-diamine, 6-Benzyloxy-N-(1-ethyl-pyrrolidin-2-ylmethyl)-N'-(3-fluoro-4-methoxy-phenyl)-[1,3,5]triazine-2,4-diamine, N-Cyclohexylmethyl-N'-(3-fluoro-4-methoxy-phenyl)-6-(1-methyl-1H-pyrrol-2-ylmethoxy)-[1,3,5]triazine-2,4-diamine, N-Cyclohexylmethyl-N'-(3-fluoro-4-methoxy-phenyl)-6-(furan-2-ylmethoxy-[1,3,5]triazine-2,4-diamine, N-Cyclohexylmethyl-N'-(3-fluoro-4-methoxy-phenyl)-6-(thiophen-2-ylmethoxy)-[1,3,5]triazine-2,4-diamine, 6-(Bicyclo[2.2.2]oct-2-yloxy)-N-cyclohexylmethyl-N-(3-fluoro-4-methoxy-phenyl)-[1,3,5]triazine-2,4-diamine, N-Cyclohexylmethyl-N'-(3-fluoro-4-methoxy-phenyl)-6-(1-methyl-pyrrolidin-2-yloxy)-[1,3,5]triazine-2,4-diamine, 4-[4-[(1-Ethyl-pyrrolidin-2-yl methyl) amino]-6-(3-fluoro-4-methoxy-phenylamino)-[1,3,5]triazin-2-yloxymethyl]-cyclohexanol, 4-[4-[(1-Ethyl-pyrrolidin-2-ylmethyl)-amino]-6-(3-fluoro-4-methoxy-phenylamino)-[1,3,5]triazin-2-yloxymethyl]-phenyl,

[4-[(1-Ethyl-pyrrolidin-2-ylmethyl)-amino]-6-(3-fluoro-4-methoxy-phenylamino)-[1,3,5]triazin-2-ylamino]-(4-hydroxy-phenyl)-acetic acid, Cyclohexyl-[4-[(1-ethyl-pyrrolidin-2-ylmethyl)-amino]-6-(3-fluoro-4-methoxy-phenylamino)-[1,3,5]triazin-2-ylamino]-acetic acid,

[4-[(1-Ethyl-pyrrolidin-2-ylmethyl)-amino]-6-(3-fluoro-4-methoxy-phenylamino)-[1,3,5]triazin-2-ylamino]-phenyl-acetic acid, 6-(2-Amino-1-phenyl-ethoxy)-N-(1-ethyl-pyrrolidin-2-ylmethyl)-N'-(3-fluoro-4-methoxy-phenyl)-[1,3,5]triazine-2,4-diamine, 2-[4-[(1-Ethyl-pyrrolidin-2-ylmethyl)-amino]-6-(3-fluoro-4-methoxy-phenylamino)-[1,3,5]triazin-2-ylamino]-2-phenyl-ethanol, N-(1-Benzyl-pyrrolidin-2-ylmethyl)N'-cyclohexylmethyl-N"-(3-fluoro-4-methoxy-phenyl)-[1,3,5]triazine-2,4,6-triamine, Amino-phenyl-acetic acid 4-[(1-ethyl-pyrrolidin-2-ylmethyl)-amino]-6-(3-fluoro-4-methoxy-phenylamino)-[1,3,5]triazin-2-yl ester, Trifluoro-acetate 2-{[4-(cyclohexylmethyl-amino)-6-(3-fluoro-4-methoxyphenylamino)-[1,3,5]triazin-2-ylamino]-methyl)-1-ethyl-pyrrolidinium, or 2-Cyclohexyl-2-[4-[(1-ethyl-pyrrolidin-2-ylmethyl)-amino]-6-(3-fluoro-4-methoxy-phenylamino)-[1,3,5]triazin-2-ylamino]-ethanol, or a stereoisomer, an enantiomer, a diastereomer, a racemic mixture, a salt, or a combination thereof.

3. The stent as claimed in claim 2, wherein the composition further comprises at least one of the following:

a pharmaceutically acceptable auxiliary;

a pharmaceutically acceptable preservative;

a pharmaceutically acceptable excipient; or any combination thereof.

4. A stent comprising a compound disposed on or within the stent, the compound having the formula

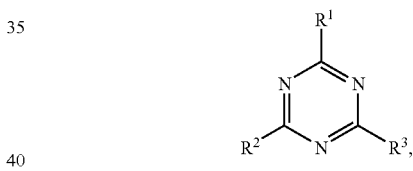

or a stereoisomer, an enantiomer, a diastereomer, a racemic mixture, a salt, or a combination thereof; wherein:

$R^1$ is selected from

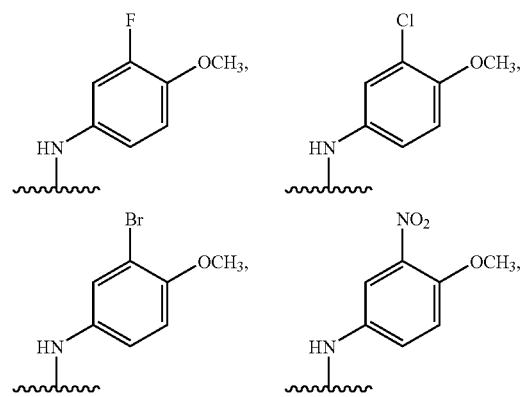

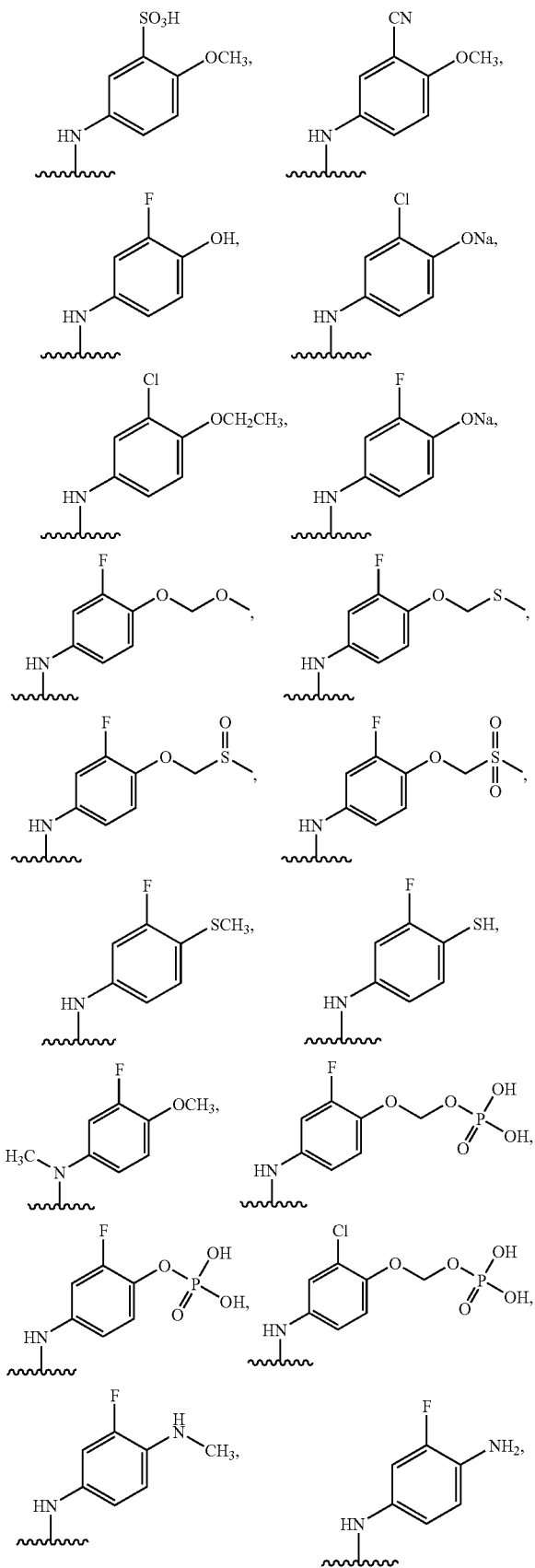

-continued
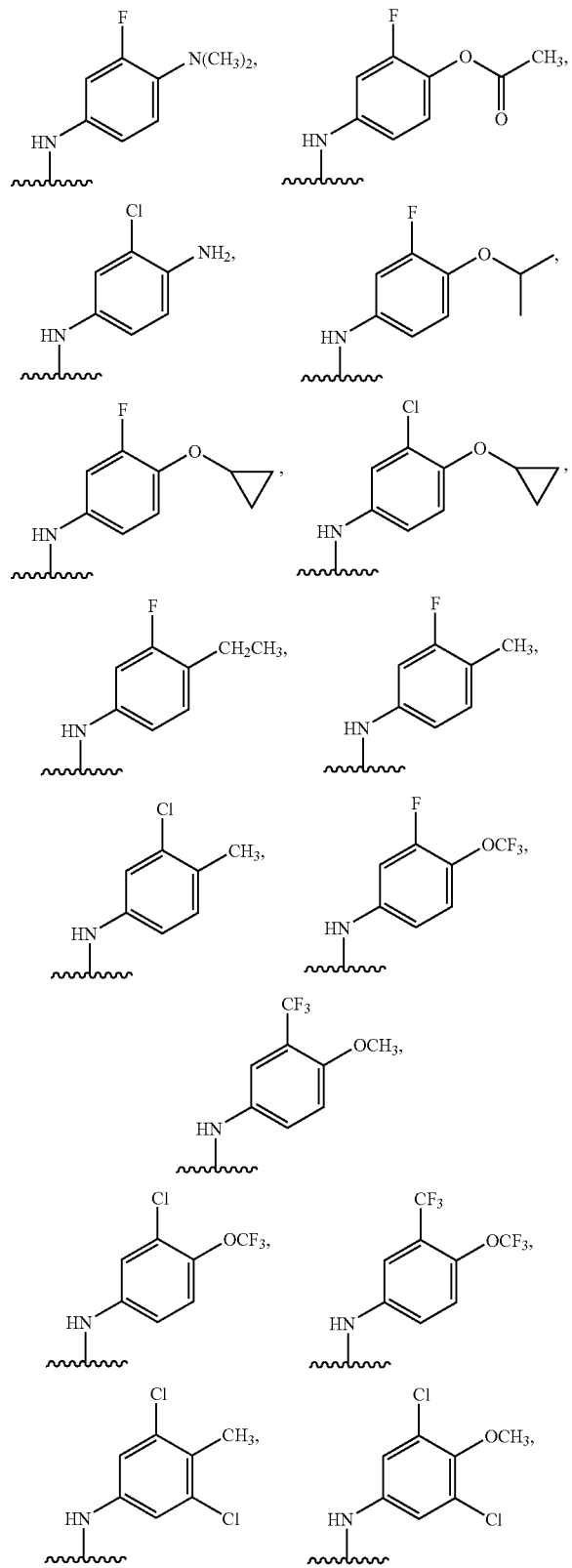

-continued
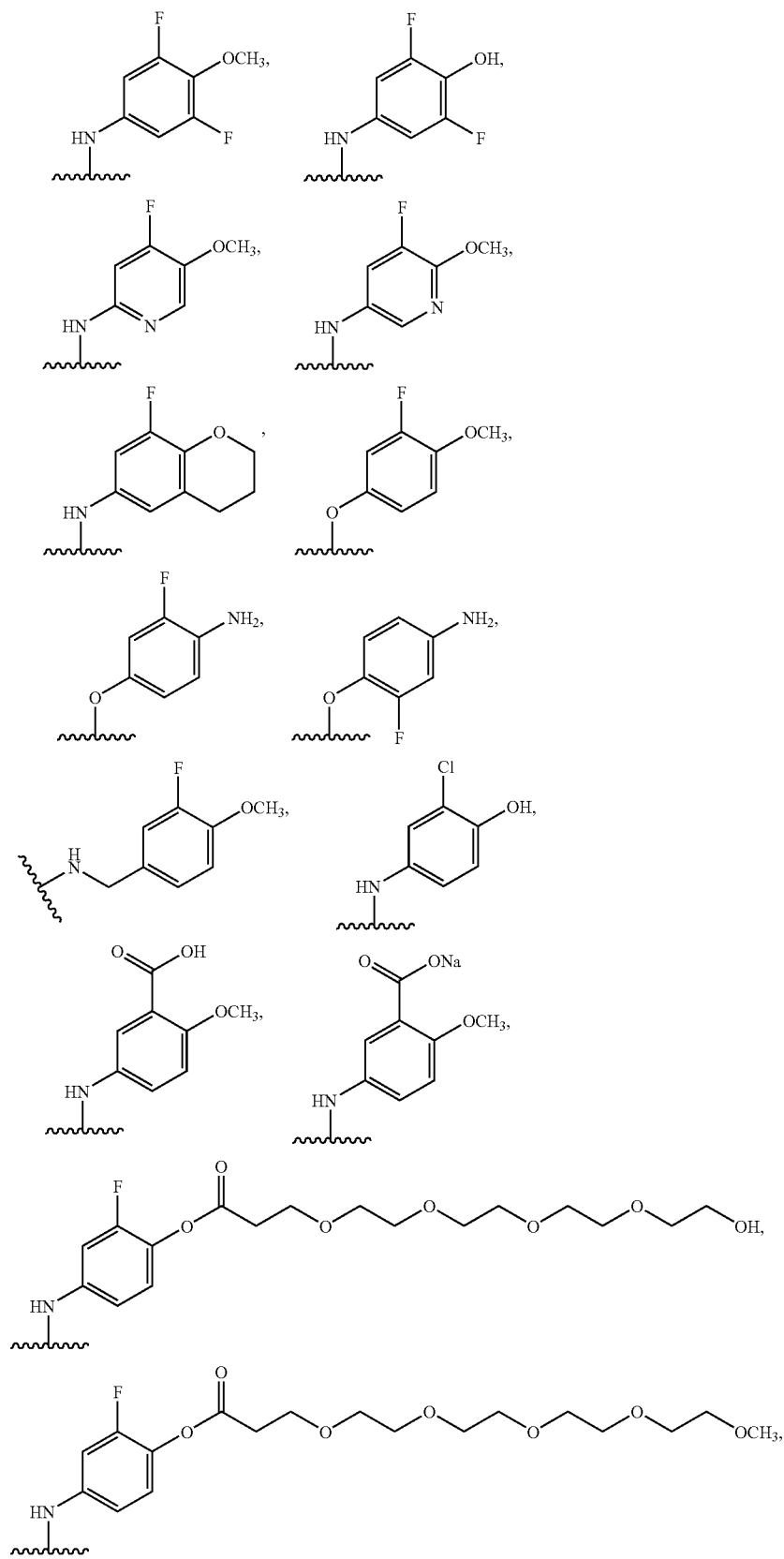

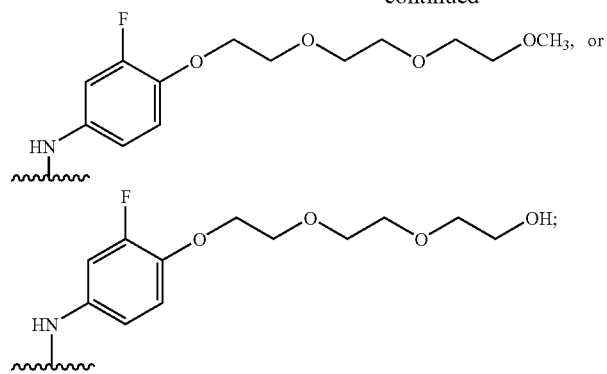
R² is selected from
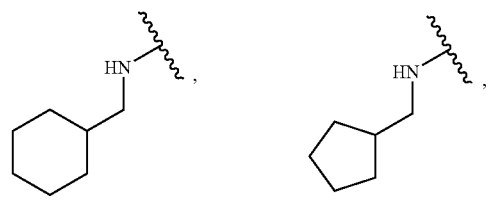
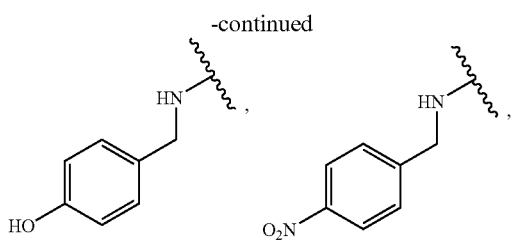
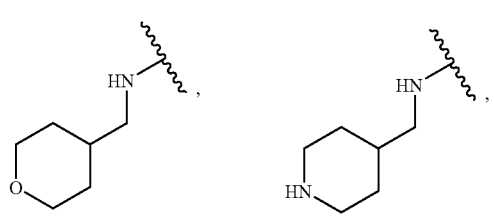
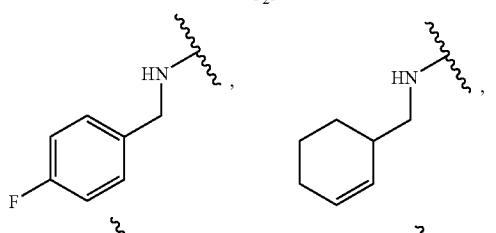
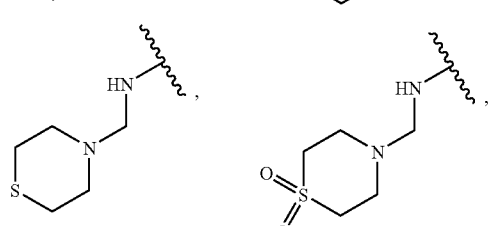
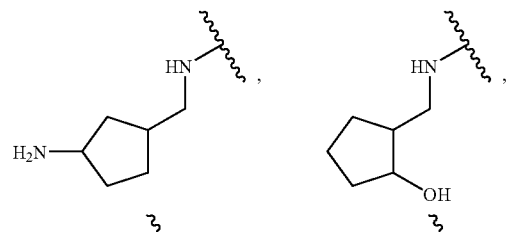
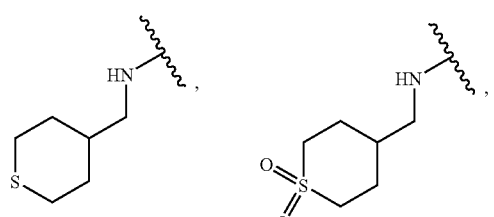
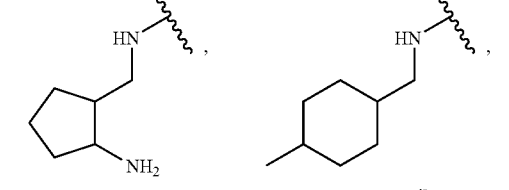
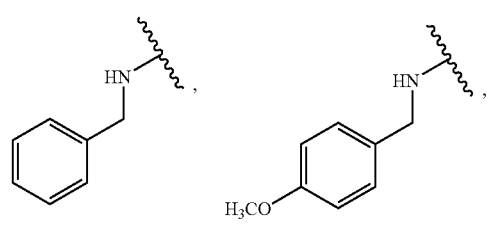
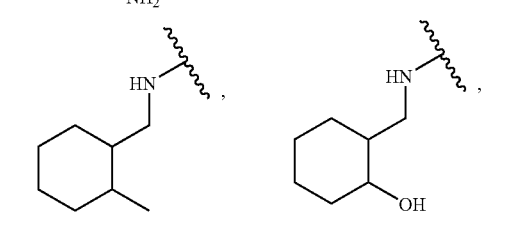

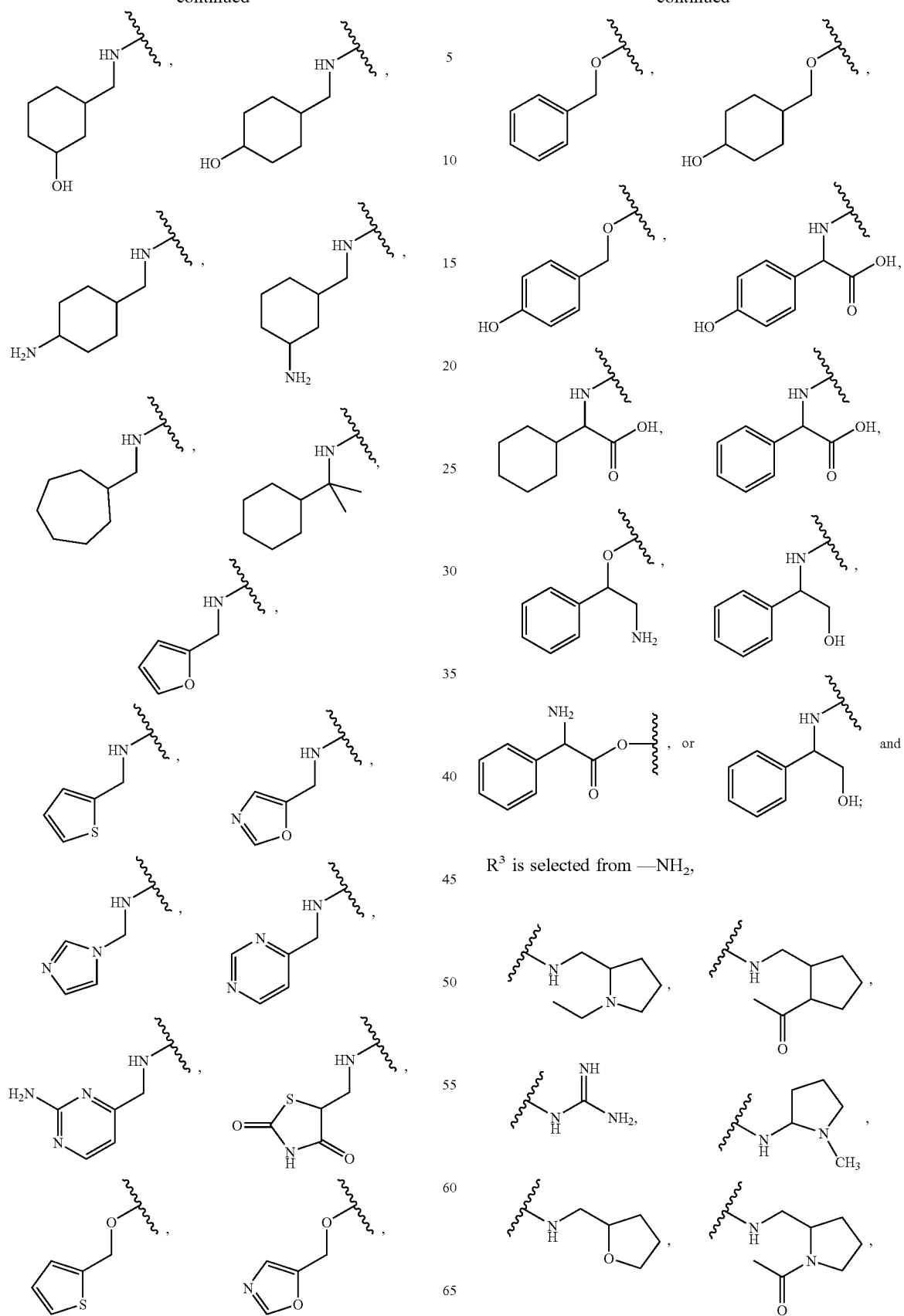
$R^3$ is selected from —$NH_2$,

-continued
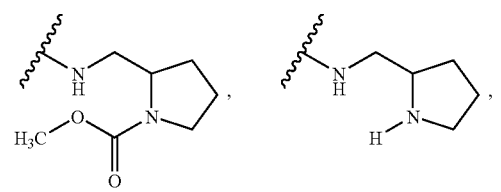 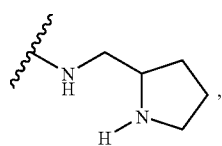
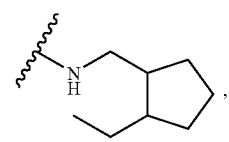 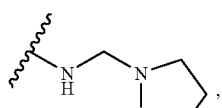
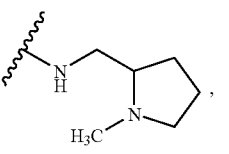 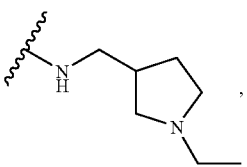
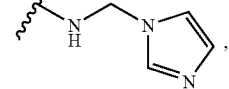 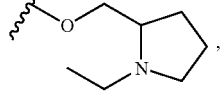
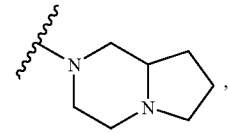 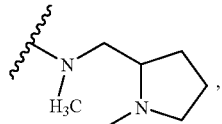
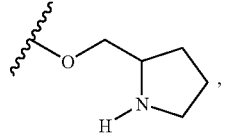 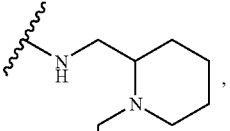
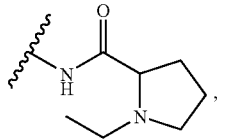 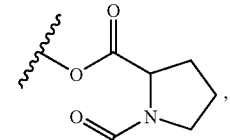
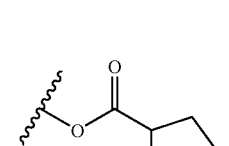 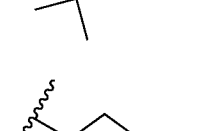
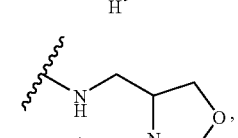 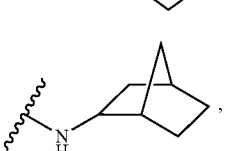
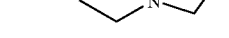 
-continued
 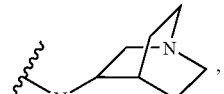
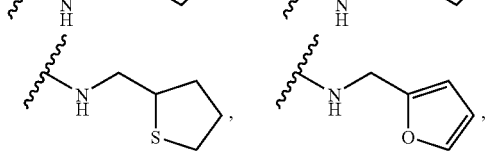 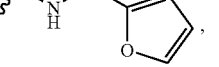
 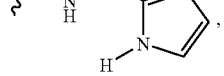
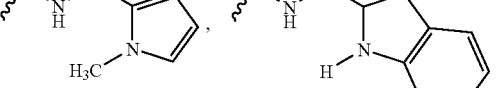
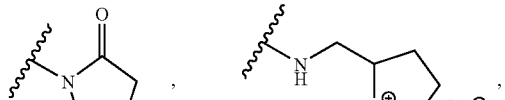
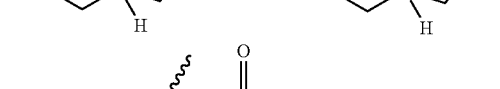
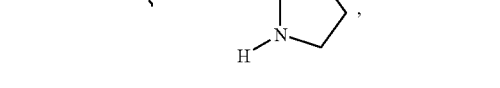

-continued
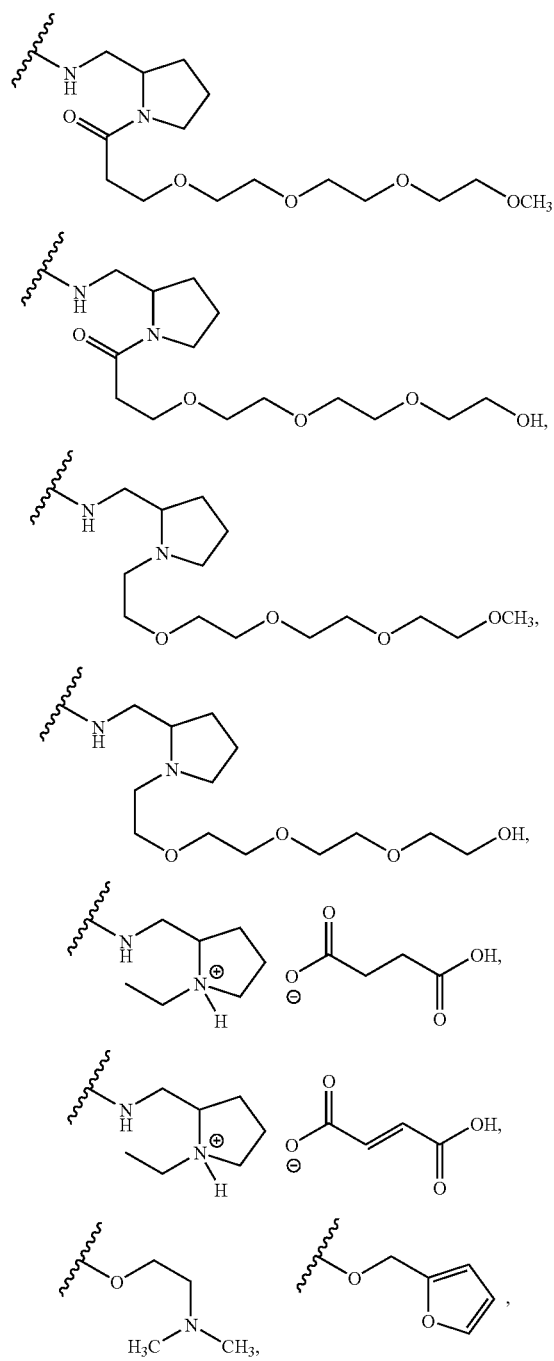
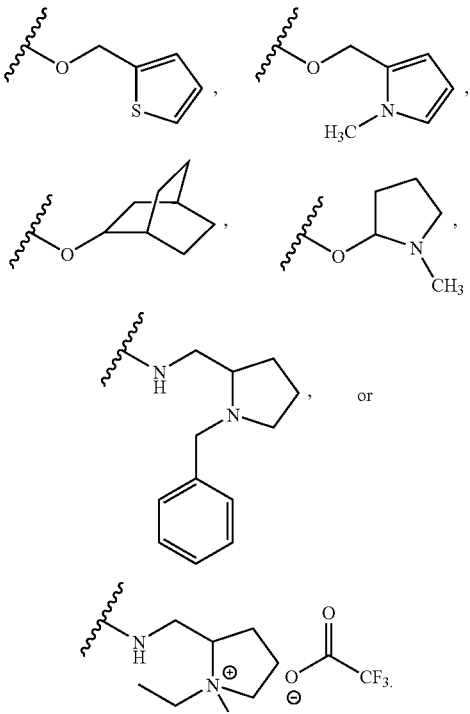
5. The stent as claimed in claim 4, wherein the compound has the formula
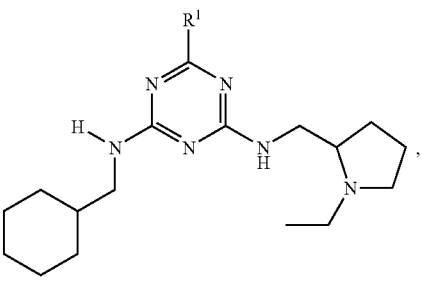
or a stereoisomer, an enantiomer, a diastereomer, a racemic mixture, a salt, or a combination thereof; wherein:
$R^1$ is selected from
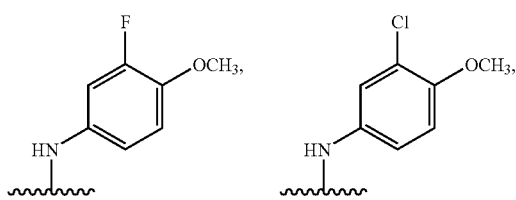

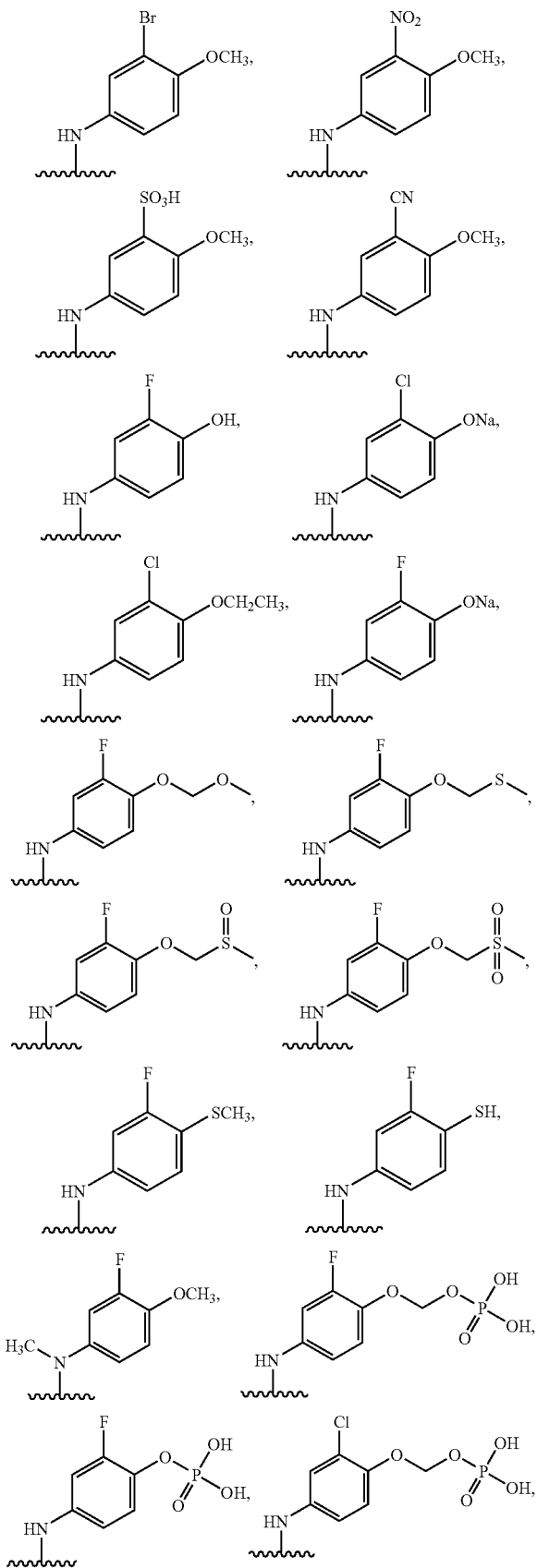

-continued
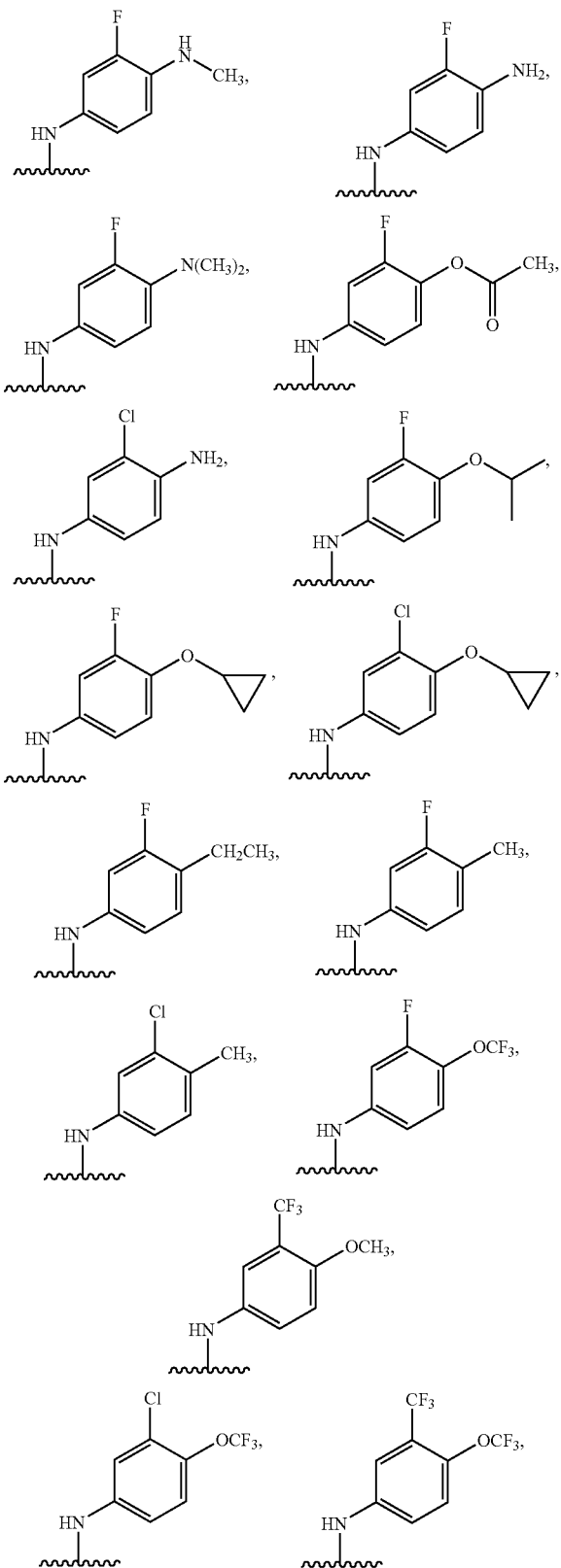

-continued
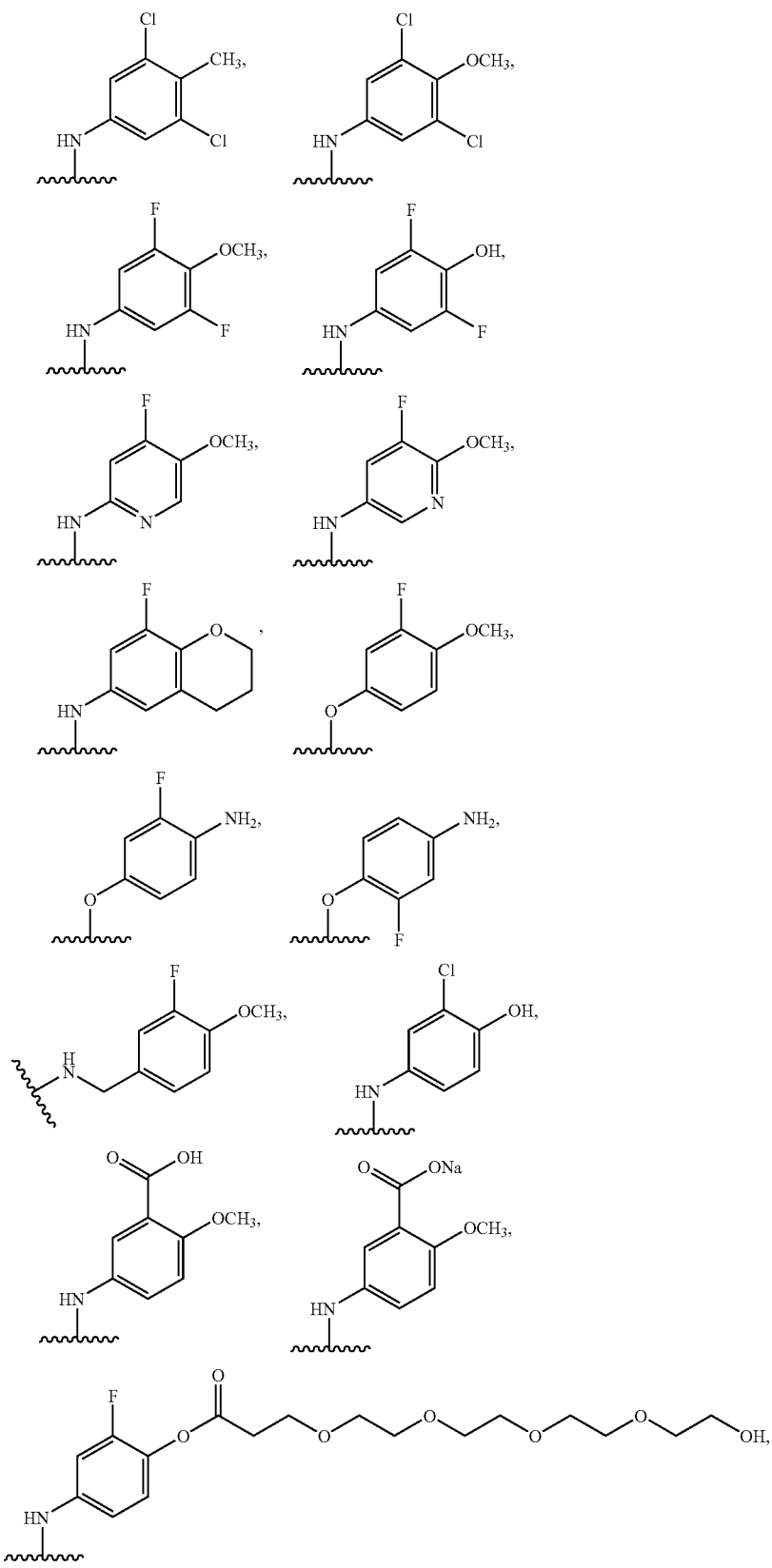

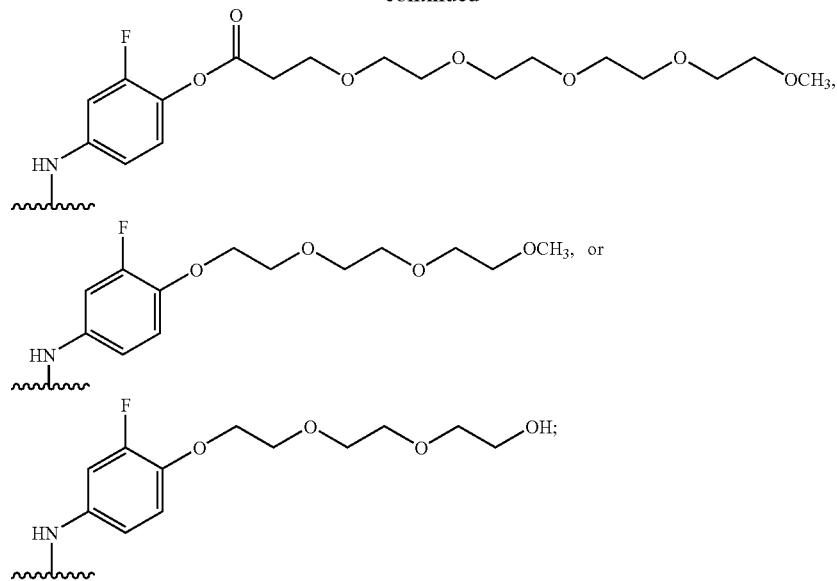
6. The stent as claimed in claim 4, wherein the compound has the formula
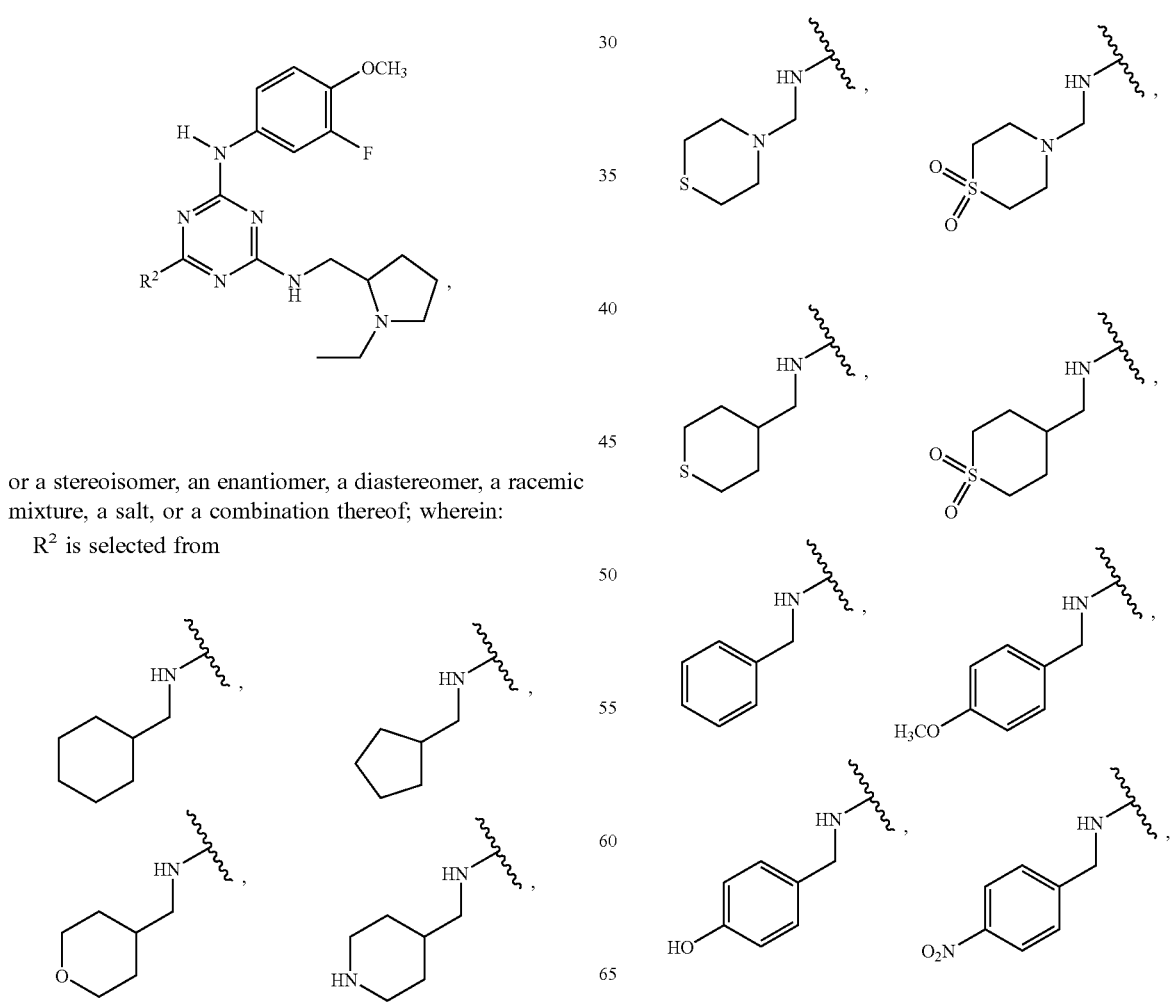
or a stereoisomer, an enantiomer, a diastereomer, a racemic mixture, a salt, or a combination thereof; wherein:
$R^2$ is selected from

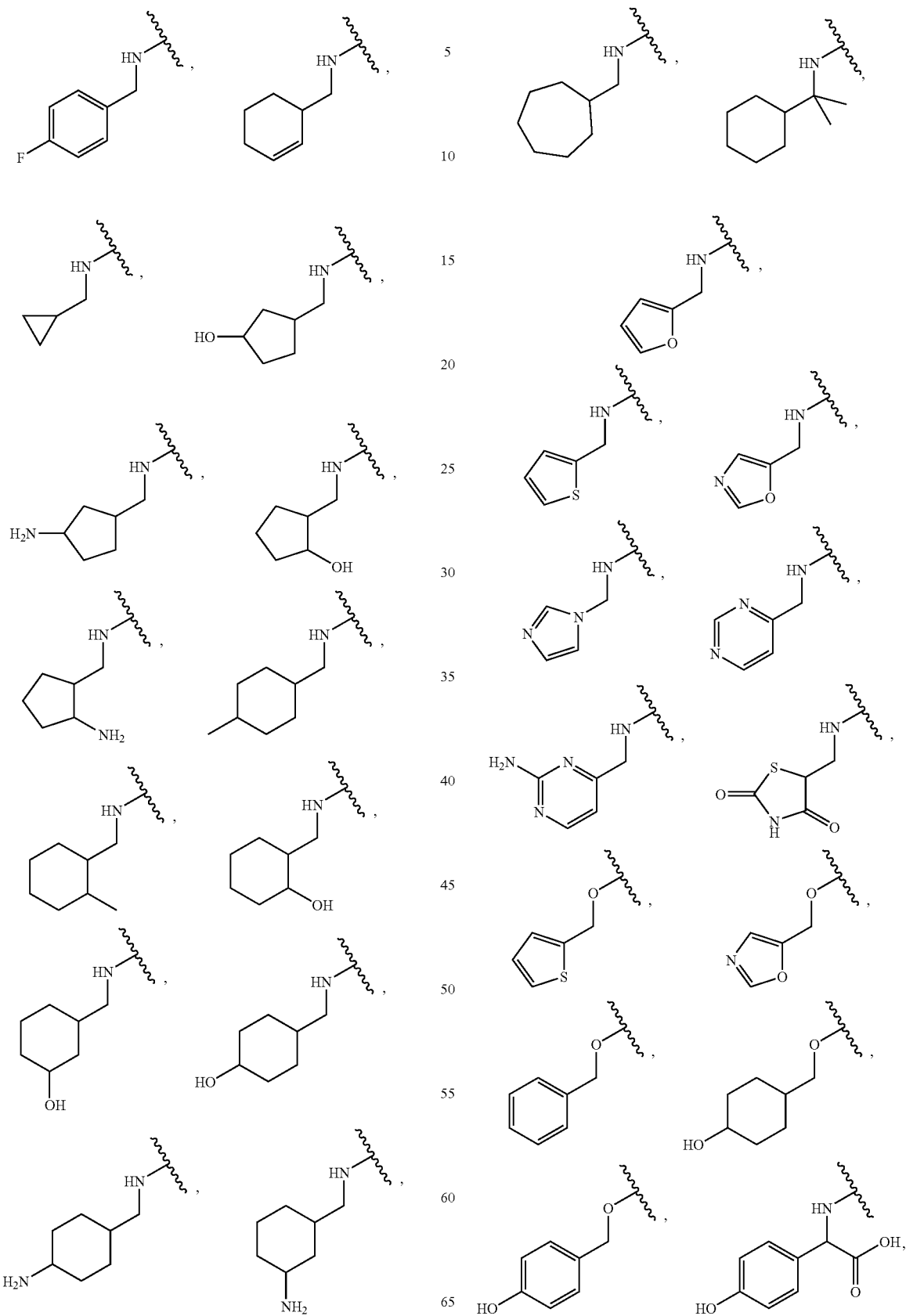

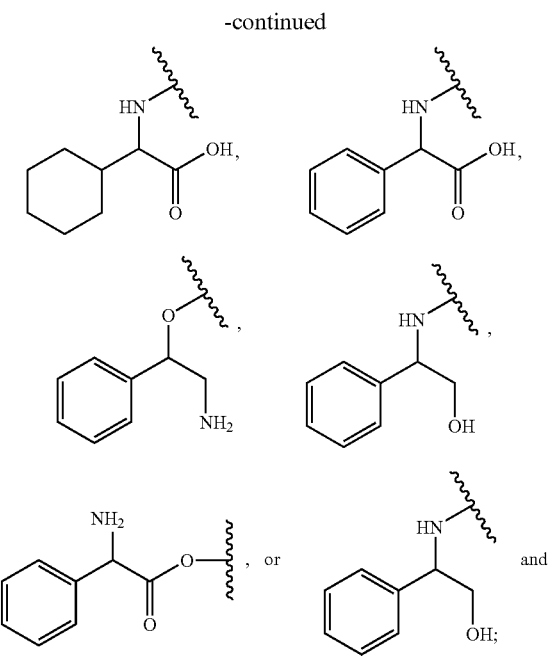
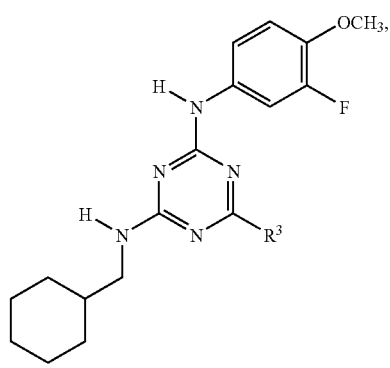
7. The stent as claimed in claim 4, wherein the compound has the formula:
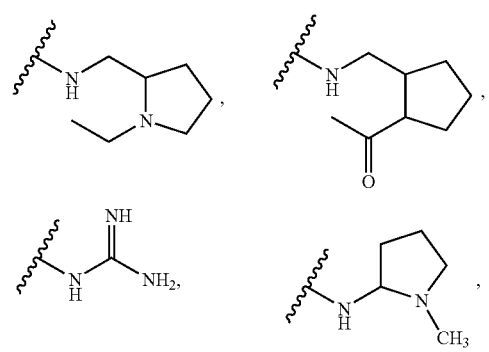
or a stereoisomer, an enantiomer, a diastereomer, a racemic mixture, a salt, or a combination thereof; wherein:
$R^3$ is selected from —$NH_2$,
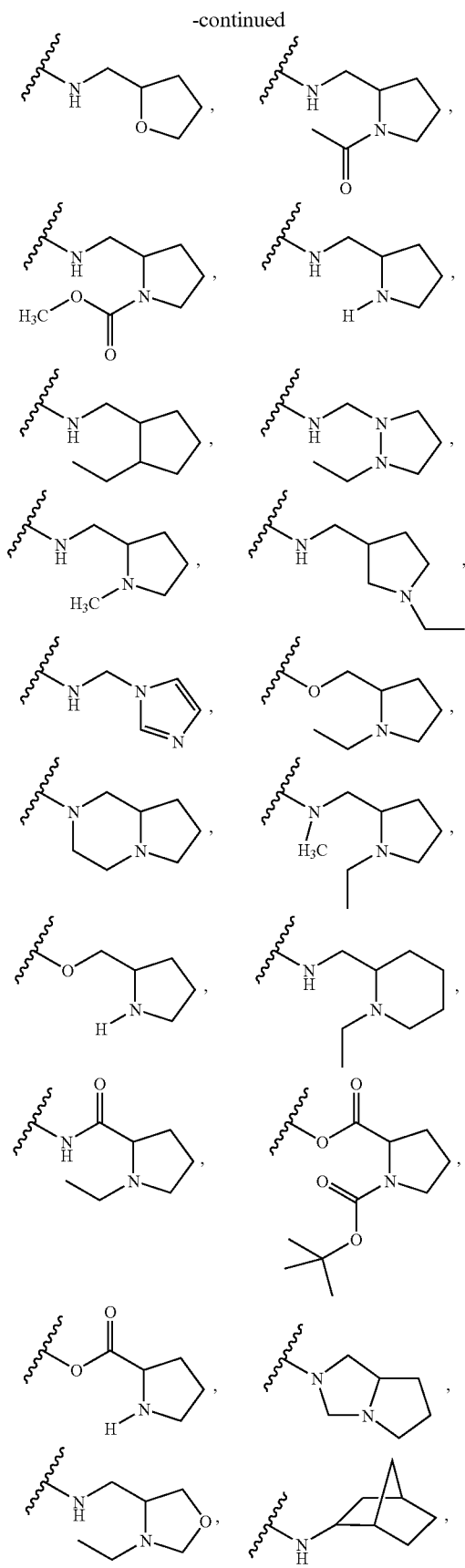

-continued
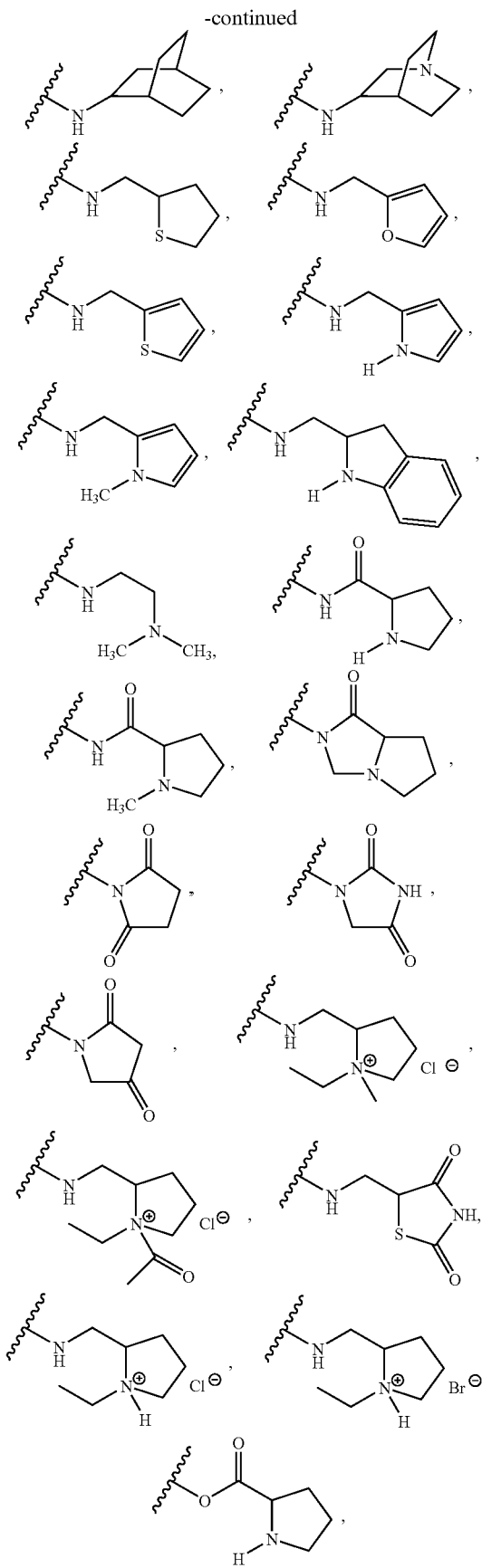
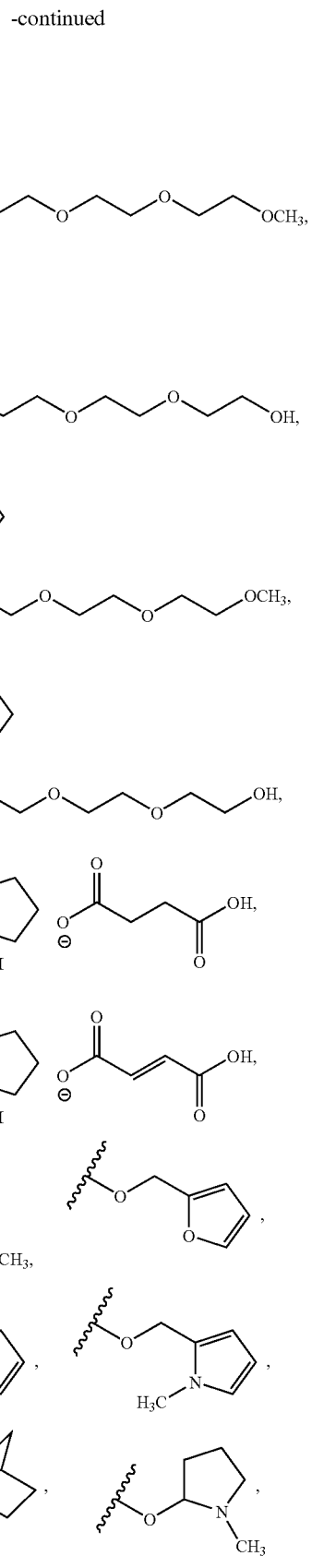

639
-continued
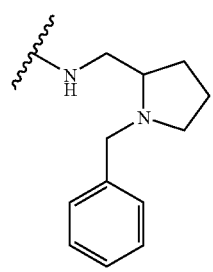, or
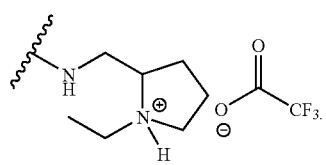
8. A stent comprising a composition disposed on or within the stent, the composition comprising a pharmaceutically acceptable carrier and a compound having the formula
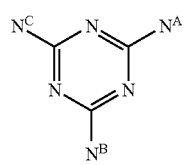
or a stereoisomer, an enantiomer, a diastereomer, a racemic mixture, a salt, or a combination thereof; wherein:
$R^1$ is selected from
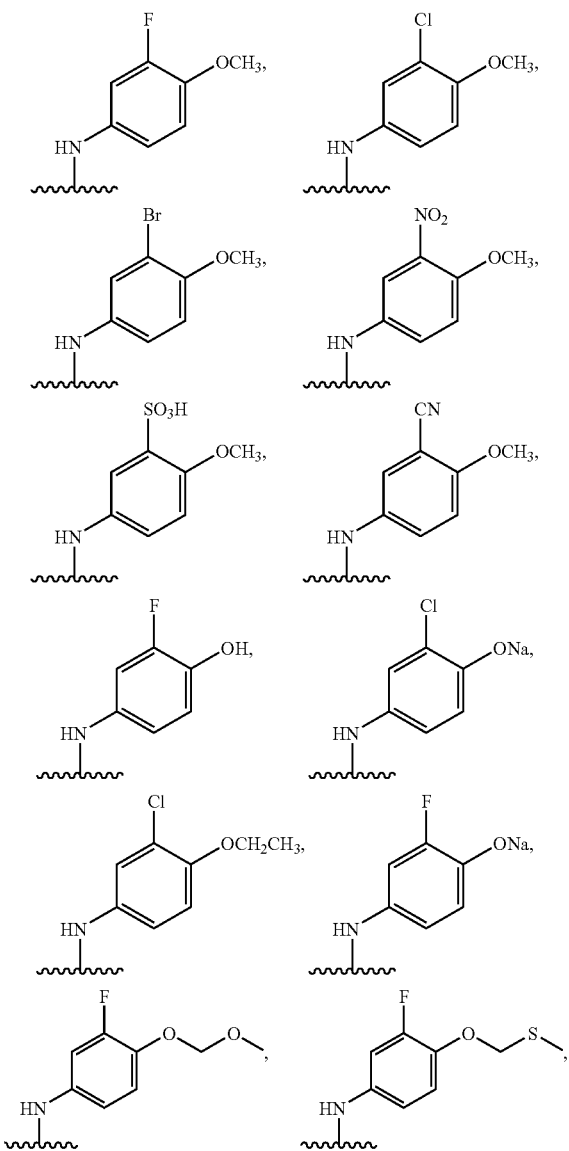

-continued
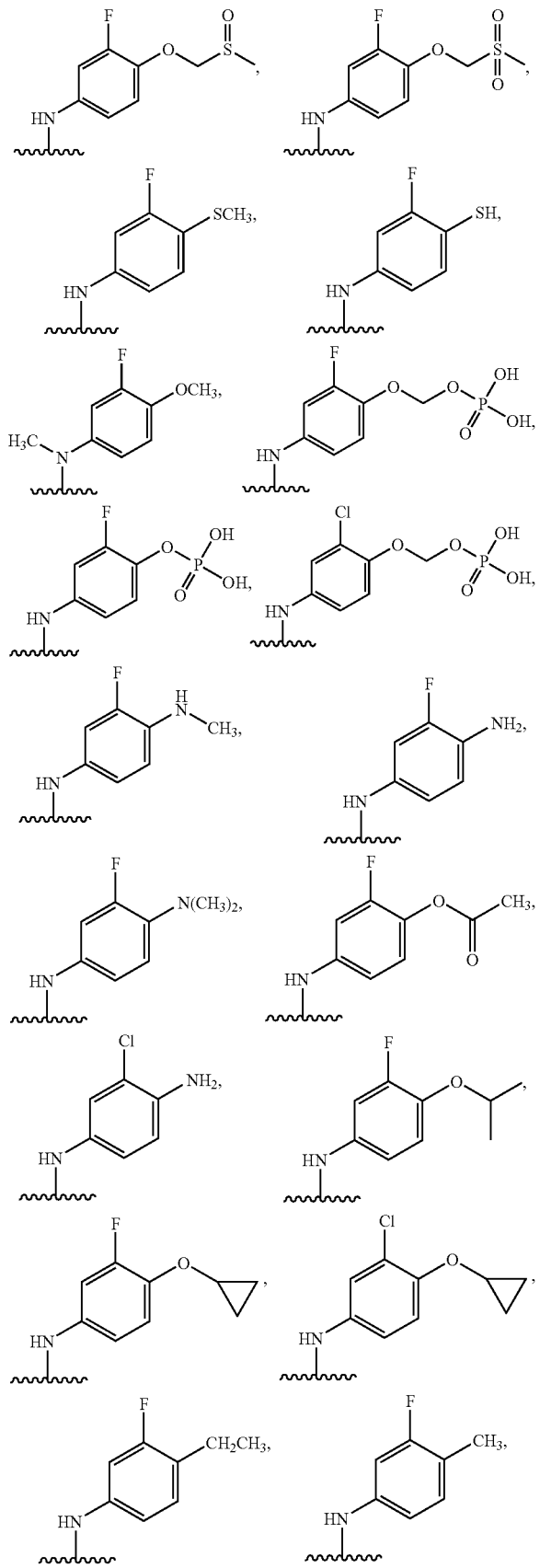

-continued
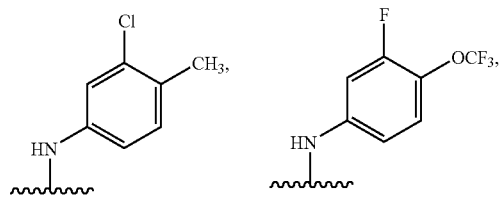
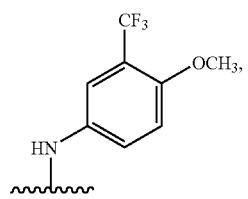
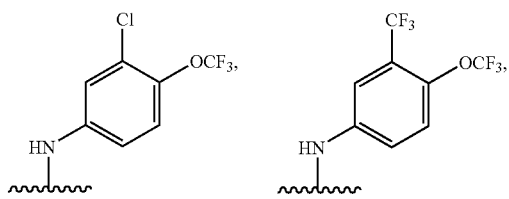
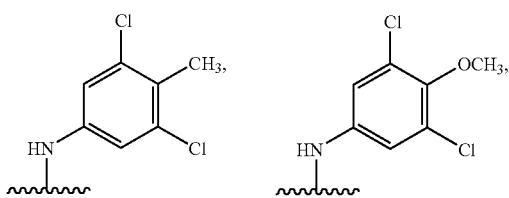
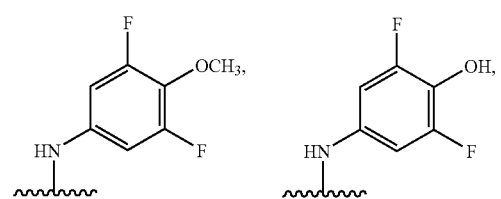
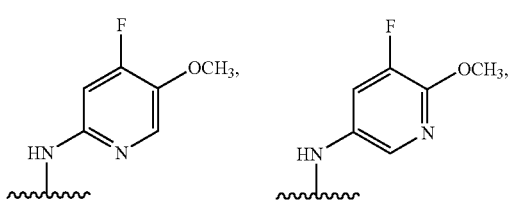
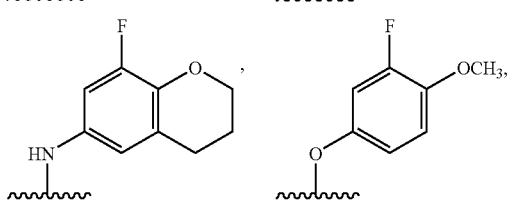
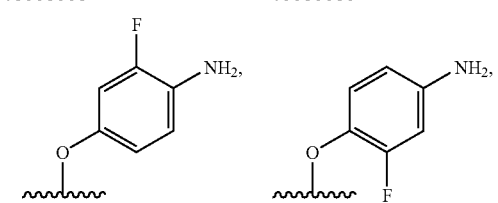

-continued
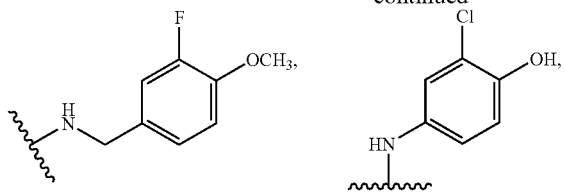
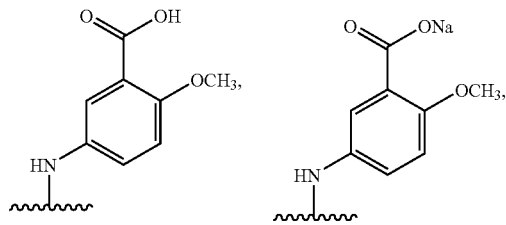
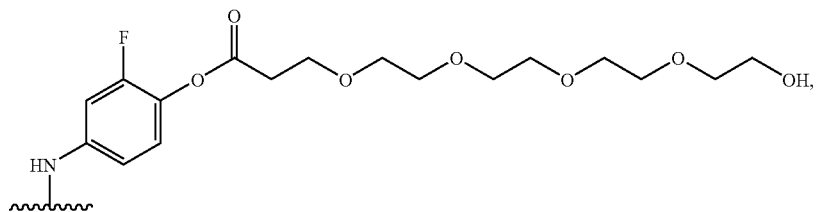
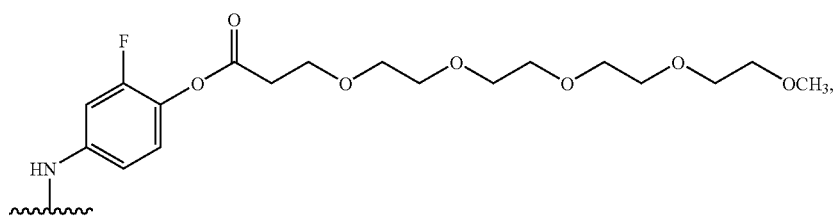
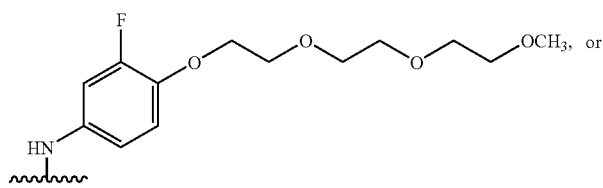
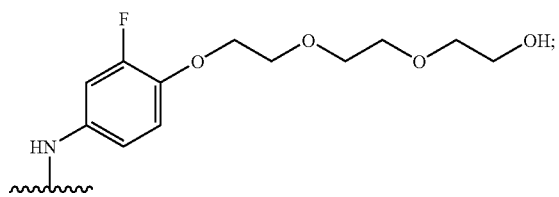

$R^2$ is selected from
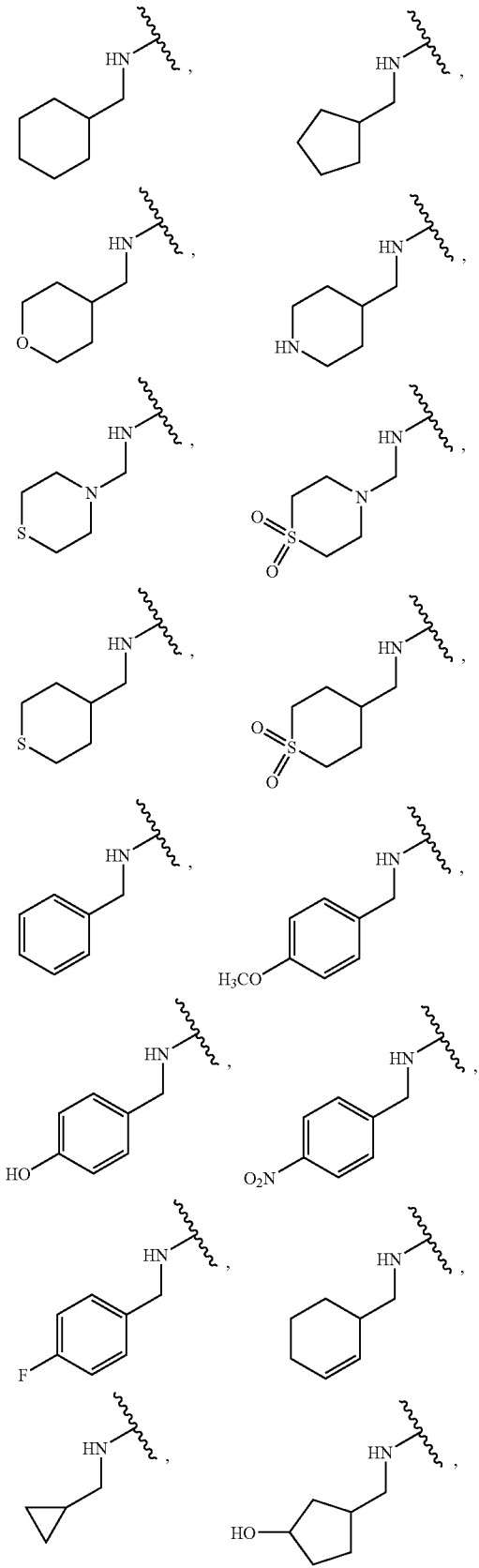
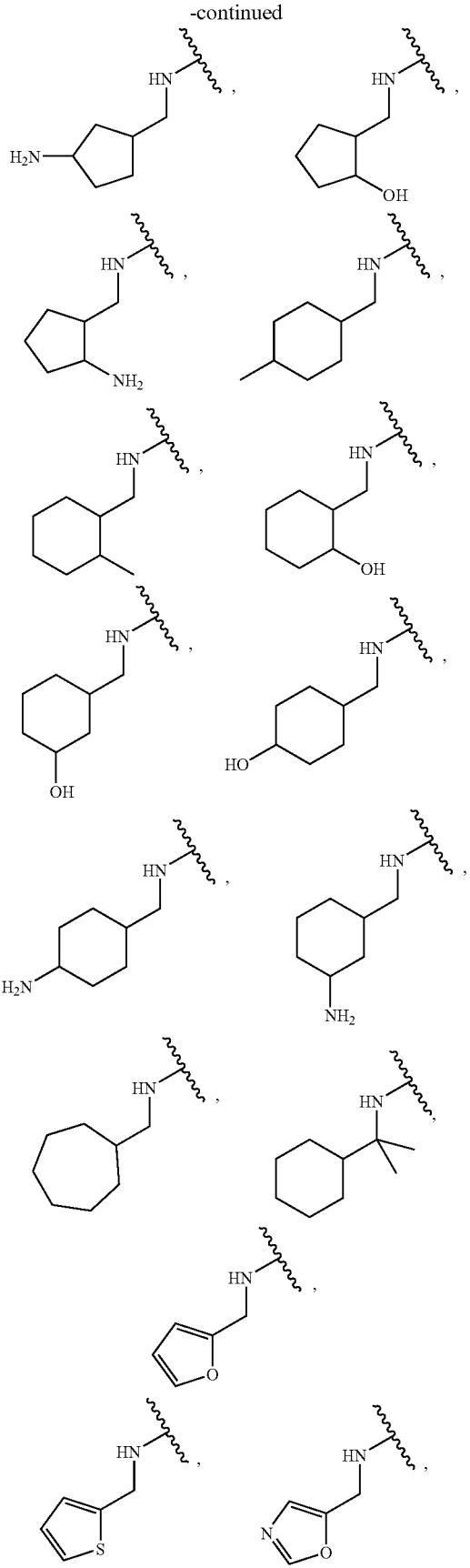
-continued

-continued
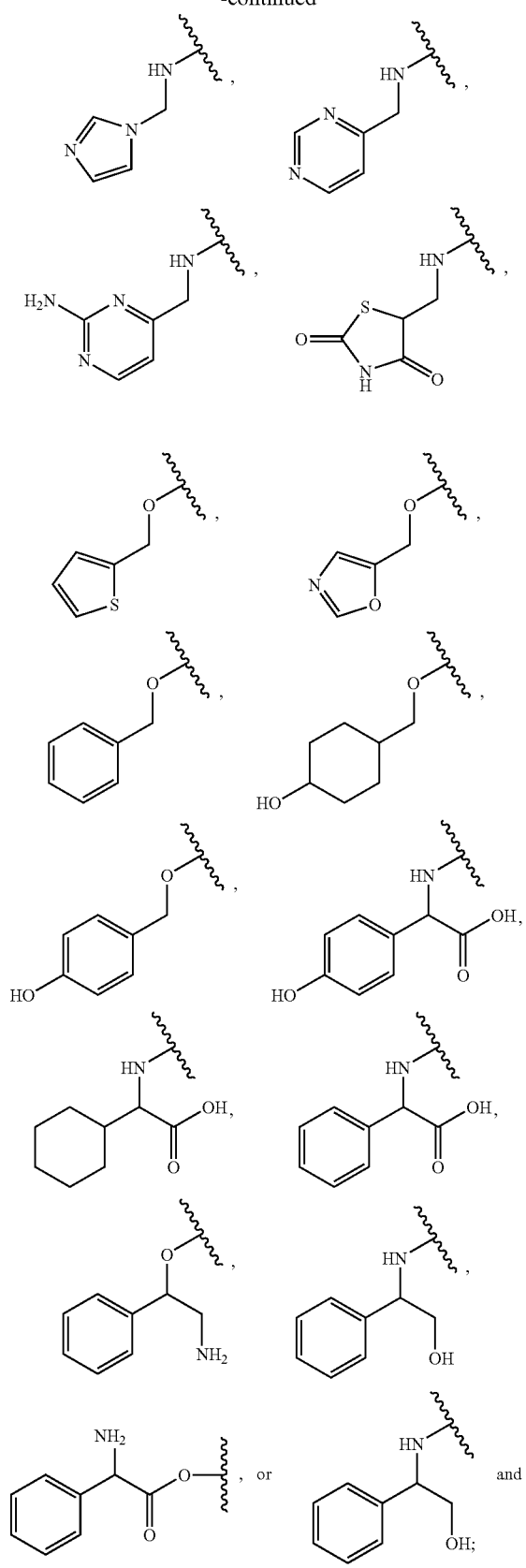
$R^3$ is selected from —$NH_2$,
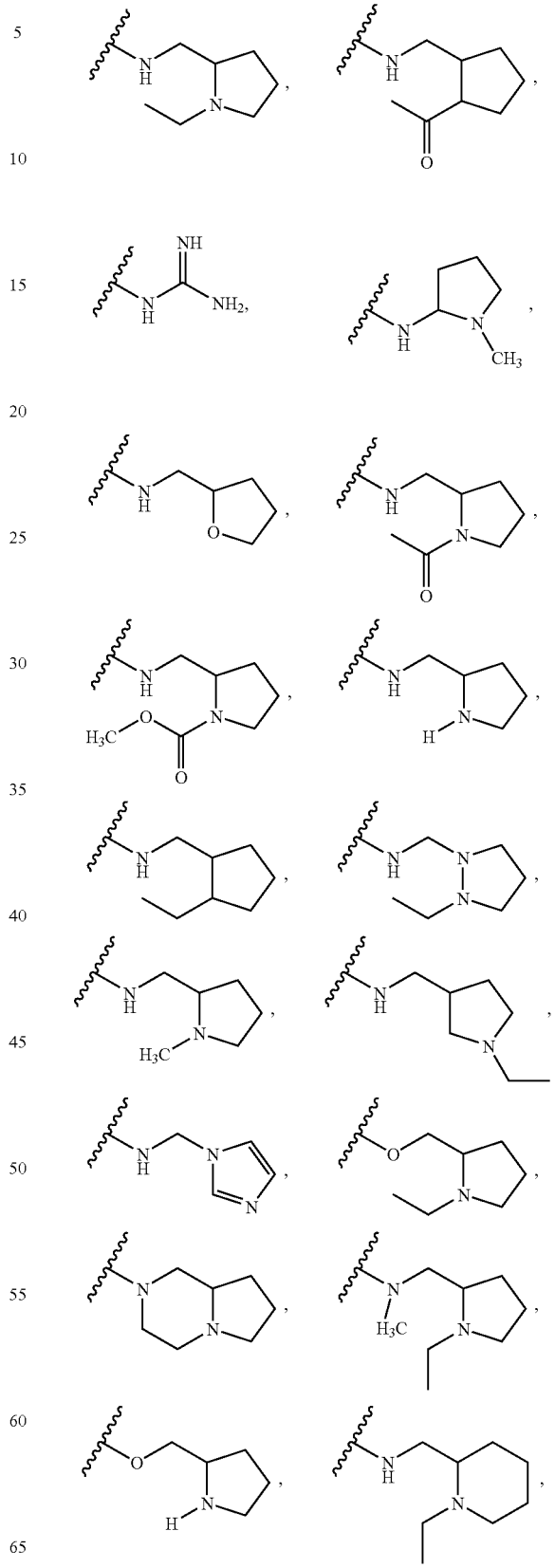

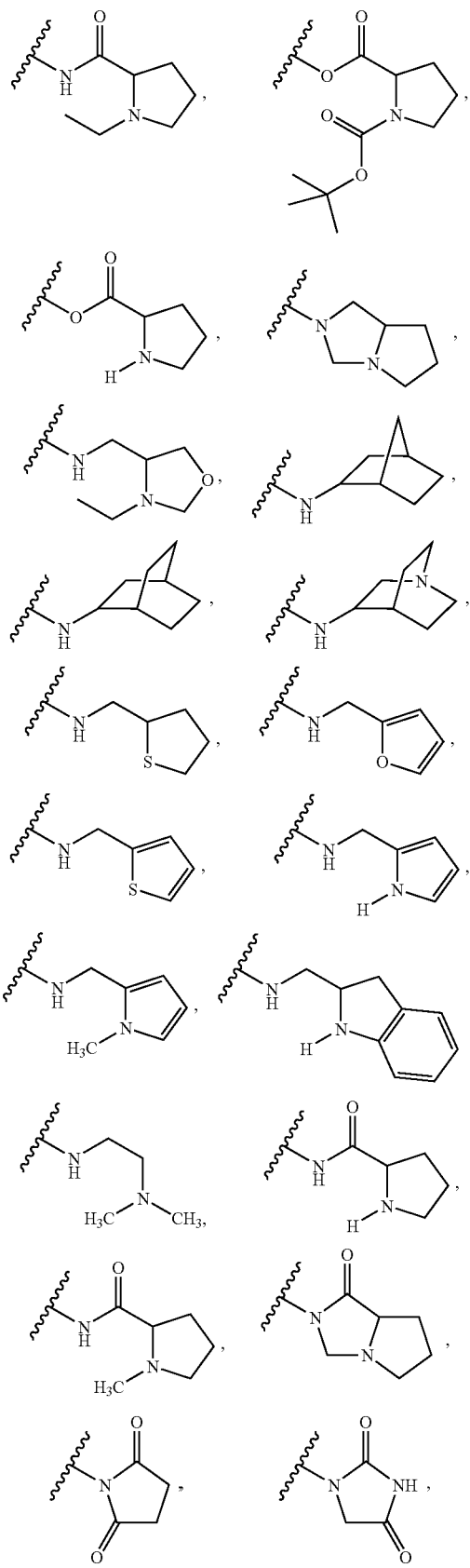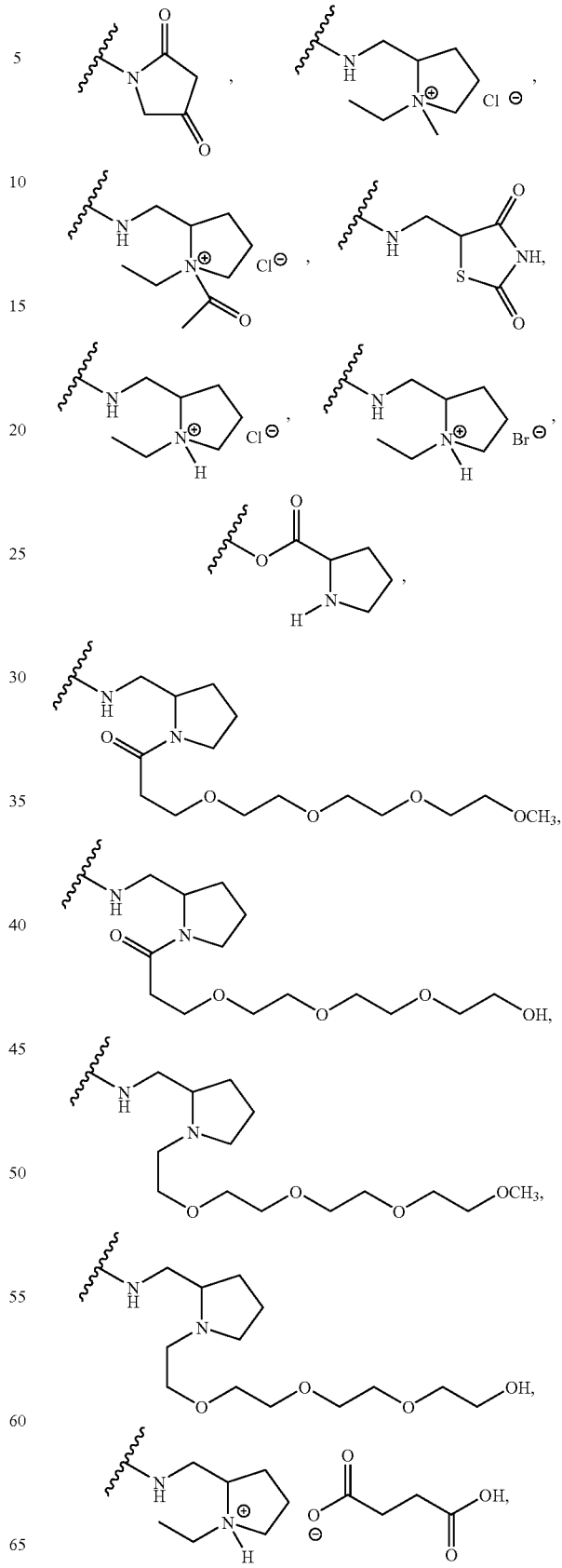

-continued

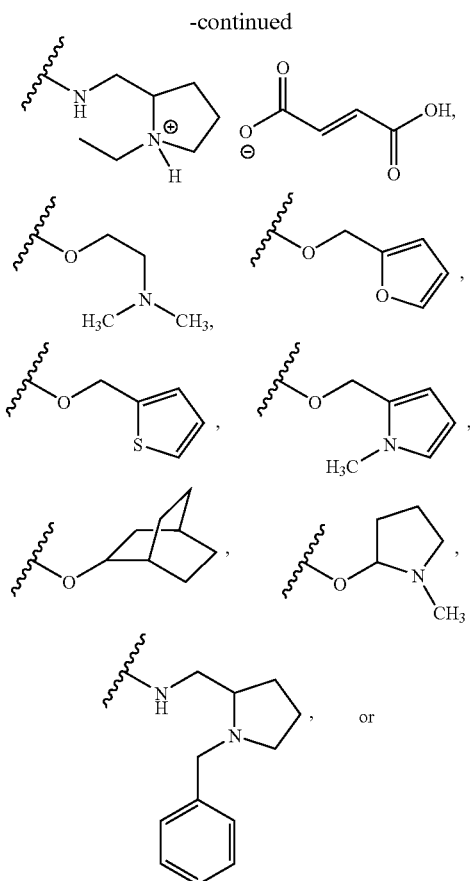

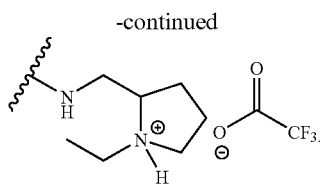

9. The stent as claimed in claim 8, wherein the composition further comprises at least one of the following:
   a pharmaceutically acceptable auxiliary;
   a pharmaceutically acceptable preservative;
   a pharmaceutically acceptable excipient; or
   any combination thereof.

10. The stent as claimed in claim 8, wherein the compound has the formula

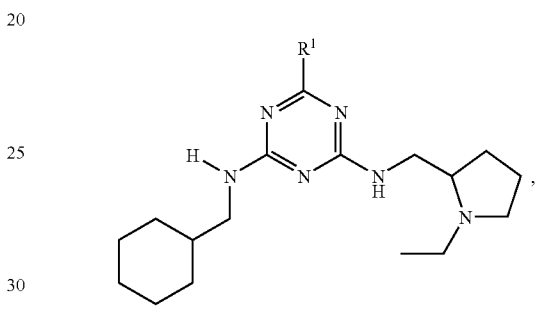

or a stereoisomer, an enantiomer, a diastereomer, a racemic mixture, a salt, or a combination thereof; wherein:
   $R^1$ is selected from

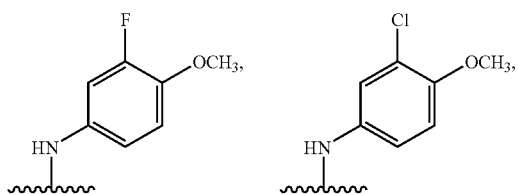

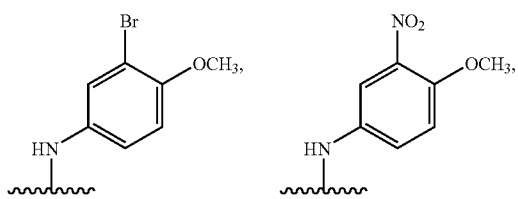

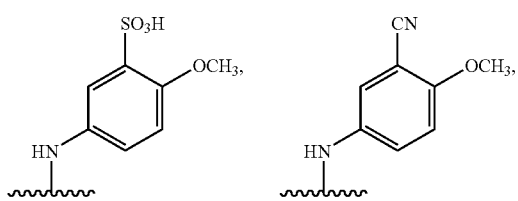

-continued
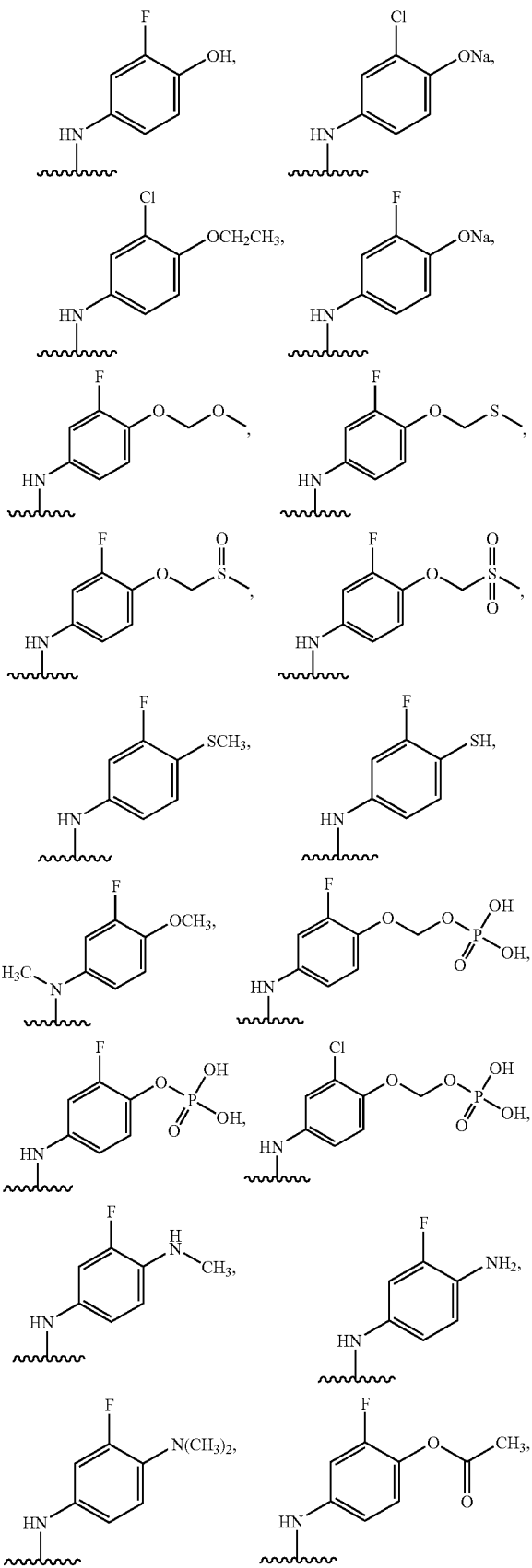

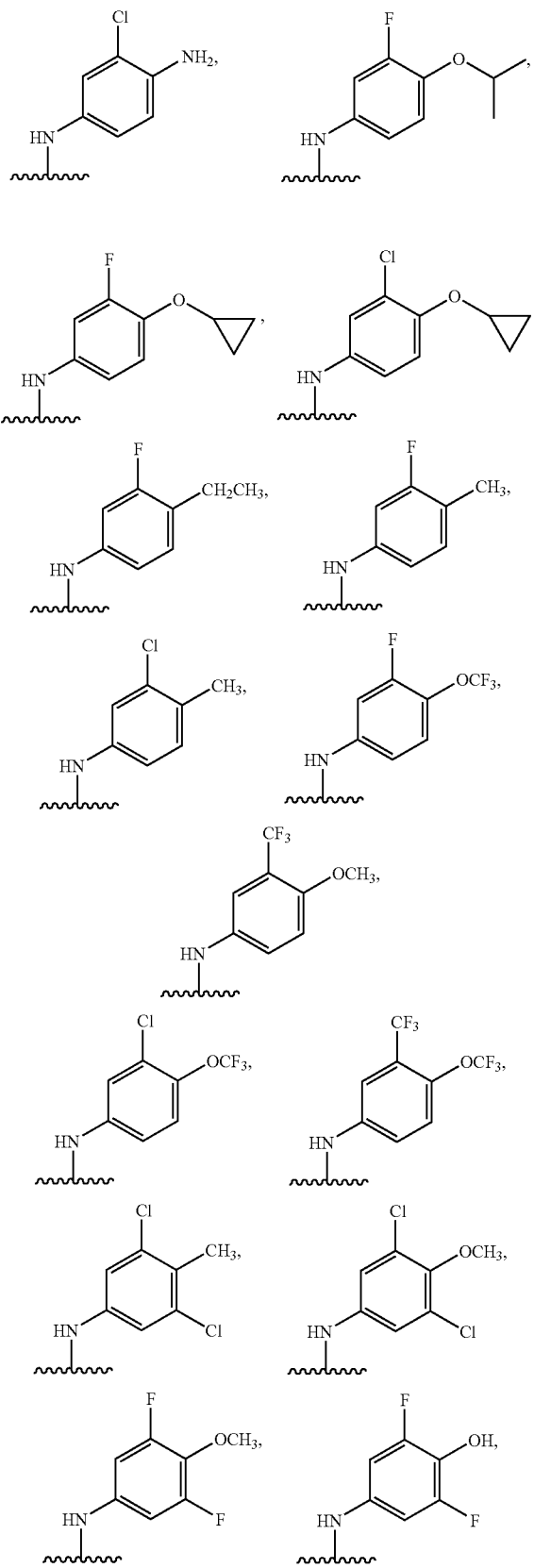

-continued
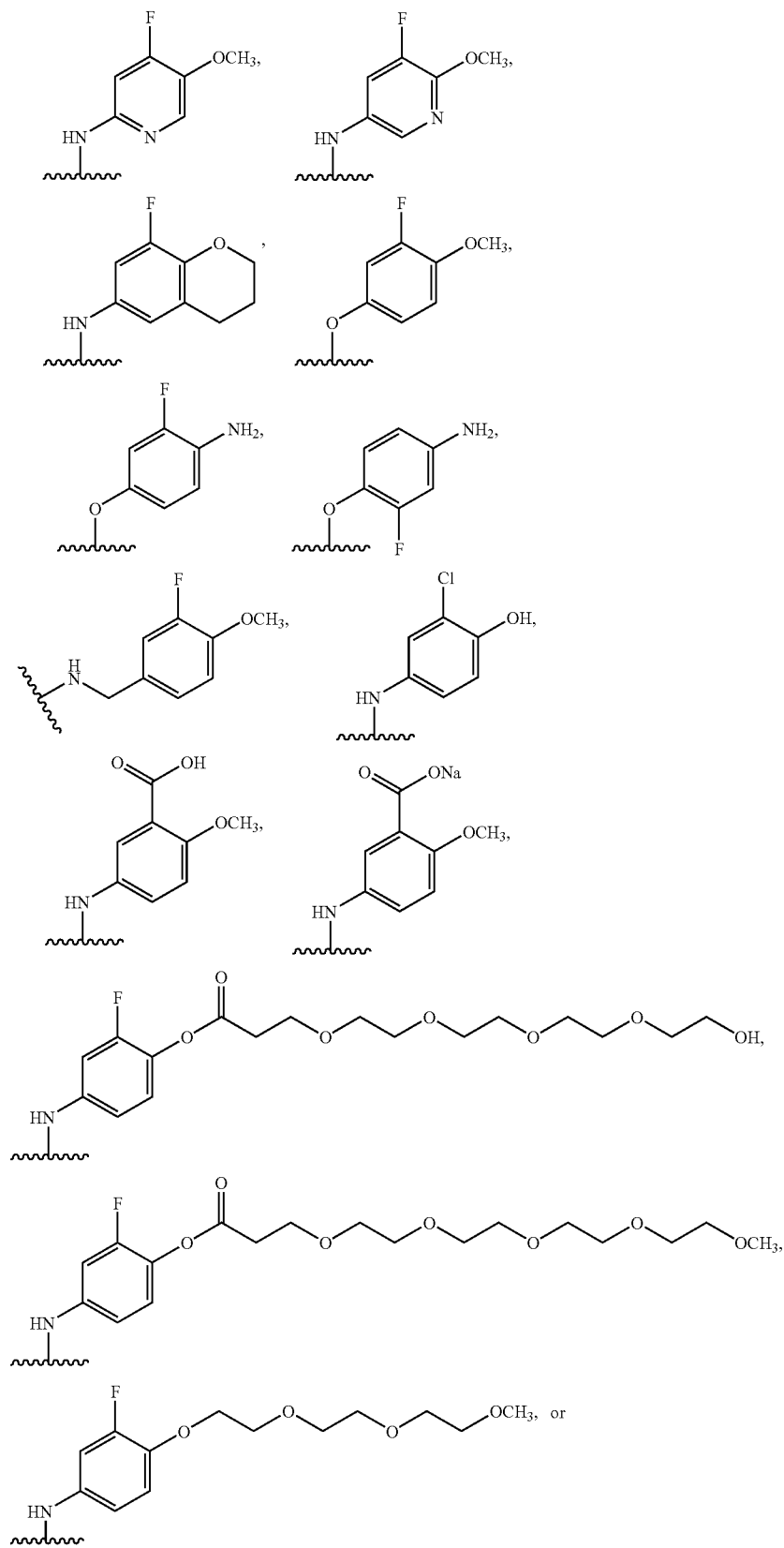

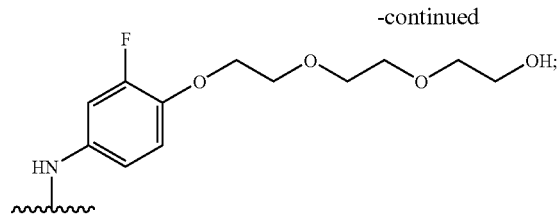
11. The stent as claimed in claim 8, wherein the compound has the formula
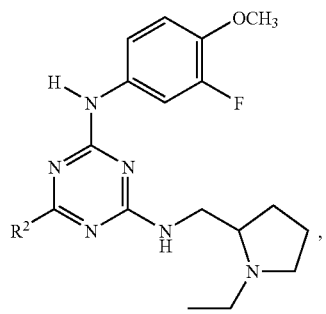
or a stereoisomer, an enantiomer, a diastereomer, a racemic mixture, a salt, or a combination thereof; wherein:
$R^2$ is selected from
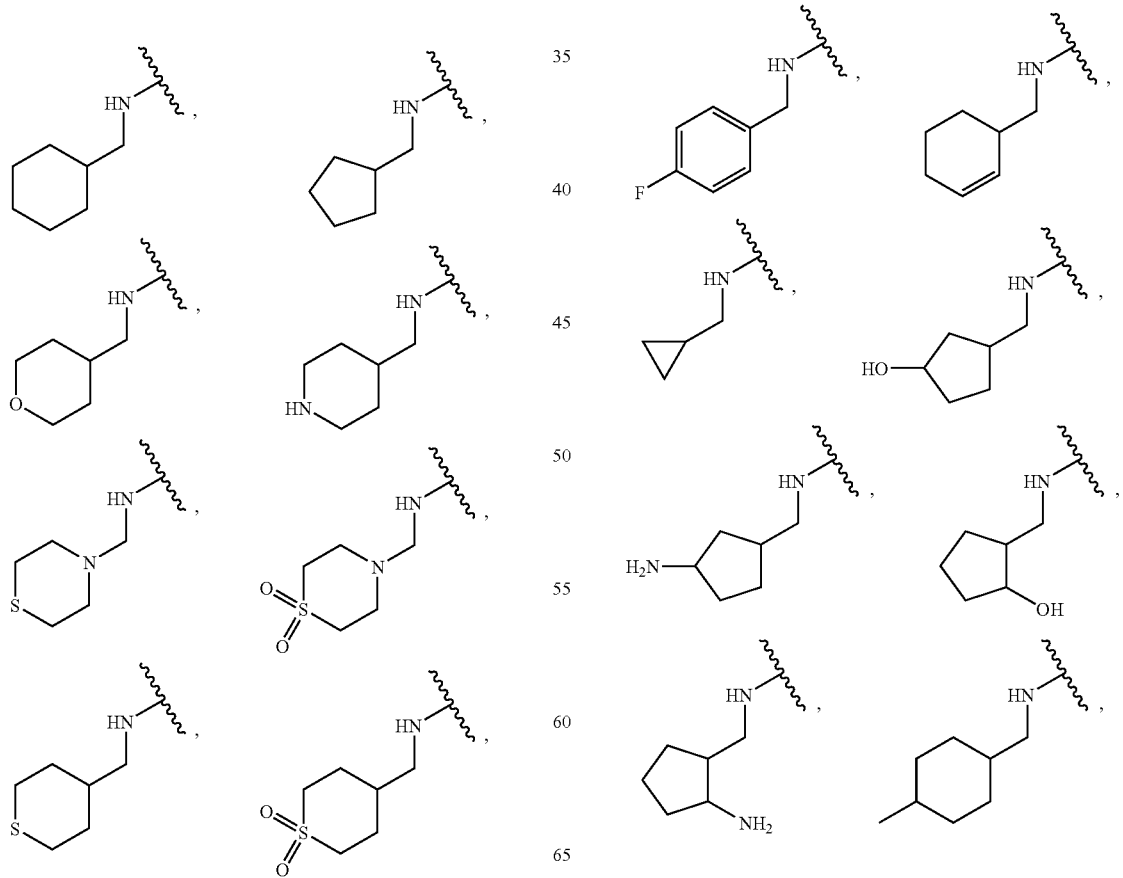

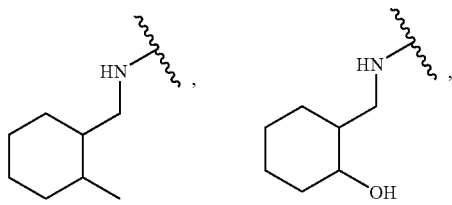
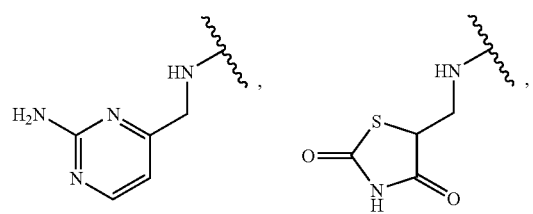
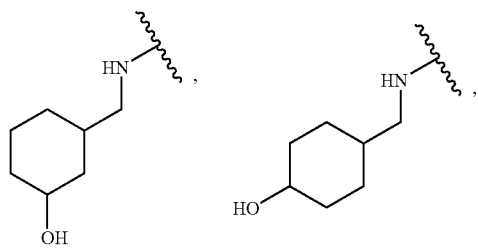
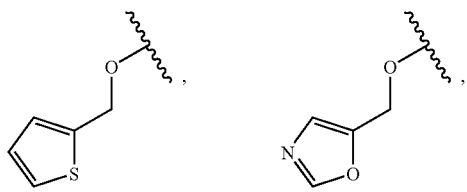
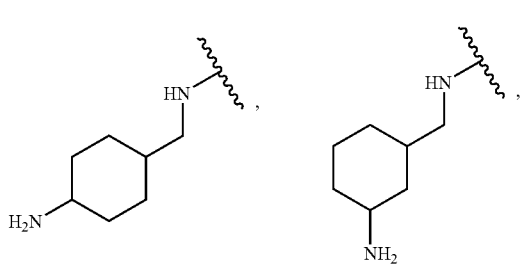
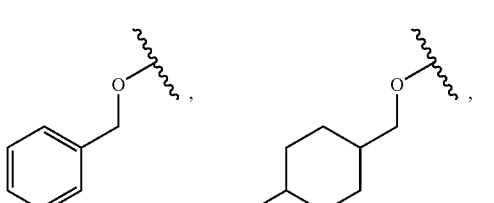
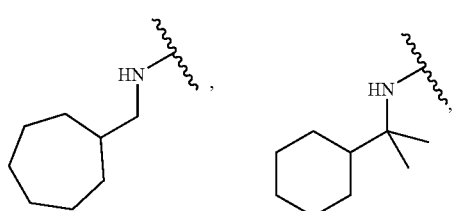
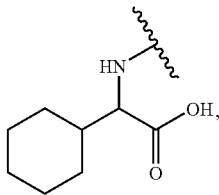
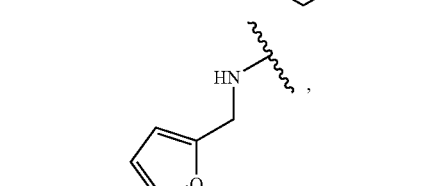
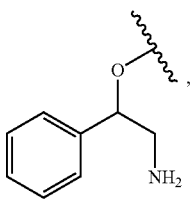
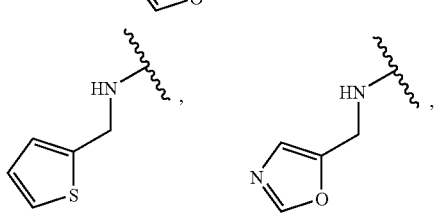
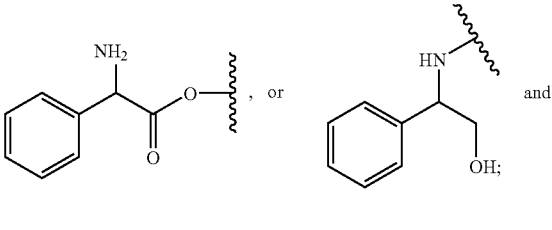

12. The stent as claimed in claim 8, wherein the compound has the formula
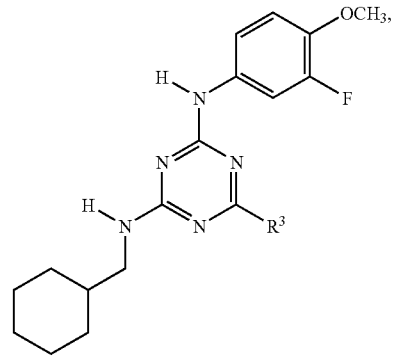
or a stereoisomer, an enantiomer, a diastereomer, a racemic mixture, a salt, or a combination thereof; wherein:
R³ is selected from —NH₂,
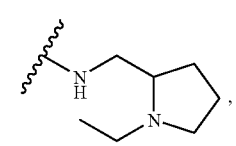 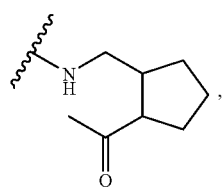
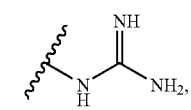 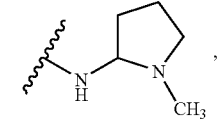
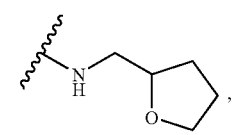 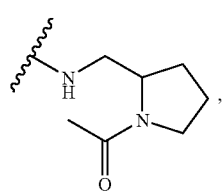
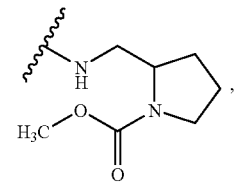 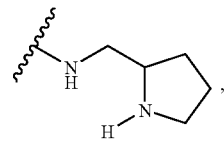
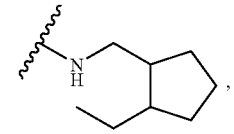 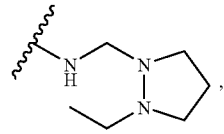
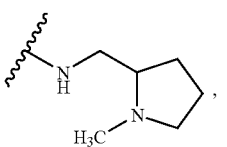 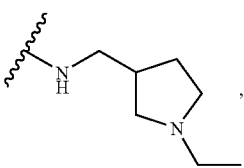
-continued
 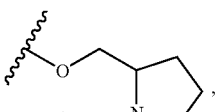
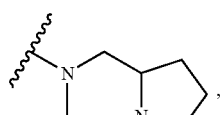 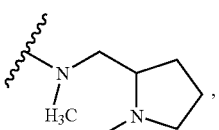
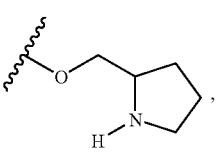 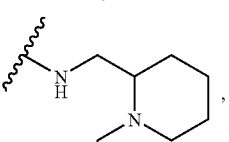
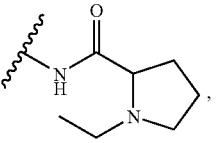 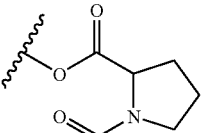
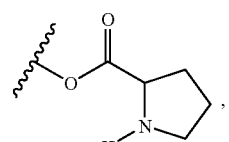 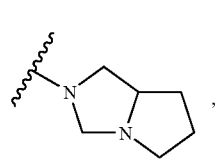
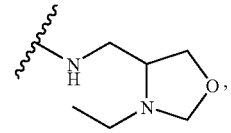 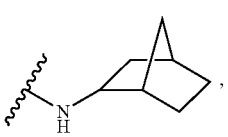
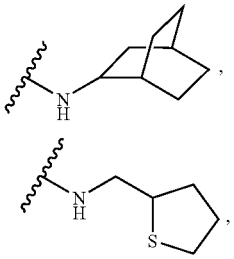 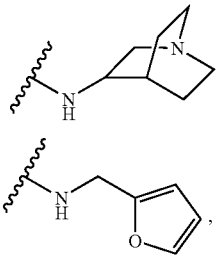
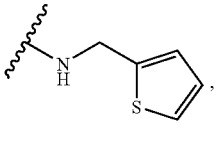 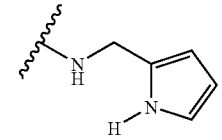
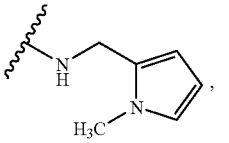 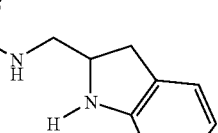

-continued
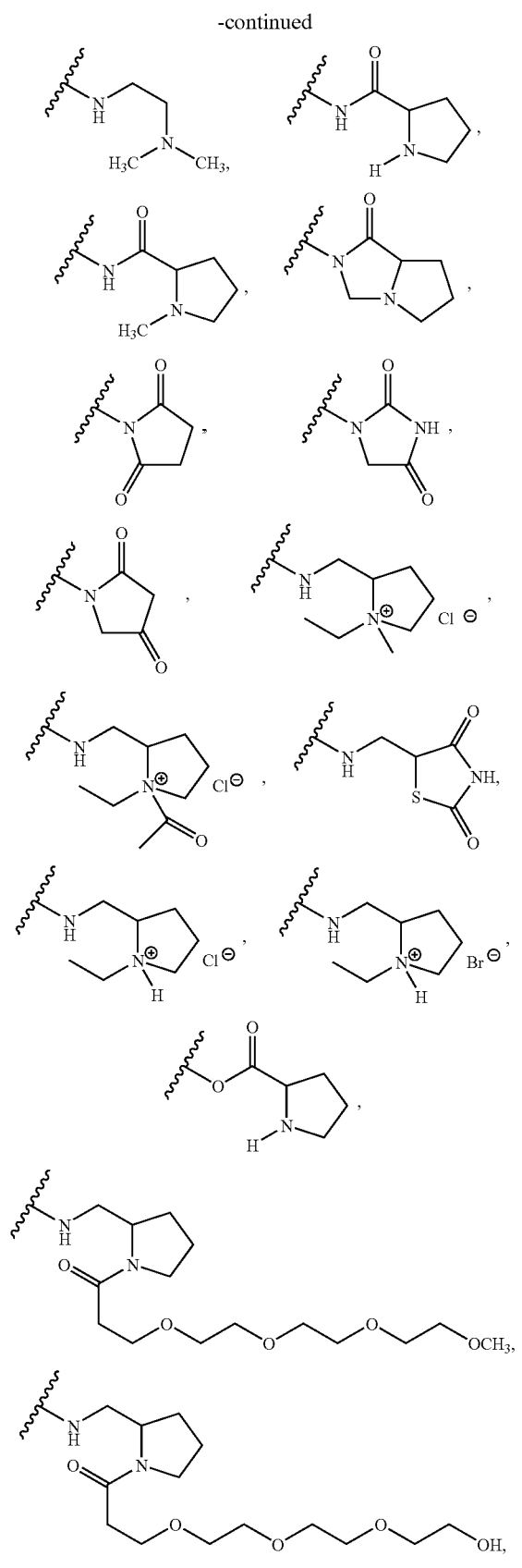
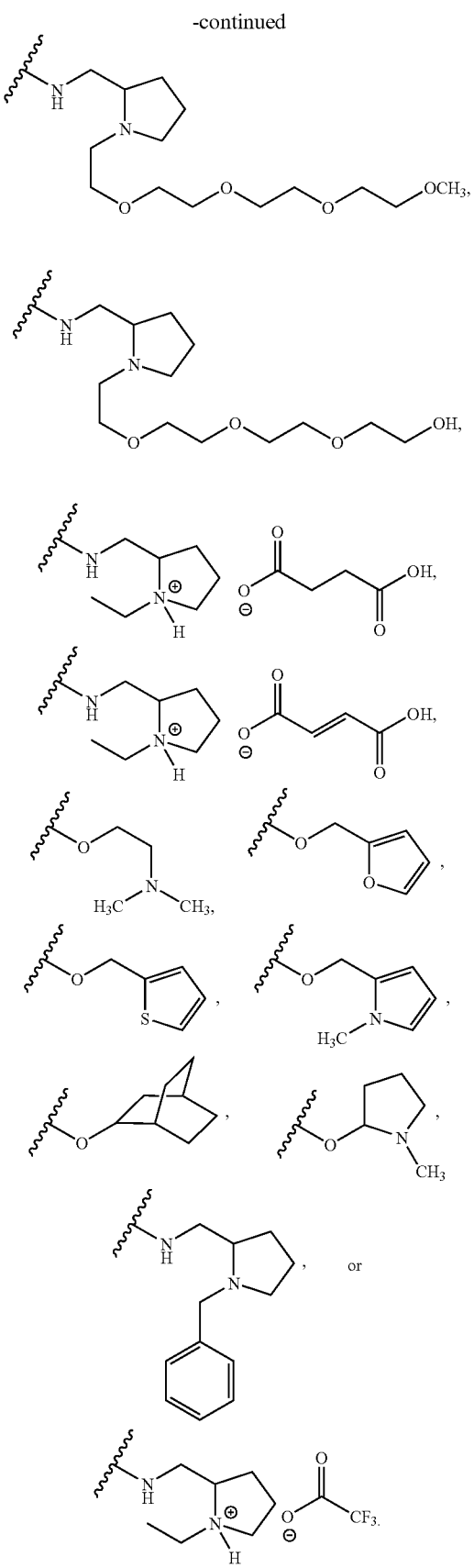

13. A stent comprising a compound disposed on or within the stent, the compound having the formula
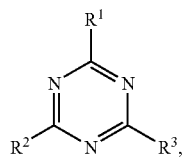
or a stereoisomer, an enantiomer, a diastereomer, a racemic mixture, a salt, or a combination thereof; wherein:
R¹ is selected from
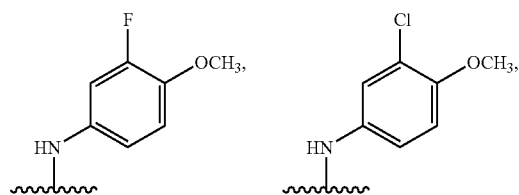
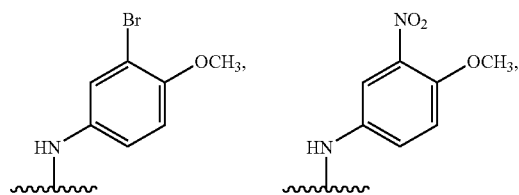
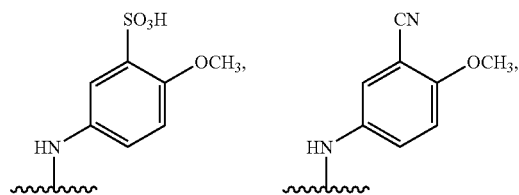
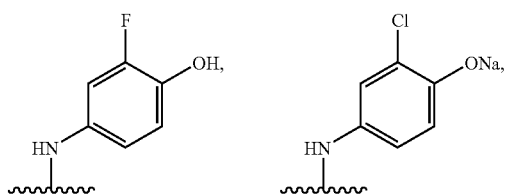
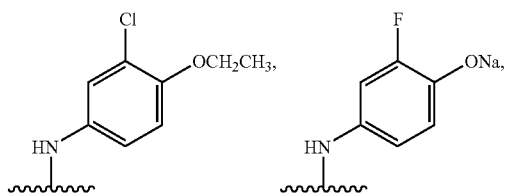

-continued
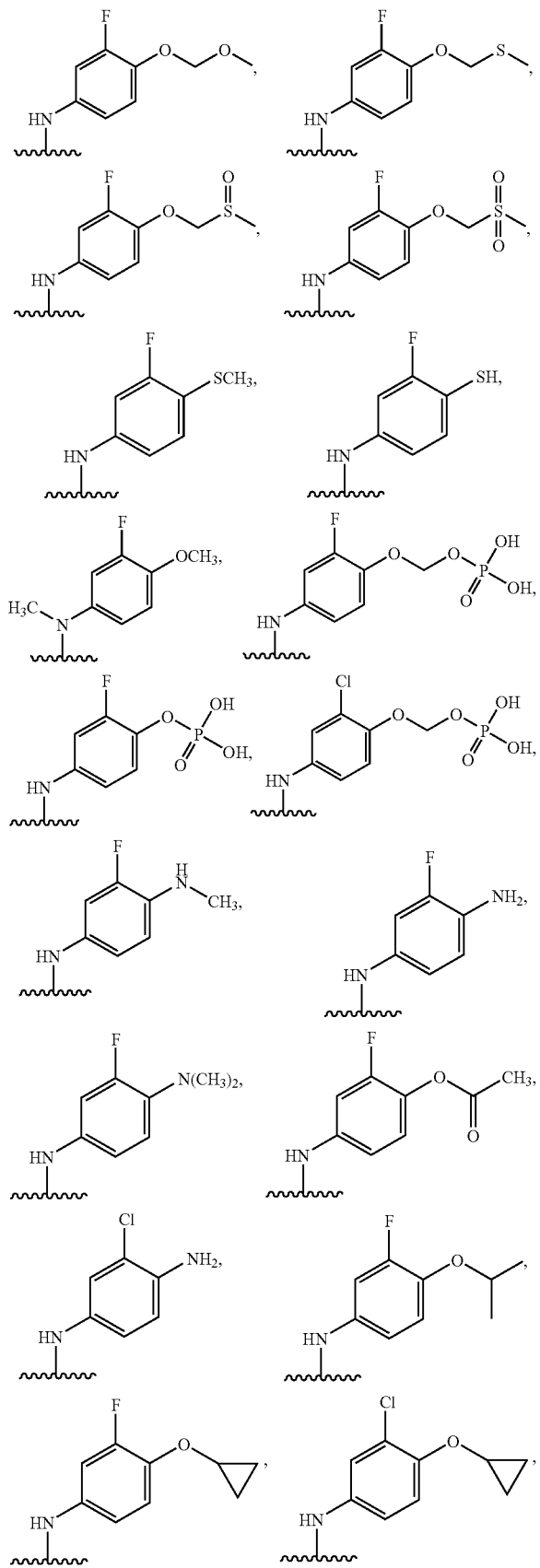

-continued
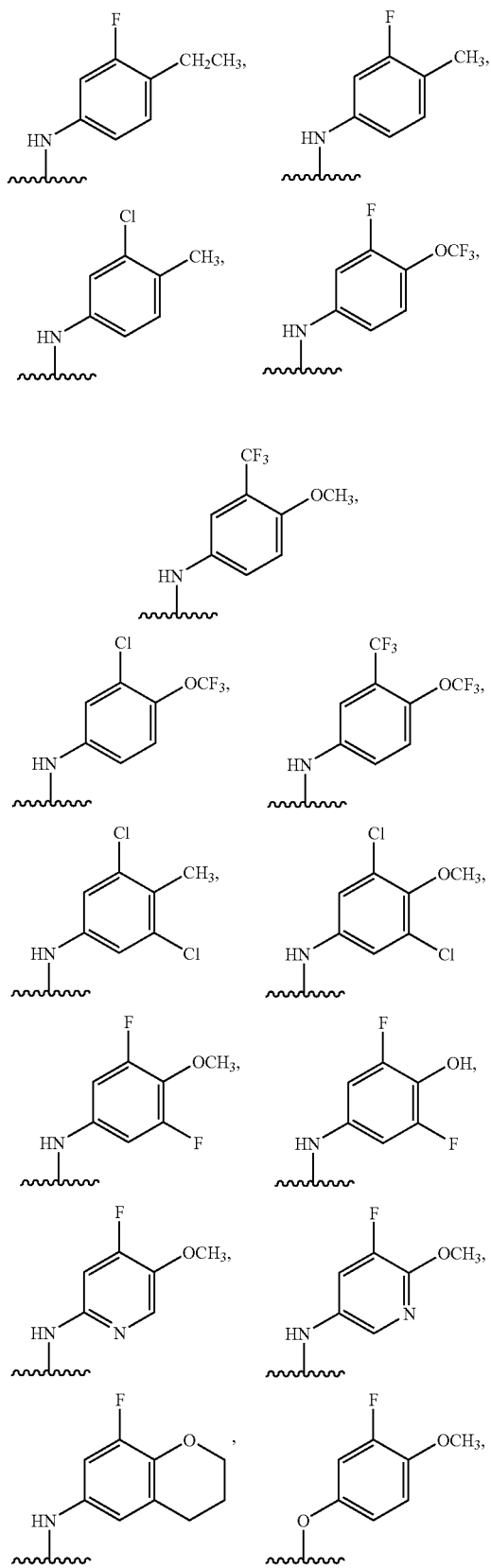

-continued
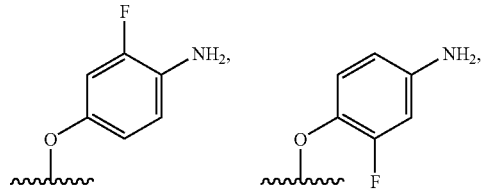
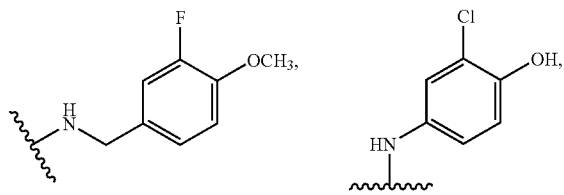
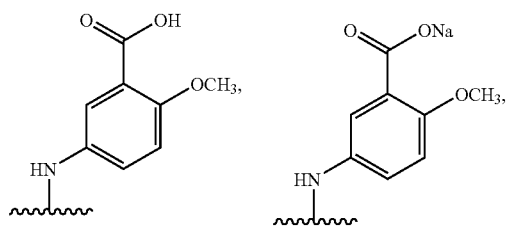
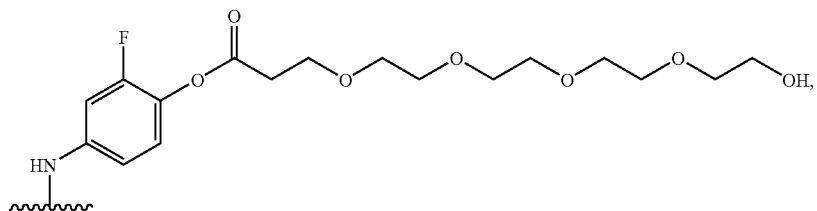
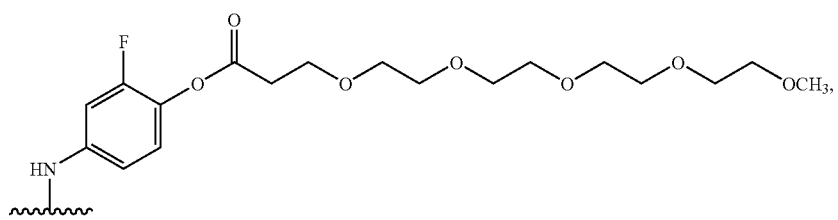
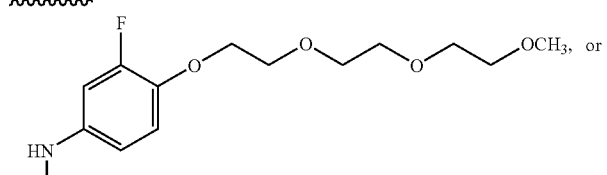
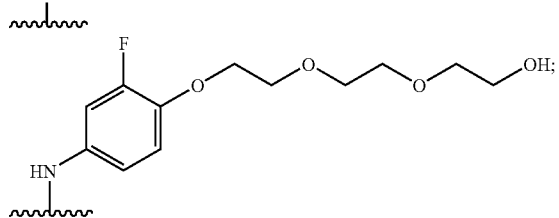

$R^2$ is selected from
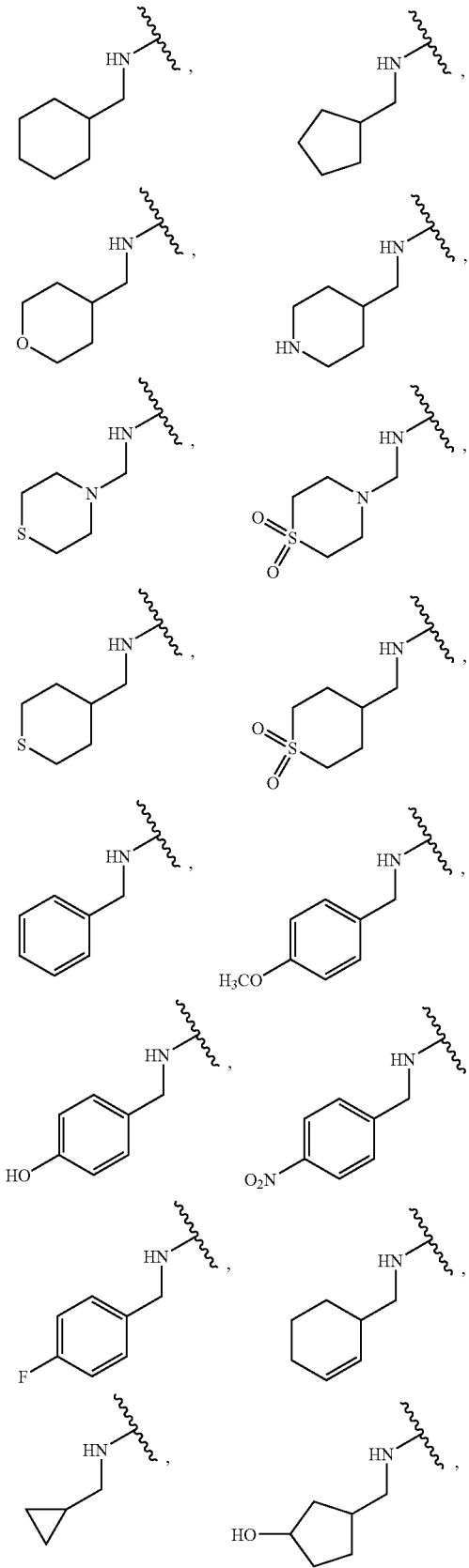
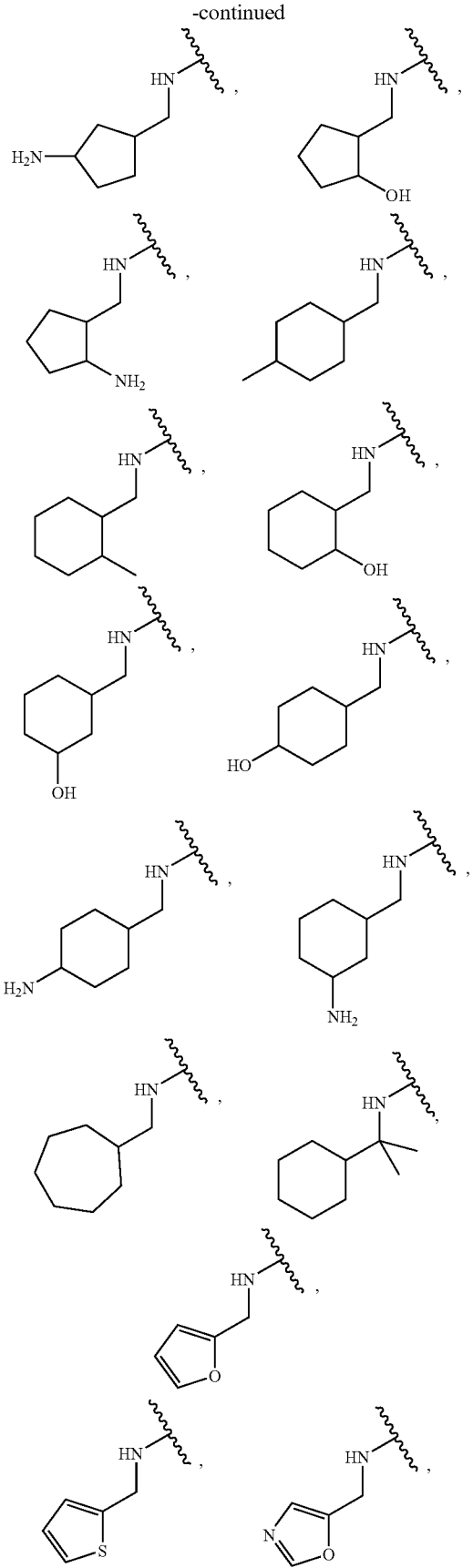

-continued
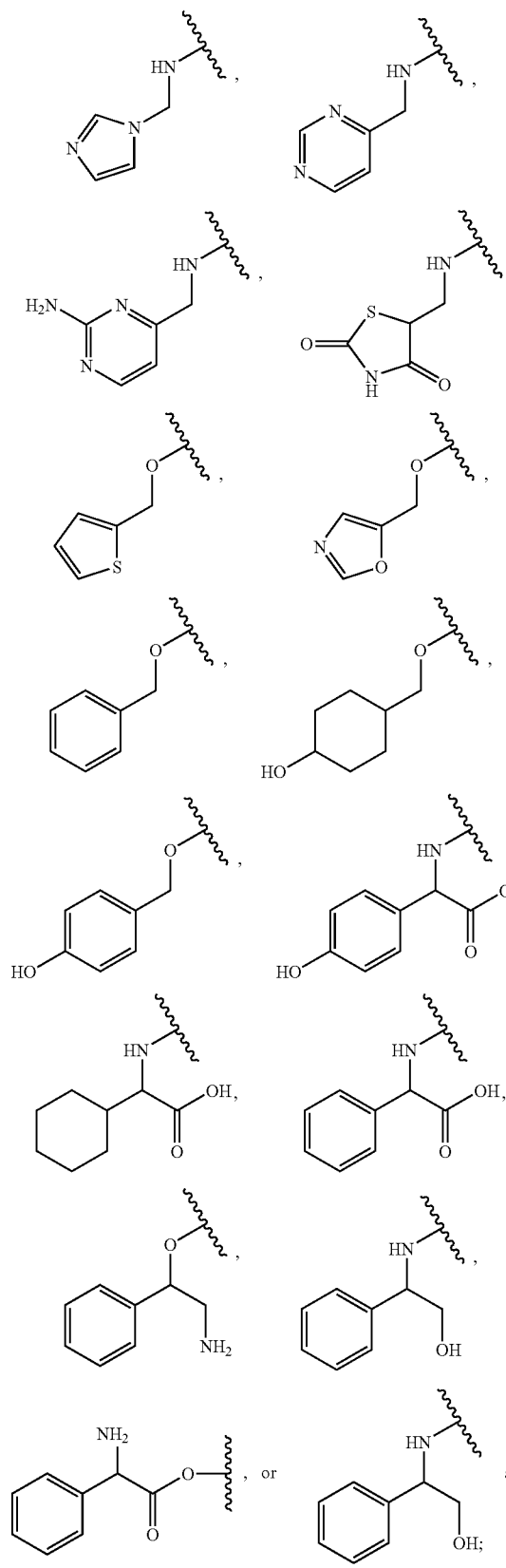
$R^3$ is selected from —$NH_2$,
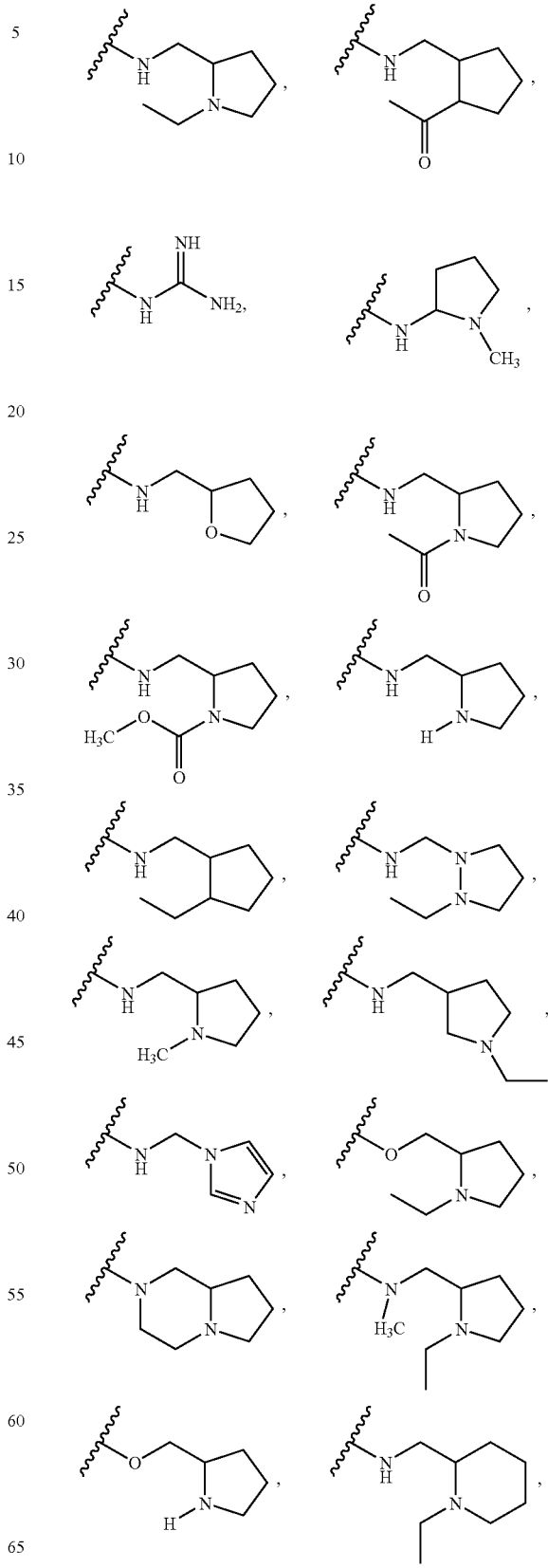

-continued
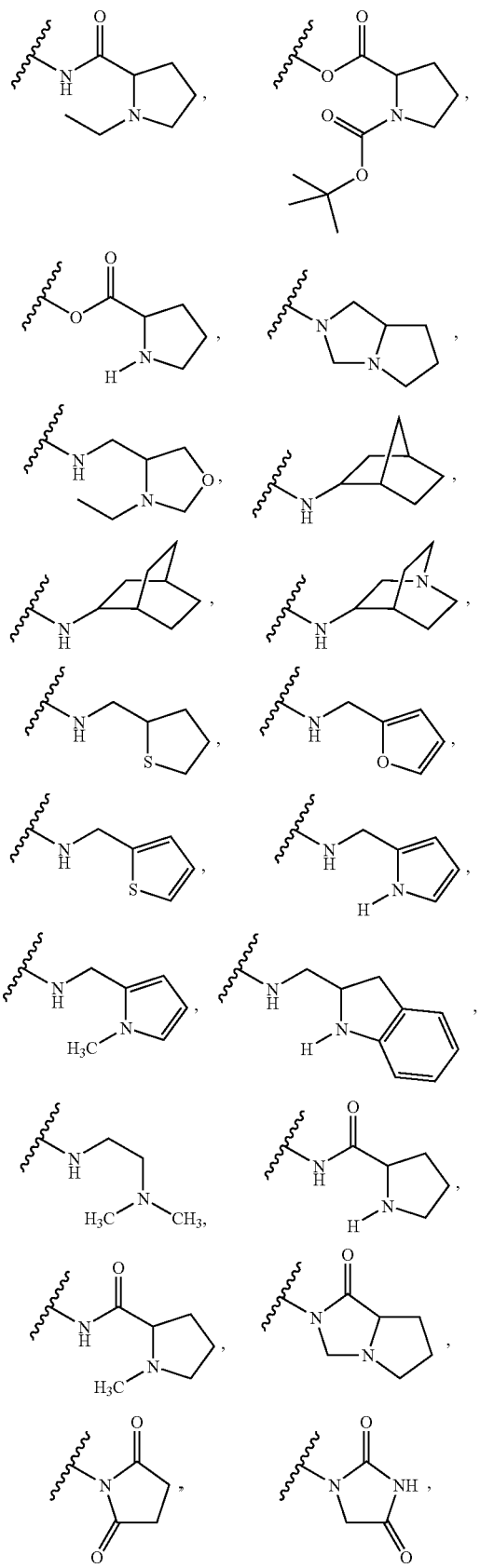
-continued
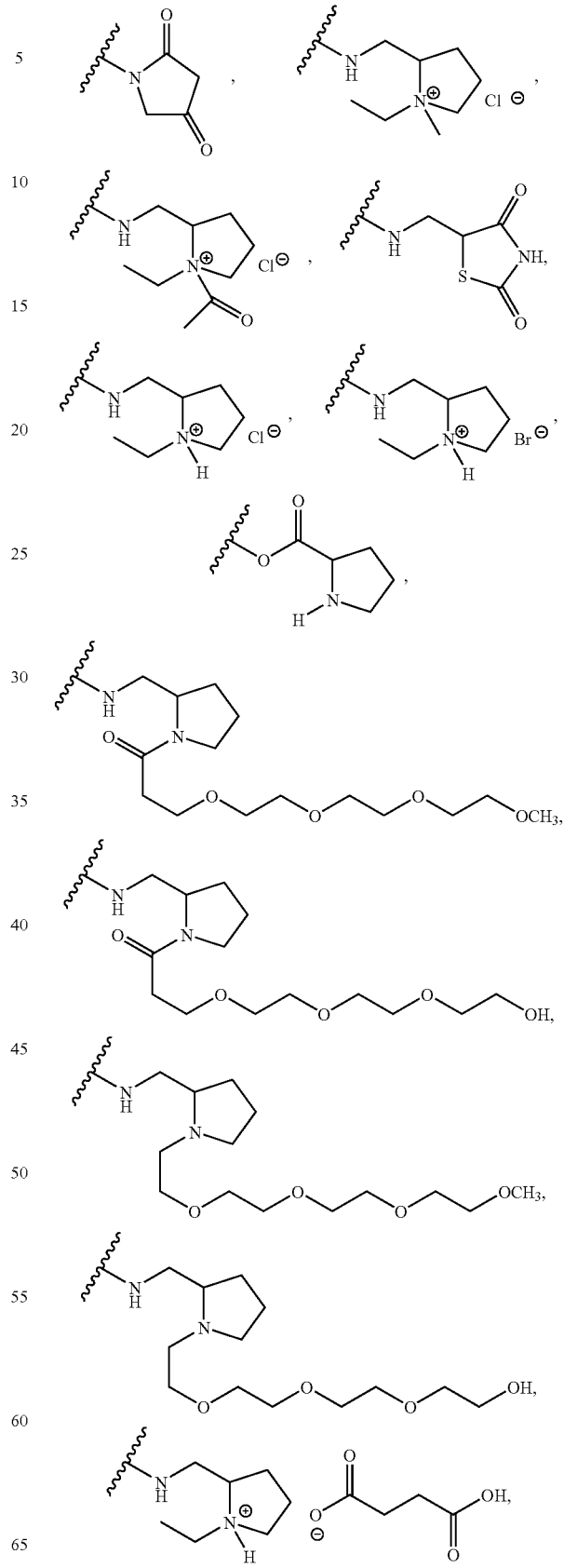

-continued

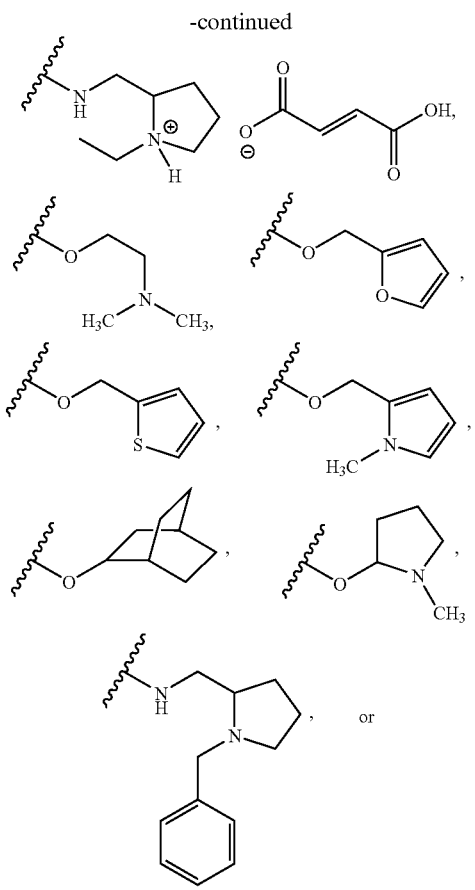

-continued

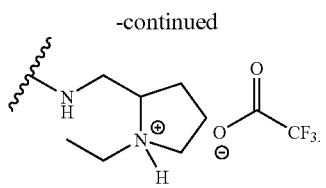

14. A stent comprising a composition disposed on or within the stent, the composition comprising a pharmaceutically acceptable carrier and a compound according to claim 13.

15. The stent as claimed in claim 14, wherein the composition further comprises at least one of the following:
   a pharmaceutically acceptable auxiliary;
   a pharmaceutically acceptable preservative;
   a pharmaceutically acceptable excipient; or
   any combination thereof.

16. A stent comprising a compound disposed on or within the stent, the compound having the formula

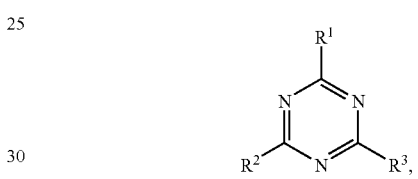

or a stereoisomer, an enantiomer, a diastereomer, a racemic mixture, a salt, or a combination thereof; wherein:
   $R^1$ is selected from

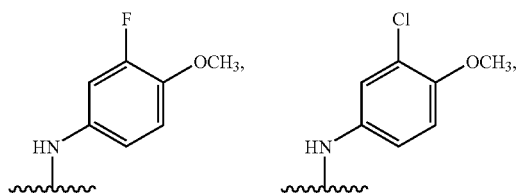

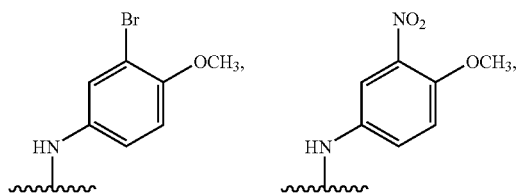

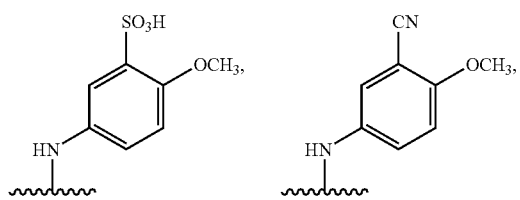

-continued
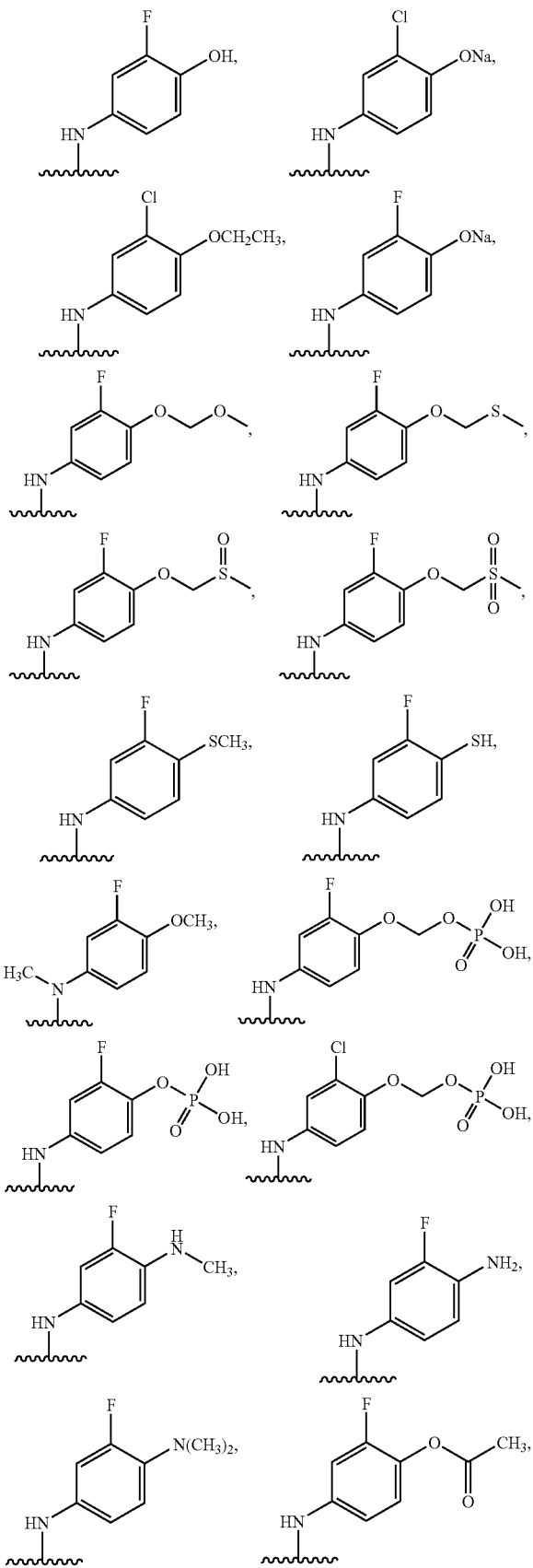

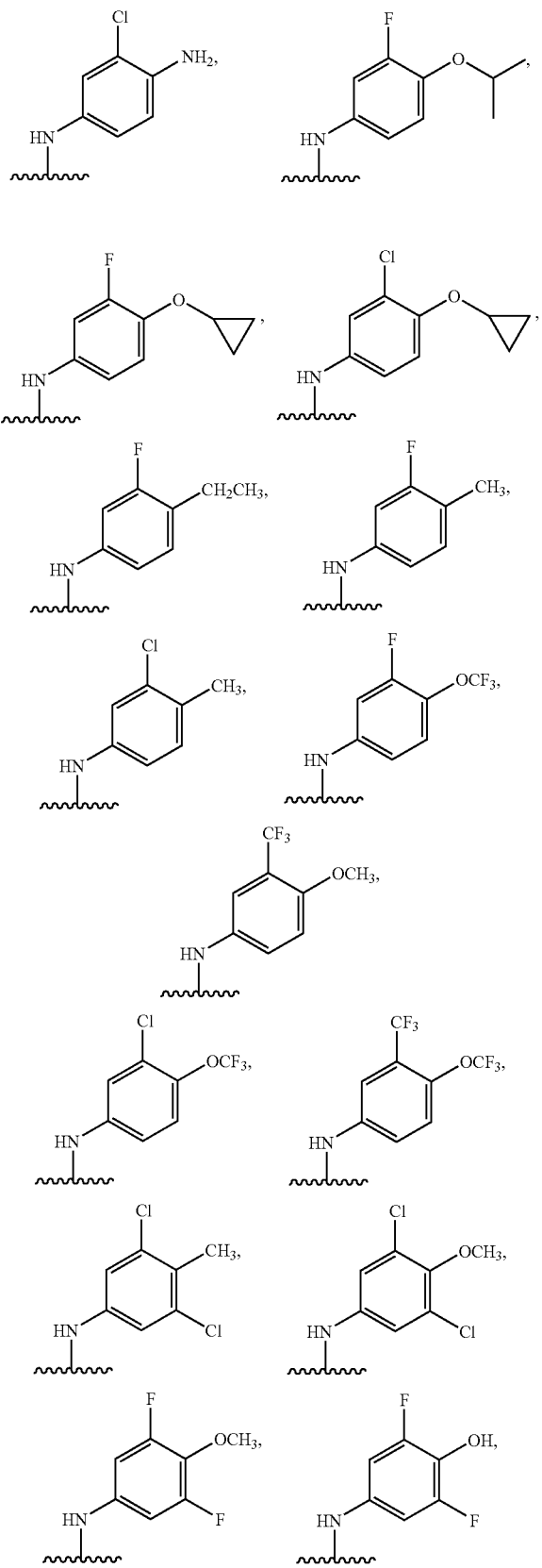

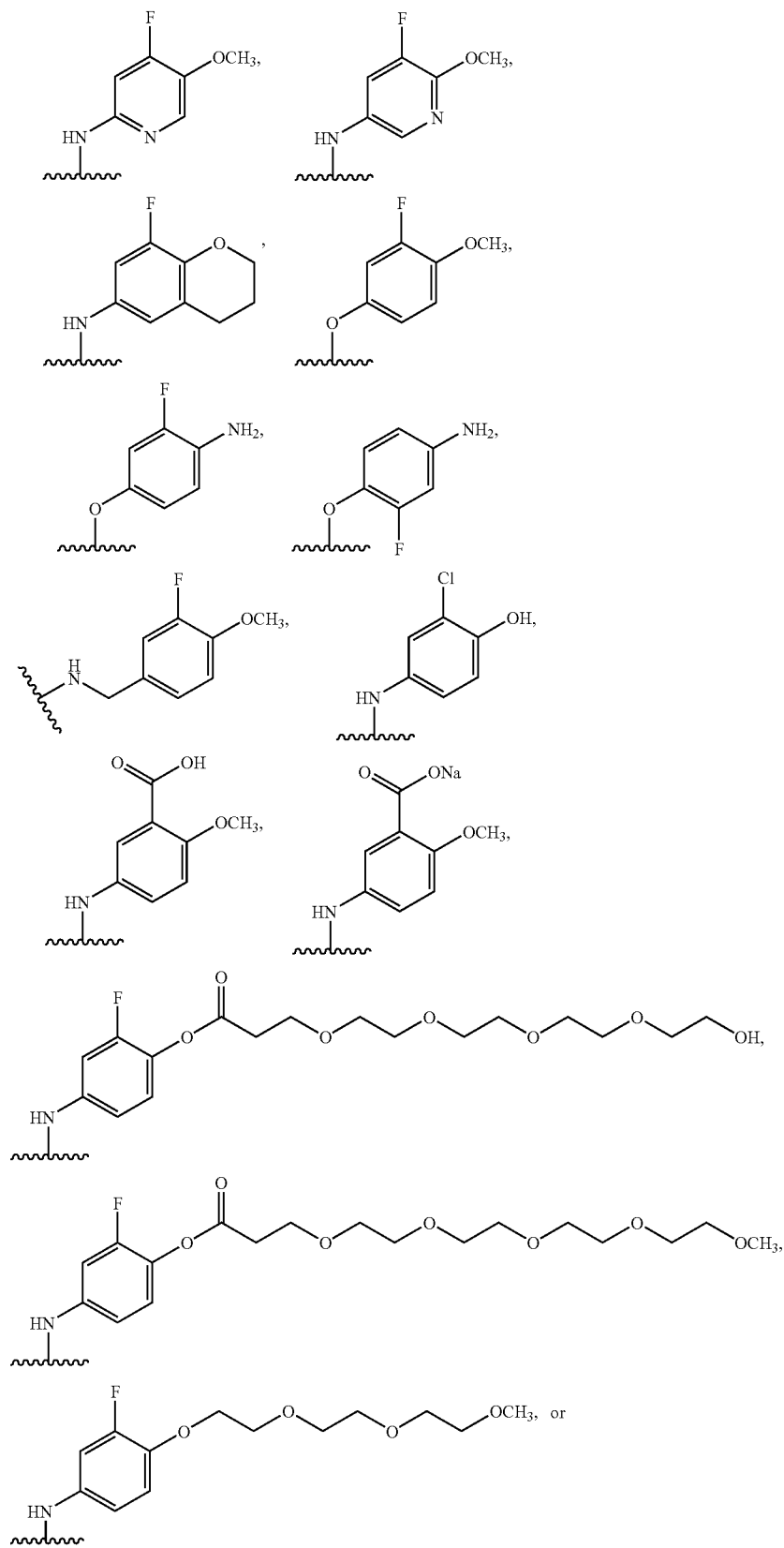

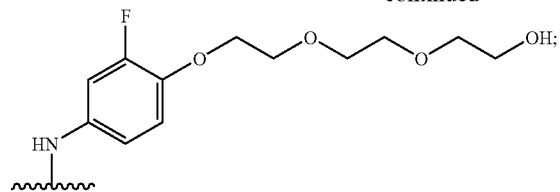
R² is selected from
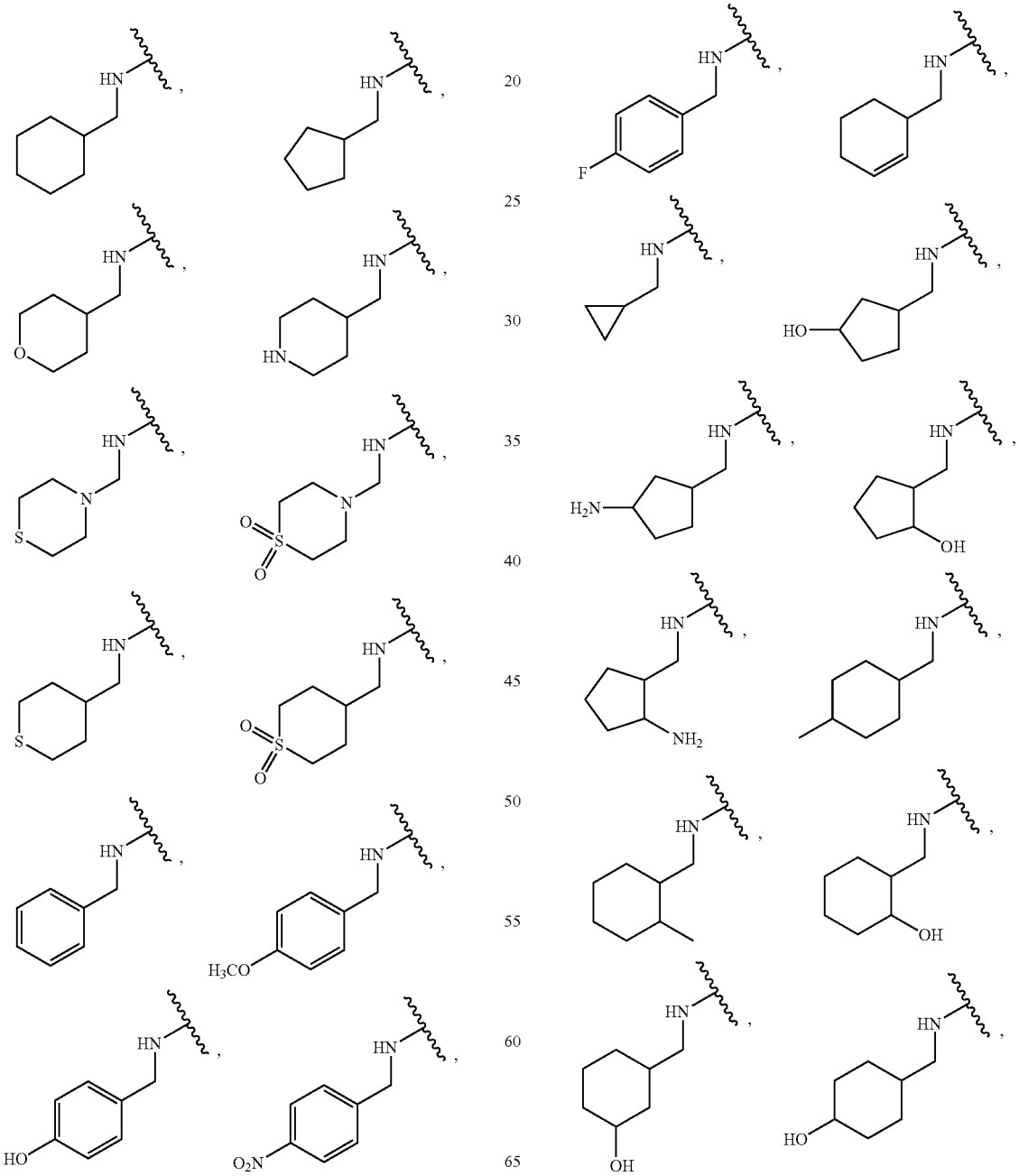

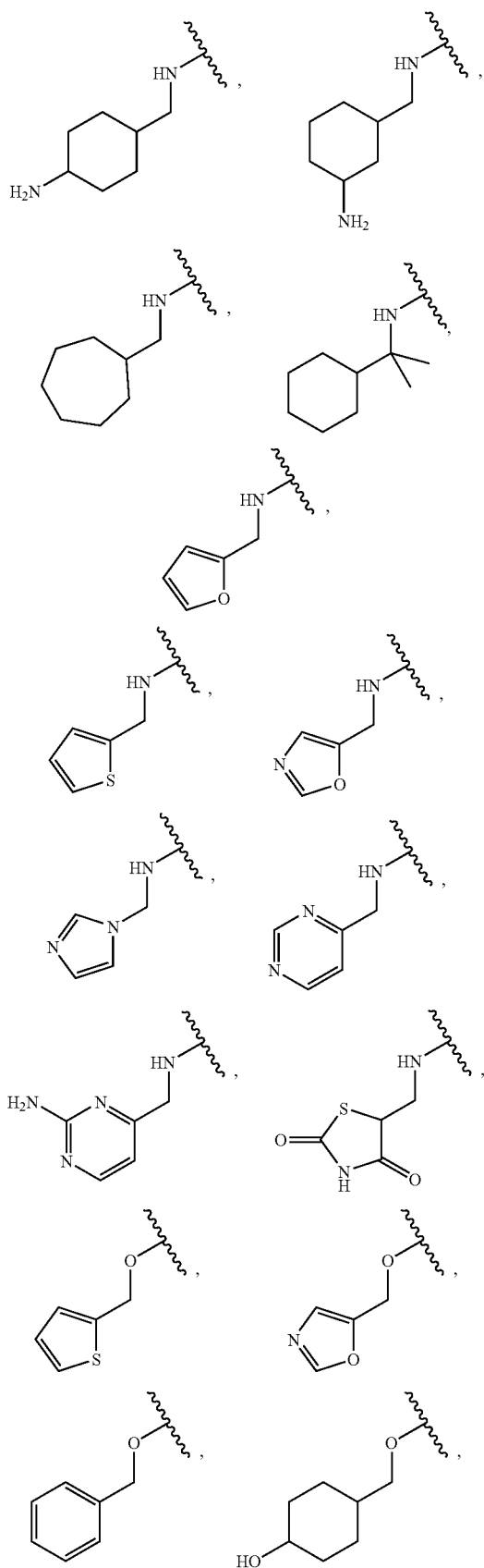
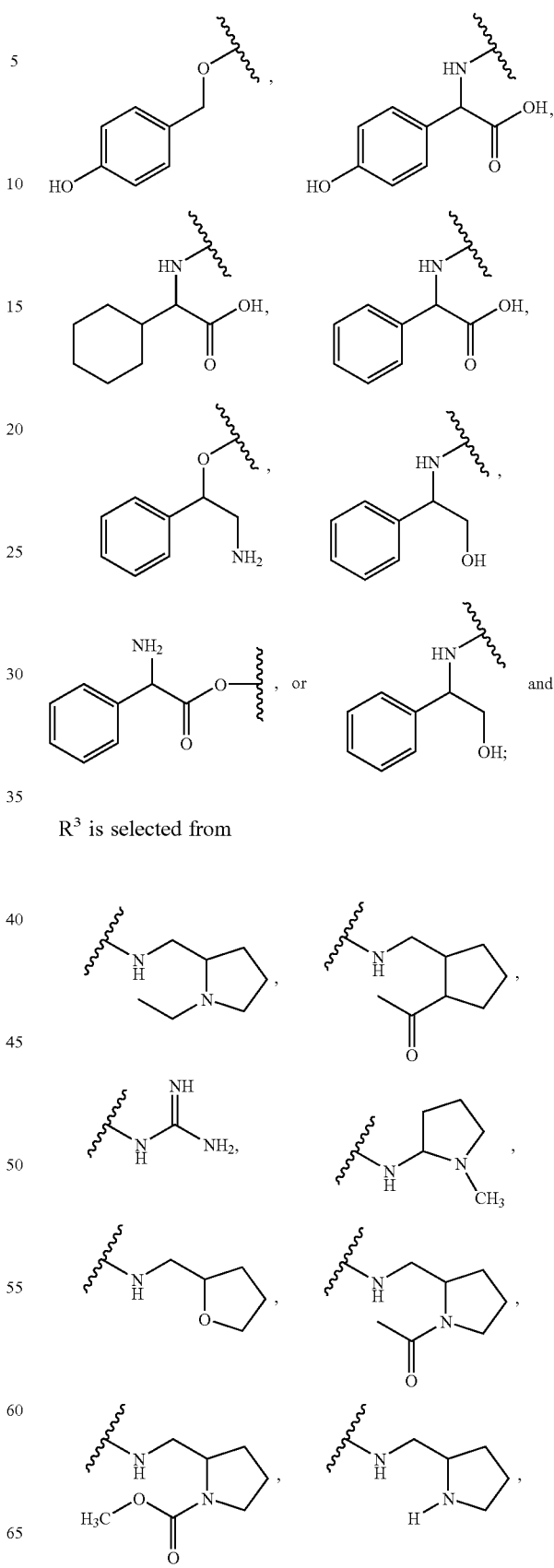
R³ is selected from

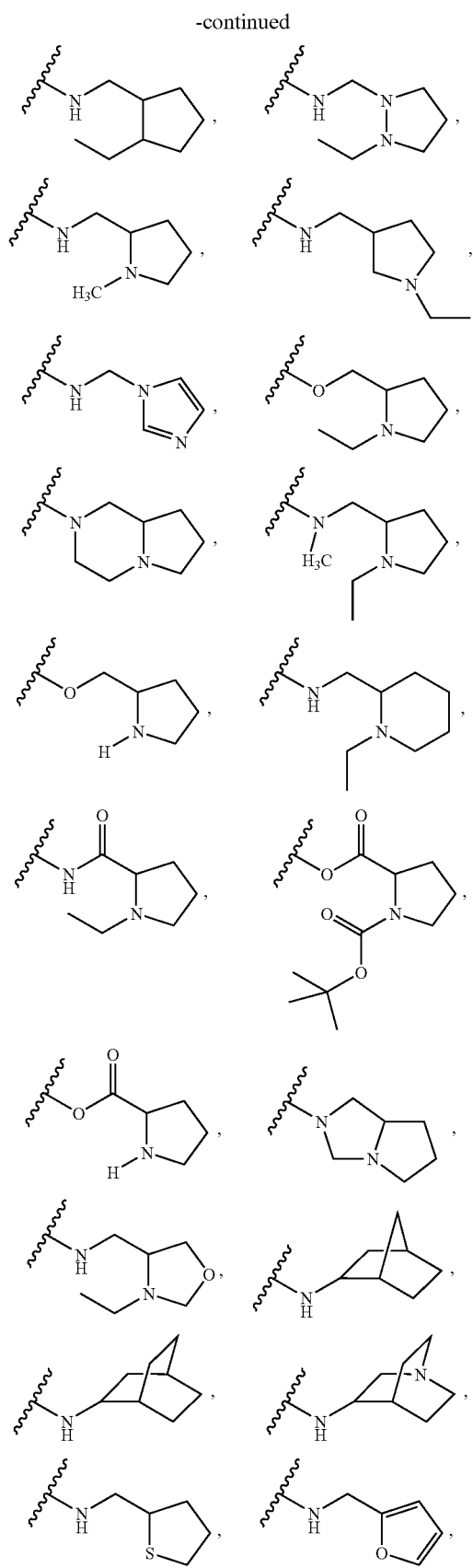
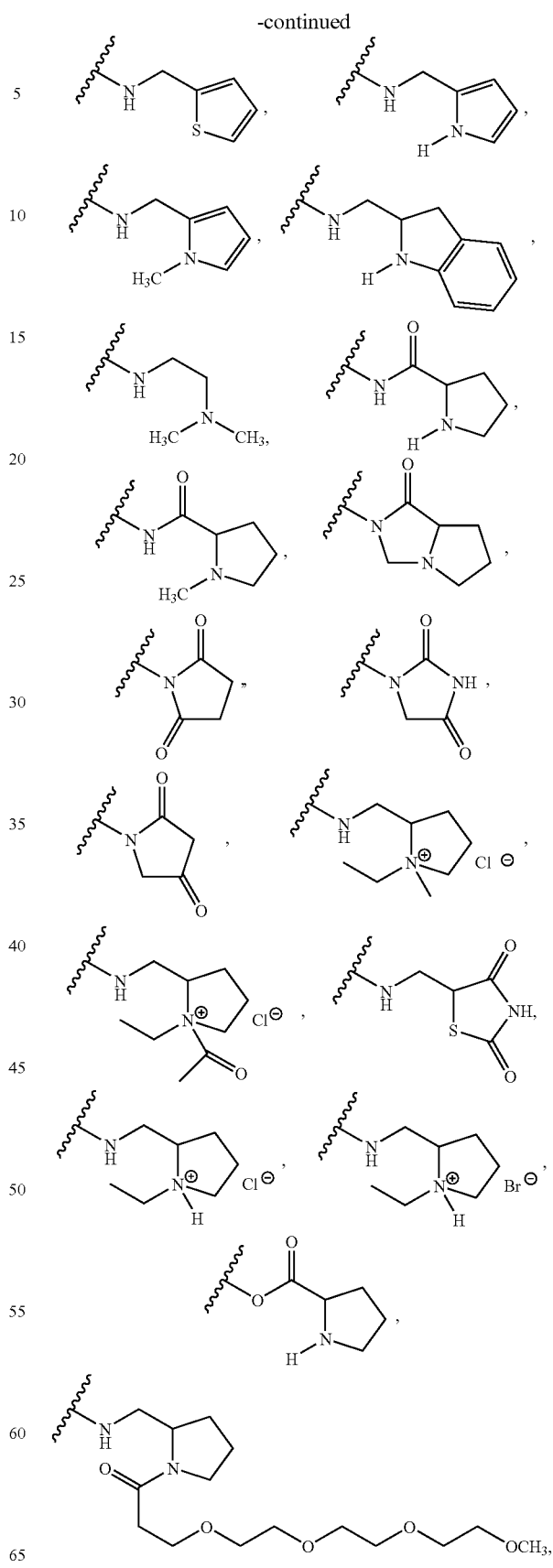

-continued

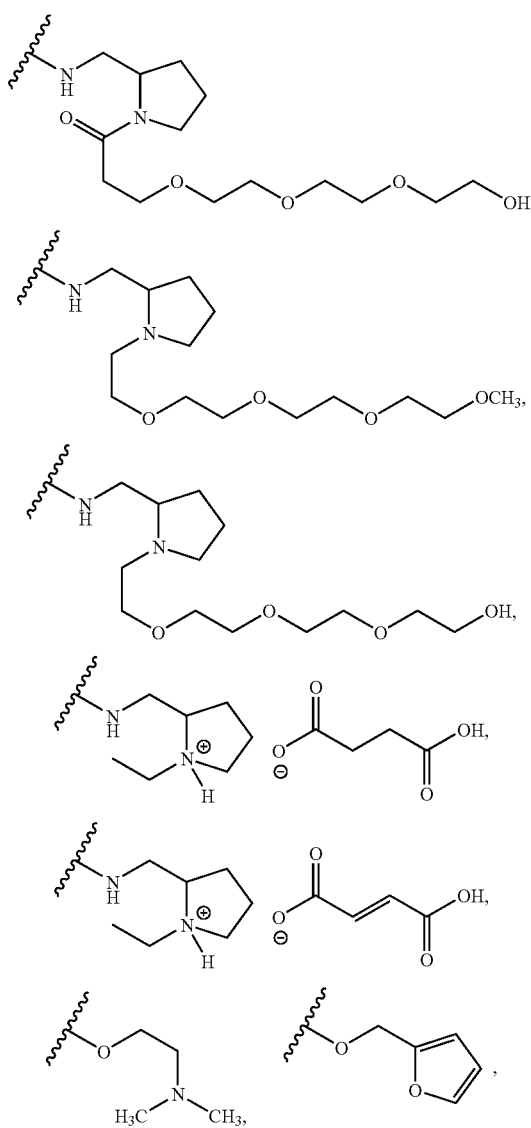

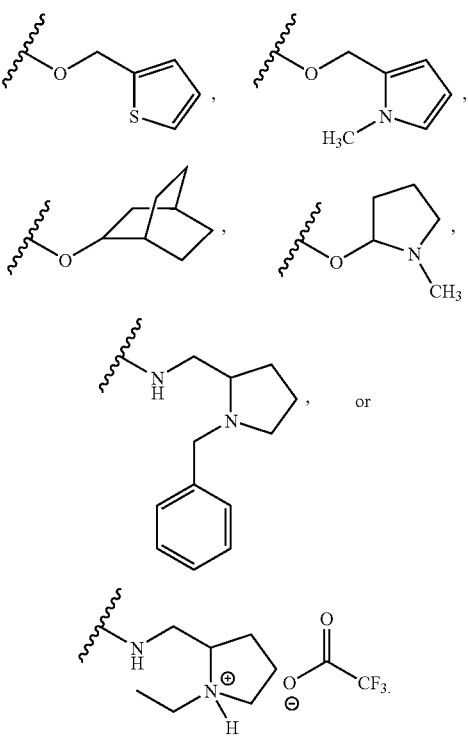

17. A stent comprising a composition disposed on or within the stent, the composition comprising a pharmaceutically acceptable carrier and a compound according to claim 16.

18. The stent as claimed in claim 17, wherein the composition further comprises at least one of the following:
a pharmaceutically acceptable auxiliary;
a pharmaceutically acceptable preservative;
a pharmaceutically acceptable excipient; or
any combination thereof.

\* \* \* \* \*